(12) United States Patent
Jacobsen et al.

(10) Patent No.: US 11,692,198 B2
(45) Date of Patent: Jul. 4, 2023

(54) TARGETED GENE ACTIVATION IN PLANTS

(71) Applicant: The Regents of the University of California, Oakland, CA (US)

(72) Inventors: Steve E. Jacobsen, Agoura Hills, CA (US); Ashot Papikian, Glendale, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/516,015

(22) Filed: Jul. 18, 2019

(65) Prior Publication Data

US 2020/0017869 A1   Jan. 16, 2020

Related U.S. Application Data

(63) Continuation-in-part of application No. PCT/US2018/014499, filed on Jan. 19, 2018.

(60) Provisional application No. 62/448,841, filed on Jan. 20, 2017.

(51) Int. Cl.
   *C12N 15/82* (2006.01)
   *C12N 15/10* (2006.01)
   *C12N 15/90* (2006.01)

(52) U.S. Cl.
   CPC ....... *C12N 15/8222* (2013.01); *C12N 15/102* (2013.01); *C12N 15/8261* (2013.01); *C12N 15/902* (2013.01)

(58) Field of Classification Search
   None
   See application file for complete search history.

(56) References Cited

U.S. PATENT DOCUMENTS

| | | |
|---|---|---|
| 4,500,707 A | 2/1985 | Caruthers et al. |
| 4,683,195 A | 7/1987 | Mullis et al. |
| 4,945,050 A | 7/1990 | Sanford et al. |
| 5,268,463 A | 12/1993 | Jefferson |
| 5,399,680 A | 3/1995 | Zhu et al. |
| 5,436,327 A | 7/1995 | Southern et al. |
| 5,466,785 A | 11/1995 | de Framond |
| 5,563,055 A | 10/1996 | Townsend et al. |
| 5,569,597 A | 10/1996 | Grimsley et al. |
| 5,604,121 A | 2/1997 | Hilder et al. |
| 5,608,142 A | 3/1997 | Barton et al. |
| 5,608,144 A | 3/1997 | Baden et al. |
| 5,608,149 A | 3/1997 | Barry et al. |
| 5,641,876 A | 6/1997 | McElroy et al. |
| 5,683,439 A | 11/1997 | Jensen |
| 5,689,049 A | 11/1997 | Cigan et al. |
| 5,689,051 A | 11/1997 | Cigan et al. |
| 5,700,637 A | 12/1997 | Southern |
| 2001/0010913 A1 | 8/2001 | Hillman et al. |
| 2014/0068797 A1 | 3/2014 | Doudna et al. |

FOREIGN PATENT DOCUMENTS

| | | | | |
|---|---|---|---|---|
| WO | WO-2015139139 A1 * | 9/2015 | ........... | C12N 15/113 |
| WO | WO-2016011070 A2 | 1/2016 | | |
| WO | WO-2017205837 A1 | 11/2017 | | |

OTHER PUBLICATIONS

Lowder et al 2015 (Plant Physiology 169: p. 971-985) (Year: 2015).*
Altschul et al., (1990). "Basic Local Alignment Search Tool," Journal of Molecular Biology, 215:403-410.
Altschul et al., (1997). "Gapped BLAST and PSI-Blast: A New Generation of Protein Database Search Programs," Nucleic Acids Research, 25(17):3389-3402.
Belanger et al., (1991). "Molecular Basis for Allelic Polymorphism of the Maize Globulin-1 Gene," Genetics, 129:863-872.
Berger et al., (1989). "Expression in Transgenic Plants of a Viral Gene Product that Mediates Insect Transmission of Potyviruses," Proc. Natl. Acad. Sci., 86:8402-8406.
Bogdanove et al., (2011). "TAL Effectors: Customizable Proteins for DNA Targeting," Science, 333:1843-1846.
Cano-Rodriguez et al., (2016). "Writing of H3K4Me3 overcomes epigenetic silencing in a sustained but context dependent manner," Nat. Commun., 7:12284, 11 pages.
Chavez et al. (2016). "Comparison of Cas9 activators in multiple species," Nat. Methods, 13:563-567, 16 pages.
Chen et al., (2013). "Fusion protein linkers: property, design and functionality," Advanced Drug Delivery Reviews, 65:1357-1369, 32 pages.
Christensen et al., (1989). "Sequence Analysis and Transcriptional Regulation by Heat Shock of Polyubiquitin Transcripts from Maize," Plant Molecular Biology, 12:619-632.
Christensen et al., (1992). "Maize Polyubiquitin Genes: Structure, Thermal Perturbation of Expression and Transcript Splicing, and Promoter Activity Following Transfer to Protoplasts by Electroporation," Plant Molecular Biology, 18:675-689.
Cokus et al., (2008). "Shotgun bisulfite sequencing of the *Arabidopsis* genome reveals DNA methylation patterning," Nature, 452(7184):215-219, 12 pages.
Cong et al., (2013). "Multiplex Genome Engineering Using CRISPR/Cas Systems," Science, 339(6121):819-823, 9 pages.
Conkling et al., (1990). "Isolation of Transcriptionally Regulated Root-Specific Genes from Tobacco," Plant Physiol. 93:1203-1211.
Corpet et al., (1988). "Multiple sequence alignment with hierarchical clustering," Nucleic Acids Res., 16:10881-90.
Deltcheva et al., (2011). "CRISPR RNA maturation by trans-encoded small RNA and host factor Rnase III," Nature, 471:602-607, 19 pages.

(Continued)

*Primary Examiner* — Matthew R Keogh
(74) *Attorney, Agent, or Firm* — Morrison & Foerster LLP

(57) ABSTRACT

The present disclosure relates to the targeting of transcriptional activators to specific loci in plants to activate transcription of the targeted loci. Specifically, the present disclosure provides methods and compositions for using guided (e.g. RNA-guided) transcriptional activators to activate transcription of specific loci in plants.

19 Claims, 39 Drawing Sheets
(39 of 39 Drawing Sheet(s) Filed in Color)
Specification includes a Sequence Listing.

(56) References Cited

OTHER PUBLICATIONS

Doudna et al., (2014). "The new frontier of genome engineering with CRISPR-Cas9," Science, 346:1258096, 10 pages.

Du et al., (2015). "DNA methylation pathways and their crosstalk with histone methylation," Nat. Rev. Mol. Cell Biol. 16:519-532, 31 pages.

Eisen, (1998). "Phylogenomics: improving functional predictions for uncharacterized genes by evolutionary analysis," Genome Res., 8: 163-167.

Esvelt et al., (2013). "Orthogonal Cas9 proteins for RNA-guided gene regulation and editing," Nature Methods, 10(11):1116-21, 19 pages.

Extended European Search Report received for Patent Application No. EP18741613.6, dated Jul. 21, 2020, 8 pages.

Gallego-Bartolome et al., (2017). "Targeted DNA demethylation of the *Arabidopsis* genome using the human TET1 catalytic domain," PNAS, 115(9):e2125-e2134.

Gates et al., (2017). "Histone Marks in the 'Driver's Seat': Functional Roles in Steering the Transcription Cycle," Trends Biochem. Sci., 42:977-989, 21 pages.

Geldner et al., (2009). "Rapid, Combinatorial Analysis of Membrane Compartments in Intact Plants with a Multicolor Marker Set," Plant Journal, 59(1):1-19.

GenBank Accession No. FJ524334.1, "Cloning vector pNIGELI6, complete sequence", Jul. 24, 2016, 4 pages.

GenBank Accession No. LT725641.1, "Gateway expression vector pAGRIKOLA-CATMA5a60920, complete sequence", Feb. 6, 2017, 4 pages.

Gilbert et al., (2014). "Genome-Scale CRISPR-Mediated Control of Gene Repression and Activation," Cell, 159:647-661.

Guo et al., (2010). "Set Domain Group2 is the major histone H3 lysine 4 trimethyltransferase in Anibidopsis," Proc Nati Acad Sci USA, 107(43):18557-62.

Higgins et al., (1989). "Fast and sensitive multiple sequence alignments on a microcomputer," Cabios, 5:151-153.

Hilson et al., (2004). "Versatile Gene-Specific Sequence Tags for *Arabidopsis* Functional Genomics: Transcript Profiling and Reverse Genetics Applications," Genome Research, 14(108):2176-2189.

Hsu et al., (2013). "DNA targeting specificity of RNA-guided Cas9 nucleases," Nature Biotechnology, 31:827-83.

Huang et al., (2017). "DNA epigenome editing using CRISPR-Cas SunTag-directed DNMT3A," Genome Biol., 18:176.

International Preliminary Report on Patentability received for PCT Patent Application No. PCT/US2018/014499, dated Aug. 1, 2019, 8 pages.

International Search Report and Written Opinion received for PCT Patent Application No. PCT/US2018/014499, dated Apr. 6, 2018, 12 pages.

Jinek et al., (2013). "RNA-programmed genome editing in human cells," eLife, 2:e00471, 9 pages.

Johnson et al., (2014). "SRA- and SET-domain-containing proteins link RNA polymerase V occupancy to DNA methylation," Nature, 507(7490):124-128.

Karlin et al., (1990). "Methods for assessing the statistical significance of molecular sequence features by using general scoring schemes," Proc. Natl. Acad. Sci. USA, 87:2264-2268.

Karlin et al., (1993). "Applications and Statistics for Multiple High-Scoring Segments in Molecular Sequences," Proc Natl Acad. Sci., 90:5873-5877.

Langridge et al., (1989). "Dual promoter of Agrobacterium tumefaciens mannopine synthase genes is regulated by plant growth hormones," PNAS USA, 86:3219-3223.

Last et al., (1991). "pEmu: an improved promoter for gene expression in cereal cells," Theor. Appl. Genet., 81:581-588.

Law et al., (2010). "Establishing, maintaining and modifying DNA methylation patterns in plants and animals," Nat. Rev. Genet., 11(3):204-220, 31 pages.

Li et al., (2013). "Multiplex and homologous recombination-mediated plant genome editing via guide RNA/Cas9,"Nature Biotechnology, 31:688-691, 8 pages.

Lowder et al., (2015). "A CRISPR/Cas9 Toolbox for Multiplexed Plant Genome Editing and Transcriptional Regulation," Plant Physiology, 169(2):971-85.

Luque et al., (2000). "A Constitutive Region is Responsible for Nuclear Targeting of 4.1 R: Modulation by Alternative Sequences Results in Differential Intracellular Localization," Journal of Cell Science, 113:2485-2496.

Mali et al., (2013). "CAS9 transcriptional activators for target specificity screening and paired nickases for cooperative genome engineering," Nature Biotechnology, 31:833-838, 17 pages.

Marton et al., (2010). "Nontransgenic Genome Modification in Plant Cells", Plant Physiology 154:1079-1087.

McCabe et al., (1988). "Stable Transformation of Soybean (Glycini Max) by Particle Acceleration," Bio/Technology, 6:923-926.

McCormick et al., (1986). "Leaf Disc Transformation of Cultivated Tomato (*L. esculentum*) using Agrobacterium Tumefaciens," Plant Cell Reports, 5:81-84.

McElroy et al., (1990). "Isolation of an efficient actin promoter for use in rice transformation," Plant Cell, 2:163-171.

Morita et al., (2016). "Targeted DNA demethylation in vivo using dCas9-peptide repeat and scFv-TET1 catalytic domain fusions," Nature Biotechnology, 34:1060-1065.

Murray et al., (1989). "Codon Usage in Plant Genes," Nucleic Acids Research, 17(2):477-498.

Myers et al., (1988). "Optimal alignments in linear space," Cabios 4:11-17.

Needleman et al., (1970). "A General Method Applicable to the Search for Similarities in the Amino Acid Sequence of Two Proteins," Journal of Molecular Biology, 48:443-453.

Odell et al., (1985). "Identification of DNA Sequences required for Activity of the Cauliflower Mosaic Virus 35S Promoter," Nature, 313:810-812.

Papikian et al., (2019). "Site-specific manipulation of *Arabidopsis* loci using CR1SPR-Cas9 SunTag systems," Nat. Commun., 10:729, 11 pages.

Paszkowski et al., (1984). "Direct Gene Transfer to Plants," The EMBO Journal, 3(12):2717-2722.

Pearson et al., (1988). "Improved Tools for Biological Sequence Comparison," Proc. Natl. Acad. Sci., 85:2444-2448.

Pflueger et al., (2018). "A modular dCas9-SunTag DNMT3A epigenome editing system overcomes pervasive off-target activity of direct fusion dCas9-DNMT3A constructs," Genome Res, 28:1193-1206.

Piatek et al., (2015). "RNA-Guided Transcriptional Regulation in Planta via Synthetic dCas9-Based Transcription Factors," Plant Biotechnology Journal, 13(4):578-589.

Qi et al., (2013). "Repurposing CRISPR as an RNA-Guided Platform for Sequence-Specific Control of Gene Expression," Cell, 152:1173-1183.

Reiss et al., (1987). "Regions in the transit peptide of SSU essential for transport into chloroplasts," Mol. Gen. Genet., 209(1):116-121.

Restriction Requirement received for U.S. Appl. No. 16/516,015, dated Aug. 26, 2020, 5 pages.

Riggs et al., (1986). "Stable transformation of tobacco by electroporation: evidence for plasmid concatenation," Proc. Natl. Acad Sci. USA, 83:5602-5606.

Rogers et al., (1987). "Improved Vectors for Plant Transformation: Expression Cassette Vectors and New Selectable Markers," Methods in Enzymology, 153:253-277.

Rutlienburg et al., (2007). "Methylation of Lysine 4 on Historie H3: Intricacy of Writing and Reading a Single Epigenetic Mark," Mol. Cell, 25:15-30.

Saitou et al., (1987). "The neighbor-joining method: a new method for reconstructing phylogenetic trees," Mol. Biol. & Evo., 4:406-425.

Schardl et al., (1987). "Design and Construction of a Versatile System for the Expression of Foreign Genes in Plants," Gene, 61:1-11.

(56) References Cited

OTHER PUBLICATIONS

Seth et al., (2016). "Current status of potential applications of repurposed Cas9 for structural and functional genomics of plants," Biochemical and Biophysical Research Communications, 480:499-507.
Settles et al., (1998). "Old and new pathways of protein export in chloroplasts and bacteria," Trends Cell Biol, 12:494-501.
Shilatifard (2012). "Compass family of H3K4 MTs: Mechanisms in Development and Disease Pathogenesis," Annu Rev Biochem., 81:65-95, 33 pages.
Smith et al., (1981). "Comparison of biosequences," Adv. Appl. Math., 2:482-489.
Soppe et al., (2000). "The late flowering phenotype of fwa mutants is caused by gain-of-function epigenetic alleles of a homeodomain gene," Mol. Cell., 6:791-802.
Stroud et al., (2014). "The roles of non-CG methylation in *Arabidopsis*," Nat. Struct. Mol. Biol., 21:64-72, 25 pages.
Tamura et al., (2007). "MEGA4: Molecular Evolutionary Genetics Analysis (MEGA) software version 4.0," Mol. Biol. & Evo., 24:1596-1599.
Tanenbaum et al., (2014). "A Protein-Tagging System for Signal Amplification in Gene Expression and Fluorescence Imaging," Cell, 159:635-46.
Thompson et al., (1994). "Clustal W: improving the sensitivity of progressive multiple sequence alignment through sequence weighting, position-specific gap penalties and weight matrix choice," Nucleic Acids Res., 22: 4673-4680.
Van Tunen et al., (1988). Cloning of the two chaicone flavanone isomerase genes from Petunia hybrida: coordinate, light-regulated and differential expression of flavonoid genes, EMBO Journal, 7(5):1257-1263.
Velten et al., (1984). "Isolation of a Dual Plant Promoter Fragment from the Ti Plasmid of Agrobacterium Tumefaciens," The EMBO Journal, 3(12):2723-2730.
Walker et al., (1987). "DNA Sequences required for Anaerobic Expression of the Maize Alcohol dehydrogenase 1 Gene," Proc. Natl. Acad. Sci., 84:6624-6628.
Xie et al., (2015). "Boosting CRISPR/Cas9 multiplex editing capability with the endogenous tRNA processing system," Proc Natl Acad Sci USA, 112(11):3570-5.
Xing et al., (2014). "A CRISPR/Cas9 toolkit for multiplex genome editing in plants," BMC Plant Biology, 14:327, 12 pages.
Zemach et al., (2013). "The *Arabidopsis* nucleosome remodeler DDM1 allows DNA methyltransferases to access H1 containing heterochromatin," Cell, 153:193-205.
Zhang et al., (2009). "Genome-wide analysis of mono-, di and trimethylation of histone H3 Tysine 4 in *Arabidopsis thaliana*," Genome Biol., 10:R62, 14 pages.

\* cited by examiner

Background fluorescence from chlorophyll

GFP

SEQUENCE LISTING

<160> NUMBER OF SEQ ID NOS: 131

<210> SEQ ID NO 1
<211> LENGTH: 7099
<212> TYPE: DNA
<213> ORGANISM: Artificial Sequence
<220> FEATURE:
<223> OTHER INFORMATION: Synthetic Construct

<400> SEQUENCE: 1

```
atgcatatga gtctagctca acagagcttt taacccaaat tggtacaata gaatacaact        60
ttagatcata attctcaaaa gaaagagatt ccttagctat tctatctgcc actccatttc       120
cttctcggct tgtatgcaca agcataaaat cctcaaactt gctaagtaga tactttatgt       180
```

-continued

```
cttggataat tggattgaga cttgacaagc ataactttca tgtaaccaaa gacacaagtt    240
gctgagaatc cacctcaaaa atgatcttcc tataattgaa tcgggataat gacagcacag    300
cccatctaag agcctccact tctacttcca gcacgcttct tacttttacc acagctcttg    360
cacctaacca taacaccttc cctgtatgat cgcgaagcac ccaccctaag ccacattta    420 atccttctgt tggccatgcc ccatcaaagt tgcacttaac ccaagattgt ggtggagctt    480
cccatgtttc tcgtctgtcc cgacggtgtt gtggttggtg ctttccttac attctgagcc    540 tcttccttc taatccactc atctgcatct tcttgtgtcc ttactaatac ctcattggtt    600
ccaaattccc tcccttaag caccagctcg tttctgttct tccacagcct cccaagtatc    660
caagggacta aagcctccac attcttcaga tcaggatatt cttgtttaag atgttgaact    720
ctatggaggt ttgtatgaac tgatgatcta ggaccggata agttcccttc ttcatagcga    780
acttattcaa agaatgtttt gtgtatcatt cttgttacat tgttattaat gaaaaaatat    840
tattggtcat tggactgaac acgagtgtta aatatggacc aggcccccaaa taagatccat    900 tgatatatga attaaataac aagaataaat cgagtcacca aaccacttgc cttttttaac    960
gagacttgtt caccaacttg atacaaaagt cattatccta tgcaaatcaa taatcataca   1020 aaatatcca ataacactaa aaaattaaaa gaaatggata atttcacaat atgttatacg   1080
ataaagaagt tacttttcca agaaattcac tgattttata agcccacttg cattagataa   1140
atggcaaaaa aaacaaaaa ggaaaagaaa taaagcacga agaattctag aaaatacgaa   1200
atacgcttca atgcagtggg acccacggtt caattattgc caattttcag ctccaccgta   1260
tatttaaaaa ataaaacgat aatgctaaaa aaatataaat cgtaacgatc gttaaatctc   1320
aacggctgga tcttatgacg accgttagaa attgtggttg tcgacgagtc agtaataaac   1380
ggcgtcaaag tggttgcagc cggcacacac gagtcgtgtt tatcaactca aagcacaaat   1440
acttttcctc aacctaaaaa taaggcaatt agccaaaaac aactttgcgt gtaaacaacg   1500
ctcaatacac gtgtcatttt attattagct attgcttcac cgccttagct ttctcgtgac   1560
ctagtcgtcc tcgtcttttc ttcttcttct tctataaaac aatacccaaa gagctcttct   1620
tcttcacaat tcagatttca atttctcaaa atcttaaaaa ctttctctca attctctcta   1680
ccgtgatcaa ggtaaatttc tgtgttcctt attctctcaa aatcttcgat tttgttttcg   1740
ttcgatccca atttcgtata tgttctttgg tttagattct gttaatctta gatcgaagac   1800
gattttctgg gtttgatcgt tagatatcat cttaattctc gattagggtt tcatagatat   1860
catccgattt gttcaaataa tttgagtttt gtcgaataat tactcttcga tttgtgattt   1920
ctatctagat ctggtgttag tttctagttt gtgcgatcga atttgtcgat taatctgagt   1980
ttttctgatt aacagggatc atcaacaagt ttgtacaaaa aagcaggctc tttaaagtat   2040
ttttacaaca attaccaaca acaacaaaca acaaacaaca ttacaattac tatttacaat   2100
tacaaaaaaa gttaacatgg acaagaagta cagcatcggc ctggccatcg gcaccaactc   2160
tgtgggctgg gccgtgatca ccgacgagta caaggtgccc agcaagaaat tcaaggtgct   2220
gggcaacacc gaccggcaca gcatcaagaa gaacctgatc ggcgccctgc tgttcgacag   2280
cggagaaaca gccgaggcca cccggctgaa gagaaccgcc agaagaagat acaccagacg   2340
gaagaaccgg atctgctatc tgcaagagat cttcagcaac gagatggcca aggtggacga   2400
cagcttcttc cacagactgg aagagtcctt cctggtggaa gaggataaga agcacgagcg   2460
gcaccccatc ttcggcaaca tcgtggacga ggtggcctac cacgagaagt accccaccat   2520
```

```
ctaccacctg agaaagaaac tggtggacag caccgacaag gccgacctgc ggctgatcta   2580
tctggccctg gcccacatga tcaagttccg gggccacttc ctgatcgagg gcgacctgaa   2640
ccccgacaac agcgacgtgg acaagctgtt catccagctg gtgcagacct acaaccagct   2700
gttcgaggaa aacccatca cgccagcgg cgtggacgcc aaggccatcc tgtctgccag   2760
actgagcaag agcagacggc tggaaaatct gatcgcccag ctgcccggcg agaagaagaa   2820
tggcctgttc ggcaacctga ttgccctgag cctgggcctg accccaact tcaagagcaa   2880
cttcgacctg gccgaggatg ccaaactgca gctgagcaag gacacctacg acgacgacct   2940
ggacaacctg ctggcccaga tcggcgacca gtacgccgac ctgtttctgg ccgccaagaa   3000
cctgtccgac gccatcctgc tgagcgacat cctgagagtg aacaccgaga tcaccaaggc   3060
cccctgagc gcctctatga tcaagagata cgacgagcac caccaggacc tgaccctgct   3120
gaaagctctc gtgcggcagc agctgcctga aagtacaaa gagatttttct tcgaccagag   3180
caagaacggc tacgccggct acatcgatgg cggagccagc caggaagagt tctacaagtt   3240
catcaagccc atcctggaaa agatggacgg caccgaggaa ctgctcgtga agctgaacag   3300
agaggacctg ctgcggaagc agcggaccttt cgacaacggc agcatccccc accagatcca   3360
cctgggagag ctgcacgcca ttctgcggcg gcaggaagat tttttacccat tcctgaagga   3420
caaccgggaa aagatcgaga gatcctgac cttccgcatc ccctactacg tgggccctct   3480
ggccagggga acagcagat cgcctggat gaccagaaag agcgaggaaa ccatcacccc   3540
ctggaacttc gaggaagtgg tggacaaggg cgccagcgcc cagagcttca tcgagcggat   3600
gaccaacttc gataagaacc tgcccaacga aaggtgctg cccaagcaca gctgctgta   3660
cgagtacttc accgtgtaca acgagctgac caaagtgaaa tacgtgaccg agggaatgag   3720
aaagcccgcc ttcctgagcg gcgagcagaa aaaagccatc gtggacctgc tgttcaagac   3780
caaccggaaa gtgaccgtga agcagctgaa agaggactac ttcaagaaaa tcgagtgctt   3840
cgactccgtg gaaatctccg gcgtggaaga tcggttcaac gcctccctgg gcacatacca   3900
cgatctgctg aaaattatca aggacaagga cttcctggac aatgaggaaa acgaggacat   3960
tctggaagat atcgtgctga cctgacact gtttgaggac agagatga tcgaggaacg   4020
gctgaaaacc tatgcccacc tgttcgacga caaagtgatg aagcagctga gcggcggag   4080
atacaccggc tggggcaggc tgagccgaa gctgatcaac ggcatccggg acaagcagtc   4140
cggcaagaca atcctggatt tcctgaagtc cgacggcttc gccaacagaa acttcatgca   4200
gctgatccac gacgacagcc tgaccttaa agaggcatc cagaaagccc aggtgtccgg   4260
ccagggcgat agcctgcacg agcacattgc caatctggcc ggcagccccg ccattaagaa   4320
gggcatcctg cagacagtga aggtggtgga cgagctcgtg aaagtgatgg gccggcacaa   4380
gcccgagaac atcgtgatcg aaatggccag agagaaccag accacccaga agggacagaa   4440
gaacagccgc gagagaatga gcggatcga agaggcatc aaagagctgg gcagccagat   4500
cctgaaagaa caccccgtgg aaaacaccca gctgcagaac gagaagctgt acctgtacta   4560
cctgcagaat gggcgggata tgtacgtgga ccaggaactg gacatcaacc ggctgtccga   4620
ctacgatgtg gacgctatcg tgcctcagag ctttctgaag gacgactcca tcgataacaa   4680
agtgctgact cggagcgaca agaaccgggg caagagcgac aacgtgccct ccgaagaggt   4740
cgtgaagaag atgaagaact actggcgcca gctgctgaat gccaagctga ttacccagag   4800
gaagttcgac aatctgacca aggccgagag aggcggctg agcgaactgg ataaggccgg   4860
cttcatcaag agacagctgg tggaaacccg gcagatcaca aagcacgtgg cacagatcct   4920
```

```
ggactcccgg atgaacacta agtacgacga gaacgacaaa ctgatccggg aagtgaaagt    4980
gatcaccctg aagtccaagc tggtgtccga tttccggaag gatttccagt tttacaaagt    5040
gcgcgagatc aacaactacc accacgccca cgacgcctac ctgaacgccg tcgtgggaac    5100
cgccctgatc aaaaagtacc ctaagctgga agcgagttc gtgtacggcg actacaaggt    5160
gtacgacgtg cggaagatga tcgccaagag cgagcaggaa atcggcaagg ctaccgccaa    5220
gtacttcttc tacagcaaca tcatgaactt tttcaagacc gagattaccc tggccaacgg    5280
cgagatccgg aagcggcctc tgatcgagac aaacggcgaa acaggcgaga tcgtgtggga    5340
taagggccgg gactttgcca ccgtgcggaa agtgctgtct atgccccaag tgaatatcgt    5400
gaaaaagacc gaggtgcaga caggcggctt cagcaaagag tctatcctgc caagaggaa     5460
cagcgacaag ctgatcgcca aagaaggc ctgggaccct aagaagtacg gcggcttcga     5520
cagcccacc gtggcctatt ctgtgctggt ggtggccaaa gtggaaaagg caagtccaa      5580
gaaactgaag agtgtgaaag agctgctggg gatcaccatc atggaaagaa gcagcttcga    5640
gaagaatccc atcgactttc tggaagccaa gggctacaaa gaagtgaaaa aggacctgat    5700
catcaagctg cctaagtact ccctgttcga gctggaaaac ggccggaaga gaatgctggc    5760
ctctgccggc gaactgcaga agggaaacga actggccctg ccctccaaat atgtgaactt    5820
cctgtacctg gccagccact atgagaagct gaagggctcc cccgaggata tgagcagaa     5880
acagctgttt gtggaacagc acaaacacta cctggacgag atcatcgagc agatcagcga    5940
gttctccaag agagtgatcc tggccgacgc taatctggac aaggtgctga gcgcctacaa    6000
caagcacaga gacaagccta tcagagagca ggccgagaat atcatccacc tgtttaccct    6060
gaccaatctg ggagcccctg ccgccttcaa gtactttgac accaccatcg accggaagag    6120
gtacaccagc accaaagagg tgctggacgc caccctgatc caccagagca tcaccggcct    6180
gtacgagaca cggatcgacc tgtctcagct gggaggcgac gcctatcccct atgacgtgcc    6240
cgattatgcc agcctgggca gcggctcccc caagaaaaaa cgcaaggtgg aagatcctaa    6300
gaaaaagcgg aaagtggacg gcattggtag tgggagcaac ggcagcagcg atccaacgg     6360
tccgactgac gccgcggaag aagaactttt gagcaagaat tatcatcttg agaacgaagt    6420
ggctcgtctt aagaaaggtt ctggcagtgg agaagaactg ctttcaaaga attaccacct    6480
ggaaaatgag gtagctagac tgaaaaaggg gagcggaagt ggggaggagt tgctgagcaa    6540
aaattatcat ttggagaacg aagtagcacg actaaagaaa gggtccggat cgggtgagga    6600
gttactctcg aaaaattatc atctcgaaaa cgaagtggct cggctaaaaa agggcagtgg    6660
ttctggagaa gagctattat ctaaaaacta ccacctcgaa aatgaggtgg cacgcttaaa    6720
aaagggaagt ggcagtggtg aagagctact atccaagaat tatcatcttg agaacgaggt    6780
agcgcgtttg aagaagggtt ccggctcagg agaggaactg ctctcgaaga actatcatct    6840
tgaaaatgag gtcgctcgat taaaaaggg atcgggcagt ggtgaggaac tactttcaaa     6900
gaattaccac ctcgaaaacg aagtagctcg attaaagaaa ggttcagggt cgggtgaaga    6960
attactgagt aaaaattatc atctggaaaa tgaggtagcg agactaaaaa aggggagtgg    7020
ttctggcgag gaattgctat cgaaaaatta tcatcttgag aacgaagttg ctaggctcaa    7080
aaagggctca ggctcaggc                                                 7099
```

<210> SEQ ID NO 2
<211> LENGTH: 1994
<212> TYPE: DNA

<213> ORGANISM: Artificial Sequence
<220> FEATURE:
<223> OTHER INFORMATION: Synthetic Construct

<400> SEQUENCE: 2

| | | | | | |
|---|---|---|---|---|---|
| atgcatatga | gtctagctca | acagagcttt | taacccaaat | tggtacaata | gaatacaact | 60 |
| ttagatcata | attctcaaaa | gaaagagatt | ccttagctat | tctatctgcc | actccatttc | 120 |
| cttctcggct | tgtatgcaca | agcataaaat | cctcaaactt | gctaagtaga | tactttatgt | 180 |
| cttggataat | tggattgaga | cttgacaagc | ataactttca | tgtaaccaaa | gacacaagtt | 240 |
| gctgagaatc | cacctcaaaa | atgatcttcc | tataattgaa | tcgggataat | gacagcacag | 300 |
| cccatctaag | agcctccact | tctacttcca | gcacgcttct | tacttttacc | acagctcttg | 360 |
| cacctaacca | taacaccttc | cctgtatgat | cgcgaagcac | ccaccctaag | ccacatttta | 420 |
| atccttctgt | tggccatgcc | ccatcaaagt | tgcacttaac | ccaagattgt | ggtggagctt | 480 |
| cccatgtttc | tcgtctgtcc | cgacggtgtt | gtggttggtg | ctttccttac | attctgagcc | 540 |
| tctttccttc | taatccactc | atctgcatct | tcttgtgtcc | ttactaatac | ctcattggtt | 600 |
| ccaaattccc | tccctttaag | caccagctcg | tttctgttct | tccacagcct | cccaagtatc | 660 |
| caagggacta | agcctccac | attcttcaga | tcaggatatt | cttgtttaag | atgttgaact | 720 |
| ctatggaggt | ttgtatgaac | tgatgatcta | ggaccggata | agttcccttc | ttcatagcga | 780 |
| acttattcaa | agaatgtttt | gtgtatcatt | cttgttacat | tgttattaat | gaaaaaatat | 840 |
| tattggtcat | tggactgaac | acgagtgtta | aatatggacc | aggccccaaa | taagatccat | 900 |
| tgatatatga | attaaataac | aagaataaat | cgagtcacca | aaccacttgc | cttttttaac | 960 |
| gagacttgtt | caccaacttg | atacaaaagt | cattatccta | tgcaaatcaa | taatcataca | 1020 |
| aaatatccaa | ataacactaa | aaattaaaa | gaaatggata | atttcacaat | atgttatacg | 1080 |
| ataaagaagt | tacttttcca | agaaattcac | tgatttata | agcccacttg | cattagataa | 1140 |
| atggcaaaaa | aaaacaaaaa | ggaaagaaa | taaagcacga | agaattctag | aaaatacgaa | 1200 |
| atacgcttca | atgcagtggg | acccacggtt | caattattgc | caatttcag | ctccaccgta | 1260 |
| tatttaaaaa | ataaaacgat | aatgctaaaa | aaatataaat | cgtaacgatc | gttaaatctc | 1320 |
| aacggctgga | tcttatgacg | accgttagaa | attgtggttg | tcgacgagtc | agtaataaac | 1380 |
| ggcgtcaaag | tggttgcagc | cggcacacac | gagtcgtgtt | tatcaactca | agcacaaat | 1440 |
| actttcctc | aacctaaaaa | taaggcaatt | agccaaaaac | aactttgcgt | gtaaacaacg | 1500 |
| ctcaatacac | gtgtcatttt | attattagct | attgcttcac | cgccttagct | ttctcgtgac | 1560 |
| ctagtcgtcc | tcgtcttttc | ttcttcttct | tctataaaac | aatacccaaa | gagctcttct | 1620 |
| tcttcacaat | tcagatttca | atttctcaaa | atcttaaaaa | ctttctctca | attctctcta | 1680 |
| ccgtgatcaa | ggtaaatttc | tgtgttcctt | attctctcaa | aatcttcgat | tttgttttcg | 1740 |
| ttcgatccca | atttcgtata | tgttctttgg | tttagattct | gttaatctta | gatcgaagac | 1800 |
| gattttctgg | gtttgatcgt | tagatatcat | cttaattctc | gattagggtt | tcatagatat | 1860 |
| catccgattt | gttcaaataa | tttgagtttt | gtcgaataat | tactcttcga | tttgtgattt | 1920 |
| ctatctagat | ctggtgttag | tttctagttt | gtgcgatcga | atttgtcgat | taatctgagt | 1980 |
| ttttctgatt | aaca | | | | | 1994 |

<210> SEQ ID NO 3
<211> LENGTH: 115
<212> TYPE: DNA
<213> ORGANISM: Artificial Sequence

```
<220> FEATURE:
<223> OTHER INFORMATION: Synthetic Construct

<400> SEQUENCE: 3
ggatcatcaa caagtttgta caaaaaagca ggctctttaa agtatttta caacaattac      60 caacaacaac aaacaacaaa caacattaca attactattt acaattacaa aaaaa          115

<210> SEQ ID NO 4
<211> LENGTH: 4107
<212> TYPE: DNA
<213> ORGANISM: Artificial Sequence
<220> FEATURE:
<223> OTHER INFORMATION: Synthetic Construct

<400> SEQUENCE: 4
atggacaaga agtacagcat cggcctggcc atcggcacca actctgtggg ctgggccgtg     60
atcaccgacg agtacaaggt gcccagcaag aaattcaagg tgctgggcaa caccgaccgg    120
cacagcatca gaagaaacct gatcggcgcc ctgctgttcg acagcggaga aacagccgag    180
gccacccggc tgaagagaac cgccagaaga agatacacca gacggaagaa ccggatctgc    240
tatctgcaag agatcttcag caacgagatg gccaaggtgg acgacagctt cttccacaga    300
ctggaagagt ccttcctggt ggaagaggat aagaagcacg agcggcaccc catcttcggc    360
aacatcgtgg acgaggtggc ctaccacgag aagtacccca ccatctacca cctgagaaag    420
aaactggtgg acagcaccga caaggccgac ctgcggctga tctatctggc cctggcccac    480
atgatcaagt tccgggggcca cttcctgatc gagggcgacc tgaaccccga caacagcgac    540
gtggacaagc tgttcatcca gctggtgcag acctacaacc agctgttcga ggaaaacccc    600
atcaacgcca gcggcgtgga cgccaaggcc atcctgtctg ccagactgag caagagcaga    660
cggctggaaa atctgatcgc ccagctgccc ggcgagaaga gaatggcct gttcggcaac    720 ctgattgccc tgagcctggg cctgaccccc aacttcaaga gcaacttcga cctggccgag    780
gatgccaaac tgcagctgag caaggacacc tacgacgacg acctggacaa cctgctggcc    840
cagatcggcg accagtacgc cgacctgttt ctggccgcca gaaacctgtc cgacgccatc    900
ctgctgagcg acatcctgag agtgaacacc gagatcacca aggcccccct gagcgcctct    960
atgatcaaga gatacgacga gcaccaccag gacctgaccc tgctgaaagc tctcgtgcgg    1020
cagcagctgc ctgagaagta caaagagatt ttcttcgacc agagcaagaa cggctacgcc    1080
ggctacatcg atggcggagc cagccaggaa gagttctaca agttcatcaa gcccatcctg    1140
gaaaagatga cggcaccga ggaactgctc gtgaagctga acagagga cctgctgcgg    1200 aagcagcgga ccttcgacaa cggcagcatc ccccaccaga tccacctggg agagctgcac    1260
gccattctgc ggcggcagga agatttttac ccattcctga aggacaaccg ggaaaagatc    1320
gagaagatcc tgaccttccg catcccctac tacgtgggcc ctctggccag ggaaacagc    1380 agattcgcct ggatgaccag aaagagcgag gaaaccatca ccccctggaa cttcgaggaa    1440
gtggtggaca agggcgccag cgcccagagc ttcatcgagc ggatgaccaa cttcgataag    1500
aacctgccca acgagaaggt gctgcccaag cacagcctgc tgtacgagta cttcaccgtg    1560
tacaacgagc tgaccaaagt gaaatacgtg accgagggaa tgagaaagcc cgccttcctg    1620
agcggcgagc agaaaaaagc catcgtggac ctgctgttca gaaccaaccg aaagtgacc    1680 gtgaagcagc tgaaagagga ctacttcaag aaaatcgagt gcttcgactc cgtggaaatc    1740
tccggcgtgg aagatcggtt caacgcctcc ctgggcacat accacgatct gctgaaaatt    1800
```

```
atcaaggaca aggacttcct ggacaatgag gaaaacgagg acattctgga agatatcgtg   1860
ctgaccctga cactgtttga ggacagagag atgatcgagg aacggctgaa aacctatgcc   1920
cacctgttcg acgacaaagt gatgaagcag ctgaagcggc ggagatacac cggctggggc   1980
aggctgagcc ggaagctgat caacggcatc cgggacaagc agtccggcaa gacaatcctg   2040
gatttcctga agtccgacgg cttcgccaac agaaacttca tgcagctgat ccacgacgac   2100
agcctgacct ttaaagagga catccagaaa gcccaggtgt ccggccaggg cgatagcctg   2160
cacgagcaca ttgccaatct ggccggcagc cccgccatta agaagggcat cctgcagaca   2220
gtgaaggtgg tggacgagct cgtgaaagtg atgggccggc acaagcccga gaacatcgtg   2280
atcgaaatgg ccagagagaa ccagaccacc cagaagggac agaagaacag ccgcgagaga   2340
atgaagcgga tcgaagaggg catcaaagag ctgggcagcc agatcctgaa agaacacccc   2400
gtggaaaaca cccagctgca gaacgagaag ctgtacctgt actacctgca gaatgggcgg   2460
gatatgtacg tggaccagga actggacatc aaccggctgt ccgactacga tgtggacgct   2520
atcgtgcctc agagctttct gaaggacgac tccatcgata caaagtgct gactcggagc   2580
gacaagaacc ggggcaagag cgacaacgtg ccctccgaag aggtcgtgaa aaagatgaag   2640
aactactggc gccagctgct gaatgccaag ctgattaccc agaggaagtt cgacaatctg   2700
accaaggccg agagaggcgg cctgagcgaa ctggataagg ccggcttcat caagagacag   2760
ctggtggaaa cccggcagat cacaaagcac gtggcacaga tcctggactc ccggatgaac   2820
actaagtacg acgagaacga caaactgatc cgggaagtga agtgatcac cctgaagtcc   2880
aagctggtgt ccgatttccg gaaggatttc cagtttttaca aagtgcgcga gatcaacaac   2940
taccaccacg cccacgacgc ctacctgaac gccgtcgtgg gaaccgccct gatcaaaaag   3000
tacccctaag ctggaaagcga gttcgtgtac ggcgactaca agtgtacga cgtgcggaag   3060
atgatcgcca agagcgagca ggaaatcggc aaggctaccg ccaagtactt cttctacagc   3120
aacatcatga actttttcaa gaccgagatt accctggcca acggcgagat ccggaagcgg   3180
cctctgatcg agacaaacgg cgaaacaggc gagatcgtgt gggataaggg ccgggacttt   3240
gccaccgtgc ggaaagtgct gtctatgccc caagtgaata tcgtgaaaaa gaccgaggtg   3300
cagacaggcg gcttcagcaa agagtctatc ctgcccaaga ggaacagcga caagctgatc   3360
gccagaaaga aggactggga ccctaagaag tacggcggct tcgacagccc caccgtggcc   3420
tattctgtgc tggtggtggc caaagtggaa aagggcaagt ccaagaaact gaagagtgtg   3480
aaagagctgc tggggatcac catcatggaa agaagcagct tcgagaagaa tcccatcgac   3540
tttctggaag ccaagggcta caaagaagtg aaaaaggacc tgatcatcaa gctgcctaag   3600
tactccctgt tcgagctgga aaacggccgg aagagaatgc tggcctctgc cggcgaactg   3660
cagaagggaa acgaactggc cctgcctcc aaatatgtga acttcctgta cctggccagc   3720
cactatgaga agctgaaggg ctccccccgag gataatgagc agaaacagct gtttgtggaa   3780
cagcacaaac actacctgga cgagatcatc gagcagatca gcgagttctc caagagagtg   3840
atcctggccg acgctaatct ggacaaggtg ctgagcgcct acaacaagca cagagacaag   3900
cctatcagag agcaggccga gaatatcatc cacctgttta ccctgaccaa tctgggagcc   3960
cctgccgcct tcaagtactt tgacaccacc atcgaccgga gaggtacac cagcaccaaa   4020
gaggtgctgg acgccaccct gatccaccag agcatcaccg gcctgtacga gacacggatc   4080
gacctgtctc agctgggagg cgacgcc                                      4107
```

```
<210> SEQ ID NO 5
<211> LENGTH: 27
<212> TYPE: DNA
<213> ORGANISM: Artificial Sequence
<220> FEATURE:
<223> OTHER INFORMATION: Synthetic Construct

<400> SEQUENCE: 5
tatccctatg acgtgcccga ttatgcc                                           27

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
cccaagaaaa aacgcaaggt g                                                 21

<210> SEQ ID NO 7
<211> LENGTH: 60
<212> TYPE: DNA
<213> ORGANISM: Artificial Sequence
<220> FEATURE:
<223> OTHER INFORMATION: Synthetic Construct

<400> SEQUENCE: 7
gacggcattg gtagtgggag caacggcagc agcggatcca acggtccgac tgacgccgcg       60

<210> SEQ ID NO 8
<211> LENGTH: 723
<212> TYPE: DNA
<213> ORGANISM: Artificial Sequence
<220> FEATURE:
<223> OTHER INFORMATION: Synthetic Construct

<400> SEQUENCE: 8
gaagaagaac ttttgagcaa gaattatcat cttgagaacg aagtggctcg tcttaagaaa       60
ggttctggca gtggagaaga actgctttca aagaattacc acctggaaaa tgaggtagct      120
agactgaaaa aggggagcgg aagtgggag gagttgctga gcaaaaatta tcatttggag       180
aacgaagtag cacgactaaa gaaagggtcc ggatcgggtg aggagttact ctcgaaaaat      240
tatcatctcg aaaacgaagt ggctcggcta aaaaagggca gtggttctgg agaagagcta      300
ttatctaaaa actaccacct cgaaaatgag gtggcacgct aaaaaagggg aagtggcagt      360
ggtgaagagc tactatccaa gaattatcat cttgagaacg aggtagcgcg tttgaagaag      420
ggttccggct caggagagga actgctctcg aagaactatc atcttgaaaa tgaggtcgct      480
cgattaaaaa agggatcggg cagtggtgag gaactacttt caagaattac cacctcgaa      540 aacgaagtag ctcgattaaa gaaaggttca gggtcgggtg aagaattact gagtaaaaat      600
tatcatctgg aaaatgaggt agcgagacta aaaaagggga gtggttctgg cgaggaattg      660
ctatcgaaaa attatcatct tgagaacgaa gttgctaggc tcaaaaaggg ctcaggctca      720
ggc                                                                    723

<210> SEQ ID NO 9
<211> LENGTH: 768
<212> TYPE: DNA
<213> ORGANISM: Artificial Sequence
<220> FEATURE:
<223> OTHER INFORMATION: Synthetic Construct
```

<400> SEQUENCE: 9

```
tagagtcctg ctttaatgag atatgcgaga cgcctatgat cgcatgatat ttgctttcaa      60
ttctgttgtg cacgttgtaa aaaacctgag catgtgtagc tcagatcctt accgccggtt     120
tcggttcatt ctaatgaata tatcacccgt tactatcgta tttttatgaa taatattctc     180
cgttcaattt actgattgta ccctactact tatatgtaca atattaaaat gaaaacaata     240
tattgtgctg aataggttta tagcgacatc tatgatagag cgccacaata acaaacaatt     300
gcgttttatt attacaaatc caatttaaa aaaagcggca gaaccggtca aacctaaaag      360
actgattaca taaatcttat tcaaatttca aaagtgcccc aggggctagt atctacgaca     420
caccgagcgg cgaactaata acgttcactg aagggaactc cggttccccg ccggcgcgca     480
tgggtgagat tccttgaagt tgagtattgg ccgtccgctc taccgaaagt tacgggcacc     540
attcaacccg gtccagcacg gcggccgggt aaccgacttg ctgccccgag aattatgcag     600
cattttttg gtgtatgtgg gccccaaatg aagtgcaggt caaaccttga cagtgacgac      660
aaatcgttgg gcgggtccag ggcgaatttt gcgacaacat gtcgaggctc agcaggaccg     720
gcatgcaagc tagcttacta gtgatattct atagtgtcac ctaaatct                 768
```

<210> SEQ ID NO 10
<211> LENGTH: 2018
<212> TYPE: DNA
<213> ORGANISM: Artificial Sequence
<220> FEATURE:
<223> OTHER INFORMATION: Synthetic Construct

<400> SEQUENCE: 10

```
ttcctaacac ctggagaacc tttatgtac ttcacaaccc tcaatgctgc ttccaggtgt       60
gactgtttgg gttgctgcat gaattgactc agcacctgca ctgcaaagct gatatctggc     120
cttgtgattg tcaagtagag aagctttccc accagtctct gataggatcc cacatcctct     180
aactctgcat catcagtctt tcctaagtgc ttgtcatatt ctacagtagt cagcctttgg     240
ttctgttcca ttggggttga cactggtctg cagcctccca gaccaacacc tgatatcagt     300
tccagtgcat acttcctctg gttcagtagg attcccttt ctgatctcag cacctcaatg      360
cctaagaagt attttagttc tcccaaatct ttcatcttga aatgctgatg cagggttgcc    420
tttgcttctg aaatcaaaac attgctgctg cctgttatta acagatcatc cacataaatc    480
aggattatga caaggtcagt cccctctctt ttggtaaaca aggagtgatc ataagcactt    540
tgcataaaac cagcctgcat aaggacagtg gtaagcttga tgttccactg ccttgatgct    600
tgctttaaac catagaggga ttcaacagcc tgcacacttt ggtctcccct ggctgtgaa     660
aaccctgagg cagagacata taacttctt ccatgaggtc accttgtaga aaagcattgt     720
tgacatccat ctggaaaagg aaccagccct tggaagcagc aacagatatg acagctttta    780
cagtgaccat tttggccact ggagaaaaag tttcatggta gtcaaggcct tcttgctgag    840
tgtatccctt ggccactagc cttgccttaa acctgtcaac ttcaccatta gctttgtatt    900
taattttgta cacccatttg gaccctatag ctgtttacc agggggtaaa gggacaatct      960
cccaggtgtt attatcctca agagcctgta tctcaaggga catggcctcc atccatttct   1020
catcttgagc tgcttctttg aaggatttag gttcagtata agtggagaaa gcactcaaat   1080
aagcttgata gtgaacaggc aagtgatcat aggaaacata gttggctata gggtatggaa   1140
catccctaga gcctttgttc agtgtcacaa agtccttgag ccagatggga ggacctgcat   1200
tgcgtttagg tctagtgtgc aggtttgctg gaactagaga gggatcagct acagcagtat   1260
```

```
ggtgctcaaa ttcagcattt gctaggtcag gctcagctga ctcaactgac tctgcaggag   1320
catgcaggtg gcctgaaggt gcagcatcag ctgaagtgat atgattttgg gtagaatgag   1380
tccccaaagt gatatcctca ttggcctcta caatgtcagg aataagaact ggagtatcat   1440
catcatcagt atgaaagctg gaaggaaaaa tatcattata cactagctgc aaagctgtat   1500
cttcagagct aagtgaacct gctcgagtga acatatcagg ttcatgggag atggactctt   1560
tgaaagggaa ctgaaactct ctgaaaacta catccctgct cactatgatc accttattat   1620
ccaagtcata caacctgtaa cccttttgag tctcagaata accaatgaag atggttcgct   1680
tggctctagg tgcaagtttg tcacctttgg gcagtgttgc tgcaaaagca agacacccaa   1740
acactctcaa gtgatcaagc ttggcatgtt tctgatagag tagttcatat ggacatttgc   1800
cttgtaagat tggagtaggg agtctattga tcaggtatac aacagtcttg acacagtctc   1860
cccaaaacct ggtaggtaca ccactctgaa acttaagtgc ccttgccatc tcaaggatgt   1920
gtctgtgctt tctctccaca acaccattct gttgtggtgt gtagggacag ctactttgat   1980
gaacaatccc aagagaggcc agcaactcat tacaactt                           2018
```

<210> SEQ ID NO 11
<211> LENGTH: 1661
<212> TYPE: PRT
<213> ORGANISM: Artificial Sequence
<220> FEATURE:
<223> OTHER INFORMATION: Synthetic Construct

<400> SEQUENCE: 11

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220
```

```
Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
```

```
                    645                 650                 655
Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala Lys
        1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
                1045                1050                1055

Ile Arg Lys Arg Pro Leu Ile Glu Thr Asn Gly Glu Thr Gly Glu Ile
                1060                1065                1070
```

-continued

```
Val Trp Asp Lys Gly Arg Asp Phe Ala Thr Val Arg Lys Val Leu Ser
        1075                1080                1085

Met Pro Gln Val Asn Ile Val Lys Lys Thr Glu Val Gln Thr Gly Gly
    1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
            1125                1130                1135

Pro Thr Val Ala Tyr Ser Val Leu Val Val Ala Lys Val Glu Lys Gly
                1140                1145                1150

Lys Ser Lys Lys Leu Lys Ser Val Lys Glu Leu Leu Gly Ile Thr Ile
    1155                1160                1165

Met Glu Arg Ser Ser Phe Glu Lys Asn Pro Ile Asp Phe Leu Glu Ala
    1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
            1205                1210                1215

Ala Gly Glu Leu Gln Lys Gly Asn Glu Leu Ala Leu Pro Ser Lys Tyr
        1220                1225                1230

Val Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys His
        1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
            1285                1290                1295

His Arg Asp Lys Pro Ile Arg Glu Gln Ala Glu Asn Ile Ile His Leu
        1300                1305                1310

Phe Thr Leu Thr Asn Leu Gly Ala Pro Ala Ala Phe Lys Tyr Phe Asp
    1315                1320                1325

Thr Thr Ile Asp Arg Lys Arg Tyr Thr Ser Thr Lys Glu Val Leu Asp
    1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp Ala Tyr Pro Tyr Asp Val Pro Asp
            1365                1370                1375

Tyr Ala Ser Leu Gly Ser Gly Ser Pro Lys Lys Lys Arg Lys Val Glu
        1380                1385                1390

Asp Pro Lys Lys Lys Arg Lys Val Asp Gly Ile Gly Ser Gly Ser Asn
    1395                1400                1405

Gly Ser Ser Gly Ser Asn Gly Pro Thr Asp Ala Ala Glu Glu Glu Leu
    1410                1415                1420

Leu Ser Lys Asn Tyr His Leu Glu Asn Glu Val Ala Arg Leu Lys Lys
1425                1430                1435                1440

Gly Ser Gly Ser Gly Glu Glu Leu Leu Ser Lys Asn Tyr His Leu Glu
            1445                1450                1455

Asn Glu Val Ala Arg Leu Lys Lys Gly Ser Gly Ser Gly Glu Glu Leu
        1460                1465                1470

Leu Ser Lys Asn Tyr His Leu Glu Asn Glu Val Ala Arg Leu Lys Lys
    1475                1480                1485
```

```
Gly Ser Gly Ser Gly Glu Glu Leu Leu Ser Lys Asn Tyr His Leu Glu
    1490                1495                1500

Asn Glu Val Ala Arg Leu Lys Lys Gly Ser Gly Ser Gly Glu Glu Leu
1505                1510                1515                1520

Leu Ser Lys Asn Tyr His Leu Glu Asn Glu Val Ala Arg Leu Lys Lys
        1525                1530                1535

Gly Ser Gly Ser Gly Glu Glu Leu Leu Ser Lys Asn Tyr His Leu Glu
    1540                1545                1550

Asn Glu Val Ala Arg Leu Lys Lys Gly Ser Gly Ser Gly Glu Glu Leu
    1555                1560                1565

Leu Ser Lys Asn Tyr His Leu Glu Asn Glu Val Ala Arg Leu Lys Lys
        1570                1575                1580

Gly Ser Gly Ser Gly Glu Glu Leu Leu Ser Lys Asn Tyr His Leu Glu
1585                1590                1595                1600

Asn Glu Val Ala Arg Leu Lys Lys Gly Ser Gly Ser Gly Glu Glu Leu
                1605                1610                1615

Leu Ser Lys Asn Tyr His Leu Glu Asn Glu Val Ala Arg Leu Lys Lys
        1620                1625                1630

Gly Ser Gly Ser Gly Glu Glu Leu Leu Ser Lys Asn Tyr His Leu Glu
    1635                1640                1645

Asn Glu Val Ala Arg Leu Lys Lys Gly Ser Gly Ser Gly
    1650                1655                1660

<210> SEQ ID NO 12
<211> LENGTH: 1369
<212> TYPE: PRT
<213> ORGANISM: Artificial Sequence
<220> FEATURE:
<223> OTHER INFORMATION: Synthetic Construct

<400> SEQUENCE: 12

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190
```

-continued

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr

```
                610                 615                 620
Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
                    645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr Ser
1025                1030                1035                1040
```

```
Asn Ile Met Asn Phe Phe Lys Thr Glu Ile Thr Leu Ala Asn Gly Glu
            1045                1050                1055

Ile Arg Lys Arg Pro Leu Ile Glu Thr Asn Gly Glu Thr Gly Glu Ile
            1060                1065                1070

Val Trp Asp Lys Gly Arg Asp Phe Ala Thr Val Arg Lys Val Leu Ser
            1075                1080                1085

Met Pro Gln Val Asn Ile Val Lys Lys Thr Glu Val Gln Thr Gly Gly
            1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
            1125                1130                1135

Pro Thr Val Ala Tyr Ser Val Leu Val Val Ala Lys Val Glu Lys Gly
            1140                1145                1150

Lys Ser Lys Lys Leu Lys Ser Val Lys Glu Leu Leu Gly Ile Thr Ile
            1155                1160                1165

Met Glu Arg Ser Ser Phe Glu Lys Asn Pro Ile Asp Phe Leu Glu Ala
            1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
            1205                1210                1215

Ala Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys His
            1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
            1285                1290                1295

His Arg Asp Lys Pro Ile Arg Glu Gln Ala Glu Asn Ile Ile His Leu
            1300                1305                1310

Phe Thr Leu Thr Asn Leu Gly Ala Pro Ala Ala Phe Lys Tyr Phe Asp
            1315                1320                1325

Thr Thr Ile Asp Arg Lys Arg Tyr Thr Ser Thr Lys Glu Val Leu Asp
            1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp Ala
            1365

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Tyr Pro Tyr Asp Val Pro Asp Tyr Ala
1               5

<210> SEQ ID NO 14
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Pro Lys Lys Lys Arg Lys Val
1               5

<210> SEQ ID NO 15
<211> LENGTH: 20
<212> TYPE: PRT
<213> ORGANISM: Artificial Sequence
<220> FEATURE:
<223> OTHER INFORMATION: Synthetic Construct

<400> SEQUENCE: 15

Asp Gly Ile Gly Ser Gly Ser Asn Gly Ser Gly Ser Asn Gly Pro
1               5                   10                  15

Thr Asp Ala Ala
            20

<210> SEQ ID NO 16
<211> LENGTH: 241
<212> TYPE: PRT
<213> ORGANISM: Artificial Sequence
<220> FEATURE:
<223> OTHER INFORMATION: Synthetic Construct

<400> SEQUENCE: 16

Glu Glu Glu Leu Leu Ser Lys Asn Tyr His Leu Glu Asn Glu Val Ala
1               5                   10                  15

Arg Leu Lys Lys Gly Ser Gly Ser Gly Glu Glu Leu Leu Ser Lys Asn
                20                  25                  30

Tyr His Leu Glu Asn Glu Val Ala Arg Leu Lys Lys Gly Ser Gly Ser
            35                  40                  45

Gly Glu Glu Leu Leu Ser Lys Asn Tyr His Leu Glu Asn Glu Val Ala
        50                  55                  60

Arg Leu Lys Lys Gly Ser Gly Ser Gly Glu Glu Leu Leu Ser Lys Asn
65                  70                  75                  80

Tyr His Leu Glu Asn Glu Val Ala Arg Leu Lys Lys Gly Ser Gly Ser
                85                  90                  95

Gly Glu Glu Leu Leu Ser Lys Asn Tyr His Leu Glu Asn Glu Val Ala
            100                 105                 110

Arg Leu Lys Lys Gly Ser Gly Ser Gly Glu Glu Leu Leu Ser Lys Asn
        115                 120                 125

Tyr His Leu Glu Asn Glu Val Ala Arg Leu Lys Lys Gly Ser Gly Ser
    130                 135                 140

Gly Glu Glu Leu Leu Ser Lys Asn Tyr His Leu Glu Asn Glu Val Ala
145                 150                 155                 160

Arg Leu Lys Lys Gly Ser Gly Ser Gly Glu Glu Leu Leu Ser Lys Asn
                165                 170                 175

Tyr His Leu Glu Asn Glu Val Ala Arg Leu Lys Lys Gly Ser Gly Ser
            180                 185                 190

Gly Glu Glu Leu Leu Ser Lys Asn Tyr His Leu Glu Asn Glu Val Ala
        195                 200                 205

Arg Leu Lys Lys Gly Ser Gly Ser Gly Glu Glu Leu Leu Ser Lys Asn
    210                 215                 220
```

Tyr His Leu Glu Asn Glu Val Ala Arg Leu Lys Lys Gly Ser Gly Ser
225                 230                 235                 240

Gly

<210> SEQ ID NO 17
<211> LENGTH: 4356
<212> TYPE: DNA
<213> ORGANISM: Artificial Sequence
<220> FEATURE:
<223> OTHER INFORMATION: Synthetic Construct

<400> SEQUENCE: 17

| | |
|---|---|
| atgcatatga gtctagctca acagagcttt taacccaaat tggtacaata gaatacaact | 60 |
| ttagatcata attctcaaaa gaaagagatt ccttagctat tctatctgcc actccatttc | 120 |
| cttctcggct tgtatgcaca agcataaaat cctcaaactt gctaagtaga tactttatgt | 180 |
| cttggataat tggattgaga cttgacaagc ataactttca tgtaaccaaa gacacaagtt | 240 |
| gctgagaatc cacctcaaaa atgatcttcc tataattgaa tcgggataat gacagcacag | 300 |
| cccatctaag agcctccact tctacttcca gcacgcttct tactttacc acagctcttg | 360 |
| cacctaacca taacaccttc cctgtatgat cgcgaagcac ccaccctaag ccacatttta | 420 |
| atccttctgt tggccatgcc ccatcaaagt tgcacttaac ccaagattgt ggtggagctt | 480 |
| cccatgtttc tcgtctgtcc cgacggtgtt gtggttggtg ctttccttac attctgagcc | 540 |
| tctttccttc taatccactc atctgcatct tcttgtgtcc ttactaatac ctcattggtt | 600 |
| ccaaattccc tccctttaag caccagctcg tttctgttct tccacagcct cccaagtatc | 660 |
| caagggacta agcctccac attcttcaga tcaggatatt cttgtttaag atgttgaact | 720 |
| ctatggaggt ttgtatgaac tgatgatcta ggaccggata agttcccttc ttcatagcga | 780 |
| acttattcaa agaatgtttt gtgtatcatt cttgttacat tgttattaat gaaaaaatat | 840 |
| tattggtcat tggactgaac acgagtgtta aatatggacc aggccccaaa taagatccat | 900 |
| tgatatatga attaaataac aagaataaat cgagtcacca accacttgc cttttttaac | 960 |
| gagacttgtt caccaacttg atacaaaagt cattatccta tgcaaatcaa taatcataca | 1020 |
| aaaatatcca ataacactaa aaaattaaaa gaaatggata atttcacaat atgttatacg | 1080 |
| ataaagaagt tacttttcca agaaattcac tgattttata agcccacttg cattagataa | 1140 |
| atggcaaaaa aaacaaaaa ggaaagaaa taaagcacga agaattctag aaaatacgaa | 1200 |
| atacgcttca atgcagtggg acccacggtt caattattgc caattttcag ctccaccgta | 1260 |
| tatttaaaaa ataaaacgat aatgctaaaa aaatataaat cgtaacgatc gttaaatctc | 1320 |
| aacggctgga tcttatgacg accgttagaa attgtggttg tcgacgagtc agtaataaac | 1380 |
| ggcgtcaaag tggttgcagc cggcacacac gagtcgtgtt tatcaactca agcacaaat | 1440 |
| acttttcctc aacctaaaaa taaggcaatt agccaaaaac aactttgcgt gtaaacaacg | 1500 |
| ctcaatacac gtgtcatttt attattagct attgcttcac cgccttagct ttctcgtgac | 1560 |
| ctagtcgtcc tcgtctttc ttcttcttct tctataaaac aatacccaaa gagctcttct | 1620 |
| tcttcacaat tcagatttca atttctcaaa atcttaaaaa ctttctctca attctctcta | 1680 |
| ccgtgatcaa ggtaaatttc tgtgttcctt attctctcaa aatcttcgat tttgttttcg | 1740 |
| ttcgatccca atttcgtata tgttctttgg tttagattct gttaatctta gatcgaagac | 1800 |
| gattttctgg gtttgatcgt tagatatcat cttaattctc gattagggtt tcatagatat | 1860 |
| catccgattt gttcaaataa tttgagtttt gtcgaataat tactcttcga tttgtgattt | 1920 |

```
ctatctagat ctggtgttag tttctagttt gtgcgatcga atttgtcgat taatctgagt    1980
ttttctgatt aacacctagg gtttatgggc cccgacatcg tgatgaccca gagcccagc     2040
agcctgagcg ccagcgtggg cgaccgcgtg accatcacct gccgcagcag caccggcgcc    2100
gtgaccacca gcaactacgc cagctgggtg caggagaagc ccggcaagct gttcaagggc    2160
ctgatcggcg gcaccaacaa ccgcgccccc ggcgtgccca gccgcttcag cggcagcctg    2220
atcggcgaca aggccaccct gaccatcagc agcctgcagc ccgaggactt cgccacctac    2280
ttctgcgccc tgtggtacag caaccactgg gtgttcggcc agggcaccaa ggtggagctg    2340
aagcgcggcg gcgcggcag cggcggcggc ggcagcggcg gcggcggcag cagcggcggc     2400
ggcagcgagg tgaagctgct ggagagcggc ggcggcctgg tgcagcccgg cggcagcctg    2460
aagctgagct gcgccgtgag cggcttcagc ctgaccgact acggcgtgaa ctgggtgcgc    2520
caggcccccg gccgcggcct ggagtggatc ggcgtgatct ggggcgacgg catcaccgac    2580
tacaacagcg ccctgaagga ccgcttcatc atcagcaagg acaacggcaa gaacaccgtg    2640
tacctgcaga tgagcaaggt gcgcagcgac gacaccgccc tgtactactg cgtgaccggc    2700
ctgttcgact actggggcca gggcaccctg gtgaccgtga gcagctaccc atacgatgtt    2760
ccagattacg ctggtggagg cggaggttct ggggggaggag gtagtggcgg tggtggttca    2820
ggaggcggcg gaagcttgga tccaggtgga ggtggaagcg gtagcaaagg agaagaactt    2880
ttcactggag ttgtcccaat tcttgttgaa ttagatggtg atgttaatgg cacaaatttt    2940
tctgtccgtg gagagggtga aggtgatgct acaaacggaa aactcaccct taaatttatt    3000
tgcactactg gaaaactacc tgttccgtgg ccaacacttg tcactactct gacctatggt    3060
gttcaatgct tttcccgtta tccggatcac atgaaacggc atgactttt caagagtgcc    3120
atgcccgaag gttatgtaca ggaacgcact atatctttca aagatgacgg gacctacaag    3180
acgcgtgctg aagtcaagtt tgaaggtgat acccttgtta atcgtatcga gttaaaggt     3240
attgatttta aagaagatgg aaacattctt ggacacaaac tcgagtacaa ctttaactca    3300
cacaatgtat acatcacggc agacaaacaa aagaatggaa tcaaagctaa cttcaaaatt    3360
cgccacaacg ttgaagatgg ttccgttcaa ctagcagacc attatcaaca aaatactcca    3420
attggcgatg gccctgtcct tttaccagac aaccattacc tgtcgacaca atctgtcctt    3480
tcgaaagatc ccaacgaaaa gcgtgaccac atggtccttc ttgagtttgt aactgctgct    3540
gggattacac atggcatgga tgagctctac aaaggtggag gtcggaccgg tcgtacgggc    3600
ggtggcggag gggatgcttt agacgatttt gacttagata tgcttggttc agacgcgtta    3660
gacgacttcg acctagacat gttaggctca gatgcattgg acgacttcga tttagatatg    3720
ttgggctccg atgccctaga tgactttgat ctagatatgc taggtagtgg cggtggcgga    3780
ggggctccaa agaagaagag aaaggtccgt acgggaggag gatctcggac cgaagagtac    3840
aagcttatcc tgaacggtaa aaccctgaaa ggtgaaacca ccaccgaagc tgttgacgct    3900
gctaccgcgg aaaaagtttt caaacagtac gctaacgaca acggtgttga cggtgaatgg    3960
acctacgacg acgctaccaa aaccttcacg gtaaccgaag gtggtggtag cggtggtggt    4020
actagtccaa aaacaaggag gagaccgcga agatcacaac ggaaaaggcc gcctacgcca    4080
tggccgtaag tttgagctcg aatttccccg atcgttcaaa catttggcaa taagtttct     4140
taagattgaa tcctgttgcc ggtcttgcga tgattatcat ataatttctg ttgaattacg    4200
ttaagcatgt aataattaac atgtaatgca tgacgttatt tatgagatgg ttttttatga    4260
ttagagtccc gcaattatac atttaatacg cgatagaaaa caaaatatag cgcgcaaact    4320
```
aggataaatt atcgcgcgcg gtgtcatcta tgttac        4356

<210> SEQ ID NO 18
<211> LENGTH: 1994
<212> TYPE: DNA
<213> ORGANISM: Artificial Sequence
<220> FEATURE:
<223> OTHER INFORMATION: Synthetic Construct

<400> SEQUENCE: 18

| | |
|---|---|
| atgcatatga gtctagctca acagagcttt taacccaaat tggtacaata gaatacaact | 60 |
| ttagatcata attctcaaaa gaaagagatt ccttagctat tctatctgcc actccatttc | 120 |
| cttctcggct tgtatgcaca agcataaaat cctcaaactt gctaagtaga tactttatgt | 180 |
| cttggataat tggattgaga cttgacaagc ataactttca tgtaaccaaa gacacaagtt | 240 |
| gctgagaatc cacctcaaaa atgatcttcc tataattgaa tcgggataat gacagcacag | 300 |
| cccatctaag agcctccact tctacttcca gcacgcttct tactttttacc acagctcttg | 360 |
| cacctaacca taacaccttc cctgtatgat cgcgaagcac ccaccctaag ccacatttta | 420 |
| atccttctgt tggccatgcc ccatcaaagt tgcacttaac ccaagattgt ggtggagctt | 480 |
| cccatgtttc tcgtctgtcc cgacggtgtt gtggttggtg ctttccttac attctgagcc | 540 |
| tctttccttc taatccactc atctgcatct tcttgtgtcc ttactaatac ctcattggtt | 600 |
| ccaaattccc tccctttaag caccagctcg tttctgttct tccacagcct cccaagtatc | 660 |
| caagggacta agcctccac attcttcaga tcaggatatt cttgtttaag atgttgaact | 720 |
| ctatggaggt ttgtatgaac tgatgatcta ggaccggata agttcccttc ttcatagcga | 780 |
| acttattcaa agaatgtttt gtgtatcatt cttgttacat tgttattaat gaaaaaatat | 840 |
| tattggtcat tggactgaac acgagtgtta aatatggacc aggccccaaa taagatccat | 900 |
| tgatatatga attaaataac aagaataaat cgagtcacca aaccacttgc cttttttaac | 960 |
| gagacttgtt caccaacttg atacaaaagt cattatccta tgcaaatcaa taatcataca | 1020 |
| aaaatatcca ataacactaa aaaattaaaa gaaatggata atttcacaat atgttatacg | 1080 |
| ataaagaagt tactttttcca agaaattcac tgattttata agcccacttg cattagataa | 1140 |
| atggcaaaaa aaaacaaaaa ggaaaagaaa taaagcacga agaattctag aaaatacgaa | 1200 |
| atacgcttca atgcagtggg acccacggtt caattattgc caattttcag ctccaccgta | 1260 |
| tatttaaaaa ataaaacgat aatgctaaaa aaatataaat cgtaacgatc gttaaatctc | 1320 |
| aacggctgga tcttatgacg accgttagaa attgtggttg tcgacgagtc agtaataaac | 1380 |
| ggcgtcaaag tggttgcagc cggcacacac gagtcgtgtt tatcaactca agcacaaat | 1440 |
| actttttcctc aacctaaaaa taaggcaatt agccaaaaac aactttgcgt gtaaacaacg | 1500 |
| ctcaatacac gtgtcatttt attattagct attgcttcac cgccttagct ttctcgtgac | 1560 |
| ctagtcgtcc tcgtcttttc ttcttcttct tctataaaac aatacccaaa gagctcttct | 1620 |
| tcttcacaat tcagatttca atttctcaaa atcttaaaaa ctttctctca attctctcta | 1680 |
| ccgtgatcaa ggtaaatttc tgtgttcctt attctctcaa aatcttcgat tttgttttcg | 1740 |
| ttcgatccca atttcgtata tgttcttttgg tttagattct gttaatctta gatcgaagac | 1800 |
| gattttctgg gtttgatcgt tagatatcat cttaattctc gattagggtt tcatagatat | 1860 |
| catccgatttt gttcaaataa tttgagtttt gtcgaataat tactcttcga tttgtgattt | 1920 |
| ctatctagat ctggtgttag tttctagttt gtgcgatcga atttgtcgat taatctgagt | 1980 |

```
tttctgatt aaca                                                      1994

<210> SEQ ID NO 19
<211> LENGTH: 831
<212> TYPE: DNA
<213> ORGANISM: Artificial Sequence
<220> FEATURE:
<223> OTHER INFORMATION: Synthetic Construct

<400> SEQUENCE: 19
atgggccccg acatcgtgat gacccagagc cccagcagcc tgagcgccag cgtgggcgac     60
cgcgtgacca tcacctgccg cagcagcacc ggcgccgtga ccaccagcaa ctacgccagc    120
tgggtgcagg agaagcccgg caagctgttc aagggcctga tcggcggcac caacaaccgc    180
gcccccggcg tgcccagccg cttcagcggc agcctgatcg cgacaaggc caccctgacc    240
atcagcagcc tgcagcccga ggacttcgcc acctacttct gcgccctgtg gtacagcaac    300
cactgggtgt tcggccaggg caccaaggtg gagctgaagc gcggcggcgg cggcagcggc    360
ggcggcggca gcggcggcgg cggcagcagc ggcggcggca gcgaggtgaa gctgctggag    420
agcggcggcg gcctggtgca gcccggcggc agcctgaagc tgagctgcgc cgtgagcggc    480
ttcagcctga ccgactacgg cgtgaactgg gtgcgccagg cccccggccg cggcctggag    540
tggatcggcg tgatctgggg cgacggcatc accgactaca cagcgccct gaaggaccgc    600
ttcatcatca gcaaggacaa cggcaagaac accgtgtacc tgcagatgag caaggtgcgc    660
agcgacgaca ccgccctgta ctactgcgtg accggcctgt cgactactg gggccagggc    720
accctggtga ccgtgagcag ctacccatac gatgttccag attacgctgg tgaggcgga    780
ggttctgggg gaggaggtag tggcggtggt ggttcaggag gcggcggaag c             831

<210> SEQ ID NO 20
<211> LENGTH: 711
<212> TYPE: DNA
<213> ORGANISM: Artificial Sequence
<220> FEATURE:
<223> OTHER INFORMATION: Synthetic Construct

<400> SEQUENCE: 20
agcaaaggag aagaactttt cactggagtt gtcccaattc ttgttgaatt agatggtgat     60
gttaatgggc acaaattttc tgtccgtgga gagggtgaag gtgatgctac aaacggaaaa    120
ctcacccctta aatttatttg cactactgga aaactacctg ttccgtggcc aacacttgtc    180
actactctga cctatggtgt tcaatgcttt tcccgttatc cggatcacat gaaacggcat    240
gacttttttca agagtgccat gcccgaaggt tatgtacagg aacgcactat atctttcaaa    300
gatgacggga cctacaagac gcgtgctgaa gtcaagtttg aaggtgatac ccttgttaat    360
cgtatcgagt taaagggtat tgattttaaa gaagatggaa acattcttgg acacaaactc    420
gagtacaact ttaactcaca caatgtatac atcacggcag acaaacaaaa gaatggaatc    480
aaagctaact tcaaaattcg ccacaacgtt gaagatggtt ccgttcaact agcagaccat    540
tatcaacaaa atactccaat tggcgatggc cctgtccttt taccagacaa ccattacctg    600
tcgacacaat ctgtcctttc gaaagatccc aacgaaaagc gtgaccacat ggtccttctt    660
gagtttgtaa ctgctgctgg gattacacat ggcatggatg agctctacaa a             711

<210> SEQ ID NO 21
<211> LENGTH: 15
<212> TYPE: DNA
<213> ORGANISM: Artificial Sequence
```

```
<220> FEATURE:
<223> OTHER INFORMATION: Synthetic Construct

<400> SEQUENCE: 21
ggcggtggcg gaggg                                                           15

<210> SEQ ID NO 22
<211> LENGTH: 156
<212> TYPE: DNA
<213> ORGANISM: Artificial Sequence
<220> FEATURE:
<223> OTHER INFORMATION: Synthetic Construct

<400> SEQUENCE: 22
gatgctttag acgattttga cttagatatg cttggttcag acgcgttaga cgacttcgac          60
ctagacatgt taggctcaga tgcattggac gacttcgatt tagatatgtt gggctccgat         120
gccctagatg actttgatct agatatgcta ggtagt                                   156

<210> SEQ ID NO 23
<211> LENGTH: 24
<212> TYPE: DNA
<213> ORGANISM: Artificial Sequence
<220> FEATURE:
<223> OTHER INFORMATION: Synthetic Construct

<400> SEQUENCE: 23
gctccaaaga agaagagaaa ggtc                                                 24

<210> SEQ ID NO 24
<211> LENGTH: 165
<212> TYPE: DNA
<213> ORGANISM: Artificial Sequence
<220> FEATURE:
<223> OTHER INFORMATION: Synthetic Construct

<400> SEQUENCE: 24
gagtacaagc ttatcctgaa cggtaaaacc ctgaaaggtg aaaccaccac cgaagctgtt          60
gacgctgcta ccgcggaaaa agttttcaaa cagtacgcta acgacaacgg tgttgacggt         120
gaatggacct acgacgacgc taccaaaacc ttcacggtaa ccgaa                         165

<210> SEQ ID NO 25
<211> LENGTH: 63
<212> TYPE: DNA
<213> ORGANISM: Artificial Sequence
<220> FEATURE:
<223> OTHER INFORMATION: Synthetic Construct

<400> SEQUENCE: 25
ccaaaaacaa ggaggagacc gcgaagatca caacggaaaa ggccgcctac gccatggccg          60
taa                                                                        63

<210> SEQ ID NO 26
<211> LENGTH: 263
<212> TYPE: DNA
<213> ORGANISM: Artificial Sequence
<220> FEATURE:
<223> OTHER INFORMATION: Synthetic Construct

<400> SEQUENCE: 26
gagctcgaat ttccccgatc gttcaaacat ttggcaataa agtttcttaa gattgaatcc          60
tgttgccggt cttgcgatga ttatcatata atttctgttg aattacgtta agcatgtaat         120
```

```
aattaacatg taatgcatga cgttatttat gagatgggtt tttatgatta gagtcccgca    180
attatacatt taatacgcga tagaaaacaa aatatagcgc gcaaactagg ataaattatc    240
gcgcgcggtg tcatctatgt tac                                           263
```

<210> SEQ ID NO 27
<211> LENGTH: 694
<212> TYPE: PRT
<213> ORGANISM: Artificial Sequence
<220> FEATURE:
<223> OTHER INFORMATION: Synthetic Construct

<400> SEQUENCE: 27

```
Met Gly Pro Asp Ile Val Met Thr Gln Ser Pro Ser Ser Leu Ser Ala
1               5                   10                  15

Ser Val Gly Asp Arg Val Thr Ile Thr Cys Arg Ser Ser Thr Gly Ala
            20                  25                  30

Val Thr Thr Ser Asn Tyr Ala Ser Trp Val Gln Glu Lys Pro Gly Lys
        35                  40                  45

Leu Phe Lys Gly Leu Ile Gly Gly Thr Asn Asn Arg Ala Pro Gly Val
    50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
            100                 105                 110

Lys Arg Gly Gly Gly Gly Ser Gly Gly Gly Gly Ser Gly Gly Gly Gly
        115                 120                 125

Ser Ser Gly Gly Gly Ser Glu Val Lys Leu Leu Glu Ser Gly Gly Gly
    130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
                165                 170                 175

Arg Gly Leu Glu Trp Ile Gly Val Ile Trp Gly Asp Gly Ile Thr Asp
            180                 185                 190

Tyr Asn Ser Ala Leu Lys Asp Arg Phe Ile Ile Ser Lys Asp Asn Gly
        195                 200                 205

Lys Asn Thr Val Tyr Leu Gln Met Ser Lys Val Arg Ser Asp Asp Thr
    210                 215                 220

Ala Leu Tyr Tyr Cys Val Thr Gly Leu Phe Asp Tyr Trp Gly Gln Gly
225                 230                 235                 240

Thr Leu Val Thr Val Ser Ser Tyr Pro Tyr Asp Val Pro Asp Tyr Ala
                245                 250                 255

Gly Gly Gly Gly Gly Ser Gly Gly Gly Gly Ser Gly Gly Gly Gly Ser
            260                 265                 270

Gly Gly Gly Gly Ser Leu Asp Pro Gly Gly Gly Ser Gly Ser Lys
        275                 280                 285

Gly Glu Glu Leu Phe Thr Gly Val Val Pro Ile Leu Val Glu Leu Asp
    290                 295                 300

Gly Asp Val Asn Gly His Lys Phe Ser Val Arg Gly Glu Gly Glu Gly
305                 310                 315                 320

Asp Ala Thr Asn Gly Lys Leu Thr Leu Lys Phe Ile Cys Thr Thr Gly
                325                 330                 335
```

Lys Leu Pro Val Pro Trp Pro Thr Leu Val Thr Thr Leu Thr Tyr Gly
                340                 345                 350

Val Gln Cys Phe Ser Arg Tyr Pro Asp His Met Lys Arg His Asp Phe
            355                 360                 365

Phe Lys Ser Ala Met Pro Glu Gly Tyr Val Gln Glu Arg Thr Ile Ser
        370                 375                 380

Phe Lys Asp Asp Gly Thr Tyr Lys Thr Arg Ala Glu Val Lys Phe Glu
385                 390                 395                 400

Gly Asp Thr Leu Val Asn Arg Ile Glu Leu Lys Gly Ile Asp Phe Lys
                405                 410                 415

Glu Asp Gly Asn Ile Leu Gly His Lys Leu Glu Tyr Asn Phe Asn Ser
            420                 425                 430

His Asn Val Tyr Ile Thr Ala Asp Lys Gln Lys Asn Gly Ile Lys Ala
        435                 440                 445

Asn Phe Lys Ile Arg His Asn Val Glu Asp Gly Ser Val Gln Leu Ala
450                 455                 460

Asp His Tyr Gln Gln Asn Thr Pro Ile Gly Asp Gly Pro Val Leu Leu
465                 470                 475                 480

Pro Asp Asn His Tyr Leu Ser Thr Gln Ser Val Leu Ser Lys Asp Pro
                485                 490                 495

Asn Glu Lys Arg Asp His Met Val Leu Leu Glu Phe Val Thr Ala Ala
            500                 505                 510

Gly Ile Thr His Gly Met Asp Glu Leu Tyr Lys Gly Gly Arg Thr
        515                 520                 525

Gly Arg Thr Gly Gly Gly Gly Asp Ala Leu Asp Asp Phe Asp Leu
530                 535                 540

Asp Met Leu Gly Ser Asp Ala Leu Asp Asp Phe Asp Leu Asp Met Leu
545                 550                 555                 560

Gly Ser Asp Ala Leu Asp Asp Phe Asp Leu Asp Met Leu Gly Ser Asp
                565                 570                 575

Ala Leu Asp Asp Phe Asp Leu Asp Met Leu Gly Ser Gly Gly Gly Gly
            580                 585                 590

Gly Ala Pro Lys Lys Lys Arg Lys Val Arg Thr Gly Gly Gly Ser Arg
        595                 600                 605

Thr Glu Glu Tyr Lys Leu Ile Leu Asn Gly Lys Thr Leu Lys Gly Glu
610                 615                 620

Thr Thr Thr Glu Ala Val Asp Ala Ala Thr Ala Glu Lys Val Phe Lys
                625                 630                 635                 640

Gln Tyr Ala Asn Asp Asn Gly Val Asp Gly Glu Trp Thr Tyr Asp Asp
            645                 650                 655

Ala Thr Lys Thr Phe Thr Val Thr Glu Gly Gly Ser Gly Gly Gly
        660                 665                 670

Thr Ser Pro Lys Thr Arg Arg Arg Pro Arg Arg Ser Gln Arg Lys Arg
            675                 680                 685

Pro Pro Thr Pro Trp Pro
    690

<210> SEQ ID NO 28
<211> LENGTH: 277
<212> TYPE: PRT
<213> ORGANISM: Artificial Sequence
<220> FEATURE:
<223> OTHER INFORMATION: Synthetic Construct

<400> SEQUENCE: 28

Met Gly Pro Asp Ile Val Met Thr Gln Ser Pro Ser Ser Leu Ser Ala
1               5                   10                  15

Ser Val Gly Asp Arg Val Thr Ile Thr Cys Arg Ser Ser Thr Gly Ala
            20                  25                  30

Val Thr Thr Ser Asn Tyr Ala Ser Trp Val Gln Glu Lys Pro Gly Lys
            35                  40                  45

Leu Phe Lys Gly Leu Ile Gly Gly Thr Asn Asn Arg Ala Pro Gly Val
        50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
            100                 105                 110

Lys Arg Gly Gly Gly Gly Ser Gly Gly Gly Gly Ser Gly Gly Gly Gly
        115                 120                 125

Ser Ser Gly Gly Gly Ser Glu Val Lys Leu Leu Glu Ser Gly Gly Gly
    130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
                165                 170                 175

Arg Gly Leu Glu Trp Ile Gly Val Ile Trp Gly Asp Gly Ile Thr Asp
            180                 185                 190

Tyr Asn Ser Ala Leu Lys Asp Arg Phe Ile Ile Ser Lys Asp Asn Gly
        195                 200                 205

Lys Asn Thr Val Tyr Leu Gln Met Ser Lys Val Arg Ser Asp Asp Thr
210                 215                 220

Ala Leu Tyr Tyr Cys Val Thr Gly Leu Phe Asp Tyr Trp Gly Gln Gly
225                 230                 235                 240

Thr Leu Val Thr Val Ser Ser Tyr Pro Tyr Asp Val Pro Asp Tyr Ala
                245                 250                 255

Gly Gly Gly Gly Gly Ser Gly Gly Gly Gly Ser Gly Gly Gly Gly Ser
            260                 265                 270

Gly Gly Gly Gly Ser
        275

<210> SEQ ID NO 29
<211> LENGTH: 237
<212> TYPE: PRT
<213> ORGANISM: Artificial Sequence
<220> FEATURE:
<223> OTHER INFORMATION: Synthetic Construct

<400> SEQUENCE: 29

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Arg Gly Glu Gly
            20                  25                  30

Glu Gly Asp Ala Thr Asn Gly Lys Leu Thr Leu Lys Phe Ile Cys Thr
            35                  40                  45

Thr Gly Lys Leu Pro Val Pro Trp Pro Thr Leu Val Thr Thr Leu Thr
        50                  55                  60

Tyr Gly Val Gln Cys Phe Ser Arg Tyr Pro Asp His Met Lys Arg His
65                  70                  75                  80

-continued

```
Asp Phe Phe Lys Ser Ala Met Pro Glu Gly Tyr Val Gln Glu Arg Thr
                85                  90                  95

Ile Ser Phe Lys Asp Asp Gly Thr Tyr Lys Thr Arg Ala Glu Val Lys
            100                 105                 110

Phe Glu Gly Asp Thr Leu Val Asn Arg Ile Glu Leu Lys Gly Ile Asp
        115                 120                 125

Phe Lys Glu Asp Gly Asn Ile Leu Gly His Lys Leu Glu Tyr Asn Phe
    130                 135                 140

Asn Ser His Asn Val Tyr Ile Thr Ala Asp Lys Gln Lys Asn Gly Ile
145                 150                 155                 160

Lys Ala Asn Phe Lys Ile Arg His Asn Val Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Val Leu Ser Lys
        195                 200                 205

Asp Pro Asn Glu Lys Arg Asp His Met Val Leu Leu Glu Phe Val Thr
    210                 215                 220

Ala Ala Gly Ile Thr His Gly Met Asp Glu Leu Tyr Lys
225                 230                 235

<210> SEQ ID NO 30
<211> LENGTH: 5
<212> TYPE: PRT
<213> ORGANISM: Artificial Sequence
<220> FEATURE:
<223> OTHER INFORMATION: Synthetic Construct

<400> SEQUENCE: 30

Gly Gly Gly Gly Gly
1               5

<210> SEQ ID NO 31
<211> LENGTH: 52
<212> TYPE: PRT
<213> ORGANISM: Artificial Sequence
<220> FEATURE:
<223> OTHER INFORMATION: Synthetic Construct

<400> SEQUENCE: 31

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Phe Asp Leu Asp
        35                  40                  45

Met Leu Gly Ser
    50

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

<400> SEQUENCE: 32

Ala Pro Lys Lys Lys Arg Lys Val
1               5
```

```
<210> SEQ ID NO 33
<211> LENGTH: 55
<212> TYPE: PRT
<213> ORGANISM: Artificial Sequence
<220> FEATURE:
<223> OTHER INFORMATION: Synthetic Construct

<400> SEQUENCE: 33

Glu Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu
    50                  55

<210> SEQ ID NO 34
<211> LENGTH: 20
<212> TYPE: PRT
<213> ORGANISM: Artificial Sequence
<220> FEATURE:
<223> OTHER INFORMATION: Synthetic Construct

<400> SEQUENCE: 34

Pro Lys Thr Arg Arg Arg Pro Arg Arg Ser Gln Arg Lys Arg Pro Pro
1               5                   10                  15

Thr Pro Trp Pro
            20

<210> SEQ ID NO 35
<211> LENGTH: 553
<212> TYPE: DNA
<213> ORGANISM: Artificial Sequence
<220> FEATURE:
<223> OTHER INFORMATION: Synthetic Construct

<400> SEQUENCE: 35
aagctttcgt tgaacaacgg aaactcgact tgccttccgc acaatacatc atttcttctt      60
agcttttttt cttcttcttc gttcatacag ttttttttg tttatcagct tacatttct      120 tgaaccgtag ctttcgtttt cttctttta actttccatt cggagttttt gtatcttgtt     180
tcatagtttg tcccaggatt agaatgatta ggcatcgaac cttcaagaat ttgattgaat     240
aaaacatctt cattcttaag atatgaagat aatcttcaaa aggcccctgg aatctgaaa      300 gaagagaagc aggcccattt atatgggaaa gaacaatagt atttcttata taggcccatt     360
taagttgaaa acaatcttca aaagtcccac atcgcttaga taagaaaacg aagctgagtt     420
tatatacagc tagagtcgaa gtagtgattg acggaaagat gtatgggctt gttttagagc     480
tagaaatagc aagttaaaat aaggctagtc cgttatcaac ttgaaaaagt ggcaccgagt     540
cggtgctttt ttt                                                       553

<210> SEQ ID NO 36
<211> LENGTH: 450
<212> TYPE: DNA
<213> ORGANISM: Artificial Sequence
<220> FEATURE:
<223> OTHER INFORMATION: Synthetic Construct

<400> SEQUENCE: 36
aagctttcgt tgaacaacgg aaactcgact tgccttccgc acaatacatc atttcttctt      60
```

-continued

```
agcttttttt cttcttcttc gttcatacag ttttttttg tttatcagct tacattttct    120
tgaaccgtag ctttcgtttt cttctttta actttccatt cggagttttt gtatcttgtt    180
tcatagtttg tcccaggatt agaatgatta ggcatcgaac cttcaagaat ttgattgaat    240
aaaacatctt cattcttaag atatgaagat aatcttcaaa aggcccctgg gaatctgaaa    300
gaagagaagc aggcccattt atatgggaaa gaacaatagt atttcttata taggcccatt    360
taagttgaaa acaatcttca aaagtcccac atcgcttaga taagaaaacg aagctgagtt    420
tatatacagc tagagtcgaa gtagtgattg                                    450
```

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct

<400> SEQUENCE: 37

```
acggaaagat gtatgggctt                                                20
```

<210> SEQ ID NO 38
<211> LENGTH: 76
<212> TYPE: DNA
<213> ORGANISM: Artificial Sequence
<220> FEATURE:
<223> OTHER INFORMATION: Synthetic Construct

<400> SEQUENCE: 38

```
gttttagagc tagaaatagc aagttaaaat aaggctagtc cgttatcaac ttgaaaaagt    60
ggcaccgagt cggtgc                                                    76
```

<210> SEQ ID NO 39
<211> LENGTH: 7
<212> TYPE: DNA
<213> ORGANISM: Artificial Sequence
<220> FEATURE:
<223> OTHER INFORMATION: Synthetic Construct

<400> SEQUENCE: 39

```
ttttttt                                                              7
```

<210> SEQ ID NO 40
<211> LENGTH: 553
<212> TYPE: DNA
<213> ORGANISM: Artificial Sequence
<220> FEATURE:
<223> OTHER INFORMATION: Synthetic Construct

<400> SEQUENCE: 40

```
aagctttcgt tgaacaacgg aaactcgact tgccttccgc acaatacatc atttcttctt    60
agcttttttt cttcttcttc gttcatacag ttttttttg tttatcagct tacattttct    120
tgaaccgtag ctttcgtttt cttctttta actttccatt cggagttttt gtatcttgtt    180
tcatagtttg tcccaggatt agaatgatta ggcatcgaac cttcaagaat ttgattgaat    240
aaaacatctt cattcttaag atatgaagat aatcttcaaa aggcccctgg gaatctgaaa    300
gaagagaagc aggcccattt atatgggaaa gaacaatagt atttcttata taggcccatt    360
taagttgaaa acaatcttca aaagtcccac atcgcttaga taagaaaacg aagctgagtt    420
tatatacagc tagagtcgaa gtagtgattg aaaactaggc catccatgga gttttagagc    480
tagaaatagc aagttaaaat aaggctagtc cgttatcaac ttgaaaaagt ggcaccgagt    540
```
cggtgctttt ttt                                                    553

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct

<400> SEQUENCE: 41
aaaactaggc catccatgga                                              20

<210> SEQ ID NO 42
<211> LENGTH: 807
<212> TYPE: DNA
<213> ORGANISM: Artificial Sequence
<220> FEATURE:
<223> OTHER INFORMATION: Synthetic Construct

<400> SEQUENCE: 42
aagctttcgt tgaacaacgg aaactcgact tgccttccgc acaatacatc atttcttctt    60
agcttttttt cttcttcttc gttcatacag ttttttttg tttatcagct tacatttct    120 tgaaccgtag ctttcgtttt cttcttttta actttccatt cggagttttt gtatcttgtt   180
tcatagtttg tcccaggatt agaatgatta ggcatcgaac cttcaagaat ttgattgaat   240
aaaacatctt cattcttaag atatgaagat aatcttcaaa aggcccctgg gaatctgaaa   300
gaagagaagc aggcccattt atatgggaaa gaacaatagt atttcttata taggcccatt   360
taagttgaaa acaatcttca aaagtcccac atcgcttaga taagaaaacg aagctgagtt   420
tatatacagc tagagtcgaa gtagtgattg aacaaagcac cagtggtcta gtggtagaat   480
agtaccctgc cacggtacag acccgggttc gattcccggc tggtgcacta tttgttgtat   540
gtcagaagtt ttagagctag aaatagcaag ttaaaataag gctagtccgt tatcaacttg   600
aaaaagtggc accgagtcgg tgcgtttaac aaagcaccag tggtctagtg gtagaatagt   660
accctgccac ggtacagacc cgggttcgat tcccggctgg tgcatcttaa gtcttaagag   720
accagtttta gagctagaaa tagcaagtta aaataaggct agtccgttat caacttgaaa   780
aagtggcacc gagtcggtgc ttttttt                                      807

<210> SEQ ID NO 43
<211> LENGTH: 77
<212> TYPE: DNA
<213> ORGANISM: Artificial Sequence
<220> FEATURE:
<223> OTHER INFORMATION: Synthetic Construct

<400> SEQUENCE: 43
aacaaagcac cagtggtcta gtggtagaat agtaccctgc cacggtacag acccgggttc    60
gattcccggc tggtgca                                                  77

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct

<400> SEQUENCE: 44
ctatttgttg tatgtcagaa                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic Construct

<400> SEQUENCE: 45

```
tcttaagtct taagagacca                                               20
```

<210> SEQ ID NO 46
<211> LENGTH: 820
<212> TYPE: DNA
<213> ORGANISM: Artificial Sequence
<220> FEATURE:
<223> OTHER INFORMATION: Synthetic Construct

<400> SEQUENCE: 46

```
aagctttcgt tgaacaacgg aaactcgact tgccttccgc acaatacatc atttcttctt    60
agcttttttt cttcttcttc gttcatacag ttttttttg tttatcagct tacatttct    120
tgaaccgtag ctttcgtttt cttcttttta actttccatt cggagttttt gtatcttgtt   180
tcatagtttg tcccaggatt agaatgatta ggcatcgaac cttcaagaat ttgattgaat   240
aaaacatctt cattcttaag atatgaagat aatcttcaaa aggcccctgg aatctgaaa    300
gaagagaagc aggcccattt atatgggaaa gaacaatagt atttcttata taggcccatt   360
taagttgaaa acaatcttca aaagtcccac atcgcttaga taagaaaacg aagctgagtt   420
tatatacagc tagagtcgaa gtagtgattg aacaaagcac cagtggtcta gtggtagaat   480
agtaccctgc cacggtacag acccgggttc gattcccggc tggtgcagac ggaaagatgt   540
atgggcttgt tttagagcta gaaatagcaa gttaaaataa ggctagtccg ttatcaactt   600
gaaaaagtgg caccgagtcg gtgcgtttaa caaagcacca gtggtctagt ggtagaatag   660
taccctgcca cggtacagac ccgggttcga ttcccggctg gtgcaaaaac taggccatcc   720
atggagtttt agagctagaa atagcaagtt aaaataaggc tagtccgtta tcaacttgaa   780
aaagtggcac cgagtcggtg cgtttaaaca aacttttttt                         820
```

<210> SEQ ID NO 47
<211> LENGTH: 24
<212> TYPE: PRT
<213> ORGANISM: Artificial Sequence
<220> FEATURE:
<223> OTHER INFORMATION: Synthetic Construct

<400> SEQUENCE: 47

```
Glu Glu Leu Leu Ser Lys Asn Tyr His Leu Glu Asn Glu Val Ala Arg
1               5                   10                  15

Leu Lys Lys Gly Ser Gly Ser Gly
            20
```

<210> SEQ ID NO 48
<211> LENGTH: 1390
<212> TYPE: PRT
<213> ORGANISM: Artificial Sequence
<220> FEATURE:
<223> OTHER INFORMATION: Synthetic Construct

<400> SEQUENCE: 48

```
Met Pro Lys Lys Lys Arg Lys Val Gly Arg Gly Met Asp Lys Lys Tyr
1               5                   10                  15
```

```
Ser Ile Gly Leu Ala Ile Gly Thr Asn Ser Val Gly Trp Ala Val Ile
            20                  25                  30

Thr Asp Glu Tyr Lys Val Pro Ser Lys Lys Phe Lys Val Leu Gly Asn
        35                  40                  45

Thr Asp Arg His Ser Ile Lys Lys Asn Leu Ile Gly Ala Leu Leu Phe
    50                  55                  60

Asp Ser Gly Glu Thr Ala Glu Ala Thr Arg Leu Lys Arg Thr Ala Arg
65                  70                  75                  80

Arg Arg Tyr Thr Arg Arg Lys Asn Arg Ile Cys Tyr Leu Gln Glu Ile
                85                  90                  95

Phe Ser Asn Glu Met Ala Lys Val Asp Asp Ser Phe Phe His Arg Leu
            100                 105                 110

Glu Glu Ser Phe Leu Val Glu Glu Asp Lys Lys His Glu Arg His Pro
        115                 120                 125

Ile Phe Gly Asn Ile Val Asp Glu Val Ala Tyr His Glu Lys Tyr Pro
    130                 135                 140

Thr Ile Tyr His Leu Arg Lys Lys Leu Val Asp Ser Thr Asp Lys Ala
145                 150                 155                 160

Asp Leu Arg Leu Ile Tyr Leu Ala Leu Ala His Met Ile Lys Phe Arg
                165                 170                 175

Gly His Phe Leu Ile Glu Gly Asp Leu Asn Pro Asp Asn Ser Asp Val
            180                 185                 190

Asp Lys Leu Phe Ile Gln Leu Val Gln Thr Tyr Asn Gln Leu Phe Glu
        195                 200                 205

Glu Asn Pro Ile Asn Ala Ser Gly Val Asp Ala Lys Ala Ile Leu Ser
    210                 215                 220

Ala Arg Leu Ser Lys Ser Arg Arg Leu Glu Asn Leu Ile Ala Gln Leu
225                 230                 235                 240

Pro Gly Glu Lys Lys Asn Gly Leu Phe Gly Asn Leu Ile Ala Leu Ser
                245                 250                 255

Leu Gly Leu Thr Pro Asn Phe Lys Ser Asn Phe Asp Leu Ala Glu Asp
            260                 265                 270

Ala Lys Leu Gln Leu Ser Lys Asp Thr Tyr Asp Asp Asp Leu Asp Asn
        275                 280                 285

Leu Leu Ala Gln Ile Gly Asp Gln Tyr Ala Asp Leu Phe Leu Ala Ala
    290                 295                 300

Lys Asn Leu Ser Asp Ala Ile Leu Leu Ser Asp Ile Leu Arg Val Asn
305                 310                 315                 320

Thr Glu Ile Thr Lys Ala Pro Leu Ser Ala Ser Met Ile Lys Arg Tyr
                325                 330                 335

Asp Glu His His Gln Asp Leu Thr Leu Leu Lys Ala Leu Val Arg Gln
            340                 345                 350

Gln Leu Pro Glu Lys Tyr Lys Glu Ile Phe Phe Asp Gln Ser Lys Asn
        355                 360                 365

Gly Tyr Ala Gly Tyr Ile Asp Gly Gly Ala Ser Gln Glu Glu Phe Tyr
    370                 375                 380

Lys Phe Ile Lys Pro Ile Leu Glu Lys Met Asp Gly Thr Glu Glu Leu
385                 390                 395                 400

Leu Val Lys Leu Asn Arg Glu Asp Leu Leu Arg Lys Gln Arg Thr Phe
                405                 410                 415

Asp Asn Gly Ser Ile Pro His Gln Ile His Leu Gly Glu Leu His Ala
            420                 425                 430

Ile Leu Arg Arg Gln Glu Asp Phe Tyr Pro Phe Leu Lys Asp Asn Arg
```

-continued

```
                435                 440                 445
Glu Lys Ile Glu Lys Ile Leu Thr Phe Arg Ile Pro Tyr Tyr Val Gly
        450                 455                 460

Pro Leu Ala Arg Gly Asn Ser Arg Phe Ala Trp Met Thr Arg Lys Ser
465                 470                 475                 480

Glu Glu Thr Ile Thr Pro Trp Asn Phe Glu Val Val Asp Lys Gly
                        485                 490                 495

Ala Ser Ala Gln Ser Phe Ile Glu Arg Met Thr Asn Phe Asp Lys Asn
                500                 505                 510

Leu Pro Asn Glu Lys Val Leu Pro Lys His Ser Leu Leu Tyr Glu Tyr
                515                 520                 525

Phe Thr Val Tyr Asn Glu Leu Thr Lys Val Lys Tyr Val Thr Glu Gly
        530                 535                 540

Met Arg Lys Pro Ala Phe Leu Ser Gly Glu Gln Lys Lys Ala Ile Val
545                 550                 555                 560

Asp Leu Leu Phe Lys Thr Asn Arg Lys Val Thr Val Lys Gln Leu Lys
                565                 570                 575

Glu Asp Tyr Phe Lys Lys Ile Glu Cys Phe Asp Ser Val Glu Ile Ser
                580                 585                 590

Gly Val Glu Asp Arg Phe Asn Ala Ser Leu Gly Thr Tyr His Asp Leu
        595                 600                 605

Leu Lys Ile Ile Lys Asp Lys Asp Phe Leu Asp Asn Glu Glu Asn Glu
        610                 615                 620

Asp Ile Leu Glu Asp Ile Val Leu Thr Leu Thr Leu Phe Glu Asp Arg
625                 630                 635                 640

Glu Met Ile Glu Glu Arg Leu Lys Thr Tyr Ala His Leu Phe Asp Asp
                        645                 650                 655

Lys Val Met Lys Gln Leu Lys Arg Arg Arg Tyr Thr Gly Trp Gly Arg
                660                 665                 670

Leu Ser Arg Lys Leu Ile Asn Gly Ile Arg Asp Lys Gln Ser Gly Lys
                675                 680                 685

Thr Ile Leu Asp Phe Leu Lys Ser Asp Gly Phe Ala Asn Arg Asn Phe
        690                 695                 700

Met Gln Leu Ile His Asp Asp Ser Leu Thr Phe Lys Glu Asp Ile Gln
705                 710                 715                 720

Lys Ala Gln Val Ser Gly Gln Gly Asp Ser Leu His Glu His Ile Ala
                        725                 730                 735

Asn Leu Ala Gly Ser Pro Ala Ile Lys Lys Gly Ile Leu Gln Thr Val
                740                 745                 750

Lys Val Val Asp Glu Leu Val Lys Val Met Gly Arg His Lys Pro Glu
        755                 760                 765

Asn Ile Val Ile Glu Met Ala Arg Glu Asn Gln Thr Thr Gln Lys Gly
        770                 775                 780

Gln Lys Asn Ser Arg Glu Arg Met Lys Arg Ile Glu Glu Gly Ile Lys
785                 790                 795                 800

Glu Leu Gly Ser Gln Ile Leu Lys Glu His Pro Val Glu Asn Thr Gln
                        805                 810                 815

Leu Gln Asn Glu Lys Leu Tyr Leu Tyr Tyr Leu Gln Asn Gly Arg Asp
                820                 825                 830

Met Tyr Val Asp Gln Glu Leu Asp Ile Asn Arg Leu Ser Asp Tyr Asp
                        835                 840                 845

Val Ala Ala Ile Val Pro Gln Ser Phe Leu Lys Asp Asp Ser Ile Asp
850                 855                 860
```

```
Asn Lys Val Leu Thr Arg Ser Asp Lys Ala Arg Gly Lys Ser Asp Asn
865                 870                 875                 880

Val Pro Ser Glu Glu Val Val Lys Lys Met Lys Asn Tyr Trp Arg Gln
            885                 890                 895

Leu Leu Asn Ala Lys Leu Ile Thr Gln Arg Lys Phe Asp Asn Leu Thr
        900                 905                 910

Lys Ala Glu Arg Gly Gly Leu Ser Glu Leu Asp Lys Ala Gly Phe Ile
        915                 920                 925

Lys Arg Gln Leu Val Glu Thr Arg Gln Ile Thr Lys His Val Ala Gln
930                 935                 940

Ile Leu Asp Ser Arg Met Asn Thr Lys Tyr Asp Glu Asn Asp Lys Leu
945                 950                 955                 960

Ile Arg Glu Val Lys Val Ile Thr Leu Lys Ser Lys Leu Val Ser Asp
                965                 970                 975

Phe Arg Lys Asp Phe Gln Phe Tyr Lys Val Arg Glu Ile Asn Asn Tyr
            980                 985                 990

His His Ala His Asp Ala Tyr Leu Asn Ala Val Val Gly Thr Ala Leu
        995                 1000                1005

Ile Lys Lys Tyr Pro Lys Leu Glu Ser Glu Phe Val Tyr Gly Asp Tyr
        1010                1015                1020

Lys Val Tyr Asp Val Arg Lys Met Ile Ala Lys Ser Glu Gln Glu Ile
1025                1030                1035                1040

Gly Lys Ala Thr Ala Lys Tyr Phe Phe Tyr Ser Asn Ile Met Asn Phe
                1045                1050                1055

Phe Lys Thr Glu Ile Thr Leu Ala Asn Gly Glu Ile Arg Lys Arg Pro
            1060                1065                1070

Leu Ile Glu Thr Asn Gly Glu Thr Gly Glu Ile Val Trp Asp Lys Gly
        1075                1080                1085

Arg Asp Phe Ala Thr Val Arg Lys Val Leu Ser Met Pro Gln Val Asn
    1090                1095                1100

Ile Val Lys Lys Thr Glu Val Gln Thr Gly Gly Phe Ser Lys Glu Ser
1105                1110                1115                1120

Ile Leu Pro Lys Arg Asn Ser Asp Lys Leu Ile Ala Arg Lys Lys Asp
                1125                1130                1135

Trp Asp Pro Lys Lys Tyr Gly Gly Phe Asp Ser Pro Thr Val Ala Tyr
            1140                1145                1150

Ser Val Leu Val Val Ala Lys Val Glu Lys Gly Lys Ser Lys Lys Leu
        1155                1160                1165

Lys Ser Val Lys Glu Leu Leu Gly Ile Thr Ile Met Glu Arg Ser Ser
        1170                1175                1180

Phe Glu Lys Asn Pro Ile Asp Phe Leu Glu Ala Lys Gly Tyr Lys Glu
1185                1190                1195                1200

Val Lys Lys Asp Leu Ile Ile Lys Leu Pro Lys Tyr Ser Leu Phe Glu
            1205                1210                1215

Leu Glu Asn Gly Arg Lys Arg Met Leu Ala Ser Ala Gly Glu Leu Gln
        1220                1225                1230

Lys Gly Asn Glu Leu Ala Leu Pro Ser Lys Tyr Val Asn Phe Leu Tyr
        1235                1240                1245

Leu Ala Ser His Tyr Glu Lys Leu Lys Gly Ser Pro Glu Asp Asn Glu
        1250                1255                1260

Gln Lys Gln Leu Phe Val Glu Gln His Lys His Tyr Leu Asp Glu Ile
1265                1270                1275                1280
```

```
Ile Glu Gln Ile Ser Glu Phe Ser Lys Arg Val Ile Leu Ala Asp Ala
            1285                1290                1295

Asn Leu Asp Lys Val Leu Ser Ala Tyr Asn Lys His Arg Asp Lys Pro
        1300                1305                1310

Ile Arg Glu Gln Ala Glu Asn Ile Ile His Leu Phe Thr Leu Thr Asn
        1315                1320                1325

Leu Gly Ala Pro Ala Ala Phe Lys Tyr Phe Asp Thr Thr Ile Asp Arg
        1330                1335                1340

Lys Arg Tyr Thr Ser Thr Lys Glu Val Leu Asp Ala Thr Leu Ile His
1345                1350                1355                1360

Gln Ser Ile Thr Gly Leu Tyr Glu Thr Arg Ile Asp Leu Ser Gln Leu
            1365                1370                1375

Gly Gly Asp Ser Arg Ala Asp Pro Lys Lys Lys Arg Lys Val
            1380                1385                1390

<210> SEQ ID NO 49
<211> LENGTH: 1139
<212> TYPE: PRT
<213> ORGANISM: Artificial Sequence
<220> FEATURE:
<223> OTHER INFORMATION: Synthetic Construct

<400> SEQUENCE: 49

Met Pro Lys Lys Lys Arg Lys Val Ser Asp Leu Val Leu Gly Leu Ala
1               5                   10                  15

Ile Gly Ile Gly Ser Val Gly Val Gly Ile Leu Asn Lys Val Thr Gly
            20                  25                  30

Glu Ile Ile His Lys Asn Ser Arg Ile Phe Pro Ala Ala Gln Ala Glu
        35                  40                  45

Asn Asn Leu Val Arg Arg Thr Asn Arg Gln Gly Arg Arg Leu Ala Arg
    50                  55                  60

Arg Lys Lys His Arg Arg Val Arg Leu Asn Arg Leu Phe Glu Glu Ser
65                  70                  75                  80

Gly Leu Ile Thr Asp Phe Thr Lys Ile Ser Ile Asn Leu Asn Pro Tyr
                85                  90                  95

Gln Leu Arg Val Lys Gly Leu Thr Asp Glu Leu Ser Asn Glu Glu Leu
            100                 105                 110

Phe Ile Ala Leu Lys Asn Met Val Lys His Arg Gly Ile Ser Tyr Leu
        115                 120                 125

Asp Asp Ala Ser Asp Asp Gly Asn Ser Ser Val Gly Asp Tyr Ala Gln
    130                 135                 140

Ile Val Lys Glu Asn Ser Lys Gln Leu Glu Thr Lys Thr Pro Gly Gln
145                 150                 155                 160

Ile Gln Leu Glu Arg Tyr Gln Thr Tyr Gly Gln Leu Arg Gly Asp Phe
                165                 170                 175

Thr Val Glu Lys Asp Gly Lys Lys His Arg Leu Ile Asn Val Phe Pro
            180                 185                 190

Thr Ser Ala Tyr Arg Ser Glu Ala Leu Arg Ile Leu Gln Thr Gln Gln
        195                 200                 205

Glu Phe Asn Pro Gln Ile Thr Asp Glu Phe Ile Asn Arg Tyr Leu Glu
    210                 215                 220

Ile Leu Thr Gly Lys Arg Lys Tyr Tyr His Gly Pro Gly Asn Glu Lys
225                 230                 235                 240

Ser Arg Thr Asp Tyr Gly Arg Tyr Arg Thr Ser Gly Glu Thr Leu Asp
                245                 250                 255
```

```
Asn Ile Phe Gly Ile Leu Ile Gly Lys Cys Thr Phe Tyr Pro Asp Glu
                260                 265                 270

Phe Arg Ala Ala Lys Ala Ser Tyr Thr Ala Gln Glu Phe Asn Leu Leu
        275                 280                 285

Asn Asp Leu Asn Asn Leu Thr Val Pro Thr Glu Thr Lys Lys Leu Ser
    290                 295                 300

Lys Glu Gln Lys Asn Gln Ile Ile Asn Tyr Val Lys Asn Glu Lys Ala
305                 310                 315                 320

Met Gly Pro Ala Lys Leu Phe Lys Tyr Ile Ala Lys Leu Leu Ser Cys
                325                 330                 335

Asp Val Ala Asp Ile Lys Gly Tyr Arg Ile Asp Lys Ser Gly Lys Ala
            340                 345                 350

Glu Ile His Thr Phe Glu Ala Tyr Arg Lys Met Lys Thr Leu Glu Thr
            355                 360                 365

Leu Asp Ile Glu Gln Met Asp Arg Glu Thr Leu Asp Lys Leu Ala Tyr
        370                 375                 380

Val Leu Thr Leu Asn Thr Glu Arg Glu Gly Ile Gln Glu Ala Leu Glu
385                 390                 395                 400

His Glu Phe Ala Asp Gly Ser Phe Ser Gln Lys Gln Val Asp Glu Leu
                405                 410                 415

Val Gln Phe Arg Lys Ala Asn Ser Ser Ile Phe Gly Lys Gly Trp His
            420                 425                 430

Asn Phe Ser Val Lys Leu Met Met Glu Leu Ile Pro Glu Leu Tyr Glu
        435                 440                 445

Thr Ser Glu Glu Gln Met Thr Ile Leu Thr Arg Leu Gly Lys Gln Lys
    450                 455                 460

Thr Thr Ser Ser Ser Asn Lys Thr Lys Tyr Ile Asp Glu Lys Leu Leu
465                 470                 475                 480

Thr Glu Glu Ile Tyr Asn Pro Val Val Ala Lys Ser Val Arg Gln Ala
                485                 490                 495

Ile Lys Ile Val Asn Ala Ala Ile Lys Glu Tyr Gly Asp Phe Asp Asn
            500                 505                 510

Ile Val Ile Glu Met Ala Arg Glu Thr Asn Glu Asp Asp Glu Lys Lys
            515                 520                 525

Ala Ile Gln Lys Ile Gln Lys Ala Asn Lys Asp Glu Lys Asp Ala Ala
        530                 535                 540

Met Leu Lys Ala Ala Asn Gln Tyr Asn Gly Lys Ala Glu Leu Pro His
545                 550                 555                 560

Ser Val Phe His Gly His Lys Gln Leu Ala Thr Lys Ile Arg Leu Trp
                565                 570                 575

His Gln Gln Gly Glu Arg Cys Leu Tyr Thr Gly Lys Thr Ile Ser Ile
            580                 585                 590

His Asp Leu Ile Asn Asn Ser Asn Gln Phe Glu Val Ala Ala Ile Leu
        595                 600                 605

Pro Leu Ser Ile Thr Phe Asp Asp Ser Leu Ala Asn Lys Val Leu Val
    610                 615                 620

Tyr Ala Thr Ala Ala Gln Glu Lys Gly Gln Arg Thr Pro Tyr Gln Ala
625                 630                 635                 640

Leu Asp Ser Met Asp Asp Ala Trp Ser Phe Arg Glu Leu Lys Ala Phe
                645                 650                 655

Val Arg Glu Ser Lys Thr Leu Ser Asn Lys Lys Lys Glu Tyr Leu Leu
            660                 665                 670

Thr Glu Glu Asp Ile Ser Lys Phe Asp Val Arg Lys Lys Phe Ile Glu
```

-continued

```
            675                 680                 685
Arg Asn Leu Val Asp Thr Arg Tyr Ala Ser Arg Val Val Leu Asn Ala
            690                 695                 700
Leu Gln Glu His Phe Arg Ala His Lys Ile Asp Thr Lys Val Ser Val
705                 710                 715                 720
Val Arg Gly Gln Phe Thr Ser Gln Leu Arg Arg His Trp Gly Ile Glu
                725                 730                 735
Lys Thr Arg Asp Thr Tyr His His Ala Val Asp Ala Leu Ile Ile
            740                 745                 750
Ala Ala Ser Ser Gln Leu Asn Leu Trp Lys Lys Gln Lys Asn Thr Leu
            755                 760                 765
Val Ser Tyr Ser Glu Asp Gln Leu Leu Asp Ile Glu Thr Gly Glu Leu
            770                 775                 780
Ile Ser Asp Asp Glu Tyr Lys Glu Ser Val Phe Lys Ala Pro Tyr Gln
785                 790                 795                 800
His Phe Val Asp Thr Leu Lys Ser Lys Glu Phe Glu Asp Ser Ile Leu
                805                 810                 815
Phe Ser Tyr Gln Val Asp Ser Lys Phe Asn Arg Lys Ile Ser Asp Ala
            820                 825                 830
Thr Ile Tyr Ala Thr Arg Gln Ala Lys Val Gly Lys Asp Lys Ala Asp
            835                 840                 845
Glu Thr Tyr Val Leu Gly Lys Ile Lys Asp Ile Tyr Thr Gln Asp Gly
            850                 855                 860
Tyr Asp Ala Phe Met Lys Ile Tyr Lys Lys Asp Lys Ser Lys Phe Leu
865                 870                 875                 880
Met Tyr Arg His Asp Pro Gln Thr Phe Glu Lys Val Ile Glu Pro Ile
                885                 890                 895
Leu Glu Asn Tyr Pro Asn Lys Gln Ile Asn Asp Lys Gly Lys Glu Val
            900                 905                 910
Pro Cys Asn Pro Phe Leu Lys Tyr Lys Glu His Gly Tyr Ile Arg
            915                 920                 925
Lys Tyr Ser Lys Lys Gly Asn Gly Pro Glu Ile Lys Ser Leu Lys Tyr
            930                 935                 940
Tyr Asp Ser Lys Leu Gly Asn His Ile Asp Ile Thr Pro Lys Asp Ser
945                 950                 955                 960
Asn Asn Lys Val Val Leu Gln Ser Val Ser Pro Trp Arg Ala Asp Val
                965                 970                 975
Tyr Phe Asn Lys Thr Thr Gly Lys Tyr Glu Ile Leu Gly Leu Lys Tyr
            980                 985                 990
Ala Asp Leu Gln Phe Asp Lys Gly Thr Gly Thr Tyr Lys Ile Ser Gln
            995                 1000                1005
Glu Lys Tyr Asn Asp Ile Lys Lys Lys Glu Gly Val Asp Ser Asp Ser
            1010                1015                1020
Glu Phe Lys Phe Thr Leu Tyr Lys Asn Asp Leu Leu Leu Val Lys Asp
1025                1030                1035                1040
Thr Glu Thr Lys Glu Gln Gln Leu Phe Arg Phe Leu Ser Arg Thr Met
                1045                1050                1055
Pro Lys Gln Lys His Tyr Val Glu Leu Lys Pro Tyr Asp Lys Gln Lys
            1060                1065                1070
Phe Glu Gly Gly Glu Ala Leu Ile Lys Val Leu Gly Asn Val Ala Asn
            1075                1080                1085
Ser Gly Gln Cys Lys Lys Gly Leu Gly Lys Ser Asn Ile Ser Ile Tyr
            1090                1095                1100
```

```
Lys Val Arg Thr Asp Val Leu Gly Asn Gln His Ile Ile Lys Asn Glu
1105                1110                1115                1120

Gly Asp Lys Pro Lys Leu Asp Phe Ser Arg Ala Asp Pro Lys Lys
                1125                1130                1135

Arg Lys Val
```

<210> SEQ ID NO 50
<211> LENGTH: 1100
<212> TYPE: PRT
<213> ORGANISM: Artificial Sequence
<220> FEATURE:
<223> OTHER INFORMATION: Synthetic Construct

<400> SEQUENCE: 50

```
Met Pro Lys Lys Arg Lys Val Ala Ala Phe Lys Pro Asn Pro Ile
1               5                   10                  15

Asn Tyr Ile Leu Gly Leu Ala Ile Gly Ile Ala Ser Val Gly Trp Ala
                20                  25                  30

Met Val Glu Ile Asp Glu Asp Glu Asn Pro Ile Cys Leu Ile Asp Leu
            35                  40                  45

Gly Val Arg Val Phe Glu Arg Ala Glu Val Pro Lys Thr Gly Asp Ser
50                  55                  60

Leu Ala Met Ala Arg Arg Leu Ala Arg Ser Val Arg Arg Leu Thr Arg
65                  70                  75                  80

Arg Arg Ala His Arg Leu Leu Arg Ala Arg Arg Leu Leu Lys Arg Glu
                85                  90                  95

Gly Val Leu Gln Ala Ala Asp Phe Asp Glu Asn Gly Leu Ile Lys Ser
            100                 105                 110

Leu Pro Asn Thr Pro Trp Gln Leu Arg Ala Ala Leu Asp Arg Lys
                115                 120                 125

Leu Thr Pro Leu Glu Trp Ser Ala Val Leu Leu His Leu Ile Lys His
130                 135                 140

Arg Gly Tyr Leu Ser Gln Arg Lys Asn Glu Gly Glu Thr Ala Asp Lys
145                 150                 155                 160

Glu Leu Gly Ala Leu Leu Lys Gly Val Ala Asp Asn Ala His Ala Leu
                165                 170                 175

Gln Thr Gly Asp Phe Arg Thr Pro Ala Glu Leu Ala Leu Asn Lys Phe
            180                 185                 190

Glu Lys Glu Ser Gly His Ile Arg Asn Gln Arg Gly Asp Tyr Ser His
        195                 200                 205

Thr Phe Ser Arg Lys Asp Leu Gln Ala Glu Leu Ile Leu Leu Phe Glu
    210                 215                 220

Lys Gln Lys Glu Phe Gly Asn Pro His Val Ser Gly Leu Lys Glu
225                 230                 235                 240

Gly Ile Glu Thr Leu Leu Met Thr Gln Arg Pro Ala Leu Ser Gly Asp
                245                 250                 255

Ala Val Gln Lys Met Leu Gly His Cys Thr Phe Glu Pro Ala Glu Pro
            260                 265                 270

Lys Ala Ala Lys Asn Thr Tyr Thr Ala Glu Arg Phe Ile Trp Leu Thr
        275                 280                 285

Lys Leu Asn Asn Leu Arg Ile Leu Glu Gln Gly Ser Glu Arg Pro Leu
    290                 295                 300

Thr Asp Thr Glu Arg Ala Thr Leu Met Asp Glu Pro Tyr Arg Lys Ser
305                 310                 315                 320
```

```
Lys Leu Thr Tyr Ala Gln Ala Arg Lys Leu Leu Gly Leu Glu Asp Thr
            325                 330                 335

Ala Phe Phe Lys Gly Leu Arg Tyr Gly Lys Asp Asn Ala Glu Ala Ser
        340                 345                 350

Thr Leu Met Glu Met Lys Ala Tyr His Ala Ile Ser Arg Ala Leu Glu
    355                 360                 365

Lys Glu Gly Leu Lys Asp Lys Lys Ser Pro Leu Asn Leu Ser Pro Glu
370                 375                 380

Leu Gln Asp Glu Ile Gly Thr Ala Phe Ser Leu Phe Lys Thr Asp Glu
385                 390                 395                 400

Asp Ile Thr Gly Arg Leu Lys Asp Arg Ile Gln Pro Glu Ile Leu Glu
                405                 410                 415

Ala Leu Leu Lys His Ile Ser Phe Asp Lys Phe Val Gln Ile Ser Leu
            420                 425                 430

Lys Ala Leu Arg Arg Ile Val Pro Leu Met Glu Gln Gly Lys Arg Tyr
        435                 440                 445

Asp Glu Ala Cys Ala Glu Ile Tyr Gly Asp His Tyr Gly Lys Lys Asn
    450                 455                 460

Thr Glu Glu Lys Ile Tyr Leu Pro Pro Ile Pro Ala Asp Glu Ile Arg
465                 470                 475                 480

Asn Pro Val Val Leu Arg Ala Leu Ser Gln Ala Arg Lys Val Ile Asn
                485                 490                 495

Gly Val Val Arg Arg Tyr Gly Ser Pro Ala Arg Ile His Ile Glu Thr
            500                 505                 510

Ala Arg Glu Val Gly Lys Ser Phe Lys Asp Arg Lys Glu Ile Glu Lys
        515                 520                 525

Arg Gln Glu Glu Asn Arg Lys Asp Arg Glu Lys Ala Ala Ala Lys Phe
    530                 535                 540

Arg Glu Tyr Phe Pro Asn Phe Val Gly Glu Pro Lys Ser Lys Asp Ile
545                 550                 555                 560

Leu Lys Leu Arg Leu Tyr Glu Gln Gln His Gly Lys Cys Leu Tyr Ser
                565                 570                 575

Gly Lys Glu Ile Asn Leu Gly Arg Leu Asn Glu Lys Gly Tyr Val Glu
            580                 585                 590

Ile Ala Ala Ala Leu Pro Phe Ser Arg Thr Trp Asp Asp Ser Phe Asn
        595                 600                 605

Asn Lys Val Leu Val Leu Gly Ser Glu Ala Gln Asn Lys Gly Asn Gln
    610                 615                 620

Thr Pro Tyr Glu Tyr Phe Asn Gly Lys Asp Asn Ser Arg Glu Trp Gln
625                 630                 635                 640

Glu Phe Lys Ala Arg Val Glu Thr Ser Arg Phe Pro Arg Ser Lys Lys
                645                 650                 655

Gln Arg Ile Leu Leu Gln Lys Phe Asp Glu Asp Gly Phe Lys Glu Arg
            660                 665                 670

Asn Leu Asn Asp Thr Arg Tyr Val Asn Arg Phe Leu Cys Gln Phe Val
        675                 680                 685

Ala Asp Arg Met Arg Leu Thr Gly Lys Gly Lys Lys Arg Val Phe Ala
    690                 695                 700

Ser Asn Gly Gln Ile Thr Asn Leu Leu Arg Gly Phe Trp Gly Leu Arg
705                 710                 715                 720

Lys Val Arg Ala Glu Asn Asp Arg His His Ala Leu Asp Ala Val Val
                725                 730                 735

Val Ala Cys Ser Thr Val Ala Met Gln Gln Lys Ile Thr Arg Phe Val
```

```
                740                 745                 750
Arg Tyr Lys Glu Met Asn Ala Phe Asp Gly Lys Thr Ile Asp Lys Glu
            755                 760                 765

Thr Gly Glu Val Leu His Gln Lys Thr His Phe Pro Gln Pro Trp Glu
        770                 775                 780

Phe Phe Ala Gln Glu Val Met Ile Arg Val Phe Gly Lys Pro Asp Gly
785                 790                 795                 800

Lys Pro Glu Phe Glu Glu Ala Asp Thr Pro Glu Lys Leu Arg Thr Leu
                805                 810                 815

Leu Ala Glu Lys Leu Ser Ser Arg Pro Glu Ala Val His Glu Tyr Val
            820                 825                 830

Thr Pro Leu Phe Val Ser Arg Ala Pro Asn Arg Lys Met Ser Gly Gln
        835                 840                 845

Gly His Met Glu Thr Val Lys Ser Ala Lys Arg Leu Asp Glu Gly Val
    850                 855                 860

Ser Val Leu Arg Val Pro Leu Thr Gln Leu Lys Leu Lys Asp Leu Glu
865                 870                 875                 880

Lys Met Val Asn Arg Glu Arg Glu Pro Lys Leu Tyr Glu Ala Leu Lys
                885                 890                 895

Ala Arg Leu Glu Ala His Lys Asp Asp Pro Ala Lys Ala Phe Ala Glu
            900                 905                 910

Pro Phe Tyr Lys Tyr Asp Lys Ala Gly Asn Arg Thr Gln Gln Val Lys
        915                 920                 925

Ala Val Arg Val Glu Gln Val Gln Lys Thr Gly Val Trp Val Arg Asn
    930                 935                 940

His Asn Gly Ile Ala Asp Asn Ala Thr Met Val Arg Val Asp Val Phe
945                 950                 955                 960

Glu Lys Gly Asp Lys Tyr Tyr Leu Val Pro Ile Tyr Ser Trp Gln Val
                965                 970                 975

Ala Lys Gly Ile Leu Pro Asp Arg Ala Val Val Gln Gly Lys Asp Glu
            980                 985                 990

Glu Asp Trp Gln Leu Ile Asp Asp Ser Phe Asn Phe Lys Phe Ser Leu
        995                 1000                1005

His Pro Asn Asp Leu Val Glu Val Ile Thr Lys Lys Ala Arg Met Phe
    1010                1015                1020

Gly Tyr Phe Ala Ser Cys His Arg Gly Thr Gly Asn Ile Asn Ile Arg
1025                1030                1035                1040

Ile His Asp Leu Asp His Lys Ile Gly Lys Asn Gly Ile Leu Glu Gly
                1045                1050                1055

Ile Gly Val Lys Thr Ala Leu Ser Phe Gln Lys Tyr Gln Ile Asp Glu
            1060                1065                1070

Leu Gly Lys Glu Ile Arg Pro Cys Arg Leu Lys Lys Arg Pro Pro Val
        1075                1080                1085

Arg Ser Arg Ala Asp Pro Lys Lys Lys Arg Lys Val
    1090                1095                1100

<210> SEQ ID NO 51
<211> LENGTH: 102
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20
```

```
<223> OTHER INFORMATION: n = A,T,C or G

<400> SEQUENCE: 51
nnnnnnnnnn nnnnnnnnnn gttttagagc tagaaatagc aagttaaaat aaggctagtc        60
cgttatcaac ttgaaaaagt ggcaccgagt cggtgctttt tt                          102

<210> SEQ ID NO 52
<211> LENGTH: 110
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20
<223> OTHER INFORMATION: n = A,T,C or G

<400> SEQUENCE: 52
nnnnnnnnnn nnnnnnnnnn gtttttgtac tctcagaaat gcagaagcta caaagataag        60
gcttcatgcc gaaatcaaca ccctgtcatt ttatggcagg gtgtttttt                   110

<210> SEQ ID NO 53
<211> LENGTH: 128
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20
<223> OTHER INFORMATION: n = A,T,C or G

<400> SEQUENCE: 53
nnnnnnnnnn nnnnnnnnnn gttgtagctc cctttctcga agagaaccg ttgctacaat         60 aaggccgtct gaaagatgt gccgcaacgc tctgcccctt aaagcttctg ctttaacggg        120
cttttttt                                                               128

<210> SEQ ID NO 54
<211> LENGTH: 4185
<212> TYPE: DNA
<213> ORGANISM: Artificial Sequence
<220> FEATURE:
<223> OTHER INFORMATION: Synthetic Construct

<400> SEQUENCE: 54
atgcatatga gtctagctca acagagcttt taacccaaat tggtacaata gaatacaact        60
ttagatcata attctcaaaa gaaagagatt ccttagctat tctatctgcc actccatttc       120
cttctcggct tgtatgcaca agcataaaat cctcaaactt gctaagtaga tactttatgt       180
cttggataat tggattgaga cttgacaagc ataactttca tgtaaccaaa gacacaagtt       240
gctgagaatc cacctcaaaa atgatcttcc tataattgaa tcgggataat gacagcacag       300
cccatctaag agcctccact tctacttcca gcacgcttct tactttacc acagctcttg       360 cacctaacca taacaccttc cctgtatgat cgcgaagcac ccaccctaag ccacatttta       420
atccttctgt tggccatgcc ccatcaaagt tgcacttaac ccaagattgt ggtggagctt       480
cccatgtttc tcgtctgtcc cgacggtgtt gtggttggtg ctttccttac attctgagcc       540
tctttccttc taatccactc atctgcatct tcttgtgtcc ttactaatac ctcattggtt       600
ccaaattccc tcccctttaag caccagctcg tttctgttct tccacagcct cccaagtatc      660
```

```
caagggacta aagcctccac attcttcaga tcaggatatt cttgtttaag atgttgaact    720
ctatggaggt ttgtatgaac tgatgatcta ggaccggata agttcccttc ttcatagcga    780
acttattcaa agaatgtttt gtgtatcatt cttgttacat tgttattaat gaaaaaatat    840
tattggtcat tggactgaac acgagtgtta aatatggacc aggcccccaaa taagatccat   900
tgatatatga attaaataac aagaataaat cgagtcacca aaccacttgc cttttttaac   960
gagacttgtt caccaacttg atacaaaagt cattatccta tgcaaatcaa taatcataca  1020
aaaatatcca ataacactaa aaaattaaaa gaaatggata atttcacaat atgttatacg  1080
ataaagaagt tacttttcca agaaattcac tgattttata agcccacttg cattagataa  1140
atggcaaaaa aaaacaaaaa ggaaaagaaa taaagcacga agaattctag aaaatacgaa  1200
atacgcttca atgcagtggg acccacggtt caattattgc caattttcag ctccaccgta  1260
tatttaaaaa ataaaacgat aatgctaaaa aaatataaat cgtaacgatc gttaaatctc  1320
aacggctgga tcttatgacg accgttagaa attgtggttg tcgacgagtc agtaataaac  1380
ggcgtcaaag tggttgcagc cggcacacac gagtcgtgtt tatcaactca aagcacaaat  1440
acttttcctc aacctaaaaa taaggcaatt agccaaaaac aactttgcgt gtaaacaacg  1500
ctcaatacac gtgtcatttt attattagct attgcttcac cgccttagct ttctcgtgac  1560
ctagtcgtcc tcgtctttc ttcttcttct tctataaaac aatacccaaa gagctcttct  1620
tcttcacaat tcagatttca atttctcaaa atcttaaaaa ctttctctca attctctcta  1680
ccgtgatcaa ggtaaatttc tgtgttcctt attctctcaa aatcttcgat tttgttttcg  1740
ttcgatccca atttcgtata tgttctttgg tttagattct gttaatctta gatcgaagac  1800
gattttctgg gtttgatcgt tagatatcat cttaattctc gattagggtt tcatagatat  1860
catccgattt gttcaaataa tttgagtttt gtcgaataat tactcttcga tttgtgattt  1920
ctatctagat ctggtgttag tttctagttt gtgcgatcga atttgtcgat taatctgagt  1980
ttttctgatt aacacctagg gtttatgggc cccgacatcg tgatgaccca gagccccagc  2040
agcctgagcg ccagcgtggg cgaccgcgtg accatcacct gccgcagcag caccggcgcc  2100
gtgaccacca gcaactacgc cagctgggtg caggagaagc ccggcaagct gttcaagggc  2160
ctgatcggcg gcaccaacaa ccgcgccccc ggcgtgccca gccgcttcag cggcagcctg  2220
atcggcgaca aggccaccct gaccatcagc agcctgcagc ccgaggactt cgccacctac  2280
ttctgcgccc tgtggtacag caaccactgg gtgttcggcc agggcaccaa ggtggagctg  2340
aagcgcggcg gcggcggcag cggcggcggc ggcagcggcg gcggcggcag cagcggcggc  2400
ggcagcgagg tgaagctgct ggagagcggc ggcggcctgg tgcagcccgg cggcagcctg  2460
aagctgagct gcgccgtgag cggcttcagc ctgaccgact acggcgtgaa ctgggtgcgc  2520
caggcccccg gccgcggcct ggagtggatc ggcgtgatct ggggcgacgg catcaccgac  2580
tacaacagcg ccctgaagga ccgcttcatc atcagcaagg acaacggcaa gaacaccgtg  2640
tacctgcaga tgagcaaggt gcgcagcgac gacaccgccc tgtactactg cgtgaccggc  2700
ctgttcgact actggggcca gggcacccct gtgaccgtga gcagctaccc atacgatgtt  2760
ccagattacg ctggtggagg cggaggttct ggggaggag gtagtggcgg tggtggttca  2820
ggaggcggcg gaagcttgga tccaggtgga ggtggaagcg gtagcaaagg agaagaactt  2880
ttcactggag ttgtccccaat tcttgttgaa ttagatggtg atgttaatgg gcacaaattt  2940
tctgtccgtg gagagggtga aggtgatgct acaaacggaa aactcaccct taaatttatt  3000
```

-continued

```
tgcactactg gaaaactacc tgttccgtgg ccaacacttg tcactactct gacctatggt    3060
gttcaatgct tttcccgtta tccggatcac atgaaacggc atgactttt caagagtgcc    3120 atgcccgaag gttatgtaca ggaacgcact atatctttca agatgacgg gacctacaag    3180 acgcgtgctg aagtcaagtt tgaaggtgat acccttgtta atcgtatcga gttaaagggt    3240
attgatttta agaagatgg aaacattctt ggacacaaac tcgagtacaa ctttaactca    3300
cacaatgtat acatcacggc agacaaacaa aagaatggaa tcaaagctaa cttcaaaatt    3360
cgccacaacg ttgaagatgg ttccgttcaa ctagcagacc attatcaaca aaatactcca    3420
attggcgatg gccctgtcct tttaccagac aaccattacc tgtcgacaca atctgtcctt    3480
tcgaaagatc ccaacgaaaa gcgtgaccac atggtccttc ttgagtttgt aactgctgct    3540
gggattacac atggcatgga tgagctctac aaaggtggag gtcggaccgg tcgtacgggc    3600
ggtggcggag gggctccaaa gaagaagaga aaggtccgta cgggaggagg atctcggacc    3660
gaagagtaca agcttatcct gaacggtaaa accctgaaag gtgaaaccac caccgaagct    3720
gttgacgctg ctaccgcgga aaaagttttc aaacagtacg ctaacgacaa cggtgttgac    3780
ggtgaatgga cctacgacga cgctaccaaa accttcacgg taaccgaagg tggtggtagc    3840
ggtggtggta ctagtccaaa acaaggagg agaccgcgaa gatcacaacg gaaaaggccg    3900
cctacgccat ggccgtaagt ttgagctcga atttccccga tcgttcaaac atttggcaat    3960
aaagtttctt aagattgaat cctgttgccg gtcttgcgat gattatcata taatttctgt    4020
tgaattacgt taagcatgta ataattaaca tgtaatgcat gacgttattt atgagatggg    4080
tttttatgat tagagtcccg caattataca tttaatacgc gatagaaaac aaaatatagc    4140
gcgcaaacta ggataaatta tcgcgcgcgg tgtcatctat gttac                    4185
```

<210> SEQ ID NO 55
<211> LENGTH: 637
<212> TYPE: PRT
<213> ORGANISM: Artificial Sequence
<220> FEATURE:
<223> OTHER INFORMATION: Synthetic Construct

<400> SEQUENCE: 55

```
Met Gly Pro Asp Ile Val Met Thr Gln Ser Pro Ser Ser Leu Ser Ala
1               5                   10                  15

Ser Val Gly Asp Arg Val Thr Ile Thr Cys Arg Ser Ser Thr Gly Ala
            20                  25                  30

Val Thr Thr Ser Asn Tyr Ala Ser Trp Val Gln Glu Lys Pro Gly Lys
        35                  40                  45

Leu Phe Lys Gly Leu Ile Gly Gly Thr Asn Asn Arg Ala Pro Gly Val
    50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
            100                 105                 110

Lys Arg Gly Gly Gly Gly Ser Gly Gly Gly Ser Gly Gly Gly Gly
        115                 120                 125

Ser Ser Gly Gly Gly Ser Glu Val Lys Leu Leu Glu Ser Gly Gly Gly
    130                 135                 140

Leu Val Gln Pro Gly Gly Ser Leu Lys Leu Ser Cys Ala Val Ser Gly
145                 150                 155                 160
```

-continued

```
Phe Ser Leu Thr Asp Tyr Gly Val Asn Trp Val Arg Gln Ala Pro Gly
                165                 170                 175

Arg Gly Leu Glu Trp Ile Gly Val Ile Trp Gly Asp Gly Ile Thr Asp
            180                 185                 190

Tyr Asn Ser Ala Leu Lys Asp Arg Phe Ile Ile Ser Lys Asp Asn Gly
        195                 200                 205

Lys Asn Thr Val Tyr Leu Gln Met Ser Lys Val Arg Ser Asp Asp Thr
    210                 215                 220

Ala Leu Tyr Tyr Cys Val Thr Gly Leu Phe Asp Tyr Trp Gly Gln Gly
225                 230                 235                 240

Thr Leu Val Thr Val Ser Ser Tyr Pro Tyr Asp Val Pro Asp Tyr Ala
                245                 250                 255

Gly Gly Gly Gly Gly Ser Gly Gly Gly Ser Gly Gly Gly Gly Ser
            260                 265                 270

Gly Gly Gly Gly Ser Leu Asp Pro Gly Gly Gly Ser Gly Ser Lys
        275                 280                 285

Gly Glu Glu Leu Phe Thr Gly Val Val Pro Ile Leu Val Glu Leu Asp
    290                 295                 300

Gly Asp Val Asn Gly His Lys Phe Ser Val Arg Gly Glu Gly Glu Gly
305                 310                 315                 320

Asp Ala Thr Asn Gly Lys Leu Thr Leu Lys Phe Ile Cys Thr Thr Gly
                325                 330                 335

Lys Leu Pro Val Pro Trp Pro Thr Leu Val Thr Thr Leu Thr Tyr Gly
            340                 345                 350

Val Gln Cys Phe Ser Arg Tyr Pro Asp His Met Lys Arg His Asp Phe
        355                 360                 365

Phe Lys Ser Ala Met Pro Glu Gly Tyr Val Gln Glu Arg Thr Ile Ser
    370                 375                 380

Phe Lys Asp Asp Gly Thr Tyr Lys Thr Arg Ala Glu Val Lys Phe Glu
385                 390                 395                 400

Gly Asp Thr Leu Val Asn Arg Ile Glu Leu Lys Gly Ile Asp Phe Lys
                405                 410                 415

Glu Asp Gly Asn Ile Leu Gly His Lys Leu Glu Tyr Asn Phe Asn Ser
            420                 425                 430

His Asn Val Tyr Ile Thr Ala Asp Lys Gln Lys Asn Gly Ile Lys Ala
        435                 440                 445

Asn Phe Lys Ile Arg His Asn Val Glu Asp Gly Ser Val Gln Leu Ala
    450                 455                 460

Asp His Tyr Gln Gln Asn Thr Pro Ile Gly Asp Gly Pro Val Leu Leu
465                 470                 475                 480

Pro Asp Asn His Tyr Leu Ser Thr Gln Ser Val Leu Ser Lys Asp Pro
                485                 490                 495

Asn Glu Lys Arg Asp His Met Val Leu Leu Glu Phe Val Thr Ala Ala
            500                 505                 510

Gly Ile Thr His Gly Met Asp Glu Leu Tyr Lys Gly Gly Gly Arg Thr
        515                 520                 525

Gly Arg Thr Gly Gly Gly Gly Ala Pro Lys Lys Arg Lys Val
    530                 535                 540

Arg Thr Gly Gly Gly Ser Arg Thr Glu Glu Tyr Lys Leu Ile Leu Asn
545                 550                 555                 560

Gly Lys Thr Leu Lys Gly Glu Thr Thr Thr Glu Ala Val Asp Ala Ala
                565                 570                 575
```

```
Thr Ala Glu Lys Val Phe Lys Gln Tyr Ala Asn Asp Asn Gly Val Asp
            580                 585                 590

Gly Glu Trp Thr Tyr Asp Asp Ala Thr Lys Thr Phe Thr Val Thr Glu
        595                 600                 605

Gly Gly Gly Ser Gly Gly Gly Thr Ser Pro Lys Thr Arg Arg Arg Pro
    610                 615                 620

Arg Arg Ser Gln Arg Lys Arg Pro Pro Thr Pro Trp Pro
625                 630                 635

<210> SEQ ID NO 56
<211> LENGTH: 450
<212> TYPE: DNA
<213> ORGANISM: Artificial Sequence
<220> FEATURE:
<223> OTHER INFORMATION: Synthetic Construct

<400> SEQUENCE: 56
aagctttcgt tgaacaacgg aaactcgact tgccttccgc acaatacatc atttcttctt      60
agcttttttt cttcttcttc gttcatacag ttttttttg tttatcagct tacatttct      120 tgaaccgtag ctttcgtttt cttcttttta actttccatt cggagttttt gtatcttgtt    180
tcatagtttg tcccaggatt agaatgatta ggcatcgaac cttcaagaat ttgattgaat    240
aaaacatctt cattcttaag atatgaagat aatcttcaaa aggcccctgg aatctgaaa     300 gaagagaagc aggcccattt atatgggaaa gaacaatagt atttcttata taggcccatt    360
taagttgaaa acaatcttca aaagtcccac atcgcttaga taagaaaacg aagctgagtt    420
tatatacagc tagagtcgaa gtagtgattg                                      450

<210> SEQ ID NO 57
<211> LENGTH: 83
<212> TYPE: DNA
<213> ORGANISM: Artificial Sequence
<220> FEATURE:
<223> OTHER INFORMATION: Synthetic Construct

<400> SEQUENCE: 57
gttttagagc tagaaatagc aagttaaaat aaggctagtc cgttatcaac ttgaaaaagt     60
ggcaccgagt cggtgctttt ttt                                             83

<210> SEQ ID NO 58
<211> LENGTH: 20
<212> TYPE: DNA
<213> ORGANISM: Artificial Sequence
<220> FEATURE:
<223> OTHER INFORMATION: Synthetic Construct

<400> SEQUENCE: 58
tgaataaagc tattatctgt                                                 20

<210> SEQ ID NO 59
<211> LENGTH: 20
<212> TYPE: DNA
<213> ORGANISM: Artificial Sequence
<220> FEATURE:
<223> OTHER INFORMATION: Synthetic Construct

<400> SEQUENCE: 59
tgataccatg aaagaatatg                                                 20

<210> SEQ ID NO 60
<211> LENGTH: 20
```

```
<212> TYPE: DNA
<213> ORGANISM: Artificial Sequence
<220> FEATURE:
<223> OTHER INFORMATION: Synthetic Construct

<400> SEQUENCE: 60
agtattgcct aatccatgaa                                                   20

<210> SEQ ID NO 61
<211> LENGTH: 20
<212> TYPE: DNA
<213> ORGANISM: Artificial Sequence
<220> FEATURE:
<223> OTHER INFORMATION: Synthetic Construct

<400> SEQUENCE: 61
tttaaatcaa cggacatcga                                                   20

<210> SEQ ID NO 62
<211> LENGTH: 20
<212> TYPE: DNA
<213> ORGANISM: Artificial Sequence
<220> FEATURE:
<223> OTHER INFORMATION: Synthetic Construct

<400> SEQUENCE: 62
atttatagcg taagcctaca                                                   20

<210> SEQ ID NO 63
<211> LENGTH: 20
<212> TYPE: DNA
<213> ORGANISM: Artificial Sequence
<220> FEATURE:
<223> OTHER INFORMATION: Synthetic Construct

<400> SEQUENCE: 63
tgtgtagtaa gtatatatag                                                   20

<210> SEQ ID NO 64
<211> LENGTH: 9
<212> TYPE: PRT
<213> ORGANISM: Artificial Sequence
<220> FEATURE:
<223> OTHER INFORMATION: Synthetic Construct

<400> SEQUENCE: 64

Ser Ser Gly Pro Pro Pro Gly Thr Gly
1               5

<210> SEQ ID NO 65
<211> LENGTH: 12
<212> TYPE: PRT
<213> ORGANISM: Artificial Sequence
<220> FEATURE:
<223> OTHER INFORMATION: Synthetic Construct

<400> SEQUENCE: 65

Ala Glu Ala Ala Ala Lys Glu Ala Ala Ala Lys Ala
1               5                   10

<210> SEQ ID NO 66
<211> LENGTH: 16
<212> TYPE: PRT
<213> ORGANISM: Artificial Sequence
<220> FEATURE:
<223> OTHER INFORMATION: Synthetic Construct
```

<400> SEQUENCE: 66

Ser Gly Ser Glu Thr Pro Gly Thr Ser Glu Ser Ala Thr Pro Glu Ser
1               5                   10                  15

<210> SEQ ID NO 67
<211> LENGTH: 43
<212> TYPE: DNA
<213> ORGANISM: Artificial Sequence
<220> FEATURE:
<223> OTHER INFORMATION: Synthetic Construct

<400> SEQUENCE: 67
tcccctaagc ccatacatcg acagataatg ttggggacga tcc                43

<210> SEQ ID NO 68
<211> LENGTH: 8423
<212> TYPE: DNA
<213> ORGANISM: Artificial Sequence
<220> FEATURE:
<223> OTHER INFORMATION: Synthetic Construct

<400> SEQUENCE: 68
agtctagctc aacagagctt ttaacccaaa ttggtacaat agaatacaac tttagatcat      60
aattctcaaa agaaagagat tccttagcta ttctatctgc cactccattt ccttctcggc     120
ttgtatgcac aagcataaaa tcctcaaact tgctaagtag atactttatg tcttggataa     180
ttggattgag acttgacaag cataactttc atgtaaccaa agacacaagt tgctgagaat     240
ccacctcaaa aatgatcttc ctataattga atcgggataa tgacagcaca gcccatctaa     300
gagcctccac ttctacttcc agcacgcttc ttactttttac cacagctctt gcacctaacc     360
ataacacctt ccctgtatga tcgcgaagca cccaccctaa gccacatttt aatccttctg     420
ttggccatgc cccatcaaag ttgcacttaa cccaagattg tggtggagct tcccatgttt     480
ctcgtctgtc ccgacggtgt tgtggttggt gctttcctta cattctgagc ctctttcctt     540
ctaatccact catctgcatc ttcttgtgtc cttactaata cctcattggt tccaaattcc     600 ctcccttaa gcaccagctc gtttctgttc ttccacagcc tcccaagtat ccaagggact     660
aaagcctcca cattcttcag atcaggatat tcttgtttaa gatgttgaac tctatggagg     720
tttgtatgaa ctgatgatct aggaccggat aagttccctt cttcatagcg aacttattca     780
aagaatgttt tgtgtatcat tcttgttaca ttgttattaa tgaaaaaata ttattggtca     840
ttggactgaa cacgagtgtt aaatatggac caggccccaa ataagatcca ttgatatatg     900
aattaaataa caagaataaa tcgagtcacc aaaccacttg cctttttaa cgagacttgt     960 tcaccaactt gatacaaaag tcattatcct atgcaaatca ataatcatac aaaaatatcc    1020
aataacacta aaaattaaa agaaatggat aatttcacaa tatgttatac gataaagaag    1080 ttactttttcc aagaaattca ctgattttat aagcccactt gcattagata aatggcaaaa    1140
aaaaacaaaa aggaaaagaa ataaagcacg aagaattcta gaaaatacga aatacgcttc    1200
aatgcagtgg gacccacggt tcaattattg ccaattttca gctccaccgt atatttaaaa    1260
aataaaacga taatgctaaa aaaatataaa tcgtaacgat cgttaaatct caacggctgg    1320
atcttatgac gaccgttaga aattgtggtt gtcgacgagt cagtaataaa cggcgtcaaa    1380
gtggttgcag ccggcacaca cgagtcgtgt ttatcaactc aaagcacaaa tacttttcct    1440
caacctaaaa ataaggcaat tagccaaaaa caactttgcg tgtaaacaac gctcaataca    1500
cgtgtcattt tattattagc tattgcttca ccgccttagc tttctcgtga cctagtcgtc    1560

```
ctcgtctttt cttcttcttc ttctataaaa caatacccaa agagctcttc ttcttcacaa    1620
ttcagatttc aatttctcaa aatcttaaaa actttctctc aattctctct accgtgatca    1680
aggtaaattt ctgtgttcct tattctctca aaatcttcga ttttgttttc gttcgatccc    1740
aatttcgtat atgttctttg gtttagattc tgttaatctt agatcgaaga cgattttctg    1800
ggtttgatcg ttagatatca tcttaattct cgattagggt tcatagata tcatccgatt     1860 tgttcaaata atttgagttt tgtcgaataa ttactcttcg atttgtgatt tctatctaga    1920
tctggtgtta gtttctagtt tgtgcgatcg aatttgtcga ttaatctgag tttttctgat    1980
taacagggat catcaacaag tttgtacaaa aaagcaggct ctttaaagta ttttacaac     2040 aattaccaac aacaacaaac aacaaacaac attacaatta ctatttacaa ttacaaaaaa    2100
agttaacatg acaagaagt acagcatcgg cctggccatc ggcaccaact ctgtgggctg     2160
ggccgtgatc accgacgagt acaaggtgcc cagcaagaaa ttcaaggtgc tgggcaacac    2220
cgaccggcac agcatcaaga gaacctgat cggcgccctg ctgttcgaca gcggagaaac     2280
agccgaggcc acccggctga agagaaccgc cagaagaaga tacaccagac ggaagaaccg    2340
gatctgctat ctgcaagaga tcttcagcaa cgagatggcc aaggtggacg acagcttctt    2400
ccacagactg aagagtcct tcctggtgga agaggataag aagcacgagc ggcaccccat     2460
cttcggcaac atcgtggacg aggtggccta ccacgagaag taccccacca tctaccacct    2520
gagaaagaaa ctggtggaca gcaccgacaa ggccgacctg cggctgatct atctggccct    2580
ggcccacatg atcaagttcc ggggccactt cctgatcgag ggcgacctga ccccgacaa     2640 cagcgacgtg acaagctgt tcatccagct ggtgcagacc tacaaccagc tgttcgagga    2700 aaacccatc aacgccagcg gcgtggacgc caaggccatc ctgtctgcca gactgagcaa    2760
gagcagacgg ctggaaaatc tgatcgccca gctgccggc gagaagaaga tggcctgtt    2820 cggcaacctg attgccctga gcctgggcct gacccccaac ttcaagagca acttcgacct    2880
ggccgaggat gccaaactgc agctgagcaa ggacacctac gacgacgacc tggacaacct    2940
gctggcccag atcggcgacc agtacgccga cctgtttctg gccgccaaga acctgtccga    3000
cgccatcctg ctgagcgaca tcctgagagt gaacaccgag atcaccaagg cccccctgag    3060
cgcctctatg atcaagagat acgacgagca ccaccaggac ctgaccctgc tgaaagctct    3120
cgtgcggcag cagctgcctg agaagtacaa agagattttc ttcgaccaga gcaagaacgg    3180
ctacgccggc tacatcgatg gcggagccag ccaggaagag ttctacaagt tcatcaagcc    3240
catcctggaa aagatggacg gcaccgagga actgctcgtg aagctgaaca gagaggacct    3300
gctgcggaag cagcggacct tcgacaacgg cagcatcccc caccagatcc acctgggaga    3360
gctgcacgcc attctgcggc ggcaggaaga ttttttaccca ttcctgaagg acaaccggga    3420
aaagatcgag aagatcctga ccttccgcat cccctactac gtgggccctc tggccagggg    3480
aaacagcaga ttcgcctgga tgaccagaaa gagcgaggaa accatcaccc cctggaactt    3540
cgaggaagtg gtggacaagg gcgccagcgc ccagagcttc atcgagcgga tgaccaactt    3600
cgataagaac ctgcccaacg agaaggtgct gcccaagcac agcctgctgt acgagtactt    3660
caccgtgtac aacgagctga ccaaagtgaa atacgtgacc gagggaatga gaaagcccgc    3720
cttcctgagc ggcgagcaga aaaagccat cgtggacctg ctgttcaaga ccaaccggaa    3780
agtgaccgtg aagcagctga aagaggacta cttcaagaaa atcgagtgct tcgactccgt    3840
ggaaatctcc ggcgtggaag atcggttcaa cgcctccctg ggcacatacc acgatctgct    3900
gaaaattatc aaggacaagg acttcctgga caatgaggaa aacgaggaca ttctggaaga    3960
```

```
tatcgtgctg accctgacac tgtttgagga cagagagatg atcgaggaac ggctgaaaac    4020
ctatgcccac ctgttcgacg acaaagtgat gaagcagctg aagcggcgga gatacaccgg    4080
ctggggcagg ctgagccgga agctgatcaa cggcatccgg acaagcagt ccggcaagac     4140 aatcctggat ttcctgaagt ccgacggctt cgccaacaga aacttcatgc agctgatcca    4200
cgacgacagc ctgaccttta aagaggacat ccagaaagcc caggtgtccg gccagggcga    4260
tagcctgcac gagcacattg ccaatctggc cggcagcccc gccattaaga agggcatcct    4320
gcagacagtg aaggtggtgg acgagctcgt gaaagtgatg ggccggcaca agcccgagaa    4380
catcgtgatc gaaatggcca gagagaacca gaccacccag aagggacaga gaacagccg     4440 cgagagaatg aagcggatcg aagagggcat caaagagctg gcagccaga tcctgaaaga    4500 acaccccgtg aaaacaccc agctgcagaa cgagaagctg tacctgtact acctgcagaa    4560
tgggcgggat atgtacgtgg accaggaact ggacatcaac cggctgtccg actacgatgt    4620
ggacgctatc gtgcctcaga gctttctgaa ggacgactcc atcgataaca aagtgctgac    4680
tcggagcgac aagaaccggg gcaagagcga caacgtgccc tccgaagagg tcgtgaagaa    4740
gatgaagaac tactgcgcc agctgctgaa tgccaagctg attacccaga ggaagttcga    4800
caatctgacc aaggccgaga gaggcggcct gagcgaactg gataaggccg gcttcatcaa    4860
gagacagctg gtgaaaccc ggcagatcac aaagcacgtg gcacagatcc tggactcccg    4920
gatgaacact aagtacgacg agaacgacaa actgatccgg gaagtgaaag tgatcaccct    4980
gaagtccaag ctggtgtccg atttccggaa ggatttccag ttttacaaag tgcgcgagat    5040
caacaactac caccacgccc acgacgccta cctgaacgcc gtcgtgggaa ccgccctgat    5100
caaaaagtac cctaagctgg aaagcgagtt cgtgtacggc gactacaagg tgtacgacgt    5160
gcggaagatg atcgccaaga gcgagcagga aatcggcaag gctaccgcca agtacttctt    5220
ctacagcaac atcatgaact ttttcaagac cgagattacc ctggccaacg gcgagatccg    5280
gaagcggcct ctgatcgaga caaacggcga aacaggcgag atcgtgtggg ataagggccg    5340
ggactttgcc accgtgcgga aagtgctgtc tatgccccaa gtgaatatcg tgaaaaagac    5400
cgaggtgcag acaggcggct tcagcaaaga gtctatcctg cccaagagga cagcgacaa    5460 gctgatcgcc agaaagaagg actgggaccc taagaagtac ggcggcttcg acagccccac    5520
cgtggcctat tctgtgctgg tggtggccaa agtggaaaag ggcaagtcca agaaactgaa    5580
gagtgtgaaa gagctgctgg ggatcaccat catggaaaga agcagcttcg agaagaatcc    5640
catcgacttt ctggaagcca agggctacaa agaagtgaaa aaggacctga tcatcaagct    5700
gcctaagtac tccctgttcg agctggaaaa cggccggaag agaatgctgg cctctgccgg    5760
cgaactgcag aagggaaacg aactggccct gccctccaaa tatgtgaact tcctgtacct    5820
ggccagccac tatgagaagc tgaagggctc ccccgaggat aatgagcaga acagctgtt    5880 tgtggaacag cacaaacact acctggacga gatcatcgag cagatcagcg agttctccaa    5940
gagagtgatc ctggccgacg ctaatctgga caaggtgctg agcgcctaca acaagcacag    6000
agacaagcct atcagagagc aggccgagaa tatcatccac ctgtttaccc tgaccaatct    6060
gggagcccct gccgccttca gtactttga caccaccatc gaccggaaga ggtacaccag    6120
caccaaagag gtgctggacg ccaccctgat ccaccagagc atcaccggcc tgtacgagac    6180
acggatcgac ctgtctcagc tgggaggcga cgcctatccc tatgacgtgc ccgattatgc    6240
cagcctgggc agcggctccc ccaagaaaaa acgcaaggtg gaagatccta agaaaaagcg    6300
```

-continued

```
gaaagtggaa gatgctccaa agaagaagag aaaggtcgac ggcattggta gtgggagcaa    6360
cggcagcagc ggatccaacg gtccgactga cgccgcggaa gaagaacttt tgagcaagaa    6420
ttatcatctt gagaacgaag tggctcgtct taagaaaggt tctggcagtg gaggttctgg    6480
ctccggatct ggtggttcgg gctcaggcgg gtccggatca ggcgaagaac tgctttcaaa    6540
gaattaccac ctggaaaatg aggtagctag actgaaaaag gggagcggaa gtgggggctc    6600
cgggtcgggc tcaggggggct ccggttcggg aggctcaggg tcgggggagg agttgctgag    6660
caaaaattat catttggaga cgaagtagc acgactaaag aaagggtccg gatcgggtgg    6720
ttcaggatct ggatccggag gatcagggtc cggtgggtcg ggctcaggag aggagttact    6780
ctcgaaaaat tatcatctcg aaaacgaagt ggctcggcta aaaaagggca gtggttctgg    6840
aggatctggg tcggggtcag gcgggtctgg atctggggga tctggatctg gtgaagagct    6900
attatctaaa aactaccacc tcgaaaatga ggtggcacgc ttaaaaaagg gaagtggcag    6960
tggtgggtcg ggatctggct ctggtggctc aggctcggga ggttcaggtt ccggggaaga    7020
gctactatcc aagaattatc atcttgagaa cgaggtagcg cgtttgaaga agggttccgg    7080
ctcaggagga tctgggtcag gatcgggggg ttccgggtca ggcgggtccg ggtcaggcga    7140
ggaactgctc tcgaagaact atcatcttga aaatgaggtc gctcgattaa aaaagggatc    7200
gggcagtggt gggtccggct ccggttccgg aggatcggga tctgggggct cgggatccgg    7260
ggaggaacta ctttcaaaga attaccacct cgaaaacgaa gtagctcgat taagaaaagg    7320
ttcagggtcg ggtggctcag gttcgggatc aggtgggtca ggctccggtg gttcaggttc    7380
gggagaagaa ttactgagta aaaattatca tctggaaaat gaggtagcga gactaaaaaa    7440
ggggagtggt tctggcggtt cgggatctgg ctctgggggc tctgggtcgg gagggtctgg    7500
gtctggcgag gaattgctat cgaaaaatta tcatcttgag aacgaagttg ctaggctcaa    7560
aaagggctca ggctcaggcg ggtccgggtc agggtcggga ggttccggat ccggggggatc    7620
aggctcaggg taacccgggg gcgcgccatg ataactagag tcctgcttta atgagatatg    7680
cgagacgcct atgatcgcat gatatttgct ttcaattctg ttgtgcacgt tgtaaaaaac    7740
ctgagcatgt gtagctcaga tccttaccgc cggtttcggt tcattctaat gaatatatca    7800
cccgttacta tcgtattttt atgaataata ttctccgttc aatttactga ttgtacccta    7860
ctacttatat gtacaatatt aaatgaaaa caatatattg tgctgaatag gtttatagcg    7920
acatctatga tagagcgcca caataacaaa caattgcgtt ttattattac aaatccaatt    7980
ttaaaaaaag cggcagaacc ggtcaaacct aaaagactga ttacataaat cttattcaaa    8040
tttcaaaagt gccccagggg ctagtatcta cgacacaccg agcggcgaac taataacgct    8100
cactgaaggg aactccggtt ccccgccggc gcgcatgggt gagattcctt gaagttgagt    8160
attggccgtc cgctctaccg aaagttacgg gcaccattca acccggtcca gcacggcggc    8220
cgggtaaccg acttgctgcc ccgagaatta tgcagcattt ttttggtgta tgtgggcccc    8280
aaatgaagtg caggtcaaac cttgacagtg acgacaaatc gttgggcggg tccagggcga    8340
atttttgcgac aacatgtcga ggctcagcag gaccggcatg caagctagct tactagtgat    8400
attctatagt gtcacctaaa tct                                            8423
```

<210> SEQ ID NO 69
<211> LENGTH: 1986
<212> TYPE: DNA
<213> ORGANISM: Artificial Sequence
<220> FEATURE:
<223> OTHER INFORMATION: Synthetic Construct

<400> SEQUENCE: 69

```
agtctagctc aacagagctt ttaacccaaa ttggtacaat agaatacaac tttagatcat      60
aattctcaaa agaaagagat tccttagcta ttctatctgc cactccattt ccttctcggc     120
ttgtatgcac aagcataaaa tcctcaaact tgctaagtag atactttatg tcttggataa     180
ttggattgag acttgacaag cataactttc atgtaaccaa agacacaagt tgctgagaat     240
ccacctcaaa aatgatcttc ctataattga atcgggataa tgacagcaca gcccatctaa     300
gagcctccac ttctacttcc agcacgcttc ttacttttac cacagctctt gcacctaacc     360
ataacacctt ccctgtatga tcgcgaagca cccaccctaa gccacatttt aatccttctg     420
ttggccatgc cccatcaaag ttgcacttaa cccaagattg tggtggagct tcccatgttt     480
ctcgtctgtc ccgacggtgt tgtggttggt gctttcctta cattctgagc ctctttcctt     540
ctaatccact catctgcatc ttcttgtgtc cttactaata cctcattggt tccaaattcc     600
ctccctttaa gcaccagctc gtttctgttc ttccacagcc tcccaagtat ccaagggact     660
aaagcctcca cattcttcag atcaggatat tcttgtttaa gatgttgaac tctatggagg     720
tttgtatgaa ctgatgatct aggaccggat aagttcccct cttcatagcg aacttattca     780
aagaatgttt tgtgtatcat tcttgttaca ttgttattaa tgaaaaaata ttattggtca     840
ttggactgaa cacgagtgtt aaatatggac caggccccaa ataagatcca ttgatatatg     900
aattaaataa caagaataaa tcgagtcacc aaaccacttg cctttttaa cgagacttgt      960
tcaccaactt gatacaaaag tcattatcct atgcaaatca ataatcatac aaaaatatcc    1020
aataacacta aaaattaaa agaaatggat aatttcacaa tatgttatac gataaagaag    1080
ttacttttcc aagaaattca ctgattttat aagcccactt gcattagata aatggcaaaa    1140
aaaaacaaaa aggaaaagaa ataaagcacg aagaattcta gaaaatacga aatacgcttc    1200
aatgcagtgg gacccacggt tcaattattg ccaattttca gctccaccgt atatttaaaa    1260
aataaaacga taatgctaaa aaaatataaa tcgtaacgat cgttaaatct caacggctgg    1320
atcttatgac gaccgttaga aattgtggtt gtcgacgagt cagtaataaa cggcgtcaaa    1380
gtggttgcag ccggcacaca cgagtcgtgt ttatcaactc aaagcacaaa tacttttcct    1440
caacctaaaa ataaggcaat tagccaaaaa caactttgcg tgtaaacaac gctcaataca    1500
cgtgtcattt tattattagc tattgcttca ccgccttagc tttctcgtga cctagtcgtc    1560
ctcgtctttt cttcttcttc ttctataaaa caatacccaa agagctcttc ttcttcacaa    1620
ttcagatttc aatttctcaa aatcttaaaa actttctctc aattctctct accgtgatca    1680
aggtaaattt ctgtgttcct tattctctca aaatcttcga ttttgttttc gttcgatccc    1740
aatttcgtat atgttctttg gtttagattc tgttaatctt agatcgaaga cgattttctg    1800
ggtttgatcg ttagatatca tcttaattct cgattagggt ttcatagata tcatccgatt    1860
tgttcaaata atttgagttt tgtcgaataa ttactcttcg atttgtgatt tctatctaga    1920
tctggtgtta gtttctagtt tgtgcgatcg aatttgtcga ttaatctgag tttttctgat    1980
taacag                                                               1986
```

<210> SEQ ID NO 70
<211> LENGTH: 115
<212> TYPE: DNA
<213> ORGANISM: Artificial Sequence
<220> FEATURE:
<223> OTHER INFORMATION: Synthetic Construct

<400> SEQUENCE: 70

```
ggatcatcaa caagtttgta caaaaaagca ggctctttaa agtattttta caacaattac    60
caacaacaac aaacaacaaa caacattaca attactattt acaattacaa aaaaa        115
```

<210> SEQ ID NO 71
<211> LENGTH: 4107
<212> TYPE: DNA
<213> ORGANISM: Artificial Sequence
<220> FEATURE:
<223> OTHER INFORMATION: Synthetic Construct

<400> SEQUENCE: 71

```
atggacaaga agtacagcat cggcctggcc atcggcacca actctgtggg ctgggccgtg    60
atcaccgacg agtacaaggt gcccagcaag aaattcaagg tgctgggcaa caccgaccgg   120
cacagcatca agaagaacct gatcggcgcc ctgctgttcg acagcggaga aacagccgag   180
gccacccggc tgaagagaac cgccagaaga agatacacca cacggaagaa ccggatctgc   240
tatctgcaag agatcttcag caacgagatg gccaaggtgg acgacagctt cttccacaga   300
ctggaagagt ccttcctggt ggaagaggat aagaagcacg agcggcaccc catcttcggc   360
aacatcgtgg acgaggtggc ctaccacgag aagtacccca ccatctacca cctgagaaag   420
aaactggtgg acagcaccga caaggccgac ctgcggctga tctatctggc cctggcccac   480
atgatcaagt tccggggcca cttcctgatc gagggcgacc tgaaccccga caacagcgac   540
gtggacaagc tgttcatcca gctggtgcag acctacaacc agctgttcga ggaaaacccc   600
atcaacgcca gcggcgtgga cgccaaggcc atcctgtctg ccagactgag caagagcaga   660
cggctggaaa atctgatcgc ccagctgccc ggcgagaaga gaatggcct gttcggcaac   720
ctgattgccc tgagcctggg cctgacccc aacttcaaga gcaacttcga cctggccgag   780
gatgccaaac tgcagctgag caaggacacc tacgacgacg acctggacaa cctgctggcc   840
cagatcggcg accagtacgc cgacctgttt ctggccgcca gaaacctgtc cgacgccatc   900
ctgctgagcg acatcctgag agtgaacacc gagatcacca aggccccct gagcgcctct   960
atgatcaaga gatacgacga gcaccaccag gacctgaccc tgctgaaagc tctcgtgcgg  1020
cagcagctgc ctgagaagta caaagagatt ttcttcgacc agagcaagaa cggctacgcc  1080
ggctacatcg atggcggagc cagccaggaa gagttctaca gtttcatcaa gcccatcctg  1140
gaaaagatgg acggcaccga ggaactgctc gtgaagctga acagagagga cctgctgcgg  1200
aagcagcgga ccttcgacaa cggcagcatc ccccaccaga tccacctggg agagctgcac  1260
gccattctgc ggcggcagga agatttttac ccattcctga aggacaaccg ggaaaagatc  1320
gagaagatcc tgaccttccg catcccctac tacgtgggcc ctctggccag gggaaacagc  1380
agattcgcct ggatgaccag aaagagcgag gaaaccatca cccctggaa cttcgaggaa  1440
gtggtggaca gggcgccag cgcccagagc ttcatcgagc ggatgaccaa cttcgataag  1500
aacctgccca acgagaaggt gctgcccaag cacagcctgc tgtacgagta cttcaccgtg  1560
tacaacgagc tgaccaaagt gaaatacgtg accgagggaa tgagaaagcc cgccttcctg  1620
agcggcgagc agaaaaaagc catcgtggac ctgctgttca gaccaaccg gaaagtgacc  1680
gtgaagcagc tgaaagagga ctacttcaag aaaatcgagt gcttcgactc cgtggaaatc  1740
tccggcgtgg aagatcggtt caacgcctcc ctgggcacat accacgatct gctgaaaatt  1800
atcaaggaca aggacttcct ggacaatgag gaaaacgagg acattctgga agatatcgtg  1860
ctgaccctga cactgtttga ggacagagag atgatcgagg aacggctgaa aacctatgcc  1920
```

```
cacctgttcg acgacaaagt gatgaagcag ctgaagcggc ggagatacac cggctggggc   1980
aggctgagcc ggaagctgat caacggcatc cgggacaagc agtccggcaa gacaatcctg   2040
gatttcctga agtccgacgg cttcgccaac agaaacttca tgcagctgat ccacgacgac   2100
agcctgacct ttaaagagga catccagaaa gcccaggtgt ccggccaggg cgatagcctg   2160
cacgagcaca ttgccaatct ggccggcagc cccgccatta agaagggcat cctgcagaca   2220
gtgaaggtgg tggacgagct cgtgaaagtg atgggccggc acaagcccga gaacatcgtg   2280
atcgaaatgg ccagagagaa ccagaccacc cagaagggac agaagaacag ccgcgagaga   2340
atgaagcgga tcgaagaggg catcaaagag ctgggcagcc agatcctgaa agaacacccc   2400
gtggaaaaca cccagctgca gaacgagaag ctgtacctgt actacctgca gaatgggcgg   2460
gatatgtacg tggaccagga actggacatc aaccggctgt ccgactacga tgtggacgct   2520
atcgtgcctc agagctttct gaaggacgac tccatcgata caaagtgct gactcggagc    2580 gacaagaacc ggcaagag cgacaacgtg ccctccgaag aggtcgtgaa gaagatgaag    2640
aactactggc gccagctgct gaatgccaag ctgattaccc agaggaagtt cgacaatctg   2700
accaaggccg agagaggcgg cctgagcgaa ctggataagg ccggcttcat caagagacag   2760
ctggtggaaa cccggcagat cacaaagcac gtggcacaga tcctggactc ccggatgaac   2820
actaagtacg acgagaacga caaactgatc cgggaagtga agtgatcac cctgaagtcc    2880 aagctggtgt ccgatttccg gaaggatttc cagttttaca aagtgcgcga gatcaacaac    2940
taccaccacg cccacgacgc ctacctgaac gccgtcgtgg aaccgccct gatcaaaaag    3000 taccctaagc tggaaagcga gttcgtgtac ggcgactaca aggtgtacga cgtgcggaag   3060
atgatcgcca agagcgagca ggaaatcggc aaggctaccg ccaagtactt cttctacagc   3120
aacatcatga actttttcaa gaccgagatt accctggcca acggcgagat ccggaagcgg   3180
cctctgatcg agacaaacgg cgaaacaggc gagatcgtgt gggataaggg ccgggacttt   3240
gccaccgtgc ggaaagtgct gtctatgccc caagtgaata tcgtgaaaaa gaccgaggtg   3300
cagacaggcg gcttcagcaa agagtctatc ctgcccaaga ggaacagcga caagctgatc   3360
gccagaaaga aggactggga ccctaagaag tacggcggct cgacagccc caccgtggcc   3420 tattctgtgc tggtggtggc caaagtggaa aagggcaagt ccaagaaact gaagagtgtg   3480
aaagagctgc tggggatcac catcatggaa agaagcagct cgagaagaa tcccatcgac   3540 tttctggaag ccaagggcta caaagaagtg aaaaaggacc tgatcatcaa gctgcctaag   3600
tactccctgt tcgagctgga aaacggccgg aagagaatgc tggcctctgc cggcgaactg   3660
cagaagggaa acgaactggc cctgccctcc aaatatgtga acttcctgta cctggccagc   3720
cactatgaga agctgaaggg ctcccccgag gataatgagc agaaacagct gtttgtggaa   3780
cagcacaaac actacctgga cgagatcatc gagcagatca gcgagttctc caagagagtg   3840
atcctggccg acgctaatct ggacaaggtg ctgagcgcct acaacaagca cagagacaag   3900
cctatcagag agcaggccga gaatatcatc cacctgtttt ccctgaccaa tctgggagcc   3960
cctgccgcct tcaagtactt tgacaccacc atcgaccgga gaggtacac cagcaccaaa   4020 gaggtgctgg acgccaccct gatccaccag agcatcaccg cctgtacga gacacggatc   4080 gacctgtctc agctgggagg cgacgcc                                      4107
```

<210> SEQ ID NO 72
<211> LENGTH: 27
<212> TYPE: DNA

```
<213> ORGANISM: Artificial Sequence
<220> FEATURE:
<223> OTHER INFORMATION: Synthetic Construct

<400> SEQUENCE: 72
tatccctatg acgtgcccga ttatgcc                                              27

<210> SEQ ID NO 73
<211> LENGTH: 21
<212> TYPE: DNA
<213> ORGANISM: Artificial Sequence
<220> FEATURE:
<223> OTHER INFORMATION: Synthetic Construct

<400> SEQUENCE: 73
cccaagaaaa aacgcaaggt g                                                    21

<210> SEQ ID NO 74
<211> LENGTH: 60
<212> TYPE: DNA
<213> ORGANISM: Artificial Sequence
<220> FEATURE:
<223> OTHER INFORMATION: Synthetic Construct

<400> SEQUENCE: 74
gacggcattg gtagtgggag caacggcagc agcggatcca acggtccgac tgacgccgcg          60

<210> SEQ ID NO 75
<211> LENGTH: 1236
<212> TYPE: DNA
<213> ORGANISM: Artificial Sequence
<220> FEATURE:
<223> OTHER INFORMATION: Synthetic Construct

<400> SEQUENCE: 75
gaagaagaac ttttgagcaa gaattatcat cttgagaacg aagtggctcg tcttaagaaa          60
ggttctggca gtggaggttc tggctccgga tctggtggtt cgggctcagg cgggtccgga         120
tcaggcgaag aactgctttc aaagaattac cacctggaaa atgaggtagc tagactgaaa         180
aaggggagcg gaagtggggg ctccgggtcg ggctcagggg gctccggttc gggaggctca         240
gggtcggggg aggagttgct gagcaaaaat tatcatttgg agaacgaagt agcacgacta         300
aagaaagggt ccggatcggg tggttcagga tctggatccg gaggatcagg gtccggtggg         360
tcgggctcag gagaggagtt actctcgaaa aattatcatc tcgaaaacga agtggctcgg         420
ctaaaaaagg gcagtggttc tggaggatct gggtcgggt caggcgggtc tggatctggg         480
ggatctggat ctggtgaaga gctattatct aaaaactacc acctcgaaaa tgaggtggca         540
cgcttaaaaa agggaagtgg cagtggtggg tcgggatctg gctctggtgg ctcaggctcg         600
ggaggttcag gttccgggga agagctacta tccaagaatt atcatcttga gaacgaggta         660
gcgcgtttga agaagggttc cggctcagga ggatctgggt caggatcggg gggttccggg         720
tcaggcgggt ccgggtcagg cgaggaactg ctctcgaaga actatcatct tgaaaatgag         780
gtcgctcgat taaaaaaggg atcgggcagt ggtgggtccg gctccggttc cggaggatcg         840
ggatctgggg gctcgggatc cggggaggaa ctactttcaa agaattacca cctcgaaaac         900
gaagtagctc gattaaagaa aggttcaggg tcgggtggct caggttcggg atcaggtggg         960
tcaggctccg gtggttcagg ttcgggagaa gaattactga gtaaaaatta tcatctggaa        1020
aatgaggtag cgagactaaa aaaggggagt ggttctggcg gttcgggatc tggctctggg        1080
ggctctgggt cgggagggtc tgggtctggc gaggaattgc tatcgaaaaa ttatcatctt        1140
```

```
gagaacgaag ttgctaggct caaaaagggc tcaggctcag gcgggtccgg gtcagggtcg    1200
ggaggttccg gatccggggg atcaggctca gggtaa                              1236

<210> SEQ ID NO 76
<211> LENGTH: 768
<212> TYPE: DNA
<213> ORGANISM: Artificial Sequence
<220> FEATURE:
<223> OTHER INFORMATION: Synthetic Construct

<400> SEQUENCE: 76
tagagtcctg ctttaatgag atatgcgaga cgcctatgat cgcatgatat ttgctttcaa      60
ttctgttgtg cacgttgtaa aaaacctgag catgtgtagc tcagatcctt accgccggtt     120
tcggttcatt ctaatgaata tatcacccgt tactatcgta tttttatgaa taatattctc     180
cgttcaattt actgattgta ccctactact tatatgtaca atattaaaat gaaaacaata     240
tattgtgctg aataggttta tagcgacatc tatgatagag cgccacaata acaaacaatt     300 gcgtttatt attacaaatc caattttaaa aaaagcggca gaaccggtca aacctaaaag      360
actgattaca taaatcttat tcaaatttca aaagtgcccc aggggctagt atctacgaca     420
caccgagcgg cgaactaata acgctcactg aagggaactc cggttccccg ccggcgcgca     480
tgggtgagat tccttgaagt tgagtattgg ccgtccgctc taccgaaagt tacgggcacc     540
attcaacccg gtccagcacg gcggccgggt aaccgacttg ctgccccgag aattatgcag     600 cattttttg gtgtatgtgg gccccaaatg aagtgcaggt caaaccttga cagtgacgac      660
aaatcgttgg gcgggtccag ggcgaatttt gcgacaacat gtcgaggctc agcaggaccg     720
gcatgcaagc tagcttacta gtgatattct atagtgtcac ctaaatct                  768

<210> SEQ ID NO 77
<211> LENGTH: 1841
<212> TYPE: PRT
<213> ORGANISM: Artificial Sequence
<220> FEATURE:
<223> OTHER INFORMATION: Synthetic Construct

<400> SEQUENCE: 77

Met Asp Lys Lys Tyr Ser Ile Gly Leu Ala Ile Gly Thr Asn Ser Val
1               5                  10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
```

```
           145                 150                 155                 160
Met Ile Lys Phe Arg Gly His Phe Leu Ile Glu Gly Asp Leu Asn Pro
                    165                 170                 175

Asp Asn Ser Asp Val Asp Lys Leu Phe Ile Gln Leu Val Gln Thr Tyr
                    180                 185                 190

Asn Gln Leu Phe Glu Glu Asn Pro Ile Asn Ala Ser Gly Val Asp Ala
                    195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                    245                 250                 255

Asp Leu Ala Glu Asp Ala Lys Leu Gln Leu Ser Lys Asp Thr Tyr Asp
                    260                 265                 270

Asp Asp Leu Asp Asn Leu Leu Ala Gln Ile Gly Asp Gln Tyr Ala Asp
                    275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                    325                 330                 335

Ala Leu Val Arg Gln Gln Leu Pro Glu Lys Tyr Lys Glu Ile Phe Phe
                    340                 345                 350

Asp Gln Ser Lys Asn Gly Tyr Ala Gly Tyr Ile Asp Gly Gly Ala Ser
                    355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                    420                 425                 430

Leu Lys Asp Asn Arg Glu Lys Ile Glu Lys Ile Leu Thr Phe Arg Ile
                    435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                    500                 505                 510

Leu Leu Tyr Glu Tyr Phe Thr Val Tyr Asn Glu Leu Thr Lys Val Lys
                    515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575
```

-continued

```
Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                    965                 970                 975

Glu Ile Asn Asn Tyr His His Ala His Asp Ala Tyr Leu Asn Ala Val
            980                 985                 990
```

-continued

```
Val Gly Thr Ala Leu Ile Lys Lys Tyr Pro Lys Leu Glu Ser Phe
            995                 1000                1005

Val Tyr Gly Asp Tyr Lys Val Tyr Asp Val Arg Lys Met Ile Ala Lys
1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
            1045                1050                1055

Ile Arg Lys Arg Pro Leu Ile Glu Thr Asn Gly Glu Thr Gly Glu Ile
            1060                1065                1070

Val Trp Asp Lys Gly Arg Asp Phe Ala Thr Val Arg Lys Val Leu Ser
            1075                1080                1085

Met Pro Gln Val Asn Ile Val Lys Lys Thr Glu Val Gln Thr Gly Gly
            1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
            1125                1130                1135

Pro Thr Val Ala Tyr Ser Val Leu Val Val Ala Lys Val Glu Lys Gly
            1140                1145                1150

Lys Ser Lys Lys Leu Lys Ser Val Lys Glu Leu Leu Gly Ile Thr Ile
            1155                1160                1165

Met Glu Arg Ser Ser Phe Glu Lys Asn Pro Ile Asp Phe Leu Glu Ala
            1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
            1205                1210                1215

Ala Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys His
            1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
            1285                1290                1295

His Arg Asp Lys Pro Ile Arg Glu Gln Ala Glu Asn Ile Ile His Leu
            1300                1305                1310

Phe Thr Leu Thr Asn Leu Gly Ala Pro Ala Ala Phe Lys Tyr Phe Asp
            1315                1320                1325

Thr Thr Ile Asp Arg Lys Arg Tyr Thr Ser Thr Lys Glu Val Leu Asp
1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp Ala Tyr Pro Tyr Asp Val Pro Asp
            1365                1370                1375

Tyr Ala Ser Leu Gly Ser Gly Ser Pro Lys Lys Lys Arg Lys Val Glu
            1380                1385                1390

Asp Pro Lys Lys Lys Arg Lys Val Glu Asp Ala Pro Lys Lys Lys Arg
            1395                1400                1405

Lys Val Asp Gly Ile Gly Ser Gly Ser Asn Gly Ser Ser Gly Ser Asn
```

```
                      1410              1415                1420
Gly Pro Thr Asp Ala Ala Glu Glu Leu Leu Ser Lys Asn Tyr His
1425                1430                1435                1440

Leu Glu Asn Glu Val Ala Arg Leu Lys Lys Gly Ser Gly Ser Gly
                1445                1450                1455

Ser Gly Ser Gly Ser Gly Gly Ser Gly Gly Ser Gly Ser Gly Gly
                1460                1465                1470

Glu Glu Leu Leu Ser Lys Asn Tyr His Leu Glu Asn Glu Val Ala Arg
            1475                1480                1485

Leu Lys Lys Gly Ser Gly Ser Gly Gly Ser Gly Ser Gly Gly
            1490                1495                1500

Ser Gly Ser Gly Gly Ser Gly Ser Gly Glu Glu Leu Leu Ser Lys Asn
1505                1510                1515                1520

Tyr His Leu Glu Asn Glu Val Ala Arg Leu Lys Lys Gly Ser Gly Ser
                1525                1530                1535

Gly Gly Ser Gly Ser Gly Ser Gly Gly Ser Gly Ser Gly Gly Ser Gly
                1540                1545                1550

Ser Gly Glu Glu Leu Leu Ser Lys Asn Tyr His Leu Glu Asn Glu Val
            1555                1560                1565

Ala Arg Leu Lys Lys Gly Ser Gly Ser Gly Gly Ser Gly Ser Gly Ser
        1570                1575                1580

Gly Gly Ser Gly Ser Gly Gly Ser Gly Glu Glu Leu Leu Ser
1585                1590                1595                1600

Lys Asn Tyr His Leu Glu Asn Glu Val Ala Arg Leu Lys Lys Gly Ser
                1605                1610                1615

Gly Ser Gly Gly Ser Gly Ser Gly Ser Gly Gly Ser Gly Ser Gly Gly
            1620                1625                1630

Ser Gly Ser Gly Glu Glu Leu Leu Ser Lys Asn Tyr His Leu Glu Asn
            1635                1640                1645

Glu Val Ala Arg Leu Lys Lys Gly Ser Gly Ser Gly Gly Ser Gly Ser
        1650                1655                1660

Gly Ser Gly Gly Ser Gly Ser Gly Gly Ser Gly Glu Glu Leu
1665                1670                1675                1680

Leu Ser Lys Asn Tyr His Leu Glu Asn Glu Val Ala Arg Leu Lys Lys
                1685                1690                1695

Gly Ser Gly Ser Gly Gly Ser Gly Ser Gly Ser Gly Gly Ser Gly Ser
            1700                1705                1710

Gly Gly Ser Gly Ser Gly Glu Glu Leu Leu Ser Lys Asn Tyr His Leu
            1715                1720                1725

Glu Asn Glu Val Ala Arg Leu Lys Lys Gly Ser Gly Ser Gly Gly Ser
        1730                1735                1740

Gly Ser Gly Ser Gly Gly Ser Gly Ser Gly Gly Ser Gly Ser Gly Glu
1745                1750                1755                1760

Glu Leu Leu Ser Lys Asn Tyr His Leu Glu Asn Glu Val Ala Arg Leu
                1765                1770                1775

Lys Lys Gly Ser Gly Ser Gly Gly Ser Gly Ser Gly Ser Gly Gly Ser
            1780                1785                1790

Gly Ser Gly Gly Ser Gly Ser Gly Glu Glu Leu Leu Ser Lys Asn Tyr
            1795                1800                1805

His Leu Glu Asn Glu Val Ala Arg Leu Lys Lys Gly Ser Gly Ser Gly
        1810                1815                1820

Gly Ser Gly Ser Gly Ser Gly Gly Ser Gly Ser Gly Gly Ser Gly Ser
1825                1830                1835                1840
```

Gly

<210> SEQ ID NO 78
<211> LENGTH: 1369
<212> TYPE: PRT
<213> ORGANISM: Artificial Sequence
<220> FEATURE:
<223> OTHER INFORMATION: Synthetic Construct

<400> SEQUENCE: 78

```
Met Asp Lys Lys Tyr Ser Ile Gly Leu Ala Ile Gly Thr Asn Ser Val
1               5                  10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350
```

```
Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
```

```
            770                 775                 780
Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala Lys
                1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
                1045                1050                1055

Ile Arg Lys Arg Pro Leu Ile Glu Thr Asn Gly Glu Thr Gly Glu Ile
                1060                1065                1070

Val Trp Asp Lys Gly Arg Asp Phe Ala Thr Val Arg Lys Val Leu Ser
                1075                1080                1085

Met Pro Gln Val Asn Ile Val Lys Lys Thr Glu Val Gln Thr Gly Gly
                1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
                1125                1130                1135

Pro Thr Val Ala Tyr Ser Val Leu Val Val Ala Lys Val Glu Lys Gly
                1140                1145                1150

Lys Ser Lys Lys Leu Lys Ser Val Lys Glu Leu Leu Gly Ile Thr Ile
                1155                1160                1165

Met Glu Arg Ser Ser Phe Glu Lys Asn Pro Ile Asp Phe Leu Glu Ala
                1170                1175                1180

Lys Gly Tyr Lys Glu Val Lys Lys Asp Leu Ile Ile Lys Leu Pro Lys
1185                1190                1195                1200
```

Tyr Ser Leu Phe Glu Leu Glu Asn Gly Arg Lys Arg Met Leu Ala Ser
            1205                1210                1215

Ala Gly Glu Leu Gln Lys Gly Asn Glu Leu Ala Leu Pro Ser Lys Tyr
        1220                1225                1230

Val Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys His
        1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
            1285                1290                1295

His Arg Asp Lys Pro Ile Arg Glu Gln Ala Glu Asn Ile Ile His Leu
            1300                1305                1310

Phe Thr Leu Thr Asn Leu Gly Ala Pro Ala Ala Phe Lys Tyr Phe Asp
            1315                1320                1325

Thr Thr Ile Asp Arg Lys Arg Tyr Thr Ser Thr Lys Glu Val Leu Asp
        1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp Ala
            1365

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct

<400> SEQUENCE: 79

Tyr Pro Tyr Asp Val Pro Asp Tyr Ala
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic Construct

<400> SEQUENCE: 80

Pro Lys Lys Lys Arg Lys Val
1               5

<210> SEQ ID NO 81
<211> LENGTH: 20
<212> TYPE: PRT
<213> ORGANISM: Artificial Sequence
<220> FEATURE:
<223> OTHER INFORMATION: Synthetic Construct

<400> SEQUENCE: 81

Asp Gly Ile Gly Ser Gly Ser Asn Gly Ser Ser Gly Ser Asn Gly Pro
1               5                   10                  15

Thr Asp Ala Ala
            20

<210> SEQ ID NO 82
<211> LENGTH: 411

```
<212> TYPE: PRT
<213> ORGANISM: Artificial Sequence
<220> FEATURE:
<223> OTHER INFORMATION: Synthetic Construct

<400> SEQUENCE: 82

Glu Glu Glu Leu Leu Ser Lys Asn Tyr His Leu Glu Asn Glu Val Ala
1               5                   10                  15

Arg Leu Lys Lys Gly Ser Gly Ser Gly Gly Ser Gly Ser Gly Ser Gly
            20                  25                  30

Gly Ser Gly Ser Gly Gly Ser Gly Ser Gly Glu Glu Leu Leu Ser Lys
        35                  40                  45

Asn Tyr His Leu Glu Asn Glu Val Ala Arg Leu Lys Lys Gly Ser Gly
    50                  55                  60

Ser Gly Gly Ser Gly Ser Gly Ser Gly Gly Ser Gly Ser Gly Gly Ser
65                  70                  75                  80

Gly Ser Gly Glu Glu Leu Leu Ser Lys Asn Tyr His Leu Glu Asn Glu
                85                  90                  95

Val Ala Arg Leu Lys Lys Gly Ser Gly Ser Gly Gly Ser Gly Ser Gly
            100                 105                 110

Ser Gly Gly Ser Gly Ser Gly Gly Ser Gly Ser Gly Glu Glu Leu Leu
        115                 120                 125

Ser Lys Asn Tyr His Leu Glu Asn Glu Val Ala Arg Leu Lys Lys Gly
    130                 135                 140

Ser Gly Ser Gly Gly Ser Gly Ser Gly Ser Gly Gly Ser Gly Ser Gly
145                 150                 155                 160

Gly Ser Gly Ser Gly Glu Glu Leu Leu Ser Lys Asn Tyr His Leu Glu
                165                 170                 175

Asn Glu Val Ala Arg Leu Lys Lys Gly Ser Gly Ser Gly Gly Ser Gly
            180                 185                 190

Ser Gly Ser Gly Gly Ser Gly Ser Gly Gly Ser Gly Ser Gly Glu Glu
        195                 200                 205

Leu Leu Ser Lys Asn Tyr His Leu Glu Asn Glu Val Ala Arg Leu Lys
    210                 215                 220

Lys Gly Ser Gly Ser Gly Gly Ser Gly Ser Gly Ser Gly Gly Ser Gly
225                 230                 235                 240

Ser Gly Gly Ser Gly Ser Gly Glu Glu Leu Leu Ser Lys Asn Tyr His
                245                 250                 255

Leu Glu Asn Glu Val Ala Arg Leu Lys Lys Gly Ser Gly Ser Gly Gly
            260                 265                 270

Ser Gly Ser Gly Ser Gly Gly Ser Gly Ser Gly Gly Ser Gly Ser Gly
        275                 280                 285

Glu Glu Leu Leu Ser Lys Asn Tyr His Leu Glu Asn Glu Val Ala Arg
    290                 295                 300

Leu Lys Lys Gly Ser Gly Ser Gly Gly Ser Gly Ser Gly Ser Gly Gly
305                 310                 315                 320

Ser Gly Ser Gly Gly Ser Gly Ser Gly Glu Glu Leu Leu Ser Lys Asn
                325                 330                 335

Tyr His Leu Glu Asn Glu Val Ala Arg Leu Lys Lys Gly Ser Gly Ser
            340                 345                 350

Gly Gly Ser Gly Ser Gly Ser Gly Gly Ser Gly Ser Gly Gly Ser Gly
        355                 360                 365

Ser Gly Glu Glu Leu Leu Ser Lys Asn Tyr His Leu Glu Asn Glu Val
    370                 375                 380
```

```
Ala Arg Leu Lys Lys Gly Ser Gly Ser Gly Gly Ser Gly Ser
385                 390                 395                 400

Gly Gly Ser Gly Ser Gly Gly Ser Gly Ser Gly
            405                 410
```

<210> SEQ ID NO 83
<211> LENGTH: 6481
<212> TYPE: DNA
<213> ORGANISM: Artificial Sequence
<220> FEATURE:
<223> OTHER INFORMATION: Synthetic Construct

<400> SEQUENCE: 83

| | | | | | |
|---|---|---|---|---|---|
| agtctagctc | aacagagctt | ttaacccaaa | ttggtacaat | agaatacaac | tttagatcat | 60 |
| aattctcaaa | agaaagagat | tccttagcta | ttctatctgc | cactccattt | ccttctcggc | 120 |
| ttgtatgcac | aagcataaaa | tcctcaaact | tgctaagtag | atactttatg | tcttggataa | 180 |
| ttggattgag | acttgacaag | cataactttc | atgtaaccaa | agacacaagt | tgctgagaat | 240 |
| ccacctcaaa | aatgatcttc | ctataattga | atcgggataa | tgacagcaca | gcccatctaa | 300 |
| gagcctccac | ttctacttcc | agcacgcttc | ttacttttac | cacagctctt | gcacctaacc | 360 |
| ataacacctt | ccctgtatga | tcgcgaagca | cccaccctaa | gccacatttt | aatccttctg | 420 |
| ttggccatgc | cccatcaaag | ttgcacttaa | cccaagattg | tggtggagct | tcccatgttt | 480 |
| ctcgtctgtc | ccgacggtgt | tgtggttggt | gctttcctta | cattctgagc | ctctttcctt | 540 |
| ctaatccact | catctgcatc | ttcttgtgtc | cttactaata | cctcattggt | tccaaattcc | 600 |
| ctccctttaa | gcaccagctc | gtttctgttc | ttccacagcc | tcccaagtat | ccaagggact | 660 |
| aaagcctcca | cattcttcag | atcaggatat | tcttgtttaa | gatgttgaac | tctatggagg | 720 |
| tttgtatgaa | ctgatgatct | aggaccggat | aagttccctt | cttcatagcg | aacttattca | 780 |
| aagaatgttt | tgtgtatcat | tcttgttaca | ttgttattaa | tgaaaaaata | ttattggtca | 840 |
| ttggactgaa | cacgagtgtt | aaatatggac | caggccccaa | ataagatcca | ttgatatatg | 900 |
| aattaaataa | caagaataaa | tcgagtcacc | aaaccacttg | cctttttaa | cgagacttgt | 960 |
| tcaccaactt | gatacaaaag | tcattatcct | atgcaaatca | ataatcatac | aaaaatatcc | 1020 |
| aataacacta | aaaattaaa | agaaatggat | aatttcacaa | tatgttatac | gataaagaag | 1080 |
| ttacttttcc | aagaaattca | ctgattttat | aagcccactt | gcattagata | aatggcaaaa | 1140 |
| aaaacaaaa | aggaaaagaa | ataaagcacg | aagaattcta | gaaaatacga | aatacgcttc | 1200 |
| aatgcagtgg | gacccacggt | tcaattattg | ccaattttca | gctccaccgt | atatttaaaa | 1260 |
| aataaaacga | taatgctaaa | aaaatataaa | tcgtaacgat | cgttaaatct | caacggctgg | 1320 |
| atcttatgac | gaccgttaga | aattgtggtt | gtcgacgagt | cagtaataaa | cggcgtcaaa | 1380 |
| gtggttgcag | ccggcacaca | cgagtcgtgt | ttatcaactc | aaagcacaaa | tactttcct | 1440 |
| caacctaaaa | ataaggcaat | tagccaaaaa | caactttgcg | tgtaaacaac | gctcaataca | 1500 |
| cgtgtcattt | tattattagc | tattgcttca | ccgccttagc | tttctcgtga | cctagtcgtc | 1560 |
| ctcgtctttt | cttcttcttc | ttctataaaa | caatacccaa | agagctcttc | ttcttcacaa | 1620 |
| ttcagatttc | aatttctcaa | aatcttaaaa | actttctctc | aattctctct | accgtgatca | 1680 |
| aggtaaattt | ctgtgttcct | tattctctca | aaatcttcga | ttttgttttc | gttcgatccc | 1740 |
| aatttcgtat | atgttctttg | gtttagattc | tgttaatctt | agatcgaaga | cgattttctg | 1800 |
| ggtttgatcg | ttagatatca | tcttaattct | cgattagggt | ttcatagata | tcatccgatt | 1860 |
| tgttcaaata | atttgagttt | tgtcgaataa | ttactcttcg | atttgtgatt | tctatctaga | 1920 |

```
tctggtgtta gtttctagtt tgtgcgatcg aatttgtcga ttaatctgag ttttttctgat    1980
taacacctag ggtttagcgc tgatgggccc cgacatcgtg atgacccaga gccccagcag    2040
cctgagcgcc agcgtgggcg accgcgtgac catcacctgc cgcagcagca ccggcgccgt    2100
gaccaccagc aactacgcca gctgggtgca ggagaagccc ggcaagctgt tcaagggcct    2160
gatcggcggc accaacaacc gcgcccccgg cgtgcccagc cgcttcagcg gcagcctgat    2220
cggcgacaag gccaccctga ccatcagcag cctgcagccc gaggacttcg ccacctactt    2280
ctgcgccctg tggtacagca accactgggt gttcggccag ggcaccaagg tggagctgaa    2340
gcgcggcggc ggcggcagcg gcggcggcgg cagcggcggc ggcggcagca gcggcggcgg    2400
cagcgaggtg aagctgctgg agagcggcgg cggcctggtg cagcccggcg gcagcctgaa    2460
gctgagctgc gccgtgagcg gcttcagcct gaccgactac ggcgtgaact gggtgcgcca    2520
ggccccggc cgcggcctgg agtggatcgg cgtgatctgg ggcgacggca tcaccgacta    2580
caacagcgcc ctgaaggacc gcttcatcat cagcaaggac aacggcaaga acaccgtgta    2640
cctgcagatg agcaaggtgc gcagcgacga caccgccctg tactactgcg tgaccggcct    2700
gttcgactac tggggccagg gcaccctggt gaccgtgagc agctacccat acgatgttcc    2760
agattacgct ggtggaggcg gaggttctgg gggaggaggt agtggcggtg gtggttcagg    2820
aggcggcgga agcttggatc caggtggagg tggaagcggt agcaaaggag aagaactttt    2880
cactggagtt gtcccaattc ttgttgaatt agatggtgat gttaatgggc acaaattttc    2940
tgtccgtgga gagggtgaag gtgatgctac aaacggaaaa ctcacccctta aatttatttg    3000
cactactgga aaactacctg ttccgtggcc aacacttgtc actactctga cctatggtgt    3060
tcaatgcttt tcccgttatc cggatcacat gaaacggcat gactttttca agagtgccat    3120
gcccgaaggt tatgtacagg aacgcactat atctttcaaa gatgacggga cctacaagac    3180
gcgtgctgaa gtcaagtttg aaggtgatac ccttgttaat cgtatcgagt taaagggtat    3240
tgattttaaa gaagatggaa acattcttgg acacaaactc gagtacaact ttaactcaca    3300
caatgtatac atcacggcag acaaacaaaa gaatggaatc aaagctaact tcaaaattcg    3360
ccacaacgtt gaagatggtt ccgttcaact agcagaccat tatcaacaaa atactccaat    3420
tggcgatggc cctgtccttt taccagacaa ccattacctg tcgacacaat ctgtcctttc    3480
gaaagatccc aacgaaaagc gtgaccacat ggtccttctt gagtttgtaa ctgctgctgg    3540
gattacacat ggcatggatg agctctacaa aggtggaggt cggaccggtc gtacggctcc    3600
aaagaagaag agaaaggtcg gcggtggcgg aggggtcga tcacaagact acgcatcga    3660
aaaatacttc acagcagacg attcttttga ttcggtgacc gaagagcgtg aatggggtgc    3720
acgcatgacc aaagctagtc ttgtgccacc tgttactagg aaatatgaag tgattgaaaa    3780
gtatgcaatt gttgcggatg aggaggaagt acaacgaaag atgcgggttt ctttgccaga    3840
ggactatggt gagaagctta atgcacaaag aaatggcatt gaagaattag atatggaact    3900
gcctgaagtc aaggagtata aaccaagaaa gcttcttggc gatgaggttt tagagcaaga    3960
ggtttatgga atcgatcctt acacccataa cctcttactt gattcaatgc ctggagaatt    4020
ggactggtca ctgcaggata acattcatt tatagaagat gtagtcttac ggaccctgaa    4080
caggcaagtt cggctgttca ctggatctgg aagcacccct atggtattcc ctttaaggcc    4140
tgtgattgaa gagctcaaag agagtgctcg tgaagagtgt gatatacgaa caatgaagat    4200
gtgtcaaggc gtcttaaagg aaatagaaag tcgttctgat gataaatatg tttcttatcg    4260
```

| | |
|---|---|
| gaagggcctt ggtgttgtgt gcaacaaaga aggtggtttt ggagaagaag attttgttgt | 4320 |
| tgaatttctt ggagaggttt atcctgtttg gaagtggttt gagaagcaag atgggatccg | 4380 |
| ttccttacag gaaaacaaaa ctgatcctgc accagagttc tacaatatat atcttgagag | 4440 |
| accaaagggt gatgctgatg gatatgattt agtcgttgtt gatgccatgc acatggctaa | 4500 |
| ctacgcaagt cgaatttgtc actcttgccg acctaattgt gaagctaagg ttactgcggt | 4560 |
| ggatggacac taccagattg gcatctattc agtacgcgct attgaatatg gcgaggagat | 4620 |
| aactttcgat tataattctg taactgagag taaggaagaa tatgaagcgt ctgtttgctt | 4680 |
| gtgtggtagc caagtatgtc gaggcagcta cttgaatctc actggtgaag gtgcatttca | 4740 |
| gaaggtgttg aaggattggc atggtctgct ggaacgacac agactgatgc tggaagcttg | 4800 |
| tgtattgaat tcagtttcag aagaagatta tcttgagttg gaagagctg gactgggaag | 4860 |
| ttgtttgctt ggtgggttgc cagattggat gattgcttat tctgctcgtc tggtccggtt | 4920 |
| catcaatttc gagagaacaa agctacccga ggaaattctt aagcacaatc tagaagaaaa | 4980 |
| gagaaaatac ttttcagata tacaccttga tgttgagaaa agtgatgctg aggttcaggc | 5040 |
| tgagggtgtc tacaatcaga ggcttcagaa tttggctgtt acacttgaca aggtgcgata | 5100 |
| tgttatgaga catgtgtttg gggatccaaa gaacgctcct cctccgctgg agaggcttac | 5160 |
| tcctgaagaa acagtgtctt ttgttttggaa cggggatggc tctttagttg atgagcttct | 5220 |
| tcagagcctg tcaccgcacc ttgaagaagg ccctcttaat gaactcagat caaagattca | 5280 |
| tggccatgat ccatctggat ctgctgatgt tttaaaggaa cttcagagat cgttactttg | 5340 |
| gttgagagat gagatccgag atctcccatg tacatacaag tgtcggaatg atgctgcagc | 5400 |
| tgatttaatt cacatatatg cctataccaa gtgctttttc aaagttcggg aataccagtc | 5460 |
| ctttatctct tctcctgtac acattagtcc gttagatttg ggggctaagt atgctgacaa | 5520 |
| gttaggtgag agtataaagg agtaccggaa gacttatggc gagaactatt gtctcgggca | 5580 |
| gctaatttac tggtataacc agacaaatac tgatccagat cttacattgg tgaaagcaac | 5640 |
| cagaggttgc ttgtctttac ccgatgttgc ttccttctat gcaaaggccc agaaaccatc | 5700 |
| gaagcatcgt gtatatggcc caaagacggt gaaaactatg gtttcacaga tgtctaagca | 5760 |
| acctcaaaga ccgtggccaa aggataaaat atggacgttc aaaagcaccc caagagtatt | 5820 |
| tggaagcccg atgttcgatg ccgtccttaa taactcatca tcactagata gagaactgtt | 5880 |
| gcagtggtta agaaatagac ggcatgtctt ccaagcgaca tgggatagtt agcgtacggg | 5940 |
| aggaggatct cggaccgaag agtacaagct tatcctgaac ggtaaaaccc tgaaaggtga | 6000 |
| aaccaccacc gaagctgttg acgctgctac cgcggaaaaa gttttcaaac agtacgctaa | 6060 |
| cgacaacggt gttgacggtg aatggaccta cgacgacgct accaaaacct tcacggtaac | 6120 |
| cgaaggtggt ggtagcggtg gtggtactag tccaaaaaca aggaggagac cgcgaagatc | 6180 |
| acaacggaaa aggccgccta cgccatggcc gtaagtttga gctcgaattt ccccgatcgt | 6240 |
| tcaaacattt ggcaataaag tttcttaaga ttgaatcctg ttgccggtct tgcgatgatt | 6300 |
| atcatataat ttctgttgaa ttacgttaag catgtaataa ttaacatgta atgcatgacg | 6360 |
| ttatttatga gatgggtttt tatgattaga gtcccgcaat tatacattta atacgcgata | 6420 |
| gaaaacaaaa tatagcgcgc aaactaggat aaattatcgc gcgcggtgtc atctatgtta | 6480 |
| c | 6481 |

<210> SEQ ID NO 84
<211> LENGTH: 1985

<212> TYPE: DNA
<213> ORGANISM: Artificial Sequence
<220> FEATURE:
<223> OTHER INFORMATION: Synthetic Construct

<400> SEQUENCE: 84

```
agtctagctc aacagagctt taacccaaa ttggtacaat agaatacaac tttagatcat      60
aattctcaaa agaaagagat tccttagcta ttctatctgc cactccattt ccttctcggc     120
ttgtatgcac aagcataaaa tcctcaaact tgctaagtag atactttatg tcttggataa     180
ttggattgag acttgacaag cataactttc atgtaaccaa agacacaagt tgctgagaat     240
ccacctcaaa aatgatcttc ctataattga atcgggataa tgacagcaca gcccatctaa     300
gagcctccac ttctacttcc agcacgcttc ttactttac cacagctctt gcacctaacc      360
ataacacctt ccctgtatga tcgcgaagca cccaccctaa gccacatttt aatccttctg     420
ttggccatgc cccatcaaag ttgcacttaa cccaagattg tggtggagct tcccatgttt     480
ctcgtctgtc ccgacggtgt tgtggttggt gctttcctta cattctgagc ctctttcctt     540
ctaatccact catctgcatc ttcttgtgtc cttactaata cctcattggt tccaaattcc     600
ctcccttaa gcaccagctc gtttctgttc ttccacagcc tcccaagtat ccaagggact      660
aaagcctcca cattcttcag atcaggatat tcttgtttaa gatgttgaac tctatggagg     720
tttgtatgaa ctgatgatct aggaccggat aagttccctt cttcatagcg aacttattca     780
aagaatgttt tgtgtatcat tcttgttaca ttgttattaa tgaaaaaata ttattggtca     840
ttggactgaa cacgagtgtt aaatatggac caggccccaa ataagatcca ttgatatatg     900
aattaaataa caagaataaa tcgagtcacc aaaccacttg ccttttttaa cgagacttgt     960
tcaccaactt gatacaaaag tcattatcct atgcaaatca ataatcatac aaaaatatcc    1020
aataacacta aaaattaaa agaaatggat aatttcacaa tatgttatac gataaagaag     1080
ttactttcc aagaaattca ctgattttat aagcccactt gcattagata aatggcaaaa     1140
aaaaacaaaa aggaaaagaa ataaagcacg aagaattcta gaaaatacga aatacgcttc    1200
aatgcagtgg gacccacggt tcaattattg ccaattttca gctccaccgt atatttaaaa    1260
aataaaacga taatgctaaa aaaatataaa tcgtaacgat cgttaaatct caacggctgg    1320
atcttatgac gaccgttaga aattgtggtt gtcgacgagt cagtaataaa cggcgtcaaa    1380
gtggttgcag ccggcacaca cgagtcgtgt ttatcaactc aaagcacaaa tactttcct    1440
caacctaaaa ataaggcaat tagccaaaaa caactttgcg tgtaaacaac gctcaataca    1500
cgtgtcattt tattattagc tattgcttca ccgccttagc tttctcgtga cctagtcgtc    1560
ctcgtctttt cttcttcttc ttctataaaa caatacccaa agagctcttc ttcttcacaa    1620
ttcagatttc aatttctcaa aatcttaaaa actttctctc aattctctct accgtgatca    1680
aggtaaattt ctgtgttcct tattctctca aaatcttcga ttttgttttc gttcgatccc    1740
aatttcgtat atgttctttg gtttagattc tgttaatctt agatcgaaga cgattttctg    1800
ggttgatcg ttagatatca tcttaattct cgattagggt tcatagata tcatccgatt       1860
tgttcaaata atttgagttt tgtcgaataa ttactcttcg atttgtgatt tctatctaga    1920
tctggtgtta gttctagtt tgtgcgatcg aatttgtcga ttaatctgag ttttctgat     1980
taaca                                                                1985
```

<210> SEQ ID NO 85
<211> LENGTH: 831
<212> TYPE: DNA

<213> ORGANISM: Artificial Sequence
<220> FEATURE:
<223> OTHER INFORMATION: Synthetic Construct

<400> SEQUENCE: 85

```
atgggcccccg acatcgtgat gacccagagc cccagcagcc tgagcgccag cgtgggcgac      60
cgcgtgacca tcacctgccg cagcagcacc ggcgccgtga ccaccagcaa ctacgccagc     120
tgggtgcagg agaagcccgg caagctgttc aagggcctga tcggcggcac caacaaccgc     180
gccccccggcg tgcccagccg cttcagcggc agcctgatcg gcgacaaggc caccctgacc     240
atcagcagcc tgcagcccga ggacttcgcc acctacttct gcgccctgtg gtacagcaac     300
cactgggtgt tcggccaggg caccaaggtg gagctgaagc gcggcggcgg cggcagcggc     360
ggcggcggca gcggcggcgg cggcagcagc ggcggcggca gcgaggtgaa gctgctggag     420
agcggcggcg gcctggtgca gcccggcggc agcctgaagc tgagctgcgc cgtgagcggc     480
ttcagcctga ccgactacgg cgtgaactgg gtgcgccagg ccccgggccg cggcctggag     540
tggatcggcg tgatctgggg cgacggcatc accgactaca cagcgccct gaaggaccgc      600
ttcatcatca gcaaggacaa cggcaagaac accgtgtacc tgcagatgag caaggtgcgc     660
agcgacgaca ccgccctgta ctactgcgtg accggcctgt cgactactg gggccagggc      720
accctggtga ccgtgagcag ctacccatac gatgttccag attacgctgg tggaggcgga     780
ggttctgggg gaggaggtag tggcggtggt ggttcaggag gcggcggaag c               831
```

<210> SEQ ID NO 86
<211> LENGTH: 711
<212> TYPE: DNA
<213> ORGANISM: Artificial Sequence
<220> FEATURE:
<223> OTHER INFORMATION: Synthetic Construct

<400> SEQUENCE: 86

```
agcaaaggag aagaactttt cactggagtt gtcccaattc ttgttgaatt agatggtgat      60
gttaatgggc acaaattttc tgtccgtgga gagggtgaag gtgatgctac aaacggaaaa     120
ctcacccctta aatttatttg cactactgga aaactacctg ttccgtggcc aacacttgtc    180
actactctga cctatggtgt tcaatgcttt tcccgttatc cggatcacat gaaacggcat     240
gactttttca agagtgccat gcccgaaggt tatgtacagg aacgcactat atctttcaaa    300
gatgacggga cctacaagac gcgtgctgaa gtcaagtttg aaggtgatac ccttgttaat    360
cgtatcgagt taaagggtat tgattttaaa gaagatggaa acattcttgg acacaaactc   420
gagtacaact ttaactcaca caatgtatac atcacggcag acaaacaaaa gaatggaatc   480
aaagctaact tcaaaattcg ccacaacgtt gaagatggtt ccgttcaact agcagaccat   540
tatcaacaaa atactccaat tggcgatggc cctgtccttt taccagacaa ccattacctg   600
tcgacacaat ctgtcctttc gaaagatccc aacgaaaagc gtgaccacat ggtccttctt   660
gagtttgtaa ctgctgctgg gattacacat ggcatggatg agctctacaa a              711
```

<210> SEQ ID NO 87
<211> LENGTH: 24
<212> TYPE: DNA
<213> ORGANISM: Artificial Sequence
<220> FEATURE:
<223> OTHER INFORMATION: Synthetic Construct

<400> SEQUENCE: 87

```
gctccaaaga agaagagaaa ggtc                                              24
```

<210> SEQ ID NO 88
<211> LENGTH: 15
<212> TYPE: DNA
<213> ORGANISM: Artificial Sequence
<220> FEATURE:
<223> OTHER INFORMATION: Synthetic Construct

<400> SEQUENCE: 88
ggcggtggcg gaggg                                                    15

<210> SEQ ID NO 89
<211> LENGTH: 2298
<212> TYPE: DNA
<213> ORGANISM: Artificial Sequence
<220> FEATURE:
<223> OTHER INFORMATION: Synthetic Construct

<400> SEQUENCE: 89
ggtcgatcac aagacttacg catcgaaaaa tacttcacag cagacgattc ttttgattcg    60
gtgaccgaag agcgtgaatg gggtgcacgc atgaccaaag ctagtcttgt gccacctgtt   120
actaggaaat atgaagtgat tgaaaagtat gcaattgttg cggatgagga ggaagtacaa   180
cgaaagatgc gggtttcttt gccagaggac tatggtgaga agcttaatgc acaaagaaat   240
ggcattgaag aattagatat ggaactgcct gaagtcaagg agtataaacc aagaaagctt   300
cttggcgatg aggttttaga gcaagaggtt tatggaatcg atccttacac ccataacctc   360
ttacttgatt caatgcctgg agaattggac tggtcactgc aggataaaca ttcatttata   420
gaagatgtag tcttacggac cctgaacagg caagttcggc tgttcactgg atctggaagc   480
acccctatgg tattcccttt aaggcctgtg attgaagagc tcaaagagag tgctcgtgaa   540
gagtgtgata tacgaacaat gaagatgtgt caaggcgtct taaggaaat agaaagtcgt   600 tctgatgata aatatgtttc ttatcggaag ggccttggtg ttgtgtgcaa caaagaaggt   660
ggttttggag aagaagattt tgttgttgaa tttcttggag aggtttatcc tgtttggaag   720
tggtttgaga agcaagatgg gatccgttcc ttacaggaaa acaaaactga tcctgcacca   780
gagttctaca atatatatct tgagagacca aagggtgatg ctgatggata tgatttagtc   840
gttgttgatg ccatgcacat ggctaactac gcaagtcgaa tttgtcactc ttgccgacct   900
aattgtgaag ctaaggttac tgcggtggat ggacactacc agattggcat ctattcagta   960
cgcgctattg aatatggcga ggagataact ttcgattata attctgtaac tgagagtaag  1020
gaagaatatg aagcgtctgt ttgcttgtgt ggtagccaag tatgtcgagg cagctacttg  1080
aatctcactg gtgaaggtgc atttcagaag gtgttgaagg attggcatgg tctgctggaa  1140
cgacacagac tgatgctgga agcttgtgta ttgaattcag tttcagaaga agattatctt  1200
gagttgggaa gagctggact gggaagttgt ttgcttggtg ggttgccaga ttggatgatt  1260
gcttattctg ctcgtctggt ccggttcatc aatttcgaga gaacaaagct acccgaggaa  1320
attcttaagc acaatctaga agaaagaga aaatactttt cagatataca ccttgatgtt  1380
gagaaaagtg atgctgaggt tcaggctgag ggtgtctaca atcagaggct tcagaatttg  1440 gctgttcacac ttgacaaggt gcgatatgtt atgagacatg tgtttgggga tccaaagaac  1500
gctcctcctc cgctggagag gcttactcct gaagaaacag tgtcttttgt ttggaacggg  1560
gatggctctt tagttgatga gcttcttcag agcctgtcac cgcaccttga agaaggccct  1620
cttaatgaac tcagatcaaa gattcatggc catgatccat ctggatctgc tgatgttta  1680

| | | | |
|---|---|---|---|
| aaggaacttc | agagatcgtt | actttggttg agagatgaga tccgagatct cccatgtaca | 1740 |
| tacaagtgtc | ggaatgatgc | tgcagctgat ttaattcaca tatatgccta taccaagtgc | 1800 |
| tttttcaaag | ttcgggaata | ccagtccttt atctcttctc ctgtacacat tagtccgtta | 1860 |
| gatttggggg | ctaagtatgc | tgacaagtta ggtgagagta taaggagta ccggaagact | 1920 |
| tatggcgaga | actattgtct | cgggcagcta atttactggt ataaccagac aaatactgat | 1980 |
| ccagatctta | cattggtgaa | agcaaccaga ggttgcttgt ctttacccga tgttgcttcc | 2040 |
| ttctatgcaa | aggcccagaa | accatcgaag catcgtgtat atggcccaaa gacggtgaaa | 2100 |
| actatggttt | cacagatgtc | taagcaacct caaagaccgt ggccaaagga taaaatatgg | 2160 |
| acgttcaaaa | gcaccccaag | agtatttgga agcccgatgt tcgatgccgt ccttaataac | 2220 |
| tcatcatcac | tagatagaga | actgttgcag tggttaagaa atagacggca tgtcttccaa | 2280 |
| gcgacatggg | atagttag | | 2298 |

<210> SEQ ID NO 90
<211> LENGTH: 165
<212> TYPE: DNA
<213> ORGANISM: Artificial Sequence
<220> FEATURE:
<223> OTHER INFORMATION: Synthetic Construct

<400> SEQUENCE: 90

| | | | |
|---|---|---|---|
| gagtacaagc | ttatcctgaa | cggtaaaacc ctgaaaggtg aaaccaccac cgaagctgtt | 60 |
| gacgctgcta | ccgcggaaaa | agttttcaaa cagtacgcta cgacaacgg tgttgacggt | 120 |
| gaatggacct | acgacgacgc | taccaaaacc ttcacggtaa ccgaa | 165 |

<210> SEQ ID NO 91
<211> LENGTH: 63
<212> TYPE: DNA
<213> ORGANISM: Artificial Sequence
<220> FEATURE:
<223> OTHER INFORMATION: Synthetic Construct

<400> SEQUENCE: 91

| | | | |
|---|---|---|---|
| ccaaaaacaa | ggaggagacc | gcgaagatca caacggaaaa ggccgcctac gccatggccg | 60 |
| taa | | | 63 |

<210> SEQ ID NO 92
<211> LENGTH: 263
<212> TYPE: DNA
<213> ORGANISM: Artificial Sequence
<220> FEATURE:
<223> OTHER INFORMATION: Synthetic Construct

<400> SEQUENCE: 92

| | | | |
|---|---|---|---|
| gagctcgaat | tccccgatc | gttcaaacat ttggcaataa agtttcttaa gattgaatcc | 60 |
| tgttgccggt | cttgcgatga | ttatcatata atttctgttg aattacgtta agcatgtaat | 120 |
| aattaacatg | taatgcatga | cgttatttat gagatgggtt tttatgatta gagtcccgca | 180 |
| attatacatt | taatacgcga | tagaaaacaa aatatagcgc gcaaactagg ataaattatc | 240 |
| gcgcgcggtg | tcatctatgt | tac | 263 |

<210> SEQ ID NO 93
<211> LENGTH: 1309
<212> TYPE: PRT
<213> ORGANISM: Artificial Sequence
<220> FEATURE:
<223> OTHER INFORMATION: Synthetic Construct

<400> SEQUENCE: 93

Met Gly Pro Asp Ile Val Met Thr Gln Ser Pro Ser Ser Leu Ser Ala
1               5                   10                  15

Ser Val Gly Asp Arg Val Thr Ile Thr Cys Arg Ser Ser Thr Gly Ala
            20                  25                  30

Val Thr Thr Ser Asn Tyr Ala Ser Trp Val Gln Glu Lys Pro Gly Lys
        35                  40                  45

Leu Phe Lys Gly Leu Ile Gly Gly Thr Asn Asn Arg Ala Pro Gly Val
    50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
            100                 105                 110

Lys Arg Gly Gly Gly Gly Ser Gly Gly Gly Gly Ser Gly Gly Gly Gly
        115                 120                 125

Ser Ser Gly Gly Gly Ser Glu Val Lys Leu Leu Glu Ser Gly Gly Gly
130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
                165                 170                 175

Arg Gly Leu Glu Trp Ile Gly Val Ile Trp Gly Asp Gly Ile Thr Asp
            180                 185                 190

Tyr Asn Ser Ala Leu Lys Asp Arg Phe Ile Ile Ser Lys Asp Asn Gly
        195                 200                 205

Lys Asn Thr Val Tyr Leu Gln Met Ser Lys Val Arg Ser Asp Asp Thr
    210                 215                 220

Ala Leu Tyr Tyr Cys Val Thr Gly Leu Phe Asp Tyr Trp Gly Gln Gly
225                 230                 235                 240

Thr Leu Val Thr Val Ser Ser Tyr Pro Tyr Asp Val Pro Asp Tyr Ala
                245                 250                 255

Gly Gly Gly Gly Gly Ser Gly Gly Gly Ser Gly Gly Gly Gly Ser
            260                 265                 270

Gly Gly Gly Gly Ser Leu Asp Pro Gly Gly Gly Ser Gly Ser Lys
        275                 280                 285

Gly Glu Glu Leu Phe Thr Gly Val Val Pro Ile Leu Val Glu Leu Asp
    290                 295                 300

Gly Asp Val Asn Gly His Lys Phe Ser Val Arg Gly Glu Gly Glu Gly
305                 310                 315                 320

Asp Ala Thr Asn Gly Lys Leu Thr Leu Lys Phe Ile Cys Thr Thr Gly
                325                 330                 335

Lys Leu Pro Val Pro Trp Pro Thr Leu Val Thr Thr Leu Thr Tyr Gly
            340                 345                 350

Val Gln Cys Phe Ser Arg Tyr Pro Asp His Met Lys Arg His Asp Phe
        355                 360                 365

Phe Lys Ser Ala Met Pro Glu Gly Tyr Val Gln Glu Arg Thr Ile Ser
    370                 375                 380

Phe Lys Asp Asp Gly Thr Tyr Lys Thr Arg Ala Glu Val Lys Phe Glu
385                 390                 395                 400

Gly Asp Thr Leu Val Asn Arg Ile Glu Leu Lys Gly Ile Asp Phe Lys

```
                405                 410                 415
Glu Asp Gly Asn Ile Leu Gly His Lys Leu Glu Tyr Asn Phe Asn Ser
            420                 425                 430
His Asn Val Tyr Ile Thr Ala Asp Lys Gln Lys Asn Gly Ile Lys Ala
            435                 440                 445
Asn Phe Lys Ile Arg His Asn Val Glu Asp Gly Ser Val Gln Leu Ala
    450                 455                 460
Asp His Tyr Gln Gln Asn Thr Pro Ile Gly Asp Gly Pro Val Leu Leu
465                 470                 475                 480
Pro Asp Asn His Tyr Leu Ser Thr Gln Ser Val Leu Ser Lys Asp Pro
                485                 490                 495
Asn Glu Lys Arg Asp His Met Val Leu Leu Glu Phe Val Thr Ala Ala
            500                 505                 510
Gly Ile Thr His Gly Met Asp Glu Leu Tyr Lys Gly Gly Gly Arg Thr
            515                 520                 525
Gly Arg Thr Ala Pro Lys Lys Lys Arg Lys Val Gly Gly Gly Gly Gly
            530                 535                 540
Gly Arg Ser Gln Asp Leu Arg Ile Glu Lys Tyr Phe Thr Ala Asp Asp
545                 550                 555                 560
Ser Phe Asp Ser Val Thr Glu Glu Arg Glu Trp Gly Ala Arg Met Thr
                565                 570                 575
Lys Ala Ser Leu Val Pro Pro Val Thr Arg Lys Tyr Glu Val Ile Glu
            580                 585                 590
Lys Tyr Ala Ile Val Ala Asp Glu Glu Val Gln Arg Lys Met Arg
            595                 600                 605
Val Ser Leu Pro Glu Asp Tyr Gly Glu Lys Leu Asn Ala Gln Arg Asn
        610                 615                 620
Gly Ile Glu Glu Leu Asp Met Glu Leu Pro Val Lys Glu Tyr Lys
625                 630                 635                 640
Pro Arg Lys Leu Leu Gly Asp Glu Val Leu Glu Gln Glu Val Tyr Gly
                645                 650                 655
Ile Asp Pro Tyr Thr His Asn Leu Leu Leu Asp Ser Met Pro Gly Glu
                660                 665                 670
Leu Asp Trp Ser Leu Gln Asp Lys His Ser Phe Ile Glu Asp Val Val
            675                 680                 685
Leu Arg Thr Leu Asn Arg Gln Val Arg Leu Phe Thr Gly Ser Gly Ser
        690                 695                 700
Thr Pro Met Val Phe Pro Leu Arg Pro Val Ile Glu Glu Leu Lys Glu
705                 710                 715                 720
Ser Ala Arg Glu Glu Cys Asp Ile Arg Thr Met Lys Met Cys Gln Gly
                725                 730                 735
Val Leu Lys Glu Ile Glu Ser Arg Ser Asp Asp Lys Tyr Val Ser Tyr
            740                 745                 750
Arg Lys Gly Leu Gly Val Val Cys Asn Lys Glu Gly Phe Gly Glu
            755                 760                 765
Glu Asp Phe Val Val Glu Phe Leu Gly Glu Tyr Pro Val Trp Lys
            770                 775                 780
Trp Phe Glu Lys Gln Asp Gly Ile Arg Ser Leu Gln Glu Asn Lys Thr
785                 790                 795                 800
Asp Pro Ala Pro Glu Phe Tyr Asn Ile Tyr Leu Glu Arg Pro Lys Gly
                805                 810                 815
Asp Ala Asp Gly Tyr Asp Leu Val Val Val Asp Ala Met His Met Ala
            820                 825                 830
```

```
Asn Tyr Ala Ser Arg Ile Cys His Ser Cys Arg Pro Asn Cys Glu Ala
        835                 840                 845

Lys Val Thr Ala Val Asp Gly His Tyr Gln Ile Gly Ile Tyr Ser Val
850                 855                 860

Arg Ala Ile Glu Tyr Gly Glu Ile Thr Phe Asp Tyr Asn Ser Val
865                 870                 875                 880

Thr Glu Ser Lys Glu Glu Tyr Glu Ala Ser Val Cys Leu Cys Gly Ser
                885                 890                 895

Gln Val Cys Arg Gly Ser Tyr Leu Asn Leu Thr Gly Glu Gly Ala Phe
            900                 905                 910

Gln Lys Val Leu Lys Asp Trp His Gly Leu Leu Glu Arg His Arg Leu
        915                 920                 925

Met Leu Glu Ala Cys Val Leu Asn Ser Val Ser Glu Glu Asp Tyr Leu
930                 935                 940

Glu Leu Gly Arg Ala Gly Leu Gly Ser Cys Leu Leu Gly Gly Leu Pro
945                 950                 955                 960

Asp Trp Met Ile Ala Tyr Ser Ala Arg Leu Val Arg Phe Ile Asn Phe
                965                 970                 975

Glu Arg Thr Lys Leu Pro Glu Glu Ile Leu Lys His Asn Leu Glu Glu
            980                 985                 990

Lys Arg Lys Tyr Phe Ser Asp Ile His Leu Asp Val Glu Lys Ser Asp
        995                 1000                1005

Ala Glu Val Gln Ala Glu Gly Val Tyr Asn Gln Arg Leu Gln Asn Leu
    1010                1015                1020

Ala Val Thr Leu Asp Lys Val Arg Tyr Val Met Arg His Val Phe Gly
1025                1030                1035                1040

Asp Pro Lys Asn Ala Pro Pro Leu Glu Arg Leu Thr Pro Glu Glu
                1045                1050                1055

Thr Val Ser Phe Val Trp Asn Gly Asp Gly Ser Leu Val Asp Glu Leu
            1060                1065                1070

Leu Gln Ser Leu Ser Pro His Leu Glu Glu Gly Pro Leu Asn Glu Leu
        1075                1080                1085

Arg Ser Lys Ile His Gly His Asp Pro Ser Gly Ser Ala Asp Val Leu
    1090                1095                1100

Lys Glu Leu Gln Arg Ser Leu Leu Trp Leu Arg Asp Glu Ile Arg Asp
1105                1110                1115                1120

Leu Pro Cys Thr Tyr Lys Cys Arg Asn Asp Ala Ala Ala Asp Leu Ile
                1125                1130                1135

His Ile Tyr Ala Tyr Thr Lys Cys Phe Phe Lys Val Arg Glu Tyr Gln
            1140                1145                1150

Ser Phe Ile Ser Ser Pro Val His Ile Ser Pro Leu Asp Leu Gly Ala
        1155                1160                1165

Lys Tyr Ala Asp Lys Leu Gly Glu Ser Ile Lys Glu Tyr Arg Lys Thr
    1170                1175                1180

Tyr Gly Glu Asn Tyr Cys Leu Gly Gln Leu Ile Tyr Trp Tyr Asn Gln
1185                1190                1195                1200

Thr Asn Thr Asp Pro Asp Leu Thr Leu Val Lys Ala Thr Arg Gly Cys
                1205                1210                1215

Leu Ser Leu Pro Asp Val Ala Ser Phe Tyr Ala Lys Ala Gln Lys Pro
            1220                1225                1230

Ser Lys His Arg Val Tyr Gly Pro Lys Thr Val Lys Thr Met Val Ser
        1235                1240                1245
```

```
Gln Met Ser Lys Gln Pro Gln Arg Pro Trp Pro Lys Asp Lys Ile Trp
    1250                1255                1260

Thr Phe Lys Ser Thr Pro Arg Val Phe Gly Ser Pro Met Phe Asp Ala
1265                1270                1275                1280

Val Leu Asn Asn Ser Ser Ser Leu Asp Arg Glu Leu Leu Gln Trp Leu
                1285                1290                1295

Arg Asn Arg Arg His Val Phe Gln Ala Thr Trp Asp Ser
            1300                1305
```

<210> SEQ ID NO 94
<211> LENGTH: 277
<212> TYPE: PRT
<213> ORGANISM: Artificial Sequence
<220> FEATURE:
<223> OTHER INFORMATION: Synthetic Construct

<400> SEQUENCE: 94

```
Met Gly Pro Asp Ile Val Met Thr Gln Ser Pro Ser Ser Leu Ser Ala
1               5                   10                  15

Ser Val Gly Asp Arg Val Thr Ile Thr Cys Arg Ser Ser Thr Gly Ala
                20                  25                  30

Val Thr Thr Ser Asn Tyr Ala Ser Trp Val Gln Glu Lys Pro Gly Lys
            35                  40                  45

Leu Phe Lys Gly Leu Ile Gly Gly Thr Asn Asn Arg Ala Pro Gly Val
50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
            100                 105                 110

Lys Arg Gly Gly Gly Gly Ser Gly Gly Gly Ser Gly Gly Gly Gly
            115                 120                 125

Ser Ser Gly Gly Gly Ser Glu Val Lys Leu Leu Glu Ser Gly Gly Gly
        130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
                165                 170                 175

Arg Gly Leu Glu Trp Ile Gly Val Ile Trp Gly Asp Gly Ile Thr Asp
            180                 185                 190

Tyr Asn Ser Ala Leu Lys Asp Arg Phe Ile Ile Ser Lys Asp Asn Gly
        195                 200                 205

Lys Asn Thr Val Tyr Leu Gln Met Ser Lys Val Arg Ser Asp Asp Thr
210                 215                 220

Ala Leu Tyr Tyr Cys Val Thr Gly Leu Phe Asp Tyr Trp Gly Gln Gly
225                 230                 235                 240

Thr Leu Val Thr Val Ser Ser Tyr Pro Tyr Asp Val Pro Asp Tyr Ala
                245                 250                 255

Gly Gly Gly Gly Gly Ser Gly Gly Gly Gly Ser Gly Gly Gly Gly Ser
            260                 265                 270

Gly Gly Gly Gly Ser
            275
```

<210> SEQ ID NO 95
<211> LENGTH: 237

```
<212> TYPE: PRT
<213> ORGANISM: Artificial Sequence
<220> FEATURE:
<223> OTHER INFORMATION: Synthetic Construct

<400> SEQUENCE: 95

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Arg Gly Glu Gly
            20                  25                  30

Glu Gly Asp Ala Thr Asn Gly Lys Leu Thr Leu Lys Phe Ile Cys Thr
        35                  40                  45

Thr Gly Lys Leu Pro Val Pro Trp Pro Thr Leu Val Thr Thr Leu Thr
50                  55                  60

Tyr Gly Val Gln Cys Phe Ser Arg Tyr Pro Asp His Met Lys Arg His
65                  70                  75                  80

Asp Phe Phe Lys Ser Ala Met Pro Glu Gly Tyr Val Gln Glu Arg Thr
                85                  90                  95

Ile Ser Phe Lys Asp Asp Gly Thr Tyr Lys Thr Arg Ala Glu Val Lys
            100                 105                 110

Phe Glu Gly Asp Thr Leu Val Asn Arg Ile Glu Leu Lys Gly Ile Asp
        115                 120                 125

Phe Lys Glu Asp Gly Asn Ile Leu Gly His Lys Leu Glu Tyr Asn Phe
130                 135                 140

Asn Ser His Asn Val Tyr Ile Thr Ala Asp Lys Gln Lys Asn Gly Ile
145                 150                 155                 160

Lys Ala Asn Phe Lys Ile Arg His Asn Val Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Val Leu Ser Lys
        195                 200                 205

Asp Pro Asn Glu Lys Arg Asp His Met Val Leu Leu Glu Phe Val Thr
210                 215                 220

Ala Ala Gly Ile Thr His Gly Met Asp Glu Leu Tyr Lys
225                 230                 235

<210> SEQ ID NO 96
<211> LENGTH: 8
<212> TYPE: PRT
<213> ORGANISM: Artificial Sequence
<220> FEATURE:
<223> OTHER INFORMATION: Synthetic Construct

<400> SEQUENCE: 96

Ala Pro Lys Lys Lys Arg Lys Val
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic Construct

<400> SEQUENCE: 97

Gly Gly Gly Gly Gly
1               5
```

<210> SEQ ID NO 98
<211> LENGTH: 765
<212> TYPE: PRT
<213> ORGANISM: Artificial Sequence
<220> FEATURE:
<223> OTHER INFORMATION: Synthetic Construct

<400> SEQUENCE: 98

```
Gly Arg Ser Gln Asp Leu Arg Ile Glu Lys Tyr Phe Thr Ala Asp Asp
1               5                   10                  15

Ser Phe Asp Ser Val Thr Glu Glu Arg Glu Trp Gly Ala Arg Met Thr
            20                  25                  30

Lys Ala Ser Leu Val Pro Pro Val Thr Arg Lys Tyr Glu Val Ile Glu
        35                  40                  45

Lys Tyr Ala Ile Val Ala Asp Glu Glu Val Gln Arg Lys Met Arg
    50                  55                  60

Val Ser Leu Pro Glu Asp Tyr Gly Glu Lys Leu Asn Ala Gln Arg Asn
65                  70                  75                  80

Gly Ile Glu Glu Leu Asp Met Glu Leu Pro Glu Val Lys Glu Tyr Lys
                85                  90                  95

Pro Arg Lys Leu Leu Gly Asp Glu Val Leu Glu Gln Glu Val Tyr Gly
            100                 105                 110

Ile Asp Pro Tyr Thr His Asn Leu Leu Leu Asp Ser Met Pro Gly Glu
        115                 120                 125

Leu Asp Trp Ser Leu Gln Asp Lys His Ser Phe Ile Glu Asp Val Val
    130                 135                 140

Leu Arg Thr Leu Asn Arg Gln Val Arg Leu Phe Thr Gly Ser Gly Ser
145                 150                 155                 160

Thr Pro Met Val Phe Pro Leu Arg Pro Val Ile Glu Glu Leu Lys Glu
                165                 170                 175

Ser Ala Arg Glu Glu Cys Asp Ile Arg Thr Met Lys Met Cys Gln Gly
            180                 185                 190

Val Leu Lys Glu Ile Glu Ser Arg Ser Asp Asp Lys Tyr Val Ser Tyr
        195                 200                 205

Arg Lys Gly Leu Gly Val Val Cys Asn Lys Glu Gly Gly Phe Gly Glu
    210                 215                 220

Glu Asp Phe Val Val Glu Phe Leu Gly Glu Val Tyr Pro Val Trp Lys
225                 230                 235                 240

Trp Phe Glu Lys Gln Asp Gly Ile Arg Ser Leu Gln Glu Asn Lys Thr
                245                 250                 255

Asp Pro Ala Pro Glu Phe Tyr Asn Ile Tyr Leu Glu Arg Pro Lys Gly
            260                 265                 270

Asp Ala Asp Gly Tyr Asp Leu Val Val Val Asp Ala Met His Met Ala
        275                 280                 285

Asn Tyr Ala Ser Arg Ile Cys His Ser Cys Arg Pro Asn Cys Glu Ala
    290                 295                 300

Lys Val Thr Ala Val Asp Gly His Tyr Gln Ile Gly Ile Tyr Ser Val
305                 310                 315                 320

Arg Ala Ile Glu Tyr Gly Glu Glu Ile Thr Phe Asp Tyr Asn Ser Val
                325                 330                 335

Thr Glu Ser Lys Glu Glu Tyr Glu Ala Ser Val Cys Leu Cys Gly Ser
            340                 345                 350

Gln Val Cys Arg Gly Ser Tyr Leu Asn Leu Thr Gly Glu Gly Ala Phe
        355                 360                 365

Gln Lys Val Leu Lys Asp Trp His Gly Leu Leu Glu Arg His Arg Leu
```

```
                370                 375                 380
Met Leu Glu Ala Cys Val Leu Asn Ser Val Ser Glu Asp Tyr Leu
385                 390                 395                 400

Glu Leu Gly Arg Ala Gly Leu Gly Ser Cys Leu Leu Gly Gly Leu Pro
                405                 410                 415

Asp Trp Met Ile Ala Tyr Ser Ala Arg Leu Val Arg Phe Ile Asn Phe
                420                 425                 430

Glu Arg Thr Lys Leu Pro Glu Glu Ile Leu Lys His Asn Leu Glu Glu
                435                 440                 445

Lys Arg Lys Tyr Phe Ser Asp Ile His Leu Asp Val Glu Lys Ser Asp
450                 455                 460

Ala Glu Val Gln Ala Glu Gly Val Tyr Asn Gln Arg Leu Gln Asn Leu
465                 470                 475                 480

Ala Val Thr Leu Asp Lys Val Arg Tyr Val Met Arg His Val Phe Gly
                485                 490                 495

Asp Pro Lys Asn Ala Pro Pro Leu Glu Arg Leu Thr Pro Glu Glu
                500                 505                 510

Thr Val Ser Phe Val Trp Asn Gly Asp Gly Ser Leu Val Asp Glu Leu
                515                 520                 525

Leu Gln Ser Leu Ser Pro His Leu Glu Glu Gly Pro Leu Asn Glu Leu
530                 535                 540

Arg Ser Lys Ile His Gly His Asp Pro Ser Gly Ser Ala Asp Val Leu
545                 550                 555                 560

Lys Glu Leu Gln Arg Ser Leu Leu Trp Leu Arg Asp Glu Ile Arg Asp
                565                 570                 575

Leu Pro Cys Thr Tyr Lys Cys Arg Asn Asp Ala Ala Ala Asp Leu Ile
                580                 585                 590

His Ile Tyr Ala Tyr Thr Lys Cys Phe Phe Lys Val Arg Glu Tyr Gln
                595                 600                 605

Ser Phe Ile Ser Ser Pro Val His Ile Ser Pro Leu Asp Leu Gly Ala
                610                 615                 620

Lys Tyr Ala Asp Lys Leu Gly Glu Ser Ile Lys Glu Tyr Arg Lys Thr
625                 630                 635                 640

Tyr Gly Glu Asn Tyr Cys Leu Gly Gln Leu Ile Tyr Trp Tyr Asn Gln
                645                 650                 655

Thr Asn Thr Asp Pro Asp Leu Thr Leu Val Lys Ala Thr Arg Gly Cys
                660                 665                 670

Leu Ser Leu Pro Asp Val Ala Ser Phe Tyr Ala Lys Ala Gln Lys Pro
                675                 680                 685

Ser Lys His Arg Val Tyr Gly Pro Lys Thr Val Lys Thr Met Val Ser
                690                 695                 700

Gln Met Ser Lys Gln Pro Gln Arg Pro Trp Pro Lys Asp Lys Ile Trp
705                 710                 715                 720

Thr Phe Lys Ser Thr Pro Arg Val Phe Gly Ser Pro Met Phe Asp Ala
                725                 730                 735

Val Leu Asn Asn Ser Ser Ser Leu Asp Arg Glu Leu Leu Gln Trp Leu
                740                 745                 750

Arg Asn Arg Arg His Val Phe Gln Ala Thr Trp Asp Ser
                755                 760                 765

<210> SEQ ID NO 99
<211> LENGTH: 553
<212> TYPE: DNA
<213> ORGANISM: Artificial Sequence
```

<220> FEATURE:
<223> OTHER INFORMATION: Synthetic Construct

<400> SEQUENCE: 99

| | | | | | |
|---|---|---|---|---|---|
| aagctttcgt | tgaacaacgg | aaactcgact | tgccttccgc | acaatacatc | atttcttctt | 60 |
| agcttttttt | cttcttcttc | gttcatacag | ttttttttg | tttatcagct | tacatttct | 120 |
| tgaaccgtag | ctttcgtttt | cttctttta | actttccatt | cggagttttt | gtatcttgtt | 180 |
| tcatagtttg | tcccaggatt | agaatgatta | ggcatcgaac | cttcaagaat | ttgattgaat | 240 |
| aaaacatctt | cattcttaag | atatgaagat | aatcttcaaa | aggcccctgg | gaatctgaaa | 300 |
| gaagagaagc | aggcccattt | atatgggaaa | gaacaatagt | atttcttata | taggcccatt | 360 |
| taagttgaaa | acaatcttca | aaagtcccac | atcgcttaga | taagaaaacg | aagctgagtt | 420 |
| tatatacagc | tagagtcgaa | gtagtgattg | acggaaagat | gtatgggctt | gttttagagc | 480 |
| tagaaatagc | aagttaaaat | aaggctagtc | cgttatcaac | ttgaaaaagt | ggcaccgagt | 540 |
| cggtgctttt | ttt | | | | | 553 |

<210> SEQ ID NO 100
<211> LENGTH: 450
<212> TYPE: DNA
<213> ORGANISM: Artificial Sequence
<220> FEATURE:
<223> OTHER INFORMATION: Synthetic Construct

<400> SEQUENCE: 100

| | | | | | |
|---|---|---|---|---|---|
| aagctttcgt | tgaacaacgg | aaactcgact | tgccttccgc | acaatacatc | atttcttctt | 60 |
| agcttttttt | cttcttcttc | gttcatacag | ttttttttg | tttatcagct | tacatttct | 120 |
| tgaaccgtag | ctttcgtttt | cttctttta | actttccatt | cggagttttt | gtatcttgtt | 180 |
| tcatagtttg | tcccaggatt | agaatgatta | ggcatcgaac | cttcaagaat | ttgattgaat | 240 |
| aaaacatctt | cattcttaag | atatgaagat | aatcttcaaa | aggcccctgg | gaatctgaaa | 300 |
| gaagagaagc | aggcccattt | atatgggaaa | gaacaatagt | atttcttata | taggcccatt | 360 |
| taagttgaaa | acaatcttca | aaagtcccac | atcgcttaga | taagaaaacg | aagctgagtt | 420 |
| tatatacagc | tagagtcgaa | gtagtgattg | | | | 450 |

<210> SEQ ID NO 101
<211> LENGTH: 20
<212> TYPE: DNA
<213> ORGANISM: Artificial Sequence
<220> FEATURE:
<223> OTHER INFORMATION: Synthetic Construct

<400> SEQUENCE: 101
acggaaagat gtatgggctt    20

<210> SEQ ID NO 102
<211> LENGTH: 76
<212> TYPE: DNA
<213> ORGANISM: Artificial Sequence
<220> FEATURE:
<223> OTHER INFORMATION: Synthetic Construct

<400> SEQUENCE: 102

| | | | | | |
|---|---|---|---|---|---|
| gttttagagc | tagaaatagc | aagttaaaat | aaggctagtc | cgttatcaac | ttgaaaaagt | 60 |
| ggcaccgagt | cggtgc | | | | | 76 |

<210> SEQ ID NO 103

-continued

```
<211> LENGTH: 7
<212> TYPE: DNA
<213> ORGANISM: Artificial Sequence
<220> FEATURE:
<223> OTHER INFORMATION: Synthetic Construct

<400> SEQUENCE: 103 ttttttt                                                                7

<210> SEQ ID NO 104
<211> LENGTH: 2335
<212> TYPE: PRT
<213> ORGANISM: Arabidopsis thaliana

<400> SEQUENCE: 104
```

| Met | Ser | Asp | Gly | Gly | Val | Ala | Cys | Met | Pro | Leu | Leu | Asn | Ile | Met | Glu |
|---|---|---|---|---|---|---|---|---|---|---|---|---|---|---|---|
| 1 | | | | 5 | | | | | 10 | | | | | 15 | |

| Lys | Leu | Pro | Ile | Val | Glu | Lys | Thr | Thr | Leu | Cys | Gly | Gly | Asn | Glu | Ser |
| | | | 20 | | | | | 25 | | | | | 30 | | |

| Lys | Thr | Ala | Ala | Thr | Thr | Glu | Asn | Gly | His | Thr | Ser | Ile | Ala | Thr | Lys |
| | | 35 | | | | | 40 | | | | | 45 | | | |

| Val | Pro | Glu | Ser | Gln | Pro | Ala | Asn | Lys | Pro | Ser | Ala | Ser | Ser | Gln | Pro |
| 50 | | | | | 55 | | | | | 60 | | | | | |

| Val | Lys | Lys | Lys | Arg | Ile | Val | Lys | Val | Ile | Arg | Lys | Val | Val | Lys | Arg |
| 65 | | | | | 70 | | | | 75 | | | | | 80 | |

| Arg | Pro | Lys | Gln | Pro | Gln | Lys | Gln | Ala | Asp | Glu | Gln | Leu | Lys | Asp | Gln |
| | | | | 85 | | | | | 90 | | | | | 95 | |

| Pro | Pro | Ser | Gln | Val | Val | Gln | Leu | Pro | Ala | Glu | Ser | Gln | Leu | Gln | Ile |
| | | | 100 | | | | | 105 | | | | | 110 | | |

| Lys | Glu | Gln | Asp | Lys | Lys | Ser | Glu | Phe | Lys | Gly | Gly | Thr | Ser | Gly | Val |
| | | | 115 | | | | | 120 | | | | | 125 | | |

| Lys | Glu | Val | Glu | Asn | Gly | Gly | Asp | Ser | Gly | Phe | Lys | Asp | Glu | Val | Glu |
| | 130 | | | | | 135 | | | | | 140 | | | | |

| Glu | Gly | Glu | Leu | Gly | Thr | Leu | Lys | Leu | His | Glu | Asp | Leu | Glu | Asn | Gly |
| 145 | | | | | 150 | | | | | 155 | | | | | 160 |

| Glu | Ile | Ser | Pro | Val | Lys | Ser | Leu | Gln | Lys | Ser | Glu | Ile | Glu | Lys | Gly |
| | | | | 165 | | | | | 170 | | | | | 175 | |

| Glu | Ile | Val | Gly | Glu | Ser | Trp | Lys | Lys | Asp | Glu | Pro | Thr | Lys | Gly | Glu |
| | | | 180 | | | | | 185 | | | | | 190 | | |

| Phe | Ser | His | Leu | Lys | Tyr | His | Lys | Gly | Tyr | Val | Glu | Arg | Arg | Asp | Phe |
| | | | 195 | | | | | 200 | | | | | 205 | | |

| Ser | Ala | Asp | Lys | Asn | Trp | Lys | Gly | Gly | Lys | Glu | Glu | Arg | Glu | Phe | Arg |
| | 210 | | | | | 215 | | | | | 220 | | | | |

| Ser | Trp | Arg | Asp | Pro | Ser | Asp | Glu | Ile | Glu | Lys | Gly | Glu | Phe | Ile | Pro |
| 225 | | | | | 230 | | | | | 235 | | | | | 240 |

| Asp | Arg | Trp | Gln | Lys | Met | Asp | Thr | Gly | Lys | Asp | Asp | His | Ser | Tyr | Ile |
| | | | | 245 | | | | | 250 | | | | | 255 | |

| Arg | Ser | Arg | Arg | Asn | Gly | Val | Arg | Glu | Lys | Thr | Trp | Lys | Tyr | Glu |
| | | | 260 | | | | | 265 | | | | | 270 | | |

| Tyr | Glu | Tyr | Glu | Arg | Thr | Pro | Pro | Gly | Gly | Arg | Phe | Val | Asn | Glu | Asp |
| | | | 275 | | | | | 280 | | | | | 285 | | |

| Ile | Tyr | His | Gln | Arg | Glu | Phe | Arg | Ser | Gly | Leu | Asp | Arg | Thr | Thr | Arg |
| | 290 | | | | | 295 | | | | | 300 | | | | |

| Ile | Ser | Ser | Lys | Ile | Val | Ile | Glu | Glu | Asn | Leu | His | Lys | Asn | Glu | Tyr |
| 305 | | | | | 310 | | | | | 315 | | | | | 320 |

| Asn | Asn | Ser | Ser | Asn | Phe | Val | Lys | Glu | Tyr | Ser | Ser | Thr | Gly | Asn | Arg |

```
            325                 330                 335
Leu Lys Arg His Gly Ala Glu Pro Asp Ser Ile Glu Arg Lys His Ser
        340                 345                 350
Tyr Ala Asp Tyr Gly Asp Tyr Gly Ser Ser Lys Cys Arg Lys Leu Ser
            355                 360                 365
Asp Asp Cys Ser Arg Ser Leu His Ser Asp His Tyr Ser Gln His Ser
        370                 375                 380
Ala Glu Arg Leu Tyr Arg Asp Ser Tyr Pro Ser Lys Asn Ser Ser Leu
385                 390                 395                 400
Glu Lys Tyr Pro Arg Lys His Gln Asp Ala Ser Phe Pro Ala Lys Ala
                405                 410                 415
Phe Ser Asp Lys His Gly His Ser Pro Ser Arg Ser Asp Trp Ser Pro
            420                 425                 430
His Asp Arg Ser Arg Tyr His Glu Asn Arg Asp Arg Ser Pro Tyr Ala
                435                 440                 445
Arg Glu Arg Ser Pro Tyr Ile Phe Glu Lys Ser His Ala Arg Lys
        450                 455                 460
Arg Ser Pro Arg Asp Arg Arg His His Asp Tyr Arg Arg Ser Pro Ser
465                 470                 475                 480
Tyr Ser Glu Trp Ser Pro His Asp Arg Ser Arg Pro Ser Asp Arg Arg
                485                 490                 495
Asp Tyr Ile Pro Asn Phe Met Glu Asp Thr Gln Ser Arg Asn Arg
            500                 505                 510
Arg Asn Gly His Arg Glu Ile Ser Arg Lys Ser Gly Val Arg Glu Arg
        515                 520                 525
Arg Asp Cys Gln Thr Gly Thr Glu Leu Glu Ile Lys His Lys Tyr Lys
    530                 535                 540
Glu Ser Asn Gly Lys Glu Ser Thr Ser Ser Ser Lys Glu Leu Gln Gly
545                 550                 555                 560
Lys Asn Ile Leu Tyr Asn Asn Ser Leu Leu Val Glu Lys Asn Ser Val
                565                 570                 575
Cys Asp Ser Ser Lys Ile Pro Val Pro Cys Ala Thr Gly Lys Glu Pro
            580                 585                 590
Val Gln Val Gly Glu Ala Pro Thr Glu Glu Leu Pro Ser Met Glu Val
        595                 600                 605
Asp Met Asp Ile Cys Asp Thr Pro Pro His Glu Pro Met Ala Ser Asp
    610                 615                 620
Ser Ser Leu Gly Lys Trp Phe Tyr Leu Asp Tyr Tyr Gly Thr Glu His
625                 630                 635                 640
Gly Pro Ala Arg Leu Ser Asp Leu Lys Ala Leu Met Glu Gln Gly Ile
                645                 650                 655
Leu Phe Ser Asp His Met Ile Lys His Ser Asp Asn Asn Arg Trp Leu
            660                 665                 670
Val Asn Pro Pro Glu Ala Pro Gly Asn Leu Leu Glu Asp Ile Ala Asp
        675                 680                 685
Thr Thr Glu Ala Val Cys Ile Glu Gln Gly Ala Gly Asp Ser Leu Pro
    690                 695                 700
Glu Leu Val Ser Val Arg Thr Leu Pro Asp Gly Lys Glu Ile Phe Val
705                 710                 715                 720
Glu Asn Arg Glu Asp Phe Gln Ile Asp Met Arg Val Glu Asn Leu Leu
                725                 730                 735
Asp Gly Arg Thr Ile Thr Pro Gly Arg Glu Phe Glu Thr Leu Gly Glu
            740                 745                 750
```

```
Ala Leu Lys Val Asn Val Glu Phe Glu Glu Thr Arg Arg Cys Val Thr
            755                 760                 765

Ser Glu Gly Val Val Gly Met Phe Arg Pro Met Lys Arg Ala Ile Glu
    770                 775                 780

Glu Phe Lys Ser Asp Asp Ala Tyr Gly Ser Glu Ser Asp Glu Ile Gly
785                 790                 795                 800

Ser Trp Phe Ser Gly Arg Trp Ser Cys Lys Gly Gly Asp Trp Ile Arg
                805                 810                 815

Gln Asp Glu Ala Ser Gln Asp Arg Tyr Tyr Lys Lys Ile Val Leu
            820                 825                 830

Asn Asp Gly Phe Pro Leu Cys Leu Met Gln Lys Ser Gly His Glu Asp
                835                 840                 845

Pro Arg Trp His His Lys Asp Asp Leu Tyr Tyr Pro Leu Ser Ser Ser
            850                 855                 860

Arg Leu Glu Leu Pro Leu Trp Ala Phe Ser Val Val Asp Glu Arg Asn
865                 870                 875                 880

Gln Thr Arg Gly Val Lys Ala Ser Leu Leu Ser Val Val Arg Leu Asn
                885                 890                 895

Ser Leu Val Val Asn Asp Gln Val Pro Pro Ile Pro Asp Pro Arg Ala
            900                 905                 910

Lys Val Arg Ser Lys Glu Arg Cys Pro Ser Arg Pro Ala Arg Pro Ser
                915                 920                 925

Pro Ala Ser Ser Asp Ser Lys Arg Glu Ser Val Glu Ser His Ser Gln
            930                 935                 940

Ser Thr Ala Ser Thr Gly Gln Asp Ser Gln Gly Leu Trp Lys Thr Asp
945                 950                 955                 960

Thr Ser Val Asn Thr Pro Arg Asp Arg Leu Cys Thr Val Asp Asp Leu
                965                 970                 975

Gln Leu His Ile Gly Asp Trp Phe Tyr Thr Asp Gly Ala Gly Gln Glu
            980                 985                 990

Gln Gly Pro Leu Ser Phe Ser Glu Leu Gln Lys Leu Val Glu Lys Gly
        995                 1000                1005

Phe Ile Lys Ser His Ser Ser Val Phe Arg Lys Ser Asp Lys Ile Trp
    1010                1015                1020

Val Pro Val Thr Ser Ile Thr Lys Ser Pro Glu Thr Ile Ala Met Leu
1025                1030                1035                1040

Arg Gly Lys Thr Pro Ala Leu Pro Ser Ala Cys Gln Gly Leu Val Val
                1045                1050                1055

Ser Glu Thr Gln Asp Phe Lys Tyr Ser Glu Met Asp Thr Ser Leu Asn
            1060                1065                1070

Ser Phe His Gly Val His Pro Gln Phe Leu Gly Tyr Phe Arg Gly Lys
        1075                1080                1085

Leu His Gln Leu Val Met Lys Thr Phe Lys Ser Arg Asp Phe Ser Ala
    1090                1095                1100

Ala Ile Asn Asp Val Val Asp Ser Trp Ile His Ala Arg Gln Pro Lys
1105                1110                1115                1120

Lys Glu Ser Glu Lys Tyr Met Tyr Gln Ser Ser Glu Leu Asn Ser Cys
                1125                1130                1135

Tyr Thr Lys Arg Ala Arg Leu Met Ala Gly Glu Ser Gly Glu Asp Ser
            1140                1145                1150

Glu Met Glu Asp Thr Gln Met Phe Gln Lys Asp Glu Leu Thr Phe Glu
        1155                1160                1165
```

-continued

```
Asp Leu Cys Gly Asp Leu Thr Phe Asn Ile Glu Gly Asn Arg Ser Ala
1170                1175                1180

Gly Thr Val Gly Ile Tyr Trp Gly Leu Asp Gly His Ala Leu Ala
1185                1190                1195                1200

Arg Val Phe His Met Leu Arg Tyr Asp Val Lys Ser Leu Ala Phe Ala
                1205                1210                1215

Ser Met Thr Cys Arg His Trp Lys Ala Thr Ile Asn Ser Tyr Lys Asp
                1220                1225                1230

Ile Ser Arg Gln Val Asp Leu Ser Ser Leu Gly Pro Ser Cys Thr Asp
                1235                1240                1245

Ser Arg Leu Arg Ser Ile Met Asn Thr Tyr Asn Lys Glu Lys Ile Asp
1250                1255                1260

Ser Ile Ile Leu Val Gly Cys Thr Asn Val Thr Ala Ser Met Leu Glu
1265                1270                1275                1280

Glu Ile Leu Arg Leu His Pro Arg Ile Ser Ser Val Asp Ile Thr Gly
                1285                1290                1295

Cys Ser Gln Phe Gly Asp Leu Thr Val Asn Tyr Lys Asn Val Ser Trp
                1300                1305                1310

Leu Arg Cys Gln Asn Thr Arg Ser Gly Glu Leu His Ser Arg Ile Arg
                1315                1320                1325

Ser Leu Lys Gln Thr Thr Asp Val Ala Lys Ser Lys Gly Leu Gly Gly
                1330                1335                1340

Asp Thr Asp Asp Phe Gly Asn Leu Lys Asp Tyr Phe Asp Arg Val Glu
1345                1350                1355                1360

Lys Arg Asp Ser Ala Asn Gln Leu Phe Arg Arg Ser Leu Tyr Lys Arg
                1365                1370                1375

Ser Lys Leu Tyr Asp Ala Arg Arg Ser Ser Ala Ile Leu Ser Arg Asp
                1380                1385                1390

Ala Arg Ile Arg Arg Trp Ala Ile Lys Lys Ser Glu His Gly Tyr Lys
                1395                1400                1405

Arg Val Glu Glu Phe Leu Ala Ser Ser Leu Arg Gly Ile Met Lys Gln
                1410                1415                1420

Asn Thr Phe Asp Phe Phe Ala Leu Lys Val Ser Gln Ile Glu Glu Lys
1425                1430                1435                1440

Met Lys Asn Gly Tyr Tyr Val Ser His Gly Leu Arg Ser Val Lys Glu
                1445                1450                1455

Asp Ile Ser Arg Met Cys Arg Glu Ala Ile Lys Asp Glu Leu Met Lys
                1460                1465                1470

Ser Trp Gln Asp Gly Ser Gly Leu Ser Ser Ala Thr Lys Tyr Asn Lys
                1475                1480                1485

Lys Leu Ser Lys Thr Val Ala Glu Lys Lys Tyr Met Ser Arg Thr Ser
                1490                1495                1500

Asp Thr Phe Gly Val Asn Gly Ala Ser Asp Tyr Gly Glu Tyr Ala Ser
1505                1510                1515                1520

Asp Arg Glu Ile Lys Arg Arg Leu Ser Lys Leu Asn Arg Lys Ser Phe
                1525                1530                1535

Ser Ser Glu Ser Asp Thr Ser Ser Glu Leu Ser Asp Asn Gly Lys Ser
                1540                1545                1550

Asp Asn Tyr Ser Ser Ala Ser Ala Ser Glu Ser Glu Ser Asp Ile Arg
                1555                1560                1565

Ser Glu Gly Arg Ser Gln Asp Leu Arg Ile Glu Lys Tyr Phe Thr Ala
                1570                1575                1580

Asp Asp Ser Phe Asp Ser Val Thr Glu Glu Arg Glu Trp Gly Ala Arg
```

```
            1585                1590                1595                1600
Met Thr Lys Ala Ser Leu Val Pro Pro Val Thr Arg Lys Tyr Glu Val
                1605                1610                1615

Ile Glu Lys Tyr Ala Ile Val Ala Asp Glu Glu Val Gln Arg Lys
        1620                1625                1630

Met Arg Val Ser Leu Pro Glu Asp Tyr Gly Lys Leu Asn Ala Gln
        1635                1640                1645

Arg Asn Gly Ile Glu Glu Leu Asp Met Glu Leu Pro Glu Val Lys Glu
    1650                1655                1660

Tyr Lys Pro Arg Lys Leu Leu Gly Asp Glu Val Leu Glu Gln Glu Val
1665                1670                1675                1680

Tyr Gly Ile Asp Pro Tyr Thr His Asn Leu Leu Asp Ser Met Pro
                1685                1690                1695

Gly Glu Leu Asp Trp Ser Leu Gln Asp Lys His Ser Phe Ile Glu Asp
            1700                1705                1710

Val Val Leu Arg Thr Leu Asn Arg Gln Val Arg Leu Phe Thr Gly Ser
        1715                1720                1725

Gly Ser Thr Pro Met Val Phe Pro Leu Arg Pro Val Ile Glu Glu Leu
            1730                1735                1740

Lys Glu Ser Ala Arg Glu Glu Cys Asp Ile Arg Thr Met Lys Met Cys
1745                1750                1755                1760

Gln Gly Val Leu Lys Glu Ile Glu Ser Arg Ser Asp Asp Lys Tyr Val
            1765                1770                1775

Ser Tyr Arg Lys Gly Leu Gly Val Val Cys Asn Lys Glu Gly Gly Phe
                1780                1785                1790

Gly Glu Glu Asp Phe Val Val Glu Phe Leu Gly Glu Val Tyr Pro Val
            1795                1800                1805

Trp Lys Trp Phe Glu Lys Gln Asp Gly Ile Arg Ser Leu Gln Glu Asn
            1810                1815                1820

Lys Thr Asp Pro Ala Pro Glu Phe Tyr Asn Ile Tyr Leu Glu Arg Pro
1825                1830                1835                1840

Lys Gly Asp Ala Asp Gly Tyr Asp Leu Val Val Val Asp Ala Met His
                1845                1850                1855

Met Ala Asn Tyr Ala Ser Arg Ile Cys His Ser Cys Arg Pro Asn Cys
                1860                1865                1870

Glu Ala Lys Val Thr Ala Val Asp Gly His Tyr Gln Ile Gly Ile Tyr
            1875                1880                1885

Ser Val Arg Ala Ile Glu Tyr Gly Glu Glu Ile Thr Phe Asp Tyr Asn
        1890                1895                1900

Ser Val Thr Glu Ser Lys Glu Glu Tyr Glu Ala Ser Val Cys Leu Cys
1905                1910                1915                1920

Gly Ser Gln Val Cys Arg Gly Ser Tyr Leu Asn Leu Thr Gly Glu Gly
            1925                1930                1935

Ala Phe Gln Lys Val Leu Lys Asp Trp His Gly Leu Leu Glu Arg His
                1940                1945                1950

Arg Leu Met Leu Glu Ala Cys Val Leu Asn Ser Val Ser Glu Glu Asp
        1955                1960                1965

Tyr Leu Glu Leu Gly Arg Ala Gly Leu Gly Ser Cys Leu Leu Gly Gly
    1970                1975                1980

Leu Pro Asp Trp Met Ile Ala Tyr Ser Ala Arg Leu Val Arg Phe Ile
1985                1990                1995                2000

Asn Phe Glu Arg Thr Lys Leu Pro Glu Glu Ile Leu Lys His Asn Leu
            2005                2010                2015
```

-continued

Glu Glu Lys Arg Lys Tyr Phe Ser Asp Ile His Leu Asp Val Glu Lys
                2020                2025                2030

Ser Asp Ala Glu Val Gln Ala Glu Gly Val Tyr Asn Gln Arg Leu Gln
            2035                2040                2045

Asn Leu Ala Val Thr Leu Asp Lys Val Arg Tyr Val Met Arg His Val
2050                2055                2060

Phe Gly Asp Pro Lys Asn Ala Pro Pro Leu Glu Arg Leu Thr Pro
2065                2070                2075                2080

Glu Glu Thr Val Ser Phe Val Trp Asn Gly Asp Gly Ser Leu Val Asp
                2085                2090                2095

Glu Leu Leu Gln Ser Leu Ser Pro His Leu Glu Glu Gly Pro Leu Asn
            2100                2105                2110

Glu Leu Arg Ser Lys Ile His Gly His Asp Pro Ser Gly Ser Ala Asp
            2115                2120                2125

Val Leu Lys Glu Leu Gln Arg Ser Leu Leu Trp Leu Arg Asp Glu Ile
2130                2135                2140

Arg Asp Leu Pro Cys Thr Tyr Lys Cys Arg Asn Asp Ala Ala Ala Asp
2145                2150                2155                2160

Leu Ile His Ile Tyr Ala Tyr Thr Lys Cys Phe Phe Lys Val Arg Glu
                2165                2170                2175

Tyr Gln Ser Phe Ile Ser Ser Pro Val His Ile Ser Pro Leu Asp Leu
                2180                2185                2190

Gly Ala Lys Tyr Ala Asp Lys Leu Gly Glu Ser Ile Lys Glu Tyr Arg
            2195                2200                2205

Lys Thr Tyr Gly Glu Asn Tyr Cys Leu Gly Gln Leu Ile Tyr Trp Tyr
            2210                2215                2220

Asn Gln Thr Asn Thr Asp Pro Asp Leu Thr Leu Val Lys Ala Thr Arg
2225                2230                2235                2240

Gly Cys Leu Ser Leu Pro Asp Val Ala Ser Phe Tyr Ala Lys Ala Gln
                2245                2250                2255

Lys Pro Ser Lys His Arg Val Tyr Gly Pro Lys Thr Val Lys Thr Met
            2260                2265                2270

Val Ser Gln Met Ser Lys Gln Pro Gln Arg Pro Trp Pro Lys Asp Lys
            2275                2280                2285

Ile Trp Thr Phe Lys Ser Thr Pro Arg Val Phe Gly Ser Pro Met Phe
            2290                2295                2300

Asp Ala Val Leu Asn Asn Ser Ser Leu Asp Arg Glu Leu Leu Gln
2305                2310                2315                2320

Trp Leu Arg Asn Arg Arg His Val Phe Gln Ala Thr Trp Asp Ser
                2325                2330                2335

<210> SEQ ID NO 105
<211> LENGTH: 2394
<212> TYPE: PRT
<213> ORGANISM: Glycine max

<400> SEQUENCE: 105

Met Gly Asp Gly Gly Val Ala Cys Met Pro Leu Gln Gln Gln His Val
1               5                   10                  15

Ile Glu Arg Leu Pro Asn Ala Ala Glu Lys Ala Leu Cys Gly Gly
                20                  25                  30

Lys Ser Gly Asn Gly Phe Asp Ser Gly Leu Leu Lys Val Ala Gly Lys
            35                  40                  45

Arg Lys Lys Lys Val Lys Val Lys Lys Val Ser Pro Ala Ala Lys

-continued

```
            50                  55                  60
Lys Val Lys Ser Glu Leu Thr Val Asp Gly Val Gly Ser Arg Gly
65                  70                  75                  80

Gly Asn Asp Val Glu Ser Gly Glu Val Cys Gly Glu Met Asp Glu Val
                85                  90                  95

Glu Glu Gly Glu Leu Gly Thr Leu Gly Cys Glu Leu Glu Asn Gly Glu
            100                 105                 110

Phe Val Pro Glu Lys Pro Val Met Leu Met Arg Arg Ser Glu Ile Glu
            115                 120                 125

Asn Gly Glu Ile Val Ser Glu Arg Trp Lys Lys Gly Glu Val Glu Arg
            130                 135                 140

Gly Glu Phe Val Ser Gly Lys Trp Arg Lys Glu Glu Asp Val Glu Lys
145                 150                 155                 160

Gly Glu Ile Val Pro Glu Lys Gly Arg Lys Gly Glu Thr Glu Lys Trp
            165                 170                 175

Glu Tyr Gly Ser Trp Arg Gly Gly Met Lys Asp Asp Ile Glu Lys Gly
            180                 185                 190

Glu Phe Ile Pro Asp Arg Trp His Arg Gly Asp Met Gly Arg Asp Asp
            195                 200                 205

Tyr Gly Tyr Ala Arg Ile Arg Arg Tyr Gln Pro Gly Arg Asp Lys Gly
            210                 215                 220

Trp Lys Asn Glu Arg Glu His Thr Pro Pro Ser Gly Arg Tyr Tyr Thr
225                 230                 235                 240

Gly Asp Glu His Phe Arg Lys Lys Glu Leu Asn Arg Ser Gly Ser Gln
            245                 250                 255

His Ala Lys Ser Ala Pro Arg Trp Glu Ser Gly Gln Glu Arg Asn Ile
            260                 265                 270

Arg Ile Ser Ser Lys Ile Val Asp Glu Lys Asn Glu His Ser Asn
            275                 280                 285

Ser Arg Thr His Met Arg Asp Tyr Ser Ser Gly Asn Arg Leu Lys Arg
            290                 295                 300

His Gly Asn Glu Ser Glu Gly Cys Glu Arg Lys Asn Tyr Gly Asp Tyr
305                 310                 315                 320

Ala Gly Ser Lys Ser Arg Arg Leu Ser Asp Asp Ser Pro Arg Leu Ala
            325                 330                 335

Tyr Ser Glu His Tyr Ser Arg Leu Ser Val Glu Arg Ser Tyr Arg Asn
            340                 345                 350

Ser Ser Ser Lys Ser Ser Ala Asp Lys Tyr Ser Ser Arg His His Glu
            355                 360                 365

Ser Leu Pro Thr Arg Ser Val Tyr Asp Lys His Gly Arg Ser Pro Gly
            370                 375                 380

Asn Ser Glu Arg Ser Pro His Asp Arg Ala Arg Tyr Tyr Asp His Lys
385                 390                 395                 400

Asp Arg Thr Pro Val Arg Pro Ser Pro Tyr Ser Cys Asp Arg Ser Pro
            405                 410                 415

Tyr Ser Ser Glu Lys Ser Pro His Gly Arg Glu Arg Ser Pro Tyr Asn
            420                 425                 430

Arg Asn Trp Asp Arg Ser Arg His His Asp His Lys Met Arg Ser Pro
            435                 440                 445

Thr His Ala Glu Arg Ser Pro Gln Asp Arg Gly Arg His His Asp Arg
            450                 455                 460

Arg Asp Pro Thr Pro Asn Leu Ile Glu Gln Ser Pro His Asp Arg Thr
465                 470                 475                 480
```

```
Arg Ser Asn Met His Arg Glu Ile Asn Ser Lys Ile Ser Ser Ser Glu
            485                 490                 495
Lys His Asn Ser Gln His Ser Cys Lys Asp Tyr Glu Asp Lys His Val
        500                 505                 510
Gln Lys Glu Ala Asn Leu Ser Asp Val Glu Ser Gln Gly Glu Arg Asn
        515                 520                 525
Val His Asn Ala Ser Lys Ser Phe Glu Ile Asp Val Cys Ser Glu Pro
    530                 535                 540
Glu Lys Glu Gln Gln Ser Ser Asn Pro Thr Val Ser Cys Lys Gly Ser
545                 550                 555                 560
Pro Cys Leu Glu Pro Leu Pro Glu Glu Leu Ala Ser Met Glu Glu Asp
                565                 570                 575
Met Asp Ile Cys Asp Thr Pro Pro His Val Pro Val Val Asp Ser
                580                 585                 590
Ser Ser Gly Lys Trp Phe Tyr Leu Asp Tyr Asn Gly Val Glu His Gly
        595                 600                 605
Pro Ser Lys Leu Ser Asp Ile Lys Val Leu Val Asp Asp Gly Val Leu
    610                 615                 620
Met Ser Asp His Phe Ile Lys His Ile Asp Ser Asp Arg Trp Leu Thr
625                 630                 635                 640
Val Glu Asn Ala Val Ser Pro Val Thr Ala Gln Ser Phe Leu Ser Val
                645                 650                 655
Val Ser Glu Thr Ile Thr Gln Leu Val Asn Pro Pro Glu Ala Pro Gly
                660                 665                 670
Asn Leu Leu Ala Asp Thr Gly Asp Ile Leu Gln Ser Gly Pro Glu Asn
        675                 680                 685
Tyr Leu Gly Ile Pro Thr Pro Ile Leu Gln Pro Met Leu Cys Ser Glu
    690                 695                 700
Asp Ser Gly Ile Ala Ser Val Leu Leu Glu Asp Leu His Ile Asp Glu
705                 710                 715                 720
Arg Val Gly Val Leu Leu Glu Gly Tyr Asp Val Ile Pro Gly Arg Glu
                725                 730                 735
Phe Glu Ala Ile Lys Glu Ser Leu Gln Met Asn Phe Glu Tyr Ala Lys
                740                 745                 750
Trp Glu Gly Leu Glu Glu Cys Glu Gly Phe Pro Gly His Asp Thr Cys
        755                 760                 765
Leu Arg Met Glu His Asp Ser Arg Ile Asp Ser Ser Arg Glu Tyr Glu
    770                 775                 780
Ser Gln Val Ser Ile Pro Ser Gly Lys Glu Asn Gly Phe Thr Leu Gly
785                 790                 795                 800
Val Pro Gly Asp Trp Phe Ser Ala Gln Trp Ser Cys Lys Gly Gly Asp
                805                 810                 815
Trp Lys Arg Asn Asp Asp Ala Gln Asp Arg Tyr Cys Asn Lys Lys Leu
                820                 825                 830
Val Leu Asn Asp Gly Phe Ser Leu Cys Gln Met Pro Lys Ser Gly Cys
        835                 840                 845
Glu Asp Pro Arg Trp Thr Arg Lys Asp Leu Tyr Tyr Pro Ser His
    850                 855                 860
Ser Arg Arg Leu Asp Leu Pro Val Trp Ala Phe Cys Thr Asp Glu Arg
865                 870                 875                 880
Gly Asp Cys Ser Thr Leu Ser Lys Pro Val Gln Thr Lys Leu Ala Ser
                885                 890                 895
```

-continued

```
Val Arg Gly Val Lys Gly Asn Ile Leu Ser Val Arg Ile Asn Ala
            900                 905                 910

Cys Val Val Lys Asp Gln Gly Ser Leu Val Ser Glu Ser Cys His Lys
            915                 920                 925

Thr Arg Ser Lys Asp Arg Tyr Pro Ser Arg Ser Thr Trp Ser Phe Ser
            930                 935                 940

Ser Thr Ser Tyr Ser Lys Arg Ser Ser Thr Glu Glu Asp Ser Gln Ser
945                 950                 955                 960

Lys Ala Ser Asn Asp Gln Gly Ser Leu Gly Ser Cys Arg Ser Met Glu
            965                 970                 975

Phe Ile Asn Ile Pro Lys Asp Tyr Cys Arg Thr Val His Asp Leu Gln
            980                 985                 990

Leu His Ser Gly Asn Trp Tyr Tyr Leu Asp Gly Ser Gly Arg Glu Arg
            995                 1000                1005

Gly Pro Ser Ser Phe Ser Glu Leu Gln Arg Leu Val Asp Gln Gly Ile
            1010                1015                1020

Val Lys Lys Tyr Ser Ser Val Phe Arg Lys Cys Asp Lys Leu Trp Val
1025                1030                1035                1040

Pro Val Thr Ser Ser Ala Glu Thr Tyr Asp Phe Asp Val Ser Leu Arg
            1045                1050                1055

Ser His Gln Glu Ser Ser Thr Leu Ser Gly Glu Cys Ser Gly Leu Pro
            1060                1065                1070

Ser Lys Gln Ile His Gly Ala Ser Val Gly Glu His Asp Ser Lys Ser
            1075                1080                1085

Asn Leu Phe Asn Ser Leu Gln Pro Gln Phe Val Gly Tyr Thr Arg Gly
            1090                1095                1100

Lys Leu His Glu Leu Val Met Arg Ser Tyr Lys Ser Arg Glu Phe Ala
1105                1110                1115                1120

Ala Val Ile Asn Glu Val Leu Asp Pro Trp Ile Asn Thr Arg Gln Pro
            1125                1130                1135

Lys Lys Glu Thr Glu Lys Gln Thr Tyr Trp Lys Ser Glu Gly Asp Gly
            1140                1145                1150

His Ala Ser Lys Arg Ala Arg Met Leu Val Asp Tyr Ser Glu Glu Asp
            1155                1160                1165

Ser Asp Phe Glu Asp Gly Ser Leu Pro Asn Trp Lys Asp Glu Ser Thr
            1170                1175                1180

Phe Glu Ala Leu Cys Gly Asp Ala Thr Phe Ser Gly Glu Gly Ser Asp
1185                1190                1195                1200

Ile Thr Asp Pro Asn Val Gly Ser Leu Gly Leu Leu Asp Gly Cys Met
            1205                1210                1215

Leu Ser Arg Val Phe His Cys Leu Arg Ser Asp Leu Lys Ser Leu Ala
            1220                1225                1230

Phe Ala Ser Met Thr Cys Lys His Trp Arg Ala Thr Val Arg Phe Tyr
            1235                1240                1245

Lys Lys Val Ser Arg His Val Asn Leu Ser Ser Leu Gly His Ser Cys
1250                1255                1260

Thr Asp Ser Ile Met Trp Asn Ile Leu Asn Ala Tyr Glu Lys Asp Lys
1265                1270                1275                1280

Ile Glu Ser Ile Val Leu Ile Gly Cys Thr Asn Ile Thr Ala Gly Met
            1285                1290                1295

Leu Glu Lys Ile Leu Leu Leu Phe Pro Gly Leu Ser Thr Val Asp Ile
            1300                1305                1310

Arg Gly Cys Ser Gln Phe Gly Glu Leu Thr Leu Lys Phe Thr Asn Val
```

```
            1315                1320                1325

Lys Trp Ile Lys Ser His Ser Ser His Ile Thr Lys Ile Ala Ser Glu
        1330                1335                1340

Ser His Lys Ile Arg Ser Val Lys Gln Phe Ala Glu Gln Thr Ser Ser
1345                1350                1355                1360

Val Ser Lys Val Ser Ile Leu Gly Ile Arg Asp Phe Gly Glu Leu
                1365                1370                1375

Lys Asp Tyr Phe Asp Ser Val Asp Lys Arg Asp Thr Ala Lys Gln Leu
                1380                1385                1390

Phe Arg Gln Asn Leu Tyr Lys Arg Ser Lys Leu Tyr Asp Ala Arg Asn
                1395                1400                1405

Ser Ser Ser Ile Leu Ser Arg Asp Ala Arg Thr Arg Arg Trp Pro Ile
        1410                1415                1420

Lys Lys Ser Glu Ser Gly Tyr Lys Arg Met Glu Gln Phe Leu Ala Ser
1425                1430                1435                1440

Arg Leu Arg Glu Ile Met Lys Ala Asn Ser Cys Asp Phe Phe Met Pro
                1445                1450                1455

Lys Val Ala Glu Ile Glu Ala Lys Met Lys Asn Gly Tyr Tyr Ser Gly
                1460                1465                1470

His Gly Leu Ser Tyr Val Lys Glu Asp Ile Ser Arg Met Cys Arg Asp
                1475                1480                1485

Ala Ile Lys Ala Lys Thr Arg Gly Asp Gly Asp Met Asn His Val
        1490                1495                1500

Ile Thr Leu Phe Ile Gln Leu Ala Thr Arg Leu Glu Glu Asn Ser Lys
1505                1510                1515                1520

Tyr Val Asn Ser Arg Asp Ala Leu Met Lys Leu Trp Gly Asn Asp Pro
                1525                1530                1535

Pro Ser Ser Leu Cys Ser Thr Ser Ser Lys Tyr Lys Lys Ser Lys Glu
                1540                1545                1550

Asn Arg Leu Leu Ser Glu Arg Lys His Arg Asn Asn Glu Thr His Gly
                1555                1560                1565

Gly Leu Asp Asn Gly Glu Tyr Ala Ser Asp Arg Glu Ile Arg Arg Arg
                1570                1575                1580

Leu Ser Lys Leu Asn Lys Lys Tyr Phe Asn Ser Glu Ser Glu Thr Ser
1585                1590                1595                1600

Asp Asp Phe Asp Arg Ser Ser Glu Asp Gly Lys Ser Asp Ser Asp Thr
                1605                1610                1615

Thr Thr Thr Asp Thr Glu Ser Asp Gln Asp Val His Ser Glu Ser Arg
                1620                1625                1630

Ile Gly Asp Ser Arg Gly Asp Gly Tyr Phe Thr Pro Asp Asp Gly Leu
                1635                1640                1645

His Phe Ile Thr Asp Glu Arg Glu Trp Gly Ala Arg Met Thr Lys Ala
                1650                1655                1660

Ser Leu Val Pro Pro Val Thr Arg Lys Tyr Asp Val Ile Asp Gln Tyr
1665                1670                1675                1680

Ile Ile Val Ala Asp Glu Glu Asp Val Arg Arg Lys Met Arg Val Ser
                1685                1690                1695

Leu Pro Asp Asp Tyr Ala Glu Lys Leu Ser Ala Gln Lys Asn Gly Ile
                1700                1705                1710

Glu Glu Ser Asp Met Glu Leu Pro Glu Val Lys Asp Tyr Lys Pro Arg
                1715                1720                1725

Lys Gln Leu Glu Asn Glu Val Val Glu Gln Glu Val Tyr Gly Ile Asp
                1730                1735                1740
```

```
Pro Tyr Thr His Asn Leu Leu Asp Ser Met Pro Lys Glu Leu Asp
1745                1750                1755                1760

Trp Ser Leu Gln Glu Lys His Leu Phe Ile Glu Asp Lys Leu Leu Arg
        1765                1770                1775

Met Leu Asn Lys Gln Val Lys His Phe Thr Gly Thr Gly Asn Thr Pro
            1780                1785                1790

Met Ser Tyr Pro Leu Gln Pro Ala Ile Glu Glu Ile Glu Arg Tyr Ala
        1795                1800                1805

Glu Glu His Cys Asp Ala Arg Thr Val Arg Met Cys Gln Gly Ile Leu
    1810                1815                1820

Lys Ala Ile Lys Ser Arg Ser Asp Asp Lys Tyr Val Ala Tyr Arg Lys
1825                1830                1835                1840

Gly Leu Gly Val Val Cys Asn Lys Glu Glu Gly Phe Gly Glu Asp Asp
                1845                1850                1855

Phe Val Val Glu Phe Leu Gly Glu Val Tyr Pro Val Trp Lys Trp Phe
            1860                1865                1870

Glu Lys Gln Asp Gly Ile Arg Ser Leu Gln Lys Asn Ser Asp Asp Pro
        1875                1880                1885

Ala Pro Glu Phe Tyr Asn Ile Tyr Leu Glu Arg Pro Lys Gly Asp Ala
    1890                1895                1900

Asp Gly Tyr Asp Leu Val Val Val Asp Ala Met His Lys Ala Asn Tyr
1905                1910                1915                1920

Ala Ser Arg Ile Cys His Ser Cys Arg Pro Asn Cys Glu Ala Lys Val
            1925                1930                1935

Thr Ala Val Asp Gly His Tyr Gln Ile Gly Ile Tyr Ser Val Arg Glu
            1940                1945                1950

Ile Gln His Gly Glu Glu Ile Thr Phe Asp Tyr Asn Ser Val Thr Glu
        1955                1960                1965

Ser Lys Glu Glu Tyr Glu Ala Ser Val Cys Leu Cys Gly Ser Gln Val
1970                1975                1980

Cys Arg Gly Ser Tyr Leu Asn Leu Thr Gly Glu Gly Ala Phe Glu Lys
1985                1990                1995                2000

Val Leu Lys Glu Trp His Gly Ile Leu Asp Arg His Tyr Leu Met Leu
                2005                2010                2015

Glu Ala Cys Glu Leu Asn Ser Val Ser Glu Glu Asp Tyr Asn Asp Leu
            2020                2025                2030

Gly Arg Ala Gly Leu Gly Ser Cys Leu Leu Gly Gly Leu Pro Asp Trp
        2035                2040                2045

Leu Val Ser Tyr Ala Ala Arg Leu Val Arg Phe Ile Asn Phe Glu Arg
    2050                2055                2060

Thr Lys Leu Pro Glu Glu Ile Leu Lys His Asn Leu Glu Glu Lys Arg
2065                2070                2075                2080

Lys Tyr Phe Ser Asp Ile Cys Leu Glu Val Glu Arg Ser Asp Ala Glu
            2085                2090                2095

Val Gln Ala Glu Gly Val Tyr Asn Gln Arg Leu Gln Asn Leu Ala Val
        2100                2105                2110

Thr Leu Asp Lys Val Arg Tyr Val Met Arg Cys Ile Phe Gly Asp Pro
    2115                2120                2125

Leu Lys Ala Pro Pro Pro Leu Glu Lys Leu Ser Pro Glu Ala Val Val
    2130                2135                2140

Ser Phe Leu Trp Lys Gly Glu Asp Ser Phe Val Glu Glu Leu Leu Gln
2145                2150                2155                2160
```

```
Cys Leu Ala Pro Tyr Val Glu Glu Ser Thr Leu Asn Asp Leu Lys Ser
                2165                2170                2175

Lys Ile His Ala His Asp Pro Ser Ser Gly Asp Ile Gln Lys Ala
            2180                2185                2190

Val Gln Lys Ser Leu Leu Trp Leu Arg Asp Glu Val Arg Asn Leu Pro
            2195                2200                2205

Cys Thr Tyr Lys Cys Arg His Asp Ala Ala Asp Leu Ile His Ile
            2210                2215                2220

Tyr Ala Tyr Thr Lys Tyr Phe Phe Arg Ile Gln Asp Tyr Gln Thr Ile
2225                2230                2235                2240

Thr Ser Pro Pro Val Tyr Ile Ser Pro Leu Asp Leu Gly Pro Lys Tyr
                2245                2250                2255

Ala Asp Lys Leu Gly Ala Gly Phe Gln Glu Tyr Arg Lys Ile Tyr Gly
                2260                2265                2270

Glu Asn Tyr Cys Leu Gly Gln Leu Ile Phe Trp His Asn Gln Ser Asn
                2275                2280                2285

Ala Glu Pro Asp Cys Thr Leu Ala Arg Ile Ser Arg Gly Cys Leu Ser
                2290                2295                2300

Leu Pro Asp Ile Ser Ser Phe Tyr Ala Lys Ala Gln Lys Pro Ser Arg
2305                2310                2315                2320

His Arg Val Tyr Gly Pro Arg Thr Val Arg Ser Met Leu Ala Arg Met
                2325                2330                2335

Glu Lys Gln Pro Gln Lys Pro Trp Pro Lys Asp Arg Ile Trp Ser Phe
                2340                2345                2350

Lys Asn Ser Pro Lys Tyr Phe Gly Ser Pro Met Leu Asp Ala Val Ile
                2355                2360                2365

Asn Asn Ser Pro Leu Asp Arg Glu Met Val His Trp Leu Lys His Arg
                2370                2375                2380

Pro Ala Ile Phe Gln Ala Leu Trp Asp Gln
2385                2390

<210> SEQ ID NO 106
<211> LENGTH: 2259
<212> TYPE: PRT
<213> ORGANISM: Zea mays

<400> SEQUENCE: 106

Met Gly Asp Gly Gly Val Ala Cys Ala Val Arg Ser Val Glu Ser Phe
1               5                   10                  15

Arg Ala Gly Ala Leu Val Arg Gly Gly Ala Gly Glu Ala Met Pro
            20                  25                  30

Asp Lys Gly Glu Arg Ala His Gly His Arg His Gln His Gln His Trp
        35                  40                  45

Lys Asn Gln Gln Ser Ala Thr Ala Ala Asp Leu Glu Gly Glu Leu
    50                  55                  60

Leu Asn Gly Glu Ala Gly Thr Asn Gly Leu Pro Glu Arg Ser Met Pro
65                  70                  75                  80

Pro Lys Lys Trp Arg Lys Val Leu Ala Ala Ser Thr Ala Ala Val Glu
                85                  90                  95

Val Glu Pro Gly Glu Ile Val Ser Thr Lys Gln Ala Val Pro Leu Lys
                100                 105                 110

Lys Glu Arg Arg Asn Gly Asp Val Glu Lys Val Glu Leu Leu Pro Glu
            115                 120                 125

Arg Gln Arg Lys Glu Lys Ser Ser Gly Lys Ser Thr Arg Lys Ser Ile
        130                 135                 140
```

```
Lys Asp Asp Val Glu Pro Gly Glu Ile Ala Leu Pro Gly Lys Arg Arg
145                 150                 155                 160

Asp Ala Lys Ser Gln Leu Ala His Asp Asn Ser Arg Arg Pro Ser Ser
            165                 170                 175

Ser Ala Gln Lys Gly Ser Leu Arg Asp Ser Asp Glu Pro Gly Glu
            180                 185                 190

Ile Lys Pro Glu Ser Gly Ile Ser Gly Ser Val Arg Lys Asn Arg Pro
            195                 200                 205

Thr Glu Pro His Ser Ser Asn His Lys His His Thr Asp Thr Ser Asp
210                 215                 220

Gln Ser Gly Ser Lys His Arg Arg Lys Gly Gly Lys Ser Ser Ser
225                 230                 235                 240

Ala Ala Arg His Leu Ser Gly Arg Ile Arg Glu Val Ser Pro Thr
                245                 250                 255

Arg Asp Arg Arg Asp Lys His Glu Arg Ser Pro Gly Ile Leu Gly Arg
            260                 265                 270

Phe Pro His Asp Arg Phe Arg His Asp Arg Tyr Asp Arg Ser Pro Ser
            275                 280                 285

Arg Leu Glu Arg Ser Pro His Arg Ala Arg His Tyr Asp Ser Arg Asp
290                 295                 300

Arg Ser Pro Tyr Ile Ser Pro Arg His Arg Ala Arg Pro Pro Gln Phe
305                 310                 315                 320

Arg Asp Asn Thr Pro Ser Arg Val Asp Asn Ser Pro Arg Gly Arg Val
            325                 330                 335

Gln His Glu Asp Ile Arg Asp Arg Ser Pro Phe Arg His Asp Arg Ser
            340                 345                 350

Pro Ser Glu Arg Cys Arg Pro Thr Asp Thr His Glu Ala Ser Lys Lys
            355                 360                 365

Ser Arg Ser Ser Asn Asn Ser Glu Lys Ser His His Lys Ser Lys Ser
    370                 375                 380

Ala Lys Gln Ser Ser Lys Ile Lys Ser Gly Ser Asn Gly Lys Asn Glu
385                 390                 395                 400

Glu Lys Ile Ser Lys Glu Lys His Thr Glu Ser Ser Gln Tyr Thr Glu
                405                 410                 415

Leu Pro Pro Pro Pro Pro Leu Pro Leu Pro Pro Pro Pro Pro Pro Pro
                420                 425                 430

Pro Pro Pro Pro Pro Leu Pro Pro Ala Val Pro Pro Leu Pro Pro
        435                 440                 445

Ser Pro Glu Pro Glu Pro Gly Val Leu Ala Glu Asp Met Ile Glu
    450                 455                 460

Asp Met Asp Ile Cys Asp Thr Pro Pro His Thr Ser Ala Val Pro Glu
465                 470                 475                 480

Pro Thr Glu Pro Ile Cys Asp Ile Gly Arg Trp Phe Tyr Leu Asp His
                485                 490                 495

Phe Gly Ile Glu Gln Gly Pro Ser Lys Leu Ala Glu Leu Lys Lys Leu
                500                 505                 510

Val Gln Asp Gly Tyr Leu Leu Ser Asp His Leu Ile Lys His Ala Asp
                515                 520                 525

Ser Asn Arg Trp Val Thr Val Glu Asn Ala Ala Ser Pro Leu Val Pro
    530                 535                 540

Ser Asp Phe Pro Ser Leu Tyr Ser Asp Thr Ser Thr Gln Leu Val Asn
545                 550                 555                 560
```

```
Pro Pro Glu Ala Pro Gly Asn Leu Leu Asp Glu Ala Leu Glu Glu Ala
            565                 570                 575
Ser Asn Leu Ser Ser Gly Ala Glu Asp Lys Gln Met Glu Glu Thr Ser
            580                 585                 590
Ala Glu Asp Ser Glu Glu Phe Cys Ile Asp Arg Val Glu Ala Leu
            595                 600                 605
Met Asp Gly Ser Ile Leu Val His Gly Gln Glu Leu Glu Ile Ile Gly
            610                 615                 620
Glu Leu Leu Gly Ala Asp Phe Gln Pro Ala Asp Trp Gln Arg Trp Ser
625                 630                 635                 640
Arg Arg Glu Asp Phe Thr Arg Leu Asn Val His Thr Glu Val Asn Asn
                    645                 650                 655
Glu Ile Asn Gly Gly Thr Glu Asn Arg Ala Thr Asp Ala Tyr Gly Leu
                    660                 665                 670
Val Ser Val Glu Lys Asn Phe His His Asn Ala Glu Ser Ser Glu Trp
                    675                 680                 685
Phe Ser Gly Arg Trp Ser Cys Lys Gly Gly Asp Trp Arg Arg Asn Asp
            690                 695                 700
Glu Leu Ser Gln Asp Thr Pro Phe Arg Lys Lys Leu Val Leu Asn Glu
705                 710                 715                 720
Gly Tyr Pro Leu Cys Gln Met Pro Lys Gly Ser Cys Glu Asp Pro Arg
                    725                 730                 735
Arg Pro Cys Lys Asp Glu Leu Tyr Tyr Pro Val Arg Ala Lys Lys Tyr
                    740                 745                 750
Glu Leu Pro Leu Trp Ala Phe Ser Leu Thr Glu Glu Asp Ile Asp Ser
                    755                 760                 765
Val Asn Asp Thr Thr Lys Ser Gly Val Val Pro Gly Arg Pro Gly Gln
            770                 775                 780
Thr Arg Gln Pro Ser Arg Gly Val Lys Gly Met Met Leu Ser Val Val
785                 790                 795                 800
Arg Ile Asn Ser Arg Val Val Lys Asp Gln Ser Ser Val Glu Pro His
                    805                 810                 815
Thr Lys Pro Arg Gly Thr Asp Arg Pro Leu Ser Arg Ser Ser Arg Ser
                    820                 825                 830
His Ser Ile Gly Ala Glu Arg Ser Val His Glu Gly Ser Ser His
                    835                 840                 845
Phe Arg Lys His His Asp His Asp Ser Gln Ser Ser His Lys Ser Lys
            850                 855                 860
Pro Val Pro Asn Ile Pro Lys Asp Arg Val Cys Thr Val Asp Glu Leu
865                 870                 875                 880
Ser Val Tyr Arg Gly Asp Trp Tyr Tyr Leu Asp Gly Thr Gly His Glu
                    885                 890                 895
His Gly Pro Phe Ser Tyr Ser Glu Leu Gln Glu Leu Val Lys Asn Gly
                    900                 905                 910
Thr Ile Ile Glu Gln Ser Ser Val Phe Arg Lys Ile Asp Asn Thr Trp
            915                 920                 925
Phe Pro Val Leu Lys Asp Leu Lys Pro Gly Ser Ser Val Pro Ser Ala
            930                 935                 940
Ala Arg Ser Ser Ser Phe Thr Ala Ala Leu Met Leu Pro Asp Gln Tyr
945                 950                 955                 960
Asn Phe Gly Val Asn Gln Gly Ser Gly Ser Phe Asn Gln Leu His Pro
                    965                 970                 975
Gln Phe Val Gly Tyr Thr Arg Gly Lys Leu His Glu Leu Val Met Lys
```

```
             980             985             990
Tyr Phe Lys Ser Arg Glu Leu Thr Leu Ala Ile Asn Glu Val Leu Asp
            995            1000            1005
Pro Trp Ile Ser Ala Lys Gln Pro Lys Lys Glu Phe Glu Ala Tyr Phe
           1010            1015            1020
Ser His Asn Ser Ala Ser Arg Asn Leu Leu Pro Glu Asp Gly Gly Ser
1025            1030            1035            1040
Ala Lys Lys Ala Lys Leu Leu Pro Asp Gln Ser Asp Glu Asp Ile His
            1045            1050            1055
Leu Ser Gln Asp Ile Leu Ala Ser Arg Lys Glu Asp Ile Cys Phe Asp
            1060            1065            1070
Glu Leu Cys Asp Ala Glu Pro Ser Val Asp Asn Asp Ser Leu Asn Pro
            1075            1080            1085
Gly Ala Gly Asn Glu Thr Trp Gly Leu Leu Asn Gly His Val Leu Ala
            1090            1095            1100
Arg Ile Phe His Phe Met Arg Ala Asp Val Lys Ala Leu Ile Ser Ser
1105            1110            1115            1120
Ala Ala Thr Cys Arg Ser Trp Asn Ala Ala Val Lys Tyr Tyr Arg Asn
            1125            1130            1135
Met Cys Arg Phe Ile Asp Leu Ser Ser Val Gly Pro Leu Cys Thr Asp
            1140            1145            1150
Ser Val Phe Cys Asp Ile Met Ala Gly Tyr Glu Lys Gln Asn Ile Arg
            1155            1160            1165
Thr Leu Ile Leu Ala Gly Cys Ser Asn Leu Ser Ser His Ala Leu Gly
            1170            1175            1180
Arg Val Leu Glu Gln Leu Pro Gln Ile Ser Tyr Val Asp Ile His Gly
1185            1190            1195            1200
Cys Gly His Leu Gly Asp Leu Lys Asn Lys Phe Gln His Val Lys Trp
            1205            1210            1215
Ile Arg Ser Ser Leu Asn Pro Glu Gly Ser Tyr Arg Lys Ile Lys Thr
            1220            1225            1230
Leu Lys Gln Ile Gly Asp Gly Asn Asn Tyr Ala Ser Lys Val Ala Arg
            1235            1240            1245
Asn Phe Thr Asn His Leu Asp Gly Ser Asp Glu Leu Asp Gly Tyr Phe
            1250            1255            1260
Ala Asp Ile Ser Asn Arg Glu Asn Ala Asn Leu Ser Phe Gly Gln Gly
1265            1270            1275            1280
Phe Tyr Lys Arg Ser Lys Leu Leu Asp Ala Arg Lys Ser Ser Ala Val
            1285            1290            1295
Leu Ser Arg Asp Ala Glu Met Arg Arg Leu Met Gln Arg Gln Ala Glu
            1300            1305            1310
Thr Ser Tyr Arg Lys Met Glu Glu Phe Ile Ile Asn Arg Leu Arg Glu
            1315            1320            1325
Ile Met Arg Ser Asn Arg Phe Asp Phe Phe Ile Pro Lys Val Ser Lys
            1330            1335            1340
Ile Glu Gly Arg Leu Lys Asn Gly Tyr Tyr Ala Arg His Gly Phe Arg
1345            1350            1355            1360
Thr Ile Lys His Asp Ile Arg Thr Met Cys Gln Asp Ala Leu Arg Tyr
            1365            1370            1375
Lys Asp Gly Asn Asp Ser Gly Asp Ile Lys Gln Ile Val Val Ser Phe
            1380            1385            1390
Ile Gln Leu Ala Lys Arg Leu Gly Asn Pro Arg Tyr Ile Ser Asp Arg
            1395            1400            1405
```

```
Tyr Gly Ala Gly Ala Gln Asp Ser Leu Asp Ile Asn Gln Tyr Ser Phe
            1410                1415                1420
Asp Thr Lys Leu Lys Lys Lys Gln Asn Lys Ile Arg Gly Ala Asn Ser
1425                1430                1435                1440
Leu Ala Ala Gly Ala Asp Asn Ser Ser Arg Ala Phe Asp Leu Glu Ile
            1445                1450                1455
Lys Arg Ser Leu Ser Lys Leu Lys Lys Lys Asp Val Tyr Ser Gly Ser
1460                1465                1470
Glu Thr Ser Asp Asp Asp Gly Tyr Ser Glu Val Asp Glu Thr Glu
            1475                1480                1485
Ser Glu Thr Thr Val Ser Asp Thr Glu Ser Asp Leu Asp Val Asn Ser
        1490                1495                1500
Gly Ala Trp Asp Leu Lys Gly Asn Ser Leu Lys Leu Ile Glu Pro Gly
1505                1510                1515                1520
Glu Ser Val Thr Asp Asp Arg Ile Leu Gly Ala Arg Met Thr Lys Ala
            1525                1530                1535
Ser Leu Val Pro Pro Val Thr Arg Lys Tyr Glu Val Ile Glu Glu Tyr
            1540                1545                1550
Leu Ile Val Ala Asp Leu Glu Glu Val Gln Arg Lys Met Arg Val Ala
        1555                1560                1565
Leu Pro Asp Asp Tyr Ser Glu Lys Leu Leu Ser Gln Lys Asn Gly Thr
        1570                1575                1580
Glu Asn Leu Glu Leu Pro Glu Val Lys Asp Tyr Gln Pro Arg Lys Val
1585                1590                1595                1600
Ala Gly Asp Glu Ile Leu Glu Gln Glu Val Tyr Gly Ile Asp Pro Tyr
            1605                1610                1615
Thr His Asn Leu Leu Ser Asp Ile Met Pro Ala Asp Leu Glu Leu Ser
            1620                1625                1630
Pro Thr Asp Lys His Ile Phe Ile Glu Glu Leu Leu Leu Asn Thr Leu
        1635                1640                1645
Asn Lys Gln Val Arg His Phe Thr Gly Ser Gly Asn Thr Pro Met Thr
1650                1655                1660
Tyr Asn Leu Arg Pro Val Ile Glu Glu Ile Gln Arg Ser Ala Glu Asp
1665                1670                1675                1680
Asn Gly Asp Lys Arg Thr Ser Lys Met Cys Leu Gly Met Leu Lys Thr
            1685                1690                1695
Met Arg Asn Arg Ser Glu Gln Asn Phe Val Ala Tyr Arg Lys Gly Leu
        1700                1705                1710
Gly Val Val Cys Asn Lys Lys Gly Phe Gly Val Asp Asp Phe Val
            1715                1720                1725
Val Glu Phe Phe Gly Glu Val Tyr Pro Ser Trp Arg Trp Tyr Glu Lys
        1730                1735                1740
Gln Asp Gly Ile Lys His Ile Gln Asn Asn Ser Glu Asp Gln Ala Pro
1745                1750                1755                1760
Glu Phe Tyr Asn Ile Met Leu Glu Arg Pro Lys Gly Asp Gly Asp Gly
            1765                1770                1775
Tyr Asp Leu Val Phe Val Asp Ala Met His Lys Ala Asn Tyr Ala Ser
            1780                1785                1790
Arg Ile Cys His Ser Cys Asn Pro Asn Cys Glu Ala Lys Val Thr Ala
        1795                1800                1805
Val Asn Gly Lys Tyr Gln Ile Gly Val Tyr Thr Leu Arg Pro Ile Ala
        1810                1815                1820
```

```
Glu Gly Glu Glu Ile Thr Phe Asp Tyr Asn Ser Val Thr Glu Ser Lys
1825                1830                1835                1840

Glu Glu His Glu Ala Ser Val Cys Leu Cys Gly Ser Gln Val Cys Arg
            1845                1850                1855

Gly Ser Tyr Leu Asn Phe Ser Gly Glu Gly Ala Phe Glu Lys Val Leu
            1860                1865                1870

Met Glu Phe His Gly Val Leu Asp Arg His Ser Leu Leu Leu Gln Ala
            1875                1880                1885

Cys Glu Thr Asp Ser Val Ser Gln Gln Asp Leu Ile Asp Leu Gly Arg
            1890                1895                1900

Ala Gly Leu Gly Thr Cys Leu Leu Ala Gly Leu Pro Gly Trp Leu Val
1905                1910                1915                1920

Ala Tyr Thr Ala His Leu Val Arg Phe Ile Tyr Leu Glu Arg Gln Lys
            1925                1930                1935

Leu Pro Asp Glu Ile Leu Arg His Asn Val Asp Glu Lys Arg Gln Phe
            1940                1945                1950

Leu Ile Glu Ile Asn Met Asp Ser Glu Lys Asn Asp Ala Glu Val Gln
            1955                1960                1965

Ala Glu Gly Val Leu Asn Ser Arg Leu Gln Gln Ile Val His Thr Leu
            1970                1975                1980

Asp Lys Val Arg Tyr Val Met Arg Cys Ile Phe Gly Asp Pro Lys Asn
1985                1990                1995                2000

Ala Pro Pro Pro Leu Val Arg Leu Ser Gly Lys Ser Leu Val Ser Ala
            2005                2010                2015

Ile Trp Lys Gly Asp Ser Ser Ile Val Ala Glu Leu Ile Gln Ser Met
            2020                2025                2030

Glu Pro His Val Glu Glu Val Leu Ser Asp Leu Lys Ala Lys Ile
            2035                2040                2045

Arg Ala His Asp Pro Ser Glu Ser Glu Asp Ile Glu Gly Gly Ile Arg
            2050                2055                2060

Asn Ser Leu Leu Trp Leu Arg Asp Glu Leu Arg Thr Leu Ser Cys Thr
2065                2070                2075                2080

Tyr Lys Cys Arg His Asp Ala Ala Ala Asp Leu Ile His Leu Tyr Ala
            2085                2090                2095

Tyr Thr Lys Cys Phe Phe Arg Val Arg Asp Tyr Lys Thr Val Lys Ser
            2100                2105                2110

Pro Pro Val His Ile Ser Pro Leu Asp Leu Gly Pro Lys Tyr Ala Asp
            2115                2120                2125

Lys Leu Gly Pro Gly Phe Gln Glu Tyr Cys Lys Thr Tyr Pro Glu Asn
            2130                2135                2140

Tyr Cys Leu Ala Gln Leu Ile Tyr Trp Tyr Ser Gln Asn Ser Glu Pro
2145                2150                2155                2160

Glu Ser Arg Leu Thr Arg Ala Arg Lys Gly Cys Met Ser Leu Pro Asp
            2165                2170                2175

Val Ser Ser Phe Tyr Val Lys Ser Ala Lys Pro Ser Gln Glu Arg Ala
            2180                2185                2190

Tyr Gly Asn Arg Thr Val Arg Phe Met Leu Ser Arg Met Glu Lys Gln
            2195                2200                2205

Ala Gln Arg Pro Trp Pro Lys Asp Arg Ile Trp Val Phe Lys Ser Asp
            2210                2215                2220

Pro Arg Phe Phe Gly Ser Pro Met Met Asp Thr Val Leu Asn Asn Ser
2225                2230                2235                2240

Pro Leu Asp Lys Glu Met Val His Trp Leu Lys Thr Arg Pro Asn Val
```

-continued

```
                    2245                2250                2255

Phe Leu Gly

<210> SEQ ID NO 107
<211> LENGTH: 1845
<212> TYPE: PRT
<213> ORGANISM: Manihot esculenta

<400> SEQUENCE: 107

Met Asn Lys Glu Glu Ser Pro Arg Val Asp Gly Pro Pro Glu Glu
1               5                   10                  15

Leu Leu Ser Met Glu Glu Asp Met Asp Ile Cys Asp Thr Pro His
                20                  25                  30

Val Pro Val Met Thr Asp Ser Ser Thr Gly Lys Trp Phe Tyr Leu Asp
            35                  40                  45

Tyr Phe Gly Met Glu Cys Gly Pro Ser Lys Leu Cys Asp Leu Lys Thr
        50                  55                  60

Leu Val Asp Glu Gly Val Leu Val Ser Asp His Leu Ile Lys His Val
65                  70                  75                  80

Asp Ser Asp Arg Trp Val Thr Ile Glu Asn Ala Val Ser Pro Leu Val
                85                  90                  95

Thr Ala Asn Phe Pro Ser Ile Thr Ser Asp Thr Ile Thr Gln Leu Val
            100                 105                 110

Ser Pro Pro Glu Ala Pro Gly Asn Leu Leu Ala Asp Thr Gly Gly Ile
        115                 120                 125

Gly Lys Ser Gly Ile Gln Ser Gly Glu Glu Val Pro Val Thr Leu Arg
130                 135                 140

Gln Ser Leu Val Ser Ile Ser Asp Ser Ser Cys Leu Ser Glu Ser Leu
145                 150                 155                 160

Glu Asp Leu Asn Ile Asp Glu Arg Val Gly Ala Leu Leu Gly Gly Phe
                165                 170                 175

Thr Val Val Pro Gly Arg Glu Leu Glu Thr Ile Gly Glu Val Leu Gln
            180                 185                 190

Met Thr Phe Glu His Ala Pro Trp Glu Lys Trp Glu Lys Ser Glu Gly
        195                 200                 205

Phe Thr Trp Asn Gln Ala Cys Ile Ser Glu Gln His Gly Glu Asp Asn
    210                 215                 220

Asp Glu Leu Ser Gly Tyr Ser Glu Met Lys Ala Lys Asp Ala Val Glu
225                 230                 235                 240

Met Arg Ser Ser Ala Ile Ser Glu Lys Asp Gln Gly Ser Val Cys Leu
                245                 250                 255

Val Asp Ala Ala Asp Trp Phe Ser Gly Arg Trp Ser Cys Lys Gly Gly
            260                 265                 270

Asp Trp Lys Arg Asn Asp Asp Thr Val Gln Asp Arg Phe Ser Arg Arg
        275                 280                 285

Lys Leu Val Leu Asn Asp Gly Phe Pro Leu Cys Gln Met Ala Lys Ser
    290                 295                 300

Gly Ser Glu Asp Pro Arg Trp His Arg Lys Asp Leu Tyr Tyr Pro
305                 310                 315                 320

Ser Gln Ser Arg Arg Leu Asp Leu Pro Pro Trp Ala Phe Ser Cys Pro
                325                 330                 335

Asp Glu Arg Asn Glu Cys Gly Gly Val Ser Arg Leu Thr Val Ala Lys
            340                 345                 350

Pro Pro Ile Pro Val Val Arg Gly Val Lys Gly Thr Met Leu Pro Val
```

-continued

```
                355                 360                 365
Val Arg Ile Asn Ala Cys Val Val Lys Asp His Gly Ser Phe Val Ser
            370                 375                 380
Glu Pro Arg Thr Lys Val Arg Gly Lys Asp Arg Tyr Pro Leu Arg Ser
385                 390                 395                 400
Ala Arg Ala Tyr Ser Ala Ala Asn Asp Gly Lys Arg Leu Thr Ala Glu
                405                 410                 415
Gly Asp Phe His Ser Lys Thr Asp Gln Asp Ser His Gly Ser Trp Lys
            420                 425                 430
Ser Ile Ser Ser Ile Asn Ile Pro Lys Asp Arg Leu Cys Thr Val Asp
            435                 440                 445
Asp Leu Gln Leu His Leu Gly Glu Trp Tyr Tyr Phe Asp Gly Ser Gly
        450                 455                 460
His Glu Arg Gly Pro Ser Ser Phe Leu Glu Leu Gln Val Leu Ala Asp
465                 470                 475                 480
Gln Gly Ser Ile Gln Lys Cys Ser Ser Ala Phe Arg Lys Phe Asp Arg
                485                 490                 495
Val Trp Val Pro Ile Thr Pro Ala Thr Glu Thr Ser Glu Ser Thr Val
            500                 505                 510
Lys Leu Gln Lys Glu Asn Leu Ala Val Cys Gly Asp Ser Ser Ala Ser
            515                 520                 525
Val Leu Gln Leu Gln Ser Ala Ala Thr Asn Glu Ser Asn Thr Asn Ser
        530                 535                 540
Ile Ser Phe His Ser Leu His Pro Gln Phe Ile Gly Tyr Thr Arg Gly
545                 550                 555                 560
Lys Leu His Glu Leu Val Met Lys Ser Tyr Lys Ser Arg Asp Phe Ala
                565                 570                 575
Ala Ala Ile Asn Asp Val Leu Asp Pro Trp Ile Asn Ala Lys Gln Pro
            580                 585                 590
Lys Lys Glu Thr Asp Asn His Ile Tyr Arg Lys Ser Glu Ile Asp Ala
            595                 600                 605
Arg Ala Gly Lys Arg Ala Arg Leu Gln Leu Asp Gly Ser Asp Tyr Asp
        610                 615                 620
Tyr Asp Met Asp Glu Asp Leu Gln Thr Ile Gln Arg Asp Asp Ala Ser
625                 630                 635                 640
Phe Glu Glu Leu Cys Gly Asp Ala Thr Phe Asn Gly Glu Ser Ser Ala
                645                 650                 655
Pro Ser Glu Thr Glu Leu Gly Ser Trp Gly Leu Leu Asp Gly His Met
            660                 665                 670
Leu Ala Arg Val Phe His Phe Leu Arg Ser Asp Met Lys Ser Leu Val
            675                 680                 685
Phe Ala Ser Leu Thr Cys Lys His Trp Arg Ala Ala Ser Phe Tyr
        690                 695                 700
Lys Asp Ile Ser Arg Gln Val Asp Leu Ser His Leu Gly Pro Asn Cys
705                 710                 715                 720
Ser Asp Leu Ile Met Trp Asn Ile Met Asn Gly Tyr Asn Lys Glu Arg
                725                 730                 735
Ile Asn Ser Met Val Leu Leu Gly Cys Thr Asn Ile Thr Ser Gly Leu
            740                 745                 750
Val Glu Asp Ile Leu Arg Thr Phe Pro Cys Leu Ser Ser Val Asp Ile
            755                 760                 765
Arg Gly Cys Ser Gln Leu Lys Glu Leu Pro Leu Lys Phe Pro Asp Leu
        770                 775                 780
```

```
Ser Trp Ile Arg Thr Arg Gly Ser Arg Gly Ile Asp Val Ser Glu Asp
785                 790                 795                 800

Ser Tyr Ser Lys Ile Arg Ser Leu Lys Gln Ile Ser Glu Thr Pro Thr
            805                 810                 815

Phe Cys Ser Asp Ala Asp Asp Phe Gly Glu Leu Lys Tyr Phe Asn
        820                 825                 830

Ser Val Asn Lys Arg Asp Ser Ala Asn Gln Leu Phe Arg Arg Ser Leu
            835                 840                 845

Tyr Lys Arg Ser Lys Leu Phe Asp Ala Arg Lys Ser Ser Ile Leu
        850                 855                 860

Ser Arg Asp Ala Arg Ile Arg Arg Trp Ala Met Lys Lys Ser Glu Ser
865                 870                 875                 880

Gly Tyr Arg Arg Met Glu Gly Phe Leu Ala Ser Gly Leu Lys Asp Ile
                885                 890                 895

Met Lys Glu Asn Thr Phe Glu Phe Val Pro Lys Val Ala Glu Ile
            900                 905                 910

Glu Asp Arg Met Lys Asn Gly Tyr Tyr Ile Gly His Gly Leu Arg Ser
            915                 920                 925

Val Lys Glu Asp Ile Ser Arg Met Cys Arg Asp Ala Ile Lys Ala Lys
            930                 935                 940

Asn Arg Gly Ala Gly Asp Met Asn His Ile Ile Thr Leu Phe Leu Lys
945                 950                 955                 960

Leu Ala Ser Arg Leu Glu Asp Ser Ser Lys Phe Ser Tyr Glu Arg Asp
                965                 970                 975

Gln Leu Met Lys Ser Trp Lys Asp Leu Ser Ala Gly Leu Gly Tyr
            980                 985                 990

Thr Pro Met Lys Tyr Lys Lys Lys Leu Ile Met Glu Lys Lys Asn Thr
            995                 1000                1005

Ile Arg Ser Asn Gly Thr Gly Tyr Ala Asn Gly Ser Cys Tyr His Gly
        1010                1015                1020

Glu Tyr Ala Ser Asp Arg Glu Ile Arg Arg Leu Ser Lys Leu Asn
1025                1030                1035                1040

Arg Lys Ser Ile Asp Ser Gly Ser Glu Thr Ser Asp Phe Asp Lys
                1045                1050                1055

Ser Ser Glu Asp Gly Arg Ser Asp Ser Glu Ser Thr Ala Ser Tyr Thr
            1060                1065                1070

Gly Ser Asp Leu Asp Phe Arg Ser Glu Ala Arg Ser Val Glu Ser Ile
        1075                1080                1085

Gly Glu Gly Phe Phe Met Gly Asp Glu Gly Leu Asp Ser Ile Thr Asp
        1090                1095                1100

Asp Arg Glu Trp Gly Ala Arg Met Thr Lys Ala Ser Leu Val Pro Pro
1105                1110                1115                1120

Val Thr Arg Lys Tyr Glu Val Ile Asp Gln Tyr Val Ile Val Ala Asp
            1125                1130                1135

Glu Glu Asp Val Gln Arg Lys Met Cys Val Ser Leu Pro Asp Asp Phe
            1140                1145                1150

Ala Glu Lys Leu Asp Ala Gln Lys Asn Gly Thr Glu Glu Leu Asp Met
        1155                1160                1165

Glu Leu Pro Glu Val Lys Asp Tyr Lys Pro Arg Lys Gln Leu Gly Asp
            1170                1175                1180

Glu Val Ile Glu Gln Glu Val Tyr Gly Ile Asp Pro Tyr Thr His Asn
1185                1190                1195                1200
```

-continued

Leu Leu Leu Asp Ser Met Pro Glu Glu Leu Asp Trp Pro Leu Ser Glu
            1205                1210                1215

Lys His Ser Phe Ile Glu Asp Met Leu Leu Gln Thr Leu Asn Lys Gln
            1220                1225                1230

Val Arg Asn Phe Thr Gly Ser Gly Asn Thr Pro Met Met Tyr Pro Leu
            1235                1240                1245

Leu Pro Val Ile Glu Asp Ile Glu Lys Ala Ala Glu Glu Cys Asp
        1250                1255                1260

Val Arg Thr Met Lys Met Cys His Gly Ile Leu Lys Ala Ile Ala Ser
1265                1270                1275                1280

Arg Pro Asp Asp Asn Tyr Val Ala Tyr Arg Lys Gly Leu Gly Val Val
            1285                1290                1295

Cys Asn Lys Gln Gly Gly Phe Gly Glu Asp Phe Val Val Glu Phe
            1300                1305                1310

Leu Gly Glu Val Tyr Pro Ala Trp Lys Trp Phe Glu Lys Gln Asp Gly
            1315                1320                1325

Ile Arg Ser Leu Gln Lys Asp Asn Lys Asp Pro Ala Pro Glu Phe Tyr
        1330                1335                1340

Asn Ile Asn Leu Glu Arg Pro Lys Gly Asp Ala Asp Gly Tyr Asp Leu
1345                1350                1355                1360

Val Val Val Asp Ala Met His Lys Ala Asn Tyr Ala Ser Arg Ile Cys
            1365                1370                1375

His Ser Cys Arg Pro Asn Cys Glu Ala Lys Val Thr Ala Val Asp Gly
            1380                1385                1390

Gln Tyr Gln Ile Gly Ile Tyr Thr Val Arg Glu Ile Gln Tyr Gly Glu
            1395                1400                1405

Glu Ile Thr Phe Asp Tyr Asn Ser Val Thr Glu Ser Lys Glu Glu Tyr
        1410                1415                1420

Glu Ala Ser Val Cys Leu Cys Gly Ser Gln Val Cys Arg Gly Ser Tyr
1425                1430                1435                1440

Leu Asn Leu Thr Gly Glu Gly Ala Phe Gln Lys Val Leu Lys Glu Trp
            1445                1450                1455

His Ala Met Leu Asp Arg His His Leu Met Leu Glu Ala Cys Glu Leu
            1460                1465                1470

Asn Ser Val Ser Glu Glu Asp Tyr Leu Asp Leu Gly Arg Ala Gly Leu
            1475                1480                1485

Gly Ser Cys Leu Leu Gly Gly Leu Pro Asp Trp Val Val Ala Tyr Ser
        1490                1495                1500

Ala Arg Leu Val Arg Phe Ile Asn Leu Glu Arg Thr Lys Leu Pro Glu
1505                1510                1515                1520

Glu Ile Leu Arg His Asn Leu Glu Glu Lys Arg Lys Tyr Phe Ser Asp
            1525                1530                1535

Ile Cys Leu Glu Val Glu Arg Ser Asp Ala Glu Val Gln Ala Glu Gly
            1540                1545                1550

Val Tyr Asn Gln Arg Leu Gln Asn Leu Ala Val Thr Leu Asp Lys Val
            1555                1560                1565

Arg Tyr Val Met Arg Cys Leu Phe Gly Asp Pro Lys Lys Ala Pro Pro
        1570                1575                1580

Pro Leu Val Arg Leu Ser Pro Glu Glu Thr Val Ser Phe Leu Trp Lys
1585                1590                1595                1600

Gly Glu Gly Ser Leu Val Glu Glu Leu Leu Gln Cys Met Ala Ser His
            1605                1610                1615

Val Glu Ala Asp Met Leu Asn Asp Leu Lys Ser Lys Ile Arg Ala Arg

```
                        1620                1625                1630
Asp Leu Ser Glu Ser Asp Asn Ile Gln Lys Glu Leu Gln Lys Ser Leu
            1635                1640                1645

Phe Trp Leu Arg Asp Glu Val Arg Ala Leu Pro Cys Thr Tyr Lys Cys
        1650                1655                1660

Arg His Asp Ala Ala Asp Leu Ile His Val Tyr Ala His Thr Lys
1665                1670                1675                1680

Cys Phe Phe Lys Val Gln Glu Tyr Lys Thr Phe Thr Ser Pro Pro Val
                1685                1690                1695

His Ile Ser Pro Leu Asp Leu Gly Pro Lys Tyr Ala Asp Lys Leu Gly
            1700                1705                1710

Ala Gly Ile His Glu Tyr Arg Lys Thr Tyr Gly Glu Asn Tyr Cys Leu
        1715                1720                1725

Gly Gln Leu Ile Tyr Trp His Ile Gln Thr Asn Ala Glu Pro Asp Cys
    1730                1735                1740

Ser Leu Ala Lys Ala Ser Arg Gly Cys Leu Ser Leu Pro Glu Ile Gly
1745                1750                1755                1760

Ser Cys Tyr Ala Lys Val Gln Lys Pro Ser Gln Gln Arg Ile Tyr Gly
                1765                1770                1775

Pro Lys Thr Val Lys Leu Leu Leu Glu Arg Met Glu Lys Tyr Pro His
            1780                1785                1790

Lys Pro Trp Pro Lys Asp Gln Ile Trp Ser Phe Lys Ser Cys Pro Lys
        1795                1800                1805

Val Ile Gly Ser Pro Met Leu Asp Ala Val Leu Ser Asn Cys Pro Leu
    1810                1815                1820

Asp Arg Glu Leu Val His Trp Leu Lys His Arg Pro Thr Ile Tyr Gln
1825                1830                1835                1840

Ala Val Trp Asp Arg
            1845

<210> SEQ ID NO 108
<211> LENGTH: 2459
<212> TYPE: PRT
<213> ORGANISM: Triticum urartu

<400> SEQUENCE: 108

Met Gly Asp Gly Gly Val Ala Cys Ala Val Pro Pro Gln Arg Ala Val
1               5                   10                  15

Glu Gly Phe Arg Ala Asp Ala Leu Val Arg Gly Glu Ala Met Pro Asn
            20                  25                  30

Lys Gly Glu Lys Ala Ala His Gly His His His His His His His
        35                  40                  45

His His Arg Lys His Tyr Ser Ala Ser Ala Ala Asp Leu Glu Glu Gly
    50                  55                  60

Glu Leu Leu Leu Asn Gly Glu Ala Asp Asn Thr Arg Asp Leu Asp Arg
65                  70                  75                  80

Thr Ile Pro Pro Lys Lys Trp Arg Lys Leu Leu Pro Ser Ser Pro Ala
                85                  90                  95

Ala Glu Leu Glu Pro Gly Glu Ile Val Ser Met Gln Ser Glu Pro Thr
            100                 105                 110

Arg Lys Ile Arg Arg Asn Val Glu Leu Asp Lys Thr Glu Phe Val Pro
        115                 120                 125

Val Thr Gln Arg Lys Gly Lys Ser Asp Lys Ile Gly Arg Lys Ser Asn
    130                 135                 140
```

```
Lys Asp Val Val Glu Pro Ala Glu Val Thr Pro Leu Gly Lys Lys Arg
145                 150                 155                 160

Asp Arg Asp His Ser Gly Lys Ile Cys Leu Ser Ala His Ile Arg Glu
            165                 170                 175

Asp Gly Lys Lys Gly Thr Ser Arg Asp Ser Asp Glu Glu Pro Gly Glu
            180                 185                 190

Ile Lys Pro Glu Ser Ser Thr Gly Ser Ala Arg Lys Ser Gln Ala
        195                 200                 205

Val Glu Pro Glu Ser Asn His Arg Lys His Gln Ala Glu Thr Phe Thr
    210                 215                 220

Gln Ser Gly Ser Arg Ser Arg Arg Lys Gly Glu Pro Lys Thr Ser Ser
225                 230                 235                 240

Gly Gly Lys His Leu Ser Gly Arg Asn His Asp Ile Leu Pro Gln Ile
            245                 250                 255

Arg Asp Arg His Asp Arg Leu Glu Arg Ser Pro Gly Ile Leu Gly Arg
            260                 265                 270

Phe Pro His Asp Arg Ile Arg His Glu Arg Ser Pro Gly Arg Met Glu
        275                 280                 285

Arg Ser Pro Arg Asp Arg Asp Arg Gly Arg His Cys Asp Asn Arg Asp
290                 295                 300

Arg Ser Pro Tyr Ile Ser Pro Arg His Arg Ala Arg Gln Ala His His
305                 310                 315                 320

Arg Asp Asn Thr Pro Ser Arg Ile Asp Asn Ser Pro Arg Gly Arg Thr
            325                 330                 335

Gln His Glu Asp Ile Arg Asp Arg Thr Ala Leu Ser His Asp Lys Ser
        340                 345                 350

Pro Ser Glu Arg Gly Arg Thr Thr Asp Ile His Glu Ala Ser Lys Lys
        355                 360                 365

Ser Arg Gly Ala Lys Leu Glu Ser Asn Asn Leu Glu Asn Val Pro His
    370                 375                 380

Lys Asn Lys Ser Met Lys Gln Pro Thr Lys Ser Asn Ser Gly Ser Asn
385                 390                 395                 400

Ile Lys Ser Glu Glu Arg Ile Ser Lys Gly Lys Ala Ser Glu Gly Val
            405                 410                 415

Gln Cys Thr Glu Leu Leu Pro Pro Pro Leu Pro Pro Pro Pro
        420                 425                 430

Pro Pro Pro Pro Pro Pro Leu Pro Pro Asn Met Pro Pro Pro Leu
        435                 440                 445

Pro Pro Pro Pro Val Pro Glu Gln Leu Asn Asp Leu Ala Glu Asp Ala
    450                 455                 460

Ser Met Glu Glu Asp Met Asp Ile Cys Asp Thr Pro His Thr Ser
465                 470                 475                 480

Glu Ala Pro Glu Leu Ser Thr Glu Pro Thr Ile Ile Met Gly Lys Trp
            485                 490                 495

Phe Tyr Leu Asp Gln Phe Gly Val Glu Gln Gly Pro Thr Lys Leu Ala
        500                 505                 510

Asp Leu Lys Lys Leu Val Glu Asp Gly Tyr Leu Leu Ser Asp His Leu
        515                 520                 525

Ile Lys His Ala Asp Ser Asn Arg Trp Val Thr Val Glu Asn Ala Ala
        530                 535                 540

Ser Pro Leu Val Pro Ser Asp Ile Pro Leu Val Tyr Ala Asp Leu Ser
545                 550                 555                 560

Ser Gln Lys Val Ser Pro Pro Glu Ala Pro Gly Asn Leu Leu Asp Glu
```

```
                    565                 570                 575
Ala Arg Glu Gly Ala Ala Leu Leu Ala Trp Ser Ala Glu Asp Glu Glu
                580                 585                 590

Glu Ala Ser Glu Glu Gln Lys Glu Asp Leu Tyr Ile Asp Asn Arg Val
                595                 600                 605

Glu Ala Leu Met Tyr Gly Ala Thr Met Val Asp Gly His Glu Leu Asp
            610                 615                 620

Ile Leu Gly Glu Val Leu Asp Ala His Phe Glu Pro Val Asp Trp Glu
625                 630                 635                 640

Arg Cys Ser Tyr Pro Glu Asp Phe Pro Arg Phe Gln Gly Gln Pro Ala
                645                 650                 655

Arg Asp Asp Gly Ile Asn Arg Ser Ile Gly Phe Val Ser Gly Val Gly
                660                 665                 670

Pro Val Gly Arg Glu Lys Phe Tyr His Asn Val Glu Cys Ser Glu Trp
            675                 680                 685

Phe Ser Gly Arg Trp Ser Cys Lys Gly Gly Asp Trp Lys Arg Asn Asp
        690                 695                 700

Glu Phe Asn Gln Asp Lys Pro Tyr Arg Lys Lys Leu Val Leu Asn Glu
705                 710                 715                 720

Gly Tyr Ala Leu Cys Gln Met Leu Lys Gly Asn His Glu Asp Pro Arg
                725                 730                 735

Trp His Cys Lys Glu Asp Leu Tyr Tyr His Val Pro Ala Lys Lys Leu
            740                 745                 750

Asp Leu Pro Leu Trp Ala Phe Ser Ser Thr Glu Glu Asp Thr Asp Ser
        755                 760                 765

Val Asp Asp Ala Ser Ala Ile Ile Pro Gly Arg Leu Cys Gln Asn Gln
770                 775                 780

Ile Arg Gln Leu Pro Lys Gly Val Lys Gly Met Thr Leu Pro Val Val
785                 790                 795                 800

Lys Ile Asn Ala Arg Val Val Lys Asp Gln Ser Ser Ile Glu Pro Cys
                805                 810                 815

Ile Lys Ser Arg Ala Ala Glu Arg Ser Leu Ser Arg Ser Ser Arg Ser
            820                 825                 830

His Ser Thr Gly Thr Asp Arg Asn Ser Val His Glu Gly Leu Ser His
        835                 840                 845

Phe Lys Lys His His Glu His Asp Leu Gln Ser Leu Gln Lys Ser Lys
    850                 855                 860

Ser Val Pro Asn Ile Pro Glu Asp His Val Cys Thr Val Glu Glu Leu
865                 870                 875                 880

Ser Val Lys Leu Gly Asp Trp Tyr Tyr Met Asp Gly Thr Gly His Glu
                885                 890                 895

His Gly Pro Phe Ser Tyr Ser Glu Leu Gln Lys Leu Val Lys Lys Gly
            900                 905                 910

Thr Ile Ile Glu Gln Ser Ser Val Phe Arg Lys Ile Asp Asn Thr Trp
        915                 920                 925

Leu Pro Val Val Lys Asp Met Lys Ser Glu Ser Ala Ala Arg Asp Gly
    930                 935                 940

Gly Pro Gly Ser Ser Asp Ser Thr Ser Ala Leu Val Glu Gln Ser Asn
945                 950                 955                 960

Thr Val Val Asn His Gly Ala Gly Arg Phe His Glu Leu His Pro Gln
                965                 970                 975

Phe Val Gly Tyr Thr Arg Gly Lys Leu His Glu Leu Val Met Lys Tyr
            980                 985                 990
```

-continued

```
Phe Lys Ser Arg Glu Leu Thr Leu Ala Ile Asn Glu Val Leu Asp Pro
    995                 1000                1005

Trp Ile Ala Ala Lys Gln Pro Lys Lys Glu Ile Glu Met Asn Phe Leu
    1010                1015                1020

Asn Asn Ser Ala Ser Arg Lys Ile Leu Pro Glu Asp Ala Gly Ser Val
1025                1030                1035                1040

Lys Arg Ala Arg Leu Leu Pro Asn Gln Ser Asp Glu Gly Ile Asn Met
                1045                1050                1055

Tyr Glu Asp Ile Leu Ala Ser Gln Asn Asp Asp Cys Ser Phe Glu Asp
                1060                1065                1070

Leu Cys His Asp Ala Ala Leu Val Glu Glu Asn Ser Thr Asn Ser Val
            1075                1080                1085

Ala Gly Ser Asp Ser Trp Gly Leu Leu Asn Val His Val Leu Ala Arg
        1090                1095                1100

Ile Phe His Phe Leu Arg Ala Asp Met Lys Ser Leu Ile Ser Ser Ala
1105                1110                1115                1120

Ala Thr Cys Lys Leu Trp Asn Thr Gly Val Gln Tyr Tyr Arg Asn Thr
                1125                1130                1135

Cys Arg Phe Val Asp Phe Ser Ser Val Gly Leu Gln Cys Thr Asp Ser
                1140                1145                1150

Val Phe His Gly Ile Met Ala Gly Tyr Glu Lys Gln Asn Ile Arg Thr
            1155                1160                1165

Leu Ile Leu Val Gly Cys Ser Asn Leu Ser Ser Leu Ala Leu Gly Glu
        1170                1175                1180

Val Leu Val Gln Phe Pro Asn Ile Cys Tyr Val His Ile Gln Gly Cys
1185                1190                1195                1200

Ser Gln Leu Trp Asp Met Lys Ser Arg Phe His His Ile Lys Trp Ile
                1205                1210                1215

Lys Ser Ser Leu Asn Pro Glu Glu Ser Leu Gln Lys Ile Lys Ser Leu
                1220                1225                1230

Lys Gln Ile Asp Asp Gly Asn Asp Tyr Ala Ser Lys Val Ala Arg Asn
                1235                1240                1245

Leu Thr Ser Gln Leu Gly Gly Ser Asp Glu Leu Asp Gly Tyr Phe Ala
            1250                1255                1260

Asp Ile Ser Asn Arg Glu Asn Ala Asn Leu Ser Phe Gly Gln Gly Phe
1265                1270                1275                1280

Tyr Lys Arg Ser Lys Trp Leu Asp Ala Arg Lys Ser Ser Ala Val Leu
                1285                1290                1295

Ser Lys Asp Ala Gln Leu Arg Arg Leu Met Gln Arg Lys Ala Glu Asn
            1300                1305                1310

Ser Tyr Arg Lys Met Glu Glu Phe Val Ile Asn Arg Leu Arg Glu Ile
            1315                1320                1325

Met Lys Ser Ser Arg Phe Asp Phe Phe Ile Pro Lys Val Ala Lys Ile
            1330                1335                1340

Glu Gly Arg Leu Lys Ser Gly Tyr Tyr Ala Arg His Gly Phe Ser Ser
1345                1350                1355                1360

Leu Lys Asn Asp Ile Arg Ser Met Cys Arg Asp Ala Leu Arg Tyr Lys
                1365                1370                1375

Gly Arg Ser Asp Leu Gly Asp Met Lys Gln Ile Val Val Ser Phe Ile
            1380                1385                1390

Gln Leu Ala Lys Arg Leu Gly Asn Pro Arg Leu Ile Ser Glu Arg Asp
        1395                1400                1405
```

```
Gly Ala Val Ala Gln Lys Asp Asn Ser Asp Thr Ser Gln Tyr Ser Ser
    1410                1415                1420

Asp Ala Lys Leu Lys Lys Gln Asn Lys Thr Thr Gly Glu Arg Arg
1425                1430                1435                1440

Gly Ala Asn Trp Ala Thr Ala Ser Ala Gly Ala Asp Ala Ser Ser Arg
                1445                1450                1455

Ala Phe Asp Arg Glu Ile Lys Arg Ser Leu Ser Lys Leu Lys Lys Met
        1460                1465                1470

Asp Val Asp Ser Gly Ser Glu Thr Ser Asp Asp Asp Gly Tyr Ser
            1475                1480                1485

Glu Gly Asp Glu Thr Glu Ser Glu Thr Thr Val Ser Asp Thr Glu Ser
        1490                1495                1500

Asp Leu Asp Ser Asn Ser Ala Ala Trp Asp Leu Arg Gly Asn Gly Met
1505                1510                1515                1520

Lys Leu Phe Glu Ser Gly Asp Ser Val Gly Asp Asp Arg Gly Trp Gly
                1525                1530                1535

Ala Arg Met Thr Lys Ala Ser Leu Val Pro Pro Val Thr Arg Lys Tyr
        1540                1545                1550

Glu Val Ile Glu Lys Tyr Leu Ile Val Ala Asp Glu Glu Val Gln
            1555                1560                1565

Arg Lys Met Arg Val Ala Leu Pro Asp Asp Tyr Ser Glu Lys Leu Leu
        1570                1575                1580

Ser Gln Lys Asn Gly Thr Glu Asn Leu Glu Ile Pro Glu Val Lys Asp
1585                1590                1595                1600

Tyr Gln Arg Arg Lys Val Pro Gly Asp Glu Val Leu Glu Gln Glu Val
            1605                1610                1615

Tyr Gly Ile Asp Pro Tyr Thr His Asn Leu Leu Arg Asp Ile Met Pro
        1620                1625                1630

Ala Asp Val Gly Leu Ser Ser Ala Asp Lys His Thr Phe Ile Glu Glu
            1635                1640                1645

Gly Leu Gly Val Val Cys Asn Lys Lys Gly Phe Gly Met Asp Asp
        1650                1655                1660

Phe Val Ile Glu Phe Phe Gly Glu Val Tyr Pro Ser Trp Arg Trp Tyr
1665                1670                1675                1680

Glu Lys Gln Asp Gly Ile Lys His Ile Gln Asn Asn Ser Glu Asp Gln
            1685                1690                1695

Ala Pro Glu Phe Tyr Asn Ile Met Leu Glu Arg Pro Lys Gly Asp Arg
        1700                1705                1710

Asp Gly Tyr Asp Leu Val Phe Val Asp Ala Met His Lys Ala Asn Tyr
            1715                1720                1725

Ala Ser Arg Ile Cys His Ser Cys Asn Pro Asn Cys Glu Ala Lys Val
        1730                1735                1740

Thr Ala Val Asp Gly Gln Tyr Gln Ile Gly Val Tyr Thr Val Arg Pro
1745                1750                1755                1760

Ile Ala Glu Gly Glu Glu Ile Thr Phe Asp Tyr Asn Ser Val Thr Glu
                1765                1770                1775

Ser Lys Glu Glu His Glu Ala Ser Val Cys Leu Cys Gly Ser Gln Val
            1780                1785                1790

Cys Arg Gly Ser Tyr Leu Asn Phe Ser Gly Glu Gly Ala Phe Glu Lys
        1795                1800                1805

Ala Cys Glu Ala Asn Thr Val Ser Gln Gln Asp Leu Ile Asp Leu Gly
        1810                1815                1820

Arg Ala Gly Leu Gly Thr Cys Leu Leu Ala Gly Leu Pro Gly Trp Leu
```

-continued

```
        1825                1830                1835                1840

Val Ala Tyr Thr Ala Gln Leu Val Arg Phe Ile Phe Glu Arg Gln
                1845                1850                1855

Lys Leu Pro Asn Glu Ile Phe Lys His Asn Met Glu Glu Lys Arg Gln
                1860                1865                1870

Phe Phe Thr Asp Ile Asn Met Asp Ser Glu Arg Asn Asp Ala Glu Val
                1875                1880                1885

Gln Ala Glu Gly Val Leu Asn Ser Arg Leu Gln His Leu Thr His Thr
                1890                1895                1900

Leu Asp Lys Val Arg Tyr Val Met Arg Cys Ile Phe Gly Asp Pro Lys
1905                1910                1915                1920

Asn Ala Pro Pro Pro Leu Val Arg Leu Thr Gly Arg Ser Leu Val Ser
                1925                1930                1935

Ala Ile Trp Lys Gly Glu Gly Ser Leu Val Asp Glu Leu Leu Gln Ser
                1940                1945                1950

Ile Glu His His Val Asp Glu Asp Val Leu Thr Asp Leu Lys Asp Lys
                1955                1960                1965

Ile Arg Leu His Asp Pro Ser Asp Ser Glu Asp Ile Asp Gly Asp Ile
                1970                1975                1980

Arg Asn Ser Leu Leu Trp Leu Arg Asp Glu Leu Arg Thr Leu Ser Cys
1985                1990                1995                2000

Thr Tyr Lys Cys Arg His Asp Ala Ala Ala Asp Leu Ile His Met Tyr
                2005                2010                2015

Ala Tyr Thr Lys Cys Phe Phe Arg Ala Arg Asp Tyr Lys Thr Val Lys
                2020                2025                2030

Ser Pro Pro Val His Ile Ser Pro Leu Asp Leu Gly Pro Lys Tyr Ala
                2035                2040                2045

Asp Lys Leu Gly Pro Gly Phe Gln Glu Tyr Ser Lys Thr Tyr Pro Glu
                2050                2055                2060

Asn Tyr Cys Leu Ala Gln Leu Ile Tyr Trp Tyr Ser Gln Asn Ala Glu
2065                2070                2075                2080

Pro Glu Ser Arg Leu Thr Arg Ala Arg Lys Gly Cys Met Ser Leu Pro
                2085                2090                2095

Asp Val Ser Ser Phe Tyr Val Lys Ser Val Lys Pro Thr Gln Glu Arg
                2100                2105                2110

Val Tyr Gly Thr Arg Thr Val Arg Phe Met Leu Ser Arg Met Glu Lys
                2115                2120                2125

Gln Ala Gln Arg Pro Trp Pro Lys Asp Arg Ile Trp Val Phe Lys Ser
                2130                2135                2140

Asp Pro Arg Phe Phe Gly Thr Pro Met Met Asp Ala Val Leu Asn Asn
2145                2150                2155                2160

Asn Ser Pro Leu Asp Lys Glu Met Arg Arg Met Asp Gly Asp Ser
                2165                2170                2175

Ser Cys Gly Gly Ser Gly Gly Glu Arg Gly Ser Thr Pro Gln Pro Gln
                2180                2185                2190

Lys His Ala Ser Ala Gly Ile Asp Pro Asp Arg Ala Val Gly Met Glu
                2195                2200                2205

Cys Arg Met Glu Thr Thr Leu Leu Ala Arg Asp Gly Thr Lys Ala Thr
                2210                2215                2220

Asn Thr Arg Phe Ser Phe Pro Phe Val Ala Asp Asn Gln Trp Thr Phe
2225                2230                2235                2240

Asn Gln Phe Arg Ser Ala Ile Cys Ala Gln Tyr Pro Trp Gly Leu Tyr
                2245                2250                2255
```

Asp Ala Val Glu Phe Arg Tyr Trp Ala Ile Asp Lys Thr Ala Trp Val
            2260                2265                2270

Pro Val Gln Cys Asp Asp Glu Leu Gly Ser Met Phe Ala Ile His Ala
    2275                2280                2285

Ser Phe Pro Ala Lys Leu Glu Ile Ser Val Ile Gln Arg Lys Arg Gly
    2290                2295                2300

Glu Ser Glu Ser Arg Gly Thr Arg Ser Gln Ser Arg Ser Arg Asp Lys
2305                2310                2315                2320

Gly Arg Thr Ser Gln Ser Arg Gly Met Lys Arg Asn Ala His Ser Arg
        2325                2330                2335

Gly Ser Ser Ser Ser Met Gln Ala Pro Gly Thr Pro Ala Val Glu Val
            2340                2345                2350

Pro Asn Asn Ala Gly Pro Ser His Ser Arg Asp Ser Val Asp Pro Tyr
        2355                2360                2365

Thr Glu Glu Gly Leu Pro Asp Asp Arg Ser Ser Asp Asp Glu Asp Glu
    2370                2375                2380

Lys Leu Phe Pro Gln Phe Val Thr Arg Lys Lys Gly Lys Glu Lys Asp
2385                2390                2395                2400

Asp Glu Gly Glu Asp Tyr Val Pro Pro Lys Gly Met Phe Asp Val
            2405                2410                2415

Leu Ile Ser Phe Phe Ala Ala Phe Asn Val Leu Val Ser Val Ala
            2420                2425                2430

Gln Gly Arg Thr Thr Lys Arg Gln Leu Ile Glu Gly Cys His Gln Pro
        2435                2440                2445

Arg Arg Asp Ser Ile Leu His Gln Ile Leu Gln
    2450                2455

<210> SEQ ID NO 109
<211> LENGTH: 1832
<212> TYPE: PRT
<213> ORGANISM: Triticum aestivum

<400> SEQUENCE: 109

Met Val Asp Lys Ala Ala Glu Thr Ser Gln Arg Glu Val Ala Ala Glu
1               5                   10                  15

Gly Val Val Leu Trp Asp Glu Ala Leu Val Lys Thr Ser Pro Glu Asp
            20                  25                  30

Leu Gln Met Arg Cys Lys Glu Leu Arg Cys Tyr Asn Asp Ile Thr Val
        35                  40                  45

Met Cys Leu Lys Lys Asp Val Asn Cys Asp Leu Glu Lys Asp Gly Leu
    50                  55                  60

Trp Pro Lys Ile Glu Ala Glu Val Ser Thr Pro Ala His Gln Asp Ser
65                  70                  75                  80

Val Pro Leu Asn Phe Gly Cys Asn Leu Ala Val Cys Leu Asp Gly Lys
                85                  90                  95

Ala Gly Glu Ile Gly Glu Val Ser Glu His Arg Thr Gly Met Glu Arg
            100                 105                 110

Ala Ala Cys Gly Ser Gln Gly Gly Met Leu Ser Phe Asp Arg Gly
        115                 120                 125

Phe Trp Lys Gly Ala Val Gly Asp Lys Asn Gln Phe Pro Arg Met Glu
    130                 135                 140

Gly Cys His Glu Asn Gly Gly Leu Ser Asp Leu Gly Asn His Asp Thr
145                 150                 155                 160

Asp Lys Phe Pro Gln Gly Ala Asp Ala Leu Ser Leu Ile Asp Asp Asn

```
              165                 170                 175
His Glu Leu Gly Arg Asp Cys Phe Leu Ala Asn Ile Asp Glu Glu Val
              180                 185                 190

Ser Phe Pro Val Asp Glu Ala Ser Ile Pro Ser Phe Tyr Gln Lys Ser
              195                 200                 205

Tyr Met Asp Val Phe Val Glu Asp Ser Lys Ser Cys Ile Glu Lys Leu
              210                 215                 220

Thr Gln Asp Ser Leu Glu Gly Asp Met Leu Ser Cys Glu Arg Asp Ala
225                 230                 235                 240

Arg Phe Arg Thr Glu Ala Ser Gly Asp Glu Asn Gln His His Arg Met
              245                 250                 255

Ala Val Ser Lys Gly Gln Val Ser Ser Ile Cys Lys Asp Ala Asn Ser
              260                 265                 270

Pro Ser Leu Asn Ala Cys Gly Leu Phe Pro Glu Ile Glu Val Leu Arg
              275                 280                 285

Gln Gln Ala Asp Lys Glu Tyr Lys Val Phe Glu Leu Pro Pro Glu Ile
              290                 295                 300

Tyr Leu Ala Arg Ser Ser Tyr Asn Pro Pro Cys Leu Asp Gly Leu Cys
305                 310                 315                 320

Arg Ser Gly Lys Glu Ser Ser Ala Val Cys Leu Gly His Gln Asp Ser
              325                 330                 335

Ser Gly Val Lys Ser Arg Cys Pro Asp His Leu Val Gln Glu Leu Asn
              340                 345                 350

Ala Tyr Asn Ser Ser Ile Asp Lys Pro Cys Ser Ala Asn Phe Val Glu
              355                 360                 365

Thr Ala Asn Asp Glu Glu Ser Gln Asn Lys Ile Ser Glu Ser Leu Asn
              370                 375                 380

Ala Ser Lys Arg Arg Asn Pro Arg Ala Ala Ser Ser Arg Asn Arg
385                 390                 395                 400

Ala Pro Ala Glu His Asp His Gln Ile Asn Lys Gly Ser Ser Ser Thr
              405                 410                 415

Cys Lys Ser Lys Lys Val Glu Ser Ser Cys Ser Leu Val Glu Ser Thr
              420                 425                 430

Leu Ile Lys Phe Pro Ser Lys Thr Thr Lys Val Arg Ser Gly Ile Asn
              435                 440                 445

Arg Pro Val Asn Ser Thr Ala Trp Gly Ser Leu Glu Lys Leu Val Asp
              450                 455                 460

Gly Phe Gly Gln Asn Cys Glu Pro Ser Thr Ser Asn Ser His Leu Ile
465                 470                 475                 480

Ser Leu Glu Asn Gly Gly Arg Ser Asn Lys Arg Ser Gly Lys Lys Glu
              485                 490                 495

Gln Pro Ile Val Arg Lys Ala Arg Ser Ser Arg Cys Pro Lys Asn Lys
              500                 505                 510

Phe Pro Ala Phe Ser Val Thr Arg Tyr Ala Pro Asp Glu Leu Asn Gly
              515                 520                 525

Glu Pro Thr Phe Ser Val Met Asp Gly Ala Tyr Gly Ser Ala Glu Gly
              530                 535                 540

Tyr Ile Gly Asn Phe Pro Lys Leu Ala Pro Arg Ala Phe Leu Asn Val
545                 550                 555                 560

Ser Asp Asp Ala His Arg Ser Val Gln His Met Ser Ile Gln Thr Asp
              565                 570                 575

Met Gln Gln Leu Asp Arg Cys Leu Asp Ser Val Ala Gln Glu Thr Cys
              580                 585                 590
```

```
Pro Ala Tyr Met Cys Gly Glu Phe Ala Lys Ser Ile Ser Glu Pro Ser
            595                 600                 605

Leu Asn Asn Gly Gly Val Gly Phe Ser Pro Asp Ser Val Leu Glu Val
610                 615                 620

Ala Ser Val Thr Cys Glu Asn Thr Ser Ala Ser His Asp Val Lys
625                 630                 635                 640

Leu Arg Gly Asn Pro Ser Tyr Pro Ala Val Leu Thr Glu Ser Asp Leu
                645                 650                 655

His Ala Ser Asp Leu Ser Ile Pro Asp Phe Gly Lys Asn His Ala Ser
                660                 665                 670

Ser Ser Thr Asp Phe Glu Gln Gln Pro Lys Thr Val Arg Gly Asp Glu
                675                 680                 685

Asn Thr Arg Ser Glu Glu Ile Asn Gln Ser His Ala Ile Ile Gly Tyr
            690                 695                 700

Val Gly Glu Gly Lys Val Gln Gly Leu Glu Lys Ser Asn Ala Val Arg
705                 710                 715                 720

Lys Thr Lys Met Leu Glu Lys Gln Lys Gly Arg Lys Lys Asp Gly Ile
                    725                 730                 735

Lys Gly Asn Asn Ile Arg Asp Gly Ser Ser Thr Lys Ile Ser Ser Ser
                740                 745                 750

Glu Ala Ser Lys Tyr Arg Val Phe Ser Asp Asp Pro Ser Ser Leu Val
                755                 760                 765

Ser Ser Gly Pro Leu Lys Phe Ser Ser Cys Phe Glu Val Val Thr Ser
770                 775                 780

Ala Thr Gln Gly Ile Ser Met His Glu His Gly Trp Val Gln Gly Pro
785                 790                 795                 800

Ser Val Ile Gly Lys Glu Lys Thr Ser Ala Leu Asn Asn Val Lys Ser
                805                 810                 815

Pro Arg Cys Lys Lys Ser Gly Gly Leu Arg Gly Lys Lys Asp Met Val
                820                 825                 830

Arg Asp Pro His Val Lys Gln Glu Ser Lys Lys Lys Asn Ile Ala Asp
                835                 840                 845

Ala Ile Phe Ile Asp Ser Gly Ser Ser Thr Leu Pro Tyr Gln Leu Ala
850                 855                 860

Thr Asp Leu Ala Thr Ser His Thr Asn Glu His Gly Tyr Arg Ser Pro
865                 870                 875                 880

Ala Ile Glu Tyr Thr Phe Gln Asn Pro Ala Ala Ile Ser Thr Glu Leu
                885                 890                 895

Pro Gly Asn Ala Ala Gly Ser Thr Gly Val Ser Val Pro Gln Pro
                900                 905                 910

Lys Arg Ala Ala Trp Ala Cys Cys Asp Asp Cys Gln Lys Trp Arg Cys
                915                 920                 925

Ile Pro Ser Glu Leu Ala Asp Val Ile Gly Glu Asn Arg Trp Thr Cys
930                 935                 940

Lys Asp Asn Asp Asp Lys Ala Phe Ala Asp Cys Ser Ile Pro Gln Ala
945                 950                 955                 960

Lys Thr Asn Ala Glu Ile Asn Ala Glu Leu Glu Leu Ser Asp Ala Ser
                965                 970                 975

Ala Asp Glu Ala Asp Lys Asp Gly Ser Asn Ser Lys Ala Ser Arg Ala
                980                 985                 990

Pro Ser Trp Thr Asn Leu Arg Ser Asn Thr Tyr Leu His Arg Asn Arg
                995                 1000                1005
```

```
Arg Asn Gln Ser Ile Asp Glu Ser Met Val Cys Asn Cys Lys Pro Pro
    1010                1015                1020

Gln Glu Gly Arg Met Gly Cys Arg Asp Gly Cys Leu Asn Arg Met Leu
1025                1030                1035                1040

Asn Ile Glu Cys Ala Lys Arg Thr Cys Pro Cys Glu Glu Gln Cys Ser
                1045                1050                1055

Asn Gln Gln Phe Gln Arg Arg Asn Tyr Ala Lys Ile Ala Trp Phe His
            1060                1065                1070

Ser Gly Lys Lys Gly Tyr Gly Leu Lys Leu Gln Glu Val Ser Glu
        1075                1080                1085

Gly Arg Phe Leu Ile Glu Tyr Val Gly Glu Val Leu Asp Ile Thr Thr
    1090                1095                1100

Tyr Glu Ser Arg Gln Arg Asp Tyr Ala Ser Lys Gly Lys Lys His Phe
1105                1110                1115                1120

Tyr Phe Met Ala Leu Asp Gly Gly Glu Val Ile Asp Ala Cys Thr Lys
                1125                1130                1135

Gly Asn Leu Gly Arg Phe Ile Asn His Ser Cys Ser Pro Asn Cys Arg
            1140                1145                1150

Thr Glu Lys Trp Met Val Asn Gly Glu Val Cys Ile Gly Ile Phe Ala
        1155                1160                1165

Met Arg Asn Ile Lys Lys Gly Glu Glu Leu Thr Phe Asp Tyr Asn Tyr
    1170                1175                1180

Val Arg Val Ser Gly Ala Ala Pro Gln Lys Cys Phe Cys Gly Thr Ala
1185                1190                1195                1200

Lys Cys Arg Gly Tyr Ile Gly Gly Asp Ile Ser Gly Ser Gly Ile Ser
                1205                1210                1215

Thr Gln His Val Ala Glu Ala Glu Tyr Phe Glu Pro Thr Val Thr Tyr
            1220                1225                1230

Lys Asp Ala Glu Glu Met Leu Gly Asn Ala Cys Ser His Gly Ala Asn
        1235                1240                1245

Pro Ile Val Val Glu Leu Glu His Glu Thr Ser Ile Gln Gln Glu Asp
    1250                1255                1260

Ser Asn Asn Cys Ile Pro Val Thr Pro Asp Ser Glu Pro His Gln Thr
1265                1270                1275                1280

Ser Pro Val Thr Pro Asp Ser Glu Pro His Gln Thr Ser Pro Ile Leu
            1285                1290                1295

Phe Glu Asn Ser Glu Leu Glu Asn Ser Trp Glu Met Trp Ser Pro Gln
        1300                1305                1310

Asp Ala Glu Asp Pro Thr Arg Thr Pro Val His Val Pro Arg Thr Ile
    1315                1320                1325

Asp Ser Thr Leu Gln Gln Leu Pro Val Tyr Asp Thr Gln Pro Leu Glu
1330                1335                1340

Phe Leu Pro Lys Ala Pro Asn Thr Met Asp Gly Ser Glu Ala Pro Asn
1345                1350                1355                1360

Val Met Asn Gln Ser Ala Arg Ser Ser Asp Leu Gly Gln Asn Leu Val
                1365                1370                1375

Val Pro Gly Phe His Ala Lys Lys Asn Asn Leu Lys Asp Gln Arg
            1380                1385                1390

Asp Val Lys Ser Ser Ser Cys Ser Thr Asp Asn Glu Asn Thr Leu Gly
        1395                1400                1405

Val Glu Ala Arg Leu Asn Asn Leu Leu Asp Arg Asp Gly Gly Ile Ser
    1410                1415                1420

Arg Arg Lys Asp Ser Thr Asn Gly Tyr Leu Arg Leu Leu Leu Phe Val
```

-continued

```
            1425                1430                1435                1440
        Thr Ala Ala Arg Asp Asn Ala Ala Ala Ala Arg Asp Asn
                        1445                1450                1455
        Ala Ala Ala Ser Ala Ala Arg Asp Asn Ala Ala Ala Ala Tyr
                        1460                1465                1470
        Asp Ala Thr Ala Met Glu His Glu Asn Ala Ala Thr Pro Ala Glu Arg
                        1475                1480                1485
        Asp Asn Ala Gly Gly Thr Ser Lys Ser Ala Arg Asp Leu Ser Leu Ile
                        1490                1495                1500
        Leu Asp Ala Leu Leu Lys Thr Lys Ser Arg Ser Val Leu Leu Asp Ile
        1505                1510                1515                1520
        Ile Asn Thr Asn Gly Leu Gln Met Leu His Asn Ile Leu Lys Gln Asn
                        1525                1530                1535
        Arg Asp Thr Phe Leu Arg Arg Pro Ile Ile Arg Lys Leu Leu Lys Val
                        1540                1545                1550
        Leu Glu Phe Leu Ala Leu Lys Gly Ile Leu Arg Ala Glu Lys Ile Asn
                        1555                1560                1565
        Glu Glu Ala Pro Arg Glu Glu Met Glu Arg Phe Arg Asp Ser Met Leu
                        1570                1575                1580
        Lys Leu Thr Arg His Ser Asp Lys Gln Val Gln Thr Ile Ala Arg His
        1585                1590                1595                1600
        Phe Cys Glu Lys Trp Ile His Pro Tyr Met Asp Gly Pro Val Ser Thr
                        1605                1610                1615
        Ser Lys Trp Cys Thr Asp Ser Tyr Ser Asn Arg Arg Lys Arg Lys Ser
                        1620                1625                1630
        Arg Trp Asp Tyr Gln Pro Glu Ser His Tyr Lys Met Val Gly Ser Leu
                        1635                1640                1645
        Val Arg Lys Val Tyr Gly Glu Leu Gly Leu Gln Ala Gly Leu Thr Arg
                        1650                1655                1660
        Asn Arg Ser Gln Pro Val Met Gly Ser Ser Thr Gly Thr Asp Asp
        1665                1670                1675                1680
        Asp Val Pro Pro Gly Phe Glu Pro Gln Gln Gly Arg Ser Val Ala Pro
                        1685                1690                1695
        Gly Phe Cys His Pro Asn Leu Asn Ile Ser Tyr Gly Ile Pro Ile Ala
                        1700                1705                1710
        His Val Gln His Leu Gly Thr Pro Glu Val Glu Gly Gly Asn Arg
                        1715                1720                1725
        Gly Gln Lys Trp Lys Val Ala Pro Gly Val Pro Phe Ile Pro Phe Pro
                        1730                1735                1740
        Gln Leu Arg Arg Gly Ser Pro Cys Pro Ser Thr Ser Thr Gln Met Ser
        1745                1750                1755                1760
        Cys His Asp Ala Met Arg Gln Asn Asn Ser Ser Gly His Arg Gly Arg
                        1765                1770                1775
        Gly Phe Asp Arg Gly Gly Arg Val Gln Arg Asn Gly Arg Asn Gly Ala
                        1780                1785                1790
        Arg Thr Arg Tyr Pro Tyr Asp His Gln Gly Arg Arg Phe Pro Ser Asn
                        1795                1800                1805
        His His Arg Ser Glu Arg Trp Gln Pro Trp Pro Asp Glu His Asp Gly
                        1810                1815                1820
        Gly Ser Gly Ser Arg Gly Arg Gln
        1825                1830

<210> SEQ ID NO 110
```

<211> LENGTH: 935
<212> TYPE: PRT
<213> ORGANISM: Oryza sativa

<400> SEQUENCE: 110

```
Met Lys Ser Ser Arg Phe Asp Phe Phe Val Pro Lys Val Ala Lys Ile
1               5                   10                  15

Glu Val Arg Leu Lys Asn Gly Tyr Tyr Ala Arg His Gly Phe Ser Tyr
            20                  25                  30

Ile Lys Asn Asp Ile Arg Ser Met Cys Arg Asp Ala Leu Arg Tyr Lys
        35                  40                  45

Gly Arg Ser Asp Leu Gly Asp Met Lys Gln Ile Val Ala Phe Ile
    50                  55                  60

Gln Leu Ala Lys Lys Leu Glu Asn Pro Arg Leu Ile Ser Asp Arg Asp
65                  70                  75                  80

Gly Thr Ala Val Gln Lys Asp Ser Ser Asp Met Ser Gln Tyr Ser Ser
                85                  90                  95

Asp Leu Lys Leu Lys Lys Gln Ser Lys Thr Met Ser Glu Arg Arg
            100                 105                 110

Gly Ala Asn Trp Thr Thr Ala Gly Ala Asp Pro Ser Ser Arg Ala Phe
            115                 120                 125

Asp Arg Glu Ile Lys Arg Ser Leu Ser Lys Leu Lys Lys Arg Asp Ile
        130                 135                 140

Asp Ser Gly Ser Glu Thr Asp Ser Asp Asp Asp Gly Tyr Ser Glu Gly
145                 150                 155                 160

Asp Glu Thr Glu Ser Glu Thr Thr Val Ser Asp Thr Glu Ser Asp Leu
                165                 170                 175

Asp Val Asn Ser Gly Ala Trp Asp Leu Lys Gly Asn Gly Met Lys Leu
            180                 185                 190

Phe Glu Ser Ser Glu Ser Leu Thr Asp Asp Arg Gly Trp Gly Ala Arg
        195                 200                 205

Met Thr Lys Ala Ser Leu Val Pro Pro Val Thr Arg Lys Tyr Glu Val
    210                 215                 220

Ile Glu Lys Tyr Leu Ile Val Ala Asp Glu Glu Val Leu Arg Lys
225                 230                 235                 240

Met Arg Val Ala Leu Pro Asp Asp Tyr Ser Glu Lys Leu Leu Ser Gln
                245                 250                 255

Lys Asn Gly Thr Glu Asn Leu Glu Leu Pro Glu Val Lys Asp Tyr Gln
            260                 265                 270

Pro Arg Lys Val Pro Gly Asp Glu Val Leu Glu Gln Glu Val Tyr Gly
        275                 280                 285

Ile Asp Pro Tyr Thr His Asn Leu Leu Leu Glu Met Met Pro Thr Glu
    290                 295                 300

Leu Asp Trp Pro Ser Ser Asp Lys His Thr Phe Val Glu Glu Leu Leu
305                 310                 315                 320

Leu Asn Thr Leu Asn Lys Gln Val Arg Gln Phe Thr Gly Ser Gly Asn
                325                 330                 335

Thr Pro Met Val Tyr Pro Leu Lys Pro Val Ile Glu Glu Ile Gln Lys
            340                 345                 350

Ser Ala Glu Glu Ser Gly Asp Arg Arg Thr Ser Lys Met Cys Leu Gly
        355                 360                 365

Met Leu Lys Ala Met Arg Asn His Pro Glu Tyr Asn Tyr Val Ala Tyr
    370                 375                 380

Arg Lys Gly Leu Gly Val Val Cys Asn Lys Thr Gly Gly Phe Gly Val
```

```
              385                 390                 395                 400
Asp Asp Phe Val Ile Glu Phe Phe Gly Glu Val Tyr Pro Ser Trp Arg
                    405                 410                 415
Trp Tyr Glu Lys Gln Asp Gly Ile Lys His Ile Gln Asn Asn Ser Asp
                420                 425                 430
Asp Gln Ala Pro Glu Phe Tyr Asn Ile Met Leu Glu Arg Pro Lys Gly
                435                 440                 445
Asp Arg Asp Gly Tyr Asp Leu Val Phe Val Asp Ala Met His Lys Ala
            450                 455                 460
Asn Tyr Ala Ser Arg Ile Cys His Ser Cys Asn Pro Asn Cys Glu Ala
465                 470                 475                 480
Lys Val Thr Ala Val Asp Gly His Tyr Gln Ile Gly Ile Tyr Thr Val
                    485                 490                 495
Arg Pro Ile Ala Glu Gly Glu Ile Thr Phe Asp Tyr Asn Ser Val
                500                 505                 510
Thr Glu Ser Lys Glu Glu His Glu Ala Ser Val Cys Leu Cys Gly Ser
            515                 520                 525
Gln Ile Cys Arg Gly Ser Tyr Leu Asn Phe Ser Gly Glu Gly Ala Phe
        530                 535                 540
Glu Lys Val Leu Met Glu Phe His Gly Val Leu Asp Arg His Ser Leu
545                 550                 555                 560
Leu Leu Gln Ala Cys Glu Ala Asn Ser Val Ser Gln Gln Asp Leu Ile
                565                 570                 575
Asp Leu Gly Arg Ala Gly Leu Gly Thr Cys Leu Leu Ala Gly Leu Pro
                580                 585                 590
Gly Trp Leu Val Ala Tyr Thr Ala His Leu Val Arg Phe Ile Phe Phe
            595                 600                 605
Glu Arg Gln Lys Leu Pro His Glu Ile Phe Lys His Asn Val Asp Glu
        610                 615                 620
Lys Arg Gln Phe Phe Thr Asp Ile Asn Met Asp Ser Glu Lys Asn Asp
625                 630                 635                 640
Ala Glu Val Gln Ala Glu Gly Val Leu Asn Ser Arg Leu Gln Asn Leu
                645                 650                 655
Thr His Thr Leu Asp Lys Val Arg Tyr Val Met Arg Cys Ile Phe Gly
                660                 665                 670
Asp Pro Lys Asn Ala Pro Pro Leu Val Arg Leu Thr Gly Arg Ser
            675                 680                 685
Leu Val Ser Ala Ile Trp Lys Gly Gly Ser Leu Val Asp Glu Leu
690                 695                 700
Leu Glu Ser Met Glu Pro His Val Glu Glu Asp Val Leu Thr Asp Leu
705                 710                 715                 720
Lys Ala Lys Ile Arg Ala His Asp Pro Ser Gly Ser Glu Asp Ile Glu
                725                 730                 735
Gly Glu Ile Arg Ser Ser Leu Leu Trp Leu Arg Asp Glu Leu Arg Thr
                740                 745                 750
Leu Ser Cys Thr Tyr Lys Cys Arg His Asp Ala Ala Asp Leu Ile
            755                 760                 765
His Met Tyr Ala Tyr Thr Lys Cys Phe Phe Arg Val Arg Asp Tyr Lys
        770                 775                 780
Thr Val Lys Ser Pro Pro Val Leu Ile Ser Pro Leu Asp Leu Gly Pro
785                 790                 795                 800
Lys Tyr Ala Asp Lys Leu Gly Pro Gly Phe Gln Glu Tyr Cys Lys Thr
                805                 810                 815
```

Tyr Pro Glu Asn Tyr Cys Leu Gly Gln Leu Ile Tyr Trp Tyr Ser Gln
            820                 825                 830

Asn Ala Glu Pro Glu Ser Arg Leu Thr Arg Ala Arg Lys Gly Cys Met
            835                 840                 845

Ser Leu Pro Asp Val Ser Phe Tyr Val Lys Ser Val Lys Pro Thr
    850                 855                 860

Gln Glu Arg Val Tyr Gly Ser Arg Thr Val Arg Phe Met Leu Ala Arg
865                 870                 875                 880

Met Glu Asn Gln Ala Gln Arg Pro Trp Pro Lys Asp Arg Ile Trp Val
            885                 890                 895

Phe Lys Ser Asp Pro Arg Phe Phe Gly Thr Pro Met Met Asp Ala Val
            900                 905                 910

Leu Asn Asn Ser Pro Leu Asp Lys Glu Met Val His Trp Leu Lys Thr
            915                 920                 925

Arg Ser Asn Val Phe Leu Gly
            930                 935

<210> SEQ ID NO 111
<211> LENGTH: 2418
<212> TYPE: PRT
<213> ORGANISM: Solanum lycopersicum

<400> SEQUENCE: 111

Met Gly Asp Gly Gly Val Ala Cys Val Pro Val Gln His Ile Met Glu
1               5                   10                  15

Pro Phe Ser Val Cys Ala Pro Lys Thr Asn Ser Ser Thr Phe Ser Thr
            20                  25                  30

Ser Ser Leu Asn Ser Thr Thr Ala Thr Val Lys Lys Lys Lys Lys Lys
        35                  40                  45

Met Asn Gly Lys Met Lys Ala Lys Arg Glu Lys Lys Val Val Asn Leu
    50                  55                  60

Ser Ser Lys Ser Val Val Lys Glu Ile Glu Ser Asn Gly Asp Ala Ala
65                  70                  75                  80

Lys Asp Glu Val Glu Glu Gly Glu Leu Gly Thr Leu Pro Val Asp Asn
                85                  90                  95

Gly Gln Leu Val Gln Glu Lys Ser Phe Ser Arg Lys Tyr Glu Ile Lys
            100                 105                 110

Ser Glu Ile Glu Lys Gly Glu Ile Thr Pro Asp Val Lys Arg Gly Glu
        115                 120                 125

Phe Leu Lys Gly Arg Trp Arg Lys Gly Glu Trp Glu Lys Ala Asn Tyr
    130                 135                 140

Ile Ser Asp Lys Ser Asp Arg Lys Gly Glu Phe Asp Lys Asn Asp Thr
145                 150                 155                 160

Gly Tyr Glu Pro Gly Glu Phe Val Pro Asp Arg Trp Arg Lys Gly Glu
                165                 170                 175

Gly Ser Ala Arg Asp Asp Phe Asn Tyr Ser Arg Thr Arg Arg Tyr Asp
            180                 185                 190

Phe Ala Lys Asp Lys Gly Trp Lys Gly Asp Leu Asp Trp Thr Pro Pro
        195                 200                 205

Leu Val Lys Asp Lys Gly Trp Arg Asp Asp Arg Glu Trp Thr Pro Pro
    210                 215                 220

Ser Val Lys Asp Lys Gly Trp Arg Asn Asp Arg Glu Trp Thr Pro Pro
225                 230                 235                 240

Leu Val Lys Asp Lys Gly Trp Arg Asn Asp Leu Glu Trp Thr Pro Pro

```
                  245                 250                 255
Ser Ala Lys Asp Lys Gly Trp Arg Asn Asp Arg Glu Trp Thr Pro Pro
            260                 265                 270
Ser Ala Lys Asp Lys Gly Trp Arg Asn Asp His Glu Trp Thr Pro Pro
            275                 280                 285
Ser Ser Gly Lys His Ser Gly Gln Lys Asp Gly Gly Arg Ser Gly Gly
            290                 295                 300
Ile Gln His Val Lys Arg Leu Ser Arg Tyr Glu Pro Ser Ile Pro Glu
305                 310                 315                 320
Arg Asn Pro Arg Ile Ser Ser Lys Ile Val Gly Glu Gly Pro Ser
                325                 330                 335
Lys Ser Glu Leu Arg Asn Gly Asn Asn Pro Ala Arg Asp Tyr Phe Ser
            340                 345                 350
Gly Asn Arg Leu Lys Arg His Gly Thr Asp Ser Asp Lys Asn Asp Arg
            355                 360                 365
Lys Phe Arg Gly Glu Tyr Asp Asp Phe Ser Ser Lys Ser Arg Lys
            370                 375                 380
Leu Ser Asp Asp Gly Ser Arg Ala Val Tyr Thr Val Asp His Ser Leu
385                 390                 395                 400
Arg Arg Ser Thr Glu Lys Leu His Lys Asn Ala Pro Ser Asn Arg Asn
                405                 410                 415
Ile Pro Pro Asp Arg Tyr Ser Ser Arg His Tyr Glu Thr Ser Lys Val
                420                 425                 430
Pro Tyr Asp Arg Leu Asn Ser Ser Pro Arg His Leu Glu Arg Ser Pro
            435                 440                 445
Arg Asp Arg Ala Arg His Leu Asp Asn Trp Asp Arg Ser Pro Ala Arg
            450                 455                 460
Arg Glu Lys Ser Pro Tyr Asp Arg Gly Arg His Phe Asp His Ser Arg
465                 470                 475                 480
Ser Pro Tyr Asp Arg Ser Arg His Tyr Asp His Arg Ser Arg Ser Pro
                485                 490                 495
Ser Tyr Ser Glu Trp Ser Pro Gln Asp Gln Gly Arg His His His Arg
            500                 505                 510
Arg Asp Arg Thr Pro Asn Phe Met Glu Pro Ser Pro Arg Asp Arg Ser
            515                 520                 525
Arg Thr Thr Tyr His Arg Asp Thr Gly Arg Lys Ser Gly Pro Ser Asp
            530                 535                 540
Lys Lys Asp Ser His Phe Glu Gly Lys Lys His Glu Gly Lys Phe Asn
545                 550                 555                 560
Asn Gln Lys Asp Val Ser Met Lys Asp Ala Lys Asp Ser Glu Val Arg
                565                 570                 575
Ser Cys Pro Glu Asn Ser Asn Cys Ser Ile Val Lys Ser Gly Asn His
                580                 585                 590
Pro Val Asn Asn Asp Gly Leu Pro Gln Cys Pro Ala Val Asn Ala Leu
            595                 600                 605
Glu Pro Ser Glu Glu Asn Gly Ala Val Glu Glu Ala Ala Ser Met Glu
            610                 615                 620
Glu Asp Met Asp Ile Cys Asn Thr Pro His Val Thr Thr Val Ala
625                 630                 635                 640
Glu Gly Ala Ile Gly Lys Trp Tyr Tyr Val Asp Gln Phe Gly Val Glu
                645                 650                 655
Gln Gly Pro Ser Arg Leu Cys Lys Leu Lys Ser Leu Val Glu Glu Gly
            660                 665                 670
```

```
Tyr Ile Val Ala Asp His Phe Val Lys His Ala Asp Ser Glu Arg Trp
        675                 680                 685
Val Thr Val Glu Asn Ala Val Ser Pro Met Ala Thr Val Asn Phe Pro
        690                 695                 700
Ser Val Val Ser Asp Val Val Thr Gln Met Val Ser Pro Pro Glu Ala
705                 710                 715                 720
Ser Gly Asn Val Leu Glu Asp Lys Cys Asp Leu Ala Gln Leu Asn Asp
                725                 730                 735
Gln Val Ala Val Asp Thr Phe Pro Pro Ser Glu Ile Val Pro Cys
            740                 745                 750
His Gly Asp Asn Leu Thr Ala Ala Glu Pro Ser Ser Glu His His Ile
        755                 760                 765
Asp Glu Arg Val Gly Ala Leu Leu Glu Gly Phe Ser Val Thr Pro Gly
        770                 775                 780
Arg Glu Leu Glu Ile Ile Gly Glu Val Leu Gln Val Thr Leu Glu His
785                 790                 795                 800
Val Glu Trp Glu Lys Trp Gly Ser Ala Glu Gly His Trp Asn Gln
                805                 810                 815
Ser Ser Asp Glu Leu Ser Leu Ser Ser Glu Val Gln Lys Glu Ser Thr
        820                 825                 830
Glu Pro Arg Thr Ser Asp Lys Glu Thr Asp Phe Phe Cys Ser Asp Pro
        835                 840                 845
Ala Glu Leu Phe Ser Gly Leu Trp Ser Cys Lys Gly Gly Asp Trp Lys
        850                 855                 860
Arg Ile Asp Glu Ala Thr Gln Asp Arg Leu Trp Lys Lys Lys Leu Val
865                 870                 875                 880
Leu Asn Asp Gly Tyr Pro Leu Cys Leu Met Ser Lys Ser Gly Ile Glu
                885                 890                 895
Asp Pro Arg Trp Pro Gln Lys Asp Glu Leu Tyr Asn Pro Ser His Ser
            900                 905                 910
Arg Lys Leu Asp Leu Pro Ser Trp Ala Phe Thr Pro Asp Glu Trp Asn
        915                 920                 925
Asp Ser Asn Val Val Gly Arg Pro Asn Gln Ser Lys Pro Pro Val Leu
        930                 935                 940
Arg Gly Thr Lys Gly Met Met Leu Pro Val Ile Arg Ile Asn Ala Cys
945                 950                 955                 960
Val Val Lys Glu His Gly Ser Phe Val Ser Glu Pro His Thr Lys Val
                965                 970                 975
Arg Gly Lys Asp Arg His Pro Gln Arg Ser Ser Arg Pro Tyr Val Val
            980                 985                 990
Thr Gly Asp Thr Lys Arg Ser Ser Glu Glu Ala Val Tyr Arg Ser Lys
        995                 1000                1005
Ser Arg Gln Asp Gln Glu Leu His Gly Ser Ser Lys Ser Ile Met Pro
        1010                1015                1020
Leu Ile Ile Pro Lys Asp Arg Leu Cys Ser Ala Asp Glu Leu Gln Leu
1025                1030                1035                1040
His Leu Gly Glu Trp Tyr Tyr Leu Asp Gly Ala Gly His Glu Arg Gly
                1045                1050                1055
Pro Phe Ser Phe Ile Glu Leu Gln Val Leu Asp Gln Gly Val Ile
            1060                1065                1070
Pro Glu Asn Ser Ser Ala Phe Arg Arg Val Asp Arg Ile Trp Val Pro
        1075                1080                1085
```

```
Val Ala Ser Ser Ser Lys Thr Ser Asp Leu Ser Lys Met Cys Gln Thr
    1090                1095                1100

Pro Asn Glu Thr Leu Gly Ala Ser Glu Ser Glu Leu Glu Asn Ser Leu
1105                1110                1115                1120

Leu Ser Ala Pro Ser Gly Ala Pro Cys Thr Phe His Gly Met His Pro
        1125                1130                1135

Gln Phe Ile Gly His Thr Gln Gly Lys Leu His Glu Leu Val Met Lys
        1140                1145                1150

Ser Tyr Lys Ser Arg Glu Leu Ala Ala Ile Asn Glu Val Leu Asp
        1155                1160                1165

Pro Trp Ile Asn Ala Arg Gln Pro Lys Lys Glu Ser Asn Pro Asp Phe
    1170                1175                1180

Arg Ala Ser Lys Lys Ala Arg Cys His Gly Ser Glu Glu Tyr Glu
1185                1190                1195                1200

Met Glu Glu Asp Ile Ser Val Phe Gln Asn Asp Glu Cys Gln Phe Asp
                1205                1210                1215

Asp Leu Cys Ser Asp Glu Thr Phe Asn Arg Glu Thr Ile Thr Thr Tyr
        1220                1225                1230

Gly Ile Lys Asn Gly Ser Trp Asp Leu Leu Asn Asp Arg Val Leu Gly
        1235                1240                1245

Arg Val Phe His Phe Leu Lys Ala Asp Val Lys Ser Leu Val Tyr Ala
    1250                1255                1260

Ser Leu Thr Cys Lys His Trp Arg Ser Ile Val Lys Ile Tyr Lys Gly
1265                1270                1275                1280

Ile Ser Pro Gln Val Asp Leu Leu Ser Val Ala Ser Ser Cys Thr Asp
        1285                1290                1295

Ser Met Met Gln Thr Ile Met Ser Gly Tyr Asn Lys Glu Lys Ile Thr
        1300                1305                1310

Ser Leu Val Leu Arg Asp Cys Thr Ser Ile Thr Pro Arg Met Leu Glu
        1315                1320                1325

Asp Val Leu Phe Ser Phe Ser Cys Leu Ser Tyr Ile Asp Ile Arg Gly
        1330                1335                1340

Cys Ser Gln Leu Asp Asp Leu Ala Val Lys Phe Pro Asn Ile Asn Trp
1345                1350                1355                1360

Ile Arg Ser Arg Ser Ser Asn Leu Lys Val Lys Ser Leu Lys Asn Phe
        1365                1370                1375

Ser Asp Arg Thr Ala Ser Ser Tyr Arg Thr Tyr Asn Ser Gln Glu Asn
        1380                1385                1390

Gln Met Asp Asp Ser Ile Gly Leu Arg Asp Tyr Leu Glu Ser Ser Asp
        1395                1400                1405

Lys Arg Glu Phe Ala Asn Gln Leu Phe Arg Arg Ser Leu Tyr Lys Arg
1410                1415                1420

Ser Lys Ala Phe Asp Ala Arg Lys Ser Ser Ser Met Leu Ser Arg Asp
1425                1430                1435                1440

Ala Gln Leu Arg His Leu Ala Met Arg Lys Ser Arg Asn Cys Phe Lys
        1445                1450                1455

Arg Met Lys Glu Phe Leu Ala Ser Ser Leu Arg Glu Ile Met Lys Glu
        1460                1465                1470

Asn Thr Phe Glu Phe Phe Val Pro Lys Val Gly Glu Ile Glu Glu Lys
        1475                1480                1485

Ile Arg Ser Gly Phe Tyr Ala Ser Arg Gly Leu Lys Ser Ala Lys Glu
        1490                1495                1500

Asp Ile Ser Arg Met Cys Arg Asp Ala Leu Lys Ser Lys Asn Arg Gly
```

-continued

```
            1505                1510                1515                1520
Asp Ala Lys Asp Met Asn Arg Ile Ile Ala Leu Phe Ile Arg Leu Ala
            1525                1530                1535

Thr Arg Leu Glu Glu Asp Pro Lys Ser Phe Arg Thr Arg Asp Glu Met
            1540                1545                1550

Met Lys Thr Ser Lys Asp Glu Ser Pro Pro Gly Phe Ser Ser Ser Thr
            1555                1560                1565

Thr Lys Tyr Lys Lys Asn Pro Ala Arg Met Ser Glu Lys Lys Tyr Phe
            1570                1575                1580

Asn Arg Ser Asn Gly Ser Ser Tyr Val Asn Gly Val Ser Asp Tyr Gly
            1585                1590                1595                1600

Glu Phe Ala Ser Asp Arg Glu Ile Lys Arg Arg Leu Ser Lys Leu Arg
            1605                1610                1615

Leu Lys Ser Leu Asp Ser Gly Ser Glu Thr Ser Asp Asp Leu Ser Gly
            1620                1625                1630

Ser Ser Gly Asp Thr Ser Ser Asp Asn Glu Ser Thr Ala Ser Glu Thr
            1635                1640                1645

Glu Ser Asp Met Asp Leu Arg Ser Glu Cys Gly Ala Ala Glu Ser Lys
            1650                1655                1660

Asp Tyr Phe Thr Pro Asp Asp Gly Phe Asp Ser Phe Ala Asp Asp Arg
1665                1670                1675                1680

Glu Trp Gly Ala Arg Met Thr Lys Ala Ser Leu Val Pro Pro Val Thr
            1685                1690                1695

Arg Lys Tyr Glu Val Ile Asp His Tyr Val Ile Val Ala Asp Glu Lys
            1700                1705                1710

Glu Val Lys Arg Lys Met Leu Val Ser Leu Pro Glu Asp Tyr Ala Gly
            1715                1720                1725

Lys Leu Ser Val Gln Lys Asn Gly Thr Glu Glu Ser Asp Met Glu Ile
            1730                1735                1740

Pro Glu Val Lys Asp Tyr Lys Pro Arg Lys Thr Leu Gly Glu Glu Val
1745                1750                1755                1760

Ile Glu Gln Glu Val Tyr Gly Ile Asp Pro Tyr Thr His Asn Leu Leu
            1765                1770                1775

Leu Asp Ser Met Pro Asp Glu Ser Asp Trp Ser Leu Leu Asp Lys His
            1780                1785                1790

Leu Phe Ile Glu Asp Val Leu Leu Arg Thr Leu Asn Lys Gln Val Arg
            1795                1800                1805

Arg Phe Thr Gly Ser His Thr Pro Met Ile Tyr Ser Leu Lys Pro Val
            1810                1815                1820

Phe Glu Glu Ile Leu Glu Thr Ala Asp Lys Asp Gln Asp Lys Arg Thr
1825                1830                1835                1840

Ile Arg Leu Cys Gln Phe Met Leu Asn Ala Ile Asp Thr Arg Pro Glu
            1845                1850                1855

Asp Asn Tyr Val Ala Tyr Arg Lys Gly Leu Gly Val Val Cys Asn Lys
            1860                1865                1870

Glu Gly Gly Phe Ser Glu Glu Asp Phe Val Val Glu Phe Leu Gly Glu
            1875                1880                1885

Val Tyr Pro Ala Trp Lys Trp Phe Glu Lys Gln Asp Gly Ile Arg Ser
            1890                1895                1900

Leu Gln Arg Asn Asn Asn Asp Pro Ala Pro Glu Phe Tyr Asn Ile Tyr
1905                1910                1915                1920

Leu Glu Arg Pro Lys Gly Asp Ala Asp Gly Tyr Asp Leu Val Val Val
            1925                1930                1935
```

```
Asp Ala Met His Lys Ala Asn Tyr Ala Ser Arg Ile Cys His Ser Cys
        1940                1945                1950

Arg Pro Asn Cys Glu Ala Lys Val Thr Ala Val Asp Gly Gln Tyr Gln
        1955                1960                1965

Ile Gly Ile Tyr Ser Thr Arg Pro Ile Ala Tyr Gly Glu Val Thr
    1970                1975                1980

Phe Asp Tyr Asn Ser Val Thr Glu Ser Lys Glu Glu Tyr Glu Ala Ser
1985                1990                1995                2000

Val Cys Leu Cys Gly Ser Gln Val Cys Arg Gly Ser Tyr Leu Asn Leu
        2005                2010                2015

Thr Gly Glu Gly Ala Phe Leu Lys Val Leu Gln Glu Tyr His Gly Leu
    2020                2025                2030

Leu Asn Arg His Gln Leu Met Leu Glu Ala Cys Glu Leu Asn Ser Val
        2035                2040                2045

Ser Glu Glu Asp Tyr Ile Asp Leu Gly Lys Ala Gly Leu Gly Ser Cys
    2050                2055                2060

Leu Leu Ala Gly Leu Pro His Trp Leu Ile Ala Tyr Ser Ala Arg Leu
2065                2070                2075                2080

Val Arg Phe Ile Asn Phe Glu Arg Thr Lys Leu Pro Asp Glu Ile Leu
        2085                2090                2095

Lys His Asn Leu Glu Glu Lys Lys Tyr Phe Ser Asp Val Cys Leu
        2100                2105                2110

Glu Val Glu Lys Asn Glu Ser Glu Ile Gln Ala Glu Gly Val Tyr Asn
        2115                2120                2125

Gln Arg Leu Gln Asn Leu Ala Leu Thr Leu Asp Lys Val Arg Tyr Val
    2130                2135                2140

Met Arg Cys Val Phe Gly Asp Pro Glu Lys Ala Pro Pro Leu Glu
2145                2150                2155                2160

Arg Leu Asn Pro Glu Glu Ala Val Ser Phe Ile Trp Arg Gly Glu Gly
        2165                2170                2175

Ser Leu Val Glu Glu Leu Leu Gln Cys Met Ala Pro His Leu Glu Asp
        2180                2185                2190

Ser Met Leu Asn Asp Leu Lys Ala Lys Ile Arg Ala His Asp Pro Ser
    2195                2200                2205

Arg Ser Asp Asp Leu Glu Thr Gly Leu Arg Lys Ser Leu Ile Trp Leu
2210                2215                2220

Arg Asp Glu Val Arg Asp Leu Pro Cys Thr Tyr Lys Ser Arg His Asp
2225                2230                2235                2240

Ala Ala Ala Asp Leu Ile His Leu Tyr Ala Tyr Thr Lys Cys Phe Phe
        2245                2250                2255

Arg Ile Arg Glu Tyr Lys Thr Val Thr Ser Pro Pro Val Tyr Ile Ser
        2260                2265                2270

Pro Leu Asp Leu Gly Pro Lys Tyr Thr Asp Lys Leu Gly Pro Gly Thr
    2275                2280                2285

His Glu Tyr Arg Lys Thr Tyr Gly Glu Asn Tyr Cys Leu Gly Gln Leu
        2290                2295                2300

Phe Tyr Trp Tyr Asn Gln Ala Asn Ala Asp Pro Glu Asn Cys Leu Phe
2305                2310                2315                2320

Lys Ala Ser Arg Gly Cys Leu Ser Leu Pro Glu Ala Gly Ser Phe Tyr
        2325                2330                2335

Ala Lys Val Gln Lys Pro Ser Arg Gln Arg Val Tyr Gly Pro Arg Thr
        2340                2345                2350
```

Val Lys Phe Met Leu Ser Arg Met Glu Lys Gln Pro Gln Arg Ala Trp
         2355                2360                2365

Pro Lys Asp Arg Ile Trp Ser Phe Lys Asn Ser Pro Asn Val Phe Gly
         2370                2375                2380

Ser Pro Met Leu Asp Gly Ile Leu Asn Lys Ser Pro Leu Glu Arg Glu
2385                2390                2395                2400

Met Val His Trp Leu Lys His Arg Pro Ala Ile Phe Gln Ala Lys Trp
                 2405                2410                2415

Asp Arg

<210> SEQ ID NO 112
<211> LENGTH: 259
<212> TYPE: PRT
<213> ORGANISM: Saccharum officinarum

<400> SEQUENCE: 112

Ala Leu Val Cys Ala Ala Gly Pro Ala Ala Gln Asn Cys Gly Cys
1               5                   10                  15

Gln Pro Asn Tyr Cys Cys Ser Lys Phe Gly Tyr Cys Gly Thr Thr Asp
                20                  25                  30

Asp Tyr Cys Gly Asp Gly Cys Gln Ser Gly Pro Cys Arg Ser Gly Gly
            35                  40                  45

Gly Ser Pro Gly Gly Gly Ser Ser Gly Val Gly Asn Val Ala Gly Val
    50                  55                  60

Val Thr Asp Ala Phe Phe Asn Gly Ile Lys Asn Gln Ala Gly Asn Gly
65                  70                  75                  80

Cys Glu Gly Lys Asn Phe Tyr Thr Arg Ser Ala Phe Leu Ser Ala Ala
                85                  90                  95

Asp Ser Tyr Lys Gly Phe Gly Gly Ser Val Glu Gly Lys Arg Glu
                100                 105                 110

Ile Ala Ala Phe Phe Ala His Val Thr His Glu Thr Gly His Phe Cys
            115                 120                 125

Tyr Ile Ser Glu Ile Asn Lys Asn Asn Ala Tyr Cys Asp Ser Ser Asn
    130                 135                 140

Arg Gln Trp Pro Cys Ala Ala Gly Gln Lys Tyr Tyr Gly Arg Gly Pro
145                 150                 155                 160

Leu Gln Ile Ser Trp Asn Tyr Asn Tyr Gly Pro Ala Gly Arg Asp Ile
                165                 170                 175

Gly Phe Asn Gly Leu Gly Asn Pro Asp Arg Val Ala Gln Asp Ala Val
            180                 185                 190

Ile Ala Phe Lys Thr Ala Leu Trp Phe Trp Thr Asn Asn Val His Arg
    195                 200                 205

Val Met Ser Gln Gly Phe Gly Ala Thr Ile Arg Ala Ile Asn Gly Val
210                 215                 220

Leu Glu Cys Asn Gly Asn Asn Pro Ala Gln Met Asn Ala Arg Val Gly
225                 230                 235                 240

Tyr Tyr Lys Gln Tyr Cys Gln Gln Leu Gly Val Asp Pro Gly Pro Asn
                245                 250                 255

Leu Thr Cys

<210> SEQ ID NO 113
<211> LENGTH: 2373
<212> TYPE: PRT
<213> ORGANISM: Solanum tuberosum

<400> SEQUENCE: 113

```
Met Asp Thr Thr Phe Gly Gly Arg Asn Asp Leu Glu Trp Thr Pro Pro
1               5                   10                  15
Leu Ala Lys Asp Arg Gly Trp Arg Asn Asp His Glu Trp Thr Pro Pro
            20                  25                  30
Leu Ala Lys Asp Lys Gly Gly Arg Asn Asp Leu Glu Trp Thr Pro Pro
            35                  40                  45
Leu Ala Lys Asp Lys Gly Trp Arg Asn Asp Leu Glu Trp Thr Pro Pro
            50                  55                  60
Leu Ala Lys Asp Lys Gly Trp Arg Asn Asp Leu Glu Trp Thr Pro Pro
65                  70                  75                  80
Leu Ala Lys Asp Lys Gly Gly Arg Asn Asp Leu Glu Trp Thr Pro Pro
            85                  90                  95
Leu Ala Lys Asp Lys Gly Gly Arg Asn Asp Leu Glu Trp Thr Pro Pro
            100                 105                 110
Leu Ala Lys Asp Arg Gly Trp Arg Asn Asp His Glu Trp Thr Pro Pro
            115                 120                 125
Leu Ala Lys Asp Arg Gly Trp Arg Asn Asp His Glu Trp Thr Pro Pro
            130                 135                 140
Leu Ala Lys Asp Lys Gly Gly Arg Asn Asp Leu Glu Trp Thr Pro Pro
145                 150                 155                 160
Leu Ala Lys Asp Arg Gly Trp Arg Asn Asp Arg Glu Trp Thr Pro Pro
            165                 170                 175
Ser Val Lys Asp Lys Gly Trp Arg Asn Asp Arg Glu Trp Thr Pro Pro
            180                 185                 190
Leu Ala Lys Asp Lys Gly Trp Arg Asn Asp Leu Glu Trp Thr Pro Pro
            195                 200                 205
Leu Ala Lys Asp Arg Gly Trp Arg Asn Asp Arg Glu Trp Thr Pro Pro
            210                 215                 220
Ser Ala Lys Asp Lys Gly Trp Arg Asn Asp His Glu Trp Thr Pro Pro
225                 230                 235                 240
Ser Ser Gly Lys His Ser Gly Glu Lys Asp Gly Gly Arg Ser Gly Gly
            245                 250                 255
Ile Gln His Met Lys Arg Leu Ser Arg Tyr Glu Pro Ser Ile Pro Glu
            260                 265                 270
Arg Asn Pro Arg Ile Ser Ser Lys Ile Val Gly Glu Gly Pro Ser
            275                 280                 285
Lys Ser Glu Leu Arg Asn Gly Asn Asn Pro Ala Arg Glu Tyr Phe Ser
            290                 295                 300
Gly Asn Arg Leu Lys Arg His Gly Thr Asp Ser Asp Lys Asn Asp Arg
305                 310                 315                 320
Lys Phe Arg Gly Glu Tyr Asp Asp Phe Ser Ser Ser Lys Ser Arg Lys
                    325                 330                 335
Leu Ser Asp Asp Gly Ser Arg Ala Val Tyr Thr Ala Asp His Ser Leu
            340                 345                 350
Arg Arg Ser Thr Glu Lys Leu His Lys Asn Ala Pro Ser Asn Arg Asn
            355                 360                 365
Ile Pro Pro Asp Arg Tyr Ser Ser Arg His Tyr Glu Thr Ser Lys Val
            370                 375                 380
Pro Tyr Asp Arg Leu Asn Ser Ser Pro Arg His Leu Glu Arg Ser Pro
385                 390                 395                 400
Arg Asp Arg Ala Arg His Leu Asp Asn Trp Asp Arg Ser Pro Ala Arg
            405                 410                 415
```

```
Arg Glu Lys Ser Pro Tyr Asp Arg Gly Arg Asn Phe Asp His Ser Arg
            420                 425                 430

Ser Pro Tyr Asp Arg Ser Arg His Tyr Asp His Arg Ser Arg Ser Pro
            435                 440                 445

Ser Tyr Ser Glu Trp Ser Pro Gln Asp Gln Gly Arg His His His Arg
            450                 455                 460

Arg Asp Arg Thr Pro Asn Phe Met Glu Pro Ser Pro Arg Asp Arg Ser
465                 470                 475                 480

Arg Thr Thr Tyr His Arg Asp Thr Gly Arg Lys Ser Gly Pro Ser Asp
                    485                 490                 495

Lys Lys Glu Ser His Phe Glu Gly Lys Lys His Glu Gly Lys Phe Ser
            500                 505                 510

Ser Gln Lys Asp Val Ser Met Lys Asp Gln Phe Ala Lys Asp Ser Glu
            515                 520                 525

Val Arg Ser Cys Pro Glu Asn Ser Asn Cys Ser Ile Val Lys Ser Gly
            530                 535                 540

Asn His Pro Val Asn Asn Asp Gly Leu Pro Gln Cys Pro Ala Val Asn
545                 550                 555                 560

Ala Leu Glu Pro Ser Glu Glu Ser Gly Ala Val Glu Glu Ala Ala Ser
                    565                 570                 575

Met Glu Glu Asp Met Asp Ile Cys Asn Thr Pro Pro His Val Thr Thr
            580                 585                 590

Val Ala Glu Gly Thr Ile Gly Lys Trp Tyr Tyr Val Asp Gln Phe Gly
            595                 600                 605

Val Glu Gln Gly Pro Ser Arg Leu Cys Lys Leu Lys Ser Leu Val Glu
            610                 615                 620

Glu Gly Tyr Ile Val Ala Asp His Phe Val Lys His Ala Asp Ser Glu
625                 630                 635                 640

Arg Trp Val Thr Val Glu Asn Ala Val Ser Pro Met Ala Thr Val Asn
                    645                 650                 655

Phe Pro Ser Val Val Ser Asp Val Val Thr Gln Met Val Ser Pro Pro
            660                 665                 670

Glu Ala Ser Gly Asn Val Leu Glu Asp Lys Cys Asp Leu Ala Gln Leu
            675                 680                 685

Asn Asp Gln Val Ala Val Asp Thr Phe Pro Pro Ser Ser Glu Ile Val
            690                 695                 700

Pro Cys His Gly Asp Asn Leu Thr Ala Ala Glu Pro Ser Leu Glu His
705                 710                 715                 720

His Ile Asp Glu Arg Val Gly Ala Leu Leu Glu Gly Phe Ser Val Thr
                    725                 730                 735

Pro Gly Arg Glu Leu Glu Ile Ile Gly Glu Val Leu Gln Val Thr Leu
            740                 745                 750

Glu His Val Glu Trp Glu Lys Trp Gly Ser Ala Glu Gly Glu His Trp
            755                 760                 765

Asn Gln Ser Ser Asp Glu Phe Leu Leu Ser Ser Glu Val Gln Lys Glu
            770                 775                 780

Ser Thr Glu Pro Arg Thr Ser Asp Lys Glu Ser Asp Phe Phe Cys Ser
785                 790                 795                 800

Asp Pro Ala Glu Leu Phe Ser Gly Leu Trp Ser Cys Lys Gly Gly Asp
                    805                 810                 815

Trp Lys Arg Ile Asp Glu Ala Thr Gln Asp Arg Leu Trp Lys Lys Lys
            820                 825                 830

Leu Val Leu Asn Asp Gly Tyr Pro Leu Cys Leu Met Ser Lys Ser Gly
```

```
                      835                 840                 845
Ile Glu Asp Pro Arg Trp Leu Gln Lys Asp Glu Leu Tyr Asn Pro Ser
850                 855                 860

His Ser Arg Lys Leu Asp Leu Pro Ser Trp Ala Phe Thr Pro Asp Glu
865                 870                 875                 880

Trp Asn Asp Ser Asn Val Val Gly Arg Pro Asn Gln Ser Lys Pro Pro
                    885                 890                 895

Val Leu Arg Gly Thr Lys Gly Met Met Leu Pro Val Ile Arg Ile Asn
                900                 905                 910

Ala Cys Val Val Lys Glu His Gly Ser Phe Val Ser Glu Pro His Thr
            915                 920                 925

Lys Val Arg Gly Lys Asp Arg His Pro Gln Arg Ser Ser Arg Pro Tyr
        930                 935                 940

Val Val Thr Gly Asp Thr Lys Arg Ser Ser Glu Glu Ala Val Tyr Arg
945                 950                 955                 960

Ser Lys Ser Arg Gln Asp Gln Glu Ser His Gly Ser Ser Lys Ser Ile
                    965                 970                 975

Met Pro Leu Ile Ile Pro Lys Asp Arg Leu Cys Ser Ala Asp Glu Leu
                980                 985                 990

Gln Leu His Leu Gly Glu Trp Tyr Tyr Leu Asp Gly Ala Gly His Glu
            995                 1000                1005

Arg Gly Pro Phe Ser Phe Ile Glu Leu Gln Val Leu Val Asp Gln Gly
        1010                1015                1020

Val Ile Pro Glu Asn Ser Ser Ala Phe Arg Arg Val Asp Arg Ile Trp
1025                1030                1035                1040

Val Pro Val Ala Ser Ser Ser Lys Thr Ser Asp Leu Ser Lys Met Cys
                    1045                1050                1055

Gln Thr Pro Asn Glu Thr Leu Gly Ala Ser Glu Ser Glu Leu Glu Ser
                1060                1065                1070

Ser Leu Gln Ser Ala Pro Ser Gly Ala Pro Cys Thr Phe His Gly Met
            1075                1080                1085

His Pro Gln Phe Ile Gly His Thr Gln Gly Lys Leu His Glu Leu Val
        1090                1095                1100

Met Lys Ser Tyr Lys Ser Arg Glu Leu Ala Ala Ala Ile Asn Glu Val
1105                1110                1115                1120

Leu Asp Pro Trp Ile Asn Ala Arg Gln Pro Lys Lys Glu Ser Asn Pro
                    1125                1130                1135

Asp Phe Arg Ala Ser Lys Lys Ala Arg Cys His Gly Ser Glu Glu Glu
                1140                1145                1150

Tyr Glu Met Glu Glu Asp Ile Ser Val Phe Gln Asn Asp Glu Cys Gln
            1155                1160                1165

Phe Asp Asp Leu Cys Gly Asp Glu Thr Phe Asn Arg Glu Thr Ile Thr
        1170                1175                1180

Thr Ser Gly Ile Lys Asn Gly Ser Trp Asp Leu Leu Asp Asp Arg Val
1185                1190                1195                1200

Leu Gly Arg Val Phe His Phe Leu Lys Ala Asp Val Lys Ser Leu Val
                    1205                1210                1215

Tyr Ala Ser Leu Thr Cys Lys His Trp Arg Ser Ile Val Lys Ile Tyr
                1220                1225                1230

Lys Gly Ile Ser Pro Gln Val Asp Leu Leu Ser Val Ala Ser Ser Cys
            1235                1240                1245

Thr Asp Ser Met Met Gln Thr Ile Met Asn Gly Tyr Asn Lys Glu Lys
        1250                1255                1260
```

```
Ile Thr Ser Leu Val Leu Arg Asp Cys Thr Ser Ile Thr Pro Arg Met
1265                1270                1275                1280

Leu Glu Asp Val Leu Phe Ser Phe Ser Cys Leu Ser Tyr Ile Asp Ile
            1285                1290                1295

Arg Gly Cys Ser Gln Leu Glu Asp Val Ala Val Lys Phe Pro Asn Ile
        1300                1305                1310

Ile Trp Ile Arg Ser Arg Ser Ser Asn Leu Lys Val Lys Ser Leu Lys
    1315                1320                1325

Asn Ile Ser Asp Arg Thr Ser Ser Ser Tyr Arg Thr Tyr Asn Ser Gln
1330                1335                1340

Glu Asn Gln Met Asp Asp Ser Ile Gly Leu Arg Asp Tyr Leu Glu Ser
1345                1350                1355                1360

Ser Asp Lys Arg Glu Phe Ala Asn Gln Leu Phe Arg Arg Ser Leu Tyr
            1365                1370                1375

Lys Arg Ser Lys Ala Phe Asp Ala Arg Lys Ser Ser Ser Met Leu Ser
        1380                1385                1390

Arg Asp Ala Gln Leu Arg His Leu Ala Met Arg Lys Ser Arg Asn Cys
    1395                1400                1405

Phe Lys Arg Met Lys Glu Phe Leu Ala Ser Ser Leu Arg Glu Ile Met
    1410                1415                1420

Lys Glu Asn Thr Phe Glu Phe Phe Val Pro Lys Val Gly Glu Ile Glu
1425                1430                1435                1440

Glu Lys Ile Arg Ser Gly Tyr Tyr Ala Ser Arg Gly Leu Lys Ser Ala
            1445                1450                1455

Lys Glu Asp Ile Ser Arg Met Cys Arg Asp Ala Leu Lys Ser Lys Asn
        1460                1465                1470

Arg Gly Asp Ala Lys Asp Met Asn Arg Ile Ile Ala Leu Phe Ile Arg
    1475                1480                1485

Leu Ala Thr Arg Leu Glu Glu Asp Pro Lys Ser Phe Arg Ser Thr Arg
    1490                1495                1500

Asp Glu Met Met Lys Thr Ser Lys Asp Glu Ser Pro Pro Gly Phe Ser
1505                1510                1515                1520

Ser Ser Thr Thr Lys Tyr Lys Lys Asn Pro Ala Arg Met Ser Glu Lys
            1525                1530                1535

Lys Tyr Phe Asn Arg Ser Asn Gly Ser Ser Tyr Val Asn Gly Val Ser
        1540                1545                1550

Asp Tyr Gly Glu Phe Ala Ser Asp Arg Glu Ile Lys Arg Arg Leu Ser
    1555                1560                1565

Lys Leu Arg Leu Lys Ser Leu Asp Ser Gly Ser Glu Thr Ser Asp Asp
    1570                1575                1580

Leu Ser Arg Ser Ser Gly Asp Thr Ser Ser Asp Asn Glu Ser Thr Ala
1585                1590                1595                1600

Ser Glu Thr Glu Ser Asp Leu Asp Leu Arg Ser Glu Cys Gly Ala Ala
            1605                1610                1615

Glu Ser Lys Asp Tyr Phe Thr Pro Asp Asp Gly Phe Asp Ser Phe Ala
        1620                1625                1630

Asp Asp Arg Glu Trp Gly Ala Arg Met Thr Lys Ala Ser Leu Val Pro
    1635                1640                1645

Pro Val Thr Arg Lys Tyr Glu Val Ile Asp His Tyr Val Ile Val Ala
    1650                1655                1660

Asp Glu Lys Glu Val Lys Arg Lys Met Leu Val Ser Leu Pro Glu Asp
1665                1670                1675                1680
```

```
Tyr Ala Gly Lys Leu Ser Val Gln Lys Asn Gly Thr Glu Glu Ser Asp
            1685                1690                1695

Met Glu Ile Pro Glu Val Lys Asp Tyr Lys Pro Arg Lys Thr Leu Gly
        1700                1705                1710

Glu Glu Val Ile Glu Gln Glu Val Tyr Gly Ile Asp Pro Tyr Thr His
            1715                1720                1725

Asn Leu Leu Leu Asp Ser Met Pro Asp Glu Ser Asp Trp Ser Leu Leu
        1730                1735                1740

Asp Lys His Leu Phe Ile Glu Asp Val Leu Leu Arg Thr Leu Asn Lys
1745                1750                1755                1760

Gln Val Arg Arg Phe Thr Gly Ser His Thr Pro Met Ile Tyr Ser Leu
            1765                1770                1775

Lys Pro Val Phe Glu Glu Ile Leu Glu Thr Ala Asp Lys Asp Gln Asp
            1780                1785                1790

Lys Arg Thr Val Arg Leu Cys Gln Phe Met Leu Asn Ala Ile Asp Thr
            1795                1800                1805

Arg Pro Glu Asp Asn Tyr Val Ala Tyr Arg Lys Gly Leu Gly Val Val
            1810                1815                1820

Cys Asn Lys Glu Gly Gly Phe Ser Glu Asp Phe Val Val Glu Phe
1825                1830                1835                1840

Leu Gly Glu Val Tyr Pro Ala Trp Lys Trp Phe Glu Lys Gln Asp Gly
            1845                1850                1855

Ile Arg Ser Leu Gln Arg Asn Asn Asp Pro Ala Pro Glu Phe Tyr
            1860                1865                1870

Asn Ile Tyr Leu Glu Arg Pro Lys Gly Asp Ala Asp Gly Tyr Asp Leu
            1875                1880                1885

Val Val Val Asp Ala Met His Lys Ala Asn Tyr Ala Ser Arg Ile Cys
            1890                1895                1900

His Ser Cys Arg Pro Asn Cys Glu Ala Lys Val Thr Ala Val Asp Gly
1905                1910                1915                1920

Gln Tyr Gln Ile Gly Ile Tyr Ser Thr Arg Pro Ile Ala Tyr Gly Glu
            1925                1930                1935

Glu Val Thr Phe Asp Tyr Asn Ser Val Thr Glu Ser Lys Glu Glu Tyr
            1940                1945                1950

Glu Ala Ser Val Cys Leu Cys Gly Ser Gln Val Cys Arg Gly Ser Tyr
            1955                1960                1965

Leu Asn Leu Thr Gly Glu Gly Ala Phe Leu Lys Val Leu Gln Glu Tyr
        1970                1975                1980

His Gly Leu Leu Asn Arg His Gln Leu Met Leu Glu Ala Cys Glu Leu
1985                1990                1995                2000

Asn Ser Val Ser Glu Glu Asp Tyr Ile Asp Leu Gly Lys Ala Gly Leu
            2005                2010                2015

Gly Ser Cys Leu Leu Ala Gly Leu Pro His Trp Leu Ile Ala Tyr Ser
            2020                2025                2030

Ala Arg Leu Val Arg Phe Ile Asn Phe Glu Arg Thr Lys Leu Pro Asp
            2035                2040                2045

Glu Ile Leu Lys His Asn Leu Glu Glu Lys Lys Tyr Phe Ser Asp
        2050                2055                2060

Val Cys Leu Glu Val Glu Lys Asn Glu Ser Glu Ile Gln Ala Glu Gly
2065                2070                2075                2080

Val Tyr Asn Gln Arg Leu Gln Asn Leu Ala Leu Thr Leu Asp Lys Val
            2085                2090                2095

Arg Tyr Val Met Arg Cys Val Phe Gly Asp Pro Glu Lys Ala Pro Pro
```

```
                        2100                2105                2110
Pro Leu Glu Arg Leu Asn Pro Glu Glu Ala Val Ser Phe Ile Trp Arg
            2115                2120                2125

Gly Glu Gly Ser Leu Val Glu Leu Leu Gln Cys Met Ala Pro His
        2130                2135                2140

Leu Glu Asp Ile Met Leu Asn Asp Leu Lys Ala Lys Ile Arg Ala His
2145                2150                2155                2160

Asp Pro Ser Arg Ser Asp Asp Leu Glu Thr Gly Leu Arg Lys Ser Leu
            2165                2170                2175

Ile Trp Leu Arg Asp Glu Val Arg Asp Leu Pro Cys Ser Tyr Lys Ser
        2180                2185                2190

Arg His Asp Ala Ala Ala Asp Leu Ile His Leu Tyr Ala Tyr Thr Lys
    2195                2200                2205

Cys Phe Phe Arg Ile Arg Glu Tyr Lys Thr Val Thr Ser Pro Pro Val
    2210                2215                2220

Tyr Ile Ser Pro Leu Asp Leu Gly Pro Lys Tyr Thr Asp Lys Leu Gly
2225                2230                2235                2240

Pro Gly Thr His Glu Tyr Arg Lys Thr Tyr Gly Glu Asn Tyr Cys Leu
            2245                2250                2255

Gly Gln Leu Phe Tyr Trp Tyr Asn Gln Ala Asn Ala Asp Pro Glu Asn
        2260                2265                2270

Cys Leu Phe Lys Ala Ser Arg Gly Cys Leu Ser Leu Pro Glu Ala Gly
    2275                2280                2285

Ser Phe Tyr Ala Lys Val Gln Lys Pro Ser Arg Gln Arg Val Tyr Gly
    2290                2295                2300

Pro Arg Thr Val Lys Phe Met Leu Ser Arg Met Glu Lys Gln Pro Gln
2305                2310                2315                2320

Arg Ala Trp Pro Lys Asp Arg Ile Trp Ser Phe Lys Asn Ser Pro Asn
            2325                2330                2335

Val Phe Gly Ser Pro Met Leu Asp Gly Ile Leu Asn Lys Ser Pro Leu
        2340                2345                2350

Glu Arg Glu Met Val His Trp Leu Lys His Arg Pro Ala Ile Phe Gln
    2355                2360                2365

Ala Lys Trp Asp Arg
    2370

<210> SEQ ID NO 114
<211> LENGTH: 2263
<212> TYPE: PRT
<213> ORGANISM: Sorghum bicolor

<400> SEQUENCE: 114

Met Gly Asp Gly Gly Val Ala Cys Ala Val Arg Ala Val Glu Gly Phe
1               5                   10                  15

Arg Ala Gly Ala Leu Val Arg Arg Gly Gly Ala Gly Glu Ala Met Pro
            20                  25                  30

Asp Lys Gly Glu Arg Ala Gln Ala His Gly His His His His Arg
        35                  40                  45

Lys Asn Gln Gln Ser Thr Thr Ala Ala Asp Leu Glu Glu Gly Glu Leu
    50                  55                  60

Leu Asn Gly Glu Ala Asp Thr Asn Gly Leu Pro Glu Arg Ser Met Pro
65                  70                  75                  80

Pro Lys Lys Trp Arg Lys Val Leu Ala Ala Ser Ala Ala Ala Ala
            85                  90                  95
```

```
Glu Val Glu Pro Gly Glu Ile Val Ser Thr Lys Gln Ala Val Pro Leu
            100                 105                 110

Lys Lys Ala Arg Arg Asn Gly Asp Val Glu Lys Val Glu Leu Leu Pro
        115                 120                 125

Glu Arg Gln Arg Lys Glu Lys Ser Ser Gly Lys Ser Thr Arg Lys Pro
    130                 135                 140

Ile Lys Asp Glu Val Glu Pro Gly Glu Ile Ala Pro Ser Glu Lys Arg
145                 150                 155                 160

Arg Asp Ala Lys Ser Gln Gln Ala Asp Asn Gly Arg Arg Pro Gly
                165                 170                 175

Ser Ser Ala Gln Lys Gly Ser Leu Arg Asp Ser Asp Glu Pro Gly
            180                 185                 190

Glu Ile Lys Pro Glu Ser Ser Ile Ser Gly Ser Ala Arg Lys Asn Arg
        195                 200                 205

Pro Thr Glu Pro Gln Ser Ile Asn His Lys His His Ala Asp Thr Ser
    210                 215                 220

Asp Gln Ser Gly Ser Lys Ser Arg Arg Lys Gly Glu Gly Lys Ser Leu
225                 230                 235                 240

Ser Ala Ser Arg His Leu Ser Gly Arg Asn Arg Glu Val Ser Pro Pro
                245                 250                 255

Thr Arg Asp Arg Arg Asp Arg His Glu Arg Ser Pro Gly Ile Leu Gly
            260                 265                 270

Arg Phe Pro His Asp Arg Phe Arg His Asp Arg Tyr Asp Arg Ser Pro
        275                 280                 285

Ser Arg Leu Glu Arg Ser Pro His Arg Glu Arg Gly Arg Gln Tyr Asp
    290                 295                 300

Ser Arg Asp Arg Ser Pro Phe Ile Ser Pro Arg His Arg Pro Arg His
305                 310                 315                 320

Pro His Leu Arg Asp Asn Thr Pro Ser Arg Val Glu Asn Ser Pro Arg
                325                 330                 335

Gly Arg Val Gln His Glu Asp Val Arg Asp Arg Ser Pro Phe Arg His
            340                 345                 350

Asp Lys Ser Pro Ser Glu Arg Cys Arg Pro Thr Asp Thr His Glu Ala
        355                 360                 365

Ser Lys Lys Ser Arg Ser Gly Ser Ser Glu Lys Ser Gln His Lys
    370                 375                 380

Ser Lys Ser Ala Lys Gln Ser Ser Lys Thr Lys Ser Gly Ser Asn Gly
385                 390                 395                 400

Lys Asn Glu Glu Lys Ile Ser Lys Glu Lys Pro Thr Glu Ser Ser Gln
                405                 410                 415

Tyr Thr Glu Leu Pro Pro Pro Pro Leu Pro Pro Pro Pro Pro
            420                 425                 430

Pro Pro Pro Pro Pro Leu Pro Pro Ala Val Pro Pro Leu Pro
        435                 440                 445

Pro Ser Pro Asp Pro Glu Pro Thr Gly Val Leu Ala Glu Asp Met Ile
    450                 455                 460

Glu Asp Met Asp Ile Cys Asp Thr Pro His Thr Ser Gly Ala Pro
465                 470                 475                 480

Glu Pro Thr Glu Pro Ile Cys Asp Ile Gly Arg Trp Phe Tyr Leu Asp
                485                 490                 495

His Phe Gly Ile Glu Gln Gly Pro Ser Lys Leu Ala Glu Leu Lys Lys
            500                 505                 510

Leu Val Glu Asp Gly Tyr Leu Leu Ser Asp His Leu Ile Lys His Ala
```

```
              515                 520                 525
Asp Ser Asn Arg Trp Val Thr Val Glu Asn Ala Ala Ser Pro Leu Val
    530                 535                 540

Pro Ser Asp Phe Pro Ser Leu Tyr Ser Asp Thr Ser Thr Gln Met Val
545                 550                 555                 560

Asn Pro Pro Glu Ala Pro Gly Asn Leu Leu Asp Glu Ala Leu Glu Glu
                565                 570                 575

Ala Ser Asn Leu Ala Ser Gly Ala Glu Asp Lys Gln Met Asp Glu Ala
                580                 585                 590

Ser Ala Glu Asp Ser Glu Glu Phe Tyr Ile Asp Asp Arg Val Glu Ala
            595                 600                 605

Leu Met Asp Gly Ser Ile Leu Val His Gly Gln Glu Leu Glu Ile Ile
        610                 615                 620

Gly Glu Leu Leu Gly Ala Asp Phe Gln Pro Ala Asp Trp Gln Ser Trp
625                 630                 635                 640

Ser His Pro Glu Asp Phe Thr Arg Phe His Val His Thr Glu Gly Asp
                645                 650                 655

Asp Gly Ile Asn Gly Gly Thr Glu Phe Leu Glu Asn Arg Ala Thr Asp
                660                 665                 670

Ala Tyr Gly Leu Val Ser Val Glu Lys Asn Asn Phe His His Tyr Val
            675                 680                 685

Glu Ser Ser Glu Trp Phe Ser Gly Arg Trp Ser Cys Lys Gly Gly Asp
690                 695                 700

Trp Met Arg Asn Asp Glu Leu Ser Gln Asp Thr Pro Phe Arg Lys Lys
705                 710                 715                 720

Leu Val Leu Asn Glu Gly Tyr Pro Leu Cys Gln Met Pro Lys Gly Ser
                725                 730                 735

Tyr Glu Asp Pro Arg Arg Pro Cys Lys Asp Glu Leu Tyr Tyr Pro Val
                740                 745                 750

Arg Ala Lys Lys His Asp Leu Pro Leu Trp Ala Phe Ser Ser Thr Glu
            755                 760                 765

Glu Asp Thr Asp Ser Val Asn Asp Thr Thr Lys Ser Gly Val Val Pro
        770                 775                 780

Gly Arg Pro Gly Gln Thr Arg Gln Pro Pro Arg Gly Val Lys Gly Met
785                 790                 795                 800

Met Leu Pro Val Val Arg Ile Asn Ser Arg Val Val Lys Asp Gln Ser
                805                 810                 815

Ser Val Glu Pro Arg Thr Lys Pro Arg Gly Thr Asp Arg Pro Leu Ser
                820                 825                 830

Arg Ser Ser Arg Ser His Ser Ile Gly Ala Glu Arg Ser Ser Val His
            835                 840                 845

Glu Gly Ser Thr His Arg Lys His His Asp His Asp Ser Gln Ser Leu
        850                 855                 860

His Lys Ser Lys Ser Val Pro Asn Ile Pro Lys Asp Arg Val Cys Thr
865                 870                 875                 880

Val Asp Glu Leu Ser Val Asn Arg Gly Asp Trp Tyr Tyr Leu Asp Gly
                885                 890                 895

Thr Gly His Glu His Gly Pro Phe Ser Tyr Ser Glu Leu Gln Glu Leu
                900                 905                 910

Val Lys Lys Gly Thr Ile Ile Glu Gln Ser Ser Val Phe Arg Lys Ile
            915                 920                 925

Asp Asn Thr Trp Phe Pro Val Leu Lys Asp Leu Lys Pro Gly Ser Ser
        930                 935                 940
```

```
Val Pro Ser Ala Ala Arg Ser Asn Ser Thr Ala Ala Leu Met His
945                 950                 955                 960

Pro Asp Gln Tyr Asn Phe Gly Val Asn Gln Gly Ser Gly Ser Phe His
                965                 970                 975

Glu Leu His Pro Gln Phe Val Gly Tyr Thr Arg Gly Lys Leu His Glu
            980                 985                 990

Leu Val Met Lys Tyr Phe Lys Ser Arg Glu Leu Thr Leu Ala Ile Asn
        995                 1000                1005

Glu Val Leu Asp Pro Trp Ile Ser Ala Lys Gln Pro Lys Lys Glu Phe
    1010                1015                1020

Glu Ala Tyr Phe Ser His Asn Ser Ala Ser Arg Asn Phe Leu Pro Asp
1025                1030                1035                1040

Gly Gly Ser Ala Lys Arg Ala Lys Leu Leu Pro Asp Gln Ser Asp Glu
                1045                1050                1055

Asp Ile His Leu Ser Glu Asp Ile Leu Ala Ser Arg Lys Glu Asp Ile
            1060                1065                1070

Cys Phe Glu Glu Leu Cys Asp Gly Ala Ser Ser Ser Val Asp Asn Asp
        1075                1080                1085

Ser Val Asn Pro Arg Ala Gly Asn Glu Ser Trp Gly Leu Leu Asn Gly
    1090                1095                1100

His Val Leu Ala Arg Ile Phe His Phe Met Arg Ala Asp Val Lys Ser
1105                1110                1115                1120

Leu Ile Ser Ser Ala Ala Thr Cys Arg Ser Trp Asn Ala Ala Ala Lys
                1125                1130                1135

Tyr Tyr Arg Asn Met Cys Arg Phe Ile Asp Leu Ser Ser Val Gly Pro
            1140                1145                1150

Leu Cys Thr Asp Ser Val Phe Cys Asp Ile Met Ala Gly Tyr Glu Lys
        1155                1160                1165

Gln Asn Ile Arg Thr Leu Ile Leu Ala Gly Cys Ser Asn Leu Ser Ser
    1170                1175                1180

His Ala Leu Gly Arg Val Leu Glu Gln Leu Pro Gln Ile Ser Tyr Val
1185                1190                1195                1200

His Ile Gln Gly Cys Gly His Leu Gly Asp Leu Lys Ser Lys Phe Gln
                1205                1210                1215

His Val Lys Trp Ile Arg Ser Ser Leu Asn Pro Glu Glu Ser Tyr Gln
            1220                1225                1230

Lys Met Lys Thr Leu Lys Gln Ile Gly Asp Gly Asn Asn Tyr Thr Ser
        1235                1240                1245

Lys Val Ala Arg Asn Phe Thr Ser Gln Leu Asp Gly Ser Asp Glu Leu
    1250                1255                1260

Asp Gly Tyr Phe Ala Asp Ile Ser Asn Arg Glu Asn Ala Asn Leu Ser
1265                1270                1275                1280

Phe Gly Gln Gly Phe Tyr Lys Arg Ser Lys Leu Leu Asp Ala Arg Lys
                1285                1290                1295

Ser Ser Ala Val Leu Ser Arg Asp Ala Glu Met Arg Arg Leu Met Gln
            1300                1305                1310

Arg Gln Ala Glu Asn Ser Tyr Arg Lys Met Glu Glu Phe Val Ile Asn
        1315                1320                1325

Arg Leu Arg Glu Ile Met Arg Ser Asn Arg Phe Asp Phe Phe Ile Pro
    1330                1335                1340

Lys Val Ala Lys Ile Glu Gly Arg Leu Lys Asn Gly Tyr Tyr Ala Arg
1345                1350                1355                1360
```

```
His Gly Phe Arg Thr Ile Lys His Asp Ile Arg Thr Met Cys Gln Asp
              1365                1370                1375

Ala Leu Arg Tyr Lys Asp Gly Asn Asp Ser Gly Asp Ile Lys Gln Ile
        1380                1385                1390

Val Val Ser Phe Ile Gln Leu Ala Lys Arg Leu Gly Asn Pro Arg His
    1395                1400                1405

Ile Ser Glu Arg Asn Gly Ala Ala His Asp Ser Leu Asp Ile Ser
1410                1415                1420

Gln Tyr Ser Phe Asp Thr Lys Leu Lys Lys Gln Asn Lys Thr Arg
1425                1430                1435                1440

Gly Ala Asn Leu Val Ala Ala Gly Ala Asp Asn Ser Ser Arg Ala Phe
                1445                1450                1455

Asp Leu Glu Ile Lys Arg Ser Leu Ser Lys Leu Lys Lys Asp Val
        1460                1465                1470

Tyr Ser Gly Ser Glu Thr Ser Asp Asp Asp Val Tyr Ser Glu Gly
            1475                1480                1485

Asp Glu Thr Glu Ser Glu Thr Thr Val Ser Asp Thr Glu Ser Asp Leu
        1490                1495                1500

Asp Val Asn Ser Gly Ala Trp Asp Leu Lys Gly Asn Gly Leu Lys Leu
1505                1510                1515                1520

Ile Glu Pro Gly Glu Ser Val Thr Asp Arg Ile Leu Gly Ala Arg
            1525                1530                1535

Met Thr Lys Ala Ser Leu Val Pro Pro Val Thr Arg Lys Tyr Glu Val
                1540                1545                1550

Ile Glu Glu Tyr Leu Ile Val Ala Asp Val Glu Glu Val Gln Arg Lys
        1555                1560                1565

Met Arg Val Ala Leu Pro Asp Asp Tyr Ser Glu Lys Leu Leu Ser Gln
        1570                1575                1580

Lys Asn Gly Thr Glu Asn Leu Glu Leu Pro Glu Val Lys Asp Tyr Gln
1585                1590                1595                1600

Pro Arg Lys Val Ala Gly Asp Glu Ile Leu Glu Gln Glu Val Tyr Gly
                1605                1610                1615

Ile Asp Pro Tyr Thr His Asn Leu Leu Ser Asp Ile Met Pro Ala Asp
            1620                1625                1630

Leu Glu Leu Ser Pro Thr Asp Lys His Ile Phe Ile Glu Glu Leu Leu
        1635                1640                1645

Leu Asn Thr Leu Asn Lys Gln Val Lys Arg Phe Thr Gly Ser Gly Asn
        1650                1655                1660

Thr Pro Met Thr Tyr Asn Leu Arg Pro Val Ile Glu Glu Ile Gln Arg
1665                1670                1675                1680

Ser Ala Glu Asp Asn Gly Asp Arg Arg Thr Ser Lys Met Cys Leu Gly
                1685                1690                1695

Met Leu Lys Thr Met Arg Asn Arg Ser Asp Gln Asn Phe Val Ala Tyr
            1700                1705                1710

Arg Lys Gly Leu Gly Val Val Cys Asn Lys Lys Gly Phe Gly Val
        1715                1720                1725

Asp Asp Phe Val Val Glu Phe Phe Gly Glu Val Tyr Pro Ser Trp Arg
        1730                1735                1740

Trp Tyr Glu Lys Gln Asp Gly Ile Lys His Ile Gln Asn Asn Ser Glu
1745                1750                1755                1760

Asp Gln Ala Pro Glu Phe Tyr Asn Ile Met Leu Glu Arg Pro Lys Gly
        1765                1770                1775

Asp Arg Asp Gly Tyr Asp Leu Val Phe Val Asp Ala Met His Lys Ala
```

```
                1780              1785              1790

Asn Tyr Ala Ser Arg Ile Cys His Ser Cys Asn Pro Asn Cys Glu Ala
        1795              1800              1805

Lys Val Thr Ala Val Asp Gly Lys Tyr Gln Ile Gly Val Tyr Thr Leu
        1810              1815              1820

Arg Pro Ile Ala Glu Gly Glu Glu Ile Thr Phe Asp Tyr Asn Ser Val
1825              1830              1835              1840

Thr Glu Ser Lys Glu Glu His Glu Ala Ser Val Cys Leu Cys Gly Ser
        1845              1850              1855

Gln Val Cys Arg Gly Ser Tyr Leu Asn Phe Ser Gly Glu Gly Ala Phe
        1860              1865              1870

Glu Lys Val Leu Met Glu Phe His Gly Val Leu Asp Arg His Ser Leu
        1875              1880              1885

Leu Leu Gln Ala Cys Glu Thr Asp Ser Val Ser Gln Gln Asp Leu Ile
        1890              1895              1900

Asp Leu Gly Arg Ala Gly Leu Gly Thr Cys Leu Leu Ala Gly Leu Pro
1905              1910              1915              1920

Gly Trp Leu Val Ala Tyr Thr Ala Asn Leu Val Arg Phe Ile Tyr Leu
            1925              1930              1935

Glu Arg Gln Lys Leu Pro Asp Glu Ile Leu Arg His Asn Val Asp Glu
        1940              1945              1950

Lys Arg Gln Phe Leu Ile Glu Ile Asn Met Asp Ser Glu Lys Asn Asp
        1955              1960              1965

Ala Glu Val Gln Ala Glu Gly Val Leu Asn Ser Arg Leu Gln Gln Ile
        1970              1975              1980

Val His Thr Leu Asp Lys Val Arg Tyr Val Met Arg Cys Val Phe Gly
1985              1990              1995              2000

Asp Pro Lys Asn Ala Pro Pro Leu Val Arg Leu Ser Gly Lys Ser
            2005              2010              2015

Leu Val Ser Ala Ile Trp Lys Gly Asp Ser Ser Ile Val Ala Glu Leu
        2020              2025              2030

Leu Gln Ser Met Glu Pro His Val Glu Glu Val Leu Ser Asp Leu
        2035              2040              2045

Lys Val Lys Ile Arg Ala His Asp Pro Pro Asp Ser Glu Asp Ile Glu
        2050              2055              2060

Gly Gly Ile Arg Asn Ser Leu Leu Trp Leu Arg Asp Glu Leu Arg Thr
2065              2070              2075              2080

Leu Pro Cys Thr Tyr Lys Cys Arg His Asp Ala Ala Ala Asp Leu Ile
            2085              2090              2095

His Leu Tyr Ala Tyr Thr Lys Cys Phe Phe Arg Val Arg Asp Tyr Lys
            2100              2105              2110

Thr Val Lys Ser Pro Pro Val His Ile Ser Pro Leu Asp Leu Gly Pro
        2115              2120              2125

Lys Tyr Ala Asp Lys Leu Gly Pro Gly Phe Gln Glu Tyr Cys Lys Thr
        2130              2135              2140

Tyr Pro Glu Asn Tyr Cys Leu Ala Gln Leu Ile Tyr Trp Tyr Ser Gln
2145              2150              2155              2160

Asn Ser Glu Pro Glu Ser Arg Leu Thr Arg Ala Arg Lys Gly Cys Met
            2165              2170              2175

Ser Leu Pro Asp Val Ser Ser Phe Tyr Val Lys Ser Ala Lys Pro Ser
            2180              2185              2190

Gln Glu Arg Val Tyr Gly Asn Arg Thr Val Arg Phe Met Leu Ser Arg
            2195              2200              2205
```

-continued

Met Glu Lys Gln Ala Gln Arg Pro Trp Pro Lys Asp Arg Ile Trp Val
                2210                2215                2220

Phe Lys Ser Asp Pro Arg Phe Phe Gly Ser Pro Met Met Asp Ala Val
2225                2230                2235                2240

Leu Asn Asn Ser Pro Leu Asp Lys Glu Met Val His Trp Leu Lys Thr
                2245                2250                2255

Arg Pro Asn Val Phe Leu Gly
            2260

<210> SEQ ID NO 115
<211> LENGTH: 2395
<212> TYPE: PRT
<213> ORGANISM: Brassica napus

<400> SEQUENCE: 115

Met Ser Asp Gly Gly Val Ala Cys Met Pro Leu Leu Asn Ile Met Glu
1               5                   10                  15

Lys Leu Pro Ala Val Glu Lys Thr Leu Cys Gly Gly Asn Asn Asp Thr
                20                  25                  30

Lys Leu Ala Gly Asn Ser Glu Asn Gly His Thr Ser Ile Ser Ala Asn
            35                  40                  45

Asp Lys Leu Pro Asp Ser Gln Pro Ala Gln Pro Lys Lys Lys Thr
        50                  55                  60

Lys Lys Ile Val Lys Val Ile Arg Lys Val Met Val Arg Lys Gln
65                  70                  75                  80

Lys Gln Pro Lys Gln Gln Ala Val Gln Leu Pro Gly Glu Ser Gln Val
                85                  90                  95

Gln Thr Lys Glu His Asp Lys Lys Ser Glu Pro Leu His Glu Asn Thr
                100                 105                 110

Cys Asn Gly Gln Leu Glu Asn Gly Gly Asp Ser Gly Phe Lys Asp Glu
            115                 120                 125

Val Glu Glu Gly Glu Leu Gly Thr Met Ser Ser His Gly Ile Leu Glu
        130                 135                 140

Asn Gly Glu Ile Ser Pro Val Lys Ser Leu Gln Arg Ser Glu Ile Glu
145                 150                 155                 160

Lys Gly Glu Ile Ser Gly Glu Ser Trp Lys Lys Asp Glu Thr Ala Asn
                165                 170                 175

Ala Glu Phe Ser Tyr Met His Tyr Asp Lys Gly Tyr Ala Glu Arg Arg
                180                 185                 190

Asp Leu Ser Ser Asp Lys Tyr Arg Lys Gly Glu Glu Arg Asp Phe Arg
            195                 200                 205

Ser Trp Arg Asp Pro Ser Asp Glu Ile Glu Lys Gly Glu Phe Ile Pro
        210                 215                 220

Asp Arg Trp His Lys Met Asp Thr Val Lys Asp His Ser Tyr Asn
225                 230                 235                 240

Arg Ser Arg Arg Asn Gly Ser Asp Arg Glu Lys Thr Trp Arg Tyr Glu
                245                 250                 255

Tyr Asp Tyr Glu His Glu Pro Thr Pro Pro Gly Gly Arg Phe Val Asn
                260                 265                 270

Glu Asp Phe Tyr Arg Arg Arg Glu Phe Arg Ser Gly Asn Asp Arg Ala
            275                 280                 285

Thr Arg Ile Ser Ser Lys Ile Val Ile Glu Asp Asn Leu His Lys Asn
        290                 295                 300

Glu Cys Asn Asp Pro Asn Gly Leu Gly Lys Glu Tyr Ser Ser Thr Val

```
                305                 310                 315                 320
Asn Lys Leu Lys Arg His Gly Ala Glu Pro Asp Ser Phe Glu Arg Lys
                    325                 330                 335
His Ser Tyr Asp Asp Tyr Gly Asp Tyr Gly Ser Ser Lys Cys Arg Lys
                    340                 345                 350
Ile Ser Asp Asp Tyr Ser Arg Ser Leu His Ser Asp His Tyr Ser Arg
                    355                 360                 365
His Ser Val Glu Arg Pro Tyr Lys Asp Ser Tyr Ser Ser Lys Thr Ser
                    370                 375                 380
Ser Leu Glu Lys Tyr Ser Arg Lys His Gln Asp Ser Ser Phe Pro Ala
385                 390                 395                 400
Arg Ala Phe Ser Asp Arg His Gly His Ser Pro Ala Arg Ser Asp Leu
                    405                 410                 415
Ser Pro His Asp Arg Ser Arg Tyr His Glu His Arg Asp Arg Ser Pro
                    420                 425                 430
Ile His Arg Glu Arg Ser Pro Tyr Ala Arg Glu Arg Ser Pro Tyr Ile
                    435                 440                 445
Phe Glu Lys Ser Ser His Ala Arg Lys Arg Ser Pro His Asp Arg Ser
            450                 455                 460
His His His Asp Tyr Arg Arg Ser Pro Ser Tyr Ser Glu Trp Ser Ser
465                 470                 475                 480
Asp Arg Arg Asp Gly Thr Ser Asn Tyr Arg Glu Asp Pro Gln Ser Asp
                    485                 490                 495
Arg Asn Arg Arg Asn Gly His Arg Glu Ile Ser Arg Lys Ser Gly Val
                    500                 505                 510
Arg Glu Lys Gly Asp Ser Gln Ala Gly Thr Glu Leu Glu His Lys Tyr
                    515                 520                 525
Arg His Arg Asp Ser Asn Gly Lys Glu Ser Ala Ser Ser Ser Lys Glu
                    530                 535                 540
Leu Gln Gly Gln Asn Ile Leu Tyr Asn Asn Asp Pro Val Val Glu Lys
545                 550                 555                 560
Ser Ser Ile Cys Asp Ser Ser Lys Ile Pro Ser Pro Cys Ala Lys Gly
                    565                 570                 575
Asn Glu Ser Val Gln Val Ser Glu Ala Pro Thr Glu Glu Leu Pro Ser
                    580                 585                 590
Met Glu Val Asp Met Asp Ile Cys Asp Thr Pro Pro His Glu Pro Ala
                    595                 600                 605
Lys Gly Lys Glu Ser Val Ala Ala Asp Ser Ser Leu Gly Lys Trp Phe
                    610                 615                 620
Tyr Leu Asp Tyr Tyr Gly Met Glu Asn Gly Pro Ala Lys Leu Ser Glu
625                 630                 635                 640
Leu Lys Ala Leu Met Glu Gln Gly Ile Leu Leu Ser Asp His Met Ile
                    645                 650                 655
Lys His Ser Asp Asn Asn Arg Trp Val Thr Ile Glu Asn Ala Thr Ser
                    660                 665                 670
Pro Thr Val Asn Ile Asn Phe Pro Ser Val Val Ser Asp Ala Val Thr
                    675                 680                 685
Arg Leu Val Asn Pro Pro Glu Ala Pro Gly Asn Leu Leu Glu Asp Ile
                    690                 695                 700
Val Asp Ala Ala Glu Ala Val Pro Met Asp Gln Glu Ala Gly Tyr Ser
705                 710                 715                 720
Leu Pro Glu Ser Val Ser Ile Pro Asp Thr Lys Glu Ile Leu Val Glu
                    725                 730                 735
```

```
His His Glu Asp Phe Gln Phe Asp Lys Arg Ile Ala Ser Leu Val Glu
            740                 745                 750

Gly Cys Thr Ile Thr Pro Gly Arg Glu Leu Glu Thr Leu Gly Glu Ala
            755                 760                 765

Met Gln Ile Lys Val Glu Leu Glu Glu Thr Arg Lys Phe Val Ser Pro
    770                 775                 780

Glu Asp Ile Thr Trp Cys Tyr Tyr Gln Val Val Asp Gln Leu Leu Gly
785                 790                 795                 800

Asp Glu Ala Ser Gly Ser Ser Glu Pro Lys Thr Arg Asp Val Glu Glu
            805                 810                 815

Leu Thr Ser Glu Asn Val Asp Gly Ser Glu Ser Asp Glu Ile Gly Ser
            820                 825                 830

Trp Leu Ser Gly Arg Trp Ser Cys Lys Gly Gly Asp Trp Ile Arg Arg
            835                 840                 845

Asp Glu Ala Ser Gln Asp Ile Tyr Tyr Lys Lys Lys Leu Val Leu Asn
850                 855                 860

Asp Gly Phe Pro Leu Cys Leu Met Gln Lys Ser Gly His Glu Asp Pro
865                 870                 875                 880

Arg Arg His Gln Lys Asp Asp Leu Tyr Tyr Ser Arg Ser Ser Ser Arg
            885                 890                 895

Leu Glu Leu Pro Leu Trp Ala Phe Ser Gly Val Asp Glu Arg Asn Gln
            900                 905                 910

Ala Arg Gly Val Lys Ala Ser Val Leu Ser Val Val Arg Leu Asn Ser
            915                 920                 925

Leu Val Val Asn Asp Gln Val Pro Ser Ile Pro Asp Pro His Val Lys
            930                 935                 940

Val Arg Gly Arg Glu Lys Cys Ser Ser Arg His Ala Arg Pro Ser Pro
945                 950                 955                 960

Ala Ser Ser Asp Ser Lys Trp Glu Ser Val Glu Thr Ile Ser Gln Ser
            965                 970                 975

Thr Ser Cys Gly Ser Gln Asp Leu Gln Gly Cys Trp Lys Thr Gly Ala
            980                 985                 990

Ser Val Ile Thr Pro Thr Asn Arg Leu Tyr Thr Val Glu Asp Leu Gln
            995                 1000                1005

Leu His Leu Gly Asp Trp Phe Tyr Ile Asp Gly Ala Gly Gln Glu Gln
    1010                1015                1020

Gly Pro Leu Pro Phe Ser Ala Leu Gln Ile Leu Val Asp Lys Gly Leu
1025                1030                1035                1040

Ile Lys Ser His Ser Ser Val Phe Arg Lys Ser Asp Lys Ile Trp Val
                1045                1050                1055

Pro Val Thr Ser Ile Thr Lys Thr Leu Glu Thr Ser Ala Lys Leu Gln
                1060                1065                1070

Gly Lys Lys Pro Ala Leu Pro Ser Asp Cys Gln Ser Leu Val Val Ser
                1075                1080                1085

Glu Ser Gln Asp Phe Lys His Ser Glu Met Asp Thr Ser Leu Ser Ser
                1090                1095                1100

Phe His Ser Met His Pro Gln Phe Leu Gly Tyr Phe Arg Gly Lys Leu
1105                1110                1115                1120

His Gln Leu Val Met Lys Thr Phe Lys Ser Arg Glu Phe Ser Ala Ala
                1125                1130                1135

Ile Asn Asp Val Leu Asp Thr Trp Ile Asn Gly Lys Gln Pro Lys Lys
                1140                1145                1150
```

-continued

```
Glu Thr Asp Lys Tyr Met Tyr His Ser Ser Glu Phe Asp Ser Ser Tyr
        1155                1160                1165

Pro Lys Arg Ala Arg Leu Met Ala Gly Glu Ile Gly Asp His Ser Glu
    1170                1175                1180

Val Asp Val Phe Gln Lys Asp Asp Leu Ala Phe Glu Asp Leu Cys
1185                1190                1195                1200

Gly Asp Ala Thr Phe His Val Glu Gly Ser Gly Ser Ser Arg Thr Ala
            1205                1210                1215

Gly Ile Tyr Trp Asp Leu Leu Asp Gly His Ala Leu Ala Arg Val Phe
        1220                1225                1230

His Leu Leu Arg Tyr Asp Val Lys Ser Leu Ala Phe Ala Ser Met Thr
    1235                1240                1245

Cys Arg His Trp Lys Ala Thr Val Asn Ser Tyr Lys Asp Ile Ser Arg
1250                1255                1260

Gln Val Asp Leu Ser Ser Leu Gly Pro Asn Cys Thr Asp Ser Arg Leu
1265                1270                1275                1280

Trp Ser Ile Met Asn Thr Tyr Asn Thr Gln Lys Ile Asp Ser Val Ile
            1285                1290                1295

Leu Val Gly Cys Thr Asn Val Thr Ser Ser Met Leu Glu Glu Val Leu
        1300                1305                1310

Arg Leu Phe Ser His Ile Ser Ser Val Asn Ile Thr Gly Cys Ser Gln
    1315                1320                1325

Phe Gly Asp Leu Thr Leu Asn Tyr Lys Lys Val Ser Trp Leu Lys Phe
    1330                1335                1340

Gln His Pro Arg Ser Gly Glu Leu Arg Ser Arg Leu Arg Ser Leu Lys
1345                1350                1355                1360

Gln Thr Thr Asp Val Ala Lys Ser Lys Gly Leu Gly Gly Asp Thr Asp
            1365                1370                1375

Asp Phe Gly Asn Leu Lys Asp Tyr Phe Asp Arg Val Glu Lys Arg Asp
        1380                1385                1390

Ser Ala Asn Gln Leu Phe Arg Lys Ser Leu Tyr Lys Arg Ser Lys Leu
    1395                1400                1405

Tyr Asp Ala Arg Lys Ser Ser Ala Ile Leu Ser Arg Asp Ala Arg Ile
    1410                1415                1420

Arg Arg Trp Ala Val Lys Lys Ser Glu His Gly Tyr Lys Arg Val Glu
1425                1430                1435                1440

Glu Phe Leu Ala Ser Ser Leu Arg Gly Ile Met Lys Gln Asn Thr Phe
            1445                1450                1455

Asp Phe Phe Thr Leu Lys Val Ala Gln Ile Glu Glu Lys Met Lys Asn
        1460                1465                1470

Gly Tyr Tyr Val Ser His Gly Leu Lys Ser Val Lys Glu Asp Ile Ser
    1475                1480                1485

Arg Met Cys Arg Glu Ala Ile Lys Gly Arg Asn Arg Gly Gly Ser Lys
    1490                1495                1500

Asp Met Asn Arg Ile Ile Val Pro Phe Ile Gln Leu Ala Thr Arg Leu
1505                1510                1515                1520

Glu Glu Val Ser Met Val Thr Ser Ser Tyr Arg Arg Asp Glu Leu Met
            1525                1530                1535

Lys Ser Trp Gln Asp Gly Ser Gly Phe Ser Ser Ala Ser Lys Tyr Asn
        1540                1545                1550

Lys Lys Leu Ser Lys Ser Val Thr Glu Lys Lys Phe Met Ser Arg Thr
    1555                1560                1565

Ser Asp Thr Leu Gly Val Asn Gly Ala Leu Asp Tyr Gly Glu Tyr Ala
```

-continued

```
            1570                1575                1580

Ser Asp Arg Glu Ile Arg Arg Leu Ser Lys Leu Asn Arg Lys Ser
1585                1590                1595                1600

Phe Gly Ser Gly Ser Glu Thr Ser Ser Glu Leu Ser Glu Asn Asp Ser
                1605                1610                1615

Tyr Ser Ser Ala Ser Ala Ser Glu Ser Glu Ser Asp Ile Arg Ser Glu
                1620                1625                1630

Gly Arg Ser Gln Asp Ser Arg Val Glu Lys Tyr Phe Thr Ser Asp Glu
                1635                1640                1645

Ser Phe Asp Ser Val Ile Glu Glu Arg Glu Trp Gly Ala Arg Met Thr
                1650                1655                1660

Lys Ala Gly Leu Val Pro Pro Val Thr Arg Lys Tyr Glu Val Ile Glu
1665                1670                1675                1680

Glu Tyr Thr Ile Val Ala Asp Glu Glu Val Gln Arg Lys Met Leu
                1685                1690                1695

Val Ser Leu Pro Glu Asp Tyr Ala Glu Lys Leu Asn Ala Gln Lys Asn
                1700                1705                1710

Gly Thr Glu Glu Leu Asp Met Glu Leu Pro Glu Val Lys Glu Tyr Lys
                1715                1720                1725

Pro Arg Lys Leu Leu Gly Asn Glu Val Leu Glu Gln Glu Val Tyr Gly
                1730                1735                1740

Ile Asp Pro Tyr Thr His Asn Leu Leu Leu Asp Ser Met Pro Glu Leu
1745                1750                1755                1760

Asp Trp Ser Leu Gln Asp Lys His Ser Phe Ile Glu Asp Val Val Leu
                1765                1770                1775

Arg Thr Leu Asn Arg Gln Ala Arg Leu Phe Thr Gly Ser Gly Asn Thr
                1780                1785                1790

Pro Met Val Phe Pro Leu Arg Pro Val Ile Glu Glu Leu Lys Glu Asn
                1795                1800                1805

Ala Arg Glu Glu Cys Asp Ile Gln Thr Met Arg Met Cys Gln Gly Ile
                1810                1815                1820

Leu Lys Ala Ile Glu Ser Arg Ser Asp Asp Asn Tyr Val Ser Tyr Arg
1825                1830                1835                1840

Lys Gly Leu Gly Val Val Cys Asn Lys Gln Ser Gly Phe Val Val Glu
                1845                1850                1855

Asp Phe Val Val Glu Phe Leu Gly Glu Val Tyr Pro Val Trp Lys Trp
                1860                1865                1870

Phe Glu Lys Gln Asp Gly Ile Arg Ser Leu Gln Glu Asn Lys Thr Asp
                1875                1880                1885

Pro Ala Pro Glu Phe Tyr Asn Ile Tyr Leu Glu Arg Pro Lys Gly Asp
                1890                1895                1900

Ala Asp Gly Tyr Asp Leu Val Val Asp Ala Met His Lys Ala Asn
1905                1910                1915                1920

Tyr Ala Ser Arg Ile Cys His Ser Cys Arg Pro Asn Cys Glu Ala Lys
                1925                1930                1935

Val Thr Ala Val Asp Gly His Tyr Gln Ile Gly Ile Tyr Ser Val Arg
                1940                1945                1950

Pro Ile Glu Tyr Gly Glu Glu Ile Thr Phe Asp Tyr Asn Ser Val Thr
                1955                1960                1965

Glu Ser Lys Glu Glu Tyr Glu Ala Ser Val Cys Leu Cys Gly Ser Gln
                1970                1975                1980

Val Cys Arg Gly Ser Tyr Leu Asn Leu Thr Gly Glu Gly Ala Phe Gln
1985                1990                1995                2000
```

Lys Val Leu Lys Glu Trp His Gly Leu Leu Asp Arg His Lys Leu Met
            2005                2010                2015

Leu Glu Ala Cys Ile Leu Asn Ser Val Ser Glu Gly Asp Tyr Leu Glu
            2020                2025                2030

Leu Gly Arg Ala Gly Leu Gly Ser Cys Leu Leu Gly Gly Leu Pro Asp
            2035                2040                2045

Trp Val Ile Ala Tyr Thr Ala Arg Leu Val Arg Phe Ile Asn Phe Glu
            2050                2055                2060

Arg Thr Lys Leu Pro Glu Glu Ile Leu Lys His Asn Met Glu Glu Lys
2065                2070                2075                2080

Arg Lys Tyr Phe Ser Asp Val His Leu Asp Val Glu Lys Ser Asp Ala
            2085                2090                2095

Glu Val Gln Ala Glu Gly Val Tyr Asn Gln Arg Leu Gln Asn Leu Ala
            2100                2105                2110

Val Thr Leu Asp Lys Val Arg Tyr Val Met Arg Arg Val Phe Gly Asp
            2115                2120                2125

Pro Lys Asn Ala Pro Pro Leu Glu Arg Leu Thr Pro Glu Glu Thr
            2130                2135                2140

Val Ser Leu Leu Trp Asn Gly Asp Gly Ser Leu Val Glu Asp Leu Leu
2145                2150                2155                2160

Gln Cys Leu Ser Pro His Val Glu Glu Gly Ile Val Asp Glu Leu Arg
            2165                2170                2175

Tyr Lys Ile Arg Ala His Asp Pro Ser Gly Ser Ala Asp Val Leu Glu
            2180                2185                2190

Glu Leu Gln Arg Ser Leu Leu Trp Leu Arg Asp Glu Ile Arg Asp Leu
            2195                2200                2205

Pro Cys Thr Tyr Lys Cys Arg Asn Asp Ala Ala Ala Asp Leu Ile His
            2210                2215                2220

Ile Tyr Ala Tyr Thr Lys Cys Phe Phe Lys Val Arg Glu Tyr Lys Ser
2225                2230                2235                2240

Phe Val Ser Ser Pro Val His Ile Ser Pro Leu Asp Leu Gly Thr Lys
            2245                2250                2255

Tyr Ala Glu Lys Leu Gly Asp Ser Ile Lys Glu Tyr Arg Lys Thr Tyr
            2260                2265                2270

Gly Glu Asn Tyr Cys Leu Gly Gln Leu Ile Tyr Trp Tyr Glu Gln Thr
            2275                2280                2285

Asn Thr Asp Pro Asp Val Thr Leu Val Lys Ala Thr Arg Gly Cys Leu
            2290                2295                2300

Ser Leu Pro Asp Val Ala Ser Phe Tyr Ala Lys Ala Gln Lys Pro Ser
2305                2310                2315                2320

Lys His Arg Val Tyr Gly Pro Lys Thr Val Lys Thr Met Val Ser Gln
            2325                2330                2335

Met Leu Lys Gln Pro Gln Lys Pro Trp Ala Lys Asp Lys Ile Trp Met
            2340                2345                2350

Phe Lys Ser Asn Pro Val Val Phe Gly Ser Pro Met Phe Asp Ala Val
            2355                2360                2365

Leu Asn Asp Ser Ser Leu Asp Arg Glu Leu Leu Gln Trp Leu Arg Ser
            2370                2375                2380

Arg Arg His Val Phe Gln Ala Thr Trp Asp Ser
2385                2390                2395

<210> SEQ ID NO 116
<211> LENGTH: 2387

```
<212> TYPE: PRT
<213> ORGANISM: Beta vulgaris subsp. vulgaris

<400> SEQUENCE: 116

Met Gly Asp Gly Gly Val Ala Cys Val Ser Leu Gln Pro Ile Met Glu
1               5                   10                  15

Lys Phe Pro Gly Ser Glu Thr Phe Cys Gly Gly Ser Ser Asn Ser
            20                  25                  30

Asn Gly Lys Leu Glu Thr Lys Ser Ile Lys Arg Thr Thr Thr Lys Arg
        35                  40                  45

Met Lys Leu Lys Arg Asp Ala Phe Phe Lys Lys Glu Glu Pro Glu Lys
    50                  55                  60

Lys Glu Leu Ile Ser Glu Lys Val Lys Ser Ser Gly Glu Val Glu Asn
65              70                  75                  80

Gly Thr Val Glu Gly Asp Lys Leu Gln Lys Glu Val Glu Glu Gly
                85                  90                  95

Glu Leu Gly Thr Leu Lys Ser Pro Lys Asn Glu Ala Glu Asn Gly Glu
            100                 105                 110

Leu Ile Pro Asp Lys Ser Tyr Lys Thr Glu Thr Glu Lys Gly Gly Ile
        115                 120                 125

Ser Thr Gly Lys Trp Arg Lys Asp Glu Gly Asp Arg Gly Glu Ile Ser
    130                 135                 140

Pro Ala Lys Trp Arg Lys Gly Glu Ala Glu Arg His Glu Cys Ser Ser
145             150                 155                 160

Gly Arg Leu Arg Gly Asp Leu Val Gln Arg Arg Asp Arg Thr Pro Glu
                165                 170                 175

Lys Tyr Arg Lys Gly Glu Tyr Glu Lys Ala Glu Phe Gly Ser Trp Arg
            180                 185                 190

Gly Ser Lys Asp Glu Val Glu Lys Gly Glu Phe Ile Pro Glu Arg Trp
        195                 200                 205

His Lys Gly Asp Ala Tyr Arg Glu Glu Tyr Tyr Ser Lys Gly Arg
    210                 215                 220

Arg His Asp Ser Ser Arg Glu Arg Arg Tyr Glu Arg Asp Trp
225                 230                 235                 240

Thr Pro Pro Ser Met Arg Tyr Ser Ala Glu Asp Val Ser Pro Val Arg
                245                 250                 255

Asp Phe Ser Arg Ser Ala Asn Asn Arg Tyr Leu Lys Thr Ala Arg
            260                 265                 270

Trp Glu Val Asn Gln Glu Arg Ser Tyr Pro Lys Met Ser Ala Lys Ile
        275                 280                 285

Met Asp Glu Leu Asn Tyr Lys Asn Glu Tyr Ser His Gly Arg Ser Gln
    290                 295                 300

Gly Arg Glu His Ser Ser Gly Ala Arg Met Lys Arg His Gly Thr Asp
305                 310                 315                 320

Ser Glu Ser Ser Asp Arg Lys Leu Tyr Asp Asp His Gly Asp Tyr Val
                325                 330                 335

Ser Ser Lys Ser Arg Arg Leu Ser Asn Ser Glu His Tyr Met Arg Gln
            340                 345                 350

Ser Ala Asp Lys Ser Phe Arg Ile Ser Asn Pro Ser Arg Ala Val Ser
        355                 360                 365

Asp Arg Leu Ser Ser Arg His Tyr Asp Asn Ala Ser Thr Arg Ala Val
    370                 375                 380

Tyr Asp Arg Gln Arg Arg Ser Pro Ser Tyr Ser Glu Arg Ser Pro His
385                 390                 395                 400
```

-continued

```
Glu Arg Gly Arg His His Asp His Arg Asp Arg Thr Pro Ala Arg His
            405                 410                 415
Glu Arg Ser Pro Cys Tyr Arg Gly His Arg His Glu Asn Arg Asn Arg
            420                 425                 430
Ser Pro Ser Tyr Val Glu Lys Ser Pro Ser Asp Arg Val Arg Val Tyr
            435                 440                 445
Glu Arg Gln Glu Lys Ser Pro Ser Tyr Ser Gly Ser Pro His Asp Arg
            450                 455                 460
Ile Arg Pro Phe Asn Asn Arg Gln Thr Ser Arg Ser Glu Val Ala Glu
465                 470                 475                 480
Thr Asn Gln Asp Asp Arg Val Gln Glu Lys Lys Pro Thr Glu Ile Ile
            485                 490                 495
Arg Asn Asp Lys Val Ser Thr Ile Ser Ala Lys Asp Pro Leu Val Ile
            500                 505                 510
Asn Asp Met Gln Asn Gly Ala Val Asp Lys Gly Ile Ser His Glu Thr
            515                 520                 525
His Val Lys Asp Glu Tyr Gln Gly Pro Cys Leu Glu Asp Lys Glu Gln
            530                 535                 540
Gln Leu Leu Val Asp Gly Thr Ile Glu Glu Leu Pro Ser Met Glu Glu
545                 550                 555                 560
Asp Met Asp Ile Cys Asp Thr Pro Pro His Val Pro Cys Val Ala Thr
                565                 570                 575
Val Asn Pro Gly Lys Trp Tyr Tyr Leu Asp His Leu Gly Glu Glu Arg
            580                 585                 590
Gly Pro Ser Arg Leu Cys Asp Leu Lys Ala Leu Ile Glu Glu Gly Ile
            595                 600                 605
Leu Met Ser Asp His Leu Val Lys His Ser Asp Ser Asp Arg Trp Glu
            610                 615                 620
Thr Val Glu Asn Ala Ala Ser Pro Val Val Thr Ala Asn Phe Thr Thr
625                 630                 635                 640
Ile Phe Ser Glu Thr Val Thr Gln Leu Val Ser Pro Pro Glu Ala Pro
                645                 650                 655
Gly Asn Leu Leu Ala Asp Val Val Asp Ala Glu His Ser Val Asp Gln
            660                 665                 670
Val Gly Ile Glu Ser Leu Asp Ser Ser Val Leu Gly Val Thr Gly Asp
            675                 680                 685
Asp Asp Leu Val Asp Asp Arg Gly Ile Asp Val Arg Val Gly Ala Leu
            690                 695                 700
Leu Asp Gly Phe Thr Val Leu Pro Gly Lys Glu Leu Glu Ile Val Gly
705                 710                 715                 720
Glu Val Leu Gln Met Thr Phe Asp His Ser Glu Trp Glu Arg Phe Gly
                725                 730                 735
Ile Ser Glu Gly Phe Met Gln Asp His Ser Gly Ser Gln Glu Pro Phe
            740                 745                 750
Glu Gln Ser Gln Glu Glu Asp Met Ser Arg Tyr Leu Glu Thr Thr Leu
            755                 760                 765
Lys Asp Ser Glu Cys Thr Ser Thr Ala Gly Leu Asp Lys Glu Cys Ser
            770                 775                 780
Phe Leu Leu Asn Glu Tyr Thr Glu Trp Phe Ser Gly Arg Trp Ser Cys
785                 790                 795                 800
Lys Gly Gly Asp Trp Gln Arg Asn Glu Glu Ala Val Gln Asp Lys Phe
                805                 810                 815
```

```
Phe Arg Lys Lys Ile Val Leu Asn Asp Gly Tyr Pro Leu Cys Gln Met
            820                 825                 830

Ser Lys Ser Gly Tyr Glu Asp Pro Arg Trp Pro Arg Lys Asp Asp Leu
        835                 840                 845

Tyr Tyr Pro Cys Gln Ser Lys Arg Leu Asp Leu Pro Ser Trp Ala Phe
    850                 855                 860

Ser Cys Pro Asp Glu Arg Asn Asp Ser Ser Ile Val Asn Lys Gln Gly
865                 870                 875                 880

Gln Ala Lys Pro Val Val Arg Gly Val Lys Gly Ser Met Met Pro
                885                 890                 895

Val Ile Arg Ile Asn Ala Cys Val Val Lys Asp His Gly Ser Ser Val
            900                 905                 910

Ser Asp Thr Arg Leu Lys Pro Arg Gly Lys Glu Lys Tyr Ser Leu Lys
        915                 920                 925

Gly Thr Lys His Tyr Ser Leu Ser Asn Asp Val Lys Lys Ser Ser Glu
    930                 935                 940

Glu Asp Ala Phe His Ser Lys Ser Phe Lys Glu Gln Asn Ser Glu Glu
945                 950                 955                 960

Ser Trp Lys Pro Ser Ile Ile Ser Lys Pro Lys Asp Arg Leu Cys Thr
                965                 970                 975

Val Asn Asp Leu Gln Leu His Leu Gly Glu Trp Tyr Tyr Leu Asp Gly
            980                 985                 990

Thr Gly His Glu Arg Gly Pro Phe Ser Cys Ser Val Leu Leu Lys Leu
        995                 1000                1005

Val Asp Glu Gly Ser Leu Lys Lys Gln Ser Ser Val Phe Arg Lys Ile
    1010                1015                1020

Asp Lys Val Trp Val Pro Val Thr Ser Val Ile Lys Ala Ser Glu Asn
1025                1030                1035                1040

Gly Gly Lys Leu Val Gly Asp Asn Ile Val Pro Val Gly Glu Ser Ser
                1045                1050                1055

Glu Thr Pro Ser Val His Gly Gly Ser Ser Ile Ser Ser Phe
            1060                1065                1070

His His Leu His Pro His Phe Ile Gly Tyr Thr Leu Gly Lys Leu His
        1075                1080                1085

Glu Leu Val Met Lys Ser Tyr Lys Ser Arg Glu Phe Ala Ala Ala Ile
    1090                1095                1100

Asn Glu Val Leu Asp Pro Trp Ile Asn Ser Arg Gln Pro Arg Lys Glu
1105                1110                1115                1120

Met Glu Lys His Arg Ser Ser Ile Tyr Val Gln Lys Ala Pro Met Gly
                1125                1130                1135

Leu Ala Phe Ser Glu Asn Glu Val Ser Met Leu Pro Glu Glu Asp Met
            1140                1145                1150

His Thr Lys Lys Arg Cys Arg Thr Leu Ile Asp Gly Val Asp Glu Asp
        1155                1160                1165

Tyr Glu Met Ile Glu Gly Val Pro Ala Leu Ser Cys Arg Glu Pro Ser
    1170                1175                1180

Phe Glu Asp Leu Cys Ser Asn Val Ala Phe Cys Lys Glu Asp Asn Asn
1185                1190                1195                1200

Cys His Lys Thr Glu Val Gly Ser Trp Gly Leu Leu Asp Gly His Ile
                1205                1210                1215

Leu Ala Arg Ile Phe His Phe Leu Arg Thr Asp Ile Lys Ser Leu Val
            1220                1225                1230

Phe Ala Ser Thr Thr Cys Lys His Trp Arg Ala Ala Val Gly Phe Tyr
```

-continued

```
             1235                1240                1245

Lys Asn Val Thr Val Arg Val Asp Leu Ser Thr Met Gly Ser Lys Cys
             1250                1255                1260

Ser Asp Ser Ile Val Gly Asn Val Met Ser Gly Tyr Asn Arg Gln Met
1265                1270                1275                1280

Ile Lys Val Leu Val Leu Asp Gly Cys Ile Asn Val Thr Ser Thr Val
                 1285                1290                1295

Leu Glu Glu Ile Leu Ser Ser Phe Ser Leu Ile Ser Cys Val Asp Ile
                 1300                1305                1310

Arg Gly Cys Ser Gln Phe Glu Glu Leu Ile Ile Lys Phe Pro His Val
                 1315                1320                1325

Asn Trp Val Glu Gly Arg Ser Ser His Gly Met Arg Thr Val Glu Glu
                 1330                1335                1340

Thr Asn Leu Lys Met Arg Ser Leu Lys Gln Met Pro Glu Gln Ser Leu
1345                1350                1355                1360

Ser Val Ser Lys Leu Gly His Gly Ser Tyr Met Glu Glu Ser Ser Gly
                 1365                1370                1375

Leu Lys Asp Tyr Phe Asp Met Val Glu Lys Arg Gly Ala Ala Asn Gln
                 1380                1385                1390

Ala Phe Arg Gln Asn Leu Tyr Lys Arg Thr Lys Leu Leu Asp Ala Arg
                 1395                1400                1405

Lys Ser Ala Ser Val Leu Ala Arg Asp Ala Arg Met Lys His Leu Ala
                 1410                1415                1420

Met Lys Lys Ala Gly Asn Gly Tyr Arg Arg Met Glu Glu Phe Leu Val
1425                1430                1435                1440

Leu Ser Leu Lys Asp Ile Met Lys Gly Asn Ser Ser Asp Tyr Phe Val
                 1445                1450                1455

Leu Lys Val Ala Glu Ile Glu Asn Arg Val Lys Ser Gly Tyr Tyr Ala
                 1460                1465                1470

Arg Arg Gly Leu Thr Ser Ala Lys Gln Asp Ile Ile Lys Met Cys Arg
                 1475                1480                1485

Glu Ala Ile Lys Ile Gln Lys Arg Gly Asp Gly Gly Asp Met Glu His
                 1490                1495                1500

Val Ile Pro Leu Phe Ile Lys Leu Gly Thr Arg Leu Asp Glu Thr Phe
1505                1510                1515                1520

Ser Ala Phe Asp Arg Asp Glu Met Val Lys Lys Gln Arg Asp Glu Thr
                 1525                1530                1535

Ser Gly Ser Ser Gly Phe Lys Lys Ser Lys Thr Val Ile Glu Lys Lys
                 1540                1545                1550

Tyr Thr Ser Arg Ala Asn Gly Thr Ser Phe Gly Asn Gly Gly Leu Asp
                 1555                1560                1565

Tyr Leu Glu Cys Ser Ser Asp Arg Glu Met Arg Lys Asn Leu Ser Arg
                 1570                1575                1580

Met Asn Lys Lys Lys Asp Leu Glu Gly Glu Ser Ser Asp Glu Phe Glu
1585                1590                1595                1600

Leu Ser Ser Asp Asp Gly Gly Ser Asp Thr Gly Ser Val Ser Asp Thr
                 1605                1610                1615

Glu Ser Asp Ser Asp Val Arg Ser Ala Val Thr Phe Gly Ser Lys Glu
                 1620                1625                1630

Glu Tyr Phe Ala Ala Glu Glu Val Phe Asp Leu Thr Pro Glu Asp Arg
                 1635                1640                1645

Glu Trp Gly Ala Arg Met Thr Lys Ala Ser Leu Val Pro Pro Val Thr
                 1650                1655                1660
```

```
Arg Lys Tyr Glu Val Ile Asp Arg Tyr Val Ile Val Ala Asp Glu Asp
1665                1670                1675                1680

Glu Val Gln Arg Lys Met Gln Val Ser Leu Pro Asp Asp Tyr Glu Asp
                1685                1690                1695

Lys Val Lys Ala Gln Lys Asn Gly Ser Asp Glu Val Asp Met Glu Ile
                1700                1705                1710

Pro Glu Val Lys Glu Tyr Lys Pro Arg Lys Gln Leu Gly Gln Glu Val
                1715                1720                1725

Ile Glu Gln Glu Val Tyr Gly Val Asp Pro Tyr Thr His Asn Leu Leu
                1730                1735                1740

Leu Asp Ser Met Pro Glu Asp Val Asp Trp Thr Ile Thr Glu Lys His
1745                1750                1755                1760

Val Phe Val Glu Glu Met Ile Leu Arg Val Leu Asn Lys Gln Val Arg
                1765                1770                1775

Gln Tyr Thr Gly Ser Gly Ser Thr Pro Met Thr Tyr Pro Leu Lys Pro
                1780                1785                1790

Val Ile Glu Glu Ile Leu Gly Ile Ala Lys Gln Asp Asn Asn Thr Arg
                1795                1800                1805

Asn Leu Lys Leu Cys Glu Ala Ile Leu Gln Ala Ile Asp Ser Arg Pro
                1810                1815                1820

Glu Asp Asn Tyr Val Ala Tyr Arg Lys Gly Leu Gly Val Val Cys Asn
1825                1830                1835                1840

Lys Glu Asp Gly Phe Thr Glu Asp Phe Val Val Glu Phe Leu Gly
                1845                1850                1855

Glu Val Tyr Pro Ala Trp Lys Trp Phe Glu Lys Gln Asp Gly Ile Arg
                1860                1865                1870

Ser Leu Gln Lys Asn Ser Lys Glu Pro Ala Pro Glu Phe Tyr Asn Ile
                1875                1880                1885

Tyr Leu Glu Arg Pro Lys Gly Asp Ala Asp Gly Tyr Asp Leu Val Val
                1890                1895                1900

Val Asp Ala Met His Lys Ala Asn Tyr Ala Ser Arg Ile Cys His Ser
1905                1910                1915                1920

Cys Arg Pro Asn Cys Glu Ala Lys Val Thr Ala Val Ser Gly Gln Tyr
                1925                1930                1935

Gln Ile Gly Ile Tyr Ser Val Arg Pro Ile Gly Phe Gly Glu Glu Val
                1940                1945                1950

Thr Phe Asp Tyr Asn Ser Val Thr Glu Ser Lys Glu Glu Tyr Glu Ala
                1955                1960                1965

Ser Val Cys Leu Cys Gly Ser Gln Val Cys Arg Gly Ser Tyr Leu Asn
                1970                1975                1980

Leu Thr Gly Glu Gly Ala Phe Gln Lys Val Leu Lys Glu Trp His Gly
1985                1990                1995                2000

Leu Leu Asp Lys His His Leu Leu Glu Ala Cys Glu Leu Asn Trp
                2005                2010                2015

Val Ser Glu Glu Asp Tyr Ile Asp Leu Gly Arg Ala Gly Leu Gly Ser
                2020                2025                2030

Cys Leu Leu Gly Asp Leu Pro Asp Trp Leu Ile Ala Tyr Ser Ala Arg
                2035                2040                2045

Leu Val Arg Phe Ile Asn Phe Glu Arg Thr Lys Leu Pro Glu Glu Ile
                2050                2055                2060

Leu Arg His Asn Leu Glu Glu Lys Lys Lys Tyr Cys Ala Glu Ile Ser
2065                2070                2075                2080
```

Leu Glu Met Glu Lys Ser Asp Ala Glu Val Gln Ala Glu Gly Val Tyr
            2085                2090                2095

Asn Gln Arg Leu Gln Asn Leu Ala Leu Thr Leu Asp Lys Val Arg Tyr
        2100                2105                2110

Val Leu Arg Cys Val Phe Gly Lys Pro Lys Ala Pro Pro Pro Leu
    2115                2120                2125

Gln Lys Leu Ser Pro Glu Met Val Ser Val Leu Trp Asn Gly Glu
2130                2135                2140

Gly Ser Leu Val Glu Gln Leu Leu Glu Cys Ile Thr Pro His Ile Ile
2145                2150                2155                2160

Asp Asp Arg Ile Leu Gln Asp Leu Arg Ser Lys Ile Arg Thr Arg Asp
            2165                2170                2175

Pro Leu Asn Ser Ala Asn Ile Glu Lys Asp Leu Arg Arg Ser Leu Leu
        2180                2185                2190

Trp Leu Arg Asp Glu Val Arg Asn Leu Pro Cys Thr Tyr Lys Ser Arg
    2195                2200                2205

His Asp Ala Ala Ala Asp Val Ile His Ile Tyr Ala Tyr Thr Lys Ser
2210                2215                2220

Leu Phe Lys Lys Arg Glu Tyr Asn Thr Val Thr Ser Pro Pro Val Tyr
2225                2230                2235                2240

Ile Ser Pro Leu Asp Leu Gly Pro Lys Cys Ala Asp Lys Leu Ser Gly
            2245                2250                2255

Met Thr Glu Tyr Cys Lys Thr Tyr Gly Glu Asn Tyr Cys Leu Gly Gln
        2260                2265                2270

Leu Ile Tyr Trp His Asn Gln Ala Asn Ala Asp Pro Asp Arg Val Leu
    2275                2280                2285

Glu Arg Ala Ser Arg Gly Cys Leu Ser Leu Pro Asp Ile Gly Ser Phe
2290                2295                2300

Tyr Ala Lys Ala Gln Lys Pro Ser Arg Gln Arg Val Tyr Gly Pro Arg
2305                2310                2315                2320

Thr Val Arg Phe Met Leu Ala Arg Met Glu Lys Gln Pro Gln Arg Pro
            2325                2330                2335

Trp Pro Lys Asp Arg Ile Trp Ser Phe Gln Cys Ser Ser Lys Phe Phe
        2340                2345                2350

Gly Ser Pro Met Leu Asp Ala Val Leu Asn Asn Ser Pro Leu Glu Arg
    2355                2360                2365

Glu Met Val Ile Trp Leu Lys Asn Arg Pro Ala Ile Phe Gln Ala Met
2370                2375                2380

Trp Asp Arg
2385

<210> SEQ ID NO 117
<211> LENGTH: 2439
<212> TYPE: PRT
<213> ORGANISM: Arachis hypogaea

<400> SEQUENCE: 117

Met Gly Asp Gly Gly Val Ala Cys Met Pro Leu Gln His Ile Met Asp
1               5                   10                  15

Lys Thr Leu Cys Glu Gly Lys Ser Ser Gly Asn Asn Val Leu Ser
            20                  25                  30

Ser Lys Leu Leu Lys Leu Pro Asp Gly Thr Arg Gly Arg Lys Lys Lys
        35                  40                  45

Lys Lys Met Lys Gln Arg Lys Asp Lys Ala Val Ser Ser Glu Leu Gly
50                  55                  60

```
Ser Asp Arg Val Asn Lys Arg Thr Cys Glu Val Glu Asn Gly Glu Ile
65                  70                  75                  80

Cys Ala Glu Lys Val Gln Lys Glu Glu Val Glu Gly Glu Leu Gly
                85                  90                  95

Thr Leu Lys Trp Pro Arg Asn Asp Leu Glu Asn Gly Glu Phe Val Pro
            100                 105                 110

Asp Met Pro Leu Pro Pro Pro Pro Leu Pro Arg Arg Arg Ser Glu
            115                 120                 125

Ile Glu Thr Gly Glu Ile Val Ser Asp Lys Trp Lys Ala Arg Glu Leu
130                 135                 140

Glu Lys Gly Glu Asn Ser Pro Gly Lys Trp Arg Glu Asp Val Glu
145                 150                 155                 160

Arg Gly Glu Val Val Pro Glu Lys Gly Arg Lys Gly Glu Ala Glu Lys
                165                 170                 175

Gly Glu Tyr Gly Ser Trp Arg Gly Met Lys Asp Ile Glu Lys Gly
            180                 185                 190

Glu Phe Ile Pro Asp Arg Trp Tyr Lys Gly Glu Met Gly Lys Asp Asp
            195                 200                 205

Tyr Gly Asn Ser Arg Ile Arg Arg Phe His Pro Gly Arg Glu Lys Ala
210                 215                 220

Trp Lys Ile Glu Arg Asp Arg Thr Pro Pro Ser Gly Arg Phe Ala Ser
225                 230                 235                 240

Asp Asp Phe Tyr Arg Lys Lys Glu Phe Asn Arg Ser Gly Gly Gln Tyr
                245                 250                 255

Ala Lys Ser Ser Pro Ser Trp Glu Ser Gly Gln Gln Arg Ser Val Arg
            260                 265                 270

Ile Ser Ser Lys Ile Val Asp Glu Gly Lys Asn Val Asn Ser Asn Gly
            275                 280                 285

Lys Asp Tyr Ser Arg Asp Tyr Asn Pro Gly Thr Arg Met Lys Arg Leu
290                 295                 300

Ser Asn Asp Ser Asp Ser Ser Asp Arg Lys Gln Phe Gly Asp Tyr Gly
305                 310                 315                 320

Ser Leu Lys Ser Arg Arg Leu Ser Asp Asp Phe Pro Arg His Gly Tyr
                325                 330                 335

Pro Glu Asn Tyr Ser Arg Arg Ser Val Glu Arg Pro Tyr Arg Ser Ser
            340                 345                 350

Asn Pro Ser Lys Leu Ser Val Asp Lys Tyr Ser Ser Arg Asn His Glu
            355                 360                 365

Ser Ser Val Ser Ser Arg Gln Ala Tyr Asp Arg His Gly His Ser Pro
370                 375                 380

Gly His Ser Asp Arg Ser Pro Arg Asp Gln Ser Arg Tyr Tyr Asp His
385                 390                 395                 400

Arg Asp Arg Thr Pro Leu Arg Arg Ser Pro Ser Gly Arg Asp Arg Ser
                405                 410                 415

Pro Tyr Arg Leu Glu Thr Cys Arg Asp Arg Ser Pro Tyr Arg Leu Glu
            420                 425                 430

Lys Ser Pro His Cys Arg Glu Arg Ser Pro Tyr Glu Arg Asn Phe Asp
            435                 440                 445

Arg Asn Arg Gln His Asp His Lys Phe Lys Ser Pro Thr Gln Gly Val
            450                 455                 460

Arg Pro Ser Pro Cys Gly Arg Asp Lys Ser Pro Tyr Ser Arg Glu Lys
465                 470                 475                 480
```

-continued

```
Ser Pro His Gly Arg Glu Arg Ser Pro His Glu Arg Met Trp Glu Arg
                485                 490                 495
Asn Arg Gln His Asp His Lys Phe Lys Ser Pro His Ala Glu Arg
            500                 505                 510
Ser Pro Gln Asp Arg Gly Arg Pro Asn Asp Arg Arg Asp His Thr Pro
            515                 520                 525
Asn Leu Val Glu Gly Ser Ser Leu Asp Gly Asn Arg Lys Asn Asn Asp
            530                 535                 540
Arg Glu Thr Ile Cys Lys Thr Leu Gln Ser Glu Lys Pro Asn Ser Glu
545                 550                 555                 560
Tyr Asn Ser Lys Glu His Glu Asp Asp Lys His Lys Arg Glu Ser Asn
                565                 570                 575
Cys Ser Ala Ala Glu Ser Gln Ser Glu Arg Asn Val Pro Asn Thr Asp
            580                 585                 590
Glu Ser Thr Asp Lys Asp Ile Ser Ser Gln Pro Thr Asn Glu Gln Leu
            595                 600                 605
Pro Arg Ser Pro Ser Ile Ser Lys Glu Ser Pro His Ile Glu Leu Val
            610                 615                 620
Pro Glu Glu Leu Pro Ser Met Glu Glu Asp Met Asp Ile Cys Asp Thr
625                 630                 635                 640
Pro Pro His Val Pro Met Val Thr Asp Ser Ala Ser Gly Lys Trp Phe
                645                 650                 655
Tyr Leu Asp Tyr Gly Gly Val Glu Asn Gly Pro Ala Lys Leu Ala Asp
                660                 665                 670
Ile Lys Val Leu Val Asp Glu Gly Val Leu Met Ser Asp His Phe Ile
            675                 680                 685
Lys His Leu Asp Ser Asp Arg Trp Leu Thr Val Glu Asn Ala Ser Ser
            690                 695                 700
Pro Leu Ala Ala Gln Pro Phe Gln Ser Ile Met Ser Asp Ala Ile Thr
705                 710                 715                 720
Gln Leu Val Asn Pro Pro Glu Ala Pro Gly Asn Leu Leu Ala Asp Thr
                725                 730                 735
Gly Asp Val Leu Gln Ser Gly Leu Asp Gln Ser Gln Glu Met Pro Ala
            740                 745                 750
Thr Leu Leu Arg Ser Asp Asp Asn Leu His Ala Ser Glu Leu Leu Glu
            755                 760                 765
Asp Leu His Ile Asp Glu Arg Val Gly Ser Leu Leu Glu Gly Tyr Asp
            770                 775                 780
Ala Thr Pro Gly Met Glu Leu Glu Ala Ile Lys Glu Ala Leu Gln Met
785                 790                 795                 800
Asn Phe Glu Tyr Ala Lys Leu Glu Gly Leu Glu Asp Cys Glu Gly Phe
                805                 810                 815
Pro Trp His Asp Ser Ser Leu Ser Glu Asp Ser Gly Ser Arg Ile Asp
                820                 825                 830
Ile Ala Pro Arg Asp Asn Glu Met Ser Met Ser Cys Glu Lys Asp Asn
            835                 840                 845
Gly Phe Ala Ala Pro Asp Asp Trp Phe Ser Ser Arg Trp Ser Cys Lys
            850                 855                 860
Gly Gly Asp Trp Lys Arg Asn Asp Asp Ala Gln Asp Arg Tyr Ser Arg
865                 870                 875                 880
Lys Lys Phe Val Leu Asn Asp Gly Phe Pro Leu Cys Leu Met Pro Lys
                885                 890                 895
Ser Gly Cys Glu Asp Pro Arg Trp Pro His Lys Asp Asp Leu Tyr Phe
```

```
                900             905             910
Pro Ser Gln Ser Arg Lys Leu Asp Leu Pro Leu Trp Ala Phe Cys Ala
            915                 920                 925

Asp Glu Arg Val Asp Tyr Cys Ala Ala Ser Arg Ser Ala Gln Ser Lys
            930                 935                 940

Pro Ala Phe Val Arg Gly Thr Lys Gly Asn Val Leu Ser Val Val Arg
945                 950                 955                 960

Ile Asn Ala Cys Val Val Lys Asp Gln Gly Ser Leu Met Ser Glu Leu
                965                 970                 975

Arg His Lys Ser Arg Gly Lys Asp Arg Tyr His Ser Arg Ser Thr Arg
            980                 985                 990

Pro His Ser Ser Ser Asp Ser Arg Arg Ser Ser Ile Glu Glu Asp
            995                 1000                1005

Ser His Ser Lys Ala Ala Ser Asp Arg Gly Ser Arg Arg Ser Met Glu
            1010                1015                1020

Phe Ile Asn Val Pro Lys Asp His Leu Cys Thr Val Lys Asp Leu Gln
1025                1030                1035                1040

Leu His Phe Gly Asp Trp Tyr Tyr Leu Asp Gly Ser Gly Arg Glu Arg
                1045                1050                1055

Gly Pro Ser Ser Phe Leu Glu Leu Gln His Leu Val Asp Gln Gly Ile
            1060                 1065                1070

Ile Lys Lys Leu Ser Ser Val Phe Arg Lys Ser Asp Lys Leu Trp Val
        1075                1080                1085

Pro Val Thr Ser Ala Thr Glu Ile Ser Asp Val Ser Leu Gly Ser His
        1090                1095                1100

Gln Glu Ser Ser Ser Thr Ser Gly Val Gln Ser Lys His Ile Gln Asp
1105                1110                1115                1120

Val Cys Val Gly Glu Pro Tyr Ala Asn Leu Ser Leu Phe Asn Ile Ile
                1125                1130                1135

His Pro Gln Phe Val Gly Tyr Thr Arg Gly Lys Leu His Glu Leu Val
            1140                1145                1150

Met Lys Ser Tyr Lys Ser Arg Glu Phe Ala Ala Ala Ile Asn Glu Val
            1155                1160                1165

Leu Asp Pro Trp Ile Asn Ala Arg Gln Pro Lys Lys Glu Ile Glu Lys
        1170                1175                1180

Gln Ile Tyr Trp Lys Ser Asp Gly Asp Ala Arg Ala Thr Lys Arg Ala
1185                1190                1195                1200

Arg Met Leu Val Asp Gly Glu Glu Asp Ser Glu Phe Glu Asp Gly Pro
                1205                1210                1215

Thr Ile Glu Lys Asp Glu Thr Thr Phe Glu Asp Leu Cys Gly Asp Ala
            1220                1225                1230

Thr Phe Ile Gly Glu Ala Ile Gly Leu Thr Asp Ser Glu Val Ala Thr
            1235                1240                1245

Trp Gly Leu Leu Asp Gly His Met Leu Ala Arg Ile Phe His Phe Leu
            1250                1255                1260

Arg Ser Asp Leu Lys Ser Leu Val Phe Ala Ser Ile Thr Cys Lys His
1265                1270                1275                1280

Trp Arg Thr Ala Val Arg Phe Tyr Lys Glu Val Ser Arg His Val Asn
                1285                1290                1295

Leu Ser Ser Leu Gly His Ser Cys Thr Asp Ser Met Leu Leu Asn Ile
            1300                1305                1310

Met Asp Ala Tyr Asp Lys Glu Lys Ile Ser Ser Met Thr Leu Met Gly
            1315                1320                1325
```

```
Cys Lys Asn Ile Ser Ala Asp Thr Leu Glu Lys Ile Leu His Ser Phe
    1330                1335                1340

Pro Gly Leu Ser Thr Ile Asp Ile Arg Gly Cys Ser Gln Phe Glu Glu
1345                1350                1355                1360

Leu Thr Pro Lys Phe Val His Val Lys Trp Ile Lys Ser Arg Phe Leu
            1365                1370                1375

Glu Glu Ser His Lys Ile Arg Ser Leu Lys His Ile Thr Asp Gln Thr
            1380                1385                1390

Ser Ser Val Ser Lys Ser Ser Ser Leu Gly Met Asp Asp Phe Gly Gln
        1395                1400                1405

Leu Lys Asp Tyr Phe Asp Ser Val Asp Lys Arg Asp Thr Ala Lys Gln
    1410                1415                1420

Leu Phe Arg Arg Asn Leu Tyr Lys Arg Ser Lys Leu Tyr Asp Ala Arg
1425                1430                1435                1440

Arg Ser Ser Ser Ile Leu Ser Arg Asp Ala Arg Thr Arg Arg Trp Ala
                1445                1450                1455

Ile Lys Lys Ser Glu Ser Gly Tyr Lys Arg Met Glu Glu Phe Leu Ala
                1460                1465                1470

Ser Arg Leu Arg Glu Ile Met Lys Thr Asn Ser Cys Asp Phe Phe Val
    1475                1480                1485

Pro Lys Val Ala Glu Ile Glu Ala Arg Met Lys Asn Gly Tyr Tyr Ile
    1490                1495                1500

Gly Arg Gly Leu Ser Ser Val Lys Glu Asp Ile Ser Arg Met Cys Arg
1505                1510                1515                1520

Asp Ala Ile Lys Ala Lys Asn Arg Gly Asp Ala Asn Asp Met Asn Arg
                1525                1530                1535

Met Ile Thr Leu Phe Ile Gln Leu Ala Thr Leu Leu Glu Glu Ser Ser
                1540                1545                1550

Ile Ser Val His Asp Arg Asp Val Leu Ser Ser Lys Tyr Lys Lys Asn
        1555                1560                1565

Arg Leu Val Thr Asp Arg Lys Tyr Arg Ser Asn Gly Thr His Gly Leu
    1570                1575                1580

Asp Asn Met Glu Tyr Thr Ser Asp Arg Glu Ile Arg Arg Leu Ser
1585                1590                1595                1600

Lys Leu Asn Lys Lys Ser Met Asp Ser Glu Ser Glu Thr Ser Asp Asp
                1605                1610                1615

Leu Asp Arg Ser Tyr Glu Asp Gly Lys Ser Asp Ser Asp Thr Thr Thr
                1620                1625                1630

Ser Glu Ala Glu Ser Asp Asp Gln Gly His Ser Glu Asn Leu Ile Gly
        1635                1640                1645

Glu Ser Arg Gly Asp Gly His Phe Thr Pro Gly Gly Asp Leu Asn Phe
    1650                1655                1660

Ile Thr Asp Asp Arg Glu Trp Gly Ala Arg Met Thr Lys Ala Ser Leu
1665                1670                1675                1680

Val Pro Pro Val Thr Arg Lys Tyr Glu Val Ile Asp Gln Tyr Val Ile
                1685                1690                1695

Val Ala Asp Glu Glu Asp Val Gln Arg Lys Met Arg Val Ser Leu Pro
                1700                1705                1710

Asp Asp Tyr Ala Glu Lys Leu Ser Ala Gln Lys Asn Gly Thr Glu Glu
        1715                1720                1725

Ser Asp Met Glu Leu Pro Glu Val Lys Asp Tyr Lys Pro Arg Lys Gln
    1730                1735                1740
```

-continued

Leu Gly Asn Glu Val Ile Glu Gln Glu Val Tyr Gly Ile Asp Pro Tyr
1745                1750                1755                1760

Thr His Asn Leu Leu Leu Asp Ser Met Pro Glu Glu Leu Asp Trp Ser
                1765                1770                1775

Leu Gln Asp Lys His Leu Phe Ile Glu Asp Val Leu Leu Arg Thr Leu
            1780                1785                1790

Asn Lys Gln Val Arg Asn Phe Thr Gly Ser Gly Ser Thr Pro Met Ser
        1795                1800                1805

Tyr Ala Leu Gln Pro Val Glu Glu Ile Lys Arg Cys Ala Glu Glu
    1810                1815                1820

Gly Cys Asp Ala Arg Thr Val Lys Met Cys Gln Gly Ile Leu Lys Ala
1825                1830                1835                1840

Ile Asp Ser Arg Pro Asp Asp Lys Tyr Val Ala Tyr Arg Lys Gly Leu
                1845                1850                1855

Gly Val Val Cys Asn Lys Glu Glu Gly Phe Ser Glu Asp Phe Val
        1860                1865                1870

Val Glu Phe Leu Gly Glu Val Tyr Pro Val Trp Lys Trp Phe Glu Lys
    1875                1880                1885

Gln Asp Gly Ile Arg Ser Leu Gln Lys Asn Ser Lys Asp Pro Ala Pro
1890                1895                1900

Glu Phe Tyr Asn Ile Tyr Leu Glu Arg Pro Lys Gly Asp Ala Asp Gly
1905                1910                1915                1920

Tyr Asp Leu Val Val Val Asp Ala Met His Lys Ala Asn Tyr Ala Ser
                1925                1930                1935

Arg Ile Cys His Ser Cys Arg Pro Asn Cys Glu Ala Lys Val Thr Ala
                1940                1945                1950

Val Asp Gly His Tyr Gln Ile Gly Ile Tyr Ser Val Arg Lys Ile Gln
        1955                1960                1965

Pro Gly Glu Glu Ile Thr Phe Asp Tyr Asn Ser Val Thr Glu Ser Lys
    1970                1975                1980

Glu Glu Tyr Glu Ala Ser Val Cys Leu Cys Gly Ser Gln Val Cys Arg
1985                1990                1995                2000

Gly Ser Tyr Leu Asn Leu Thr Gly Glu Gly Ala Phe Gln Lys Val Leu
                2005                2010                2015

Lys Asp Ser His Gly Ile Leu Asp Arg His Tyr Leu Met Leu Glu Ala
        2020                2025                2030

Cys Glu Leu Asn Ser Val Ser Glu Glu Asp Tyr Asn Asp Leu Gly Arg
            2035                2040                2045

Ala Gly Leu Gly Ser Cys Leu Leu Glu Gly Leu Pro Asp Trp Leu Val
2050                2055                2060

Ala Tyr Ala Ala Arg Leu Val Cys Leu Ile Thr Tyr Val Leu Leu Gly
2065                2070                2075                2080

Ile Phe Leu Ser Phe Cys Ser Leu Phe Leu Val Leu Met Phe Leu Ala
                2085                2090                2095

Phe Asp Val Val Lys Val Arg Phe Ile Asn Phe Glu Thr Lys Leu
            2100                2105                2110

Pro Glu Glu Ile Leu Lys His Asn Leu Glu Glu Lys Arg Lys Tyr Phe
        2115                2120                2125

Ser Asp Ile Cys Leu Glu Val Glu Arg Ser Asp Ala Glu Val Gln Ala
    2130                2135                2140

Glu Gly Val Tyr Asn Gln Arg Leu Gln Asn Leu Ala Val Thr Leu Asp
2145                2150                2155                2160

Lys Val Arg Tyr Val Met Arg Cys Ile Phe Gly Asp Pro Arg Lys Ala

```
                      2165                2170                2175

Pro Pro Pro Leu Glu Lys Ile Ser Pro Glu Ala Ala Val Ser Phe Leu
            2180                2185                2190

Trp Lys Gly Glu Gly Ser Phe Val Glu Glu Leu Leu Gln Cys Ile Ala
            2195                2200                2205

Pro His Val Glu Glu Asp Ala Leu Asn Glu Leu Arg Ser Lys Ile Asp
            2210                2215                2220

Ala His Asp Pro Ser Ser Gly Asp Ile Gln Lys Glu Val Gln Lys
2225                2230                2235                2240

Ser Leu Leu Trp Leu Arg Asp Glu Val Arg Asp Leu Leu Cys Thr Tyr
            2245                2250                2255

Lys Cys Arg His Asp Ala Ala Ala Asp Leu Ile His Ile Tyr Ala Tyr
            2260                2265                2270

Thr Lys Tyr Phe Phe Arg Ile Arg Ala Tyr Glu Thr Ile Thr Ser Pro
            2275                2280                2285

Pro Val Tyr Ile Ser Pro Leu Asp Leu Gly Pro Lys Tyr Ala Asn Lys
            2290                2295                2300

Leu Gly Ala Gly Phe Gln Glu Tyr Arg Lys Ile Tyr Gly Glu Asn Tyr
2305                2310                2315                2320

Cys Leu Gly Gln Leu Ile Phe Trp His Asn Gln Ser Asn Val Asp Pro
            2325                2330                2335

Asp His Ser Leu Gly Arg Ala Ser Arg Gly Cys Leu Ser Leu Pro Asp
            2340                2345                2350

Ile Ser Ser Phe Tyr Ala Lys Ala Leu Lys Pro Ser Lys His Arg Val
            2355                2360                2365

Tyr Gly Pro Arg Thr Val Arg Ser Met Leu Ala Arg Met Glu Lys Gln
            2370                2375                2380

Pro Gln Arg Pro Trp Pro Lys Asp Gln Ile Trp Thr Phe Lys Ser Phe
2385                2390                2395                2400

Pro Lys Phe Phe Gly Ser Pro Met Leu Asp Ala Val Ile Asn Asn Thr
            2405                2410                2415

Pro Leu Asp Arg Glu Met Val His Trp Leu Lys His Arg Pro Ala Ile
            2420                2425                2430

Tyr Gln Ala Met Trp Asp Arg
            2435

<210> SEQ ID NO 118
<211> LENGTH: 2394
<212> TYPE: PRT
<213> ORGANISM: Raphanus sativus

<400> SEQUENCE: 118

Met Arg Asn Gly Gly Val Ala Thr Cys Met Pro Leu Leu Asn Ile Met
1               5                   10                  15

Asp Lys Leu Pro Thr Met Glu Lys Lys Thr Leu Cys Gly Gly Gly Asn
            20                  25                  30

Asn Asn Asp Ser Lys Val Ala Ala Thr Ser Glu Asn Gly His Thr Thr
        35                  40                  45

Asp Asn Lys Leu Pro Glu Phe Gln Pro Ala Lys Pro Ser Ala Ser Gln
    50                  55                  60

Pro Pro Lys Lys Lys Lys Ile Val Lys Val Ile Arg Lys Val Val
65                  70                  75                  80

Val Arg Lys Pro Lys Gln Arg Lys Asp Gln Gly Val Gln Leu Ser Gly
                85                  90                  95
```

-continued

```
Glu Ser Gln Val Gln Lys Lys Glu Gln Asp Lys Lys Ser Glu Val Val
                100                 105                 110
Gln Gly Lys Gly Gly Glu Ser Ser Asn Lys Glu Glu Asn Gly Gly Asp
            115                 120                 125
Ser Gly Phe Lys Asp Glu Val Glu Glu Gly Glu Leu Gly Thr Leu Asn
        130                 135                 140
Pro Asp Gly Val Leu Glu Asn Gly Glu Ile Ser Pro Val Lys Ser Leu
145                 150                 155                 160
Gln Arg Ser Glu Val Glu Lys Gly Glu Ile Ser Gly Glu Thr Trp Lys
                165                 170                 175
Lys Asp Glu Thr Thr Lys Gly Asp Tyr Ser Asn Leu Gln Tyr Asn Lys
            180                 185                 190
Trp Asn Val Glu Arg Arg Asp Leu Pro Ala Asp Lys Tyr Arg Lys Glu
        195                 200                 205
Glu Arg Glu Phe Arg Ser Trp Arg Asp Pro Gly Asp Glu Ile Glu Lys
    210                 215                 220
Gly Glu Phe Ile Pro Asp Arg Trp His Lys Met Asp Thr Val Lys Asp
225                 230                 235                 240
Asp His Ser Tyr Asn Arg Ser Arg Arg Asn Gly Val Asp Arg Glu Lys
                245                 250                 255
Tyr Asp Tyr Asp Tyr Glu His Glu Arg Thr Pro Pro Gly Gly Arg Phe
            260                 265                 270
Ala Asn Glu Asp Thr Tyr Arg Arg Glu Phe Arg Ser Gly Asn Asp
        275                 280                 285
Arg Ala Thr Lys Ile Ser Ser Lys Ile Val Ile Glu Glu Ser Leu His
    290                 295                 300
Lys Asn Glu Tyr Asn Asp Pro Asn Asn Leu Gly Lys Glu Tyr Ser Ser
305                 310                 315                 320
Thr Val Asn Lys Leu Lys Arg His Gly Ala Glu Pro Asp Ser Phe Glu
                325                 330                 335
Arg Lys His Phe Tyr Ala Asp His Gly Asp Tyr Gly Ser Ser Lys Tyr
            340                 345                 350
Arg Lys Leu Ser Asp Asp Ser Ser Arg Ser Leu His Pro Asp His Tyr
        355                 360                 365
Ser Arg Asn Ser Val Glu Arg Asp Tyr Arg Asp Ser Tyr Ser Ser Lys
    370                 375                 380
Asn Ser Ser Leu Glu Lys Tyr Pro Arg Lys His Gln Asp Ser Tyr Phe
385                 390                 395                 400
Pro Ala Arg Ser Val Ser Asp Arg His Ala His Ser Pro Ala Arg Ser
                405                 410                 415
Asp Leu Ser Pro His Asp Arg Ser Arg Tyr His Gly His Arg Asp Arg
            420                 425                 430
Ser Ser Leu His Arg Glu Arg Ser Pro Tyr Ala Arg Glu Arg Ser Pro
        435                 440                 445
Tyr Thr Phe Glu Lys Pro Ser His Ala Arg Lys Lys Ser Pro His Asp
    450                 455                 460
Arg Ser His His His Asp Tyr Arg Arg Ser Pro Ser Tyr Ser Glu Trp
465                 470                 475                 480
Ser Ser Asp Arg Arg Asp Gly Thr Ser Arg Tyr Met Glu Asp Pro Gln
                485                 490                 495
Ser Asp Arg Thr Arg Arg Asn Gly His Arg Glu Ile Ser Arg Lys Ser
            500                 505                 510
Gly Val Arg Glu Arg Arg Asp Ser Gln Ala Gly Met Glu Leu Glu His
```

```
            515                 520                 525
Lys His Arg His Arg Asp Ser Asn Gly Lys Glu Ser Thr Pro Ser Arg
    530                 535                 540
Lys Asp Leu Gln Gly Lys Asn Ile Leu Tyr Asn Asn Pro Val Val
545                 550                 555                 560
Glu Lys Asp Ser Val Cys Asp Ser Ser Lys Ile Pro Ser Ala Cys Ala
                565                 570                 575
Lys Gly Lys Glu Ser Val Gln Val Gly Glu Ala Pro Thr Glu Leu
            580                 585                 590
Pro Ser Met Glu Val Asp Met Asp Ile Cys Asp Thr Pro Pro His Glu
            595                 600                 605
Glu Pro Leu Ala Ala Asp Ser Ser Leu Gly Lys Trp Phe Tyr Leu Asp
    610                 615                 620
Tyr Tyr Gly Thr Glu His Gly Pro Ala Lys Leu Ser Glu Leu Lys Ala
625                 630                 635                 640
Leu Met Glu Gln Gly Ile Leu Phe Ser Asp His Met Ile Lys His Ser
                645                 650                 655
Asp Asn Asn Arg Trp Val Thr Ile Glu Asn Ala Thr Ser Pro Val Val
            660                 665                 670
Asn Ile Asn Thr Pro Ser Ile Val Ser Asp Thr Val Thr Gln Leu Val
    675                 680                 685
Asn Pro Pro Glu Ala Pro Gly Asn Leu Leu Glu Asp Ile Ala Asp Ala
690                 695                 700
Ala Gln Ala Val Pro Met Glu Gln Gly Ala Gly Asp Ser Leu Pro Glu
705                 710                 715                 720
Ser Leu Ser Ile Pro Asp Ser Asn Asp Ile Val Val Gly His Arg Glu
                725                 730                 735
Asp Phe Gln Phe Asp Asn Arg Ile Ala Ser Leu Leu Glu Gly Tyr Thr
            740                 745                 750
Ile Thr Pro Gly Arg Glu Leu Glu Thr Leu Gly Glu Ala Met Gln Ile
    755                 760                 765
Glu Val Glu Leu Glu Glu Thr Arg Arg Phe Val Ser Ser Glu Asp Ile
    770                 775                 780
Val Trp Cys Tyr Tyr Gln Val Val Asn Gln Leu Leu Leu Asn Glu Glu
785                 790                 795                 800
Ser Cys Gly Arg Ser Glu Pro Lys Thr Val Ala Ile Glu Glu Leu Lys
                805                 810                 815
Ser Glu Asn Val Asp Asn Ser Glu Ser Asp Glu Thr Gly Ser Trp Phe
            820                 825                 830
Ser Gly Arg Trp Ser Cys Lys Gly Gly Asp Trp Ile Arg His Asp Glu
    835                 840                 845
Ala Phe Gln Asp Arg Asp Tyr Lys Thr Lys Met Val Leu Asn Asp Gly
    850                 855                 860
Phe Pro Leu Cys Leu Met Gln Lys Ser Gly Tyr Glu Asp Pro Arg Trp
865                 870                 875                 880
His His Lys Asp Asp Leu Tyr Asn Pro Cys Ser Ser Lys Leu Glu
                885                 890                 895
Leu Pro Leu Trp Ala Phe Ser Gly Ala Asp Glu Arg Asn Gln Ala Arg
            900                 905                 910
Gly Val Lys Ala Asn Val Leu Ser Val Arg Leu Asn Ser Leu Val
    915                 920                 925
Val Ser Asp Gln Val Pro Ser Val Pro Asp Pro Leu Val Lys Val Arg
    930                 935                 940
```

```
Ser Arg Glu Lys Phe Ser Ser Arg His Ala Arg Pro Ser Pro Ala Ser
945                 950                 955                 960

Cys Asp Ser Lys Arg Glu Ser Val Glu Thr Ile Ser Gln Thr Thr Ala
                965                 970                 975

Cys Ser Ser Gln Asp Leu Gln Arg Phe Trp Lys Thr Asp Ala Ser Val
                980                 985                 990

Ser Thr Pro Gly Asp Arg Leu Tyr Thr Val Asp Asp Leu His Leu His
                995                 1000                1005

Leu Gly Asp Trp Phe Tyr Met Asp Gly Ala Gly Gln Glu Gln Gly Pro
            1010                1015                1020

Leu Pro Phe Ser Glu Leu Gln Ile Leu Val Asp Lys Gly Leu Ile Lys
1025                1030                1035                1040

Arg His Thr Ser Val Phe Arg Lys Ser Asp Lys Ile Trp Val Pro Val
                1045                1050                1055

Thr Ser Ile Thr Lys Thr Ser Glu Ile Ser Ala Lys Leu Gln Gly Lys
            1060                1065                1070

Thr Pro Ala Leu Pro Ser Asp Cys Gln Ser Leu Asp Val Ser Glu Ser
            1075                1080                1085

Gln Asp Phe Arg His Ser Glu Met Asp Thr Ser Leu Ser Ser Phe His
1090                1095                1100

Ala Met His Pro Gln Phe Leu Gly Tyr Phe Arg Gly Lys Leu His Gln
1105                1110                1115                1120

Leu Ile Met Lys Thr Tyr Lys Thr Arg Glu Phe Ser Ala Ala Ile Asn
                1125                1130                1135

Asp Val Leu Asp Ser Trp Ile His Ala Arg Gln Pro Lys Lys Glu Thr
            1140                1145                1150

Asp Lys Tyr Met His Gln Asn Ser Glu Phe Gly Ser Ser Ser Tyr Thr
            1155                1160                1165

Lys Arg Ala Arg Leu Met Ala Gly Glu Ser Arg Asp His Ser Glu Val
            1170                1175                1180

Glu Asp Ala Gln Met Phe Gln Lys Asp Glu Leu Ala Phe Glu Asp Leu
1185                1190                1195                1200

Cys Gly Asp Ala Thr Phe His Val Glu Gly Ser Gly Ser Ser Gly Thr
                1205                1210                1215

Val Gly Met Tyr Trp Asp Leu Leu Asp Gly His Val Leu Ala Arg Val
            1220                1225                1230

Phe His Leu Leu Arg Tyr Asp Val Lys Ser Leu Ala Phe Ala Ser Met
            1235                1240                1245

Thr Cys Arg His Trp Lys Ala Val Val Ser Ser Tyr Lys Asp Ile Ser
            1250                1255                1260

Arg Gln Val Asp Leu Ser Ser Leu Gly Thr Asn Cys Thr Asp Ser Arg
1265                1270                1275                1280

Leu Trp Ser Ile Met Asn Thr Tyr Asn Thr Glu Lys Ile Asp Ser Ile
                1285                1290                1295

Ile Leu Val Gly Cys Thr Asn Val Thr Ser Ser Met Leu Glu Glu Ile
            1300                1305                1310

Leu Arg Leu Phe Pro His Ile Ser Ser Val Asp Ile Thr Gly Cys Ser
            1315                1320                1325

Gln Phe Gly Asn Leu Thr Leu Lys Tyr Lys Lys Leu Ser Trp Leu Lys
            1330                1335                1340

Cys Gln His Pro Arg Ser Gly Asp Leu His Ser Arg Leu Thr Ser Leu
1345                1350                1355                1360
```

-continued

Lys Gln Thr Asn Val Asn Lys Ser Lys Gly Leu Gly Gly Asp Thr Asp
                1365                1370                1375

Asp Phe Gly Asn Leu Lys Asp Tyr Phe Asp Arg Val Glu Lys Arg Asp
            1380                1385                1390

Ser Ala Asn Gln Leu Phe Arg Arg Ser Leu Tyr Lys Arg Ser Lys Leu
        1395                1400                1405

Tyr Asp Ala Arg Lys Ser Ser Ala Ile Leu Ser Arg Asp Ala Arg Ile
    1410                1415                1420

Arg Arg Trp Ala Ile Lys Lys Ser Glu His Gly Tyr Lys Arg Val Glu
1425                1430                1435                1440

Glu Phe Leu Ala Ser Ser Leu Arg Gly Ile Met Met Gln Asn Thr Phe
                1445                1450                1455

Asp Phe Phe Val Leu Lys Val Ala Gln Ile Glu Glu Lys Met Lys Asn
            1460                1465                1470

Gly Tyr Tyr Val Ser His Gly Leu Lys Ser Val Lys Glu Asp Ile Ser
        1475                1480                1485

Arg Met Cys Arg Gln Ala Ile Lys Glu Arg Asn Arg Gly Asp Ser Lys
    1490                1495                1500

Asp Met Asn Arg Ile Ile Ile Leu Phe Ile Gln Leu Ala Thr Cys Leu
1505                1510                1515                1520

Glu Glu Val Ser Met Ala Thr Ser Ser Tyr Arg Arg Asp Glu Leu Met
                1525                1530                1535

Lys Ser Trp Gln Asp Gly Ser Gly Leu Ser Ser Ala Ser Lys Tyr Asn
            1540                1545                1550

Thr Lys Leu Ser Lys Ser Val Thr Glu Lys Lys Tyr Met Ser Arg Thr
        1555                1560                1565

Gly Asp Thr Phe Gly Val Asn Gly Ala Leu Asp Tyr Gly Glu Tyr Ala
    1570                1575                1580

Ser Asp Arg Glu Ile Lys Arg Arg Leu Ser Lys Leu Asn Arg Lys Ser
1585                1590                1595                1600

Phe Gly Ser Gly Ser Glu Thr Ser Ser Glu Leu Ser Asp Asn Asp Asn
                1605                1610                1615

Tyr Ser Ser Ala Ser Glu Ser Glu Ser Asp Ile Arg Ser Glu Gly Arg
            1620                1625                1630

Ser Gln Asp Thr Arg Val Glu Lys Tyr Phe Thr Ala Asp Glu Ser Phe
        1635                1640                1645

Asp Ser Val Thr Glu Glu Arg Glu Trp Gly Ala Arg Met Thr Lys Ala
    1650                1655                1660

Ser Leu Val Pro Pro Val Thr Arg Lys Tyr Glu Leu Ile Glu Glu Tyr
1665                1670                1675                1680

Thr Ile Val Ala Asp Glu Glu Val Arg Arg Lys Met Arg Val Ser
                1685                1690                1695

Leu Pro Glu Asp Tyr Gly Glu Lys Leu Asn Ala Gln Arg Asn Gly Ile
            1700                1705                1710

Glu Glu Leu Asp Met Glu Leu Pro Glu Val Lys Glu Tyr Lys Pro Arg
        1715                1720                1725

Lys Leu Leu Gly Asn Glu Val Leu Glu Gln Glu Val Tyr Gly Ile Asp
    1730                1735                1740

Pro Tyr Thr His Asn Leu Leu Asp Ser Met Pro Gly Glu Leu Asp
1745                1750                1755                1760

Trp Ser Leu Gln Asp Lys His Ser Phe Ile Glu Asp Val Val Leu Arg
                1765                1770                1775

Ala Leu Asn Arg Lys Val Arg Phe Leu Thr Gly Ser Gly Asn Thr Pro

```
            1780             1785              1790
Met Val Tyr Pro Leu Arg Pro Val Ile Glu Glu Leu Lys Glu Asn Ser
        1795              1800             1805

Arg Glu Glu Cys Asp Ile Gln Thr Met Arg Met Cys Gln Gly Val Leu
        1810              1815             1820

Lys Ala Ile Glu Ser Arg Ser Gly Asp Thr Tyr Val Ser Tyr Arg Lys
1825              1830             1835             1840

Gly Leu Gly Val Val Cys Asn Lys Gln Gly Gly Phe Val Glu Asp Asp
                  1845             1850             1855

Phe Val Val Glu Phe Leu Gly Glu Val Tyr Pro Val Trp Lys Trp Phe
                  1860             1865             1870

Glu Lys Gln Asp Gly Ile Arg Ser Leu Gln Glu Asn Lys Thr Asp Pro
        1875             1880              1885

Ala Pro Glu Phe Tyr Asn Ile Tyr Leu Glu Arg Pro Lys Gly Asp Ala
        1890              1895             1900

Asp Gly Tyr Asp Leu Val Val Val Asp Ala Met His Lys Ala Asn Tyr
1905              1910             1915             1920

Ala Ser Arg Ile Cys His Ser Cys Arg Pro Asn Cys Glu Ala Lys Val
                  1925             1930             1935

Thr Ala Val Asp Gly His Tyr Gln Ile Gly Ile Tyr Ser Val Arg Pro
                  1940             1945             1950

Ile Glu Tyr Gly Glu Glu Ile Thr Phe Asp Tyr Asn Ser Val Thr Glu
        1955             1960              1965

Ser Lys Glu Glu Tyr Glu Ala Ser Val Cys Leu Cys Gly Ser His Val
        1970              1975             1980

Cys Arg Gly Ser Tyr Leu Asn Leu Thr Gly Glu Gly Ala Phe Gln Lys
1985              1990             1995             2000

Val Leu Lys Glu Trp His Gly Leu Leu Asp Arg His Arg Leu Met Leu
                  2005             2010             2015

Glu Ala Cys Met Leu Asn Ser Val Ser Glu Glu Asp Tyr Leu Glu Leu
                  2020             2025             2030

Gly Arg Ala Gly Leu Gly Ser Cys Leu Leu Gly Gly Leu Pro Asp Trp
                  2035             2040             2045

Val Ile Ala Tyr Ser Ala His Leu Val Arg Phe Ile Asn Phe Glu Arg
        2050              2055             2060

Thr Lys Leu Pro Val Glu Ile Leu Lys His Asn Met Glu Glu Lys Ile
2065              2070             2075             2080

Lys Tyr Phe Ser Asp Ile His Leu Asp Val Glu Lys Ser Asp Ala Glu
                  2085             2090             2095

Val Gln Ala Glu Gly Val Tyr Asn Gln Arg Leu Gln Asn Leu Ala Val
                  2100             2105             2110

Thr Leu Asp Lys Val Arg Tyr Val Met Arg Arg Val Phe Gly Asp Pro
                  2115             2120             2125

Lys Asn Ala Pro Pro Leu Glu Lys Leu Thr Pro Glu Glu Thr Val
        2130              2135             2140

Ser Phe Leu Trp Asn Gly Asp Gly Ser Leu Val Glu Glu Leu Leu Gln
2145              2150             2155             2160

Cys Leu Ser Pro His Val Glu Val Gly Ile Val Asp Lys Leu Arg Ser
                  2165             2170             2175

Lys Ile Arg Ala His Asp Pro Ser Gly Ser Ala Asp Val Leu Lys Asp
                  2180             2185             2190

Leu Gln Arg Ser Leu Leu Trp Leu Arg Asp Glu Ile Arg Asp Leu Pro
                  2195             2200             2205
```

-continued

```
Cys Thr Tyr Lys Cys Arg Asn Asp Ala Ala Asp Leu Ile His Ile
        2210                2215                2220

Tyr Ala Tyr Thr Lys Cys Leu Phe Lys Val Arg Glu Tyr Lys Ser Phe
2225                2230                2235                2240

Met Ser Ser Pro Val His Ile Ser Pro Leu Asp Leu Gly Ala Lys Tyr
                2245                2250                2255

Ala Asp Lys Leu Gly Glu Gly Ile Lys Glu Tyr Arg Lys Thr Tyr Gly
        2260                2265                2270

Glu Asn Tyr Cys Leu Gly Gln Leu Ile Tyr Trp Tyr Glu Gln Thr Asn
        2275                2280                2285

Thr Asp Pro Asp Leu Thr Leu Val Lys Ala Thr Arg Gly Cys Leu Ser
        2290                2295                2300

Leu Pro Glu Val Ala Ser Phe Tyr Ala Lys Ala His Lys Pro Ser Lys
2305                2310                2315                2320

His Arg Val Tyr Gly Pro Lys Thr Val Lys Thr Met Val Ser Gln Met
                2325                2330                2335

Ser Lys Gln Pro Gln Lys Pro Trp Ala Lys Asp Lys Ile Trp Met Phe
        2340                2345                2350

Lys Ser Ser Leu Gly Val Leu Gly Ser Pro Met Phe Asp Thr Val Leu
        2355                2360                2365

Asn Asn Ser Ser Leu Asp Arg Glu Leu Val Gln Trp Leu Arg Asn Arg
        2370                2375                2380

Arg His Val Phe Gln Ala Thr Trp Asp Ser
2385                2390

<210> SEQ ID NO 119
<211> LENGTH: 762
<212> TYPE: PRT
<213> ORGANISM: Glycine max

<400> SEQUENCE: 119

Arg Ile Gly Asp Ser Arg Gly Asp Gly Tyr Phe Thr Pro Asp Asp Gly
1               5                   10                  15

Leu His Phe Ile Thr Asp Glu Arg Glu Trp Gly Ala Arg Met Thr Lys
            20                  25                  30

Ala Ser Leu Val Pro Pro Val Thr Arg Lys Tyr Asp Val Ile Asp Gln
        35                  40                  45

Tyr Ile Ile Val Ala Asp Glu Glu Asp Val Arg Arg Lys Met Arg Val
    50                  55                  60

Ser Leu Pro Asp Asp Tyr Ala Glu Lys Leu Ser Ala Gln Lys Asn Gly
65                  70                  75                  80

Ile Glu Glu Ser Asp Met Glu Leu Pro Glu Val Lys Asp Tyr Lys Pro
                85                  90                  95

Arg Lys Gln Leu Glu Asn Glu Val Val Glu Gln Val Tyr Gly Ile
            100                 105                 110

Asp Pro Tyr Thr His Asn Leu Leu Asp Ser Met Pro Lys Glu Leu
            115                 120                 125

Asp Trp Ser Leu Gln Glu Lys His Leu Phe Ile Glu Asp Lys Leu Leu
130                 135                 140

Arg Met Leu Asn Lys Gln Val Lys His Phe Thr Gly Thr Gly Asn Thr
145                 150                 155                 160

Pro Met Ser Tyr Pro Leu Gln Pro Ala Ile Glu Glu Ile Glu Arg Tyr
                165                 170                 175

Ala Glu Glu His Cys Asp Ala Arg Thr Val Arg Met Cys Gln Gly Ile
```

-continued

```
                180                 185                 190
Leu Lys Ala Ile Lys Ser Arg Ser Asp Asp Lys Tyr Val Ala Tyr Arg
            195                 200                 205
Lys Gly Leu Gly Val Val Cys Asn Lys Glu Glu Gly Phe Gly Glu Asp
            210                 215                 220
Asp Phe Val Val Glu Phe Leu Gly Glu Val Tyr Pro Val Trp Lys Trp
225                 230                 235                 240
Phe Glu Lys Gln Asp Gly Ile Arg Ser Leu Gln Lys Asn Ser Asp Asp
            245                 250                 255
Pro Ala Pro Glu Phe Tyr Asn Ile Tyr Leu Glu Arg Pro Lys Gly Asp
            260                 265                 270
Ala Asp Gly Tyr Asp Leu Val Val Asp Ala Met His Lys Ala Asn
            275                 280                 285
Tyr Ala Ser Arg Ile Cys His Ser Cys Arg Pro Asn Cys Glu Ala Lys
            290                 295                 300
Val Thr Ala Val Asp Gly His Tyr Gln Ile Gly Ile Tyr Ser Val Arg
305                 310                 315                 320
Glu Ile Gln His Gly Glu Glu Ile Thr Phe Asp Tyr Asn Ser Val Thr
                325                 330                 335
Glu Ser Lys Glu Glu Tyr Glu Ala Ser Val Cys Leu Cys Gly Ser Gln
            340                 345                 350
Val Cys Arg Gly Ser Tyr Leu Asn Leu Thr Gly Glu Gly Ala Phe Glu
            355                 360                 365
Lys Val Leu Lys Glu Trp His Gly Ile Leu Asp Arg His Tyr Leu Met
            370                 375                 380
Leu Glu Ala Cys Glu Leu Asn Ser Val Ser Glu Asp Tyr Asn Asp
385                 390                 395                 400
Leu Gly Arg Ala Gly Leu Gly Ser Cys Leu Leu Gly Gly Leu Pro Asp
            405                 410                 415
Trp Leu Val Ser Tyr Ala Ala Arg Leu Val Arg Phe Ile Asn Phe Glu
            420                 425                 430
Arg Thr Lys Leu Pro Glu Glu Ile Leu Lys His Asn Leu Glu Glu Lys
            435                 440                 445
Arg Lys Tyr Phe Ser Asp Ile Cys Leu Glu Val Glu Arg Ser Asp Ala
            450                 455                 460
Glu Val Gln Ala Glu Gly Val Tyr Asn Gln Arg Leu Gln Asn Leu Ala
465                 470                 475                 480
Val Thr Leu Asp Lys Val Arg Tyr Val Met Arg Cys Ile Phe Gly Asp
            485                 490                 495
Pro Leu Lys Ala Pro Pro Leu Glu Lys Leu Ser Pro Glu Ala Val
            500                 505                 510
Val Ser Phe Leu Trp Lys Gly Glu Asp Ser Phe Val Glu Glu Leu Leu
            515                 520                 525
Gln Cys Leu Ala Pro Tyr Val Glu Glu Ser Thr Leu Asn Asp Leu Lys
            530                 535                 540
Ser Lys Ile His Ala His Asp Pro Ser Ser Gly Asp Ile Gln Lys
545                 550                 555                 560
Ala Val Gln Lys Ser Leu Leu Trp Leu Arg Asp Glu Val Arg Asn Leu
            565                 570                 575
Pro Cys Thr Tyr Lys Cys Arg His Asp Ala Ala Ala Asp Leu Ile His
            580                 585                 590
Ile Tyr Ala Tyr Thr Lys Tyr Phe Phe Arg Ile Gln Asp Tyr Gln Thr
            595                 600                 605
```

-continued

Ile Thr Ser Pro Pro Val Tyr Ile Ser Pro Leu Asp Leu Gly Pro Lys
610                 615                 620

Tyr Ala Asp Lys Leu Gly Ala Gly Phe Gln Glu Tyr Arg Lys Ile Tyr
625                 630                 635                 640

Gly Glu Asn Tyr Cys Leu Gly Gln Leu Ile Phe Trp His Asn Gln Ser
            645                 650                 655

Asn Ala Glu Pro Asp Cys Thr Leu Ala Arg Ile Ser Arg Gly Cys Leu
        660                 665                 670

Ser Leu Pro Asp Ile Ser Ser Phe Tyr Ala Lys Ala Gln Lys Pro Ser
    675                 680                 685

Arg His Arg Val Tyr Gly Pro Arg Thr Val Arg Ser Met Leu Ala Arg
690                 695                 700

Met Glu Lys Gln Pro Gln Lys Pro Trp Pro Lys Asp Arg Ile Trp Ser
705                 710                 715                 720

Phe Lys Asn Ser Pro Lys Tyr Phe Gly Ser Pro Met Leu Asp Ala Val
            725                 730                 735

Ile Asn Asn Ser Pro Leu Asp Arg Glu Met Val His Trp Leu Lys His
            740                 745                 750

Arg Pro Ala Ile Phe Gln Ala Leu Trp Asp
        755                 760

<210> SEQ ID NO 120
<211> LENGTH: 737
<212> TYPE: PRT
<213> ORGANISM: Zea mays

<400> SEQUENCE: 120

Glu Ser Val Thr Asp Asp Arg Ile Leu Gly Ala Arg Met Thr Lys Ala
1               5                   10                  15

Ser Leu Val Pro Pro Val Thr Arg Lys Tyr Glu Val Ile Glu Glu Tyr
                20                  25                  30

Leu Ile Val Ala Asp Leu Glu Glu Val Gln Arg Lys Met Arg Val Ala
            35                  40                  45

Leu Pro Asp Asp Tyr Ser Glu Lys Leu Leu Ser Gln Lys Asn Gly Thr
50                  55                  60

Glu Asn Leu Glu Leu Pro Glu Val Lys Asp Tyr Gln Pro Arg Lys Val
65                  70                  75                  80

Ala Gly Asp Glu Ile Leu Glu Gln Val Tyr Gly Ile Asp Pro Tyr
                85                  90                  95

Thr His Asn Leu Leu Ser Asp Ile Met Pro Ala Asp Leu Glu Leu Ser
            100                 105                 110

Pro Thr Asp Lys His Ile Phe Ile Glu Glu Leu Leu Leu Asn Thr Leu
        115                 120                 125

Asn Lys Gln Val Arg His Phe Thr Gly Ser Gly Asn Thr Pro Met Thr
130                 135                 140

Tyr Asn Leu Arg Pro Val Ile Glu Glu Ile Gln Arg Ser Ala Glu Asp
145                 150                 155                 160

Asn Gly Asp Lys Arg Thr Ser Lys Met Cys Leu Gly Met Leu Lys Thr
            165                 170                 175

Met Arg Asn Arg Ser Glu Gln Asn Phe Val Ala Tyr Arg Lys Gly Leu
            180                 185                 190

Gly Val Val Cys Asn Lys Lys Gly Gly Phe Gly Val Asp Asp Phe Val
        195                 200                 205

Val Glu Phe Phe Gly Glu Val Tyr Pro Ser Trp Arg Trp Tyr Glu Lys

```
            210                 215                 220
Gln Asp Gly Ile Lys His Ile Gln Asn Asn Ser Glu Asp Gln Ala Pro
225                 230                 235                 240

Glu Phe Tyr Asn Ile Met Leu Glu Arg Pro Lys Gly Asp Gly Asp Gly
                    245                 250                 255

Tyr Asp Leu Val Phe Val Asp Ala Met His Lys Ala Asn Tyr Ala Ser
                260                 265                 270

Arg Ile Cys His Ser Cys Asn Pro Asn Cys Glu Ala Lys Val Thr Ala
            275                 280                 285

Val Asn Gly Lys Tyr Gln Ile Gly Val Tyr Thr Leu Arg Pro Ile Ala
        290                 295                 300

Glu Gly Glu Glu Ile Thr Phe Asp Tyr Asn Ser Val Thr Glu Ser Lys
305                 310                 315                 320

Glu Glu His Glu Ala Ser Val Cys Leu Cys Gly Ser Gln Val Cys Arg
                    325                 330                 335

Gly Ser Tyr Leu Asn Phe Ser Gly Glu Gly Ala Phe Glu Lys Val Leu
                340                 345                 350

Met Glu Phe His Gly Val Leu Asp Arg His Ser Leu Leu Gln Ala
            355                 360                 365

Cys Glu Thr Asp Ser Val Ser Gln Gln Asp Leu Ile Asp Leu Gly Arg
        370                 375                 380

Ala Gly Leu Gly Thr Cys Leu Leu Ala Gly Leu Pro Gly Trp Leu Val
385                 390                 395                 400

Ala Tyr Thr Ala His Leu Val Arg Phe Ile Tyr Leu Glu Arg Gln Lys
                    405                 410                 415

Leu Pro Asp Glu Ile Leu Arg His Asn Val Asp Glu Lys Arg Gln Phe
                420                 425                 430

Leu Ile Glu Ile Asn Met Asp Ser Glu Lys Asn Asp Ala Glu Val Gln
            435                 440                 445

Ala Glu Gly Val Leu Asn Ser Arg Leu Gln Gln Ile Val His Thr Leu
        450                 455                 460

Asp Lys Val Arg Tyr Val Met Arg Cys Ile Phe Gly Asp Pro Lys Asn
465                 470                 475                 480

Ala Pro Pro Leu Val Arg Leu Ser Gly Lys Ser Leu Val Ser Ala
                    485                 490                 495

Ile Trp Lys Gly Asp Ser Ser Ile Val Ala Glu Leu Ile Gln Ser Met
                500                 505                 510

Glu Pro His Val Glu Glu Val Leu Ser Asp Leu Lys Ala Lys Ile
            515                 520                 525

Arg Ala His Asp Pro Ser Glu Ser Glu Asp Ile Glu Gly Gly Ile Arg
        530                 535                 540

Asn Ser Leu Leu Trp Leu Arg Asp Glu Leu Arg Thr Leu Ser Cys Thr
545                 550                 555                 560

Tyr Lys Cys Arg His Asp Ala Ala Ala Asp Leu Ile His Leu Tyr Ala
                    565                 570                 575

Tyr Thr Lys Cys Phe Phe Arg Val Arg Asp Tyr Lys Thr Val Lys Ser
                580                 585                 590

Pro Pro Val His Ile Ser Pro Leu Asp Leu Gly Pro Lys Tyr Ala Asp
            595                 600                 605

Lys Leu Gly Pro Gly Phe Gln Glu Tyr Cys Lys Thr Tyr Pro Glu Asn
        610                 615                 620

Tyr Cys Leu Ala Gln Leu Ile Tyr Trp Tyr Ser Gln Asn Ser Glu Pro
625                 630                 635                 640
```

-continued

```
Glu Ser Arg Leu Thr Arg Ala Arg Lys Gly Cys Met Ser Leu Pro Asp
                645                 650                 655

Val Ser Ser Phe Tyr Val Lys Ser Ala Lys Pro Ser Gln Glu Arg Ala
            660                 665                 670

Tyr Gly Asn Arg Thr Val Arg Phe Met Leu Ser Arg Met Glu Lys Gln
        675                 680                 685

Ala Gln Arg Pro Trp Pro Lys Asp Arg Ile Trp Val Phe Lys Ser Asp
690                 695                 700

Pro Arg Phe Phe Gly Ser Pro Met Met Asp Thr Val Leu Asn Asn Ser
705                 710                 715                 720

Pro Leu Asp Lys Glu Met Val His Trp Leu Lys Thr Arg Pro Asn Val
                725                 730                 735

Phe

<210> SEQ ID NO 121
<211> LENGTH: 755
<212> TYPE: PRT
<213> ORGANISM: Manihot esculenta

<400> SEQUENCE: 121

Glu Gly Phe Phe Met Gly Asp Glu Gly Leu Asp Ser Ile Thr Asp Asp
1               5                   10                  15

Arg Glu Trp Gly Ala Arg Met Thr Lys Ala Ser Leu Val Pro Pro Val
                20                  25                  30

Thr Arg Lys Tyr Glu Val Ile Asp Gln Tyr Val Ile Val Ala Asp Glu
            35                  40                  45

Glu Asp Val Gln Arg Lys Met Cys Val Ser Leu Pro Asp Asp Phe Ala
50                  55                  60

Glu Lys Leu Asp Ala Gln Lys Asn Gly Thr Glu Glu Leu Asp Met Glu
65                  70                  75                  80

Leu Pro Glu Val Lys Asp Tyr Lys Pro Arg Lys Gln Leu Gly Asp Glu
                85                  90                  95

Val Ile Glu Gln Glu Val Tyr Gly Ile Asp Pro Tyr Thr His Asn Leu
            100                 105                 110

Leu Leu Asp Ser Met Pro Glu Glu Leu Asp Trp Pro Leu Ser Glu Lys
        115                 120                 125

His Ser Phe Ile Glu Asp Met Leu Leu Gln Thr Leu Asn Lys Gln Val
130                 135                 140

Arg Asn Phe Thr Gly Ser Gly Asn Thr Pro Met Met Tyr Pro Leu Leu
145                 150                 155                 160

Pro Val Ile Glu Asp Ile Glu Lys Ala Ala Glu Glu Cys Asp Val
                165                 170                 175

Arg Thr Met Lys Met Cys His Gly Ile Leu Lys Ala Ile Ala Ser Arg
            180                 185                 190

Pro Asp Asp Asn Tyr Val Ala Tyr Arg Lys Gly Leu Gly Val Val Cys
        195                 200                 205

Asn Lys Gln Gly Gly Phe Gly Glu Asp Asp Phe Val Val Glu Phe Leu
210                 215                 220

Gly Glu Val Tyr Pro Ala Trp Lys Trp Phe Glu Lys Gln Asp Gly Ile
225                 230                 235                 240

Arg Ser Leu Gln Lys Asp Asn Lys Asp Pro Ala Pro Glu Phe Tyr Asn
                245                 250                 255

Ile Asn Leu Glu Arg Pro Lys Gly Asp Ala Asp Gly Tyr Asp Leu Val
            260                 265                 270
```

```
Val Val Asp Ala Met His Lys Ala Asn Tyr Ala Ser Arg Ile Cys His
            275                 280                 285

Ser Cys Arg Pro Asn Cys Glu Ala Lys Val Thr Ala Val Asp Gly Gln
    290                 295                 300

Tyr Gln Ile Gly Ile Tyr Thr Val Arg Glu Ile Gln Tyr Gly Glu Glu
305                 310                 315                 320

Ile Thr Phe Asp Tyr Asn Ser Val Thr Glu Ser Lys Glu Glu Tyr Glu
                325                 330                 335

Ala Ser Val Cys Leu Cys Gly Ser Gln Val Cys Arg Gly Ser Tyr Leu
                340                 345                 350

Asn Leu Thr Gly Glu Gly Ala Phe Gln Lys Val Leu Lys Glu Trp His
            355                 360                 365

Ala Met Leu Asp Arg His His Leu Met Leu Glu Ala Cys Glu Leu Asn
    370                 375                 380

Ser Val Ser Glu Glu Asp Tyr Leu Asp Leu Gly Arg Ala Gly Leu Gly
385                 390                 395                 400

Ser Cys Leu Leu Gly Gly Leu Pro Asp Trp Val Val Ala Tyr Ser Ala
                405                 410                 415

Arg Leu Val Arg Phe Ile Asn Leu Glu Arg Thr Lys Leu Pro Glu Glu
            420                 425                 430

Ile Leu Arg His Asn Leu Glu Glu Lys Arg Lys Tyr Phe Ser Asp Ile
    435                 440                 445

Cys Leu Glu Val Glu Arg Ser Asp Ala Glu Val Gln Ala Glu Gly Val
    450                 455                 460

Tyr Asn Gln Arg Leu Gln Asn Leu Ala Val Thr Leu Asp Lys Val Arg
465                 470                 475                 480

Tyr Val Met Arg Cys Leu Phe Gly Asp Pro Lys Lys Ala Pro Pro Pro
                485                 490                 495

Leu Val Arg Leu Ser Pro Glu Glu Thr Val Ser Phe Leu Trp Lys Gly
            500                 505                 510

Glu Gly Ser Leu Val Glu Glu Leu Leu Gln Cys Met Ala Ser His Val
        515                 520                 525

Glu Ala Asp Met Leu Asn Asp Leu Lys Ser Lys Ile Arg Ala Arg Asp
    530                 535                 540

Leu Ser Glu Ser Asp Asn Ile Gln Lys Glu Leu Gln Lys Ser Leu Phe
545                 550                 555                 560

Trp Leu Arg Asp Glu Val Arg Ala Leu Pro Cys Thr Tyr Lys Cys Arg
                565                 570                 575

His Asp Ala Ala Ala Asp Leu Ile His Val Tyr Ala His Thr Lys Cys
            580                 585                 590

Phe Phe Lys Val Gln Glu Tyr Lys Thr Phe Thr Ser Pro Pro Val His
    595                 600                 605

Ile Ser Pro Leu Asp Leu Gly Pro Lys Tyr Ala Asp Lys Leu Gly Ala
    610                 615                 620

Gly Ile His Glu Tyr Arg Lys Thr Tyr Gly Glu Asn Tyr Cys Leu Gly
625                 630                 635                 640

Gln Leu Ile Tyr Trp His Ile Gln Thr Asn Ala Glu Pro Asp Cys Ser
                645                 650                 655

Leu Ala Lys Ala Ser Arg Gly Cys Leu Ser Leu Pro Glu Ile Gly Ser
            660                 665                 670

Cys Tyr Ala Lys Val Gln Lys Pro Ser Gln Gln Arg Ile Tyr Gly Pro
    675                 680                 685
```

```
Lys Thr Val Lys Leu Leu Leu Glu Arg Met Glu Lys Tyr Pro His Lys
        690                 695                 700

Pro Trp Pro Lys Asp Gln Ile Trp Ser Phe Lys Ser Cys Pro Lys Val
705                 710                 715                 720

Ile Gly Ser Pro Met Leu Asp Ala Val Leu Ser Asn Cys Pro Leu Asp
                725                 730                 735

Arg Glu Leu Val His Trp Leu Lys His Arg Pro Thr Ile Tyr Gln Ala
            740                 745                 750

Val Trp Asp
        755

<210> SEQ ID NO 122
<211> LENGTH: 530
<212> TYPE: PRT
<213> ORGANISM: Triticum urartu

<400> SEQUENCE: 122

Ser Ala Asp Lys His Thr Phe Ile Glu Glu Gly Leu Gly Val Val Cys
1               5                   10                  15

Asn Lys Lys Gly Gly Phe Gly Met Asp Asp Phe Val Ile Glu Phe Phe
            20                  25                  30

Gly Glu Val Tyr Pro Ser Trp Arg Trp Tyr Glu Lys Gln Asp Gly Ile
        35                  40                  45

Lys His Ile Gln Asn Asn Ser Glu Asp Gln Ala Pro Glu Phe Tyr Asn
    50                  55                  60

Ile Met Leu Glu Arg Pro Lys Gly Asp Arg Asp Gly Tyr Asp Leu Val
65                  70                  75                  80

Phe Val Asp Ala Met His Lys Ala Asn Tyr Ala Ser Arg Ile Cys His
                85                  90                  95

Ser Cys Asn Pro Asn Cys Glu Ala Lys Val Thr Ala Val Asp Gly Gln
            100                 105                 110

Tyr Gln Ile Gly Val Tyr Thr Val Arg Pro Ile Ala Glu Gly Glu Glu
        115                 120                 125

Ile Thr Phe Asp Tyr Asn Ser Val Thr Glu Ser Lys Glu Glu His Glu
    130                 135                 140

Ala Ser Val Cys Leu Cys Gly Ser Gln Val Cys Arg Gly Ser Tyr Leu
145                 150                 155                 160

Asn Phe Ser Gly Glu Gly Ala Phe Glu Lys Ala Cys Glu Ala Asn Thr
                165                 170                 175

Val Ser Gln Gln Asp Leu Ile Asp Leu Gly Arg Ala Gly Leu Gly Thr
            180                 185                 190

Cys Leu Leu Ala Gly Leu Pro Gly Trp Leu Val Ala Tyr Thr Ala Gln
        195                 200                 205

Leu Val Arg Phe Ile Phe Glu Arg Gln Lys Leu Pro Asn Glu Ile
    210                 215                 220

Phe Lys His Asn Met Glu Glu Lys Arg Gln Phe Phe Thr Asp Ile Asn
225                 230                 235                 240

Met Asp Ser Glu Arg Asn Asp Ala Glu Val Gln Ala Glu Gly Val Leu
                245                 250                 255

Asn Ser Arg Leu Gln His Leu Thr His Thr Leu Asp Lys Val Arg Tyr
            260                 265                 270

Val Met Arg Cys Ile Phe Gly Asp Pro Lys Asn Ala Pro Pro Leu
        275                 280                 285

Val Arg Leu Thr Gly Arg Ser Leu Val Ser Ala Ile Trp Lys Gly Glu
    290                 295                 300
```

```
Gly Ser Leu Val Asp Glu Leu Leu Gln Ser Ile Glu His His Val Asp
305                 310                 315                 320

Glu Asp Val Leu Thr Asp Leu Lys Asp Lys Ile Arg Leu His Asp Pro
                325                 330                 335

Ser Asp Ser Glu Asp Ile Asp Gly Asp Ile Arg Asn Ser Leu Leu Trp
            340                 345                 350

Leu Arg Asp Glu Leu Arg Thr Leu Ser Cys Thr Tyr Lys Cys Arg His
        355                 360                 365

Asp Ala Ala Asp Leu Ile His Met Tyr Ala Tyr Thr Lys Cys Phe
    370                 375                 380

Phe Arg Ala Arg Asp Tyr Lys Thr Val Lys Ser Pro Val His Ile
385                 390                 395                 400

Ser Pro Leu Asp Leu Gly Pro Lys Tyr Ala Asp Lys Leu Gly Pro Gly
                405                 410                 415

Phe Gln Glu Tyr Ser Lys Thr Tyr Pro Glu Asn Tyr Cys Leu Ala Gln
            420                 425                 430

Leu Ile Tyr Trp Tyr Ser Gln Asn Ala Glu Pro Glu Ser Arg Leu Thr
        435                 440                 445

Arg Ala Arg Lys Gly Cys Met Ser Leu Pro Asp Val Ser Ser Phe Tyr
450                 455                 460

Val Lys Ser Val Lys Pro Thr Gln Glu Arg Val Tyr Gly Thr Arg Thr
465                 470                 475                 480

Val Arg Phe Met Leu Ser Arg Met Glu Lys Gln Ala Gln Arg Pro Trp
                485                 490                 495

Pro Lys Asp Arg Ile Trp Val Phe Lys Ser Asp Pro Arg Phe Phe Gly
            500                 505                 510

Thr Pro Met Met Asp Ala Val Leu Asn Asn Asn Ser Pro Leu Asp Lys
        515                 520                 525

Glu Met
    530

<210> SEQ ID NO 123
<211> LENGTH: 144
<212> TYPE: PRT
<213> ORGANISM: Triticum aestivum

<400> SEQUENCE: 123

Phe His Ser Gly Lys Lys Gly Tyr Gly Leu Lys Leu Gln Glu Glu Val
1               5                   10                  15

Ser Glu Gly Arg Phe Leu Ile Glu Tyr Val Gly Glu Val Leu Asp Ile
                20                  25                  30

Thr Thr Tyr Glu Ser Arg Gln Arg Asp Tyr Ala Ser Lys Gly Lys Lys
            35                  40                  45

His Phe Tyr Phe Met Ala Leu Asp Gly Gly Glu Val Ile Asp Ala Cys
    50                  55                  60

Thr Lys Gly Asn Leu Gly Arg Phe Ile Asn His Ser Cys Ser Pro Asn
65                  70                  75                  80

Cys Arg Thr Glu Lys Trp Met Val Asn Gly Glu Val Cys Ile Gly Ile
                85                  90                  95

Phe Ala Met Arg Asn Ile Lys Lys Gly Glu Glu Leu Thr Phe Asp Tyr
            100                 105                 110

Asn Tyr Val Arg Val Ser Gly Ala Ala Pro Gln Lys Cys Phe Cys Gly
        115                 120                 125

Thr Ala Lys Cys Arg Gly Tyr Ile Gly Gly Asp Ile Ser Gly Ser Gly
```

<210> SEQ ID NO 124
<211> LENGTH: 757
<212> TYPE: PRT
<213> ORGANISM: Oryza sativa

<400> SEQUENCE: 124

Asn Ser Gly Ala Trp Asp Leu Lys Gly Asn Gly Met Lys Leu Phe Glu
1               5                   10                  15

Ser Ser Glu Ser Leu Thr Asp Asp Arg Gly Trp Gly Ala Arg Met Thr
            20                  25                  30

Lys Ala Ser Leu Val Pro Pro Val Thr Arg Lys Tyr Glu Val Ile Glu
        35                  40                  45

Lys Tyr Leu Ile Val Ala Asp Glu Glu Val Leu Arg Lys Met Arg
    50                  55                  60

Val Ala Leu Pro Asp Asp Tyr Ser Glu Lys Leu Leu Ser Gln Lys Asn
65                  70                  75                  80

Gly Thr Glu Asn Leu Glu Leu Pro Glu Val Lys Asp Tyr Gln Pro Arg
                85                  90                  95

Lys Val Pro Gly Asp Glu Val Leu Glu Gln Glu Val Tyr Gly Ile Asp
            100                 105                 110

Pro Tyr Thr His Asn Leu Leu Leu Glu Met Met Pro Thr Glu Leu Asp
        115                 120                 125

Trp Pro Ser Ser Asp Lys His Thr Phe Val Glu Glu Leu Leu Leu Asn
    130                 135                 140

Thr Leu Asn Lys Gln Val Arg Gln Phe Thr Gly Ser Gly Asn Thr Pro
145                 150                 155                 160

Met Val Tyr Pro Leu Lys Pro Val Ile Glu Glu Ile Gln Lys Ser Ala
                165                 170                 175

Glu Glu Ser Gly Asp Arg Arg Thr Ser Lys Met Cys Leu Gly Met Leu
            180                 185                 190

Lys Ala Met Arg Asn His Pro Glu Tyr Asn Tyr Val Ala Tyr Arg Lys
        195                 200                 205

Gly Leu Gly Val Val Cys Asn Lys Thr Gly Gly Phe Gly Val Asp Asp
    210                 215                 220

Phe Val Ile Glu Phe Phe Gly Glu Val Tyr Pro Ser Trp Arg Trp Tyr
225                 230                 235                 240

Glu Lys Gln Asp Gly Ile Lys His Ile Gln Asn Asn Ser Asp Asp Gln
                245                 250                 255

Ala Pro Glu Phe Tyr Asn Ile Met Leu Glu Arg Pro Lys Gly Asp Arg
            260                 265                 270

Asp Gly Tyr Asp Leu Val Phe Val Asp Ala Met His Lys Ala Asn Tyr
        275                 280                 285

Ala Ser Arg Ile Cys His Ser Cys Asn Pro Asn Cys Glu Ala Lys Val
    290                 295                 300

Thr Ala Val Asp Gly His Tyr Gln Ile Gly Ile Tyr Thr Val Arg Pro
305                 310                 315                 320

Ile Ala Glu Gly Glu Glu Ile Thr Phe Asp Tyr Asn Ser Val Thr Glu
                325                 330                 335

Ser Lys Glu Glu His Glu Ala Ser Val Cys Leu Cys Gly Ser Gln Ile
            340                 345                 350

Cys Arg Gly Ser Tyr Leu Asn Phe Ser Gly Glu Gly Ala Phe Glu Lys
        355                 360                 365

Val Leu Met Glu Phe His Gly Val Leu Asp Arg His Ser Leu Leu Leu
370                 375                 380

Gln Ala Cys Glu Ala Asn Ser Val Ser Gln Gln Asp Leu Ile Asp Leu
385                 390                 395                 400

Gly Arg Ala Gly Leu Gly Thr Cys Leu Leu Ala Gly Leu Pro Gly Trp
            405                 410                 415

Leu Val Ala Tyr Thr Ala His Leu Val Arg Phe Ile Phe Glu Arg
            420                 425                 430

Gln Lys Leu Pro His Glu Ile Phe Lys His Asn Val Asp Glu Lys Arg
            435                 440                 445

Gln Phe Phe Thr Asp Ile Asn Met Asp Ser Glu Lys Asn Asp Ala Glu
450                 455                 460

Val Gln Ala Glu Gly Val Leu Asn Ser Arg Leu Gln Asn Leu Thr His
465                 470                 475                 480

Thr Leu Asp Lys Val Arg Tyr Val Met Arg Cys Ile Phe Gly Asp Pro
            485                 490                 495

Lys Asn Ala Pro Pro Leu Val Arg Leu Thr Gly Arg Ser Leu Val
            500                 505                 510

Ser Ala Ile Trp Lys Gly Glu Gly Ser Leu Val Asp Glu Leu Leu Glu
515                 520                 525

Ser Met Glu Pro His Val Glu Glu Asp Val Leu Thr Asp Leu Lys Ala
530                 535                 540

Lys Ile Arg Ala His Asp Pro Ser Gly Ser Glu Asp Ile Glu Gly Glu
545                 550                 555                 560

Ile Arg Ser Ser Leu Leu Trp Leu Arg Asp Glu Leu Arg Thr Leu Ser
            565                 570                 575

Cys Thr Tyr Lys Cys Arg His Asp Ala Ala Ala Asp Leu Ile His Met
            580                 585                 590

Tyr Ala Tyr Thr Lys Cys Phe Phe Arg Val Arg Asp Tyr Lys Thr Val
            595                 600                 605

Lys Ser Pro Pro Val Leu Ile Ser Pro Leu Asp Leu Gly Pro Lys Tyr
            610                 615                 620

Ala Asp Lys Leu Gly Pro Gly Phe Gln Glu Tyr Cys Lys Thr Tyr Pro
625                 630                 635                 640

Glu Asn Tyr Cys Leu Gly Gln Leu Ile Tyr Trp Tyr Ser Gln Asn Ala
            645                 650                 655

Glu Pro Glu Ser Arg Leu Thr Arg Ala Arg Lys Gly Cys Met Ser Leu
            660                 665                 670

Pro Asp Val Ser Ser Phe Tyr Val Lys Ser Val Lys Pro Thr Gln Glu
            675                 680                 685

Arg Val Tyr Gly Ser Arg Thr Val Arg Phe Met Leu Ala Arg Met Glu
            690                 695                 700

Asn Gln Ala Gln Arg Pro Trp Pro Lys Asp Arg Ile Trp Val Phe Lys
705                 710                 715                 720

Ser Asp Pro Arg Phe Phe Gly Thr Pro Met Met Asp Ala Val Leu Asn
            725                 730                 735

Asn Ser Pro Leu Asp Lys Glu Met Val His Trp Leu Lys Thr Arg Ser
            740                 745                 750

Asn Val Phe Leu Gly
            755

<210> SEQ ID NO 125
<211> LENGTH: 752
<212> TYPE: PRT

<213> ORGANISM: Solanum lycopersicum

<400> SEQUENCE: 125

```
Tyr Phe Thr Pro Asp Asp Gly Phe Asp Ser Phe Ala Asp Asp Arg Glu
1               5                   10                  15

Trp Gly Ala Arg Met Thr Lys Ala Ser Leu Val Pro Pro Val Thr Arg
            20                  25                  30

Lys Tyr Glu Val Ile Asp His Tyr Val Ile Val Ala Asp Glu Lys Glu
        35                  40                  45

Val Lys Arg Lys Met Leu Val Ser Leu Pro Glu Asp Tyr Ala Gly Lys
    50                  55                  60

Leu Ser Val Gln Lys Asn Gly Thr Glu Glu Ser Asp Met Glu Ile Pro
65                  70                  75                  80

Glu Val Lys Asp Tyr Lys Pro Arg Lys Thr Leu Gly Glu Glu Val Ile
                85                  90                  95

Glu Gln Glu Val Tyr Gly Ile Asp Pro Tyr Thr His Asn Leu Leu Leu
            100                 105                 110

Asp Ser Met Pro Asp Glu Ser Asp Trp Ser Leu Leu Asp Lys His Leu
        115                 120                 125

Phe Ile Glu Asp Val Leu Leu Arg Thr Leu Asn Lys Gln Val Arg Arg
    130                 135                 140

Phe Thr Gly Ser His Thr Pro Met Ile Tyr Ser Leu Lys Pro Val Phe
145                 150                 155                 160

Glu Glu Ile Leu Glu Thr Ala Asp Lys Asp Gln Asp Lys Arg Thr Ile
                165                 170                 175

Arg Leu Cys Gln Phe Met Leu Asn Ala Ile Asp Thr Arg Pro Glu Asp
            180                 185                 190

Asn Tyr Val Ala Tyr Arg Lys Gly Leu Gly Val Val Cys Asn Lys Glu
        195                 200                 205

Gly Gly Phe Ser Glu Glu Asp Phe Val Val Glu Phe Leu Gly Glu Val
    210                 215                 220

Tyr Pro Ala Trp Lys Trp Phe Glu Lys Gln Asp Gly Ile Arg Ser Leu
225                 230                 235                 240

Gln Arg Asn Asn Asn Asp Pro Ala Pro Glu Phe Tyr Asn Ile Tyr Leu
                245                 250                 255

Glu Arg Pro Lys Gly Asp Ala Asp Gly Tyr Asp Leu Val Val Val Asp
            260                 265                 270

Ala Met His Lys Ala Asn Tyr Ala Ser Arg Ile Cys His Ser Cys Arg
        275                 280                 285

Pro Asn Cys Glu Ala Lys Val Thr Ala Val Asp Gly Gln Tyr Gln Ile
    290                 295                 300

Gly Ile Tyr Ser Thr Arg Pro Ile Ala Tyr Gly Glu Glu Val Thr Phe
305                 310                 315                 320

Asp Tyr Asn Ser Val Thr Glu Ser Lys Glu Glu Tyr Glu Ala Ser Val
                325                 330                 335

Cys Leu Cys Gly Ser Gln Val Cys Arg Gly Ser Tyr Leu Asn Leu Thr
            340                 345                 350

Gly Glu Gly Ala Phe Leu Lys Val Leu Gln Tyr His Gly Leu Leu
        355                 360                 365

Asn Arg His Gln Leu Met Leu Glu Ala Cys Glu Leu Asn Ser Val Ser
    370                 375                 380

Glu Glu Asp Tyr Ile Asp Leu Gly Lys Ala Gly Leu Gly Ser Cys Leu
385                 390                 395                 400
```

```
Leu Ala Gly Leu Pro His Trp Leu Ile Ala Tyr Ser Ala Arg Leu Val
                405                 410                 415

Arg Phe Ile Asn Phe Glu Arg Thr Lys Leu Pro Asp Glu Ile Leu Lys
            420                 425                 430

His Asn Leu Glu Glu Lys Lys Lys Tyr Phe Ser Asp Val Cys Leu Glu
        435                 440                 445

Val Glu Lys Asn Glu Ser Glu Ile Gln Ala Glu Gly Val Tyr Asn Gln
    450                 455                 460

Arg Leu Gln Asn Leu Ala Leu Thr Leu Asp Lys Val Arg Tyr Val Met
465                 470                 475                 480

Arg Cys Val Phe Gly Asp Pro Glu Lys Ala Pro Pro Leu Glu Arg
                485                 490                 495

Leu Asn Pro Glu Glu Ala Val Ser Phe Ile Trp Arg Gly Glu Gly Ser
                500                 505                 510

Leu Val Glu Glu Leu Leu Gln Cys Met Ala Pro His Leu Glu Asp Ser
            515                 520                 525

Met Leu Asn Asp Leu Lys Ala Lys Ile Arg Ala His Asp Pro Ser Arg
        530                 535                 540

Ser Asp Asp Leu Glu Thr Gly Leu Arg Lys Ser Leu Ile Trp Leu Arg
545                 550                 555                 560

Asp Glu Val Arg Asp Leu Pro Cys Thr Tyr Lys Ser Arg His Asp Ala
                565                 570                 575

Ala Ala Asp Leu Ile His Leu Tyr Ala Tyr Thr Lys Cys Phe Phe Arg
                580                 585                 590

Ile Arg Glu Tyr Lys Thr Val Thr Ser Pro Pro Val Tyr Ile Ser Pro
            595                 600                 605

Leu Asp Leu Gly Pro Lys Tyr Thr Asp Lys Leu Gly Pro Gly Thr His
        610                 615                 620

Glu Tyr Arg Lys Thr Tyr Gly Glu Asn Tyr Cys Leu Gly Gln Leu Phe
625                 630                 635                 640

Tyr Trp Tyr Asn Gln Ala Asn Ala Asp Pro Glu Asn Cys Leu Phe Lys
                645                 650                 655

Ala Ser Arg Gly Cys Leu Ser Leu Pro Glu Ala Gly Ser Phe Tyr Ala
                660                 665                 670

Lys Val Gln Lys Pro Ser Arg Gln Arg Val Tyr Gly Pro Arg Thr Val
            675                 680                 685

Lys Phe Met Leu Ser Arg Met Glu Lys Gln Pro Gln Arg Ala Trp Pro
690                 695                 700

Lys Asp Arg Ile Trp Ser Phe Lys Asn Ser Pro Asn Val Phe Gly Ser
705                 710                 715                 720

Pro Met Leu Asp Gly Ile Leu Asn Lys Ser Pro Leu Glu Arg Glu Met
                725                 730                 735

Val His Trp Leu Lys His Arg Pro Ala Ile Phe Gln Ala Lys Trp Asp
                740                 745                 750

<210> SEQ ID NO 126
<211> LENGTH: 752
<212> TYPE: PRT
<213> ORGANISM: Solanum tuberosum

<400> SEQUENCE: 126

Tyr Phe Thr Pro Asp Asp Gly Phe Asp Ser Phe Ala Asp Asp Arg Glu
1               5                   10                  15

Trp Gly Ala Arg Met Thr Lys Ala Ser Leu Val Pro Pro Val Thr Arg
            20                  25                  30
```

```
Lys Tyr Glu Val Ile Asp His Tyr Val Ile Ala Asp Glu Lys Glu
            35                  40                  45

Val Lys Arg Lys Met Leu Val Ser Leu Pro Glu Asp Tyr Ala Gly Lys
 50                  55                  60

Leu Ser Val Gln Lys Asn Gly Thr Glu Ser Asp Met Glu Ile Pro
 65              70                  75                  80

Glu Val Lys Asp Tyr Lys Pro Arg Lys Thr Leu Gly Glu Val Ile
                85                  90                  95

Glu Gln Glu Val Tyr Gly Ile Asp Pro Tyr Thr His Asn Leu Leu
                100                 105                 110

Asp Ser Met Pro Asp Glu Ser Asp Trp Ser Leu Leu Asp Lys His Leu
            115                 120                 125

Phe Ile Glu Asp Val Leu Leu Arg Thr Leu Asn Lys Gln Val Arg Arg
            130                 135                 140

Phe Thr Gly Ser His Thr Pro Met Ile Tyr Ser Leu Lys Pro Val Phe
145                 150                 155                 160

Glu Glu Ile Leu Glu Thr Ala Asp Lys Asp Gln Asp Lys Arg Thr Val
                165                 170                 175

Arg Leu Cys Gln Phe Met Leu Asn Ala Ile Asp Thr Arg Pro Glu Asp
                180                 185                 190

Asn Tyr Val Ala Tyr Arg Lys Gly Leu Gly Val Val Cys Asn Lys Glu
                195                 200                 205

Gly Gly Phe Ser Glu Glu Asp Phe Val Val Glu Phe Leu Gly Glu Val
            210                 215                 220

Tyr Pro Ala Trp Lys Trp Phe Glu Lys Gln Asp Gly Ile Arg Ser Leu
225                 230                 235                 240

Gln Arg Asn Asn Asn Asp Pro Ala Pro Glu Phe Tyr Asn Ile Tyr Leu
                245                 250                 255

Glu Arg Pro Lys Gly Asp Ala Asp Gly Tyr Asp Leu Val Val Val Asp
                260                 265                 270

Ala Met His Lys Ala Asn Tyr Ala Ser Arg Ile Cys His Ser Cys Arg
            275                 280                 285

Pro Asn Cys Glu Ala Lys Val Thr Ala Val Asp Gly Gln Tyr Gln Ile
            290                 295                 300

Gly Ile Tyr Ser Thr Arg Pro Ile Ala Tyr Gly Glu Glu Val Thr Phe
305                 310                 315                 320

Asp Tyr Asn Ser Val Thr Glu Ser Lys Glu Glu Tyr Glu Ala Ser Val
                325                 330                 335

Cys Leu Cys Gly Ser Gln Val Cys Arg Gly Ser Tyr Leu Asn Leu Thr
            340                 345                 350

Gly Glu Gly Ala Phe Leu Lys Val Leu Gln Glu Tyr His Gly Leu Leu
            355                 360                 365

Asn Arg His Gln Leu Met Leu Glu Ala Cys Glu Leu Asn Ser Val Ser
            370                 375                 380

Glu Glu Asp Tyr Ile Asp Leu Gly Lys Ala Gly Leu Gly Ser Cys Leu
385                 390                 395                 400

Leu Ala Gly Leu Pro His Trp Leu Ile Ala Tyr Ser Ala Arg Leu Val
                405                 410                 415

Arg Phe Ile Asn Phe Glu Arg Thr Lys Leu Pro Asp Glu Ile Leu Lys
                420                 425                 430

His Asn Leu Glu Glu Lys Lys Tyr Phe Ser Asp Val Cys Leu Glu
            435                 440                 445
```

Val Glu Lys Asn Glu Ser Glu Ile Gln Ala Glu Gly Val Tyr Asn Gln
    450                 455                 460

Arg Leu Gln Asn Leu Ala Leu Thr Leu Asp Lys Val Arg Tyr Val Met
465                 470                 475                 480

Arg Cys Val Phe Gly Asp Pro Glu Lys Ala Pro Pro Leu Glu Arg
                485                 490                 495

Leu Asn Pro Glu Glu Ala Val Ser Phe Ile Trp Arg Gly Glu Gly Ser
        500                 505                 510

Leu Val Glu Glu Leu Leu Gln Cys Met Ala Pro His Leu Glu Asp Ile
            515                 520                 525

Met Leu Asn Asp Leu Lys Ala Lys Ile Arg Ala His Asp Pro Ser Arg
    530                 535                 540

Ser Asp Asp Leu Glu Thr Gly Leu Arg Lys Ser Leu Ile Trp Leu Arg
545                 550                 555                 560

Asp Glu Val Arg Asp Leu Pro Cys Ser Tyr Lys Ser Arg His Asp Ala
                565                 570                 575

Ala Ala Asp Leu Ile His Leu Tyr Ala Tyr Thr Lys Cys Phe Phe Arg
            580                 585                 590

Ile Arg Glu Tyr Lys Thr Val Thr Ser Pro Pro Val Tyr Ile Ser Pro
    595                 600                 605

Leu Asp Leu Gly Pro Lys Tyr Thr Asp Lys Leu Gly Pro Gly Thr His
        610                 615                 620

Glu Tyr Arg Lys Thr Tyr Gly Glu Asn Tyr Cys Leu Gly Gln Leu Phe
625                 630                 635                 640

Tyr Trp Tyr Asn Gln Ala Asn Ala Asp Pro Glu Asn Cys Leu Phe Lys
                645                 650                 655

Ala Ser Arg Gly Cys Leu Ser Leu Pro Glu Ala Gly Ser Phe Tyr Ala
            660                 665                 670

Lys Val Gln Lys Pro Ser Arg Gln Arg Val Tyr Gly Pro Arg Thr Val
    675                 680                 685

Lys Phe Met Leu Ser Arg Met Glu Lys Gln Pro Gln Arg Ala Trp Pro
        690                 695                 700

Lys Asp Arg Ile Trp Ser Phe Lys Asn Ser Pro Asn Val Phe Gly Ser
705                 710                 715                 720

Pro Met Leu Asp Gly Ile Leu Asn Lys Ser Pro Leu Glu Arg Glu Met
                725                 730                 735

Val His Trp Leu Lys His Arg Pro Ala Ile Phe Gln Ala Lys Trp Asp
            740                 745                 750

<210> SEQ ID NO 127
<211> LENGTH: 737
<212> TYPE: PRT
<213> ORGANISM: Sorghum bicolor

<400> SEQUENCE: 127

Glu Ser Val Thr Asp Asp Arg Ile Leu Gly Ala Arg Met Thr Lys Ala
1               5                   10                  15

Ser Leu Val Pro Pro Val Thr Arg Lys Tyr Glu Val Ile Glu Glu Tyr
            20                  25                  30

Leu Ile Val Ala Asp Val Glu Val Gln Arg Lys Met Arg Val Ala
        35                  40                  45

Leu Pro Asp Asp Tyr Ser Glu Lys Leu Leu Ser Gln Lys Asn Gly Thr
    50                  55                  60

Glu Asn Leu Glu Leu Pro Glu Val Lys Asp Tyr Gln Pro Arg Lys Val
65                  70                  75                  80

```
Ala Gly Asp Glu Ile Leu Glu Gln Glu Val Tyr Gly Ile Asp Pro Tyr
                85                  90                  95

Thr His Asn Leu Leu Ser Asp Ile Met Pro Ala Asp Leu Glu Leu Ser
                100                 105                 110

Pro Thr Asp Lys His Ile Phe Ile Glu Glu Leu Leu Leu Asn Thr Leu
            115                 120                 125

Asn Lys Gln Val Lys Arg Phe Thr Gly Ser Gly Asn Thr Pro Met Thr
130                 135                 140

Tyr Asn Leu Arg Pro Val Ile Glu Glu Ile Gln Arg Ser Ala Glu Asp
145                 150                 155                 160

Asn Gly Asp Arg Arg Thr Ser Lys Met Cys Leu Gly Met Leu Lys Thr
                165                 170                 175

Met Arg Asn Arg Ser Asp Gln Asn Phe Val Ala Tyr Arg Lys Gly Leu
                180                 185                 190

Gly Val Val Cys Asn Lys Lys Gly Phe Gly Val Asp Asp Phe Val
        195                 200                 205

Val Glu Phe Phe Gly Glu Val Tyr Pro Ser Trp Arg Trp Tyr Glu Lys
            210                 215                 220

Gln Asp Gly Ile Lys His Ile Gln Asn Asn Ser Glu Asp Gln Ala Pro
225                 230                 235                 240

Glu Phe Tyr Asn Ile Met Leu Glu Arg Pro Lys Gly Asp Arg Asp Gly
                245                 250                 255

Tyr Asp Leu Val Phe Val Asp Ala Met His Lys Ala Asn Tyr Ala Ser
                260                 265                 270

Arg Ile Cys His Ser Cys Asn Pro Asn Cys Glu Ala Lys Val Thr Ala
            275                 280                 285

Val Asp Gly Lys Tyr Gln Ile Gly Val Tyr Thr Leu Arg Pro Ile Ala
    290                 295                 300

Glu Gly Glu Glu Ile Thr Phe Asp Tyr Asn Ser Val Thr Glu Ser Lys
305                 310                 315                 320

Glu Glu His Glu Ala Ser Val Cys Leu Cys Gly Ser Gln Val Cys Arg
                325                 330                 335

Gly Ser Tyr Leu Asn Phe Ser Gly Glu Gly Ala Phe Glu Lys Val Leu
                340                 345                 350

Met Glu Phe His Gly Val Leu Asp Arg His Ser Leu Leu Leu Gln Ala
            355                 360                 365

Cys Glu Thr Asp Ser Val Ser Gln Gln Asp Leu Ile Asp Leu Gly Arg
    370                 375                 380

Ala Gly Leu Gly Thr Cys Leu Leu Ala Gly Leu Pro Gly Trp Leu Val
385                 390                 395                 400

Ala Tyr Thr Ala Asn Leu Val Arg Phe Ile Tyr Leu Glu Arg Gln Lys
                405                 410                 415

Leu Pro Asp Glu Ile Leu Arg His Asn Val Asp Glu Lys Arg Gln Phe
                420                 425                 430

Leu Ile Glu Ile Asn Met Asp Ser Glu Lys Asn Asp Ala Glu Val Gln
            435                 440                 445

Ala Glu Gly Val Leu Asn Ser Arg Leu Gln Gln Ile Val His Thr Leu
    450                 455                 460

Asp Lys Val Arg Tyr Val Met Arg Cys Val Phe Gly Asp Pro Lys Asn
465                 470                 475                 480

Ala Pro Pro Pro Leu Val Arg Leu Ser Gly Lys Ser Leu Val Ser Ala
                485                 490                 495
```

```
Ile Trp Lys Gly Asp Ser Ser Ile Val Ala Glu Leu Leu Gln Ser Met
            500                 505                 510
Glu Pro His Val Glu Glu Val Leu Ser Asp Leu Lys Val Lys Ile
        515                 520                 525
Arg Ala His Asp Pro Pro Asp Ser Glu Asp Ile Glu Gly Gly Ile Arg
        530                 535                 540
Asn Ser Leu Leu Trp Leu Arg Asp Glu Leu Arg Thr Leu Pro Cys Thr
545                 550                 555                 560
Tyr Lys Cys Arg His Asp Ala Ala Asp Leu Ile His Leu Tyr Ala
                565                 570                 575
Tyr Thr Lys Cys Phe Phe Arg Val Arg Asp Tyr Lys Thr Val Lys Ser
                580                 585                 590
Pro Pro Val His Ile Ser Pro Leu Asp Leu Gly Pro Lys Tyr Ala Asp
                595                 600                 605
Lys Leu Gly Pro Gly Phe Gln Glu Tyr Cys Lys Thr Tyr Pro Glu Asn
        610                 615                 620
Tyr Cys Leu Ala Gln Leu Ile Tyr Trp Tyr Ser Gln Asn Ser Glu Pro
625                 630                 635                 640
Glu Ser Arg Leu Thr Arg Ala Arg Lys Gly Cys Met Ser Leu Pro Asp
                645                 650                 655
Val Ser Ser Phe Tyr Val Lys Ser Ala Lys Pro Ser Gln Glu Arg Val
                660                 665                 670
Tyr Gly Asn Arg Thr Val Arg Phe Met Leu Ser Arg Met Glu Lys Gln
                675                 680                 685
Ala Gln Arg Pro Trp Pro Lys Asp Arg Ile Trp Val Phe Lys Ser Asp
        690                 695                 700
Pro Arg Phe Phe Gly Ser Pro Met Met Asp Ala Val Leu Asn Asn Ser
705                 710                 715                 720
Pro Leu Asp Lys Glu Met Val His Trp Leu Lys Thr Arg Pro Asn Val
                725                 730                 735
Phe

<210> SEQ ID NO 128
<211> LENGTH: 764
<212> TYPE: PRT
<213> ORGANISM: Brassica napus

<400> SEQUENCE: 128

Gly Arg Ser Gln Asp Ser Arg Val Glu Lys Tyr Phe Thr Ala Asp Glu
1               5                   10                  15
Ser Phe Asp Ser Val Thr Glu Glu Arg Glu Trp Gly Ala Arg Met Thr
            20                  25                  30
Lys Ala Ser Leu Val Pro Pro Val Thr Arg Lys Tyr Glu Leu Ile Glu
        35                  40                  45
Glu Tyr Thr Ile Val Ala Asp Glu Glu Val Gln Arg Lys Met Arg
    50                  55                  60
Val Ser Leu Pro Glu Asp Tyr Asp Lys Leu Asn Ala Gln Arg Asn
65                  70                  75                  80
Gly Ile Glu Glu Leu Asp Met Glu Leu Pro Glu Val Lys Glu Tyr Lys
                85                  90                  95
Pro Arg Lys Leu Leu Gly Asn Glu Val Leu Glu Gln Glu Val Tyr Gly
            100                 105                 110
Ile Asp Pro Tyr Thr His Asn Leu Leu Leu Asp Ser Met Pro Gly Glu
        115                 120                 125
```

-continued

Leu Asp Trp Ser Leu Gln Asp Lys His Ser Phe Ile Glu Asp Val Val
130                 135                 140

Leu Arg Ala Leu Asn Arg Lys Val Arg Phe Leu Thr Gly Ser Gly Asn
145                 150                 155                 160

Thr Pro Met Val Phe Pro Leu Arg Pro Val Ile Glu Glu Leu Lys Glu
            165                 170                 175

Asn Ala Arg Glu Glu Cys Asp Ile Gln Thr Met Lys Met Cys Gln Gly
            180                 185                 190

Val Leu Lys Ala Ile Glu Ser Arg Ser Gly Asp Asn Tyr Val Ser Tyr
        195                 200                 205

Arg Lys Gly Leu Gly Val Val Cys Asn Lys Gln Gly Phe Val Glu
210                 215                 220

Asp Asp Phe Val Val Glu Phe Leu Gly Glu Val Tyr Pro Val Trp Lys
225                 230                 235                 240

Trp Phe Glu Lys Gln Asp Gly Ile Arg Ser Leu Gln Glu Asn Lys Thr
            245                 250                 255

Asp Pro Ala Pro Glu Phe Tyr Asn Ile Tyr Leu Glu Arg Pro Lys Gly
            260                 265                 270

Asp Ala Asp Gly Tyr Asp Leu Val Val Val Asp Ala Met His Lys Ala
        275                 280                 285

Asn Tyr Ala Ser Arg Ile Cys His Ser Cys Arg Pro Asn Cys Glu Ala
290                 295                 300

Lys Val Thr Ala Val Asp Gly His Tyr Gln Ile Gly Ile Tyr Ser Val
305                 310                 315                 320

Arg Pro Ile Glu Tyr Gly Glu Glu Ile Thr Phe Asp Tyr Asn Ser Val
            325                 330                 335

Thr Glu Ser Lys Glu Glu Tyr Glu Ala Ser Val Cys Leu Cys Gly Ser
            340                 345                 350

Gln Val Cys Arg Gly Ser Tyr Leu Asn Leu Thr Gly Glu Gly Ala Phe
        355                 360                 365

Gln Lys Val Leu Lys Glu Trp His Gly Leu Leu Asp Arg His Arg Leu
370                 375                 380

Met Leu Glu Ala Cys Ile Leu Asn Ser Val Ser Glu Glu Asp Tyr Leu
385                 390                 395                 400

Glu Leu Gly Arg Ala Gly Leu Gly Ser Cys Met Leu Gly Gly Leu Pro
            405                 410                 415

Asp Trp Val Ile Ala Tyr Ser Ala His Leu Val Arg Phe Ile Asn Phe
            420                 425                 430

Glu Arg Thr Lys Leu Pro Glu Glu Ile Leu Lys His Asn Met Glu Glu
        435                 440                 445

Lys Arg Lys Tyr Phe Ser Asp Ile His Leu Asp Val Glu Lys Ser Asp
450                 455                 460

Ala Glu Val Gln Ala Glu Gly Val Tyr Asn Gln Arg Leu Gln Asn Leu
465                 470                 475                 480

Ala Val Thr Leu Asp Lys Val Arg Tyr Val Met Arg Arg Val Phe Gly
            485                 490                 495

Asp Pro Lys Asn Ala Pro Pro Leu Glu Lys Leu Thr Pro Glu Glu
            500                 505                 510

Thr Val Ser Phe Leu Trp Asn Gly Asp Gly Ser Leu Val Glu Glu Ile
        515                 520                 525

Leu Gln Cys Leu Ser Pro His Val Glu Glu Gly Ile Val Asp Glu Leu
530                 535                 540

Arg Ser Lys Ile Arg Ala His Asp Pro Ser Gly Ser Ala Asp Val Leu

```
            545                 550                 555                 560
Lys Asp Leu Gln Arg Ser Leu Leu Trp Leu Arg Asp Glu Val Arg Asp
                565                 570                 575

Leu Pro Cys Thr Tyr Lys Cys Arg Asn Asp Ala Ala Ala Asp Leu Ile
                580                 585                 590

His Ile Tyr Ala Tyr Thr Lys Cys Phe Phe Lys Val Arg Glu Tyr Lys
                595                 600                 605

Ser Phe Met Ser Ser Pro Val Gln Ile Ser Pro Leu Asp Leu Gly Ala
                610                 615                 620

Lys Tyr Ala Asp Lys Leu Gly Glu Gly Ile Lys Glu Tyr Arg Lys Thr
625                 630                 635                 640

Tyr Gly Glu Asn Tyr Cys Leu Gly Gln Leu Ile Tyr Trp Tyr Glu Gln
                645                 650                 655

Thr Asn Thr Asp Pro Asp Leu Thr Leu Val Lys Ala Thr Arg Gly Cys
                660                 665                 670

Leu Ser Leu Pro Glu Val Ala Ser Phe Tyr Ala Lys Ala His Lys Pro
                675                 680                 685

Ser Lys His Arg Val Tyr Gly Pro Lys Thr Val Lys Thr Met Val Ser
                690                 695                 700

Gln Met Ser Lys Gln Pro Gln Lys Pro Trp Ala Lys Asp Lys Ile Trp
705                 710                 715                 720

Met Phe Lys Ser Thr Leu Gly Val Leu Gly Ser Pro Met Phe Asp Ala
                725                 730                 735

Val Val Asn Asn Ser Ser Leu Asp Arg Glu Leu Leu Gln Trp Leu Lys
                740                 745                 750

Asn Arg Arg His Val Phe Gln Ala Thr Trp Asp Ser
                755                 760

<210> SEQ ID NO 129
<211> LENGTH: 755
<212> TYPE: PRT
<213> ORGANISM: Beta vulgaris subsp. vulgaris

<400> SEQUENCE: 129

Glu Glu Tyr Phe Ala Ala Glu Glu Val Phe Asp Leu Thr Pro Glu Asp
1               5                   10                  15

Arg Glu Trp Gly Ala Arg Met Thr Lys Ala Ser Leu Val Pro Pro Val
                20                  25                  30

Thr Arg Lys Tyr Glu Val Ile Asp Arg Tyr Val Ile Val Ala Asp Glu
            35                  40                  45

Asp Glu Val Gln Arg Lys Met Gln Val Ser Leu Pro Asp Asp Tyr Glu
50                  55                  60

Asp Lys Val Lys Ala Gln Lys Asn Gly Ser Asp Glu Val Asp Met Glu
65                  70                  75                  80

Ile Pro Glu Val Lys Glu Tyr Lys Pro Arg Lys Gln Leu Gly Gln Glu
                85                  90                  95

Val Ile Glu Gln Glu Val Tyr Gly Val Asp Pro Tyr Thr His Asn Leu
            100                 105                 110

Leu Leu Asp Ser Met Pro Glu Asp Val Asp Trp Thr Ile Thr Glu Lys
            115                 120                 125

His Val Phe Val Glu Glu Met Ile Leu Arg Val Leu Asn Lys Gln Val
            130                 135                 140

Arg Gln Tyr Thr Gly Ser Gly Ser Thr Pro Met Thr Tyr Pro Leu Lys
145                 150                 155                 160
```

-continued

```
Pro Val Ile Glu Glu Ile Leu Gly Ile Ala Lys Gln Asp Asn Asn Thr
            165                 170                 175
Arg Asn Leu Lys Leu Cys Glu Ala Ile Leu Gln Ala Ile Asp Ser Arg
        180                 185                 190
Pro Glu Asp Asn Tyr Val Ala Tyr Arg Lys Gly Leu Gly Val Val Cys
        195                 200                 205
Asn Lys Glu Asp Gly Phe Thr Glu Asp Phe Val Glu Phe Leu
        210                 215                 220
Gly Glu Val Tyr Pro Ala Trp Lys Trp Phe Lys Gln Asp Gly Ile
225                 230                 235                 240
Arg Ser Leu Gln Lys Asn Ser Lys Glu Pro Ala Pro Glu Phe Tyr Asn
            245                 250                 255
Ile Tyr Leu Glu Arg Pro Lys Gly Asp Ala Asp Gly Tyr Asp Leu Val
            260                 265                 270
Val Val Asp Ala Met His Lys Ala Asn Tyr Ala Ser Arg Ile Cys His
        275                 280                 285
Ser Cys Arg Pro Asn Cys Glu Ala Lys Val Thr Ala Val Ser Gly Gln
        290                 295                 300
Tyr Gln Ile Gly Ile Tyr Ser Val Arg Pro Ile Gly Phe Gly Glu Glu
305                 310                 315                 320
Val Thr Phe Asp Tyr Asn Ser Val Thr Glu Ser Lys Glu Tyr Glu
                325                 330                 335
Ala Ser Val Cys Leu Cys Gly Ser Gln Val Cys Arg Gly Ser Tyr Leu
            340                 345                 350
Asn Leu Thr Gly Glu Gly Ala Phe Gln Lys Val Leu Lys Glu Trp His
        355                 360                 365
Gly Leu Leu Asp Lys His His Leu Leu Leu Glu Ala Cys Glu Leu Asn
370                 375                 380
Trp Val Ser Glu Glu Asp Tyr Ile Asp Leu Gly Arg Ala Gly Leu Gly
385                 390                 395                 400
Ser Cys Leu Leu Gly Asp Leu Pro Asp Trp Leu Ile Ala Tyr Ser Ala
                405                 410                 415
Arg Leu Val Arg Phe Ile Asn Phe Glu Arg Thr Lys Leu Pro Glu Glu
            420                 425                 430
Ile Leu Arg His Asn Leu Glu Glu Lys Lys Tyr Cys Ala Glu Ile
            435                 440                 445
Ser Leu Glu Met Glu Lys Ser Asp Ala Glu Val Gln Ala Glu Gly Val
450                 455                 460
Tyr Asn Gln Arg Leu Gln Asn Leu Ala Leu Thr Leu Asp Lys Val Arg
465                 470                 475                 480
Tyr Val Leu Arg Cys Val Phe Gly Lys Pro Lys Lys Ala Pro Pro Pro
                485                 490                 495
Leu Gln Lys Leu Ser Pro Glu Glu Met Val Ser Val Leu Trp Asn Gly
            500                 505                 510
Glu Gly Ser Leu Val Glu Gln Leu Leu Glu Cys Ile Thr Pro His Ile
            515                 520                 525
Ile Asp Asp Arg Ile Leu Gln Asp Leu Arg Ser Lys Ile Arg Thr Arg
        530                 535                 540
Asp Pro Leu Asn Ser Ala Asn Ile Glu Lys Asp Leu Arg Arg Ser Leu
545                 550                 555                 560
Leu Trp Leu Arg Asp Glu Val Arg Asn Leu Pro Cys Thr Tyr Lys Ser
                565                 570                 575
Arg His Asp Ala Ala Ala Asp Val Ile His Ile Tyr Ala Tyr Thr Lys
```

```
                580             585              590
Ser Leu Phe Lys Lys Arg Glu Tyr Asn Thr Val Thr Ser Pro Pro Val
            595                 600             605

Tyr Ile Ser Pro Leu Asp Leu Gly Pro Lys Cys Ala Asp Lys Leu Ser
            610                 615             620

Gly Met Thr Glu Tyr Cys Lys Thr Tyr Gly Glu Asn Tyr Cys Leu Gly
625                 630                 635                 640

Gln Leu Ile Tyr Trp His Asn Gln Ala Asn Ala Asp Pro Asp Arg Val
                645                 650                 655

Leu Glu Arg Ala Ser Arg Gly Cys Leu Ser Leu Pro Asp Ile Gly Ser
            660                 665                 670

Phe Tyr Ala Lys Ala Gln Lys Pro Ser Arg Gln Arg Val Tyr Gly Pro
            675                 680                 685

Arg Thr Val Arg Phe Met Leu Ala Arg Met Glu Lys Gln Pro Gln Arg
            690                 695                 700

Pro Trp Pro Lys Asp Arg Ile Trp Ser Phe Gln Cys Ser Ser Lys Phe
705                 710                 715                 720

Phe Gly Ser Pro Met Leu Asp Ala Val Leu Asn Asn Ser Pro Leu Glu
                725                 730                 735

Arg Glu Met Val Ile Trp Leu Lys Asn Arg Pro Ala Ile Phe Gln Ala
            740                 745                 750

Met Trp Asp
        755

<210> SEQ ID NO 130
<211> LENGTH: 767
<212> TYPE: PRT
<213> ORGANISM: Arachis hypogaea

<400> SEQUENCE: 130

Gly His Ser Glu Asn Leu Ile Gly Glu Ser Arg Gly Asp Gly His Phe
1               5                   10                  15

Thr Pro Glu Gly Asp Leu Asn Phe Ile Thr Asp Asp Arg Glu Trp Gly
                20                  25                  30

Ala Arg Met Thr Lys Ala Ser Leu Val Pro Pro Val Thr Arg Lys Tyr
            35                  40                  45

Glu Val Ile Asp Gln Tyr Val Ile Val Ala Asp Glu Glu Asp Val Gln
        50                  55                  60

Arg Lys Met Arg Val Ser Leu Pro Asp Asp Tyr Ala Glu Lys Leu Ser
65                  70                  75                  80

Ala Gln Lys Asn Gly Thr Glu Glu Ser Asp Met Glu Leu Pro Glu Val
                85                  90                  95

Lys Asp Tyr Lys Pro Arg Lys Gly Leu Gly Asn Glu Val Ile Glu Gln
            100                 105                 110

Glu Val Tyr Gly Ile Asp Pro Tyr Thr His Asn Leu Leu Leu Asp Ser
        115                 120                 125

Met Pro Glu Glu Leu Asp Trp Ser Leu Gln Asp Lys His Leu Phe Ile
130                 135                 140

Glu Asp Val Leu Leu Arg Thr Leu Asn Lys Gln Val Arg Asn Phe Thr
145                 150                 155                 160

Gly Ser Gly Ser Thr Pro Met Ser Tyr Ala Leu Gln Pro Val Ile Glu
                165                 170                 175

Glu Ile Lys Arg Cys Ala Glu Glu Gly Cys Asp Ala Arg Thr Val Lys
            180                 185                 190
```

```
Met Cys Gln Gly Ile Leu Lys Ala Ile Asp Ser Arg Pro Asp Asp Lys
            195                 200                 205

Tyr Val Ala Tyr Arg Lys Gly Leu Gly Val Val Cys Asn Lys Glu Glu
        210                 215                 220

Gly Phe Ser Glu Asp Asp Phe Val Val Glu Phe Leu Gly Glu Val Tyr
225                 230                 235                 240

Pro Val Trp Lys Trp Phe Glu Lys Gln Asp Gly Ile Arg Ser Leu Gln
                245                 250                 255

Lys Asn Ser Lys Asp Pro Ala Pro Glu Phe Tyr Asn Ile Tyr Leu Glu
            260                 265                 270

Arg Pro Lys Gly Asp Ala Asp Gly Tyr Asp Leu Val Val Val Asp Ala
        275                 280                 285

Met His Lys Ala Asn Tyr Ala Ser Arg Ile Cys His Ser Cys Arg Pro
    290                 295                 300

Asn Cys Glu Ala Lys Val Thr Ala Val Asp Gly His Tyr Gln Ile Gly
305                 310                 315                 320

Ile Tyr Ser Val Arg Lys Ile Gln Pro Gly Glu Glu Ile Thr Phe Asp
                325                 330                 335

Tyr Asn Ser Val Thr Glu Ser Lys Glu Glu Tyr Glu Ala Ser Val Cys
            340                 345                 350

Leu Cys Gly Ser Gln Val Cys Arg Gly Ser Tyr Leu Asn Leu Thr Gly
        355                 360                 365

Glu Gly Ala Phe Gln Lys Val Leu Lys Asp Ser His Gly Ile Leu Asp
    370                 375                 380

Arg His Tyr Leu Met Leu Glu Ala Cys Glu Leu Asn Ser Val Ser Glu
385                 390                 395                 400

Glu Asp Tyr Asn Asp Leu Gly Arg Ala Gly Leu Gly Ser Cys Leu Leu
                405                 410                 415

Glu Gly Leu Pro Asp Trp Leu Val Ala Tyr Ala Ala Arg Leu Val Arg
            420                 425                 430

Phe Ile Asn Phe Glu Arg Thr Lys Leu Pro Glu Ile Leu Lys His
        435                 440                 445

Asn Leu Glu Glu Lys Arg Lys Tyr Phe Ser Asp Ile Cys Leu Glu Val
450                 455                 460

Glu Arg Ser Asp Ala Glu Val Gln Ala Glu Gly Val Tyr Asn Gln Arg
465                 470                 475                 480

Leu Gln Asn Leu Ala Val Thr Leu Asp Lys Val Arg Tyr Val Met Arg
                485                 490                 495

Cys Ile Phe Gly Asp Pro Arg Lys Ala Pro Pro Leu Glu Lys Ile
            500                 505                 510

Ser Pro Glu Ala Ala Val Ser Phe Leu Trp Lys Gly Glu Gly Ser Phe
        515                 520                 525

Val Glu Glu Leu Leu Gln Cys Ile Ala Pro His Val Glu Glu Asp Ala
530                 535                 540

Leu Asn Glu Leu Arg Ser Lys Ile Asp Ala His Asp Pro Ser Ser Ser
545                 550                 555                 560

Gly Asp Ile Gln Lys Glu Val Gln Lys Ser Leu Leu Trp Leu Arg Asp
                565                 570                 575

Glu Val Arg Asp Leu Leu Cys Thr Tyr Lys Cys Arg His Asp Ala Ala
            580                 585                 590

Ala Asp Leu Ile His Ile Tyr Ala Tyr Thr Lys Tyr Phe Phe Arg Ile
        595                 600                 605

Arg Ala Tyr Glu Thr Ile Thr Ser Pro Pro Val Tyr Ile Ser Pro Leu
```

```
                  610                 615                 620
Asp Leu Gly Pro Lys Tyr Ala Asn Lys Leu Gly Ala Gly Phe Gln Glu
625                 630                 635                 640

Tyr Arg Lys Ile Tyr Gly Glu Asn Tyr Cys Leu Gly Gln Leu Ile Phe
                    645                 650                 655

Trp His Asn Gln Ser Asn Val Asp Pro Asp His Ser Leu Gly Arg Ala
                660                 665                 670

Ser Arg Gly Cys Leu Ser Leu Pro Asp Ile Ser Ser Phe Tyr Ala Lys
                675                 680                 685

Ala Leu Lys Pro Ser Lys His Arg Val Tyr Gly Pro Arg Thr Val Arg
            690                 695                 700

Ser Met Leu Ala Arg Met Glu Lys Gln Pro Gln Arg Pro Trp Pro Lys
705                 710                 715                 720

Asp Gln Ile Trp Thr Phe Lys Ser Phe Pro Lys Phe Phe Gly Ser Pro
                    725                 730                 735

Met Leu Asp Ala Val Ile Asn Asn Thr Pro Leu Asp Arg Glu Met Val
                740                 745                 750

His Trp Leu Lys His Arg Pro Ala Ile Tyr Gln Ala Met Trp Asp
                755                 760                 765

<210> SEQ ID NO 131
<211> LENGTH: 764
<212> TYPE: PRT
<213> ORGANISM: Raphanus sativus

<400> SEQUENCE: 131

Gly Arg Ser Gln Asp Thr Arg Val Glu Lys Tyr Phe Thr Ala Asp Glu
1               5                   10                  15

Ser Phe Asp Ser Val Thr Glu Glu Arg Glu Trp Gly Ala Arg Met Thr
                20                  25                  30

Lys Ala Ser Leu Val Pro Pro Val Thr Arg Lys Tyr Glu Leu Ile Glu
            35                  40                  45

Glu Tyr Thr Ile Val Ala Asp Glu Glu Val Arg Arg Lys Met Arg
    50                  55                  60

Val Ser Leu Pro Glu Asp Tyr Gly Glu Lys Leu Asn Ala Gln Arg Asn
65                  70                  75                  80

Gly Ile Glu Glu Leu Asp Met Glu Leu Pro Glu Val Lys Glu Tyr Lys
                85                  90                  95

Pro Arg Lys Leu Leu Gly Asn Glu Val Leu Glu Gln Glu Val Tyr Gly
                100                 105                 110

Ile Asp Pro Tyr Thr His Asn Leu Leu Asp Ser Met Pro Gly Glu
            115                 120                 125

Leu Asp Trp Ser Leu Gln Asp Lys His Ser Phe Ile Glu Asp Val Val
130                 135                 140

Leu Arg Ala Leu Asn Arg Lys Val Arg Phe Leu Thr Gly Ser Gly Asn
145                 150                 155                 160

Thr Pro Met Val Tyr Pro Leu Arg Pro Val Ile Glu Glu Leu Lys Glu
                165                 170                 175

Asn Ser Arg Glu Glu Cys Asp Ile Gln Thr Met Arg Met Cys Gln Gly
                180                 185                 190

Val Leu Lys Ala Ile Glu Ser Arg Ser Gly Asp Thr Tyr Val Ser Tyr
            195                 200                 205

Arg Lys Gly Leu Gly Val Val Cys Asn Lys Gln Gly Gly Phe Val Glu
    210                 215                 220
```

-continued

```
Asp Asp Phe Val Val Glu Phe Leu Gly Glu Val Tyr Pro Val Trp Lys
225                 230                 235                 240

Trp Phe Glu Lys Gln Asp Gly Ile Arg Ser Leu Gln Glu Asn Lys Thr
            245                 250                 255

Asp Pro Ala Pro Glu Phe Tyr Asn Ile Tyr Leu Glu Arg Pro Lys Gly
        260                 265                 270

Asp Ala Asp Gly Tyr Asp Leu Val Val Asp Ala Met His Lys Ala
    275                 280                 285

Asn Tyr Ala Ser Arg Ile Cys His Ser Cys Arg Pro Asn Cys Glu Ala
290                 295                 300

Lys Val Thr Ala Val Asp Gly His Tyr Gln Ile Gly Ile Tyr Ser Val
305                 310                 315                 320

Arg Pro Ile Glu Tyr Gly Glu Ile Thr Phe Asp Tyr Asn Ser Val
                325                 330                 335

Thr Glu Ser Lys Glu Glu Tyr Glu Ala Ser Val Cys Leu Cys Gly Ser
            340                 345                 350

His Val Cys Arg Gly Ser Tyr Leu Asn Leu Thr Gly Glu Gly Ala Phe
        355                 360                 365

Gln Lys Val Leu Lys Glu Trp His Gly Leu Leu Asp Arg His Arg Leu
370                 375                 380

Met Leu Glu Ala Cys Met Leu Asn Ser Val Ser Glu Asp Tyr Leu
385                 390                 395                 400

Glu Leu Gly Arg Ala Gly Leu Gly Ser Cys Leu Leu Gly Gly Leu Pro
                405                 410                 415

Asp Trp Val Ile Ala Tyr Ser Ala His Leu Val Arg Phe Ile Asn Phe
        420                 425                 430

Glu Arg Thr Lys Leu Pro Val Glu Ile Leu Lys His Asn Met Glu Glu
    435                 440                 445

Lys Ile Lys Tyr Phe Ser Asp Ile His Leu Asp Val Glu Lys Ser Asp
450                 455                 460

Ala Glu Val Gln Ala Glu Gly Val Tyr Asn Gln Arg Leu Gln Asn Leu
465                 470                 475                 480

Ala Val Thr Leu Asp Lys Val Arg Tyr Val Met Arg Arg Val Phe Gly
            485                 490                 495

Asp Pro Lys Asn Ala Pro Pro Leu Glu Lys Leu Thr Pro Glu Glu
        500                 505                 510

Thr Val Ser Phe Leu Trp Asn Gly Asp Gly Ser Leu Val Glu Glu Leu
    515                 520                 525

Leu Gln Cys Leu Ser Pro His Val Glu Val Gly Ile Val Asp Lys Leu
530                 535                 540

Arg Ser Lys Ile Arg Ala His Asp Pro Ser Gly Ser Ala Asp Val Leu
545                 550                 555                 560

Lys Asp Leu Gln Arg Ser Leu Leu Trp Leu Arg Asp Glu Ile Arg Asp
            565                 570                 575

Leu Pro Cys Thr Tyr Lys Cys Arg Asn Asp Ala Ala Ala Asp Leu Ile
        580                 585                 590

His Ile Tyr Ala Tyr Thr Lys Cys Leu Phe Lys Val Arg Glu Tyr Lys
    595                 600                 605

Ser Phe Met Ser Ser Pro Val His Ile Ser Pro Leu Asp Leu Gly Ala
                610                 615                 620

Lys Tyr Ala Asp Lys Leu Gly Glu Gly Ile Lys Glu Tyr Arg Lys Thr
625                 630                 635                 640

Tyr Gly Glu Asn Tyr Cys Leu Gly Gln Leu Ile Tyr Trp Tyr Glu Gln
```

-continued

```
                        645                 650                 655
Thr Asn Thr Asp Pro Asp Leu Thr Leu Val Lys Ala Thr Arg Gly Cys
            660                 665                 670

Leu Ser Leu Pro Glu Val Ala Ser Phe Tyr Ala Lys Ala His Lys Pro
        675                 680                 685

Ser Lys His Arg Val Tyr Gly Pro Lys Thr Val Lys Thr Met Val Ser
    690                 695                 700

Gln Met Ser Lys Gln Pro Gln Lys Pro Trp Ala Lys Asp Lys Ile Trp
705                 710                 715                 720

Met Phe Lys Ser Ser Leu Gly Val Leu Gly Ser Pro Met Phe Asp Thr
                725                 730                 735

Val Leu Asn Asn Ser Ser Leu Asp Arg Glu Leu Val Gln Trp Leu Arg
            740                 745                 750

Asn Arg Arg His Val Phe Gln Ala Thr Trp Asp Ser
        755                 760
```

TARGETED GENE ACTIVATION IN PLANTS

CROSS-REFERENCE TO RELATED APPLICATIONS

This application is a continuation-in-part application of International Patent Application No. PCT/US2018/014499, filed on Jan. 19, 2018, which claims the benefit of U.S. Provisional Application No. 62/448,841, filed on Jan. 20, 2017, the disclosures of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 262232001420SUBSEQLIST.txt, date recorded: Sep. 25, 2019, size: 534 KB).

FIELD

The present disclosure relates to the targeting of transcriptional activators to specific loci in plants to activate transcription of the targeted loci. Specifically, the present disclosure provides methods and compositions for using guided (e.g. RNA-guided) transcriptional activators to activate transcription of specific loci in plants.

BACKGROUND

Transcriptional regulation is a key aspect of the growth and development of many organisms. In plants, transcriptional regulation plays a pivotal role in growth and development, as well as a multitude of biological pathways and processes. Indeed, the manipulation of gene expression in plants, such as the activation of a gene of interest, can have profound phenotypic impacts. In addition to influencing a phenotype, the activation of gene expression or transcriptional activation of a locus of interest can be useful for a wide variety of research purposes.

There is currently no robust method for selectively activating the expression of plant genes or other plant loci of interest. Accordingly, a need exists for methods of inducing transcriptional activation of specific loci in plants.

BRIEF SUMMARY

In one aspect, the present disclosure provides a method for activating expression of a target nucleic acid in a plant, including: (a) providing a plant including: a first recombinant polypeptide including a nuclease-deficient CAS9 polypeptide (dCAS9) or fragment thereof and a multimerized epitope; a second recombinant polypeptide including a transcriptional activator and an affinity polypeptide that specifically binds to the epitope; a crRNA and a tracrRNA, or fusions thereof; and (b) growing the plant under conditions whereby the first and second recombinant polypeptides are targeted to the target nucleic acid, thereby activating expression of the target nucleic acid. In some embodiments; the dCAS9 polypeptide has an amino acid sequence that is at least 80% identical to SEQ ID NO: 12. In some embodiments that may be combined with any of the preceding embodiments, the multimerized epitope includes a GCN4 epitope. In some embodiments, the multimerized epitope includes about 2 to about 10 copies of a GCN4 epitope. In some embodiments that may be combined with any of the preceding embodiments, the first polypeptide includes one or more linkers that link polypeptide units in the recombinant polypeptide. In some embodiments that may be combined with any of the preceding embodiments, the first polypeptide includes a nuclear localization signal (NLS). In some embodiments that may be combined with any of the preceding embodiments, the transcriptional activator is a VP64 polypeptide. In some embodiments, the VP64 polypeptide includes an amino acid sequence that is at least 80% identical to SEQ ID NO: 31. In some embodiments that may be combined with any of the preceding embodiments, the affinity polypeptide is an antibody. In some embodiments, the antibody is an scFv antibody. In some embodiments, the antibody includes an amino acid sequence that is at least 80% identical to SEQ ID NO: 28. In some embodiments that may be combined with any of the preceding embodiments, the second polypeptide includes one or more linkers that link polypeptide units in the recombinant polypeptide. In some embodiments that may be combined with any of the preceding embodiments, the second polypeptide includes an SV40-type NLS. In some embodiments, the SV40-type NLS includes an amino acid sequence that is at least 80% identical to SEQ. ID NO: 32. In some embodiments that may be combined with any of the preceding embodiments, the crRNA and the tracrRNA are fused together, thereby forming a guide RNA (gRNA). In some embodiments that may be combined with any of the preceding embodiments; expression of the activated nucleic acid is increased in the range of about 100-fold to about 10,000-fold as compared to a corresponding control. In some embodiments that may be combined with any of the preceding embodiments, the transcriptional activator is an SDG2 polypeptide.

In another aspect, the present disclosure provides a recombinant vector including: a first nucleic acid sequence including a plant promoter and that encodes a recombinant polypeptide including a nuclease-deficient CAS9 polypeptide (dCAS9) or fragment thereof and a multimerized epitope; a second nucleic acid sequence including a plant promoter and that encodes a recombinant polypeptide including a transcriptional activator and an affinity polypeptide that specifically binds to the epitope; and a third nucleic acid sequence including a promoter and that encodes a crRNA and a tracrRNA, or fusions thereof. In some embodiments, the plant promoter in the first nucleic acid sequence is a UBQ10 promoter. In some embodiments, the UBQ10 promoter includes a nucleic acid sequence that is at least 80% identical to SEQ ID NO: 2. In some embodiments that may be combined with any of the preceding embodiments, the first nucleic acid sequence includes a terminator sequence. In some embodiments, the terminator is an OCS terminator. In some embodiments, the OCS terminator includes a nucleic acid sequence that is at least 80% identical to SEQ ID NO: 9. In some embodiments that may be combined with any of the preceding embodiments, the dCAS9 polypeptide includes an amino acid sequence that is at least 80% identical to SEQ ID NO: 12. In some embodiments that may be combined with any of the preceding embodiments, the multimerized epitope includes a GCN4 epitope. In some embodiments, the multimerized epitope includes about 2 to about 10 copies of a GCN4 epitope. In some embodiments that may be combined with any of the preceding embodiments, the first polypeptide includes one or more linkers that link polypeptide units in the recombinant polypeptide. In some embodiments that may be combined with any of the preceding embodiments, the first polypeptide includes a nuclear localization signal (NLS). In some embodiments that may be combined with any of the preceding embodiments, the plant promoter in the second nucleic acid sequence is a UBQ10 promoter. In some embodiments, the UBQ10 promoter includes a nucleic acid sequence that is at least 80% identical to SEQ ID NO: 2. In some embodiments that may be combined with any of the preceding embodiments, the second nucleic acid sequence includes a terminator sequence. In some embodiments, the terminator is a NOS terminator. In some embodiments, the NOS terminator includes a nucleic acid sequence that is at least 80% identical to SEQ ID NO: 26. In some embodiments that may be combined with any of the preceding embodiments, the transcriptional activator is a VP64 polypeptide. In some embodiments, the VP64 polypeptide includes an amino acid sequence that is at least 80% identical to SEQ ID NO: 31. In some embodiments that may be combined with any of the preceding embodiments, the affinity polypeptide is an antibody. In some embodiments, the antibody is an scFv antibody. In some embodiments, the antibody includes an amino acid sequence that is at least 80% identical to SEQ ID NO: 28. In some embodiments that may be combined with any of the preceding embodiments, the second polypeptide includes one or more linkers that link polypeptide units in the recombinant polypeptide. In some embodiments that may be combined with any of the preceding embodiments, the second polypeptide includes an SV40-type NLS. In some embodiments, the SV40-type NLS includes an amino acid sequence that is at least 80% identical to SEQ ID NO: 32. In some embodiments that may be combined with any of the preceding embodiments, the crRNA and the tracrRNA are fused together, thereby forming a guide RNA (gRNA). In some embodiments that may be combined with any of the preceding embodiments, the first and second nucleic acids are separated by a TBS insulator. In some embodiments, the TBS insulator includes a nucleic acid sequence that is at least 80% identical to SEQ ID NO: 10. In some embodiments that may be combined with any of the preceding embodiments, the transcriptional activator is an SDG2 polypeptide.

In another aspect, the present disclosure provides a plant or plant cell including the vector of any of the preceding embodiments.

In another aspect, the present disclosure provides a method for activating expression of a target nucleic acid in a plant, including: (a) providing a plant including a vector of any one of the preceding embodiments; and (b) growing the plant under conditions whereby the first, second, and third nucleic acids in the vector are expressed and the resulting polypeptides are targeted to the target nucleic acid, thereby activating expression of the target nucleic acid. In some embodiments, expression of the activated nucleic acid is increased in the range of about 100-fold to about 10,000-fold as compared to a corresponding control.

In another aspect, the present disclosure provides a plant or plant cell including: a) a first recombinant polypeptide including a nuclease-deficient CAS9 polypeptide (dCAS9) or fragment thereof and a multimerized epitope, b) a second recombinant polypeptide including a transcriptional activator and an affinity polypeptide that specifically binds to the epitope, and c) a crRNA and a tracrRNA, or fusions thereof. In some embodiments, the plant or plant cell includes a nucleic acid that has increased expression as compared to a corresponding control.

In another aspect, the present disclosure provides a plant or plant cell including: first nucleic acid including a plant promoter and that encodes a recombinant polypeptide including a nuclease-deficient CAS9 polypeptide (dCAS9) or fragment thereof and a multimerized epitope, b) a second nucleic acid including a plant promoter and that encodes a recombinant polypeptide including a transcriptional activator and an affinity polypeptide that specifically binds to the epitope, and c) a third nucleic acid including a promoter and that encodes a crRNA and a tracrRNA, or fusions thereof. In some embodiments, the plant or plant cell includes a nucleic acid that has increased expression as compared to a corresponding control.

In another aspect, the present disclosure provides a method for producing a plant with increased expression of a target nucleic acid, including: (a) providing a plant including a recombinant nucleic acid, where the recombinant nucleic acid encodes a recombinant SDG2 polypeptide capable of being targeted to a target nucleic acid; and (b) growing the plant under conditions whereby the recombinant SDG2 polypeptide encoded by the recombinant nucleic acid is expressed and is targeted to the target nucleic acid, thereby increasing expression of the target nucleic acid to produce the plant with increased expression of the target nucleic acid. In some embodiments, the recombinant SDG2 polypeptide is targeted to the target nucleic acid via a SunTag targeting system. In some embodiments that may be combined with any of the preceding embodiments, the plant includes: a first recombinant nucleic acid encoding a first recombinant polypeptide including a nuclease-deficient CAS9 polypeptide (dCAS9) and a multimerized epitope; a second recombinant nucleic acid encoding a second recombinant polypeptide including an SDG2 polypeptide and an affinity polypeptide that specifically binds to the epitope; and a crRNA and a tracrRNA, or fusions thereof in some embodiments that may be combined with any of the preceding embodiments, the SDG2 polypeptide includes an H3K4 methyltransferase domain. In some embodiments, the SDG2 polypeptide includes an amino acid sequence that is at least 80% identical to SEQ ID NO: 98. In some embodiments that may be combined with any of the preceding embodiments, the dCAS9 polypeptide has an amino acid sequence that is at least 80% identical to SEQ ID NO: 78. In some embodiments that may be combined with any of the preceding embodiments, the multimerized epitope includes a GCN4 epitope. In some embodiments, the multimerized epitope includes about 2 to about 10 copies of a GCN4 epitope. In some embodiments that may be combined with any of the preceding embodiments, the first polypeptide includes one or more linkers that link polypeptide units in the recombinant polypeptide. In some embodiments that may be combined with any of the preceding embodiments; the first polypeptide includes a nuclear localization signal (NLS). In some embodiments that may be combined with any of the preceding embodiments, the affinity, polypeptide is an antibody. In some embodiments, the antibody is an scFv antibody. In some embodiments, the antibody includes an amino acid sequence that is at least 80% identical to SEQ ID NO: 94. In some embodiments that may be combined with any of the preceding embodiments; the second polypeptide includes one or more linkers that link polypeptide units in the recombinant polypeptide. In some embodiments that may be combined with any of the preceding embodiments, the second polypeptide includes a nuclear localization signal (NLS). In some embodiments that may be combined with any of the preceding embodiments, the crRNA and the tracrRNA are fused together, thereby forming a guide RNA (gRNA). In some embodiments that may be combined with any of the preceding embodiments, expression of the target nucleic acid is increased by at least 10% as compared to a corresponding control. In some embodiments that may be combined with any of the preceding embodiments, the target nucleic acid with increased expression exhibits a decrease in DNA methylation. In some embodiments that may be combined with any of the preceding embodiments, the method further includes crossing the plant with increased expression of the target nucleic acid to a second plant to produce one or more F1 plants.

In another aspect, the present disclosure provides a method for producing a plant with increased expression of a target nucleic acid, including: (a) providing a plant including: a first recombinant nucleic acid encoding a first recombinant polypeptide including a nuclease-deficient CAS9 polypeptide (dCAS9) and a multimerized epitope; a second recombinant nucleic acid encoding a second recombinant polypeptide including an SDG2 polypeptide and an affinity polypeptide that specifically binds to the epitope; a crRNA and a tracrRNA, or fusions thereof; and (h) growing the plant under conditions whereby the first and second recombinant polypeptides encoded by the first and second recombinant nucleic acids are expressed and are targeted to the target nucleic acid, thereby increasing expression of the target nucleic acid to produce the plant with increased expression of the target nucleic acid.

In another aspect, the present disclosure provides a recombinant vector including: (a) a first nucleic acid sequence that encodes a recombinant polypeptide including a nuclease-deficient CAS9 polypeptide (dCAS9) and a multimerized epitope; (b) a second nucleic acid sequence that encodes a recombinant polypeptide including an SDG2 polypeptide and an affinity polypeptide that specifically binds to the epitope; and (c) a third nucleic acid sequence that encodes a crRNA and a tracrRNA, or fusions thereof.

In another aspect, the present disclosure provides a plant cell including a recombinant vector including: (a) a first nucleic acid sequence that encodes a recombinant polypeptide including a nuclease-deficient CAS9 polypeptide (dCAS9) and a multimerized epitope; (b) a second nucleic acid sequence that encodes a recombinant polypeptide including an SDG2 polypeptide and an affinity polypeptide that specifically binds to the epitope; and (c) a third nucleic acid sequence that encodes a crRNA and a tracrRNA, or fusions thereof.

DESCRIPTION OF THE FIGURES

The patent or application file contains at least one drawing executed in color. Copies of this patent or patent application publication with color drawings will be provided by the office upon request and payment of the necessary fee.

FIG. 6A illustrates FWA expression in the following Arabidopsis backgrounds: wild-type Col-0, fwa mutants, and two independent T1 lines housing the SunTag VP64 construct that contains gRNA4. FIG. 6B illustrates FWA expression in the following Arabidopsis backgrounds: wild-type Col-0, a T1 line housing the SunTag VP64 construct that does not contain any gRNA, and two independent T2 lines housing the SunTag VP64 construct that contains gRNA4.

DETAILED DESCRIPTION

Figure 1:
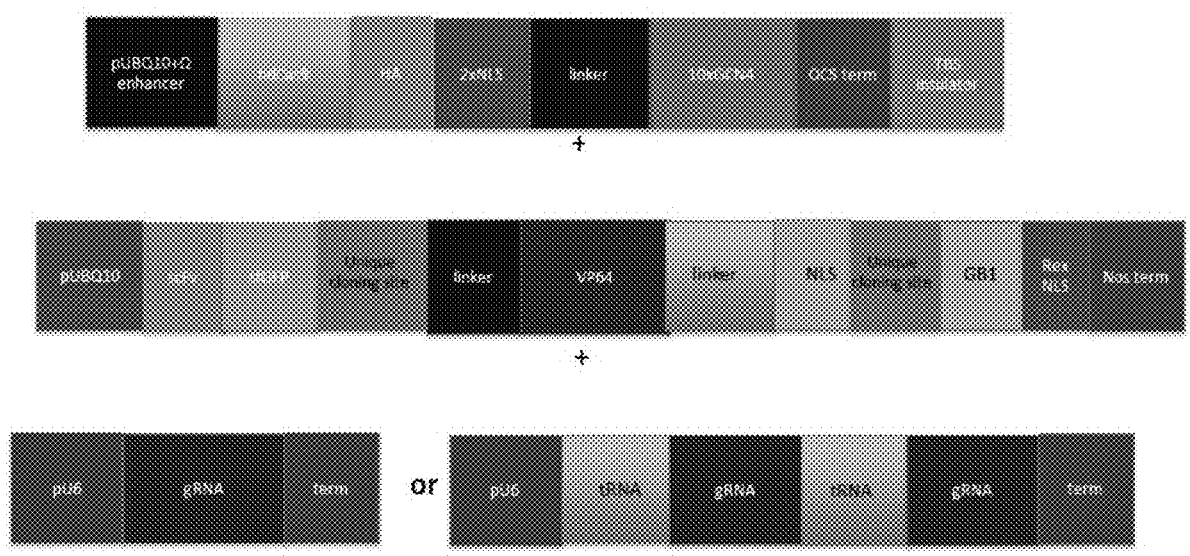
FIG. 1 illustrates a schematic of the expression cassettes present in the vector housing the SunTag VP64 expression system.

The following description is presented to enable a person of ordinary skill in the art to make and use the various embodiments. Descriptions of specific devices, techniques, methods, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure relates to the targeting of transcriptional activators to specific loci in plants to activate transcription of the targeted loci. Specifically, the present disclosure provides methods and compositions for using RNA-guided transcriptional activators to activate transcription of specific loci in plants.

The present disclosure also relates generally to the targeting of SDG2 polypeptides to specific loci in plants to activate transcription of the targeted loci. Methods and compositions are provided for facilitating SDG2 polypeptide-mediated transcriptional activation of targeted loci and reduction of DNA methylation at the targeted loci. Accordingly, the present disclosure provides compositions and methods for facilitating SDG2 polypeptide-mediated transcriptional activation of targeted loci and reduction of DNA methylation at the targeted loci.

The present disclosure relates to the amplification of transcriptional activation at a target nucleic acid. Recruitment of multiple copies of a protein to a target substrate (e.g. DNA, RNA, or protein) may amplify signals in biological systems. When the protein is a transcriptional activator, providing multiple copies of that transcriptional activator may result in amplification of the expression of that nucleic acid.

A synthetic system was previously developed for use in mammals for recruiting multiple copies of a protein to a target polypeptide chain, and this system was called a SunTag system (Tanenbaum et al., 2014) (WO2016011070).

This system was also adapted so that the multiple copies of the protein using the SunTag system could be targeted to a nucleic acid using the CRISPR-Cas9 system (Tanenbaum et al., 2014). However, this system was developed for use in mammals.

The present disclosure is based, at least in part, on Applicant's development of a SunTag gene activation system that is functional in plants. The present disclosure provides the successful construction of a SunTag system that is operable in plants and uses CRISPR-based targeting to target a transcriptional activator to specific nucleic acids. This SunTag system was able to substantially increase expression of targeted genes as compared to corresponding controls. In some instances, many thousands-fold increases in gene expression were observed. This work presents the opportunity for robust and selective activation of plant genes or other nucleic acids in plants, which may serve both research purposes as well as be used in applications for crop improvement.

The present disclosure is also based, at least in part, on Applicant's development of a system for activating transcription in plants by targeting SDG2 polypeptides to specific loci. Specifically, Applicant targeted the silenced and DNA methylated FWA gene in *Arabidopsis* with a CRISPR-Cas9 SunTag construct to recruit the catalytic domain of the H3K4 methyltransferase SDG2 (SDG2C) to chromatin. The SDG2C polypeptide included the C-terminal region of SDG2 including the SET domain and its flanking regions. This was sufficient to drive strong expression and DNA demethylation of the target locus, demonstrating that SDG2 can act as a targeted transcriptional activator. This represents the development of a method, using a plant-specific protein, to target gene activation and DNA demethylation at specific areas of chromatin.

Accordingly, the present disclosure provides methods and compositions for the recruitment of multiple copies of a transcriptional activator (e.g. VP64, SDG2) to a target nucleic acid in plants via CRISPR-based targeting in a manner that allows for transcriptional activation of the target nucleic acid. In certain aspects, this specific targeting involves the use of a system that includes (1) a nuclease-deficient CAS9 polypeptide that is recombinantly fused to a multimerized epitope, (2) a transcriptional activator polypeptide that is recombinantly fused to an affinity polypeptide, and (3) a guide RNA (gRNA). In this aspect, the dCAS9 portion of the dCAS9-multimerized epitope fusion protein is involved with targeting a target nucleic acid as directed by the guide RNA. The multimerized epitope portion of the dCAS9-multimerized epitope fusion protein is involved with binding to the affinity polypeptide (which is recombinantly fused to a transcriptional activator). The affinity polypeptide portion of the transcriptional activator-affinity polypeptide fusion protein is involved with binding to the multimerized epitope so that the transcriptional activator can be in association with dCAS9. The transcriptional activator portion of the transcriptional activator-affinity polypeptide fusion protein is involved with activating transcription of a target nucleic acid, once the complex has been targeted to a target nucleic acid via the guide RNA.

As described above, certain aspects of the present disclosure involve CRISPR-based targeting of a target nucleic acid, which involves use of a CRISPR-CAS9 targeting system. CRISPR-CAS9 systems involve the use of a CRISPR RNA (crRNA), a trans-activating CRISPR RNA (tracrRNA), and a CAS9 protein. The crRNA and tracrRNA aid in directing the CAS9 protein to a target nucleic acid sequence, and these RNA molecules can be specifically engineered to target specific nucleic acid sequences. In particular, certain aspects of the present disclosure involve the use of a single guide RNA (gRNA) that reconstitutes the function of the crRNA and the tracrRNA. Further, certain aspects of the present disclosure involve a CAS9 protein that does not exhibit DNA cleavage activity (dCAS9). As disclosed herein, gRNA molecules may be used to direct a dCAS9 protein to a target nucleic acid sequence.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments of the disclosure and does not pose a limitation on the scope of the disclosure unless otherwise claimed. No language in the specification should be construed as indicating any non-claimed element as essential to the practice of the embodiments of the disclosure.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects and embodiments of the present disclosure described herein include "comprising," "consisting," and "consisting essentially of" aspects and embodiments.

It is to be understood that one, some, or all of the properties of the various embodiments described herein may be combined to form other embodiments of the present disclosure. These and other aspects of the present disclosure will become apparent to one of skill in the art. These and other embodiments of the present disclosure are further described by the detailed description that follows.

The terms "isolated" and "purified" as used herein refers to a material that is removed from at least one component with which it is naturally associated (e.g., removed from its original environment). The term "isolated," when used in reference to an isolated protein, refers to a protein that has been removed from the culture medium of the host cell that expressed the protein. As such an isolated protein is free of extraneous or unwanted compounds (e.g., nucleic acids; native bacterial or other proteins, etc.).

Recombinant Polypeptides

The present disclosure relates to the use of recombinant polypeptides to activate expression of a target nucleic acid (e.g. recombinant VP64 polypeptides, recombinant SDG2 polypeptides). In certain aspects, the targeting involves the use of a nuclease-deficient CAS9 polypeptide that is recombinantly fused to a multimerized epitope. In certain aspects, the targeting involves the use of a transcriptional activator polypeptide that is recombinantly fused to an affinity polypeptide.

As used herein, a "polypeptide" is an amino acid sequence including a plurality of consecutive polymerized amino acid residues (e.g., at least about 15 consecutive polymerized amino acid residues). "Polypeptide" refers to an amino acid sequence, oligopeptide, peptide, protein, or portions thereof, and the terms "polypeptide" and "protein" are used interchangeably.

Polypeptides as described herein also include polypeptides having various amino acid additions, deletions, or substitutions relative to the native amino acid sequence of a polypeptide of the present disclosure. In some embodiments, polypeptides that are homologs of a polypeptide of the present disclosure contain non-conservative changes of certain amino acids relative to the native sequence of a polypeptide of the present disclosure. In some embodiments, polypeptides that are homologs of a polypeptide of the present disclosure contain conservative changes of certain amino acids relative to the native sequence of a polypeptide of the present disclosure, and thus may be referred to as conservatively modified variants. A conservatively modified variant may include individual substitutions, deletions or additions to a polypeptide sequence which result in the substitution of an amino acid with a chemically similar amino acid. Conservative substitution tables providing functionally similar amino acids are well-known in the art. Such conservatively modified variants are in addition to and do not exclude polymorphic variants, interspecies homologs, and alleles of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). A modification of an amino acid to produce a chemically similar amino acid may be referred to as an analogous amino acid.

Recombinant polypeptides of the present disclosure that are composed of individual polypeptide domains may be described based on the individual polypeptide domains of the overall recombinant polypeptide. A domain in such a recombinant polypeptide refers to the particular stretches of contiguous amino acid sequences with a particular function or activity. For example, a recombinant polypeptide that is a fusion of a transcriptional activator polypeptide and an affinity polypeptide, the contiguous amino acids that encode the transcriptional activator polypeptide may be described as the transcriptional activator domain in the overall recombinant polypeptide, and the contiguous amino acids that encode the affinity polypeptide may be described as the affinity domain in the overall recombinant polypeptide. Individual domains in an overall recombinant protein may also be referred to as units of the recombinant protein. Recombinant polypeptides that are composed of individual polypeptide domains may also be referred to as fusion polypeptides.

Certain aspects of the present disclosure relate to a nuclease-deficient CAS9 polypeptide that is recombinantly fused to a multimerized epitope (e.g. dCAS9-multimerized epitope fusion protein). The dCAS9 polypeptide domain of a dCAS9-multimerized epitope fusion protein may be in an N-terminal orientation or a C-terminal orientation relative to the multimerized epitope domain. The multimerized epitope domain of a dCAS9-multimerized epitope fusion protein may be in an N-terminal orientation or a C-terminal orientation relative to the dCAS9 polypeptide domain. In some embodiments, a dCAS9-multimerized epitope fusion protein may be a direct fusion of a dCAS9 polypeptide domain and a multimerized epitope domain. In some embodiments, a dCAS9-multimerized epitope fusion protein may be an indirect fusion of a dCAS9 polypeptide domain and a multimerized epitope domain. In embodiments where the fusion is indirect, a linker domain or other contiguous amino acid sequence may separate the dCAS9 polypeptide domain and the multimerized epitope domain.

Certain aspects of the present disclosure relate to a transcriptional activator polypeptide (e.g. VP64, SDGC2) that is recombinantly fused to an affinity polypeptide (e.g. transcriptional activator-affinity polypeptide fusion protein). The transcriptional activator polypeptide domain of a transcriptional activator-affinity polypeptide fusion protein may be in an N-terminal orientation or a C-terminal orientation relative to the affinity polypeptide. The affinity polypeptide domain of a transcriptional activator-affinity polypeptide fusion protein may be in an N-terminal orientation or a C-terminal orientation relative to the transcriptional activator polypeptide domain. In some embodiments, a transcriptional activator-affinity polypeptide fusion protein may be a direct fusion of a transcriptional activator polypeptide domain and an affinity polypeptide domain. In some embodiments, a transcriptional activator-affinity polypeptide fusion protein may be an indirect fusion of a transcriptional activator polypeptide domain and an affinity polypeptide domain. In embodiments where the fusion is indirect, a linker domain or other contiguous amino acid sequence may separate the transcriptional activator polypeptide domain and the affinity polypeptide domain.

Linkers

Various linkers may be used in the construction of recombinant proteins as described herein. In general, linkers are short peptides that separate the different domains in a multi-domain protein. They may play an important role in fusion proteins, affecting the crosstalk between the different domains, the yield of protein production, and the stability and/or the activity of the fusion proteins. Linkers are generally classified into 2 major categories: flexible or rigid. Flexible linkers are typically used when the fused domains require a certain degree of movement or interaction, and these linkers are usually composed of small amino acids such as, for example, glycine (G), serine (S) or proline (P).

The certain degree of movement between domains allowed by flexible linkers is an advantage in some fusion proteins. However, it has been reported that flexible linkers can sometimes reduce protein activity due to an inefficient separation of the two domains. In this case, rigid linkers may be used since they enforce a fixed distance between domains and promote their independent functions. A thorough description of several linkers has been provided in Chen X et al., 2013, Advanced Drug Delivery Reviews 65 (2013) 1357-1369).

Various linkers may be used in, for example, the construction of recombinant polypeptides as described herein. Linkers may be used in e.g. dCAS9-multimerized epitope fusion proteins as described herein to separate the coding sequences of the dCAS9 polypeptide and the multimerized epitope polypeptide. Linkers may be used in e.g. transcriptional activator-affinity polypeptide fusion proteins as described herein to separate the coding sequences of the transcriptional activator polypeptide and the affinity polypeptide. For example, a variety of wiggly/flexible linkers, stiff/rigid linkers, short linkers, and long linkers may be used as described herein. Various linkers as described herein may be used in the construction of recombinant proteins as described herein.

A variety of shorter or longer linker regions are known in the art, for example corresponding to a series of glycine residues, a series of adjacent glycine-serine dipeptides, a series of adjacent glycine-glycine-serine tripeptides, or known linkers from other proteins. A flexible linker may include, for example, the amino acid sequence: SSGPPPGTG (SEQ ID NO: 64) and variants thereof. A rigid linker may include, for example, the amino acid sequence: AEAAAKEAAAKA (SEQ ID NO: 65) and variants thereof. The XTEN linker, SGSETPGTSESATPES (SEQ ID NO: 66), and variants thereof, described in Guilinget et al, 2014 (Nature Biotechnology 32, 577-582), may also be used. This particular linker was previously shown to produce the best results among other linkers in a protein fusion between dCAS9 and the nuclease FokI.

Recombinant polypeptides of the present disclosure may contain one or more linkers that contain an amino acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% amino acid identity to the amino acid sequence of any one of SEQ ID NO: 15 and/or SEQ ID NO: 30.

Nuclear Localization Signals (NLS)

Recombinant polypeptides of the present disclosure may contain one or more nuclear localization signals (NLS). Nuclear localization signals may also be referred to as nuclear localization sequences, domains, peptides, or other terms readily apparent to those of skill in the art. Nuclear localization signals are a translocation sequence that, when present in a polypeptide, direct that polypeptide to localize to the nucleus of a eukaryotic cell.

Various nuclear localization signals may be used in recombinant polypeptides of the present disclosure. For example, one or more SV40-type NLS or one or more REX NLS may be used in recombinant polypeptides. Recombinant polypeptides may also contain two or more tandem copies of a nuclear localization signal. For example, recombinant polypeptides may contain at least two, at least three, at least for, at least five, at least six, at least seven, at least eight, at least nine, or at least ten copies, either tandem or not, of a nuclear localization signal.

Recombinant polypeptides of the present disclosure may contain one or more nuclear localization signals that contain an amino acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% amino acid identity to the amino acid sequence of any one of SEQ ID NO: 14, SEQ ID NO: 32, and/or SEQ ID NO: 34.

Tags, Reporters, and Other Features

Recombinant polypeptides of the present disclosure may contain one or more tags that allow for e.g. purification and/or detection of the recombinant polypeptide. Various tags may be used herein and are well-known to those of skill in the art. Exemplary tags may include HA, GST, FLAG, MBP, etc., and multiple copies of one or more tags may be present in a recombinant polypeptide.

Recombinant polypeptides of the present disclosure may contain one or more reporters that allow for e.g. visualization and/or detection of the recombinant polypeptide. A reporter polypeptide encodes a protein that may be readily detectable due to its biochemical characteristics such as, for example, enzymatic activity or chemifluorescent features. Reporter polypeptides may be detected in a number of ways depending on the characteristics of the particular reporter. For example, a reporter polypeptide may be detected by its ability to generate a detectable signal (e.g. fluorescence), by its ability to form a detectable product, etc. Various reporters may be used herein and are well-known to those of skill in the art. Exemplary reporters may include GFP, GUS, mCherry, luciferase, etc., and multiple copies of one or more tags may be present in a recombinant polypeptide.

Recombinant polypeptides of the present disclosure may contain one or more polypeptide domains that serve a particular purpose depending on the particular goal/need. For example, recombinant polypeptides may contain a GB1 polypeptide. Recombinant polypeptides may contain translocation sequences that target the polypeptide to a particular cellular compartment or area. Suitable features will be readily apparent to those of skill in the art.

Transcriptional Activators

Certain aspects of the present disclosure involve targeting a transcriptional activator to a target nucleic acid such that the transcriptional activator activates the expression/transcription of the target nucleic acid. In some embodiments, a transcriptional activator is present in a recombinant polypeptide that contains a transcriptional activator polypeptide and an affinity polypeptide.

Transcriptional activators are polypeptides that facilitate the activation of transcription/expression of a nucleic acid (e.g. a gene). Transcriptional activators may be DNA-binding proteins that bind to enhancers, promoters, or other regulatory elements of a nucleic acid, which then promotes expression of the nucleic acid. Transcriptional activators may interact with proteins that are components of transcriptional machinery or other proteins that are involved in regulation of transcription in a manner that promotes expression of the nucleic acid.

Transcriptional activators of the present disclosure may be endogenous to the host plant, or they may be exogenous/heterologous to the host plant. In some embodiments, the transcriptional activator is a viral transcriptional activator. In some embodiments, the transcriptional activator is derived from Herpes Simplex Virus. For example, one or more copies of a Herpes Simplex Virus Viral Protein 16 (VP16) domain may be used herein. In some embodiments, at least two, at least three, or at least four or more copies of a VP16 domain may be used as a transcriptional activator. A polypeptide containing 4 copies of the Herpes Simplex Virus Viral Protein 16 (VP16) domain is known as a VP64 domain.

In some embodiments, the transcriptional activator is a VP64 polypeptide. A VP64 polypeptide of the present disclosure may contain an amino acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% amino acid identity to the amino acid sequence of SEQ ID NO: 31.

Other exemplary transcriptional activators include, for example, the the EDLL motif present in the ERF/EREBP family of transcriptional regulators in plants, activation domains of or full-length transcription factors, the TAL activation domain derived from the transcription activator-like effector (TALE) proteins from the plant pathogen *Xanthomonas*, plant endogenous and exogenous histone acetylases (e.g. p300 from mammals), histone methylases (e.g. H3K4 methylation depositors (SDG2)), histone demethylases (e.g. H3K9 demethylases (IBM1)), Polymerase II subunits, and various combinations of the above mentioned transcriptional activators. For example, VP64 and EDLL may each be fused to an scFv antibody in the SunTag system and co-expressed for targeted activation. In the latter case, each fusion would bind to the epitope tail fused to dCas9.

Additional transcriptional activators that may be used in the methods and compositions described herein will be readily apparent to those of skill in the art.

SDG2 Polypeptides

In some embodiments, a transcriptional activator of the present disclosure is a recombinant SDG2 polypeptide. Certain aspects of the present disclosure therefore relate to recombinant SDG2 polypeptides. SDG2 proteins are known in the art and are described herein. In *Arabidopsis thaliana*, locus AT4G15180 codes for SDG2. SDG2 is a histone methyltransferase, and functions to catalyze methylation of histone 3 (H3) at position lysine 4 (K4). Accordingly, SDG2 is an H3K4 histone methyltransferase. SDG2 proteins generally catalyze tri-methylation (me3) of H3K4, producing H3K4me3. However, without wishing to be bound by theory, SDG2 may also catalyze some quantity of mono-methylation (me1) or di-methylation (me2) of H3K4.

Recombinant SDG2 polypeptides of the present disclosure may contain an SDG2 polypeptide domain and a domain involved in facilitating the targeting of the recombinant SDG2 polypeptide to a target nucleic acid. In some embodiments, recombinant SDG2 polypeptides include an SDG2 polypeptide domain and a heterologous DNA-binding domain. In some embodiments, recombinant SDG2 polypeptides include an SDG2 polypeptide domain and a dCAS9 polypeptide domain. In some embodiments, recombinant SDG2 polypeptides include an SDG2 polypeptide domain and an scFv antibody polypeptide domain.

Various SDG2 polypeptides may be used in the methods and compositions of the present disclosure, including full-length SDG2 proteins and fragments thereof. In some embodiments, an SDG2 polypeptide contains at least 20 consecutive amino acids, at least 30 consecutive amino acids, at least 40 consecutive amino acids, at least 50 consecutive amino acids, at least 60 consecutive amino acids, at least 70 consecutive amino acids, at least 80 consecutive amino acids, at least 90 consecutive amino acids, at least 100 consecutive amino acids, at least 120 consecutive amino acids, at least 140 consecutive amino acids, at least 160 consecutive amino acids, at least 180 consecutive amino acids, at least 200 consecutive amino acids, at least 220 consecutive amino acids, at least 240 consecutive amino acids, at least 260 consecutive amino acids, at least 280 consecutive amino acids, at least 300 consecutive amino acids, at least 350 consecutive amino acids, at least 400 consecutive amino acids, at least 450 consecutive amino acids, at least 500 consecutive amino acids, at least 550 consecutive amino acids, at least 600 consecutive amino acids, at least 650 consecutive amino acids, or at least 750 consecutive amino acids or more of a full-length SDG2 protein. In some embodiments, an SDG2 polypeptide may include sequences with one or more amino acids removed from the consecutive amino acid sequence of a full-length SDG2 protein. In some embodiments, an SDG2 polypeptide may include sequences with one or more amino acids replaced/substituted with an amino acid different from the endogenous amino acid present at a given amino acid position in a consecutive amino acid sequence of a full-length SDG2 protein. In some embodiments, an SDG2 polypeptide may include sequences with one or more amino acids added to an otherwise consecutive amino acid sequence of a full-length SDG2 protein.

Suitable SDG2 proteins may be identified and isolated from monocot and dicot plants. Examples of suitable SDG2 proteins may include, for example, those listed in Table 1, homologs thereof, and orthologs thereof.

TABLE 1

SDG2 Proteins

| Organism | Gene Name | SED ID NO. |
|---|---|---|
| *Arabidopsis thaliana* | AT4G15180 | 104 |
| *Glycine max* | XP_006592400.1 | 105 |
| *Zea mays* | PWZ45175.1 | 106 |
| *Manihot esculenta* | XP_021633431.1 | 107 |
| *Triticum urartu* | EMS63882.1 | 108 |
| *Triticum aestivum* | SPT15485.1 | 109 |
| *Oryza sativa* | Os08g08210.1 | 110 |
| *Solanum lycopersicum* | XP_010323788.1 | 111 |
| *Saccharum officinarum* | ABP37821.1 | 112 |
| *Solanum tuberosum* | XP_006360591.1 | 113 |
| *Sorghum bicolor* | XP_021320942.1 | 114 |
| *Brassica napus* | XP_022560579.1 | 115 |
| *Beta vulgaris* subsp. *vulgaris* | XP_010689485.1 | 116 |
| *Arachis hypogaea* | RYR43245.1 | 117 |
| *Raphanus sativus* | XP_018470209.1 | 118 |

In some embodiments, an SDG2 polypeptide of the present disclosure has an amino acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% amino acid identity to the amino acid sequence of the *A. thaliana* SDG2 protein (SEQ ID NO: 104).

An SDG2 polypeptide may include the amino acid sequence or a fragment thereof of any SDG2 homolog or ortholog, such as any one of those listed in Table 1. One of skill would readily recognize that additional SDG2 protein homologs and/or orthologs may exist and may be used herein.

SDG2 Catalytic Domain (SDG2C) Polypeptides

As described above, in some embodiments, the SDG2 polypeptide is a fragment of a full-length SDG2 protein. In some embodiments, the fragment includes the catalytic (H3K4 histone methyltransferase) domain of SDG2 (SDG2C). Accordingly, in some embodiments, the SDG2 polypeptide is a fragment of a full-length SDG2 protein that includes that SDG2 catalytic domain (SDG2C polypeptides).

Examples of suitable SDG2C polypeptides may include, for example, those listed in Table 2, homologs thereof, and orthologs thereof.

TABLE 2

SDG2C Polypeptides

| Organism | Gene Name | SED ID NO. |
|---|---|---|
| *Arabidopsis thaliana* | AT4G15180 | 98 |
| *Glycine max* | XP_006592400.1 | 119 |
| *Zea mays* | PWZ45175.1 | 120 |
| *Manihot esculenta* | XP_021633431.1 | 121 |
| *Triticum urartu* | EMS63882.1 | 122 |
| *Triticum aestivum* | SPT15485.1 | 123 |
| *Oryza sativa* | Os08g08210.1 | 124 |
| *Solanum lycopersicum* | XP_010323788.1 | 125 |
| *Solanum tuberosum* | XP_006360591.1 | 126 |
| *Sorghum bicolor* | XP_021320942.1 | 127 |
| *Brassica napus* | CDY22935.1 | 128 |
| *Beta vulgaris* subsp. *vulgaris* | XP_010689485.1 | 129 |
| *Arachis hypogaea* | XP_025614375.1 | 130 |
| *Raphanus sativus* | XP_018470209.1 | 131 |

In some embodiments, an SDG2C polypeptide of the present disclosure has an amino acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% amino acid identity to the amino acid sequence of SEQ ID NO: 98 (*Arabidopsis thaliana* SDG2C).

An SDG2C polypeptide may include the amino acid sequence or a fragment thereof of any SDG2C polypeptide homolog or ortholog, such as any one of those listed in Table 2. One of skill would readily recognize that additional SDG2C polypeptide homologs and/or orthologs may exist and may be used herein.

Targeting Using DNA-Binding Domains

Certain aspects of the present disclosure relate to targeting SDG2 polypeptides to specific loci. Targeted loci may also be referred to as target nucleic acids. Various methods for targeting polypeptides to a specific nucleic acid are known in the art and are described herein. In some embodiments, an RNA-guided DNA-binding protein or system is used to facilitate targeting of an SDG2 polypeptide to a target nucleic acid (e.g. CRISPR-CAS9 targeting systems, such as a SunTag system). In some embodiments, a DNA-binding domain may be used to facilitate targeting of an SDG2 polypeptide to a target nucleic acid.

In addition to the CRISPR-based targeting systems described herein, recombinant SDG2 polypeptides of the present disclosure may be targeted to a target nucleic acid via a DNA-binding domain. Accordingly, certain aspects of the present disclosure relate to recombinant SDG2 polypeptides that have DNA-binding activity. In some embodiments, this DNA-binding activity is achieved through a heterologous DNA-binding domain (e.g. binds with a sequence affinity other than that of any DNA-binding domain that may be present in the endogenous protein). In some embodiments, recombinant SDG2 polypeptides of the present disclosure contain a DNA-binding domain. Recombinant SDG2 polypeptides of the present disclosure may contain one DNA binding domain or they may contain more than one DNA-binding domain. Heterologous DNA-binding domains may be recombinantly fused to an SDG2 polypeptide of the present disclosure such that the SDG2 polypeptide is then able to be targeted to a specific nucleic acid sequence.

In some embodiments, the DNA-binding domain is a zinc finger domain. A zinc finger domain generally refers to a DNA-binding protein domain that contains zinc fingers, which are small protein structural motifs that can coordinate one or more zinc ions to help stabilize their protein folding. Zinc fingers were first identified as DNA-binding motifs (Miller et al., 1985), and numerous other variations of them have been characterized. Recent progress has been made that allows the engineering of DNA-binding proteins that specifically recognize any desired DNA sequence. For example, it was shown that a three-finger zinc finger protein could be constructed to block the expression of a human oncogene that was transformed into a mouse cell line (Chop and Klug, 1994).

Zinc fingers can generally be classified into several different structural families and typically function as interaction modules that bind DNA, RNA, proteins, or small molecules. Suitable zinc finger domains of the present disclosure may contain two, three, four, five, six, seven, eight, or nine zinc fingers. Examples of suitable zinc finger domains may include, for example, Cys2His2 (C2H2) zinc finger domains, C-x8-C-x5-C-x3-H (CCCH) zinc finger domains, multi-cysteine zinc finger domains, and zinc binuclear cluster domains.

In some embodiments, the DNA-binding domain binds a specific nucleic acid sequence. For example, the DNA-binding domain may bind a sequence that is at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, or a higher number of nucleotides in length.

In some embodiments, a recombinant SDG2 polypeptide of the present disclosure may contain two N-terminal CCCH zinc finger domains.

In some embodiments, the zinc finger domain is an engineered zinc finger array, such as a C2H2 zinc finger array. Engineered arrays of C2H2 zinc fingers can be used to create DNA-binding proteins capable of targeting desired genomic DNA sequences. Methods of engineering zinc finger arrays are well known in the art, and include, for example, combining smaller zinc fingers of known specificity.

In some embodiments, recombinant SDG2 polypeptides of the present disclosure may contain a DNA-binding domain other than a zinc finger domain. Examples of such DNA-binding domains may include, for example, TAL (transcription activator-like) effector targeting domains, helix-turn-helix family DNA-binding domains, basic domains, ribbon-helix-helix domains, TBP (TATA-box binding protein) domains, barrel dimer domains, RIB domains homology domain), BAH (bromo-adjacent homology) domains, SANT domains, Chromodomains, Tudor domains, Bromodomains, PHD domains (plant homed domain), WD40 domains, and MBD domains (methyl-CpG-binding domain).

In some embodiments, the DNA-binding domain is a TAL effector targeting domain. TAL effectors generally refer to secreted bacterial proteins, such as those secreted by *Xanthomonas* or *Ralstonia* bacteria when infecting various plant species. Generally, TAL effectors are capable of binding promoter sequences in the host plant, and activate the expression of plant genes that aid in bacterial infection. TAL effectors recognize plant DNA sequences through a central repeat targeting domain that contains a variable number of approximately 34 amino acid repeats. Moreover, TAL effector targeting domains can be engineered to target specific DNA sequences. Methods of modifying TAL effector targeting domains are well known in the art, and described in Bogdanove and Voytas, Science. 2011 Sep. 30; 333(6051): 1843-6.

Other DNA-binding domains for use in the methods and compositions of the present disclosure will be readily apparent to one of skill in the art, in view of the present disclosure.

Affinity Polypeptides

Certain aspects of the present disclosure relate to recombinant polypeptides that contain an affinity polypeptide. Affinity polypeptides of the present disclosure may bind to one or more epitopes (e.g. a multimerized epitope). In some embodiments, an affinity polypeptide is present in a recombinant polypeptide that contains a transcriptional activator polypeptide and an affinity polypeptide.

A variety of affinity polypeptides are known in the art and may be used herein. Generally, the affinity polypeptide should be stable in the conditions present in the intracellular environment of a plant cell. Additionally, the affinity polypeptide should specifically bind to its corresponding epitope with minimal cross-reactivity.

The affinity polypeptide may be an antibody such as, for example, an scFv. The antibody may be optimized for stability in the plant intracellular environment. When a GCN4 epitope is used in the methods described herein, a suitable affinity polypeptide that is an antibody may contain an anti-GCN4 scFv domain.

In embodiments where the affinity polypeptide is an scFv antibody, the polypeptide may contain an amino acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% amino acid identity to the amino acid sequence of SEQ ID NO: 28.

Other exemplary affinity polypeptides include, for example, proteins with SH2 domains or the domain itself, 14-3-3 proteins, proteins with SH3 domains or the domain itself, the Alpha-Syntrophin PDZ protein interaction domain, the PDZ signal sequence, or proteins from plants which can recognize AGO hook motifs (e.g. AGO4 from *Arabidopsis thaliana*).

Additional affinity polypeptides that may be used in the methods and compositions described herein will be readily apparent to those of skill in the art.

Epitopes and Multimerized Epitopes

Certain aspects of the present disclosure relate to recombinant polypeptides that contain an epitope or a multimerized epitope. Epitopes of the present disclosure may bind to an affinity polypeptide. In some embodiments, an epitope or multimerized epitope is present in a recombinant polypeptide that contains a dCAS9 polypeptide.

Epitopes of the present disclosure may be used for recruiting affinity polypeptides (and any polypeptides they may be recombinantly fused to) to a dCAS9 polypeptide. In embodiments where a dCAS9 polypeptide is fused to an epitope or a multimerized epitope, the dCAS9 polypeptide may be fused to one copy of an epitope, multiple copies of an epitope, more than one different epitope, or multiple copies of more than one different epitope as further described herein.

A variety of epitopes and multimerized epitopes are known in the art and may be used herein. In general, the epitope or multimerized epitope may be any polypeptide sequence that is specifically recognized by an affinity polypeptide of the present disclosure. Exemplary epitopes may include a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, a VSV-G epitope, and a GCN4 epitope.

Other exemplary amino acid sequences that may serve as epitopes and multimerized epitopes include, for example, phosphorylated tyrosines in specific sequence contexts recognized by SH2 domains, characteristic consensus sequences containing phosphoserines recognized by 14-3-3 proteins, proline rich peptide motifs recognized by SH3 domains, the PDZ protein interaction domain or the PDZ signal sequence, and the AGO hook motif from plants.

Epitopes described herein may also be multimerized. Multimerized epitopes may include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, or at least 24 or more copies of an epitope.

Multimerized epitopes may be present as tandem copies of an epitope, or each individual epitope may be separated from another epitope in the multimerized epitope by a linker or other amino acid sequence. Suitable linker regions are known in the art and are described herein. The linker may be configured to allow the binding of affinity polypeptides to adjacent epitopes without, or without substantial, steric hindrance. Linker sequences may also be configured to provide an unstructured or linear region of the polypeptide to which they are recombinantly fused. The linker sequence may comprise e.g. one or more glycines and/or serines. The linker sequences may be e.g. at least 2, at least 3, at least 4, at least 5, at least 6, at least 7, at least 8, at least 9, or at least 10 or more amino acids in length.

In some embodiments, the epitope is a GCN4 epitope (SEQ ID NO: 47). In some embodiments, the multimerized epitope contains at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, or at least 24 copies of a GCN4 epitope (SEQ ID NO: 47). In some embodiments, the multimerized epitope contains 10 copies of a GCN4 epitope (SEQ ID NO: 16).

Additional epitopes and multimerized epitopes that may be used in the methods and compositions described herein will be readily apparent to those of skill in the art.

CRISPR-CAS9

Certain aspects of the present disclosure involve CRISPR-based targeting of a transcriptional activator to a target nucleic acid, which involves use of a CRISPR-CAS9 targeting system. In some embodiments, an epitope or multimerized epitope of the present disclosure is present in a recombinant polypeptide that contains dCAS9 polypeptide.

CRISPR systems naturally use small base-pairing guide RNAs to target and cleave foreign DNA elements in a sequence-specific manner (Wiedenheft et al., 2012). There are diverse CRISPR systems in different organisms that may be used to target proteins of the present disclosure to a target nucleic acid. One of the simplest systems is the type II CRISPR system from *Streptococcus pyogenes*. Only a single gene encoding the CAS9 protein and two RNAs, a mature CRISPR RNA (crRNA) and a partially complementary trans-acting RNA (tracrRNA), are necessary and sufficient for RNA-guided silencing of foreign DNAs (Jinek et al, 2012). Maturation of crRNA requires tracrRNA and RNase III (Deltcheva et al., 2011). However, this requirement can be bypassed by using an engineered small guide RNA (gRNA) containing a designed hairpin that mimics the tracrRNA-crRNA complex (Jinek et al., 2012). Base pairing between the gRNA and target DNA normally causes double-strand breaks (DSBs) due to the endonuclease activity of CAS9.

It is known that the endonuclease domains of the CAS9 protein can be mutated to create a programmable RNA-dependent DNA-binding protein (dCAS9) (Qi et al., 2013). The fact that duplex gRNA-dCAS9 binds target sequences without endonuclease activity has been used to tether regulatory proteins, such as transcriptional activators or repressors, to promoter regions in order to modify gene expression (Gilbert et al., 2013), and CAS9 transcriptional activators have been used for target specificity screening and paired nickases for cooperative genome engineering (Mali et al., 2013, Nature Biotechnology 31:833-838). Thus, dCAS9 may be used as a modular RNA-guided platform to recruit different proteins to DNA in a highly specific manner. One of skill in the art would recognize other RNA-guided DNA binding protein/RNA complexes that can be used equivalently to CRISPR-CAS9.

The CRISPR-CAS9 system may be used to target a transcriptional activator polypeptide (e.g. VP64, SDG2) to a specific nucleic acid. Targeting using CRISPR-CAS9 may be beneficial over other genome targeting techniques in certain instances. For example, one need only change the guide RNAs in order to target recombinant polypeptides to a new genomic location, or even multiple locations simultaneously. Further, CAS9-mediated targeting has been shown to be insensitive to the methylation state of the target nucleic acid (Nature Biotechnology 31, 827-832 (2013)). In addition, guide RNAs can be extended to include sites for binding to certain proteins which can be fused to polypeptides of interest (e.g. VP64 and SDG2 polypeptides).

CAS9 Proteins

A variety of CAS9 proteins may be used in the methods of the present disclosure. There are several CAS9 genes present in different bacteria species (Esvelt, K et al, 2013, Nature Methods). One of the most characterized CAS9 proteins is the CAS9 protein from *S. pyogenes* that, in order to be active, needs to bind a gRNA with a specific sequence and the presence of a PAM motif (NGG, where N is any nucleotide) at the 3' end of the target locus. However, other CAS9 proteins from different bacterial species show differences in 1) the sequence of the gRNA they can bind and 2) the sequence of the PAM motif. Therefore, it is possible that other CAS9 proteins such as, for example, those from *Streptococcus thermophilus* or *N. meningitidis* may also be utilized herein. Indeed, these two CAS9 proteins have a smaller size (around 1100 amino acids) as compared to *S. pyogenes* CAS9 (1400 amino acids), which may confer some advantages during cloning or protein expression.

CAS9 proteins from a variety of bacteria have been used successfully in engineered CRISPR-CAS9 systems. There are also versions of CAS9 proteins available in which the codon usage has been more highly optimized for expression in eukaryotic systems, such as human codon optimized CAS9 (Cell, 152:1173-1183) and plant optimized CAS9 (Nature Biotechnology, 31:688-691).

CAS9 proteins may also be modified for various purposes. For example, CAS9 proteins may be engineered to contain a nuclear-localization sequence (NLS). CAS9 proteins may be engineered to contain an NLS at the N-terminus of the protein, at the C-terminus of the protein, or at both the N- and C-terminus of the protein. Engineering a CAS9 protein to contain an NLS may assist with directing the protein to the nucleus of a host cell. CAS9 proteins may be engineered such that they are unable to cleave nucleic acids (e.g. nuclease-deficient dCAS9 polypeptides). One of skill in the art would be able to readily identify a suitable CAS9 protein for use in the methods and compositions of the present disclosure.

Exemplary CAS9 proteins that may be used in the methods and compositions of the present disclosure may include, for example, a CAS9 protein having the amino acid sequence of any one of SEQ ID NO: 48, SEQ ID NO: 49, and/or SEQ ID NO: 50, homologs thereof, and fragments thereof. In some embodiments, the CAS9 polypeptide is a dCAS9 polypeptide. dCAS9 polypeptides may contain an amino acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% amino acid identity to the amino acid sequence of SEQ ID NO: 12.

CRISPR RNAs

The CRISPR RNA (crRNA) of the present disclosure may take a variety of forms. As described above, the sequence of the crRNA is involved in conferring specificity to targeting a specific nucleic acid.

Many different crRNA molecules can be designed to target many different sequences. With respect to targeting, target nucleic acids generally require the PAM sequence, NGG, at the end of the 20 base pair target sequence. crRNAs of the present disclosure may be expressed as a single crRNA molecule, or they may be expressed in the form of a crRNA/tracrRNA hybrid molecule where the crRNA and the tracrRNA have been fused together, forming a guide RNA (gRNA). crRNA molecules and/or guide RNA molecules may be extended to include sites for the binding of RNA binding proteins.

Multiple crRNAs and/or guide RNAs can be encoded into a single CRISPR array to enable simultaneous targeting to several sites (Science 2013: Vol. pp. 819-823). For example, the tracrRNA may be expressed separately, and two adjacent target sequences may be encoded in a pre-crRNA array interspaced with repeats.

A variety of promoters may be used to drive expression of the crRNA and/or the guide RNA. crRNAs and/or guide RNAs may be expressed using a Pol III promoter such as, for example, the U6 promoter or the H1 promoter (eLife 2013 2:e00471). For example, an approach in plants has been described using three different Pol III promoters from three different *Arabidopsis* U6 genes, and their corresponding gene terminators (BMC Plant Biology 2014 14:327). One skilled in the art would readily understand that many additional Pol III promoters could be utilized to simultaneously express many crRNAs and/or guide RNAs to many different locations in the genome simultaneously. The use of different Pol III promoters for each crRNA and/or gRNA expression cassette may be desirable to reduce the chances of natural gene silencing that can occur when multiple copies of identical sequences are expressed in plants. In addition, crRNAs and/or guide RNAs can be modified to improve the efficiency of their function in guiding CAS9 to a target nucleic acid. For example, it has been shown that adding either 8 or 20 additional nucleotides to the gRNA in order to extend the hairpin by 4 or 10 base pairs resulted in more efficient CAS9 activity (eLife 2013 2:e00471).

In some embodiments, the guide RNA is driven by a U6 promoter. In some embodiments, the guide RNA is driven by a promoter having a nucleic acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% nucleic acid sequence identity to the nucleic acid sequence of SEQ ID NO: 36.

Alternatively, a tRNA-gRNA expression cassette (Xie, X et al, 2015, Proc Natl Acad Sci USA. 2015 Mar. 17; 112(11):3570-5) may be used to deliver multiple gRNAs simultaneously with high expression levels. In such an embodiment, a tRNA in such a cassette may have a nucleic acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at leak about 92%, at least about 93%, at least about 94%, at least about 95%, at least about 96%, at least about 97%, at least about 98%, at least about 99%, or at least about 100% nucleic acid sequence identity to the nucleic acid sequence of SEQ ID NO: 43.

Trans-Activating CRISPR RNAs

The trans-activating CRISPR RNA (tracrRNA) of the present disclosure may take a variety of forms, as will be readily understood by one of skill in the art. As described above, tracrRNAs are involved in the maturation of a crRNA. tracrRNAs of the present disclosure may be expressed as a single tracrRNA molecule, or they may be expressed in the form of a crRNA/tracrRNA hybrid molecule where the crRNA and the tracrRNA have been fused together, forming a guide RNA (gRNA). tracrRNA molecules and/or guide RNA molecules may be extended to include sites for the binding of RNA binding proteins.

As CRISPR systems naturally exist n a variety of bacteria, the framework of the crRNA and tracrRNA in these bacteria may be adapted for use in the methods and compositions described herein. crRNAs, tracrRNAs, and/or guide RNAs of the present disclosure may be constructed based on the framework of one or more of these molecules in, for example, *S. pyogenes, Streptococcus thermophilus*, and/or *N. meningitidis*. For example, a guide RNA of the present disclosure may be constructed based on the framework of the crRNA and tracrRNA from *S. pyogenes* (SEQ ID NO: 51), *Streptococcus thermophilus* (SEQ ID NO: 52), and/or *N. meningitidis* (SEQ ID NO: 53). In these exemplary frameworks, the 5' end of the sequence contains 20 generic nucleotides (N) that correspond to the crRNA targeting sequence. This sequence will vary depending on the sequence of the particular nucleic acid being targeted.

In some embodiments, the tracrRNA component may have a nucleic acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% nucleic acid sequence identity to the nucleic acid sequence of SEQ ID NO: 38.

Recombinant Nucleic Acids Encoding Recombinant Proteins

Certain aspects of the present disclosure relate to recombinant nucleic acids encoding recombinant proteins of the present disclosure. Certain aspects of the present disclosure relate to recombinant nucleic acids encoding various portions/domains of recombinant proteins of the present disclosure.

As used herein, the terms "polynucleotide," "nucleic acid," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications. As used herein, the symbols for nucleotides and polynucleotides are those recommended by the IUPAC-IUB Commission of Biochemical Nomenclature.

In some embodiments, a recombinant nucleic acid is provided that encodes a recombinant SDG2 polypeptide. In some embodiments, the recombinant nucleic acid encodes an SDG2 polypeptide that has an amino acid sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 98.

In some embodiments, a recombinant nucleic acid is provided containing a plant promoter and that encodes a recombinant polypeptide containing a nuclease-deficient CAS9 polypeptide (dCAS9) and a multimerized epitope. This recombinant nucleic acid may encode a recombinant polypeptide having an amino acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% amino acid identity to the amino acid sequence of SEQ. ID NO: 11.

In some embodiments, a recombinant nucleic acid is provided containing a plant promoter and that encodes recombinant polypeptide containing a transcriptional activator and an affinity polypeptide. This recombinant nucleic acid may encode a recombinant polypeptide having an amino acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% amino acid identity to the amino acid sequence of SEQ ID NO: 27.

Recombinant nucleic acids are also provided that have a nucleic acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% nucleic acid sequence identity to the nucleic acid sequence of any one of SEQ ID NO: 1, SEQ NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 26, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 83, SEQ ID NO: 84, SEQ NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 99, SEQ ID NO: 100, SEQ ID NO: 101, SEQ ID NO: 102, and SEQ ID NO: 103.

Sequences of the polynucleotides of the present disclosure may be prepared by various suitable methods known in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteucci et al., (1980) Tetrahedron Lett 21:719-722; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired polynucleotide sequence from the gel via techniques known to those of ordinary skill in the art, such as utilization of polymerase chain reactions (PCR; e.g., U.S. Pat. No. 4,683,195).

The nucleic acids employed in the methods and compositions described herein may be codon optimized relative to a parental template for expression in a particular host cell. Cells differ in their usage of particular codons, and codon bias corresponds to relative abundance of particular tRNAs in a given cell type. By altering codons in a sequence so that they are tailored to match with the relative abundance of corresponding tRNAs, it is possible to increase expression of a product (e.g. a polypeptide) from a nucleic acid. Similarly, it is possible to decrease expression by deliberately choosing codons corresponding to rare tRNAs. Thus, codon optimization/deoptimization can provide control over nucleic acid expression in a particular cell type (e.g. bacterial cell, plant cell, mammalian cell, etc.). Methods of codon optimizing a nucleic acid for tailored expression in a particular cell type are well-known to those of skill in the art.

Methods of Identifying Sequence Similarity

Various methods are known to those of skill in the art for identifying similar (e.g. homologs, orthologs, paralogs, etc.) polypeptide and/or polynucleotide sequences, including phylogenetic methods, sequence similarity analysis, and hybridization methods.

Phylogenetic trees may be created for a gene family by using a program such as CLUSTAL (Thompson et al. Nucleic Acids Res. 22: 4673-4680 (1994); Higgins et al. Methods Enzymol 266: 383-402 (1996)) or MEGA (Tamura et al. Mol. Biol. & Evo. 24:1596-1599 (2007)). Once an initial tree for genes from one species is created, potential orthologous sequences can be placed in the phylogenetic tree and their relationships to genes from the species of interest can be determined. Evolutionary relationships may also be inferred using the Neighbor-Joining method (Saitou and Nei, Mol. Biol. & Evo. 4:406-425 (1987)). Homologous sequences may also be identified by a reciprocal BLAST strategy. Evolutionary distances may, be computed using the Poisson correction method (Zuckerkandl and Pauling, pp. 97-166 in Evolving Genes and Proteins, edited by V. Bryson and H. J. Vogel. Academic Press, New York (1965)).

In addition, evolutionary information may be used to predict gene function. Functional predictions of genes can be greatly improved by focusing on how genes became similar in sequence (i.e. by evolutionary processes) rather than on the sequence similarity itself (Eisen, Genome Res. 8: 163-167 (1998)). Many specific examples exist in which gene function has been shown to correlate well with gene phylogeny (Eisen, Genome Res. 8: 163-167 (1998)). By using a phylogenetic analysis, one skilled in the art would recognize that the ability to deduce similar functions conferred by closely-related polypeptides is predictable.

When a group of related sequences are analyzed using a phylogenetic program such as CLUSTAL, closely related sequences typically cluster together or in the same clade (a group of similar genes). Groups of similar genes can also be identified with pair-wise BLAST analysis (Feng and Doolittle, J. Mol. Evol. 25: 351-360 (1987)). Analysis of groups of similar genes with similar function that fall within one clade can yield sub-sequences that are particular to the clade. These sub-sequences, known as consensus sequences, can not only be used to define the sequences within each chide, but define the functions of these genes; genes within a clade may contain paralogous sequences, or orthologous sequences that share the same function (see also, for example, Mount, Bioinformatics: Sequence and Genome Analysis Cold Spring Harbor Laboratory Press, Cold Spring Harbor, N.Y., page 543 (2001)).

To find sequences that are homologous to a reference sequence, BLAST nucleotide searches can be performed with the BLASTN program, score=100, wordlength=12, to obtain nucleotide sequences homologous to a nucleotide sequence encoding a protein of the disclosure. BLAST protein searches can be performed with the BLASTX program, score=50, wordlength=3, to obtain amino acid sequences homologous to a protein or polypeptide of the disclosure. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used.

Methods for the alignment of sequences and for the analysis of similarity and identity of polypeptide and polynucleotide sequences are well-known in the art.

As used herein "sequence identity" refers to the percentage of residues that are identical in the same positions in the sequences being analyzed. As used herein "sequence similarity" refers to the percentage of residues that have similar biophysical/biochemical characteristics in the same positions (e.g. charge, size, hydrophobicity) in the sequences being analyzed.

Methods of alignment of sequences for comparison are well-known in the art, including manual alignment and computer assisted sequence alignment and analysis. This latter approach is a preferred approach in the present disclosure, due to the increased throughput afforded by computer assisted methods. As noted below, a variety of computer programs for performing sequence alignment are available, or can be produced by one of skill.

The determination of percent sequence identity and/or similarity between any two sequences can be accomplished using a mathematical algorithm. Examples of such mathematical algorithms are the algorithm of Myers and Miller, CABIOS 4:11-17 (1988); the local homology algorithm of Smith et al., Adv. Appl. Math. 2:482 (1981); the homology alignment algorithm of Needleman and Wunsch, J. Mol. Biol. 48:443-453 (1970); the search-for-similarity-method of Pearson and Lipman, Proc. Natl. Acad. Sci. 85:2444-2448 (1988); the algorithm of Karlin and Altschul; Proc. Natl. Acad. Sci. USA 87:2264-2268 (1990), modified as in Karlin and Altschul, Proc. Natl. Acad. Sci. USA 90:5873-5877 (1993).

Computer implementations of these mathematical algorithms can be utilized for comparison of sequences to determine sequence identity and/or similarity. Such implementations include, for example: CLUSTAL in the PC/Gene program (available from Intelligenetics, Mountain View, Calif.); the AlignX program, version10.3.0 (Invitrogen, Carlsbad, Calif.) and GAP, BESTFIT, BLAST, FASTA, and TFASTA in the Wisconsin Genetics Software Package, Version 8 (available from Genetics Computer Group (GCG), 575 Science Drive; Madison; Wis., USA). Alignments using these programs can be performed using the default parameters. The CLUSTAL program is well described by Higgins et al. Gene 73:237-244 (1988); Higgins et al. CABIOS 5:151-153 (1989); Corpet et al., Nucleic Acids Res. 16:10881-90 (1988); Huang et al. CABIOS 8:155-65 (1992); and Pearson et al., Meth. Mol. Biol. 24:307-331 (1994). The BLAST programs of Altschul et al. Mol. Biol. 215:403-410 (1990) are based on the algorithm of Karlin and Altschul (1990) supra.

Polynucleotides homologous to a reference sequence can be identified by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives; solvents, etc. present in both the hybridization and wash solutions and incubations (and number thereof), as described in more detail in references cited below (e.g., Sambrook et al., Molecular Cloning: A Laboratory Manual, 2nd Ed., Vol. 1-3, Cold Spring Harbor Laboratory, Cold Spring Harbor, N.Y. ("Sambrook") (1989); Berger and Kimmel, Guide to Molecular Cloning Techniques, Methods in Enzymology, vol. 152 Academic Press, Inc., San Diego, Calif. ("Berger and Kimmel") (1987); and Anderson and Young, "Quantitative Filter Hybridisation." In: Flames and Higgins, ed., Nucleic Acid Hybridisation, A Practical Approach. Oxford; TRL Press, 73-111 (1985)).

Encompassed by the disclosure are polynucleotide sequences that are capable of hybridizing to the disclosed polynucleotide sequences and fragments thereof under various conditions of stringency (see, for example, Wahl and Berger, Methods Enzymol. 152: 399-407 (1987); and Kimmel, Methods Enzymo. 152: 507-511, (1987)). Full length cDNA, homologs, orthologs, and paralogs of polynucleotides of the present disclosure may be identified and isolated using well-known polynucleotide hybridization methods.

With regard to hybridization, conditions that are highly stringent; and means for achieving them, are well known in the art. See, for example, Sambrook et al, (1989) (supra); Berger and Kimmel (1987) pp. 467-469 (supra); and Anderson and Young (1985)(supra).

Hybridization experiments are generally conducted in a buffer of pH between 6.8 to 7.4, although the rate of hybridization is nearly independent of pH at ionic strengths likely to be used in the hybridization buffer (Anderson and Young (1985) (supra)). In addition; one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency. As a general guideline, high stringency is typically performed at $T_m-5°$ C. to $T_m-20°$ C., moderate stringency at $T_m-20°$ C. to $T_m-35°$ C. and low stringency at $T_m-35°$ C. to $T_m-50°$ C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m-25°$ C. for DNA-DNA duplex and $T_m-15°$ C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH.

Hybridization and wash conditions that may be used to bind and remove polynucleotides with less than the desired homology to the nucleic acid sequences or their complements of the present disclosure include, for example: 6×SSC and 1% SDS at 65° C.; 50% formamide, 4×SSC at 42° C.; 0.5×SSC to 2.0×SSC, 0.1% SDS at 50° C. to 65° C.; or 0.1×SSC to 2×SSC, 0.1% SDS at 50° C.-65° C.; with a first wash step of, for example, 10 minutes at about 42° C. with about 20% (v/v) formamide in 0.1×SSC, and with, for example, a subsequent wash step with 0.2×SSC and 0.1% SUS at 65° C. for 10, 20 or 30 minutes.

For identification of less closely related homologs, wash steps may be performed at a lower temperature, e.g., 50° C. An example of a low stringency wash step employs a solution and conditions of at least 25° C. in 30 mM NaCl, 3 mM trisodium citrate, and 0.1% SDS over 30 min. Greater stringency may be obtained at 42° C. in 15 mM NaCl, with 1.5 mM trisodium citrate, and 0.1% SDS over 30 min. Wash procedures will generally employ at least two final wash steps. Additional variations on these conditions will be readily apparent to those skilled in the art (see, for example, US Patent Application No. 20010010913).

If desired, one may employ wash steps of even greater stringency, including conditions of 65° C.-68° C. in a solution of 15 mM NaCl, 1.5 mM trisodium citrate, and 0.1% SDS, or about 0.2×SSC, 0.1% SDS at 65° C. and washing twice, each wash step of 10, 20 or 30 min in duration, or about 0.1×SSC, 0.1% SDS at 65° C. and washing twice for 10, 20 or 30 min. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C.

Target Nucleic Acids

Transcriptional activators of the present disclosure may be targeted to specific target nucleic acids to induce activation/expression of the target nucleic acid. In some embodiments, the transcriptional activator polypeptide is targeted to the target nucleic acid via a heterologous DNA-binding domain. In this sense, a target nucleic acid of the present disclosure is targeted based on the particular nucleotide sequence in the target nucleic acid that is recognized by the targeting portion of the DNA-binding domain. In some embodiments, transcriptional activators activate expression of a target nucleic acid by being targeted to the nucleic acid with the assistance of a guide RNA (via. CRISPR-based targeting). In some embodiments, the CRISPR-based targeting scheme may be a SunTag targeting system. With CRISPR-based targeting, a target nucleic acid of the present disclosure is targeted based on the particular nucleotide sequence in the target nucleic acid that is recognized by the targeting portion of the crRNA or guide RNA that is used according to the methods of the present disclosure.

Various types of nucleic acids may be targeted for activation of expression, as will be readily apparent to one of skill in the art. The target nucleic acid may be located within the coding region of a target gene or upstream or downstream thereof. Moreover, the target nucleic acid may reside endogenously in a target gene or may be inserted into the gene, e.g., heterologous, for example, using techniques such as homologous recombination. For example, a target gene of the present disclosure can be operably linked to a control region, such as a promoter, that contains a sequence that can be recognized by e.g. a crRNA/tracrRNA and/or a guide RNA of the present disclosure such that a transcriptional activator of the present disclosure may be targeted to that sequence. In some embodiments, the target nucleic acid is not a target of and/or does not naturally associate with the naturally-occurring transcriptional activator polypeptide (e.g. VP64, SDG2).

In some embodiments, the target nucleic acid is endogenous to the plant where the expression of one or more genes is activated according to the methods described herein. In some embodiments, the target nucleic acid is a transgene of interest that has been inserted into a plant. Methods of introducing transgenes into plants are well known in the art. Transgenes may be inserted into plants in order to provide a production system for a desired protein, or may be added to the genetic compliment in order to modulate the metabolism of a plant.

Suitable target nucleic acids will be readily apparent to one of skill in the art depending on the particular need or outcome. The target nucleic acid may be in e.g. a region of euchromatin (e.g. highly expressed gene), or the target nucleic acid may be in a region of heterochromatin (e.g. centromere DNA). Use of transcriptional activators according to the methods described herein to induce transcriptional activation in a region of heterochromatin or other highly methylated region of a plant genome may be especially useful in certain research embodiments. For example, activation of a retrotransposon in a plant genome may find use in inducing mutagenesis of other genomic regions in that genome. A target nucleic acid of the present disclosure may be methylated or it may be unmethylated.

Exemplary target genes for e.g. research or other purposes may include, for example, AS1, PHYB, DWF4, CLV3; and API. The methods of the present disclosure may also provide a quantitative approach to comparing guide RNA efficiency at activating expression of target genes using plant-based. SunTag expression systems.

Plants of the Present Disclosure

Certain aspects of the present disclosure relate to plants containing transcriptional activators that are targeted to one or more target nucleic acids in the plant in order to activate transcription and/or increase expression of the target nucleic acid.

As used herein, a "plant" refers to any of various photosynthetic, eukaryotic multi-cellular organisms of the kingdom Plantae, characteristically producing embryos, containing chloroplasts, having cellulose cell walls and lacking locomotion. As used herein, a "plant" includes any plant or part of a plant at any stage of development, including seeds, suspension cultures, plant cells, embryos, meristematic regions, callus tissue, leaves, roots, shoots, gametophytes, sporophytes, pollen, microspores, and progeny thereof. Also included are cuttings, and cell or tissue cultures. As used in conjunction with the present disclosure, plant tissue includes, for example, whole plants, plant cells, plant organs, e.g., leafs, stems, roots, meristems, plant seeds, protoplasts, callus, cell cultures, and any groups of plant cells organized into structural and/or functional units.

Any plant cell may be used in the present disclosure so long as it remains viable after being transformed with a sequence of nucleic acids. Preferably, the plant cell is not adversely affected by the transduction of the necessary nucleic acid sequences, the subsequent expression of the proteins or the resulting intermediates.

As disclosed herein, a broad range of plant types may be modified to incorporate recombinant polypeptides and/or polynucleotides of the present disclosure. Suitable plants that may be modified include both monocotyledonous (monocot) plants and dicotyledonous (dicot) plants.

Examples of suitable plants may include, for example, species of the Family Gramineae, including *Sorghum bicolor* and *Zea mays*; species of the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale*, and *Triticum*.

In some embodiments, plant cells may include, for example, those from corn (*Zea mays*), canola (*Brassica napus, Brassica rapa* ssp.), *Brassica* species useful as sources of seed oil, alfalfa (*Medicago sativa*), rice (*Oryza sativa*), rye (*Secale cereale*), Sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), duckweed (*Lemna*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucijra*), pineapple (*Ananas comosus*), *Citrus* trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), Papaya (*Carica papaya*), cashew (*Anacardium occidentale*), Macadamia (*Macadamia* spp.), almond (*Prunus amygdalus*), sugar beets (*Beta vulgaris*), sugarcane (*Saccharum* spp), oats, barley, vegetables, ornamentals, and conifers.

Examples of suitable vegetables plants may include, for example, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*).

Examples of suitable ornamental plants may include, for example, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Examples of suitable conifer plants may include, for example, loblolly pine (*Pinus taeda*), slash pine (*Pinus elliotii*), Ponderosa pine (*Pinus ponderosa*), lodgepole pine (*Pinus contorta*), Monterey pine (*Pinus radiata*), Douglas-fir (*Pseudotsuga menziesii*), Western hemlock (*Isuga canadensis*), Sitka spruce (*Picea glauca*), redwood (*Sequoia sempervirens*), silver fir (*Abies amabilis*), balsam fir (*Abies balsamea*), Western red cedar (*Thuja plicata*), and Alaska yellow-cedar (*Chamaecyparis nootkatensis*).

Examples of suitable leguminous plants may include, for example, guar, locust bean, fenugreek, soybean, garden beans, cowpea, mungbean, lima bean, fava bean, lentils, chickpea, peanuts (*Arachis* sp.), crown vetch (*Vicia* sp.), hairy vetch, adzuki bean, lupine (*Lupinus* sp.), trifolium, common bean (*Phaseolus* sp.), field bean (*Pisum* sp.), clover (*Melilotus* sp.) Lotus, trefoil, lens, and false indigo.

Examples of suitable forage and turf grass may include, for example, alfalfa (*Medicago* s sp.), orchard grass, tall fescue, perennial ryegrass, creeping bent grass, and redtop.

Examples of suitable crop plants and model plants may include, for example, *Arabidopsis*, corn, rice, alfalfa, sunflower, canola, soybean, cotton, peanut, *Sorghum*, wheat, tobacco, and *Lemna*.

The plants of the present disclosure may be genetically modified in that recombinant nucleic acids have been introduced into the plants, and as such the genetically modified plants do not occur in nature. A suitable plant of the present disclosure is one capable of expressing one or more nucleic acid constructs encoding one or more recombinant proteins. The recombinant proteins encoded by the nucleic acids may be e.g. recombinant polypeptides containing a nuclease-deficient CAS9 polypeptide (dCAS9) and a multimerized epitope, as well as recombinant polypeptides containing a transcriptional activator and an affinity polypeptide.

As used herein, the terms "transgenic plant" and "genetically modified plant" are used interchangeably and refer to a plant which contains within its genome a recombinant nucleic acid. Generally, the recombinant nucleic acid is stably integrated within the genome such that the polynucleotide is passed on to successive generations. However, in certain embodiments, the recombinant nucleic acid is transiently expressed in the plant. The recombinant nucleic acid may be integrated into the genome alone or as part of a recombinant expression cassette. "Transgenic" is used herein to include any cell, cell line, callus, tissue, plant part or plant, the genotype of which has been altered by the presence of exogenous nucleic acid including those transgenics initially so altered as well as those created by sexual crosses or asexual propagation from the initial transgenic.

"Recombinant nucleic acid" or "heterologous nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids contains two or more subsequences that are not found in the same relationship to each other in nature. For example, regarding instance (c), a recombinant nucleic acid sequence will have two or more sequences from unrelated genes arranged to make a new functional nucleic acid. Specifically, the present disclosure describes the introduction of an expression vector into a plant cell, where the expression vector contains a nucleic acid sequence coding for a protein that is not normally found in a plant cell or contains a nucleic acid coding for a protein that is normally found in a plant cell but is under the control of different regulatory sequences. With reference to the plant cell's genome, then, the nucleic acid sequence that codes for the protein is recombinant. A protein that is referred to as recombinant generally implies that it is encoded by a recombinant nucleic acid sequence which may be present in the plant cell. Recombinant proteins of the present disclosure may also be exogenously supplied directly to host cells (e.g. plant cells).

A "recombinant" polypeptide, protein, or enzyme of the present disclosure, is a polypeptide, protein, or enzyme that may be encoded by a "recombinant nucleic acid" or "heterologous nucleic acid" or "recombinant polynucleotide."

In some embodiments, the genes encoding the recombinant proteins in the plant cell may be heterologous to the plant cell. In certain embodiments, the plant cell does not naturally produce one or more polypeptides of the present disclosure, and contains heterologous nucleic acid constructs capable of expressing one or more genes necessary for producing those molecules. In certain embodiments, the plant cell does not naturally produce one or more polypeptides of the present disclosure, and is provided the one or more polypeptides through exogenous delivery of the polypeptides directly to the plant cell without the need to express a recombinant nucleic acid encoding the recombinant polypeptide in the plant cell.

Recombinant nucleic acids and/or recombinant proteins of the present disclosure may be present in host cells (e.g. plant cells). In some embodiments, recombinant nucleic acids are present in an expression vector, and the expression vector may be present in host cells (e.g. plant cells).

Expression of Recombinant Proteins in Plants

Recombinant polypeptides of the present disclosure may be introduced into plant cells via any suitable methods known in the art. For example, a recombinant polypeptide can be exogenously added to plant cells and the plant cells are maintained under conditions such that the recombinant polypeptide is involved with targeting one or more target nucleic acids to activate the expression of the target nucleic acids in the plant cells. Alternatively, a recombinant nucleic acid encoding a recombinant polypeptide of the present disclosure can be expressed in plant cells and the plant cells are maintained under conditions such that the recombinant polypeptides of the present disclosure are targeted to one or more target nucleic acids and activate the expression of the target gene in the plant cells. Additionally, in some embodiments, a recombinant polypeptide of the present disclosure may be transiently expressed in a plant via viral infection of the plant, or by introducing a recombinant polypeptide-encoding RNA into a plant to activate the expression of a target nucleic acid of interest. Methods of introducing recombinant proteins via viral infection or via the introduction of RNAs into plants are well known in the art. For example, Tobacco rattle virus (TRV) has been successfully used to introduce zinc finger nucleases in plants to cause genome modification ("Nontransgenic Genome Modification in Plant Cells", Plant Physiology 154:1079-1087 (2010)).

A recombinant nucleic acid encoding a recombinant polypeptide of the present disclosure can be expressed in a plant with any suitable plant expression vector. Typical vectors useful for expression of recombinant nucleic acids in higher plants are well known in the art and include, for example, vectors derived from the tumor-inducing (Ti) plasmid of *Agrobacterium tumefaciens* (e.g., see Rogers et al., Meth. in Enzymol. (1987) 153:253-277). These vectors are plant integrating vectors in that on transformation, the vectors integrate a portion of vector DNA into the genome of the host plant. Exemplary *A. tumefaciens* vectors useful herein are plasmids pKYLX6 and pKYLX7 (e.g., see Schardl et al., Gene (1987) 61:1-11; and Berger et al., Proc. Natl. Acad. Sci. USA (1989) 86:8402-8406); and plasmid pBI 101.2 that is available from Clontech Laboratories, Inc. (Palo Alto, Calif.).

In addition to regulatory domains, recombinant polypeptides of the present disclosure can be expressed as a fusion protein that is coupled to, for example, a maltose binding protein ("MBP"), glutathione S transferase (GST), hexahistidine, c-myc, or the FLAG epitope for ease of purification, monitoring expression, or monitoring cellular and subcellular localization.

Moreover, a recombinant nucleic acid encoding a recombinant polypeptide of the present disclosure can be modified to improve expression of the recombinant protein in plants by using codon preference. When the recombinant nucleic acid is prepared or altered synthetically, advantage can be taken of known codon preferences of the intended plant host where the nucleic acid is to be expressed. For example, recombinant nucleic acids of the present disclosure can be modified to account for the specific codon preferences and GC content preferences of monocotyledons and dicotyledons, as these preferences have been shown to differ (Murray et al., Nucl. Acids Res. (1989) 17: 477-498).

In some embodiments, recombinant polypeptides of the present disclosure can be used to create functional "over-expression" mutations in a plant by releasing repression of the target gene expression as a consequence of transcriptional activation of the target nucleic acid. Release of gene expression repression, which may lead to activation of gene expression, may be of a structural gene, one encoding a protein having for example enzymatic activity, or of a regulatory gene, e.g., one encoding a protein that in turn regulates expression of a structural gene.

The present disclosure further provides expression vectors encoding recombinant polypeptides of the present disclosure. A nucleic acid sequence coding for the desired recombinant nucleic acid of the present disclosure can be used to construct a recombinant expression vector which can be introduced into the desired host cell. A recombinant expression vector will typically contain a nucleic acid encoding a recombinant protein of the present disclosure, operably linked to transcriptional initiation regulatory sequences which will direct the transcription of the nucleic acid in the intended host cell, such as tissues of a transformed plant.

Recombinant nucleic acids e.g. encoding recombinant polypeptides of the present disclosure may be expressed on multiple expression vectors or they may be expressed on a single expression vector. In some embodiments, recombinant nucleic acids encoding (1) recombinant polypeptides containing a nuclease-deficient CAS9 polypeptide (dCAS9) and a multimerized epitope, (2) recombinant polypeptides containing a transcriptional activator and an affinity polypeptide, and (3) a crRNA and a tracrRNA, or fusions thereof (guide RNA), are all expressed on a single vector.

For example, plant expression vectors may include (1) a cloned gene under the transcriptional control of 5 and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

In some embodiments, an expression vector containing recombinant nucleic acids of the present disclosure may contain a plant-specific TBS insulator sequence having a nucleic acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% nucleic acid sequence identity to the nucleic acid sequence of SEQ ID NO: 10.

In some embodiments, expression of a nucleic acid of the present disclosure may be driven (in operable linkage) with a promoter (e.g. a promoter functional in plants or a plant-specific promoter). A plant promoter, or functional fragment thereof, can be employed to control the expression of a recombinant nucleic acid of the present disclosure in regenerated plants. The selection of the promoter used in expression vectors will determine the spatial and temporal expression pattern of the recombinant nucleic acid in the modified plant, e.g., the nucleic acid encoding the recombinant polypeptide of the present disclosure is only expressed in the desired tissue or at a certain time in plant development or growth. Certain promoters will express recombinant nucleic acids in all plant tissues and are active under most environmental conditions and states of development or cell differentiation (i.e., constitutive promoters). Other promoters will express recombinant nucleic acids in specific cell types (such as leaf epidermal cells, mesophyll cells, root cortex cells) or in specific tissues or organs (roots, leaves or flowers; for example) and the selection will reflect the desired location of accumulation of the gene product. Alternatively, the selected promoter may drive expression of the recombinant nucleic acid under various inducing conditions.

Examples of suitable constitutive promoters may include, for example, the core promoter of the Rsyn7, the core CaMV 35S promoter (Odell et al., Nature (1985) 313:810-812), CaMV 19S (Lawton et al., 1987), rice actin (Wang et al., 1992; U.S. Pat. No. 5,641,876; and McElroy et al., Plant Cell (1985) 2:163-171); ubiquitin (Christensen et al., Plant Mol. Biol. (1989) 12:619-632; and Christensen et al., Plant Mol. Biol. (1992) 18:675-689), pEMU (Last et al., Theor. Appl. Genet. (1991) 81:581-588), MAS (Velton et al., EMBO J. (1984) 3:2723-2730), nos (Ebert et al., 1987), Adh (Walker et al.; 1987), the P- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the pEmu promoter, the rubisco promoter, the GRP 1-8 promoter, and other transcription initiation regions from various plant genes known to those of skilled artisans, and constitutive promoters described in, for example, U.S. Pat. Nos. 5,608,149; 5,608,144; 5,604,121; 5,569,597; 5,466,785; 5,399,680; 5,268,463; and 5,608,142.

In some embodiments, expression of a nucleic acid of the present disclosure may be driven (in operable linkage) with a UBQ10 promoter. In some embodiments, expression of a nucleic acid of the present disclosure may be driven (in operable linkage) with a promoter having a nucleic acid sequence with at least about 20%, at least about 25%, at least about 30%, at least about 40%; at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% nucleic acid sequence identity to the nucleic acid sequence of SEQ ID NO: 2.

Examples of suitable tissue specific promoters may include, for example, the lectin promoter (Vodkin et al., 1983; Lindstrom et al., 1990), the corn alcohol dehydrogenase 1 promoter (Vogel et al., 1989; Dennis et al., 1984), the corn light harvesting complex promoter (Simpson, 1986; Bansal et al., 1992); the corn heat shock protein promoter (Odell et al., Nature (1985) 313:810-812; Rochester et al., 1986), the pea small subunit RuBP carboxylase promoter (Poulsen et al., 1986; Cashmore et al., 1983), the Ti plasmid mannopine synthase promoter (Langridge et al., 1989), the Ti plasmid nopaline synthase promoter (Langridge et al., 1989), the *Petunia chalcone* isomerase promoter (Van Tunen et al., 1988), the bean glycine rich protein 1 promoter (Keller et al., 1989), the truncated CaMV 35s promoter (Odell et al., Nature (1985) 313:810-812), the potato patatin promoter (Wenzler et al., 1989), the root cell promoter (Conkling et al., 1990); the maize zein promoter (Reina et al., 1990; Kriz et al., 1987; Wandelt and Feix, 1989; Langridge and Feix, 1983; Reina et al., 1990), the globulin-1 promoter (Belanger and Kriz et al., 1991), the α-tubulin promoter, the cab promoter (Sullivan et al., 1989), the PEPCase promoter (Hudspeth & Grula, 1989), the R gene complex-associated promoters (Chandler et al., 1989), and the chalcone synthase promoters (Franken et al., 1991).

Alternatively, the plant promoter can direct expression of a recombinant nucleic acid of the present disclosure in a specific tissue or may be otherwise under more precise environmental or developmental control. Such promoters are referred to here as "inducible" promoters. Environmental conditions that may affect transcription by inducible promoters include, for example, pathogen attack, anaerobic conditions, or the presence of light. Examples of inducible promoters include, for example, the AdhI promoter which is inducible by hypoxia or cold stress; the Hsp70 promoter which is inducible by heat stress, and the PPDK promoter which is inducible by light. Examples of promoters under developmental control include, for example, promoters that initiate transcription only, or preferentially, in certain tissues, such as leaves, roots, fruit, seeds, or flowers. An exemplary promoter is the anther specific promoter 5126 (U.S. Pat. Nos. 5,689,049 and 5,689,051). The operation of a promoter may also vary depending on its location in the genome. Thus, an inducible promoter may become fully or partially constitutive in certain locations.

Moreover, any combination of a constitutive or inducible promoter, and a non-tissue specific or tissue specific promoter may be used to control the expression of various recombinant polypeptides of the present disclosure.

The recombinant nucleic acids of the present disclosure and/or a vector housing a recombinant nucleic acid of the present disclosure, may also contain a regulatory sequence that serves as a 3' terminator sequence. One of skill in the art would readily recognize a variety of terminators that may be used in the recombinant nucleic acids of the present disclosure. For example, a recombinant nucleic acid of the present disclosure may contain a 3' NOS terminator.

In some embodiments, recombinant nucleic acids of the present disclosure contain a transcriptional termination site. Transcription termination sites may include, for example, OCS terminators and NOS terminators.

In some embodiments, recombinant nucleic acids of the present disclosure contain a transcriptional termination site having a nucleic acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% nucleic acid sequence identity to the nucleic acid sequence of SEQ ID NO: 9.

In some embodiments, recombinant nucleic acids of the present disclosure contain a transcriptional termination site having a nucleic acid sequence with at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% nucleic acid sequence identity to the nucleic acid sequence of SEQ ID NO: 26.

Plant transformation protocols as well as protocols for introducing recombinant nucleic acids of the present disclosure into plants may vary depending on the type of plant or plant cell, e.g., monocot or dicot, targeted for transformation. Suitable methods of introducing recombinant nucleic acids of the present disclosure into plant cells and subsequent insertion into the plant genome include, for example, microinjection (Crossway et al., Biotechniques (1986) 4:320-334), electroporation (Riggs et al., Proc. Natl. Acad Sci. USA (1986) 83:5602-5606), *Agrobacterium*-mediated transformation (U.S. Pat. No. 5,563,055), direct gene transfer (Paszkowski et al., EMBO J. (1984) 3:2717-2722), and ballistic particle acceleration (U.S. Pat. No. 4,945,050; Tomes et al. (1995). "Direct DNA Transfer into Intact Plant Cells via Microprojectile Bombardment," in Plant Cell, Tissue, and Organ Culture: Fundamental Methods; ed. Gamborg and Phillips (Springer-Verlag, Berlin); and McCabe et al., Biotechnology (1988) 6:923-926).

Additionally, recombinant polypeptides of the present disclosure can be targeted to a specific organelle within a plant cell. Targeting can be achieved by providing the recombinant protein with an appropriate targeting peptide sequence. Examples of such targeting peptides include, for example, secretory signal peptides (for secretion or cell wall or membrane targeting), plastid transit peptides, chloroplast transit peptides, mitochondrial target peptides, vacuole targeting peptides, nuclear targeting peptides, and the like (e.g., see Reiss et al., Mol. Gen. Genet. (1987) 209(1):116-121; Settles and Martienssen, Trends Cell Biol (1998) 12:494-501; Scott et al, J Biol Chem (2000) 10:1074; and Luque and Correas, J Cell Sci (2000) 113:2485-2495).

The modified plant may be grown into plants in accordance with conventional ways (e.g., see McCormick et al., Plant Cell. Reports (1986) 81-84). These plants may then be grown, and pollinated with either the same transformed strain or different strains, with the resulting hybrid having the desired phenotypic characteristic. Two or more generations may be grown to ensure that the subject phenotypic characteristic is stably maintained and inherited and then seeds harvested to ensure the desired phenotype or other property has been achieved.

The present disclosure also provides plants derived from plants having increased or activated expression as a consequence of the methods of the present disclosure. A plant having increased or activated expression as a consequence of the methods of the present disclosure may be crossed with itself or with another plant to produce an F1 plant. In some embodiments, one or more of the resulting F1 plants may also have increased expression of the target nucleic acid and/or reduced methylation of the target nucleic acid.

Further provided are methods of screening plants derived from plants having increased or activated expression as a consequence of the methods of the present disclosure. In some embodiments, the derived plants (e.g. F1 or F2 plants resulting from or derived from crossing the plant having increased or activated expression as a consequence of the methods of the present disclosure with another plant) can be selected from a population of derived plants. For example, provided are methods of selecting one or more of the derived plants that (i) lack recombinant nucleic acids, and (ii) have increased or activated expression of the target nucleic acid.

Methods of Activating or Increasing Expression of a Target Nucleic Acid in Plants Growing conditions sufficient for the recombinant polypeptides of the present disclosure to be expressed in the plant to be targeted to and activate the expression of one or more target nucleic acids of the present disclosure are well known in the art and include any suitable growing conditions disclosed herein. Typically, the plant is grown under conditions sufficient to express a recombinant polypeptide of the present disclosure, and for the expressed recombinant polypeptides to be localized to the nucleus of cells of the plant in order to be targeted to and activate the expression of the target nucleic acids (if those targets are present in the nucleus). Generally, the conditions sufficient for the expression of the recombinant polypeptide will depend on the promoter used to control the expression of the recombinant polypeptide. For example, if an inducible promoter is utilized, expression of the recombinant polypeptide in a plant will require that the plant to be grown in the presence of the inducer.

As noted above, growing conditions sufficient for the recombinant polypeptides of the present disclosure to be expressed in the plant to be targeted to and activate the expression of one or more target nucleic acids may vary depending on a number of factors (e.g. species of plant, use of inducible promoter, etc.). Suitable growing conditions may include, for example, ambient environmental conditions, standard greenhouse conditions, growth in long days under standard environmental conditions (e.g. 16 hours of light, 8 hours of dark), growth in 12 hour light: 12 hour dark day/night cycles, etc.

Various time frames may be used to observe activation in expression of a target nucleic acid according to the methods of the present disclosure. Plants may be observed/assayed for activation in expression of a target nucleic acid after, for example, about 5 days of growth, about 10 days of growth, about 15 days after growth, about 20 days after growth, about 25 days after growth, about 30 days after growth, about 35 days after growth, about 40 days after growth, about 50 days after growth, or 55 days or more of growth.

A target nucleic acid of the present disclosure in a plant cell housing recombinant polypeptides of the present disclosure may have its expression increased/upregulated/activated by at least about 5%, at least about 10%, at least about 15%, at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% as compared to a corresponding control. Various controls will be readily apparent to one of skill in the art. For example, a control may be a corresponding plant or plant cell that does not contain recombinant polypeptides of the present disclosure (e.g. wild-type plant or plant cell).

A target nucleic acid of the present disclosure may have its expression increased/upregulated/activated as compared to a corresponding control nucleic acid. A target nucleic acid may have its expression increased/upregulated/activated at least about 1-fold, at least about 2-fold, at least about 3-fold, at least about 4-fold, at least about 5-fold, at least about 10-fold, at least about 15-fold, at least about 20-fold, at leak about 25-fold, at least about 30-fold, at least about 40-fold, at least about 50-fold, at least about 75-fold, at least about 100-fold, at least about 150-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 1,250-fold, at least about 1,500-fold, at least about 1,750-fold, at least about 2,000-fold, at least about 2,500-fold, at least about 3,000-fold, at least about 3,500-fold, at least about 4,000-fold, at least about 4,500-fold, at least about 5,000-fold, at least about 5,500-fold, at least about 6,000-fold, at least about 6,500-fold, at least about 7,000-fold, at least about 7,500-fold, at least about 8,000-fold, at least about 8,500-fold, at least about 9,000-fold, at least about 9,500-fold, at least about 10,000-fold, at least about 12,000-fold, at least about 14,00-fold, at least about 16,000-fold, at least about 18,000-fold, or at least about 20,000-fold or more as compared to a corresponding control nucleic acid. In some embodiments, a target nucleic acid may have its expression upregulated in the range of about 1,000-fold to about 10,000-fold as compared to a corresponding control nucleic acid. As stated above, various controls will be readily apparent to one of skill in the art. For example, a control nucleic acid may be a corresponding nucleic acid from a plant or plant cell that does not contain a nucleic acid encoding a recombinant polypeptide of the present disclosure.

In some embodiments, nucleic acids targeted by a transcriptional activator polypeptide (e.g. SDG2) according to the methods of the present disclosure may experience a reduction or loss in DNA methylation at and/or in proximity of the targeted nucleic acid after the transcriptional activator polypeptide has been targeted to the target nucleic acid.

A target nucleic acid of the present disclosure in a plant cell housing a recombinant transcriptional activator polypeptide of the present disclosure may have its level of methylation reduced by at least about 5%, at least about 10%, at least about 15%, at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% as compared to a corresponding control. Various controls will be readily apparent to one of skill in the art. For example, a control may be a corresponding plant or plant cell that does not contain a nucleic acid encoding a recombinant transcriptional activator polypeptide of the present disclosure (e.g. a wild-type plant or plant cell).

A target nucleic acid of the present disclosure having reduced methylation as compared to a corresponding control nucleic acid (as a consequence of the methods of the present disclosure) may exhibit a reduction in methylation over a number of nucleotides including and adjacent to the targeted nucleotide sequences in a target nucleic acid. For example, the reduction in methylation may be present over one nucleotide, over about 5 nucleotides, over about 10 nucleotides, over about 15 nucleotides, over about 20 nucleotides, over about 25 nucleotides, over about 30 nucleotides, over about 35 nucleotides, over about 40 nucleotides, over about 45 nucleotides, over about 50 nucleotides, over about 55 nucleotides, over about 60 nucleotides, over about 75 nucleotides, over about 100 nucleotides, over about 125 nucleotides, over about 150 nucleotides, over about 175 nucleotides, over about 200 nucleotides, over about 225 nucleotides, over about 250 nucleotides, over about 275 nucleotides, over about 300 nucleotides, over about 350 nucleotides, over about 400 nucleotides, over about 450 nucleotides, over about 500 nucleotides, over about 600 nucleotides, over about 700 nucleotides, over about 800 nucleotides, over about 900 nucleotides, over about 1,000 nucleotides, over about 1,500 nucleotides, over about 2,000 nucleotides, over about 2,500 nucleotides, or over about 3,000 nucleotides or more as compared to corresponding nucleotides in a corresponding control nucleic acid. The reduction in methylation of nucleotides adjacent to the target nucleotides in the target nucleic acid may occur in nucleotides that are 5' to the target nucleotide sequences, 3' to the target nucleotides sequences, or both 5' and 3' to the target nucleotide sequences.

Reduced methylation of a target nucleic acid induced by targeting a recombinant transcriptional activator polypeptide to the target nucleic acid may be stable in plants even in the absence of the recombinant transcriptional activator polypeptide in the plant. Accordingly, the methods of the present disclosure may allow one or more target nucleic acids in a plant to maintain a reduced level of methylation after a nucleic acid encoding a recombinant transcriptional activator polypeptide has been crossed out or otherwise removed from the plant. For example, after targeting a particular genomic region with a recombinant transcriptional activator polypeptide according to the methods of the present disclosure, the reduced level of methylation of the targeted region may remain stable even after crossing away the transgenes. It is an object of the present disclosure to provide plants having reduced methylation of one or more target nucleic acids according to the methods of the present disclosure. As the methods of the present disclosure may allow one or more target nucleic acids in a plant to remain in their state of reduced methylation after a recombinant transcriptional activator polynucleotide encoding a recombinant transcriptional activator polypeptide of the present disclosure has been crossed out of the plant, the progeny plants of these plants may have reduced methylation of one or more target nucleic acids even in the absence of the recombinant polynucleotides that produce the recombinant polypeptides of the present disclosure.

Comparisons in the present disclosure may also be in reference to corresponding control plants. Various control plants will be readily apparent to one of skill in the art. For example, a control plant may be a plant that does not contain one or more of: (1) a recombinant polypeptide including a nuclease-deficient CAS9 polypeptide (dCAS9) or fragment thereof and a multimerized epitope, (2) a recombinant polypeptide including a transcriptional activator and an affinity polypeptide, and/or (3) a crRNA and a tracrRNA, or fusions thereof.

Methods of probing the expression level of a nucleic acid are well-known to those of skill in the art. For example, qRT-PCR analysis may be used to determine the expression level of a population of nucleic acids isolated from a nucleic acid-containing sample (e.g. plants, plant tissues, or plant cells).

Methods of probing the methylation status of a nucleic acid are well-known to those of skill in the art. For example, bisulfite sequencing and nucleic acid analysis may be used to determine the methylation status, on a nucleotide-by-nucleotide basis, of a population of nucleic acids isolated from a nucleic acid-containing sample (e.g. plants, plant tissues, or plant cells).

It is to be understood that while the present disclosure has been described in conjunction with the preferred specific embodiments thereof, the foregoing description is intended to illustrate and not limit the scope of the present disclosure. Other aspects, advantages, and modifications within the scope of the present disclosure will be apparent to those skilled in the art to which the present disclosure pertains.

EXAMPLES

The following examples are offered to illustrate provided embodiments and are not intended to limit the scope of the present disclosure.

Example 1: SunTag VP64 System for Targeted Gene Activation in Plants

This Example demonstrates the targeting of the VP64 transcriptional activator, using a SunTag system, to specific loci in plants and the subsequent transcriptional activation of the targeted loci.

Introduction

Recently, a technique called SunTag was developed to recruit many effector proteins simultaneously to a location via one dCAS9 protein. In this way, there is an amplification of the effect of targeting, and improved magnitude of gene regulation (Tanenbaum et al, 2014). Tanenbaum et al. described that a dCas9 protein was fused to an unstructured peptide that contains up to 24 copies of the GCN4 epitope. A single chain antibody, scFV, designed to bind this peptide sequence with high affinity and specificity, was fused to an effector protein for gene regulation. Co-expression of the two components allows binding of up to 24 copies of the antibody-fused effector protein to each CAS9-GCN4 fusion protein. In the case of VP64 as an effector protein, this procedure resulted in very high activation of gene expression compared to simple CAS9-VP64 fusion proteins.

Although the SunTag system described above (Tanenbaum et al, 2014) resulted in targeted activation of gene expression, this system was designed for and tested in mammalian cells, and such a method has not been shown to work in plants. Moreover, given the multitude of differences in the cellular environment between plant and animal cells, as well as the differences in nucleic acid structure and function between plant and animal cells, it was not known that such a method could even work in plants.

The present Example describes Applicant's development of a SunTag system capable of specifically activating target gene expression in plants.

Materials and Methods

Plasmid Construction

The SunTag system described in Tanenbaum et al, 2014 was designed to upregulate/activate genes in mammalian systems. Therefore, transferring this system directly into plants would fail to upregulate/activate selected genomic targets. New SunTag constructs thus needed to be constructed and tested in plants as a first step to seeing if this system could be used to activate gene expression of a specific locus in plants.

The SunTag VP64 constructs as described in Tanenbaum et al, 2014 were ordered from Addgene (pHRdSV40-dCas9-10×GCN4_v4-P2A-BFP and pHRdSV40-scFv-GCN4-sfGFP-VP64-GB1-NLS). In order for the SunTag system to successfully be expressed and work in plants, various components of the system needed to be modified and adapted for use in plants.

Plant-specific promoters and transcriptional terminators were used in the new construct, although a human codon-optimized, nuclease-deficient (hdCAS9) was also used. Human codon optimized dCas9 expression, which is fused to one HA tag, two nuclear localization signals, and a linker followed by a 10× epitope tail (10×GCN4), was driven by the plant UBIQUITIN10 (UBQ10) promoter, which is ubiquitously expressed in *Arabidopsis*. The UBQ10 promoter preceding dCas9-10×GCN4 was followed by an Omega translational enhancer sequence. The single chain antibody (scFV) portion of the system, which was also driven by the UBQ10 promoter, was fused to superfolder UP, followed by a linker, VP64, another linker, an NLS that was added for plant nuclear localization, GB1, and a REX NIS The dCas9-10×GCN4 and scFv-VP64 cassettes were separated by a plant-specific TBS insulator sequence (SEQ ID NO: 10). gRNA expression was controlled by the Pol III specific U6 promoter and termination was controlled by the Poll III termination sequence.

All features of the constructed SunTag VP64 system were present on a single vector. The dCAS9-10×GCN4 cassette, scFv-VP64 cassette, and respective gRNA cassette were cloned into a binary vector using In-Fusion cloning. Only one respective gRNA cassette was present in the SunTag vector transformed into plants. For evaluating the different gRNA cassettes, different independent SunTag vectors were constructed, each housing a respective gRNA cassette. A schematic of the expression cassettes for the SunTag VP64 system is presented in FIG. 1.

Construction of dCAS9-10×GCN4 Cassette

The dCAS9-10×GCN4 portion of the SunTag VP64 vector that was constructed is contained in expression cassette pUBQ10_Omega RBC_dCas9_1×HA2×NLS_flexible linker_10×GCN4 (nucleic acid sequence presented in SEQ ID NO: 1). This cassette contains the following features and nucleic acid sequences are provided: UBQ10 promoter (SEQ ID NO: 2), Omega RBC translation enhancer (SEQ ID NO: 3), dCas9 (SEQ ID NO: 4), 1×HA (SEQ ID NO: 5), 2×NLS (SEQ ID NO: 6), flexible linker (SEQ ID NO: 7), 10×GCN4 (SEQ ID NO: 8). The expression cassette further included an OCS terminator (SEQ ID NO: 9).

This expression cassette produces a recombinant dCas9-10×GCN4 fusion protein (SEQ ID NO: 11): dCAS9-1×HA-2×NLS-flexible linker-10×GCN4. The amino acid sequences of features present in the recombinant fusion protein expressed from this expression cassette are: dCAS9 (SEQ 11) NO: 12), 1×HA (SEQ ID NO: 13), 2×NLS (SEQ ID NO: 14), flexible linker (SEQ ID NO: 15), and 10×GCN4 (SEQ ID NO: 16).

Construction of scFv-VP64 Cassette

The scFv-VP64 portion of the SunTag VP64 vector that was constructed is contained in expression cassette pUBQ10-scFv-sfGFP-glycine linker-VP64-glycine linker-SV40 type NLS-GB1-REX NLS-NOS terminator (nucleic acid sequence presented in SEQ ID NO: 17). This cassette contains the following features and nucleic acid sequences are provided: UBQ10 promoter (SEQ ID NO: 18), scFv single chain antibody (SEQ ID NO: 19), sfGFP (SEQ ID NO: 20), glycine linker (SEQ ID NO: 21), VP64 (SEQ ID NO: 22), glycine linker (SEQ ID NO: 21), SV40 type NES (SEQ NO: 23), GB1 (SEQ ID NO: 24), REX NLS (SEQ ID NO: 25), and NOS terminator (SEQ ID NO: 26).

This expression cassette produces a recombinant scFv-VP64 fusion protein (SEQ ID NO: 27): scFv-sfGFP-glycine linker-VP64-glycine linker-SV40 type NLS-GB1-REX NLS. The amino acid sequences of features present in the recombinant fusion protein expressed from this expression cassette are: scFv (SEQ ID NO: 28), sfGFP (SEQ ID NO: 29), glycine linker (SEQ ID NO: 30), VP64 (SEQ ID NO: 31), SV40-type NLS (SEQ ID NO: 32), GB1 (SEQ ID NO: 33), and REX NLS (SEQ ID NO: 34).

Construction of gRNA Cassettes

For targeting the FWA gene promoter, a number of different gRNA expression cassettes were constructed. One such expression cassette was U6:gRNA4 (nucleic acid sequence presented in SEQ ID NO: 35). This cassette contains the following features and nucleic acid sequences are provided: U6 promoter (SEQ ID NO: 36), protospacer 44 (SEQ ID NO: 37), gRNA backbone (SEQ ID NO: 38), and PolIII terminator (SEQ ID NO: 39).

A similar expression cassette that was constructed was U6:gRNA17 (nucleic acid sequence presented in SEQ ID NO: 40). This cassette contains the following features and nucleic acid sequences are provided: U6 promoter (SEQ ID NO: 36), protospacer #17 (SEQ ID NO: 41), gRNA backbone (SEQ ID NO: 38), and Pol III terminator (SEQ ID NO: 39).

For targeting the GIS gene promoter, a tRNA:gRNA expression cassette was constructed. This cassette contained two different gRNA molecules targeting different regions of the GIS promoter. The nucleic acid sequence for the GIS tRNA:gRNA expression cassette is presented in SEQ ID NO: 42. The structure of this cassette is as follows: U6 promoter-tRNA-protospacer #1-gRNA backbone-tRNA-protospacer #2-gRNA backbone-Pol III terminator. Nucleic acid sequences of the features include U6 promoter (SEQ ID NO: 36), tRNA (SEQ ID NO: 43), protospacer #1 (SEQ ID NO: 44), gRNA backbone (SEQ ID NO: 38), protospacer #2 (SEQ ID NO: 45), and Pol III terminator (SEQ ID NO: 39).

Design of tRNA:gRNA Cassette for Targeting the FWA Promoter

A tRNA:gRNA expression cassette was designed for targeting the FWA promoter.

This cassette has a similar structure as the tRNA:gRNA cassette described above for the GIS promoter. This cassette for targeting FWA includes two different gRNA molecules and uses protospacer #4 and protospacer #17 as described above. The sequence of this cassette is presented in SEQ ID NO: 46, Construct Transformation into *Arabidopsis*

The vector described above housing the SunTag VP64 expression system was transformed into *Agrobacterium*. The vector was then introduced into Col-0 wild-type *Arabidopsis thaliana* plants using *Agrobacterium*-mediated transformation via the floral dip method. T1 transgenic plants were selected based on their resistance to Hygromycin.

Flowering Time Assays

Flowering time in plants was scored by measuring the number of rosette and caulinar leaves.

Fluorescent Microscopy

Visualization of sfGFP fluorescence was performed using a Zeiss confocal microscope and recommended wavelengths to visualize GFP fluorescence. Leaf sections were taken from transgenic SunTag VP64 plants and placed on microscope slides for visualization. Other tissues imaged included roots. In the latter case, seeds from transgenic plants were plated on plates containing Murashige and Skoog (MS) media and Hygromycin, and plates were then grown vertically to allow roots to extend. Once grown, seedlings were placed on microscope slides and GFP was visualized using a confocal microscope.

qRT-PCR qRT-PCR assays were conducted according to standard methods and the manufacturer's protocol. The Superscript III First-Strand synthesis kit (Invitrogen) was used for these assays.

Bisulfate Sequencing

BS-Seq libraries were generated as previously reported (Cokes et al., 2008) and all libraries were sequenced using the HiSeq 2000 platform following manufacturer instructions (Illumina) at a length of 50 bp. Bisulfite-Seq (BS-Seq) reads were aligned to the TAIR10 version of the *Arabidopsis thaliana* reference genome using BS-seeker. For BS-Seq, up to 2 mismatches were allowed and only uniquely mapped reads were used.

Chromatin Immunoprecipitation (ChIP) and ChIP-Seq

Transgenic SunTag VP64 seeds were plated on MS media and grown. Tissue was collected and two grams were used to grind the tissue. Nuclear Isolation Buffer, protease inhibitors, and 1% formaldehyde was then added to the powder. This solution was incubated at room temperature on a rotator for 10 minutes. Glycine was then added to stop crosslinking. The solution was filtered, spun down, and the resulting pellet was resuspended with extraction buffer 2+ inhibitors. This was spun down, and the resulting pellet was resuspended with extraction buffer 3+ inhibitors. This was spun and resuspended with Nuclear Lysis Buffer. The solution was moved to a new tube and diluted with CUP dilution buffer. Samples were then sonicated (30 seconds on, 30 seconds off at maximum power for 15 minutes). dCas9 and the SunTag system were then immunoprecipitated using an anti-HA antibody. Samples were then washed and eluted. DNA was then extracted using phenol-chloroform and libraries were then made for sequencing by following the procedures recommended by the NuGEN kit used. Sequencing reads were then aligned using bowtie2.

Results

Figure 2A:
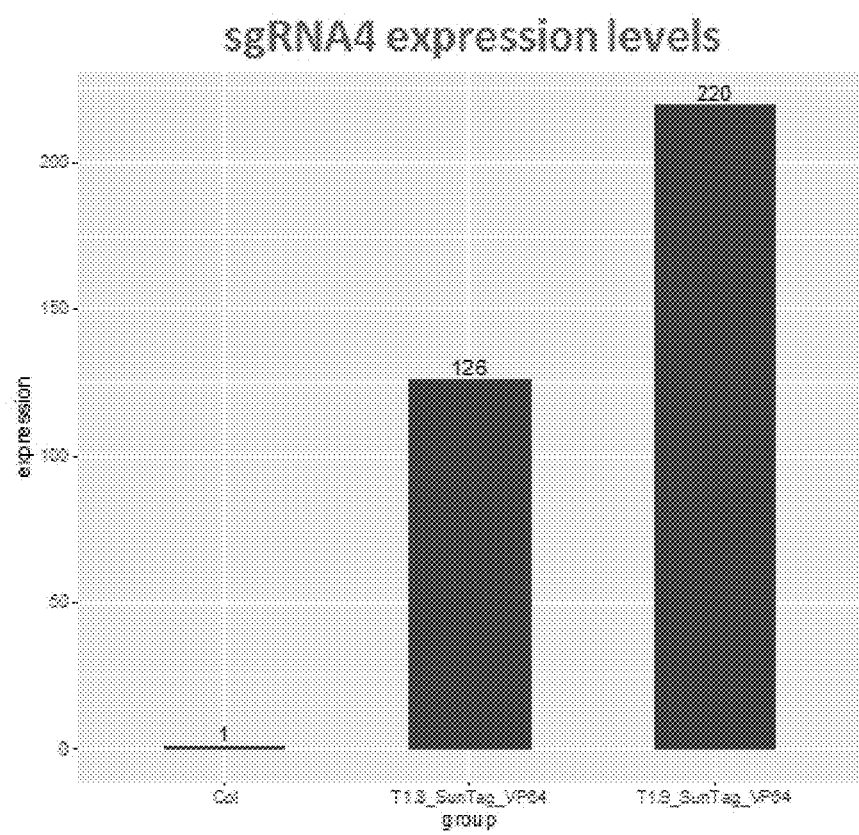
FIG. 2A-FIG. 2B illustrates expression levels of sgRNA4 (FIG. 2A) and dCAS9 (FIG. 2B) in two independent T1 lines housing the SunTag VP64 construct, as well as in wild-type plants.
Figure 2B:
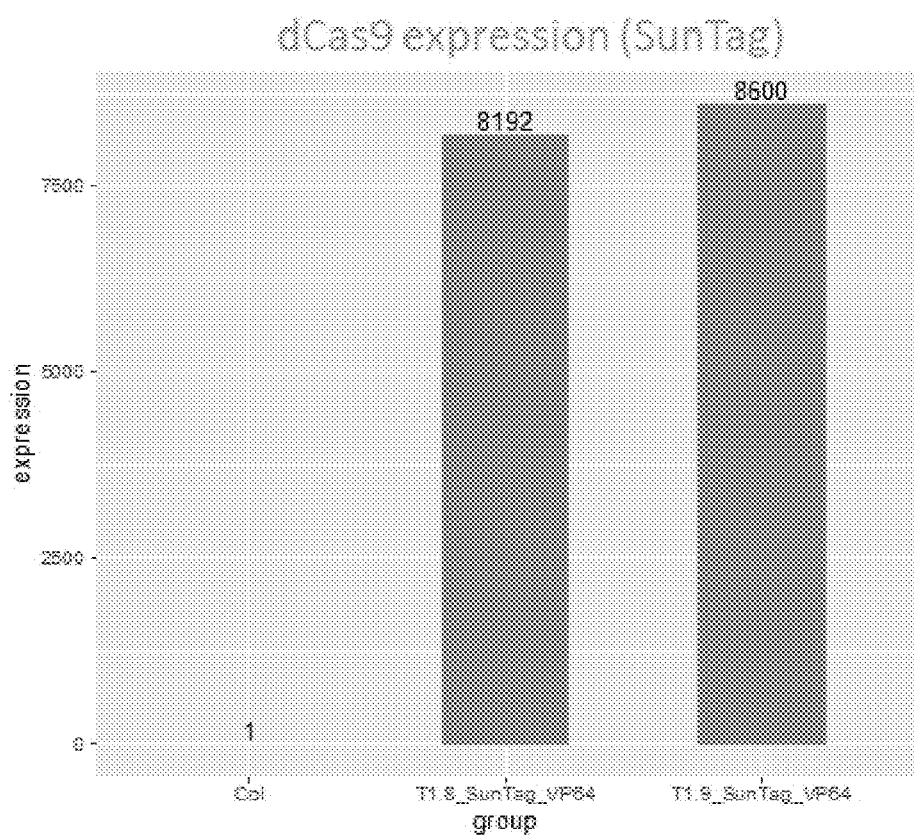

Evaluating Component Expression qRT-PCR of plants housing the SunTag VP64 expression system was performed to determine if the various components were being properly expressed. Specifically, expression of the guide RNAs and dCAS9 was evaluated as a proxy for expression of the system. As shown in FIG. 2A and FIG. 2B, it was found that both sgRNA4 and dCAS9 in the T1 plants were being expressed.

Evaluating Component Nuclear Localization

After determining that the components of the SunTag VP64 expression system were being expressed in T1 plants as described above, plants were evaluated using fluorescent microscopy to determine if the scFv-VP64 fusion protein was being targeted to the nucleus well as to probe proper production of the fusion protein). Nuclear localization was evaluated using transient expression assays and fluorescent microscopy analysis in *N. benthamiana* plants transfected with the SunTag VP64 vector. Because the scFv-VP64 fusion protein also contained sfGFP, probing for GFP nuclear localization provides a read-out of nuclear localization of the fusion protein.

Figure 3:
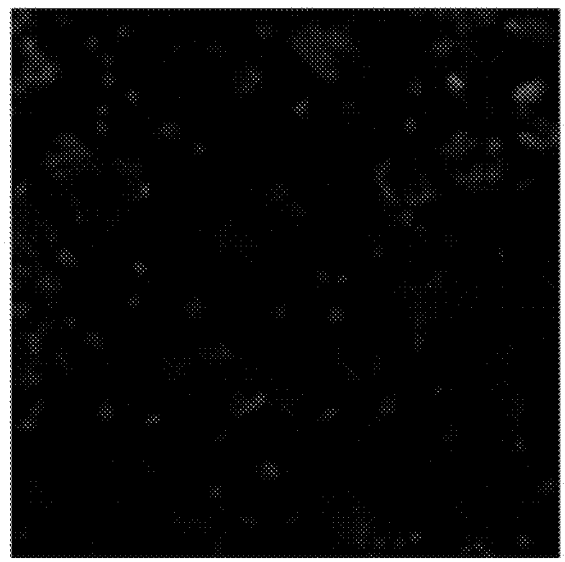
FIG. 3 illustrates fluorescence microscopy of N. benthamiana plants transfected with the iteration of the SunTag VP64 vector where VP64 was fused to the NLS from Tanenbaum et al, 2014.
Figure 3:
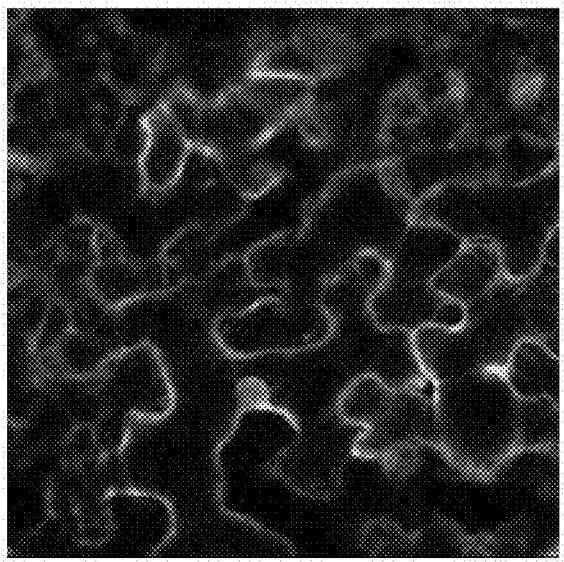
Figure 3:
Figure 3:
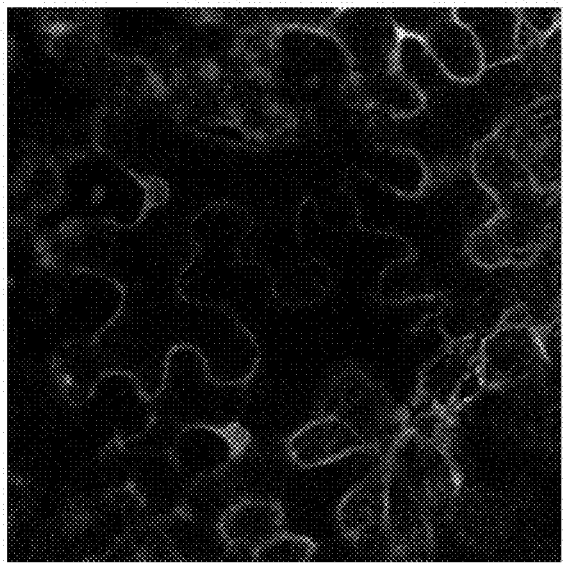

In an earlier iteration of the SunTag VP64 vector that was constructed, the first nuclear localization signal (NLS) following VP64 in the scFv-VP64 cassette (added to C-terminus of VP64) was the same as that used in Tanenbaum et al, 2014. However, with that NLS, the scFv-VP64 fusion protein did not localize to the nucleus in plants evaluated (FIG. 3).

Figure 4:
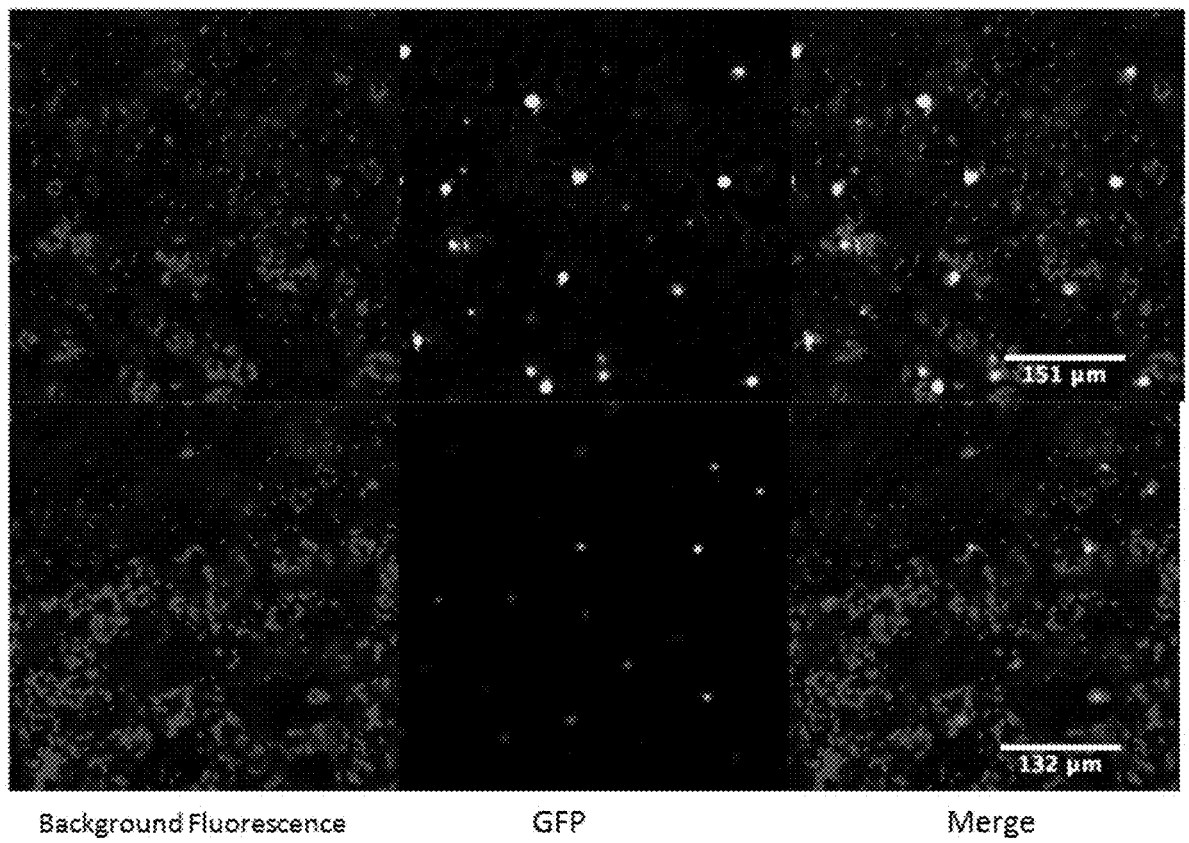
FIG. 4 illustrates fluorescence microscopy of N. benthamiana plants transfected with the iteration of the SunTag VP64 vector where VP64 was fused to an SV40-type NLS.

The earlier SunTag VP64 vector was thus re-designed to replace the failed NLS described above with a linker followed by a modified SV40-type NLS. This is the vector described above in the Materials and Methods. T1 plants housing this SunTag VP64 vector were similarly evaluated for nuclear localization of the scFv-VP64 fusion protein. As can be seen in FIG. 4, the SV40-type NLS was able to facilitate nuclear localization of the scFv-VP64 fusion protein.

Figure 5:
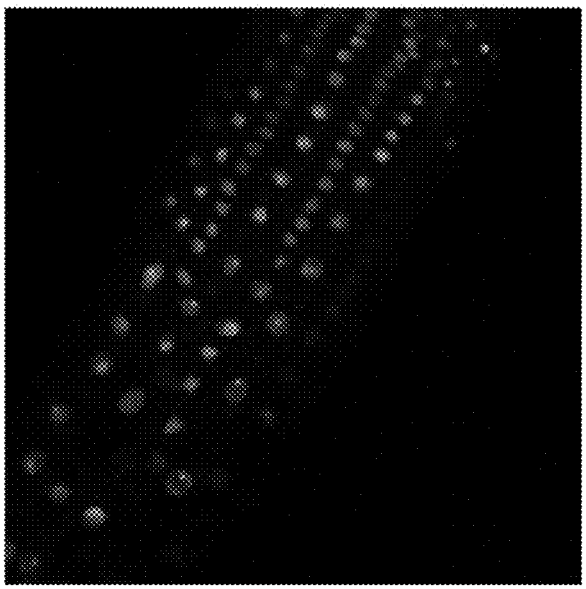
FIG. 5 illustrates fluorescence microscopy of T2 A. thaliana plants transformed with the iteration of the SunTag VP64 vector where VP64 was fused to an SV40-type NLS. Tissue shown is root tissue.
Figure 5:
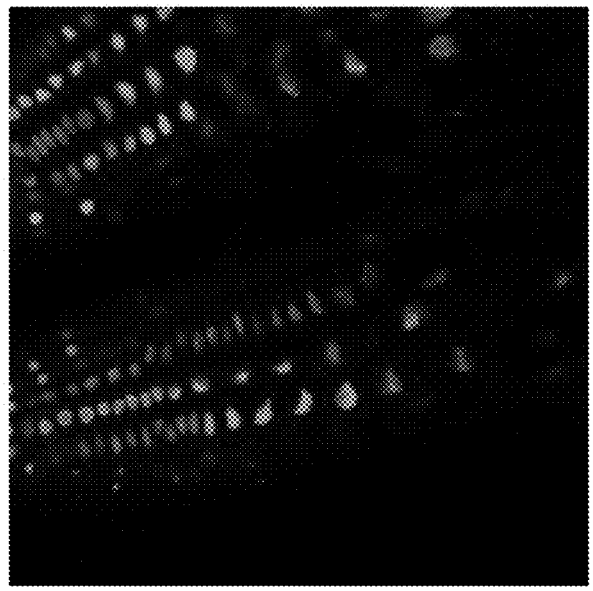

Nuclear localization of the scFv-VP64 fusion protein containing the SV40-type NLS was also evaluated in T2 *A. thaliana* plants housing the SunTag VP64 construct. The roots of these plants were evaluated for nuclear localization. As can be seen in FIG. 5, the SV40-type NLS was able to facilitate nuclear localization of the sav-VP64 fusion protein.

Activation of FWA Expression Using gRNA4

Following confirmation that the SunTag VP64 expression system components were being expressed and localized to the nucleus as described above, various plant lines were evaluated for whether this system could activate expression of a targeted gene. Various T1 and/or T2 lines housing the SunTag VP64 construct that contains gRNA4 (which targets the FWA promoter) were evaluated for expression levels of FWA.

Figure 6A:
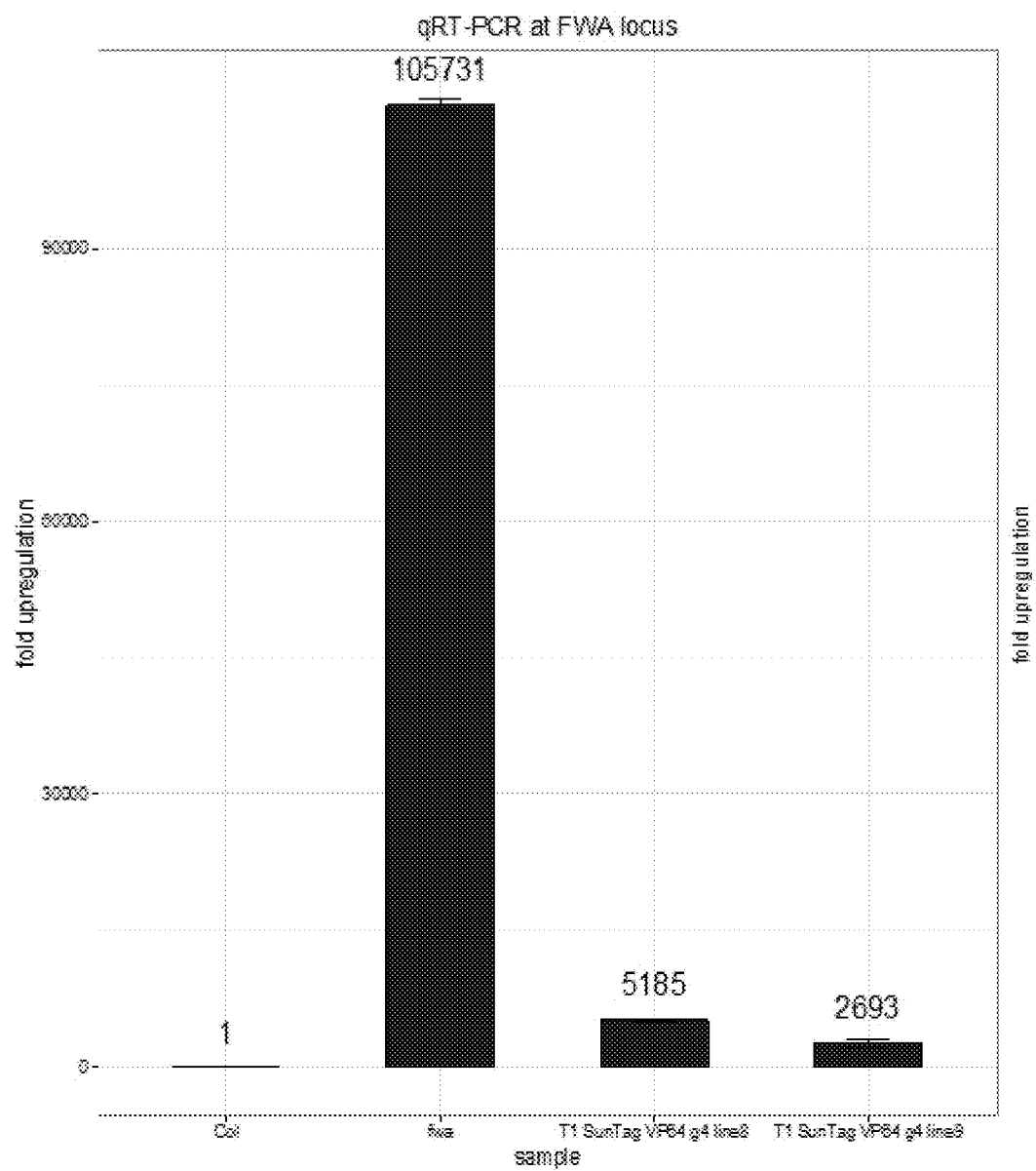
FIG. 6A-FIG. 6B illustrates FWA expression levels as determined by qRT-PCR in various lines.

As can be seen in FIG. 6A, two independent T1 lines housing the SunTag VP64 construct that contains gRNA4 showed substantially increased expression of FWA as compared to wild-type plants (Col). In wild-type plants, the promoter of FWA is methylated, which results in very low (if any) levels of expression of this gene. However, the SunTag VP64 expression system was able to activate FWA expression in an otherwise wild-type genetic background. In fwa mutants, an epimutation results in loss of methylation from the FWA promoter and subsequent high levels of expression of this gene, as was observed in FIG. 6A.

Figure 6B:
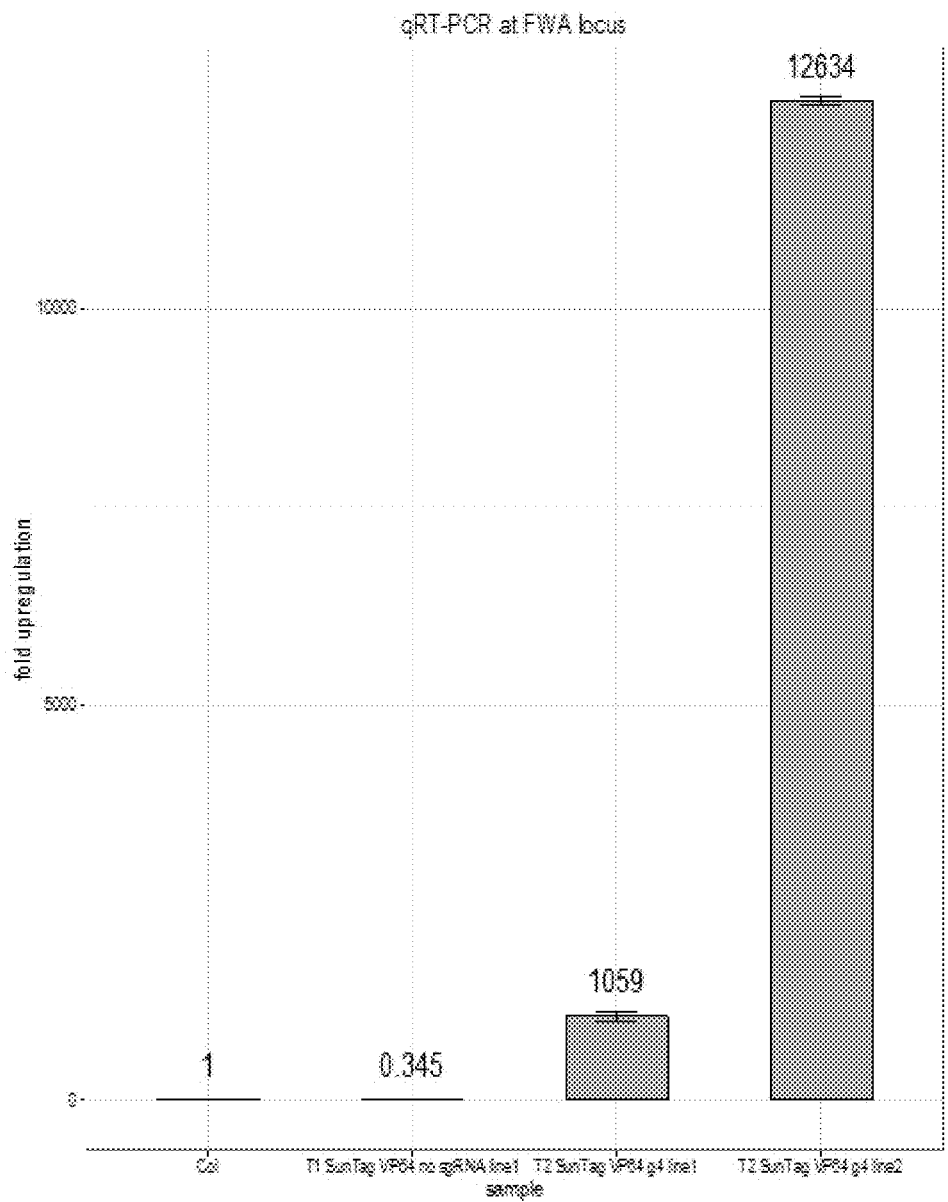
Figure 7:
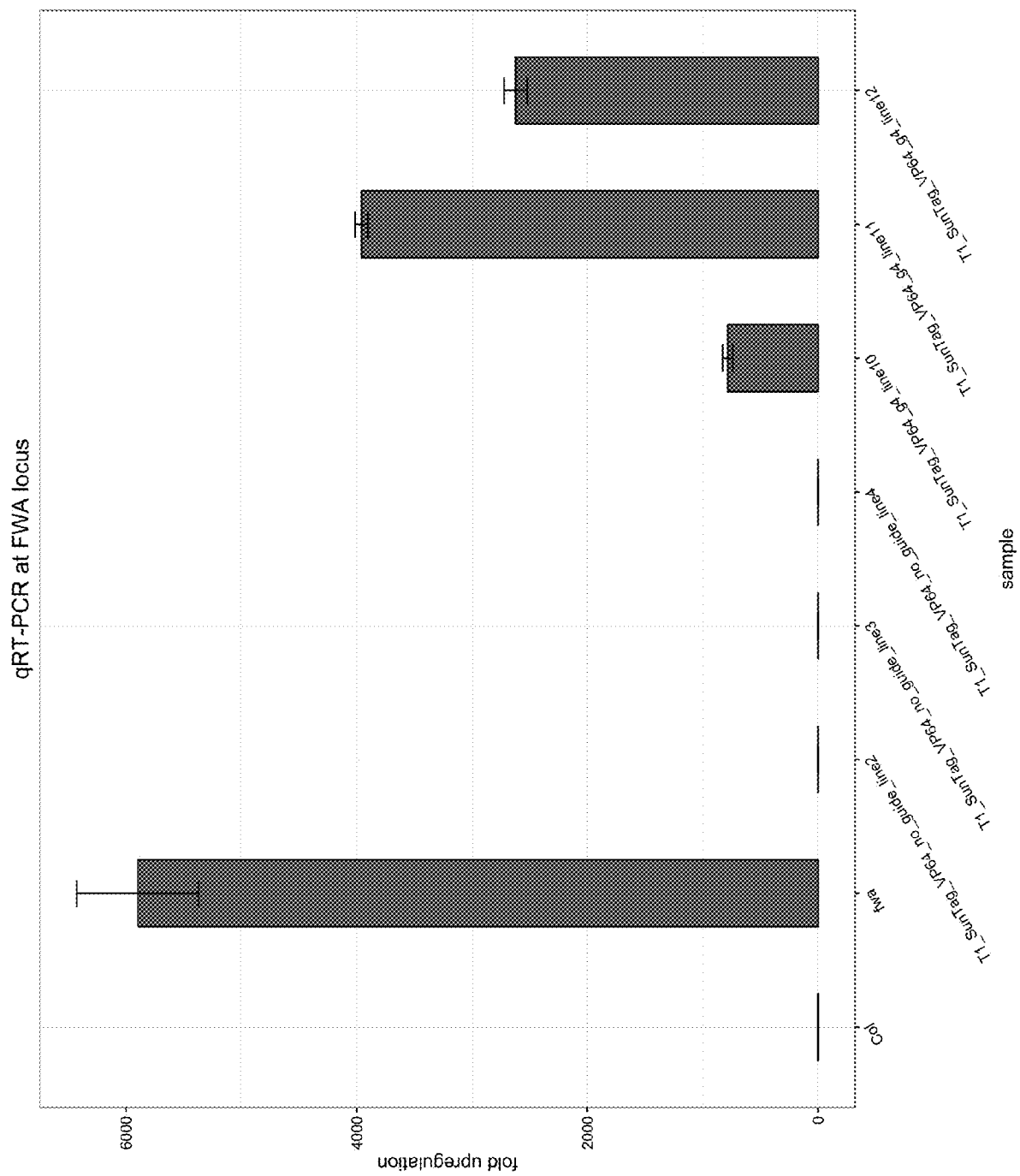
FIG. 7 illustrates FWA expression levels as determined by qRT-PCR in various lines. Shown is FWA expression in the following Arabidopsis backgrounds: wild-type Col-0, fwa mutant, T1 lines housing the SunTag VP64 construct that does not contain any gRNA (lines 2, 3, and 4), and T1 lines housing the SunTag VP64 construct that contains gRNA4 (lines 10, 11, and 12).
Figure 8:
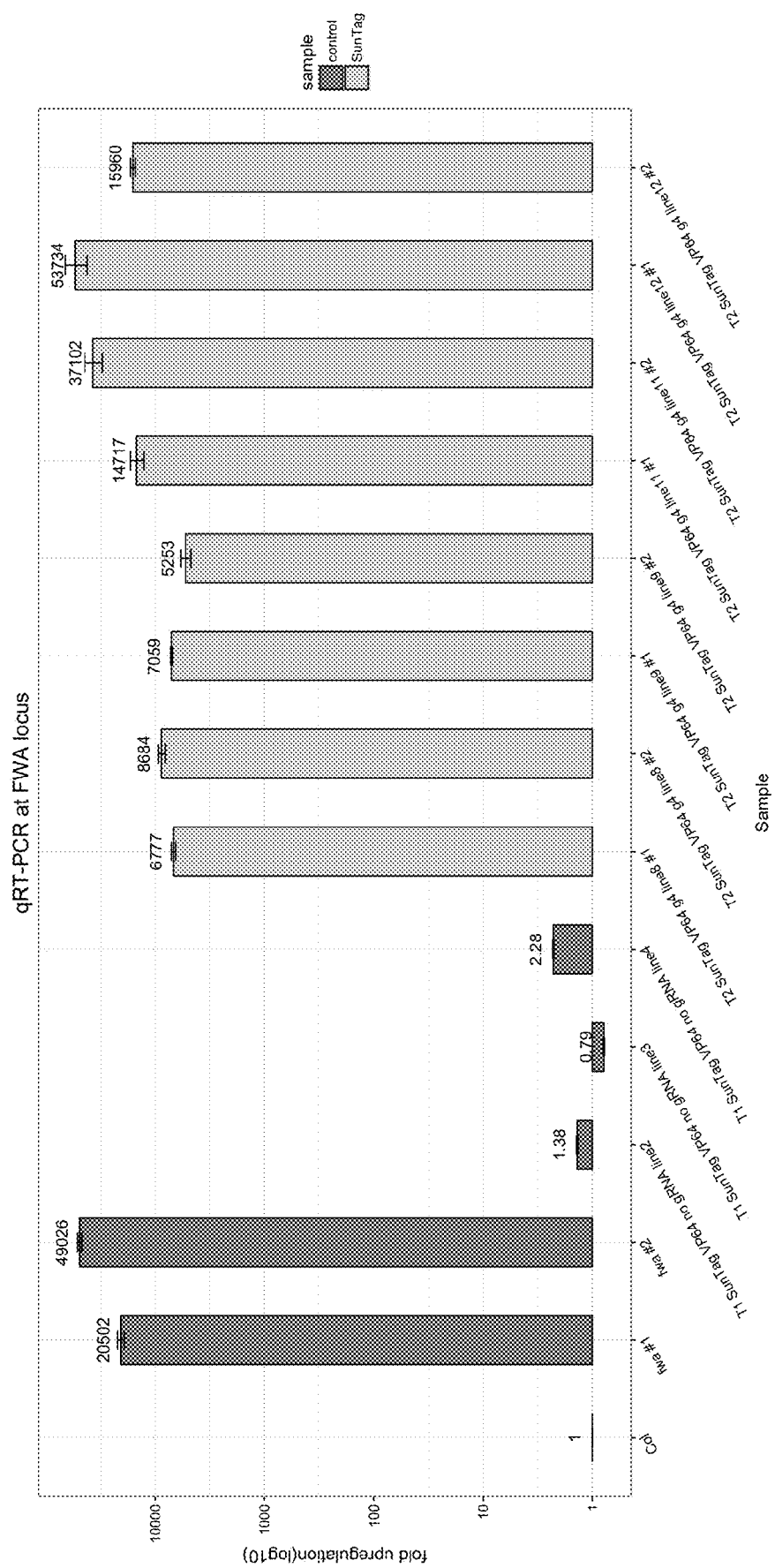
FIG. 8 illustrates FWA expression levels as determined by qRT-PCR in various lines. Shown is FWA expression in the following Arabidopsis backgrounds: wild-type Col-0 fwa mutants, T1 lines housing the SunTag VP64 construct that does not contain any gRNA (lines 2, 3, and 4), and T2 lines housing the SunTag VP64 construct that contains gRNA4 (lines 8, 9, 11, and 12).

As can be seen in FIG. 6B, two independent T2 lines housing the SunTag VP64 construct that contains gRNA4 showed substantially increased expression of FWA as compared to wild-type plants (Col). FWA expression was also substantially increased in the T2 lines as compared to a T1 SunTag VP64 line that did not contain any gRNA. Additional control and experimental SunTag VP64+gRNA lines were evaluated for FWA expression, which produced similar results as described above (FIG. 7 and FIG. 8).

Figure 9:
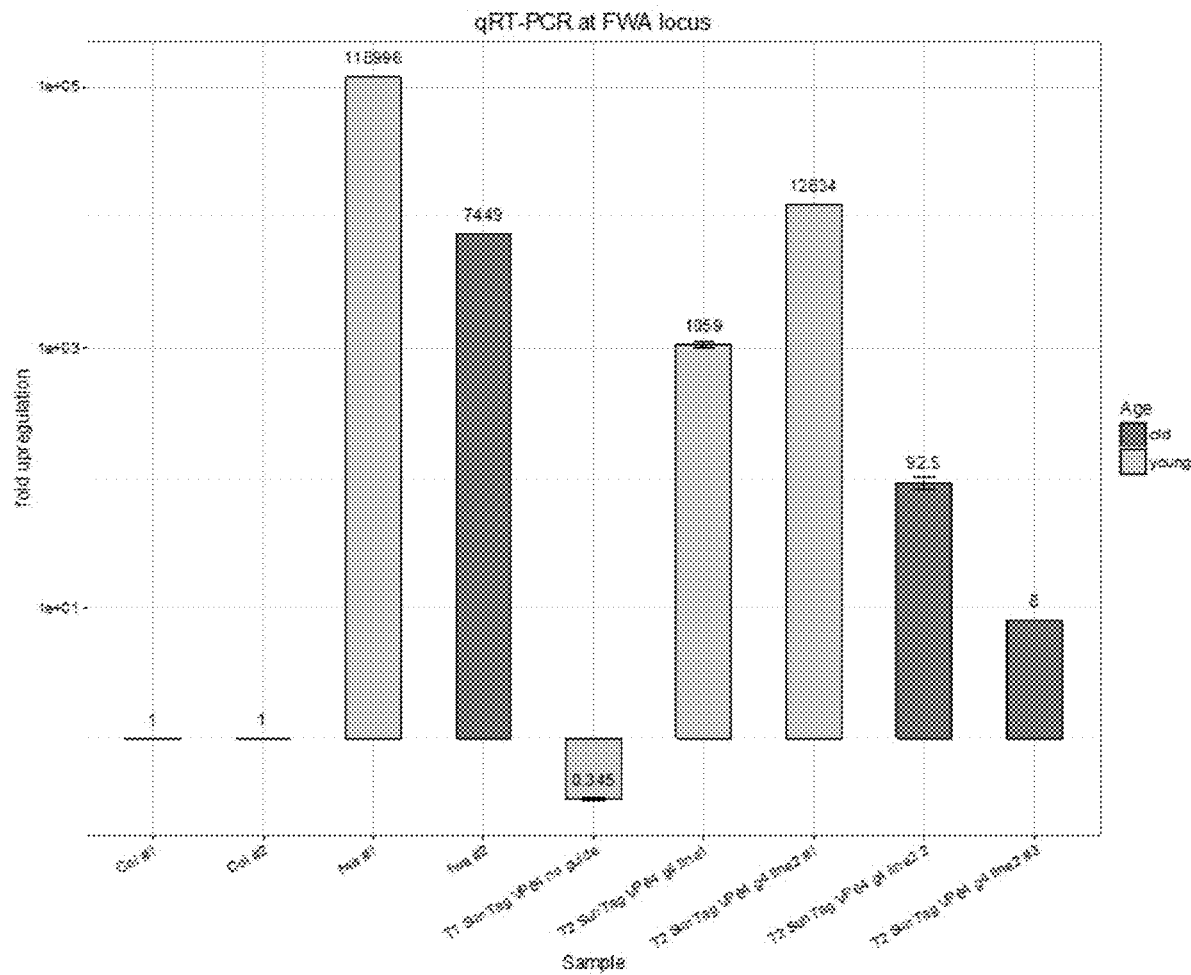
FIG. 9 illustrates FWA expression levels as determined by qRT-PCR in old and young leaf tissue from various Arabidopsis lines. The line samples include two wild-type Col-0 samples, two fwa mutant samples, a T1 line housing the SunTag VP64 construct that does not contain any gRNA, and multiple T2 lines housing the SunTag VP64 construct that contains gRNA4.

In a related assay, both old and young leaf tissue from various *Arabidopsis* lines was evaluated for FWA expression. As can be seen in FIG. 9, SunTag VP64 *Arabidopsis* lines containing gRNA4 showed upregulation of FWA expression as compared to wild-type plants and as compared to a T1 SunTag VP64 line that did not contain any gRNA. Further, the data demonstrates that older leaves have reduced levels of FWA RNA, which is consistent with previous reports.

Figure 10:
FIG. 10 illustrates flowering time in a SunTag VP64+ gRNA4 line and a control line that does not contain any guide RNA.

Given that FWA is a repressor of flowering time, the timing of flowering could serve as a phenotypic illustration of activation of the FWA gene. Accordingly, flowering time was evaluated in SunTag VP64 *Arabidopsis* lines containing gRNA4, as well as in control lines that do not contain any gRNA. It was found that the SunTag VP64 *Arabidopsis* lines containing gRNA4 were slightly late flowering as compared to the no gRNA control lines (FIG. 10). This delayed flowering phenotype is consistent with activation of the FWA gene.

Overall, the results suggest that, in the SunTag VP64 lines containing a gRNA that targets the FWA promoter (gRNA4), the gRNA is able to successfully guide Cas9 to the FWA locus, and that VP64 is then able to activate expression of FWA.

Activation of FWA Expression Using gRNA17

The results described above indicate that SunTag VP64 constructs containing gRNA4 were able to successfully activate FWA expression. Another gRNA that targets the FWA promoter (gRNA17) was also tested in a SunTag VP64 construct to evaluate if lines containing this construct also exhibited activation of FWA expression.

Figure 11:
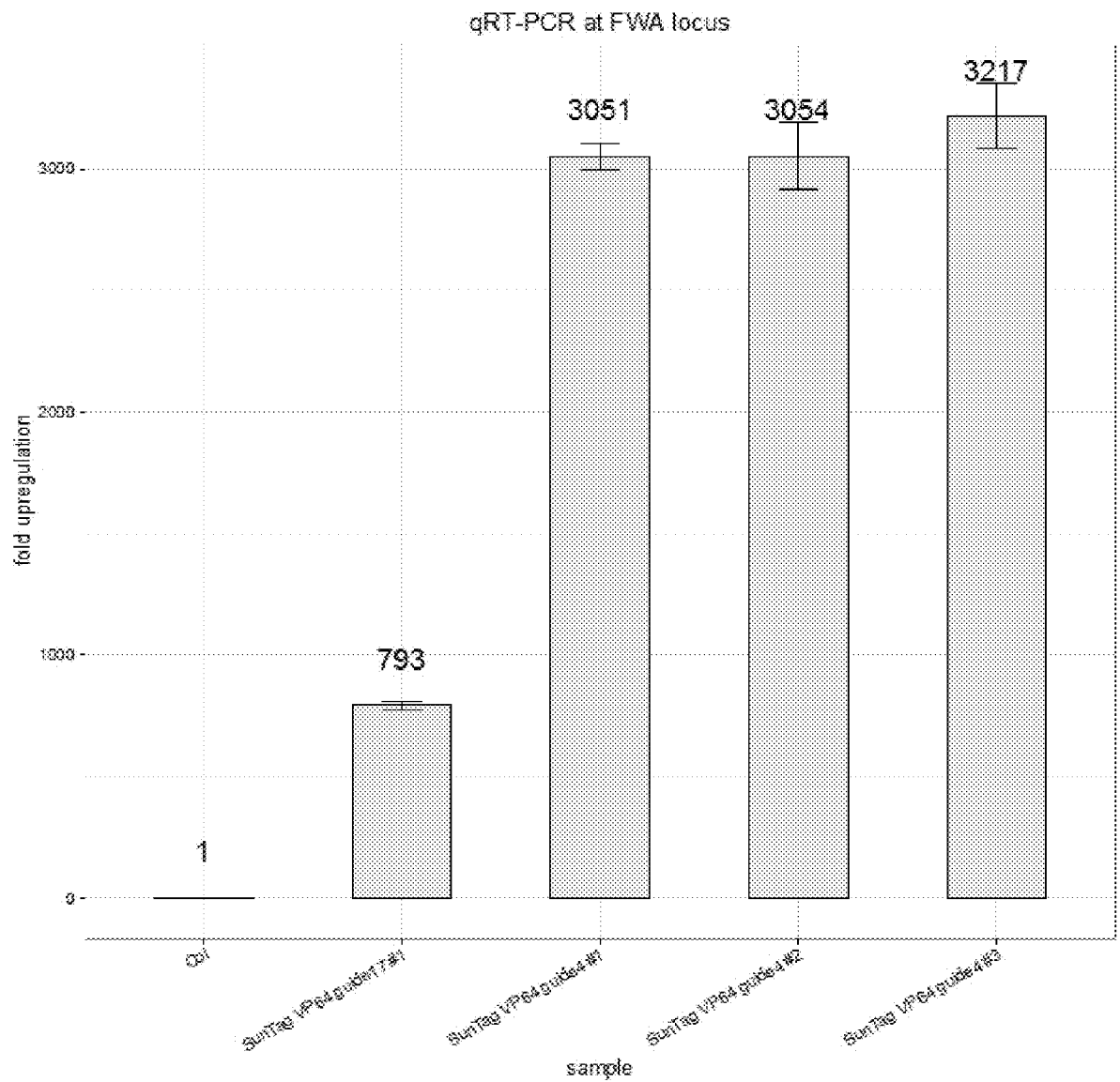
FIG. 11 illustrates FWA expression levels as determined by qRT-PCR in various lines. Shown is FWA expression in the following Arabidopsis backgrounds: wild-type Col-0, a line housing the SunTag VP64 construct that contains gRNA17, and samples from lines housing the SunTag VP64 construct that contains gRNA4.
Figure 12:
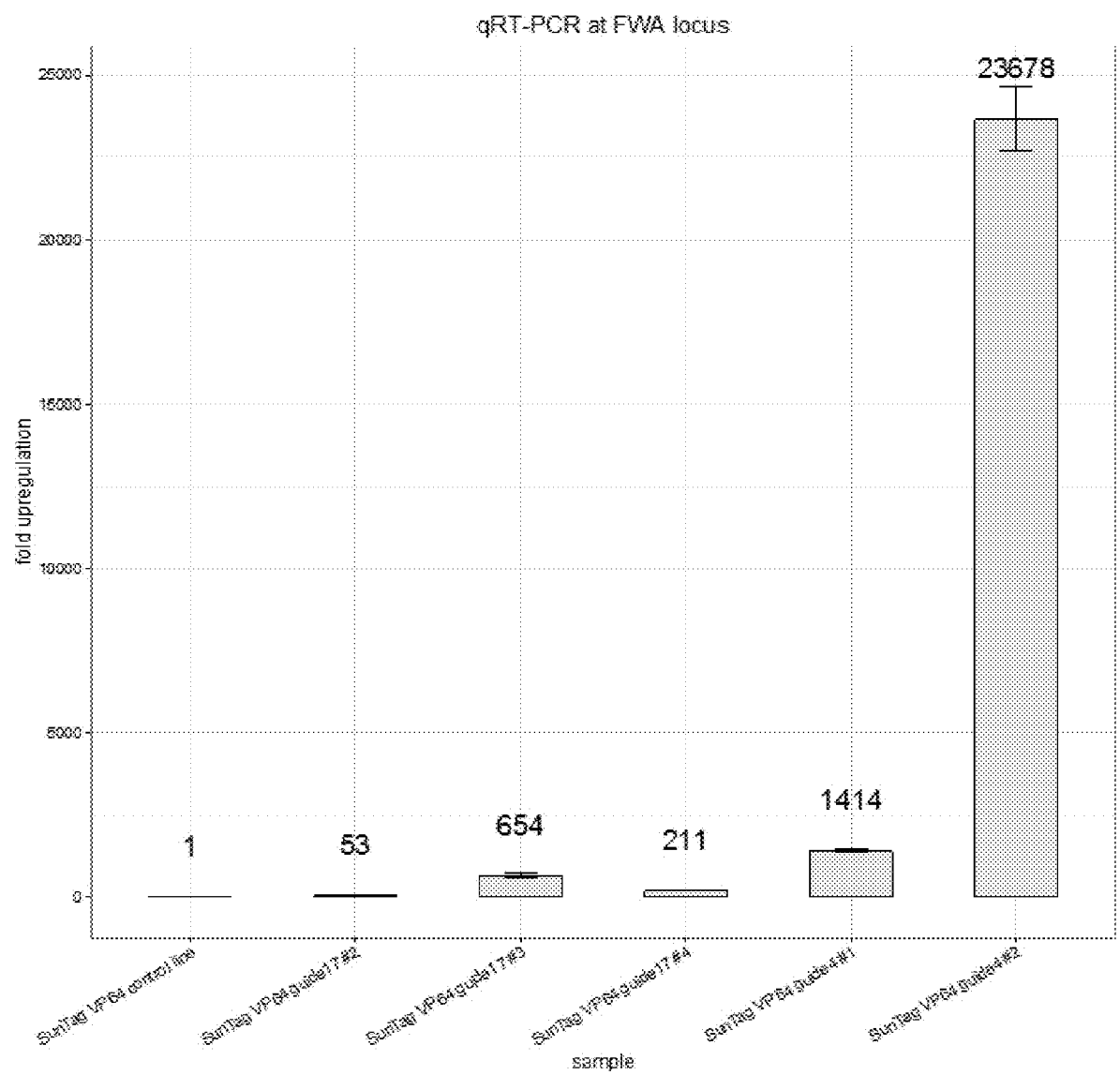
FIG. 12 illustrates FWA expression levels as determined by qRT-PCR in various lines. Shown is FWA expression in the following Arabidopsis backgrounds: wild-type Col-0, a control line housing the SunTag VP64 construct that does not contain any gRNA, samples from lines housing the SunTag VP64 construct that contains gRNA17, and samples from lines housing the SunTag VP64 construct that contains gRNA4.

As can be seen in FIG. 11, a line housing the SunTag VP64 construct that contains gRNA17 also showed substantially increased expression of FWA as compared to wild-type plants (Col). In this assay, lines containing a SunTag VP64 construct that contains gRNA4 showed greater activation of FWA than achieved in lines containing gRNA17, but all SunTag VP64 lines containing a gRNA that targets the FWA promoter showed substantially increased expression of FWA as compared to wild-type plants (Col). Additional control and experimental SunTag VP64+gRNA lines were evaluated for FWA expression, which produced similar results as described above (FIG. 12).

Taken together, the results suggest that, in the SunTag VP64 lines containing a gRNA that targets the FWA promoter, the gRNA is able to successfully guide Cas9 to the FWA locus, and that VP64 is then able to activate expression of FWA.

Methylation Status of FWA Promoter in FWA-Activated Lines

The results above suggest that, in the SunTag VP64 lines containing a gRNA that targets the FWA promoter, the gRNA is able to successfully guide Cas9 to the FWA locus, and that VP64 is then able to activate expression of FWA. Also, as described above, the SunTag VP64+gRNA lines are in an otherwise wild-type genetic background, and in wild-type *Arabidopsis* plants, the FWA promoter is highly methylated such that FWA expression is effectively silenced. To investigate the methylation status of the FWA promoter in SunTag VP64+gRNA lines, bisulfite sequencing and analysis assays in various lines were conducted.

Figure 13:
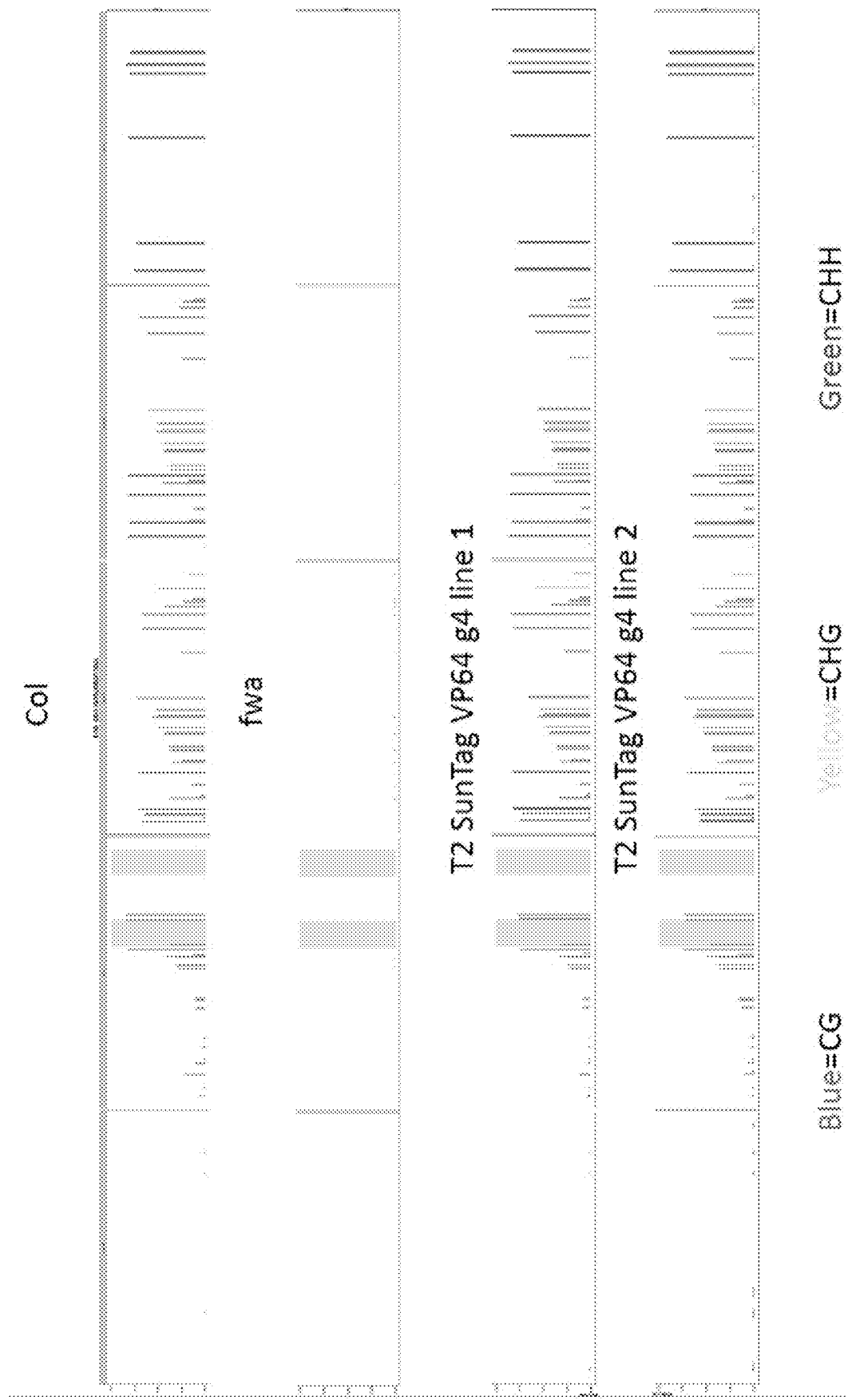
FIG. 13 illustrates methylation analysis of the FWA promoter in various lines: wild-type Col-0, fwa mutants, and T2 lines (lines 1 and 2) housing the SunTag VP64 construct that contains gRNA4.
Figure 14:
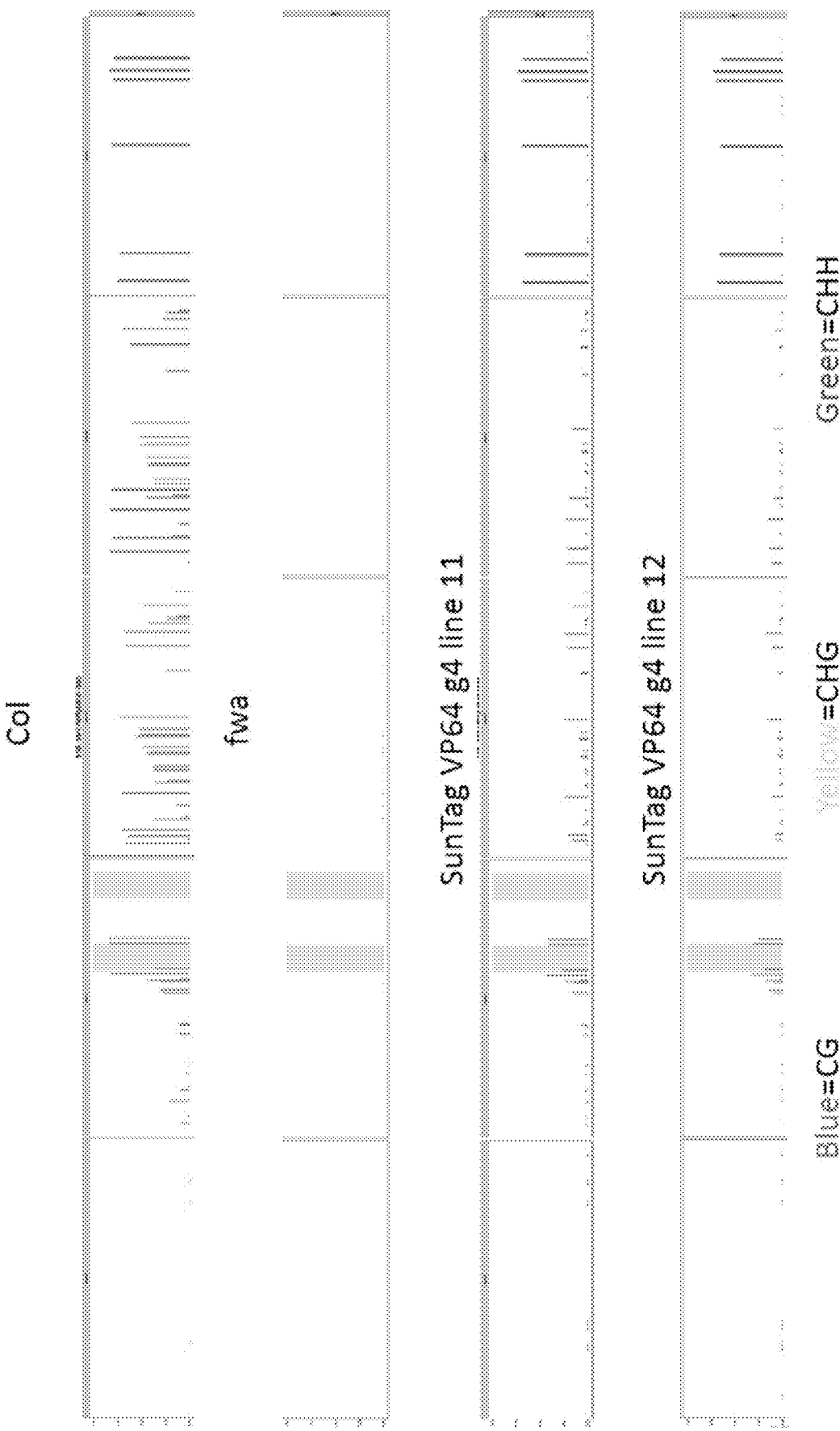
FIG. 14 illustrates methylation analysis of the FWA promoter in various lines: wild-type Col-0, fwa mutants, and two lines (lines 11 and 12) housing the SunTag VP64 construct that contains gRNA4.

From FIG. 13, it was seen that two independent T2 SunTag VP64+gRNA4 lines did not show differential methylation in the FWA promoter as compared to wild-type plants. However, as can be seen in FIG. 14, two different lines containing SunTag VP64+gRNA4 did show a moderate level of decreased methylation in the FWA promoter as compared to wild-type plants. These results suggest that there is not a clear link between FWA activation and methylation status of the FWA promoter in SunTag VP64+gRNA lines. However, taken together, the data does indicate that the SunTag VP64 system described herein can activate expression of a methylated gene.

ChIP Analysis of Cas9-Bound Targets

Figure 15:
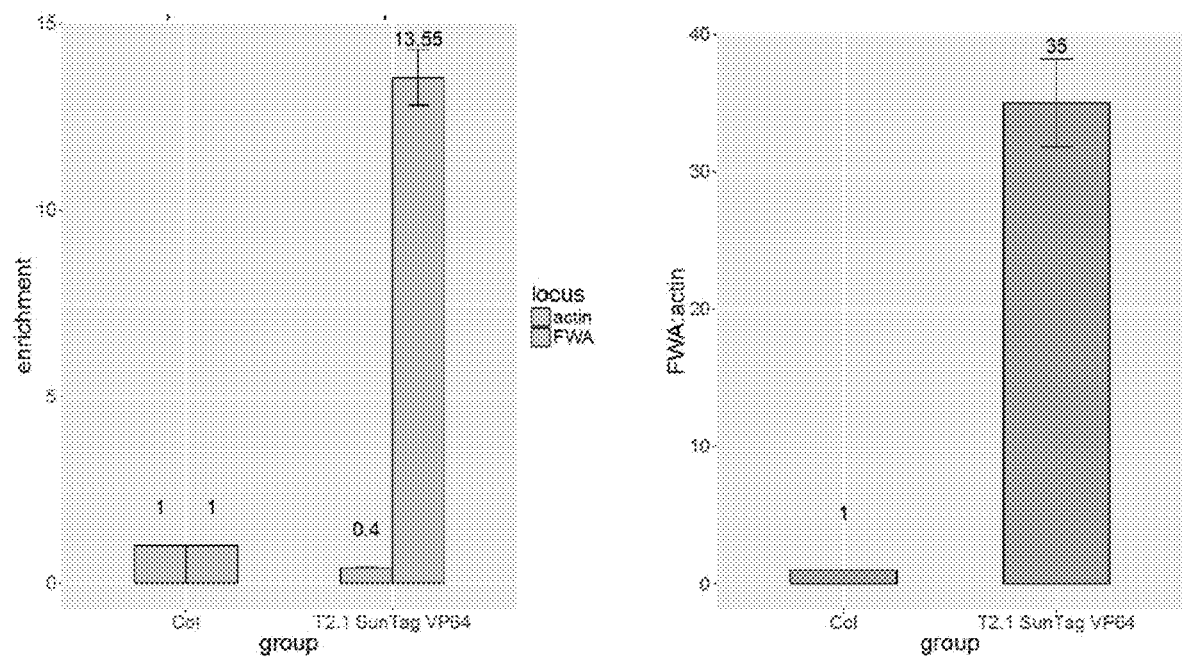
FIG. 15 illustrates ChIP-qPCR results in wild-type plants and T2 lines housing the SunTag VP64 construct that contains gRNA4.

As described above, the results suggest that, in the SunTag VP64 lines containing a gRNA that targets the FWA promoter, the gRNA is able to successfully guide Cas9 to the FWA locus, and that VP64 is then able to activate expression of FWA. To confirm that Cas9 was targeted to the FWA promoter in these lines (specifically the SunTag VP64+gRNA4 line), ChIP-qPCR of Cas9 using an anti-HA antibody (Cas9 is 1×HA tagged) was performed. As can be seen in FIG. 15, ChIP-qPCR confirmed Cas9 binding to FWA via gRNA4.

Figure 16:
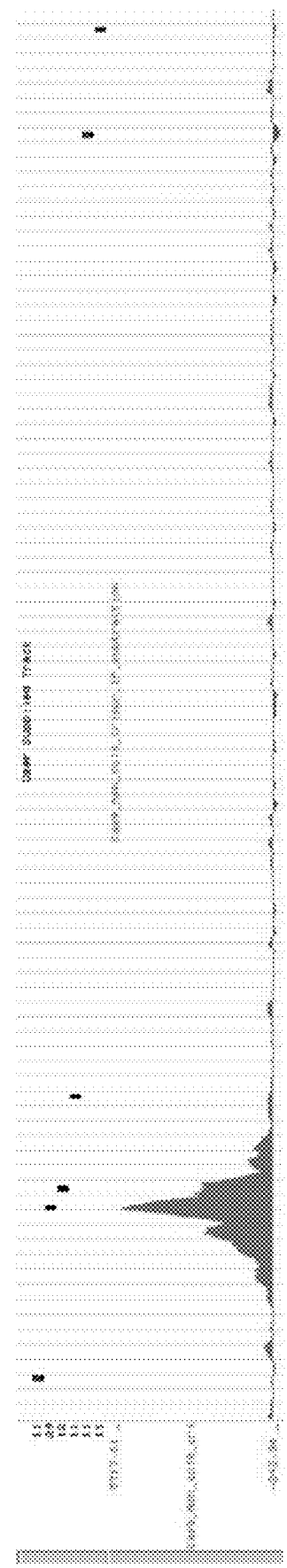
FIG. 16 illustrates a screenshot of the genome browser analyzing the FWA promoter region in Cas9 CUP samples from the SunTag VP64+gRNA4 lines.
Figure 17:
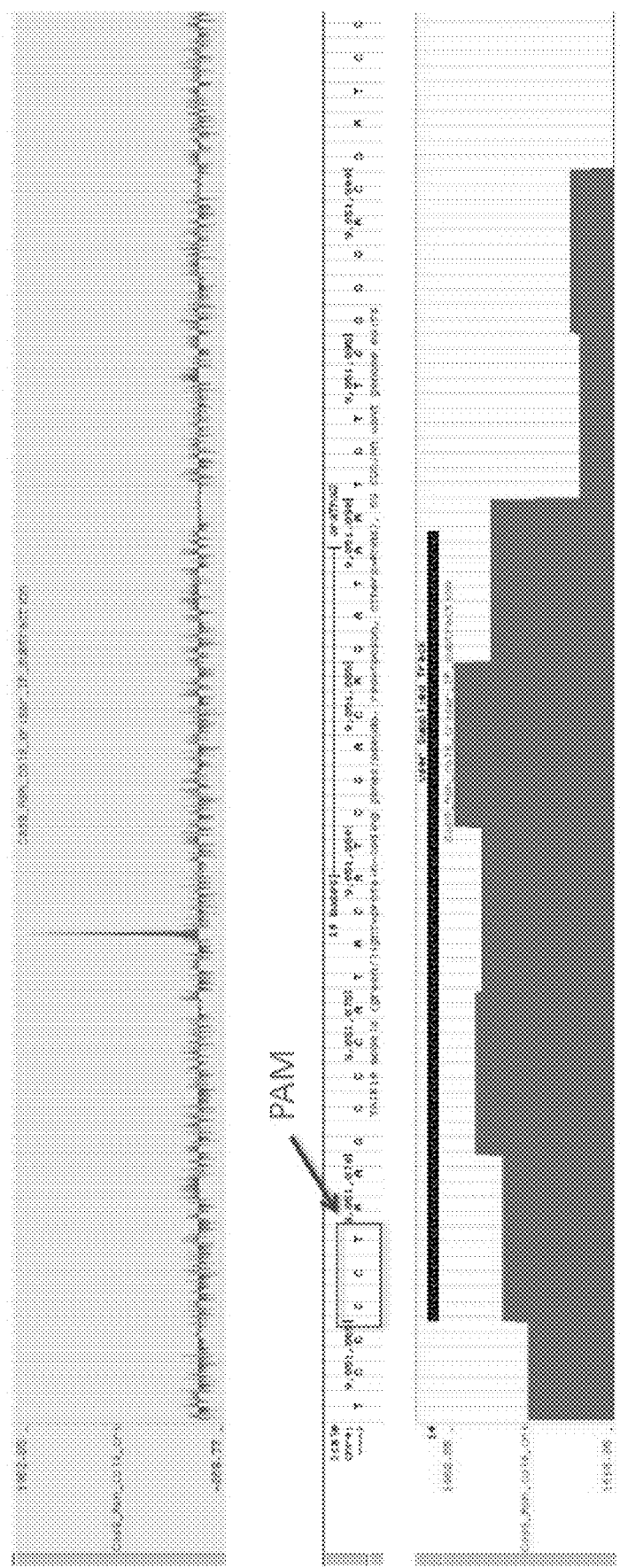
FIG. 17 illustrates a screenshot of the genome browser analyzing a region of the genome (SEQ ID NO: 67) in Cas9 ChIP samples from the SunTag VP64+gRNA4 lines that was bound by Cas9.

ChIP samples were further subjected to ChIP-seq to analyze genome-wide binding of Cas9 to genomic regions. The results illustrated in FIG. 16 demonstrate an enrichment of Cas9 over the FWA promoter. ChIP-seq analysis also revealed only one major off-target of gRNA4 (FIG. 17). This off-target contained a PAM sequence+14 base pairs that were complementary to gRNA4.

These results demonstrate that, in the SunTag VP64+gRNA system, Cas9 is able to be guided to its targets as specified by the gRNA, and that Cas9 is able to bind these targets. The results further suggest that this successful targeting is responsible for the activation of FWA by VP64.

Activation of GIS Expression Using tRNA:gRNA

The data described above indicates that the SunTag VP64+gRNA construct that was designed to target the FWA promoter was successful in doing so, and also successful at activating expression of FWA. To evaluate nucleic acid targets other than FWA, a SunTag VP64 construct was designed that contained a tRNA:gRNA cassette that targeted the GIS locus. CRISPR-targeting technology involving tRNA-gRNA expression cassettes is described in Xie et al, PNAS (2015). This tRNA:gRNA system utilizes a plant's endogenous tRNA processing system to produce mature gRNAs from a single transcript, and allows for the delivery of multiple gRNAs simultaneously with high expression level. The tRNA:gRNA cassette that was designed to target GIS is further described in the Materials and Methods. This SunTag VP64 construct was transformed into wild-type plants, and expression of GIS in these transformed plants was evaluated.

Figure 18:
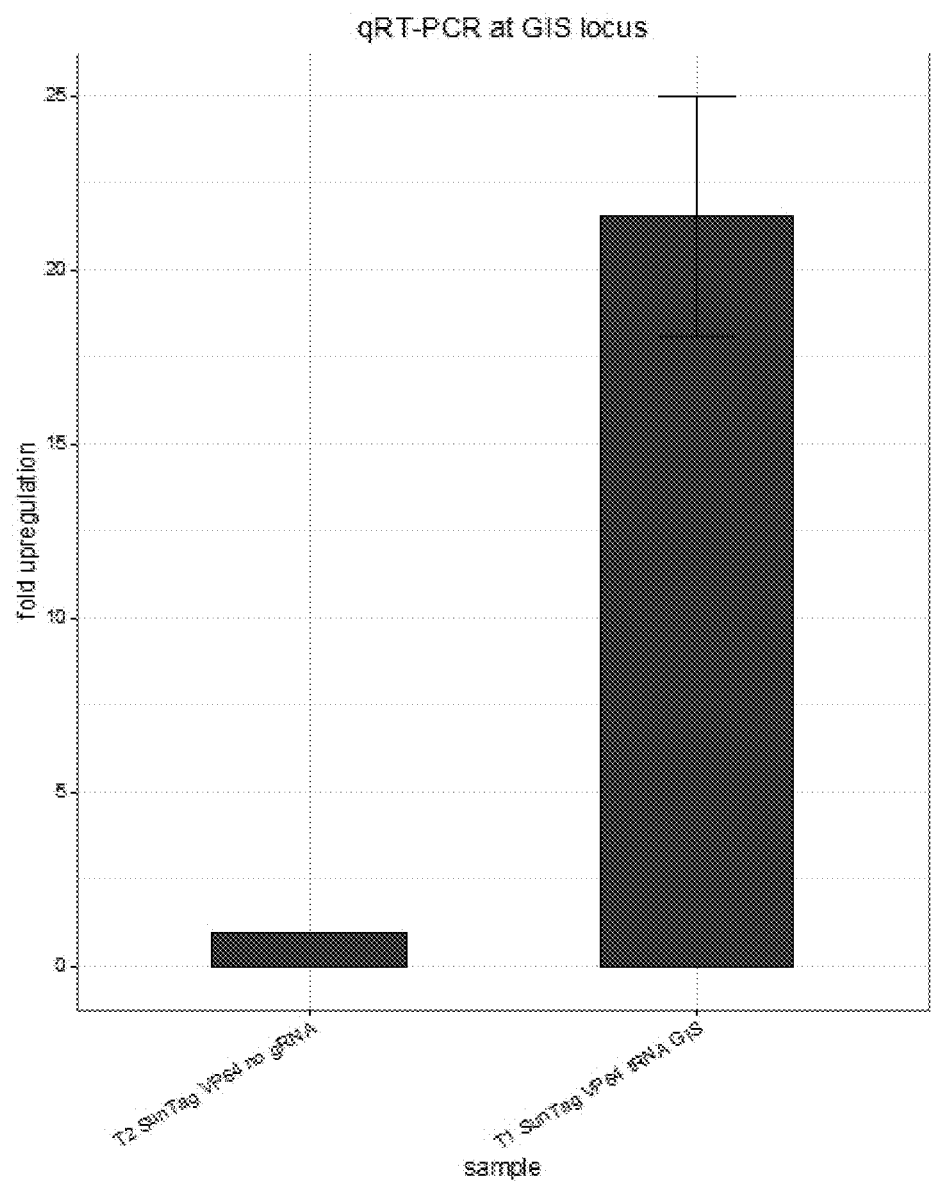
FIG. 18 illustrates GIS expression levels as determined by qRT-PCR in various lines. Shown is GIS expression in the following *Arabidopsis* backgrounds: a T2 SunTag VP64 line that did not contain any gRNA, and a T1 line housing the SunTag VP64 construct that contains the tRNA:gRNA that targets GIS.

As can be seen in FIG. 18, a T1 line housing the SunTag VP64 construct that contains the tRNA:gRNA that targets GIS showed substantially increased expression of GIS as compared to a T2 SunTag VP64 line that did not contain any gRNA. As above, the results suggest that, in the SunTag VP64 lines containing a gRNA that targets GIS, the gRNA is able to successfully guide Cas9 to the GIS locus, and that VP64 is then able to activate expression of GIS.

Conclusion

The data presented in this Example demonstrates the successful construction of a SunTag VP64+gRNA system that is operable in plants. The SunTag system was able to substantially increase expression of targeted genes as compared to corresponding controls. In some instances, many thousands-fold increases in gene expression were observed, and the system was also able to activate expression of a normally methylated gene (FWA). This work presents the opportunity for robust and selective activation of plant genes or other nucleic acids in plants, which may serve both research purposes as well as be used in applications for crop improvement.

Example 2: SunTag without VP64 does not Activate the Expression of FWA

This Example demonstrates that the targeting of SunTag to the FWA promoter with guide RNA 4, but without the VP64 transcriptional activator (no effector), does not lead to the activation of FWA expression.

Materials and Methods

Relevant and applicable Materials and Methods for this Example are as described in Example 1. One difference is that instead of fusing linker-VP64-linker-NLS to the antibody, only linker-NLS was fused to obtain a no effector control in this Example. DNA and protein sequence information for the antibody region without a VP64 fusion is provided below. Further, the guide RNA 4 previously described in Example 1 was used in this Example to evaluate the no effector control constructs.

The relevant control vector used in this Example contained the scFv antibody region without VP64. This vector contained the following features: UBQ10 promoter-scFv-sfGFP-unique BsiWI site for cloning effectors-glycine linker-NLS added for plant nuclear localization-unique BsiWI site for cloning effectors-GB1-REX NLS-NOS terminator. The nucleotide sequence of this expression cassette is presented in SEQ ID NO: 54.

The fusion polypeptide encoded from the cassette described above contained the following features: scFv-sfGFP-glycinelinker-NLS added for plant nuclear localization-GB1-REX NLS. The amino acid sequence is presented in SEQ ID NO: 55.

Results

Figure 19:
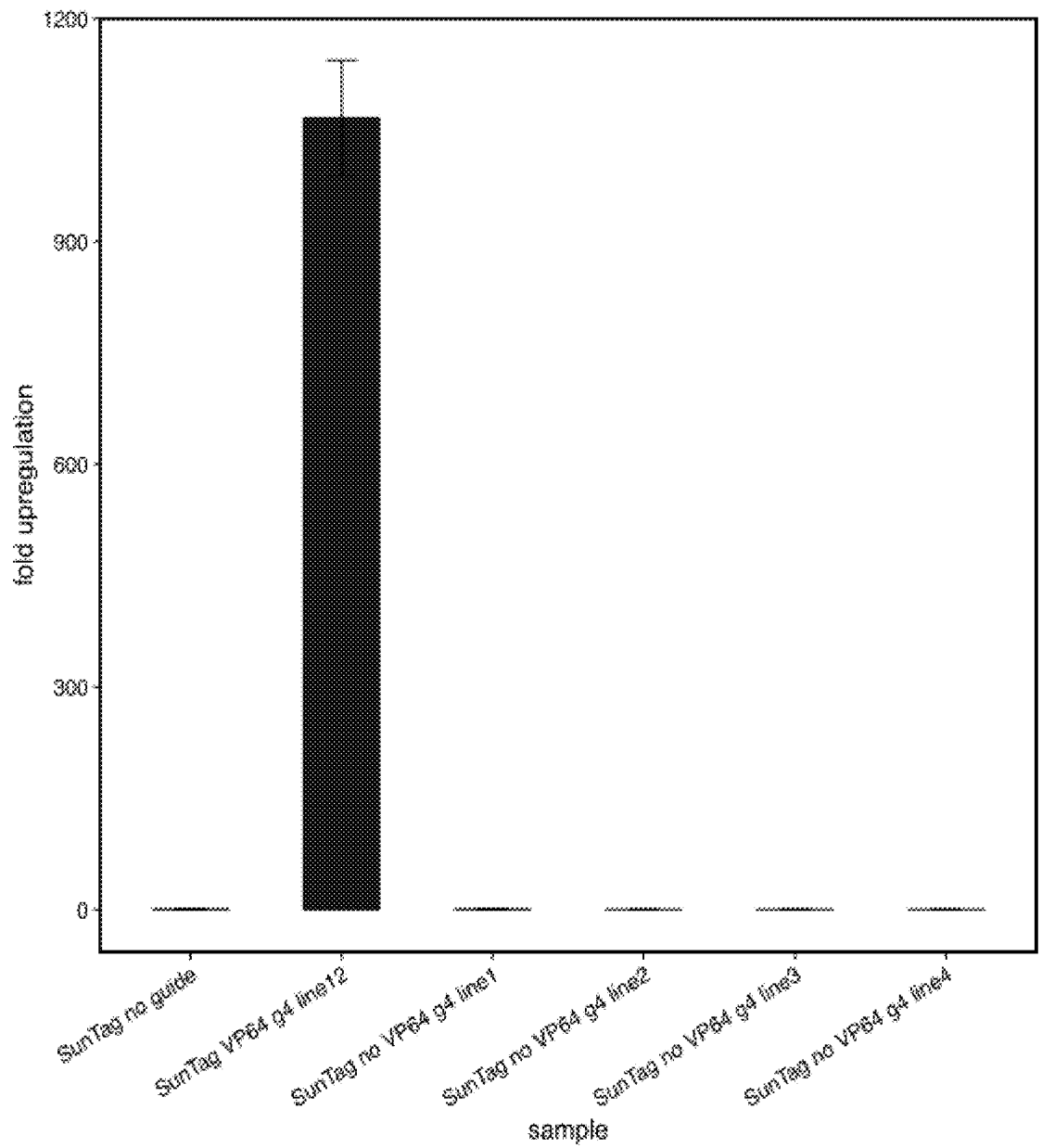
FIG. 19 illustrates qRT-PCR data of the FWA locus. One SunTag, no guide negative control line, one SunTag VP64 sgRNA4 positive control line, and four independent T1 SunTag no VP64 sgRNA4 lines are shown. Fold upregulation is plotted and a housekeeping gene, IPP2, was used as an internal control. Error bars indicate standard error of the mean of two replicates.
Figure 20A:
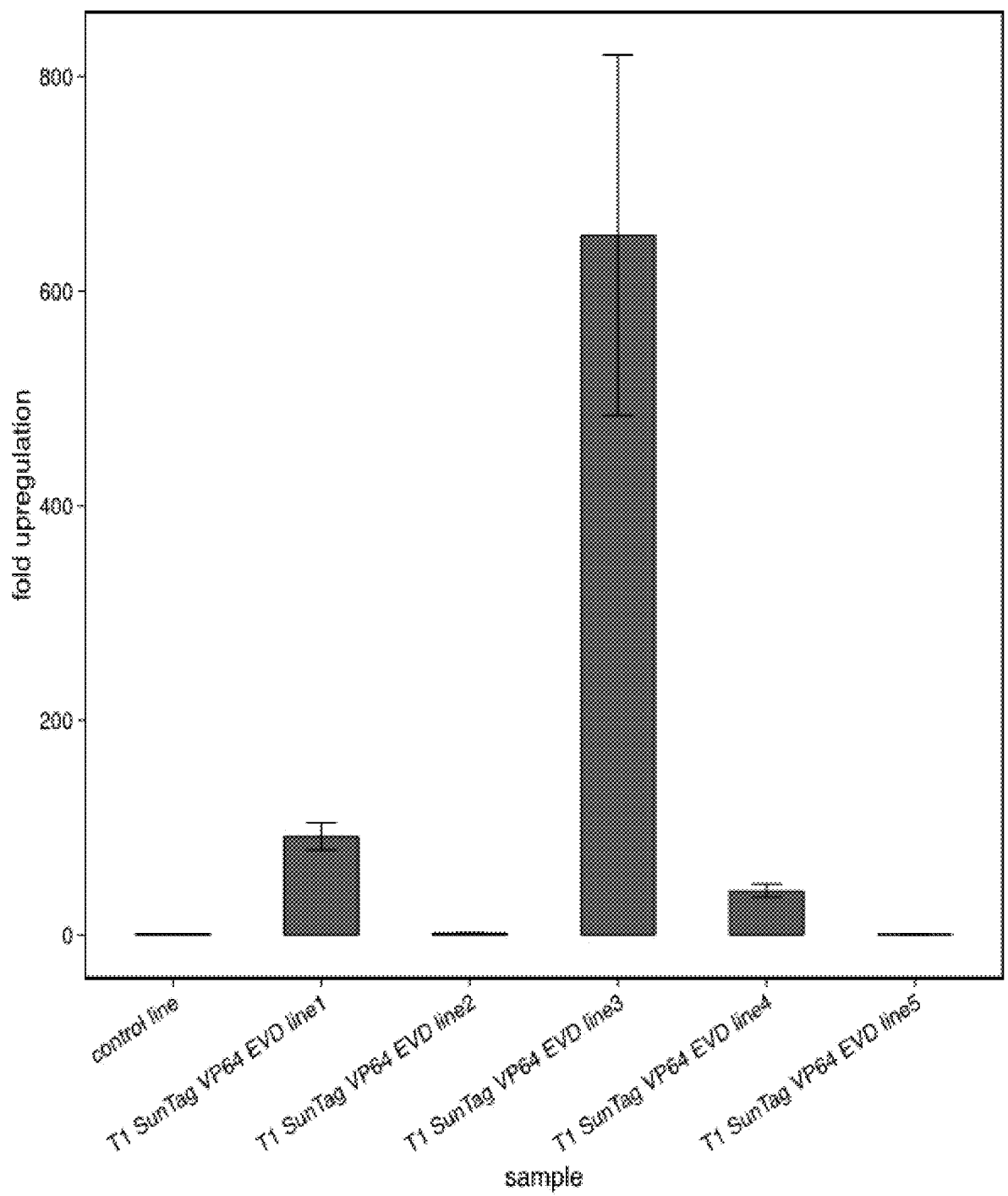
FIG. 20A, FIG. 20B, and FIG. 20C illustrate qRT-PCR data for EVD in T1 plants. Each of FIG. 20A, FIG. 20B, and FIG. 20C represent a separate experiment screening different T1 plants. Each T1 plant contains two guides targeting EVD. Col (wild type) and no guide samples are included as negative controls. "Control line" indicates a control with guides targeting the unrelated. SUPERMAN gene. Fold upregulation is plotted and a housekeeping gene, IPP2, was used as an internal control. Error bars indicate standard error of the mean of two replicates.
Figure 20B:
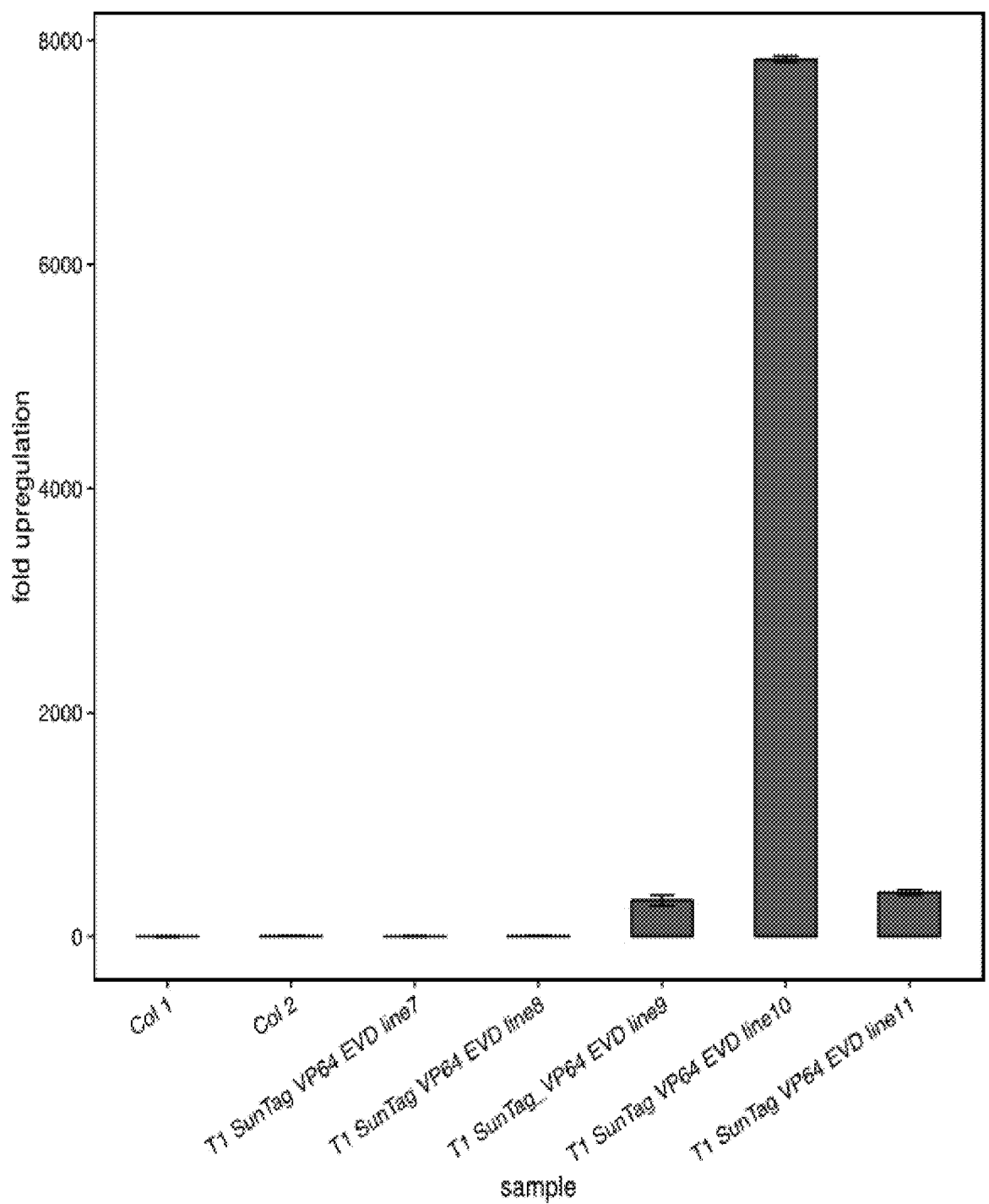
Figure 20C:
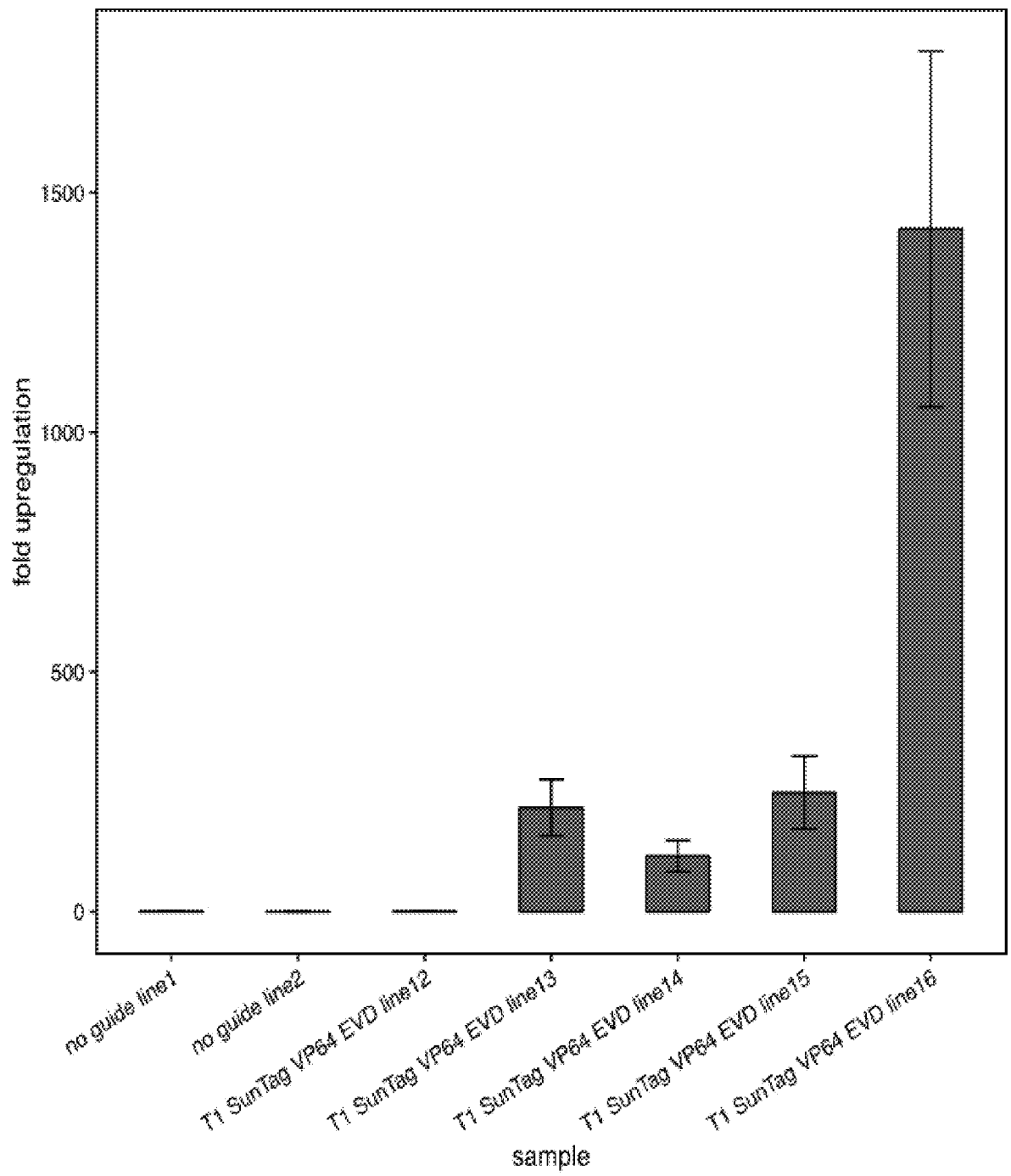

To confirm that the physical binding of Cas9 to the FWA promoter does not activate transcription, qRT-PCR was done with RNA from plants expressing SunTag guide 4 without an effector. Four T1 lines were screened for transcriptional activation. As shown in FIG. 19, expression of FWA was not activated when VP64 was omitted. A negative control with no guide RNA, and a positive control with VP64 and guide 4 are also plotted for comparison. These results show that the recruitment of VP64 is responsible for the ectopic expression of FWA.

Example 3: SunTag VP64-Mediated Activation of a Diverse Set of Genomic Targets

This Example demonstrates that SunTag VP64 is able to activate a methylated transposable element (EVADE), and two additional genes involved in development which have no promoter methylation.

Materials and Methods

Relevant and applicable Materials and Methods for this Example are as described in Example 1. A notable difference is that different guide RNAs are used to target each respective locus. All sgRNA expression is driven by the U6 promoter in each case. For each target, both guides are on the same binary vector and are cloned in tandem. Sequence information is provided below.

For the guide RNAs (sgRNA), each guide RNA was driven by the U6 promoter, the nucleotide sequence of which is presented in SEQ ID NO: 56. The sgRNA backbone sequence used for each guide RNA is presented in SEQ ID NO: 57. The two spacer sequences used in the EVD guide RNAs are presented in SEQ ID NO: 58 (spacer 1 for EVD) and SEQ ID NO: 59 (spacer 2 for EVD). The two spacer sequences used in the AP3 guide RNAs are presented in SEQ ID NO: 60 (spacer 1 for AP3) and SEQ ID NO: 61 (spacer 2 for AP3). The two spacer sequences used in the CLV3 guide RNAs are presented in SEQ ID NO: 62 (spacer 1 for CLV3) and SEQ ID NO: 63 (spacer 2 for CLV3).

Results

Figure 21:
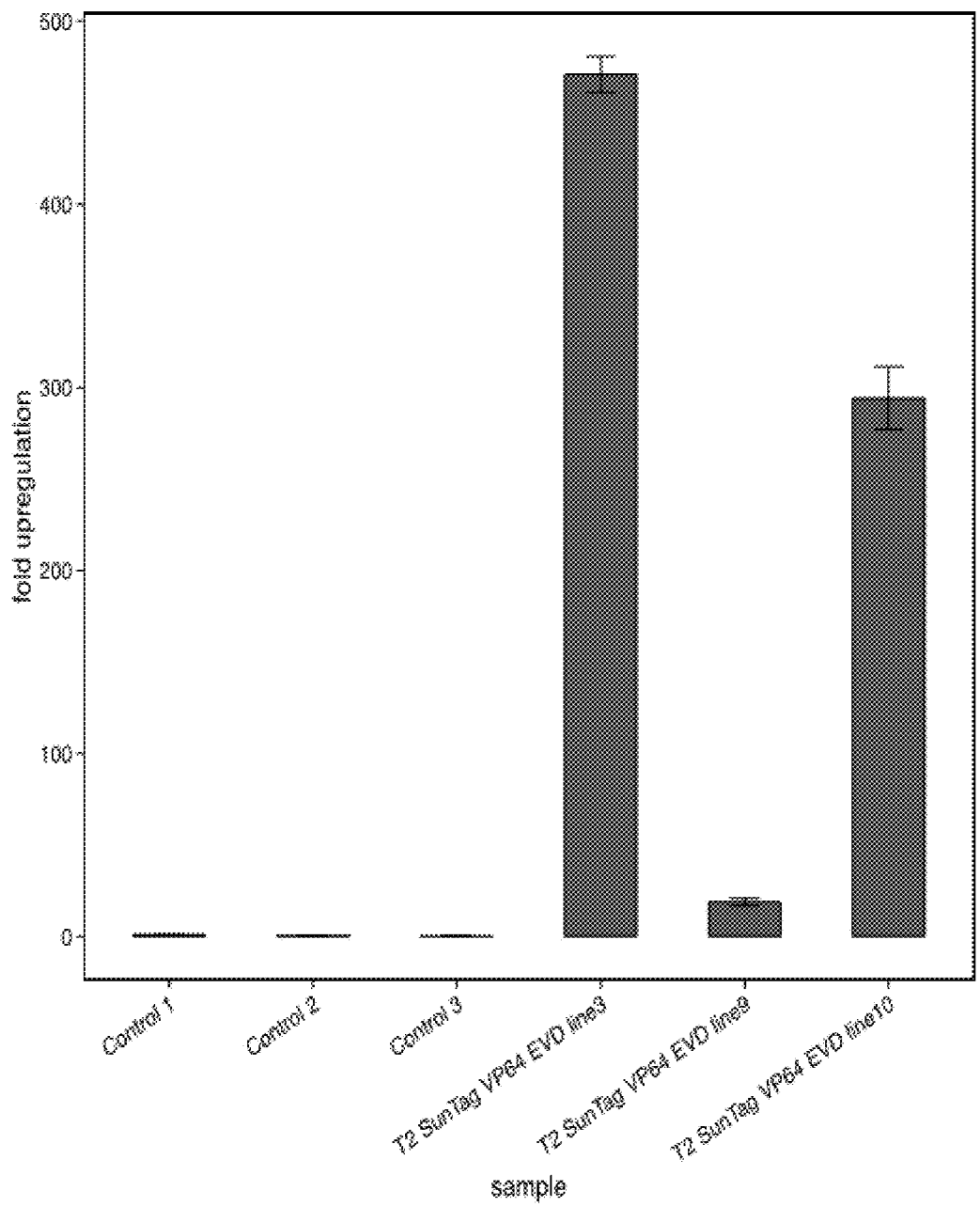
FIG. 21 illustrates qRT-PCR data for EVD. Expression data is from T2 plants from three independent lines with two guides targeting EVD. Three control lines are included as negative controls. The first one corresponds to a no guide control, while the next two correspond to plants expressing gRNAs targeting the unrelated SUPERMAN gene. Fold upregulation is plotted and a housekeeping gene, IPP2, was used as an internal control. Error bars indicate standard error of the mean of two replicates.

SunTag VP64 was targeted to the retrotransposon EVD, which is normally DNA methylated and silenced. Two separate guides (both driven by the U6 promoter) were targeted simultaneously to the 5' end of the coding region. As shown in FIG. 20A-20C, 15 different T1 lines were screened by qRT-PCR for EVD transcripts. Numerous positive lines ectopically expressing EVD were found, indicating that SunTag VP64 can be utilized for targeted activation of transposons or transposon families. It also provides further evidence that methylated loci are amenable to VP64 mediated activation in plants.

qRT-PCR measurement of RNA expression of three independent EVD targeting SunTag VP64 T2 lines provides further confirmation of the activation of EVD (FIG. 21), and showed that the activation is stable over multiple generations.

Figure 22A:
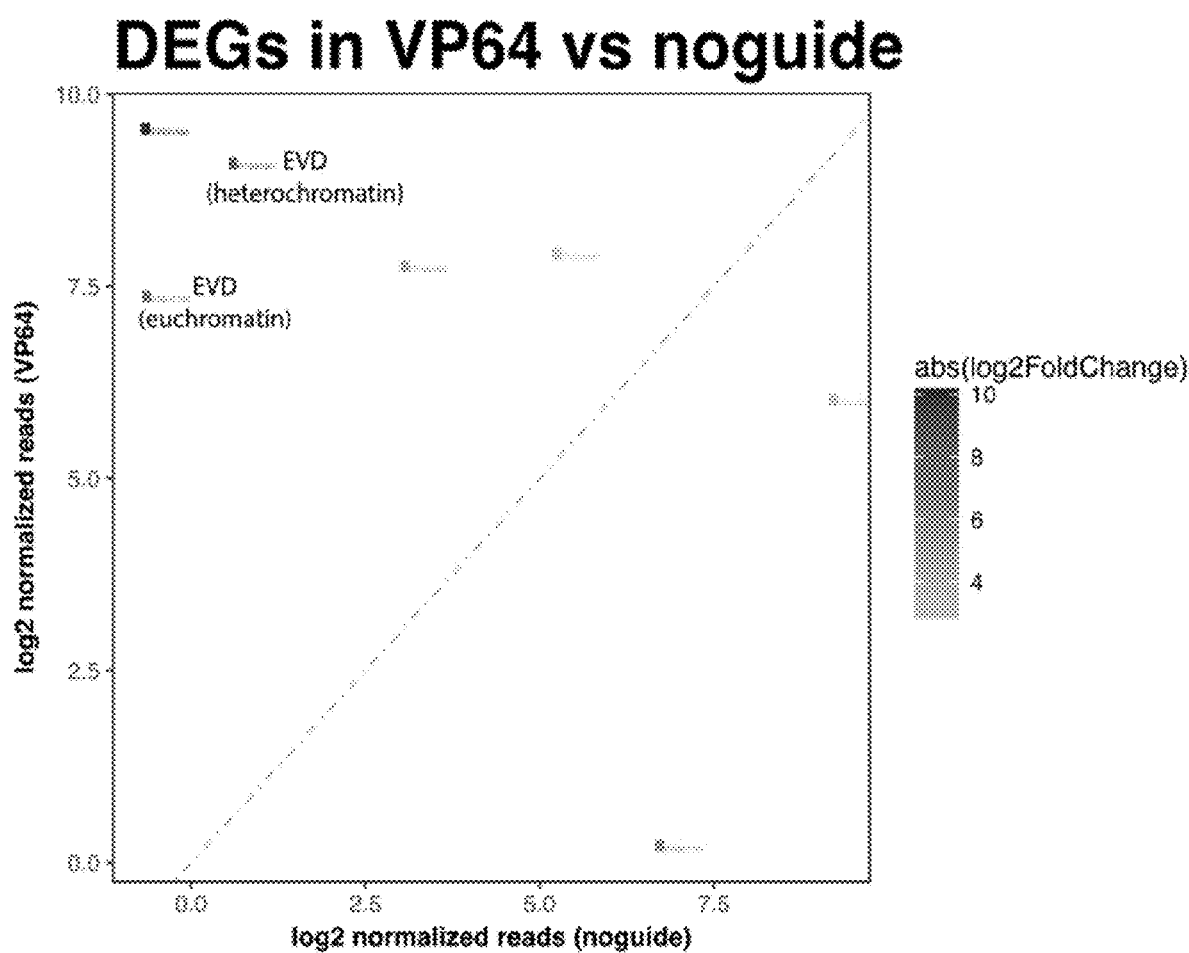
FIG. 22A-FIG. 22B illustrate scatterplots showing significantly differentially expressed genes (Dais) in T2 plants targeting EVD with two guides. Results for line 3 (FIG. 22A) and line 10 (FIG. 22B) are shown. Genes which showed at least a four-fold change are shown. Both upregulated copies of the EVD locus are labeled.
Figure 22B:
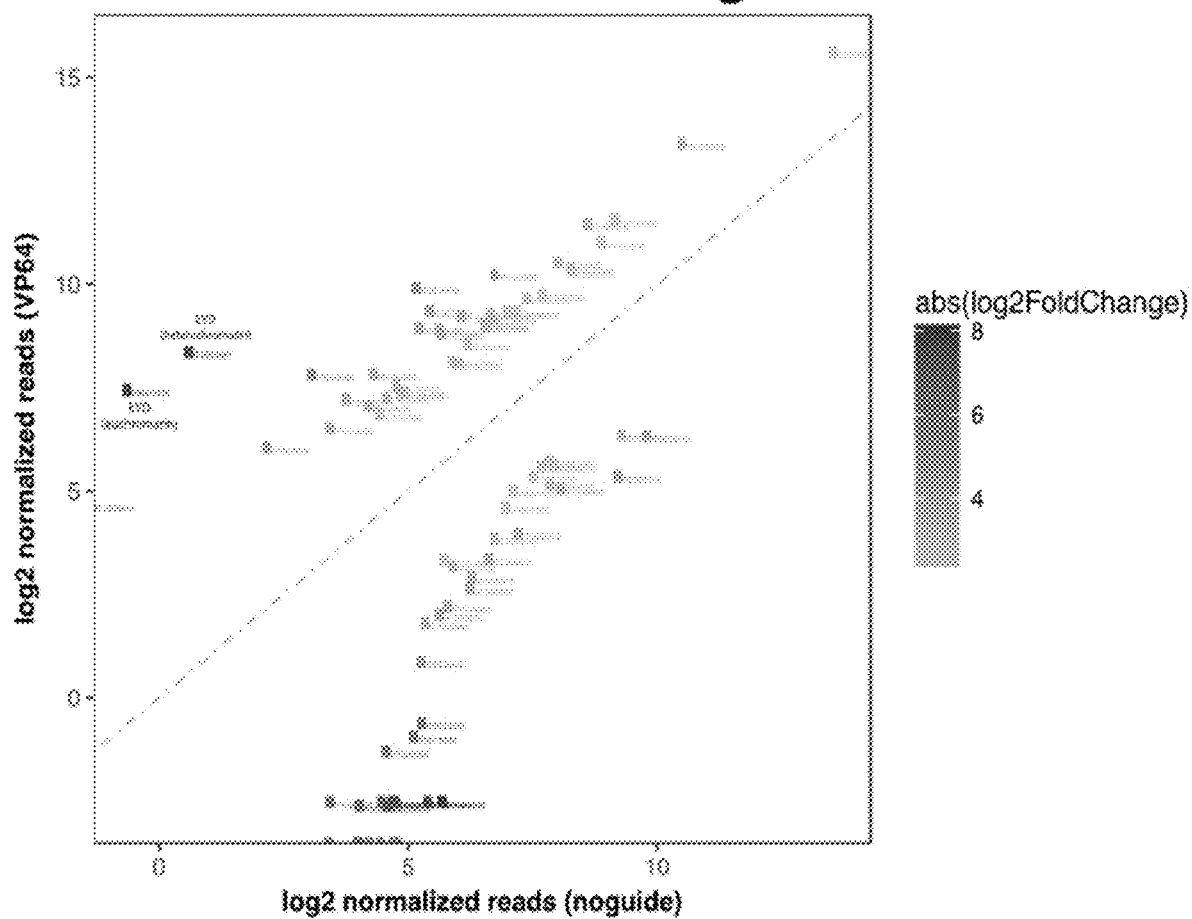

RNA-seq was also performed to confirm the upregulation of EVD. There are two copies of the EVD transposon in the *Arabidopsis* genome that are predicted to be upregulated by the guide RNAs used, one that resides in a region of heterochromatin near the centromere on chromosome 1 (At1g34967), and one that resides in an area of the genome that is generally euchromatic on chromosome 5 (At5g17125). It was found that both copies were highly upregulated and genome-wide analyses indicated that the activation of EVD was highly specific, with very few other genes affected (FIG. 22A-FIG. 22B). These results show that SunTag VP64 can be used to specifically activate genes in both heterochromatin and euchromatin.

Figure 23:
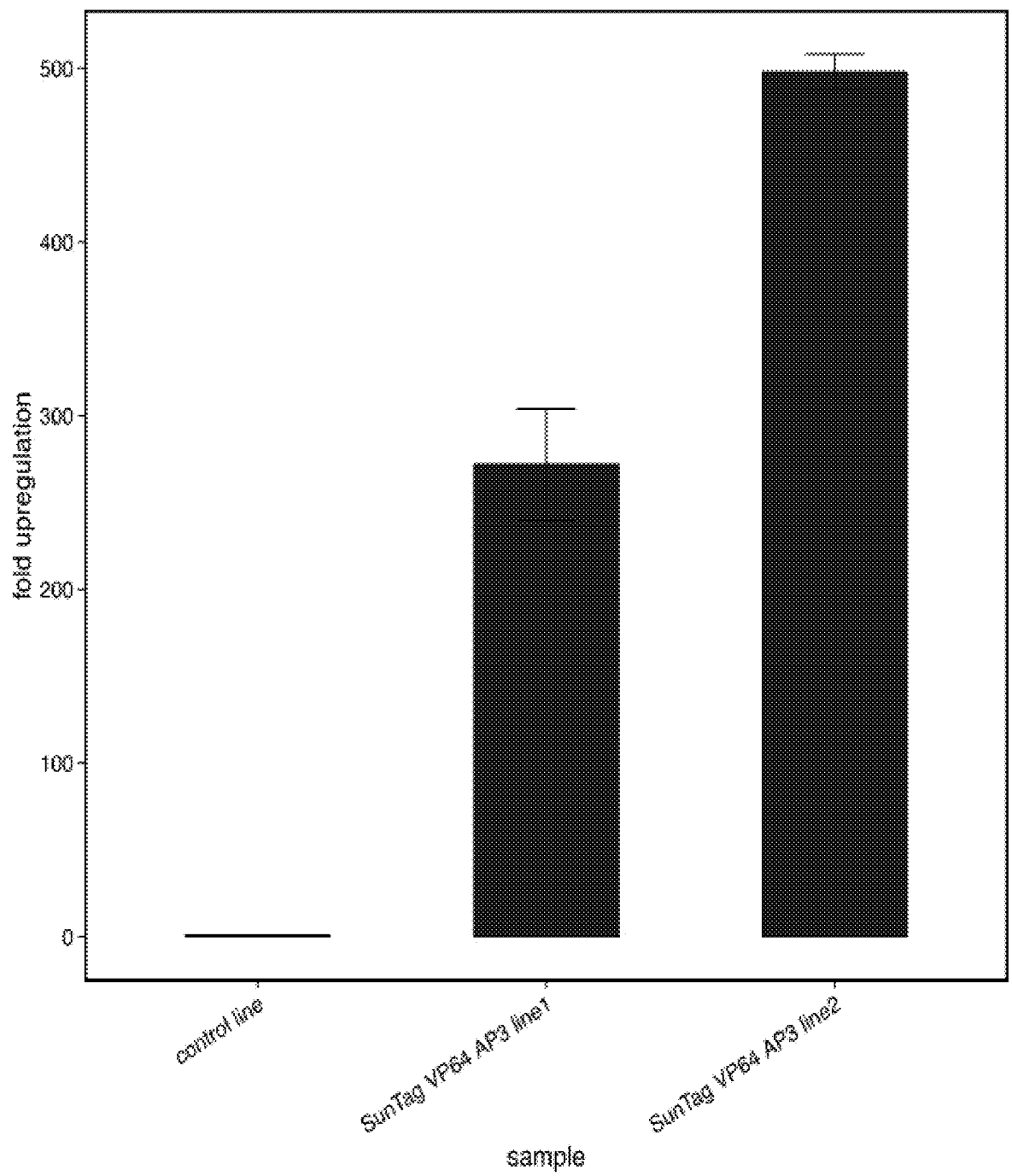
FIG. 23 illustrates qRT-PCR data for AP3. Expression data is from two independent T1 lines with two guides targeting the promoter region of AP3. A control line expressing guides targeting the unrelated EVD gene is included as a negative control. Fold upregulation is plotted and a housekeeping gene, IPP2, was used as an internal control. Error bars indicate standard error of the mean of two replicates.
Figure 24:
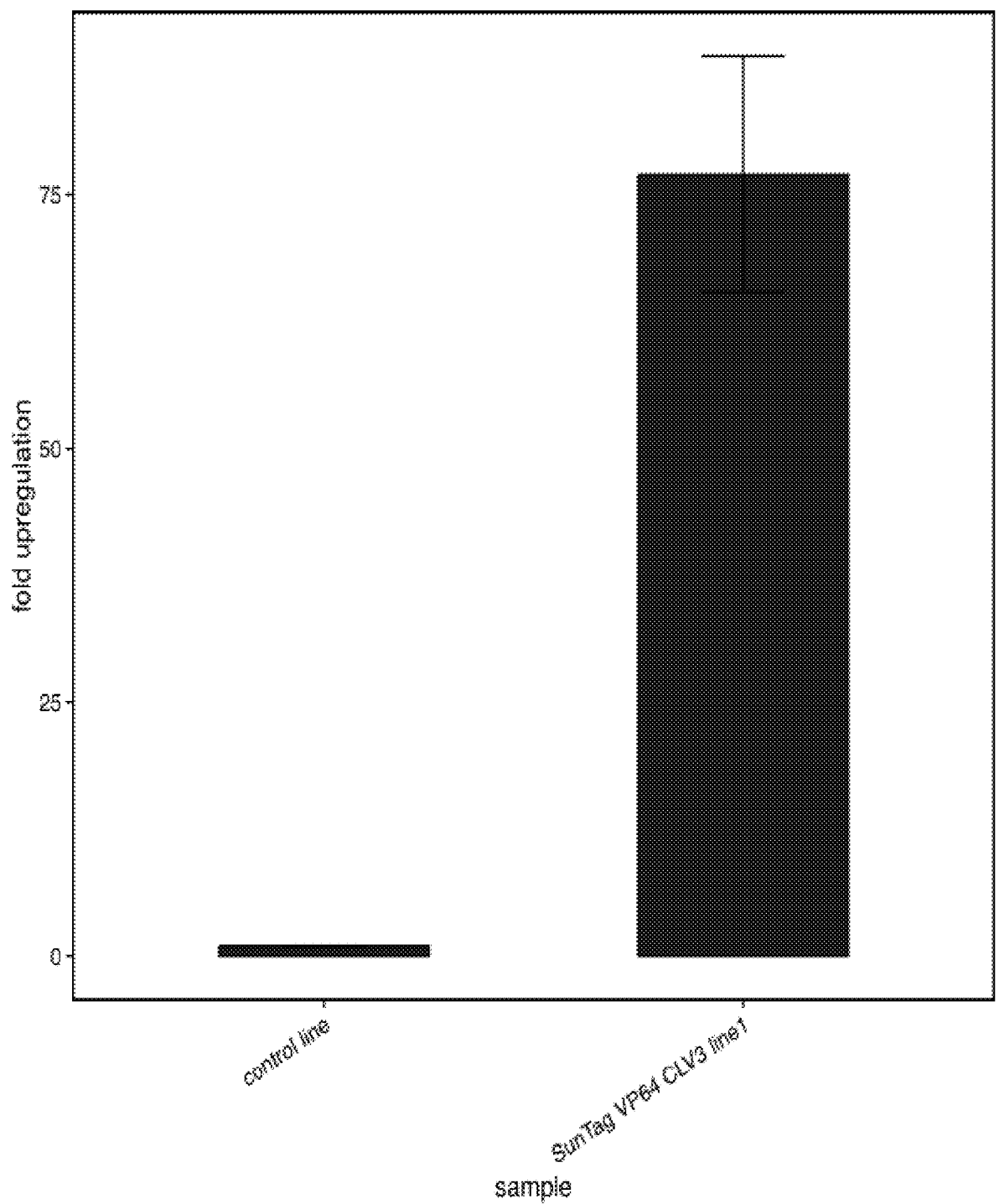
FIG. 24 illustrates qRT-PCR data for CLV3. Expression data is from one T1 line with two guides targeting the promoter region of CLV3. A wild type sample is included as a negative control. Fold upregulation is plotted and a housekeeping gene, IPP2, was used as an internal control. Error bars indicate standard error of the mean of two replicates.

Two additional genes were targeted for activation using the SunTag VP64 activation system. One gene is AP3, which regulates floral development. It has no methylation present in its promoter. Two designed sgRNAs were targeted to its promoter and as shown by qRT-PCR in FIG. 23, two independent T1 lines displayed an upregulation of AP3 transcription. CLV3, which controls the development of the shoot apical meristem among other functions, is another gene that was targeted with two guides simultaneously. The CLV3 locus is not methylated in its promoter. FIG. 24 shows qRT-PCR expression data of one T1 SunTag VP64 line, and displays an upregulation of the CLV3 transcript.

Overall, these results suggest that Applicant's SunTag VP64 system for use in plants is a highly robust activation tool that is able to access multiple chromatin contexts through sgRNA complementarity and can subsequently activate transcription of a diverse set of genomic targets. This tool can also be used to activate genes with promoter methylation as well as genes with no promoter methylation. The observation that SunTag VP64 can be used to transiently activate transposons raises the possibility of using this tool to create new transposition events in the genome, with very few off target effects and without the use of reagents that demethylate the entire genome.

REFERENCES

Tanenbaum et al. A Protein-Tagging System for Signal Amplification in Gene Expression and Fluorescence Imaging. Cell 159, 635-646, Oct. 23, 2014.

Example 4: SDG2-Mediated Gene Activation and the Loss of DNA Methylation

This Example demonstrates the targeting of an SDG2 polypeptide to a locus of interest. Certain histone marks have been shown to be associated with particular transcriptional states. The trimethylation of lysine 4 of histone H3 at the 5' ends of genes usually corresponds to a state of active transcription. However, whether H3K4 methylation can directly activate transcription, or results from transcription itself was previously unknown in plants. In this Example, the C-terminal region of the *Arabidopsis thaliana* histone methyltransferase SDG2 was targeted to genes in various chromatin contexts using the CRISPR-Cas9 SunTag system, and the results show that SDG2 can directly activate transcription. In addition, the activation of targets containing DNA methylation leads to a decrease of DNA methylation at those regions. The ability to target histone methylation may serve e.g. as a tool for studying the direct effects of histone modifications, as well as for biotechnology applications.
Introduction Histone modifications play important roles in regulating the expression of genes in distinct cell types and throughout various stages of development. However, the association of epigenetic marks and transcriptional status is mainly based on evidence that relies on correlations between epigenomic profiling and expression data. Numerous reports have shown how histone marks can directly influence transcription[1]. Further research and the development of epigenome editing tools will further characterize the effects of histone modifications upon gene expression.

H3K4me3 is present at the 5' ends of certain genes, and is correlated with active transcription[1]. In *Saccharomyces cerevisiae*, Set1/COMPASS is responsible for the deposition of H3K4 methylation in mono-, di-, and tri-form[2]. In humans, Set1 homologs consist of the Mixed Lineage Leukemia family of proteins, which consist of MLL1-MLL4, SET1A, and SET1B. In both yeast and humans, the presence of H3K4me3 positively correlates with Pol II occupancy and the presence of histone acetyl marks[3]. In *Arabidopsis thaliana*, similar to yeast and mammals, genes with H3K4me3 are highly expressed. H3K4me3 and -me2 are mainly present in promoters and the 5' ends of genes, whereas H3K4me1 is mainly localized to gene bodies, similar to the localization of gene body CG methylation[4]. However, both H3K4me2 and -me3 marks are anticorrelated with DNA methylation.

In plants, DNA methylation exists in three different contexts: CG, CHG, and CHH, where H=A, T, or C. De novo methylation in all three contexts is catalyzed by the RNA-directed DNA methylation (RdDM) pathway[5]. Maintenance methylation is catalyzed by distinct pathways for each sequence context. CG methylation is maintained by DNA METHYLTRANSFERASE 1 (MET1), CHG methylation is maintained by CHROMOMETHYLASE 3 (CMT3) and a self-reinforcing feedback loop involving H3K9me2 and SUPPRESSOR OF VARIEGATION 3-9 HOMOLOGUE 4 (SUVH4), SUVH5, and SUVH6. CHH methylation in euchromatic contexts and the edges of long TEs is maintained by the RdDM pathway[5]. CHH methylation in heterochromatin is maintained by CMT2 and a feedback loop involving SUVH4-6, through a similar mechanism involving CMT3 and CHG maintenance[6-8].

The CRISPR-Cas systems for genome engineering have made (epi)genome editing approaches much more feasible for multiplexing and have increased the specificity of targeting approaches[9]. The catalytic HNH and RuvC-like domains of Cas9 have been mutated to create deactivated versions of Cas9 (dCas9), thus transforming Cas9 to an RNA-guided DNA-binding domain[9]. Different types of effector proteins can be fused to dCas9 in order to endow it with different capabilities. For example, straight fusions of dCas9 with transcriptional activators, as well as other $2^{nd}$ generation transcriptional activator CRISPR-Cas-based systems have been made to activate the expression of genes at specific loci[10]. The SunTag system has been shown to robustly activate the expression of genes by recruiting multiple copies of the transcriptional activator VP64[11,12]. This system has also been adapted to remove and target DNA methylation in mammals[13-15]. The SunTag system has also been adapted for targeted DNA demethylation and targeted transcriptional activation in plants[16,17].

It was previously shown that targeting SunTag VP64 to the promoter of the methylated FWA locus was able to activate its expression[17], circumventing CG methylation mediated silencing of FWA[18] and reaching or surpassing FWA transcript levels seen in fwa epigenetic mutant plants, where all FWA promoter methylation is lost, leading to reactivation[19]. It has been shown in mammalian cell lines that targeting H3K4me3 can directly activate gene expression[20]. In plants, however, it has previously been unknown whether H3K4me3 can initiate transcription, or whether it is a consequence of transcription itself. Here, the C-terminal region of SDG2 (SDG2C), the major H3K4me3 methyltransferase in *Arabidopsis thaliana*, was targeted to a specific locus using a SunTag system to determine if the targeting of histone methylation to specific loci can directly activate gene expression, and to characterize how H3K4me3 and/or the act of transcription affect DNA methylation levels.

Materials and Methods

Plasmid Construction

The components of the SunTag construct were synthesized using GenScript services and PCR amplified and cloned into a binary vector. The SunTag system was adapted from Tanenbaum et al., 2014 in order to create a SunTag-based histone methylation targeting system in plants. For this purpose, the C-terminal region of the histone methyltransferase SDG2 (SDG2C), as described in Guo et al., 2010, was cloned into the SunTag vector. dCas9, single chain variable fragment (scFv) antibodies, and guide RNAs (gRNA) comprise the SunTag system and were cloned into a binary vector using In-Fusion cloning, which would then be used for floral dipping in *Arabidopsis thaliana*. The expression and localization of the SunTag construct components were systematically tested in plants to ensure proper protein production and localization.

The components of the SunTag system were all cloned into one binary vector, as described in Papikian et al., 2019, *Nature Communications*. Human codon optimized dCas9 expression, which is fused to one HA tag, three nuclear localization signals, and a linker followed by a 10× epitope tail, is driven by the plant UBIQUITIN10 (UBQ10) promoter. A TBS insulator sequence separates dCas9 and the single chain antibody portion of the system, which is also driven by the UBQ10 promoter. The single chain antibody is fused to superfolder-GFP, followed by an SV40-type NLS that was added for plant nuclear localization, a linker, the catalytic domain of SDG2, GB1, and a REX NLS. The catalytic domain of SDG2 (described in Guo et al., 2010 (*Proc. Natl. Acad. Sci. USA*)) was amplified from cDNA with the stop codon included and cloned into the SunTag binary vector. The stop codon was included to exclude GB1 and the REX NLS from translation, as they are unnecessary for the present purpose. sgRNA expression was driven by the U6 promoter. The final construct was used for plant transformation.

Construction of dCAS9-10×GCN4 Cassette

The dCAS9-10×GCN4 portion of the SunTag vector that was constructed is contained in expression cassette UBQ10_OmegaRBC_dCas9_1×HA_NLSNLSNLS_flexible linker_GCN4×10_OCS-terminator (nucleic acid sequence presented in SEQ ID NO: 68). This cassette contains the following features and nucleic acid sequences are provided: UBQ10 promoter (SEQ ID NO: 69), Omega RBC translation enhancer (SEQ ID NO: 70), dCas9 (SEQ ID NO: 71), 1×HA (SEQ ID NO: 72), 3×NLS (SEQ ID NO: 73), flexible linker (SEQ ID NO: 74), GCN4×10 (SEQ ID NO: 75). The expression cassette further included an OCS terminator (SEQ ID NO: 76).

This expression cassette produces a recombinant dCas9-10×GCN4 fusion protein (SEQ ID NO: 77): dCAS9-1×HA-3×NLS-flexible linker-GCN4×10. The amino acid sequences of features present in the recombinant fusion protein expressed from this expression cassette are: dCAS9 (SEQ ID NO: 78), 1×HA (SEQ ID NO: 79), 3×NLS (SEQ ID NO: 80), flexible linker (SEQ ID NO: 81), and 10×GCN4 (SEQ ID NO: 82). In the dCAS9-1×HA-3×NLS-flexible linker-GCN4×10 fusion polypeptide (SEQ ID NO: 77), in the third sequence of the NLS in the 3×NLS sequence, there is an "A" amino acid residue that precedes the rest of the NLS sequence.

Construction of scFv-SDG2C Cassette

The scFv-SDG2C portion of the SunTag vector that was constructed is contained in expression cassette UBQ10_scFv_sfGFP_NLS_glycine linker_SDG2C_GB1_REX NLS_NOS terminator (nucleic acid sequence presented in SEQ ID NO: 83). This cassette contains the following features and nucleic acid sequences are provided: UBQ10 promoter (SEQ ID NO: 84), scFv antibody (SEQ ID NO: 85), sfGFP (SEQ ID NO: 86), NLS (SEQ ID NO: 87), glycine linker (SEQ ID NO: 88), SDG2C (SEQ ID NO: 89), GB1 (SEQ ID NO: 90), REX NLS (SEQ ID NO: 91), and NOS terminator (SEQ ID NO: 92).

This expression cassette produces a recombinant scFv-SDG2C fusion protein (SEQ ID NO: 93): scFv-sfGFP-NLS-glycine linker-SDG2C. The amino acid sequences of features present in the recombinant fusion protein expressed from this expression cassette are: scFv (SEQ ID NO: 94), sfGFP (SEQ ID NO: 95), NLS (SEQ ID NO: 96), glycine linker (SEQ ID NO: 97), and SDG2C (SEQ ID NO: 98).

Construction of gRNA Cassette

For targeting the FWA promoter, a gRNA expression cassette was constructed: U6:gRNA4 (nucleic acid sequence presented in SEQ ID NO: 99). This cassette contains the following features and nucleic acid sequences are provided: U6 promoter (SEQ ID NO: 100), protospacer #4 (SEQ ID NO: 101), gRNA backbone (SEQ ID NO: 102), and PolIII terminator (SEQ ID NO: 103).

Construct Transformation into *Arabidopsis*

The SunTag vector described above was transformed into *Agrobacterium*. The vector was then introduced into Col-0 wild-type *Arabidopsis thaliana* plants using *Agrobacterium*-mediated transformation via the floral dip method. T1 transgenic plants were selected.

qRT-PCR qRT-PCR assays were conducted according to standard methods and the manufacturer's protocol. The Superscript III First-Strand synthesis kit (Invitrogen) was used for these assays.

Bisulfite Sequencing

BS-Seq libraries were generated as previously reported (Papikian et al., 2019) and all libraries were sequenced using the HiSeq 4000 platform following manufacturer instructions (Illumina) at a length of 50 bp. Bisulfite-Seq (BS-Seq) reads were aligned to the TAIR10 version of the *Arabidopsis thaliana* reference genome using BS-seeker2. For BS-Seq, up to 2 mismatches were allowed and only uniquely mapped reads were used.

Results

Figure 25:
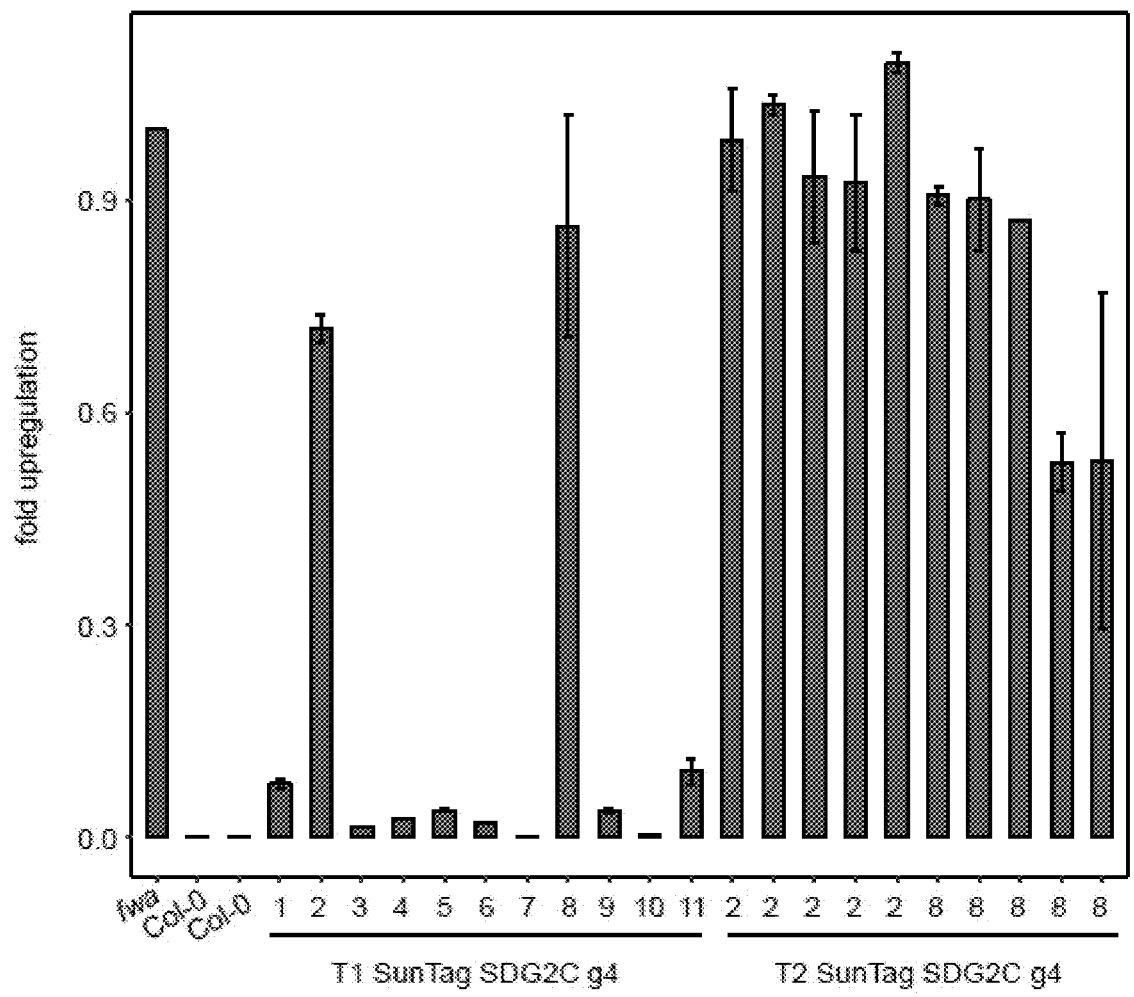
FIG. 25 illustrates that SunTag SDG2C is able to activate the expression of FWA. Shown are qRT-PCR results of FWA transcript levels in an fwa epiallele control plant, 2 Col-Q control plants, 11 independent T1 lines of SunTag SDG2C gRNA4 (g4), and multiple progeny from 2 independent lines of 12 plants. Expression fold change relative to the fwa epiallele plant is plotted and error bars represent the mean±s.e. of 2 technical replicates.

In order to make a CRISPR-Cas-based system to target histone methylation in plants, a SunTag SDG2C fusion using a 22aa SunTag system was developed and initially targeted to the FWA locus with gRNA4[16,17] in *Arabidopsis thaliana* wild type (Col-0) plants to see if H3K4me3 can be recruited and subsequently lead to the reactivation of FWA expression. qRT-PCR analysis of T1 and T2 SunTag SDG2C gRNA4 plants indicated that FWA expression was reactivated in these lines (FIG. 25).

Figure 26:
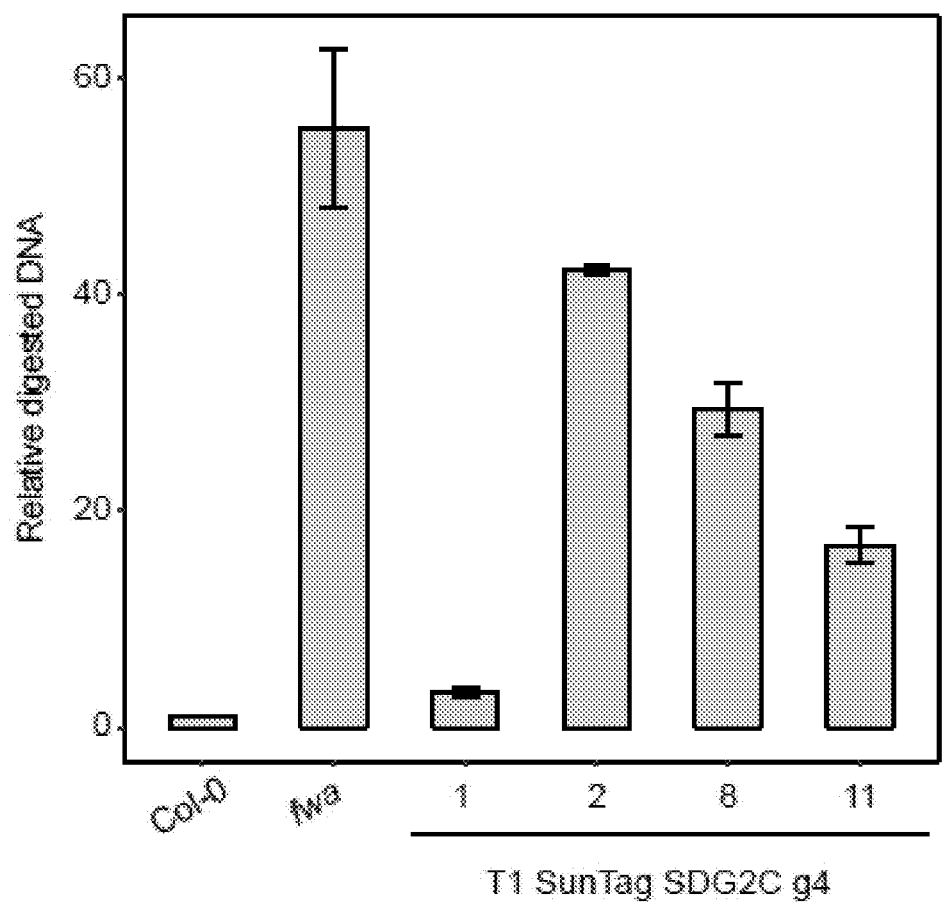
FIG. 26 illustrates that SDG2C-mediated activation of FWA leads to a reduction in DNA methylation. Shown are qPCR results quantifying McrBC digested genomic DNA at the 5' end of the FWA locus in Col-0, fwa, and 4 independent T1 lines of SunTag SDG2C gRNA4. Data is displayed relative to Col-0 and error bars represent the mean±s.e. of 2 technical replicates.
Figure 27:
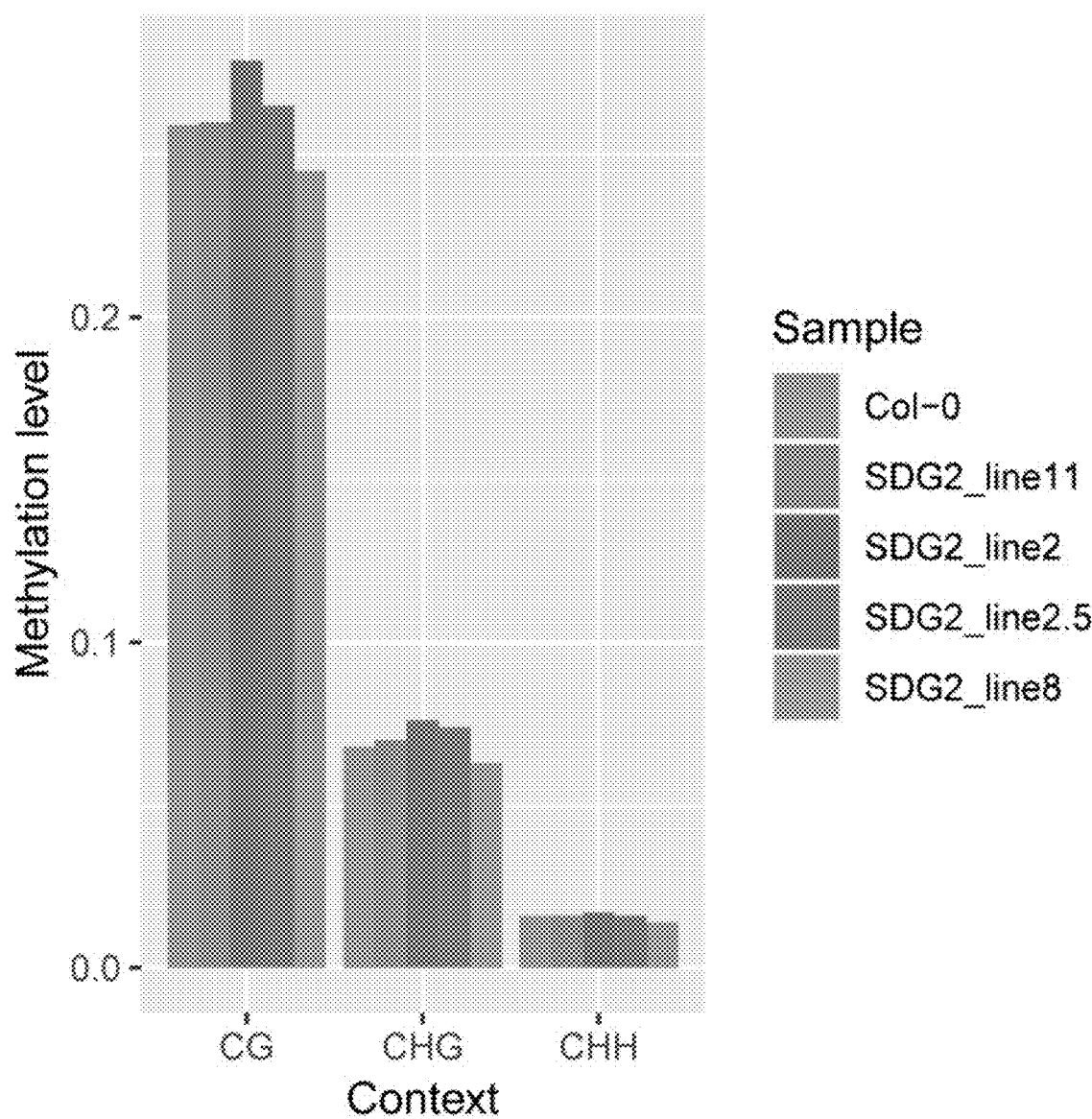
FIG. 27 illustrates the genome wide level of DNA methylation (ratio of methylated to unmethylated) in Col-0 and SDG2C SunTag lines for all three methylation contexts (CG, CHG, CHH). For FIG. 27-FIG. 35, a plant is a 12 generation plant if it contains a decimal point (.) in its identifier. For example, "SDG2_line2.5" is a 12 plant from line 2, plant #5.
Figure 28:
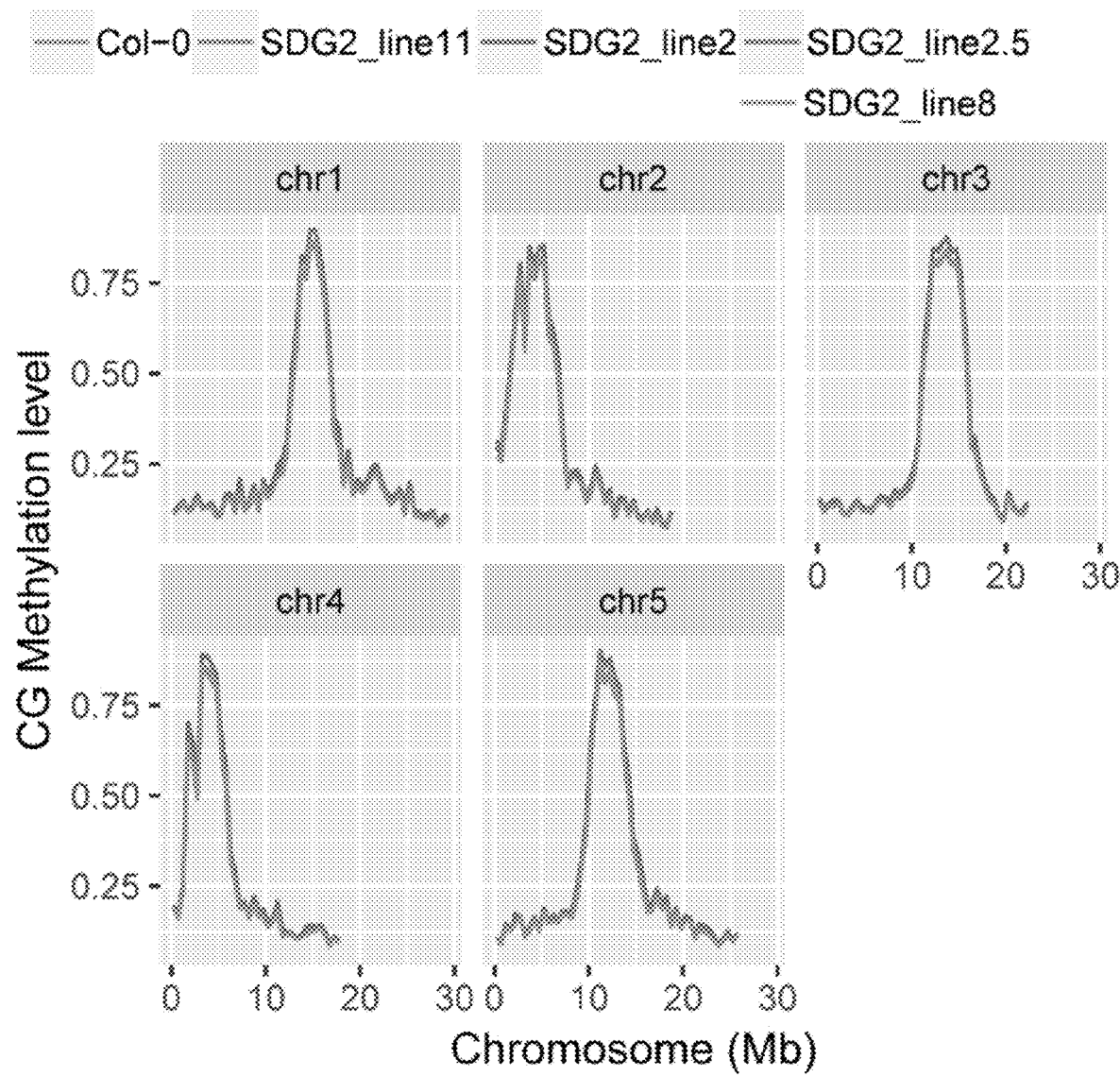
FIG. 28 illustrates the per-chromosome pattern of CU DNA methylation in Col-0 and SDG2C SunTag lines.
Figure 29:
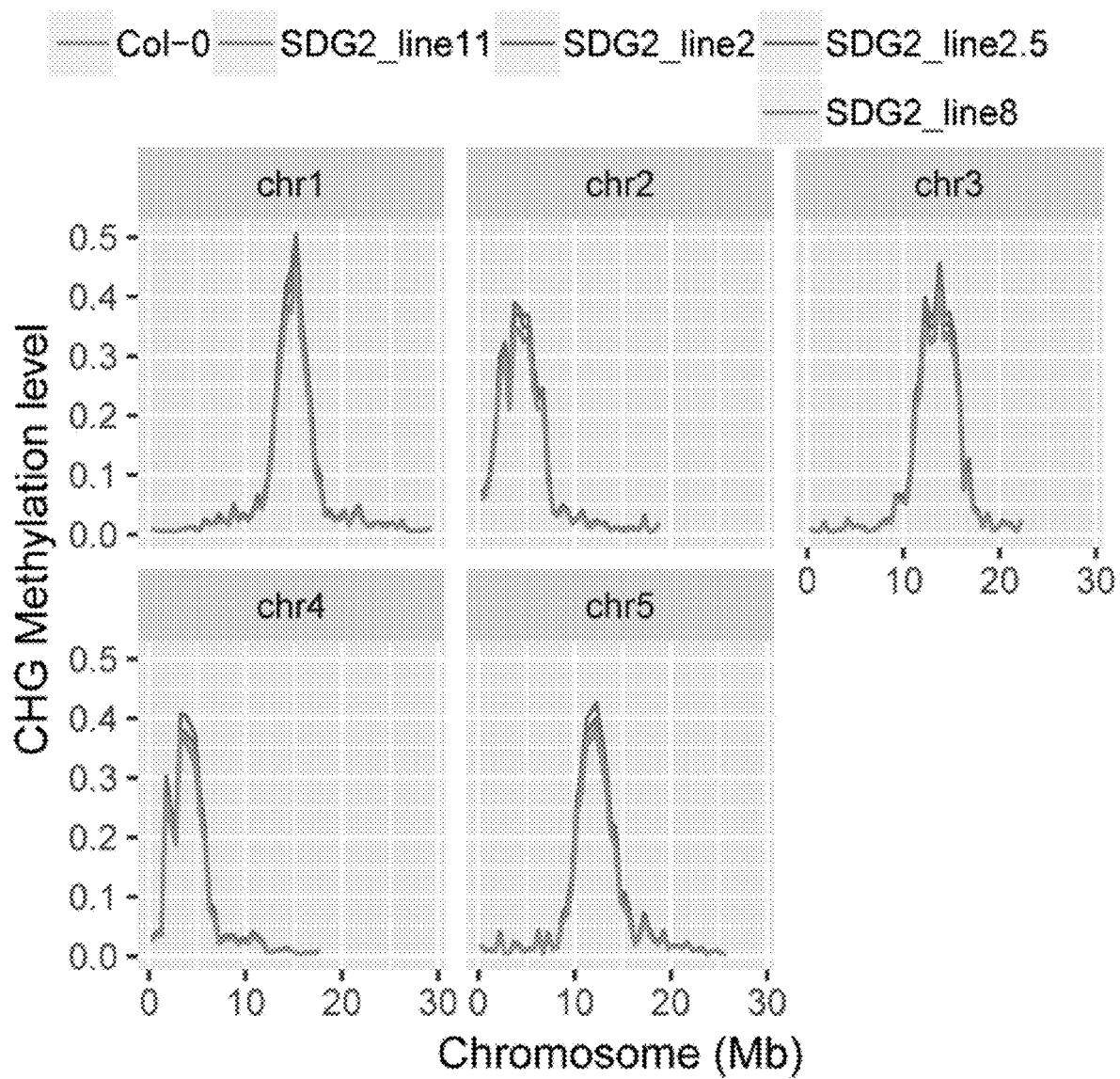
FIG. 29 illustrates the per-chromosome pattern of CHG DNA methylation in Col-0 and SDG2C SunTag lines.
Figure 30:
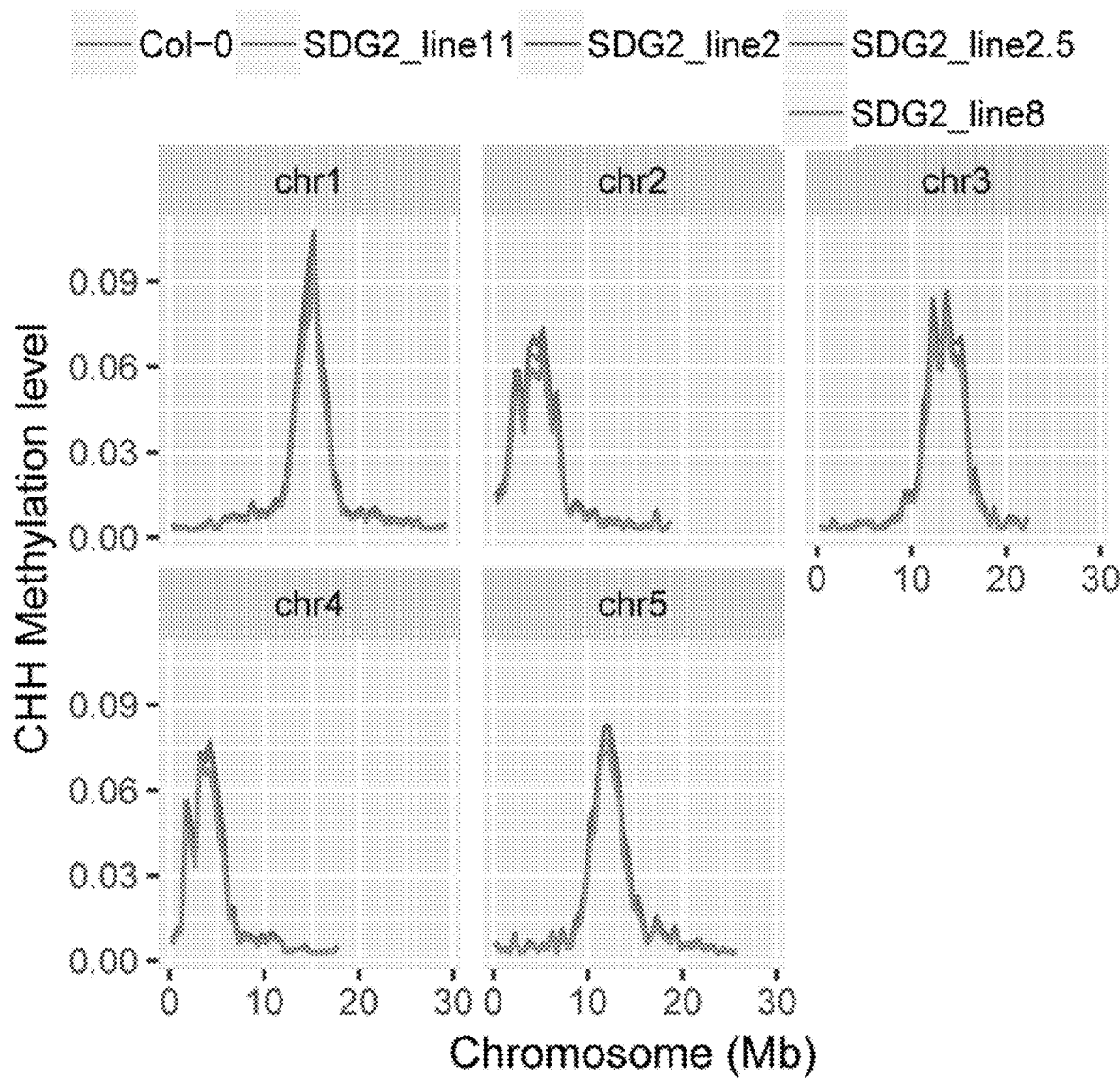
FIG. 30 illustrates the per-chromosome pattern of CHH DNA methylation in Col-0 and SDG2C SunTag lines.
Figure 31:
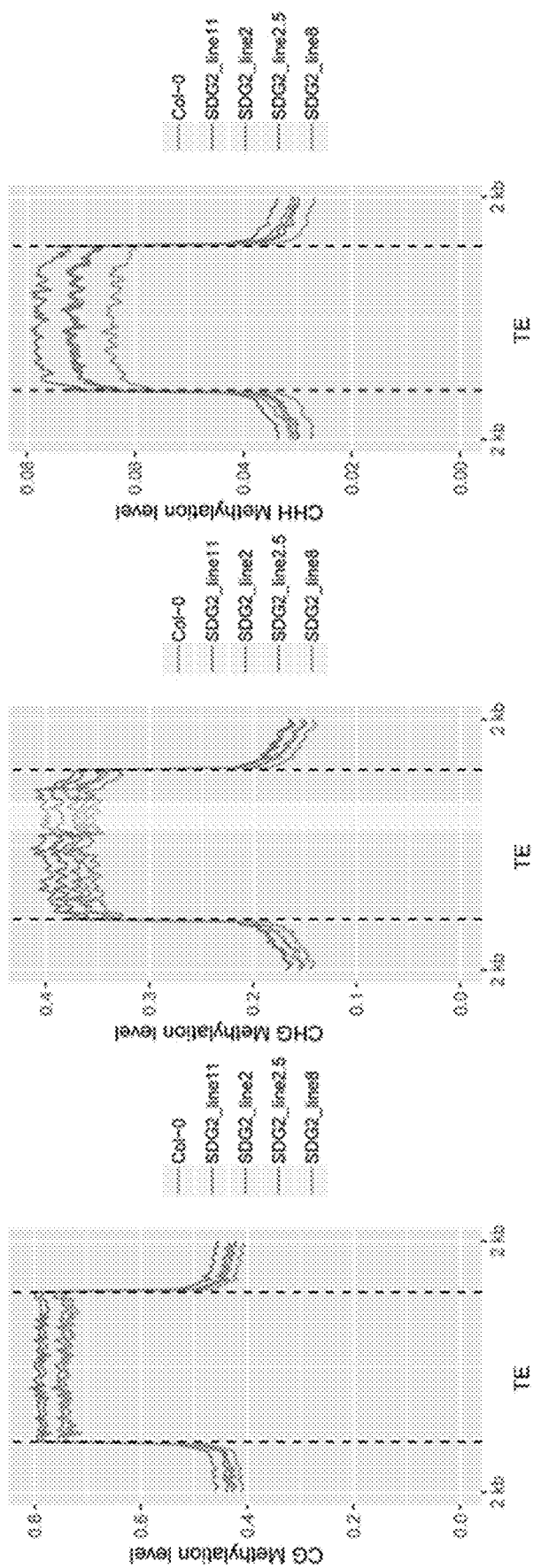
FIG. 31 illustrates the pattern of DNA methylation across transposable elements (TEs) in Col-0 and SDG2C SunTag lines for all three methylation contexts (CG, CHG, CHH).
Figure 32:
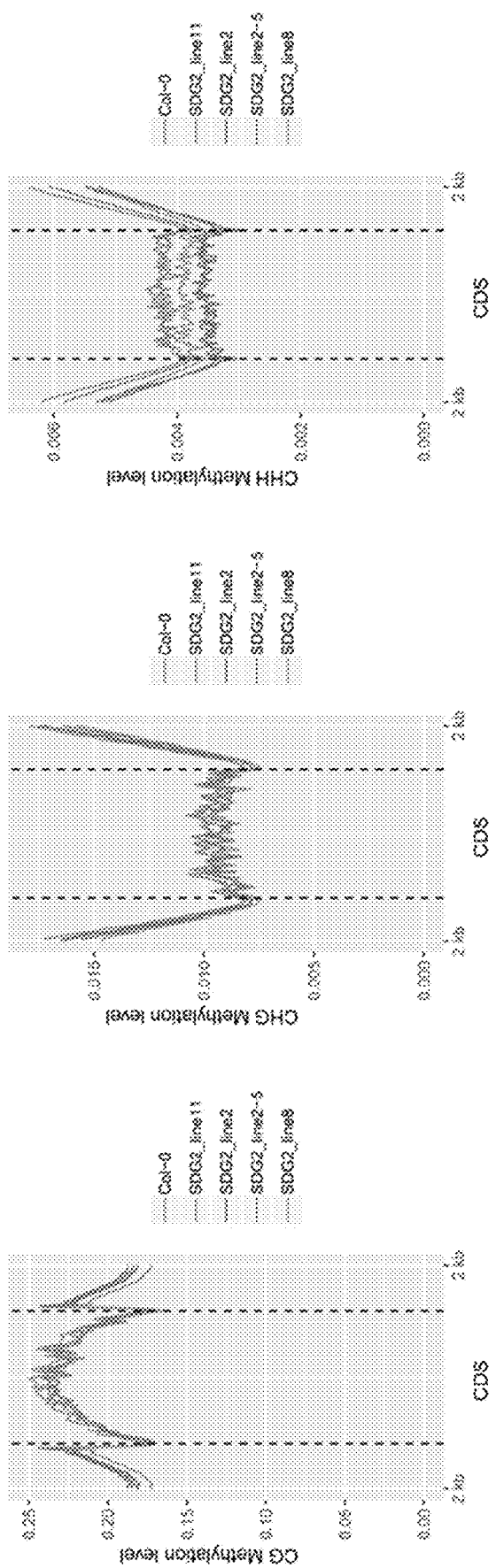
FIG. 32 illustrates the pattern of DNA methylation across coding sequences (CDS) in Col-0 and SDG2C SunTag lines for all three methylation contexts (CG, CHG, CHH).
Figure 33:
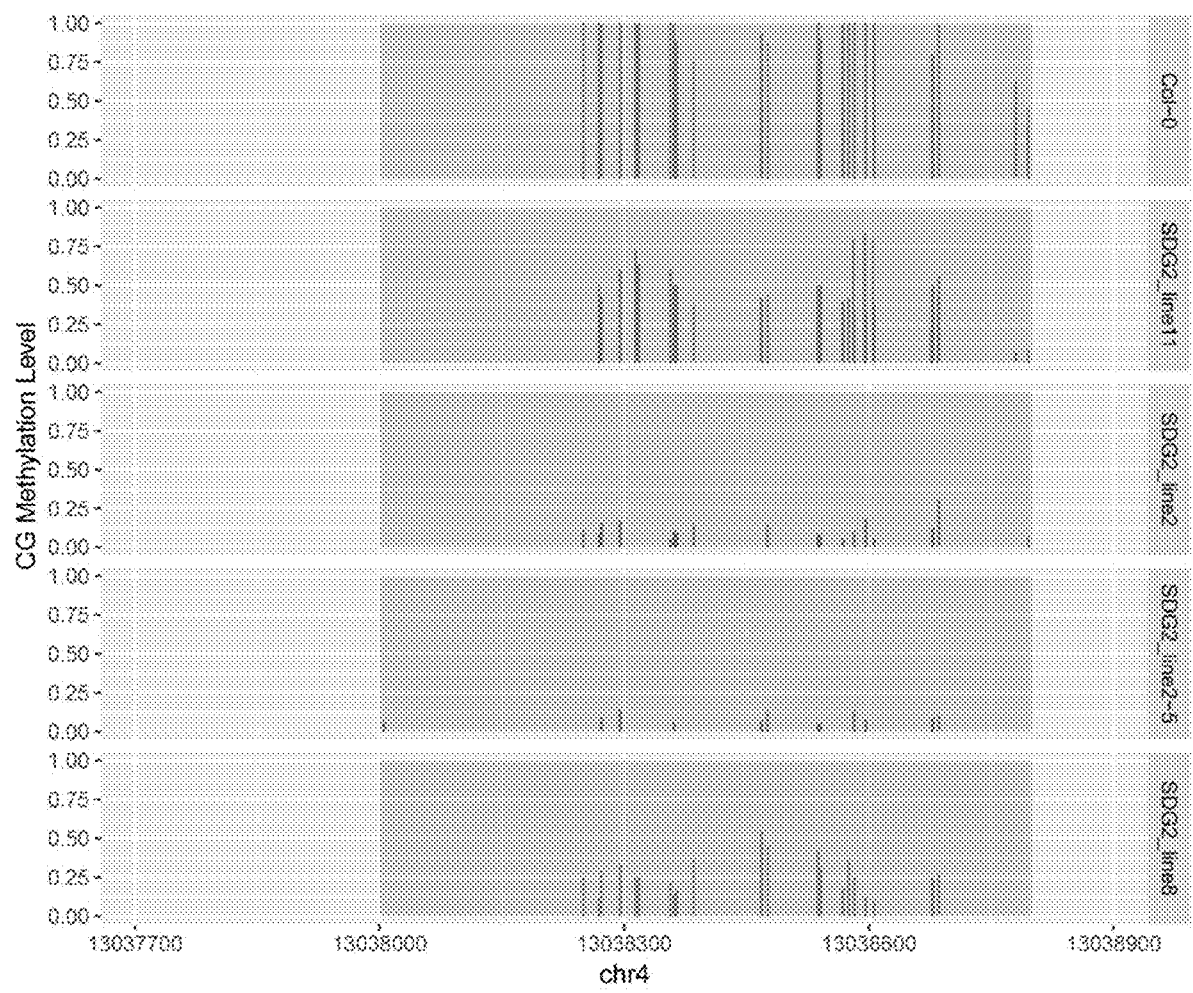
FIG. 33 illustrates the pattern of CG DNA methylation at the FWA locus in Col-0 and SDG2C SunTag lines.
Figure 34:
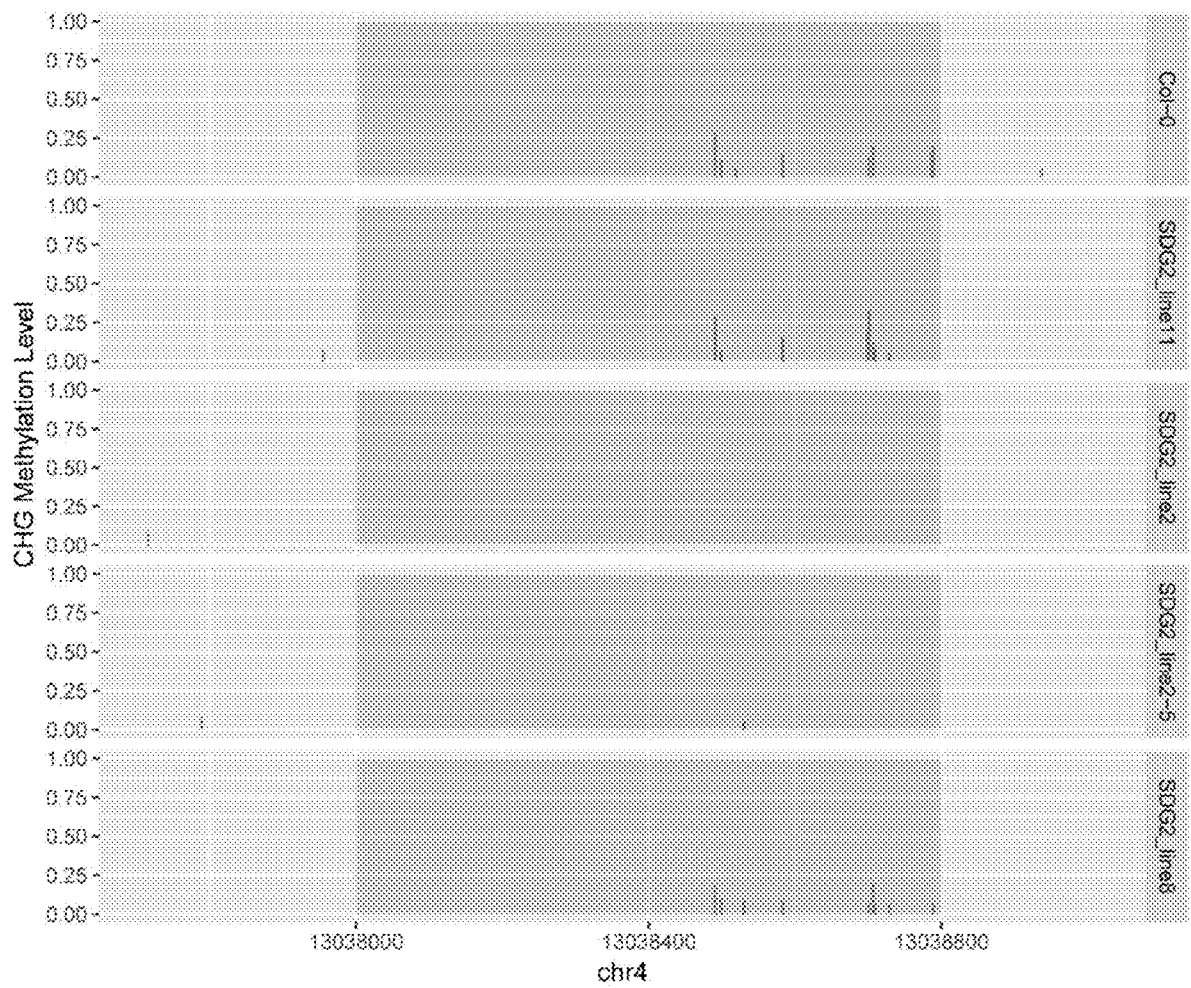
FIG. 34 illustrates the pattern of CHG DNA methylation at the FWA locus in Col-0 and SDG2C SunTag lines.
Figure 35:
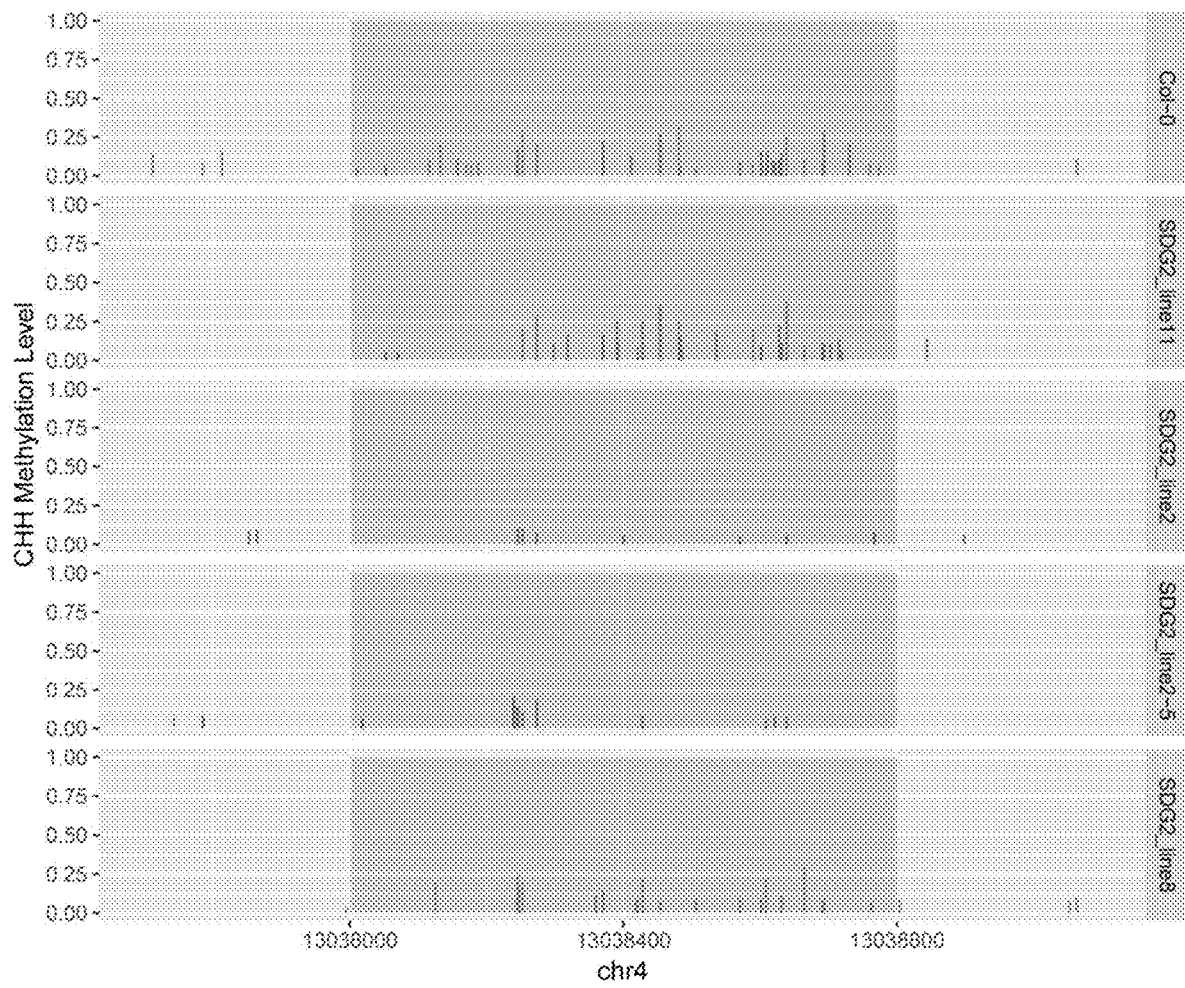
FIG. 35 illustrates the pattern of CHH DNA methylation at the FWA locus in Col-0 and SDG2C SunTag lines.

It was previously shown that SunTag VP64-mediated activation of FWA expression can lead to a reduction or total loss of FWA promoter methylation[17]. Interestingly, T1 SunTag SDG2C gRNA4 transgenic plants showed a similar effect, indicating that activation was coupled with the demethylation of DNA (FIG. 26). This surprising result was further investigated using whole genome bisulfite sequencing (WGBS). Global analysis of DNA methylation patterns suggested comparable levels of global DNA methylation between the Col-0 and SDG2C SunTag lines (FIG. 27-FIG. 30). However, specific differences in DNA methylation at the FWA locus were observed, notably that the SDG2C SunTag lines had markedly reduced levels of DNA methylation in all three sequence contexts (CG, CHG, and CHH) as compared to wild-type Col-0 plants (FIG. 33-FIG. 35).

Discussion

This Example illustrates how targeting SunTag SDG2C to specific loci in different chromatin contexts in *Arabidopsis* directly leads to gene activation, and in addition, activation of methylated targets leads to a decrease or complete loss of proximal methylation. This observation is similar to what was observed upon FWA and EVD/ATR upregulation with SunTag VP64[17].

SunTag SDG2C represents a new tool for plants in order to directly study the effects on gene expression and chromatin at targeted loci with ectopic H3K4me3. In addition to unmethylated loci, the targeting of methylated loci may lead to H3K4me3 and expression-mediated DNA demethylation. This tool also represents another SunTag system for the manipulation of gene expression and epigenome engineering, having implications in both basic research and in plant biotechnology (e.g. to activate or overexpress loci critical to crop yield).

REFERENCES

1. Gates, L. A., Foulds, C. E. & O'Malley, B. W. Histone Marks in the 'Driver's Seat': Functional Roles in Steering the Transcription Cycle. Trends Biochem. Sci. 42, 977-989 (2017).
2. Shilatifard, A. COMPASS family of H3K4 MTs: Mechanisms in Development and Disease Pathogenesis. 65-95 (2014). doi:10.1146/annurev-biochem-051710-134100. The
3. Ruthenburg, A. J., Allis, C. D. & Wysocka, J. Methylation of Lysine 4 on Histone H3: Intricacy of Writing and Reading a Single Epigenetic Mark. Mol. Cell 25, 15-30 (2007).
4. Zhang, X., Bernatavichute, Y. V. Cokus. S., Pellegrini, M. & Jacobsen, S. E. Genome-wide analysis of mono-, di- and trimethylation of histone H3 lysine 4 in *Arabidopsis thaliana*. Genome Biol. 10, R62 (2009).
5. Law, J. A. & Jacobsen, S. E. Establishing, maintaining and modifying DNA methylation patterns in plants and animals. Nat. Rev. Genet. 11, 204-220 (2010).
6. Du. J., Johnson, L. M., Jacobsen, S. E. & Patel. D. J. DNA methylation pathways and their crosstalk with histone methylation. Nat. Rev. Mol. Cell Biol. 16, 519-532 (2015).
7. Zemach, A. et al. The *Arabidopsis* nucleosome remodeler DDM1 allows DNA methyltransferases to access H1-containing heterochromatin. Cell 153, 193-205 (2013).
8. Stroud, H. et al. Non-CG methylation patterns shape the epigenetic landscape in *Arabidopsis*. Nat Struct. Mol. Biol. 21, 64-72 (2013).
9. Doudna, J. A. & Charpentier, E. The new frontier of genome engineering with CRISPR-Cas9. Science (80-.). 346, 1258096-1258096 (2014).
10. Chavez, A. et al. Comparison of Cas9 activators in multiple species. Nat. Methods 13, 563-567 (2016).
11. Tanenbaum, M. E., Gilbert, L. A., Qi. L. S., Weissman, J. S. & Vale, R. D. A protein-tagging system for signal amplification in gene expression and fluorescence imaging. Cell 159, 635-646 (2014).
12. Gilbert, L. A. et al. Genome-Scale CRISPR-Mediated Control of Gene Repression and Activation. Cell 159, 647-661 (2014).
13. Morita, S. et al. Targeted DNA demethylation in vivo using dCas9-peptide repeat and scFv-TET1 catalytic domain fusions. Nat. Biotechnol. 34, 1060-1065 (2016).
14. Huang. Y.-H. et al. DNA epigenome editing using CRISPR-Cas SunTag-directed DNMT3A. Genome Biol. 18, 176 (2017).
15. Ford. E. et al. A modular dCas9-SunTag DNMT3 A epigenome editing system overcomes pervasive off-target activity of direct fusion dCas9-DNMT3A constructs. Genome Res. 28, 1193-1206 (2018).
16. Gallego-Bartolomé, J. et al. Targeted DNA demethylation of the *Arabidopsis* genome using the human TET1 catalytic domain. Proc. Natl. Acad. Sci. 115, 201716945 (2018).
17. Papikian. A., Liu, W., Gallego-Bartolome. J. & Jacobsen, S. E. Site-specific manipulation of *Arabidopsis* loci using CRISPR-Cas9 SunTag systems. Nat Commun. 1-11 doi: 10.1038/s41467-019-08736-7
18. Johnson, L. M. et al. SRA- and SET-domain-containing proteins link RNA polymerase V occupancy to DNA methylation. Nature 507, 124-128 (2014).
19. Soppe, W. J. J. et al. The late flowering phenotype of fwa mutants is caused by gain-of-function epigenetic alleles of a homeodomain gene. Mol. Cell 6, 791-802 (2000).
20. Dokter-Fokkens, J. et al. Writing of H3K4Me3 overcomes epigenetic silencing in a sustained but context-dependent manner. Nat. Conmun. 7, 1-11 (2016).
21. Guo et al., SET DOMAIN GROUP2 is the major histone H3 lysine [corrected] 4 trimethyltransferase in *Arabidopsis*. Proc Natl Acad Sci USA. 2010 Oct. 26; 107(43): 18557-62.

What is claimed is:

1. A method for activating expression of a target nucleic acid in a plant, comprising:
   (a) providing a plant comprising:
      a first recombinant polypeptide comprising 1) a nuclease-deficient CAS9 polypeptide (dCAS9) or fragment thereof and 2) a multimerized epitope;
      a second recombinant polypeptide comprising 1) a histone methyltransferase domain at least 90% identical to SEQ ID NO: 98 and 2) an affinity polypeptide that specifically binds to the epitope;
      a crRNA and a tracrRNA, or fusions thereof; and
   (b) growing the plant under conditions whereby the first and second recombinant polypeptides are targeted to the target nucleic acid, thereby activating expression of the target nucleic acid.

2. The method of claim 1, wherein the multimerized epitope comprises a GCN4 epitope.

3. The method of claim 1, wherein the first polypeptide comprises a nuclear localization signal (NLS).

4. The method of claim 1, wherein the affinity polypeptide is an antibody.

5. The method of claim 4, wherein the antibody is an scFv antibody.

6. The method of claim 1, wherein the second polypeptide comprises an SV40-type NLS.

7. The method of claim 1, wherein expression of the activated nucleic acid is increased in the range of about 100-fold to about 10,000-fold as compared to a corresponding control.

8. A recombinant vector comprising:
   a first nucleic acid sequence comprising a plant promoter and that encodes a recombinant polypeptide comprising 1) a nuclease-deficient CAS9 polypeptide (dCAS9) or fragment thereof and 2) a multimerized epitope;
   a second nucleic acid sequence comprising a plant promoter and that encodes a recombinant polypeptide comprising 1) a histone methyltransferase domain at least 90% identical to SEQ ID NO: 98 and 2) an affinity polypeptide that specifically binds to the epitope; and
   a third nucleic acid sequence comprising a promoter and that encodes a crRNA and a tracrRNA, or fusions thereof.

9. The vector of claim 8, wherein the plant promoter in the first nucleic acid sequence is a UBQ10 promoter.

10. The vector of claim 8, wherein the first nucleic acid sequence comprises a terminator sequence.

11. The vector of claim 8, wherein the multimerized epitope comprises a GCN4 epitope.

12. The vector of claim 8, wherein the first polypeptide comprises a nuclear localization signal (NLS).

13. The vector of claim 8, wherein the plant promoter in the second nucleic acid sequence is a UBQ10 promoter.

14. The vector of any claim 8, wherein the second nucleic acid sequence comprises a terminator sequence.

15. The vector of claim 8, wherein the affinity polypeptide is an antibody.

16. The vector of claim 15, wherein the antibody is an scFv antibody.

17. The vector of claim 8, wherein the second polypeptide comprises an SV40-type NLS.

18. A plant or plant cell comprising the vector of claim 8.

19. A method for producing a plant with increased expression of a target nucleic acid, comprising:
   (a) providing a plant comprising a recombinant nucleic acid, wherein the recombinant nucleic acid encodes a recombinant polypeptide comprising: 1) histone methyltransferase domain at least 90% identical to SEQ ID NO: 98, and 2) a heterologous DNA-binding domain comprising a zinc finger domain and capable of binding a target nucleic acid; and
   (b) growing the plant under conditions whereby the recombinant polypeptide encoded by the recombinant nucleic acid is expressed and is targeted to the target nucleic acid, thereby increasing expression of the target nucleic acid to produce the plant with increased expression of the target nucleic acid.

* * * * *